US010065990B2

(12) United States Patent
Jiang et al.

(10) Patent No.: US 10,065,990 B2
(45) Date of Patent: Sep. 4, 2018

(54) CYCLIC PEPTIDE COMPOUND, AND PREPARATION METHOD, PHARMACEUTICAL COMPOSITION AND USE THEREOF

(71) Applicant: HANGZHOU GUANYU BIO-MEDICAL CO., LTD, Zhejiang (CN)

(72) Inventors: Sheng Jiang, Shanghai (CN); Zhiyi Yao, Shanghai (CN); Yiwu Yao, Shanghai (CN); Yatao Qiu, Shanghai (CN); Changyin Lu, Shanghai (CN); Kun Su, Shanghai (CN); Xiaoming Yao, Shanghai (CN)

(73) Assignee: HANGZHOU GUANYU BIO-MEDICAL CO., LTD., Zhejiang (CN)

( * ) Notice: Subject to any disclaimer, the term of this patent is extended or adjusted under 35 U.S.C. 154(b) by 255 days.

(21) Appl. No.: 14/915,740

(22) PCT Filed: Sep. 2, 2014

(86) PCT No.: PCT/CN2014/085705
§ 371 (c)(1),
(2) Date: May 20, 2016

(87) PCT Pub. No.: WO2015/027959
PCT Pub. Date: Mar. 5, 2015

(65) Prior Publication Data

US 2016/0280736 A1 Sep. 29, 2016

(30) Foreign Application Priority Data

Sep. 2, 2013 (CN) .......................... 2013 1 0393529

(51) Int. Cl.

| | |
|---|---|
| ***C07K 5/062*** | (2006.01) |
| ***C07K 5/02*** | (2006.01) |
| ***C07K 1/12*** | (2006.01) |
| *A61K 38/00* | (2006.01) |

(52) U.S. Cl.
CPC .......... *C07K 5/06017* (2013.01); *C07K 1/126* (2013.01); *C07K 5/0207* (2013.01); *C07K 5/06026* (2013.01); *C07K 5/06034* (2013.01); *A61K 38/00* (2013.01); *Y02A 50/411* (2018.01)

(58) Field of Classification Search
None
See application file for complete search history.

(56) References Cited

FOREIGN PATENT DOCUMENTS

| | | | | |
|---|---|---|---|---|
| CN | 102391359 A | 3/2012 | | |
| CN | 102946732 A | 2/2013 | | |
| JP | 2013528182 | 7/2013 | | |
| WO | WO2011150283 A1 * | 12/2011 | ........... | A61K 31/435 |
| WO | 2013071715 A1 | 5/2013 | | |

OTHER PUBLICATIONS

WIPO translation of CN102391359A.*
International Search Report issued in corresponding application No. PCT/CN2014/085705 dated Nov. 26, 2014.
Chung-gi Shin et al., "Practical Synthesis of Oligodehydroalanine Derivatives by Repetition of Stepwise Elongation of Serine Derivative and b-Elimination" Chemistry Letters, The Chemical Society of Japan, 1994, pp. 1301-1304.
Japanese Office Action issued in corresponding Application No. 2016-539409 dated Apr. 11, 2017, 11 pages.
Extended European Search Report issued in corresponding Application No. EP 14840656.4 dated Jul. 26, 2016, 8 pages.

* cited by examiner

*Primary Examiner* — Marcela M Cordero Garcia
*Assistant Examiner* — Jia-Hai Lee
(74) *Attorney, Agent, or Firm* — Carter, Deluca, Farrell & Schmidt, LLP

(57) ABSTRACT

The present invention relates to a cyclic peptide compound, and a preparation method, pharmaceutical composition and use thereof. In particular, the cyclic peptide compound of the present invention has a structure as shown by general formula (I). The compound of general formula (I), and isomers, racemates, pharmaceutically acceptable salts, crystalline hydrates, solvates or mixtures thereof have a use in the preparation of medicaments for preventing or treating mammalian diseases associated with histone deacetylase dysregulations.

(I)

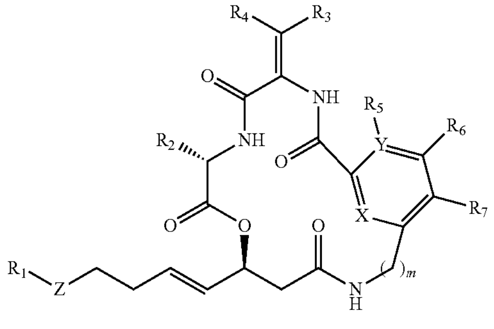

10 Claims, No Drawings

CYCLIC PEPTIDE COMPOUND, AND PREPARATION METHOD, PHARMACEUTICAL COMPOSITION AND USE THEREOF

TECHNICAL FIELD

The present invention relates to the field of medicinal chemistry and chemotherapy domain. More specifically, the present invention relates to a compound with a chemical structure shown as formula (I), its preparation, pharmaceutical compositions and applications of in preparing pharmaceuticals for preventing or treating mammalian diseases related to the dysregulation of histone deacetylase, especially cancer, neurodegenerative diseases, malaria and diabetes, etc.

BACKGROUND TECHNOLOGY

Histone deacetylase HDAC (histone) is a kind of protease, which plays an important role in the structural modification and regulation of gene expression. Under normal circumstances, the acetylation of histone is suitable for DNA and histone octamer dissociated, nucleosome structure relaxation, so that a variety of transcription factors and synergistic transcription factors to DNA binding site specificity combined activation of gene transcription. In the nucleus, histone acetylation and histone to acetylation process is in a dynamic balance, and the histone acetyl transfer enzymes (histone acetyltransferase, hat) and histone deacetylases (histone deacetylase, HDAC) common regulation.

Histone acetylation modification plays an important role in the occurrence and development of tumor. In the normal cell body, once there is an imbalance between the acetylation of histone and histone acetylation, which'd leads to the change of normal cell cycle and cell metabolism behavior and induce tumors accordingly. Histone to acetylation enzyme catalyzed by histone deacetylation, maintain histone acetylation and de acetylation state of equilibrium, many processes and cancer related gene expression, cell proliferation, differentiation and apoptosis is closely related. In cancer cells, HDAC overexpression leads to the enhancement of acetylation and histone through a return to positive charge, thereby increasing the gravitational force between DNA and histone, the relaxation of the nucleosome becomes very closely, is not conducive to the specific gene expression, including several tumor suppressor genes.

With the further development of life science, molecular biology research on the pathogenesis and mechanism of tumor has provided the basis for the development of anti-tumor drugs with low toxicity and high efficiency. Histone deacetylases (HDACs) is one of the key enzymes for the maintenance of chromosomal basic composition unit of the nucleosome organization protein acetylation balance, the catalyzed by histone acetylation, and transcriptional repressor of genes that are closely related, involved in promoting gene silencing of many processes is a hot target for anti-cancer drug design. Histone deacetylase inhibitors (HDACi) can increase acetylation of protein in a specific region of chromatin histone acetylation, thereby regulating the expression and stability of apoptosis and differentiation-related protein, induction of apoptosis and differentiation, become a new class of anticancer drugs. HDACi not only have a good therapeutic effect against a variety of hematological malignancies and solid tumors, but also has a relatively high selectivity and low toxicity advantages of tumor cells.

SUMMARY OF THE INVENTION

One aspect of the invention is to provide a cyclic peptide compound with a chemical structure shown as formula (I) and its isomer, racemic body, pharmacy acceptable salt, crystalline hydrate, solvents or their mixtures.

Another aspect of the present invention is to provide processes for preparing formula (I).

Another aspect of the invention is to provide a pharmaceutical composition comprised a therapeutically effective amount of a compound selected from the compound of formula (I), its isomers, racemates, pharmaceutically acceptable salts, crystalline hydrate, solvate or their mixture, and one or more pharmaceutically acceptable carrier.

Another aspect of the invention provides applications of the compound of Formula (I), its isomers, racemates, pharmaceutically acceptable salts, crystalline hydrate, solvate or their mixture in preparing pharmaceuticals for preventing or treating mammalian diseases related to the dysregulation of histone deacetylase.

According to one aspect of the invention, it provides a cyclic peptide compound with a chemical structure shown as formula (I), its isomer, racemic body, pharmacy acceptable salt, crystalline hydrate, solvents or their mixtures:

(I)

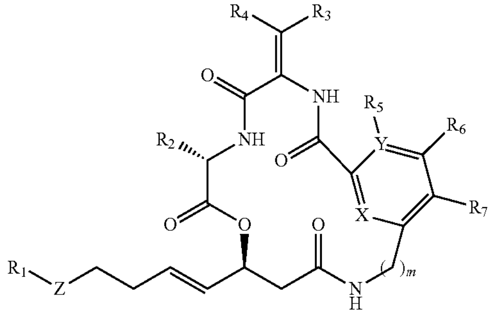

Wherein: $R_1$ is hydrogen, $C_{1-16}$ alkyl, $C_{3-16}$ cycloalkyl, —(C═O)—($C_{1-16}$ alkyl), —(C═S)—($C_{1-16}$ alkyl) or —S—($C_{1-16}$ alkyl);

$R_2$ is hydrogen, $C_{1-12}$ alkyl, —$CH_2$—O—($C_{1-12}$ alkyl), —$CH_2$—NH—($C_{1-12}$ alkyl), —$CH_2$—S—($C_{1-12}$ alkyl), $C_{6-12}$ aryl, heteroaryl, —$CH_2$—($C_{6-12}$ aryl)-$CH_2$— or heteroaryl; wherein the $C_{6-12}$ aryl, heteroaryl, —$CH_2$—$C_{6-12}$ aryl, —$CH_2$-heteroaryl, can contain one or more substituents, the substituents can be halo, amino, hydroxy, nitro, cyano, $C_{1-12}$ alkyl, $C_{1-12}$ alkoxy, amino $C_{1-12}$ alkyl, acyl, acyloxy, thio $C_{1-12}$ alkyl, phenyl or carboxyl;

$R_3$, $R_4$ are each independently selected from hydrogen, $C_{1-12}$ alkyl, —O—($C_{1-12}$ alkyl), —NH—($C_{1-12}$ alkyl), —S—($C_{1-12}$ alkyl), $C_{6-12}$ aryl and heteroaryl;

One of X and Y is C, and the other is N, or both X and Y are N;

$R_5$, $R_6$, $R_7$ are independently selected from hydrogen, halo, —S—($C_{1-12}$ alkyl), $C_{1-12}$ alkyl or t-butoxycarbonyl;

Z is —$CH_2$—, —NH—, —O—, —S— or

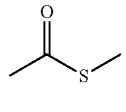

;

M is 0, 1, 2, 3, 4, 5 or 6.

In the preferred embodiment, $R_1$ are hydrogen, $C_{1-16}$ alkyl, $C_{3-16}$ cycloalkyl, —(C═O)—($C_{1-16}$ alkyl), —(C═S)—($C_{1-16}$ alkyl) or —S—($C_{1-16}$ alkyl);

$R_2$ is hydrogen, $C_{1-12}$ alkyl, —CH2-O—($C_{1-12}$-alkyl), —$CH_2$—NH—($C_{1-12}$ alkyl), —$CH_2$—S—($C_{1-12}$ alkyl), $C_{6-12}$ aryl, heteroaryl, —$CH_2$—($C_{6-12}$ aryl)-$CH_2$— or heteroaryl;

$R_3$, $R_4$ are each independently selected from hydrogen, $C_{1-12}$ alkyl, —O—($C_{1-12}$ alkyl), —NH—($C_{1-12}$ alkyl), —S—($C_{1-12}$ alkyl), $C_{6-12}$ aryl and heteroaryl;

One of X and Y is C, and the other is N, or both X and Y is N;

$R_5$, $R_6$, $R_7$ are independently selected from hydrogen, halo, —S—($C_{1-12}$ alkyl), $C_{1-12}$ alkyl and t-butoxycarbonyl;

Z is —O—, —S— or

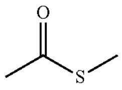;

m is 0, 1 or 2.

In the further preferred embodiments, $R_1$ is hydrogen or $C_{1-16}$ alkyl;

$R_2$ is hydrogen, $C_{1-12}$ alkyl, or $C_{6-12}$ aryl;

$R_3$, $R_4$ groups are each independently selected from hydrogen, $C_{1-12}$ alkyl, —O—($C_{1-12}$ alkyl), —NH—($C_{1-12}$ alkyl), —S—($C_{1-12}$ alkyl), $C_{6-12}$ aryl and heteroaryl;

X is N;

Y is C;

$R_5$, $R_6$, $R_7$ are independently selected from hydrogen, F, —S—(C1-12 alkyl);

Z is —S— or

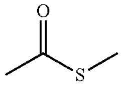;

m is 0, 1 or 2.

In a more preferred embodiment of the invention, the compound of Formula (I) is particularly preferred compound as follows:

1

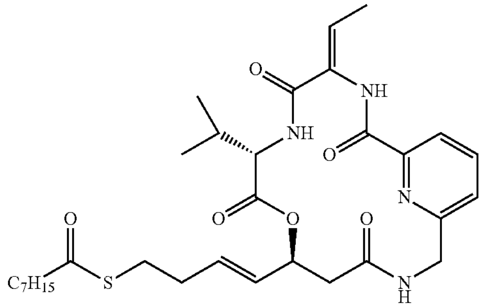

-continued

2

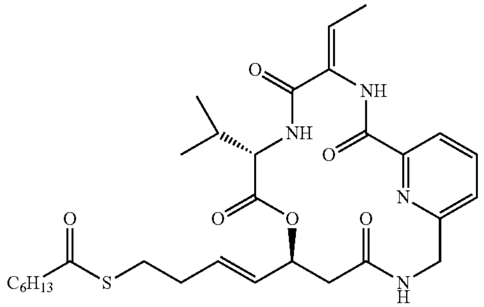

3

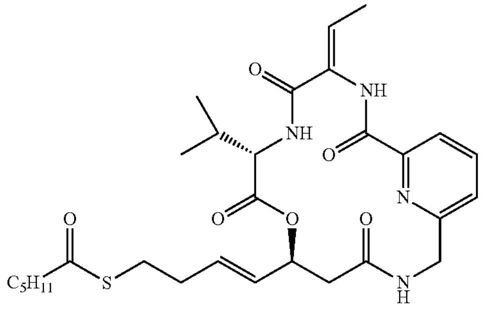

4

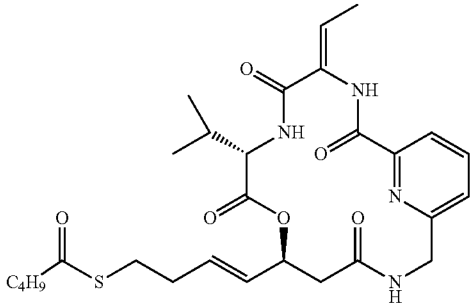

5

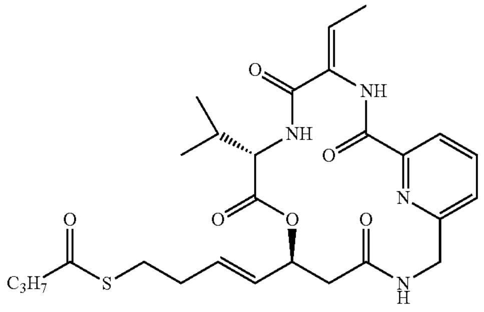

6

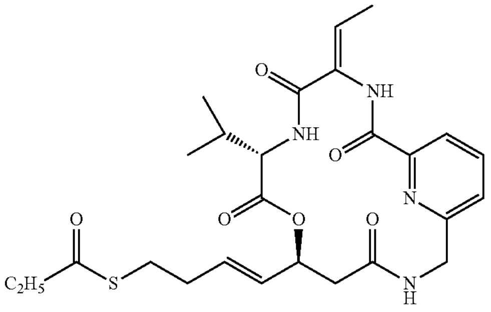

-continued
7
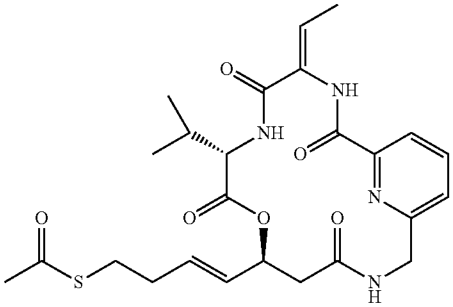
8
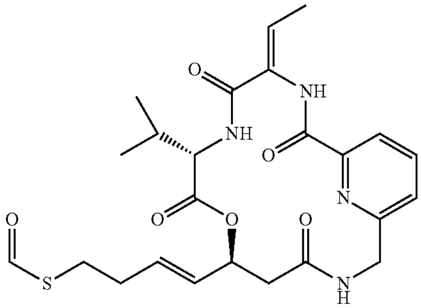
9
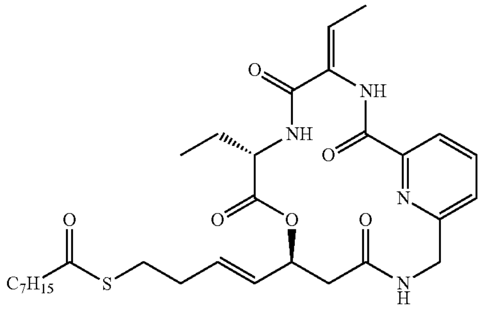
10
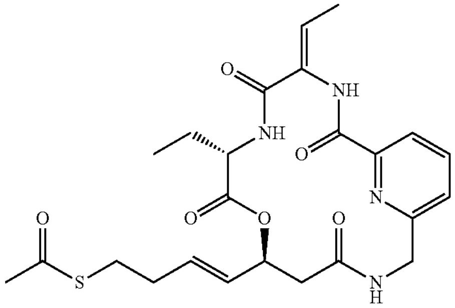
11
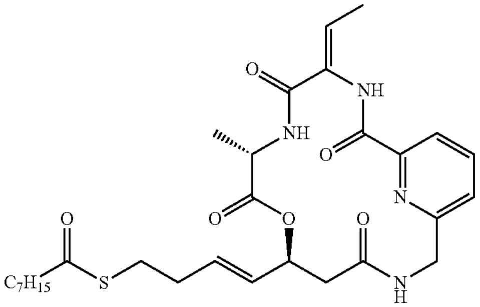
-continued
12
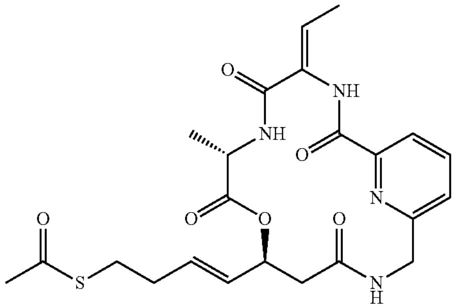
13
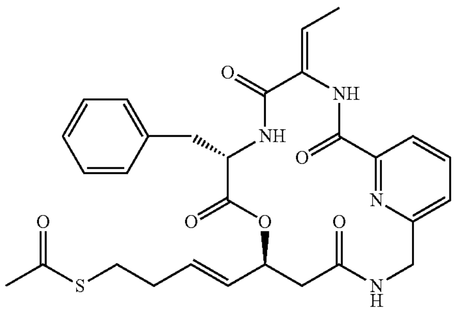
14
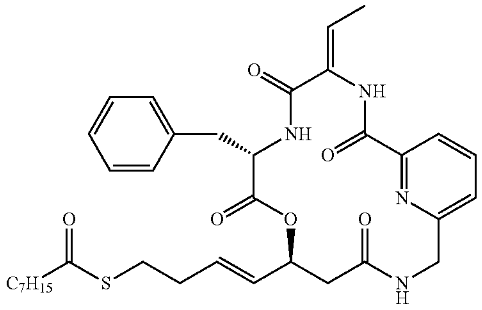
15
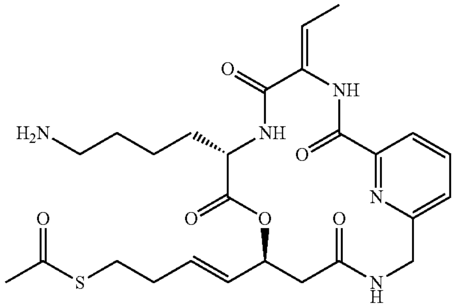
16
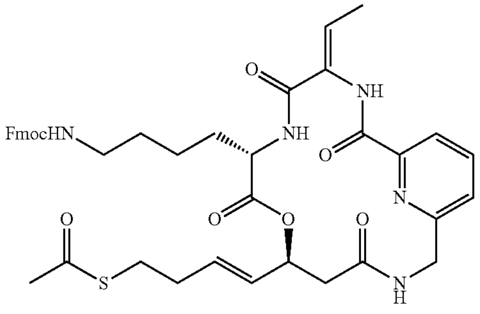

-continued
17
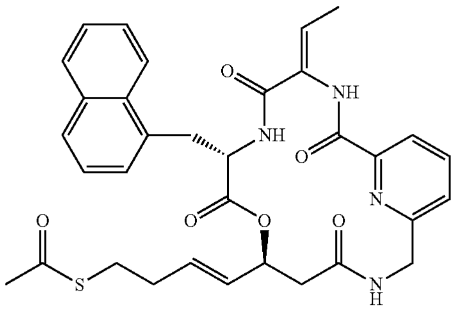
18
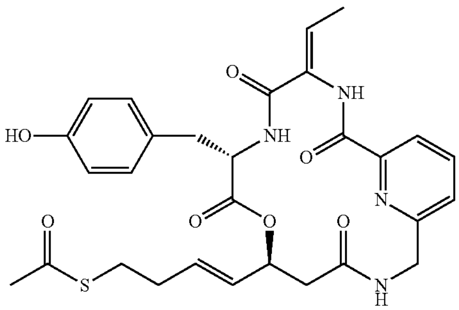
19
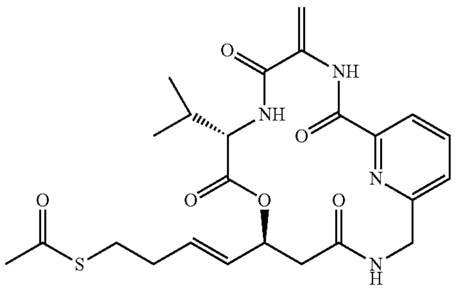
20
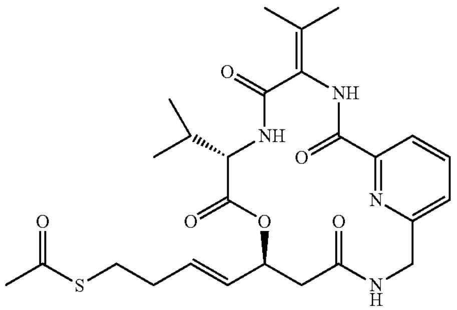
21
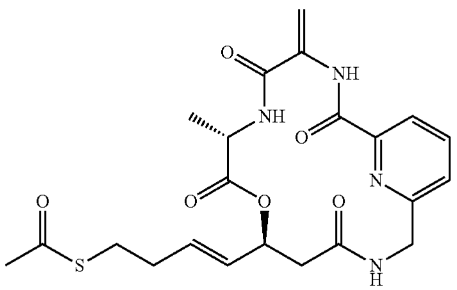
-continued
22
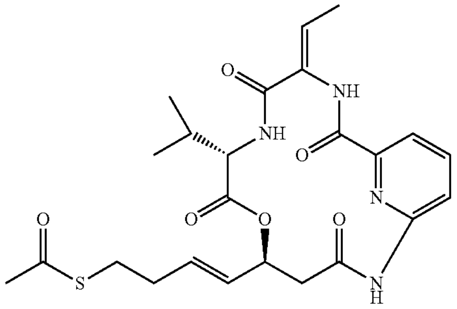
23
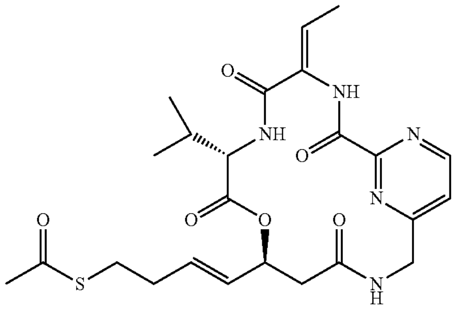
24
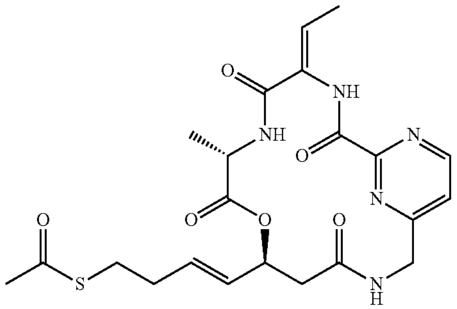
25
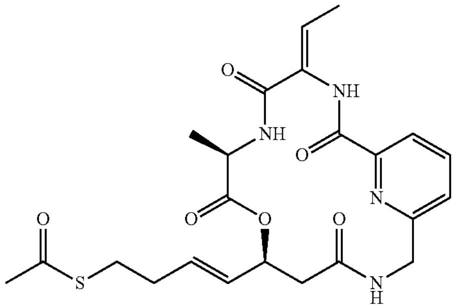
26
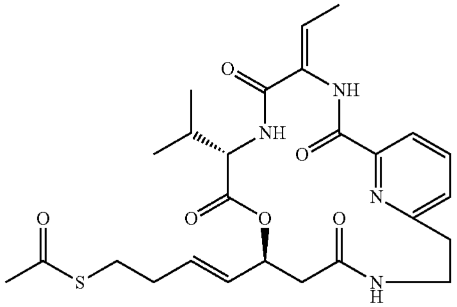

-continued
27
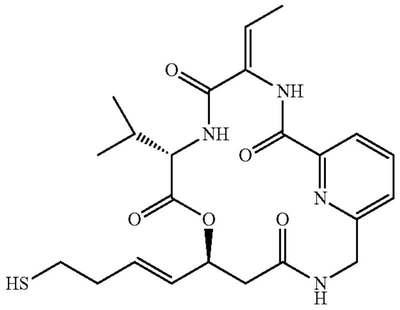
28
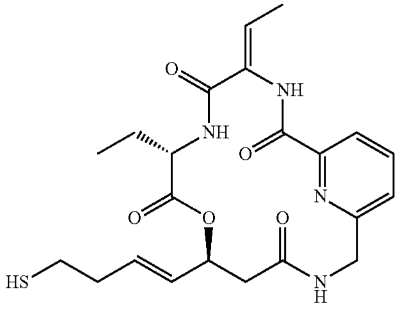
29
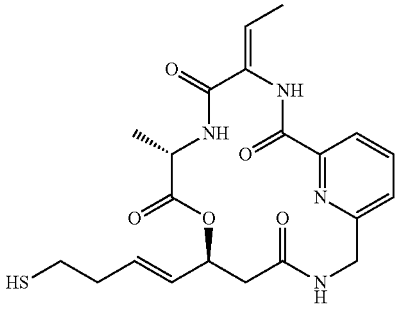
30
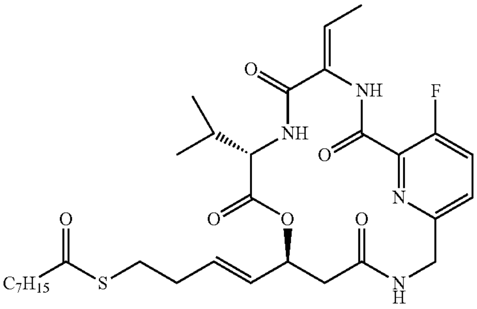
31
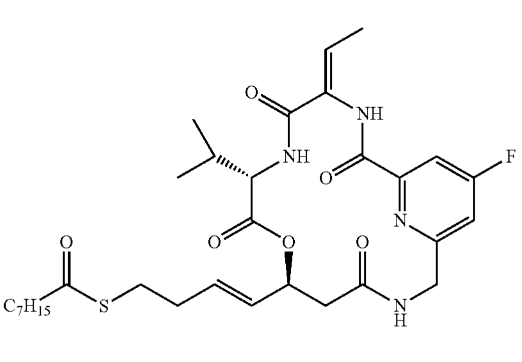
-continued
32
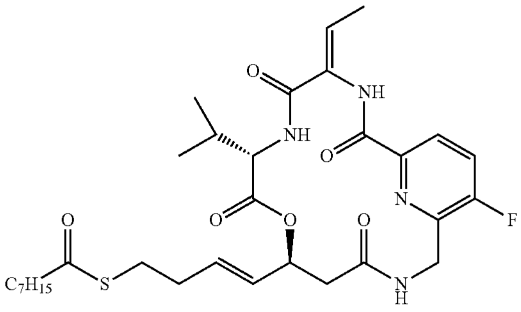
33
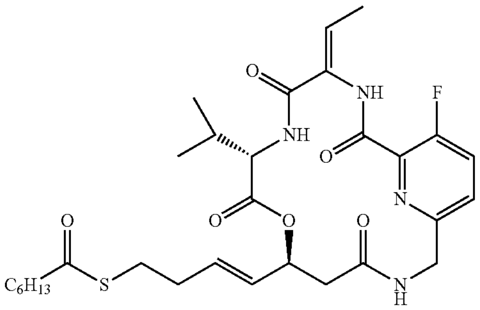
34
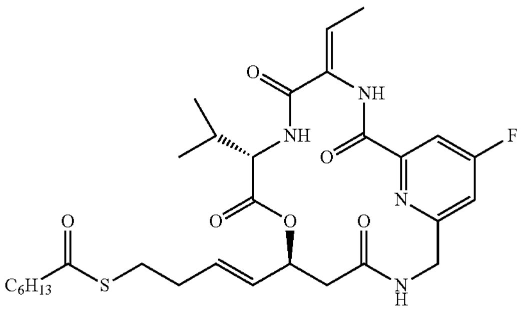
35
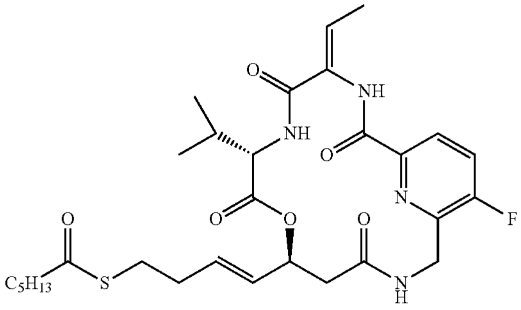
36
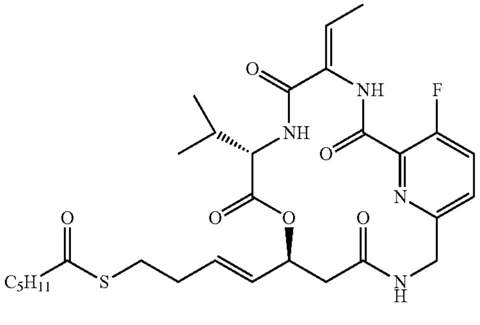

-continued
37
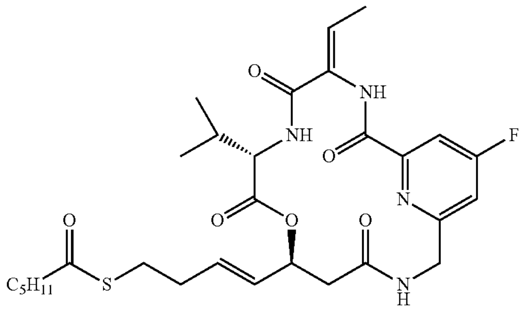
38
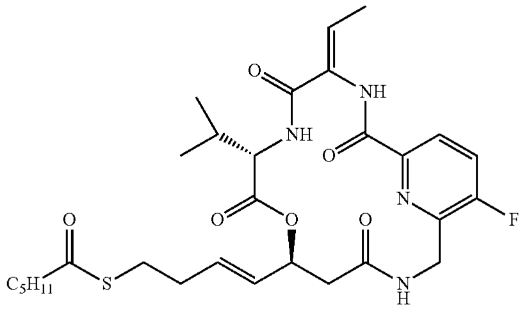
39
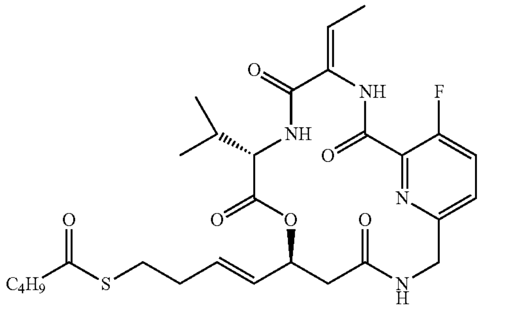
40
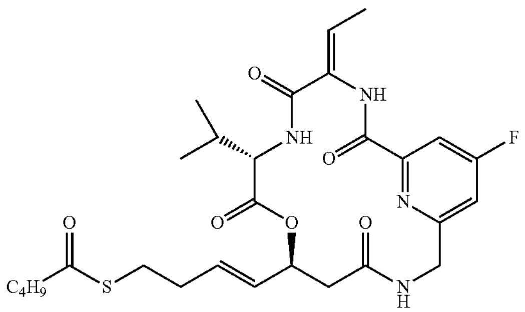
41
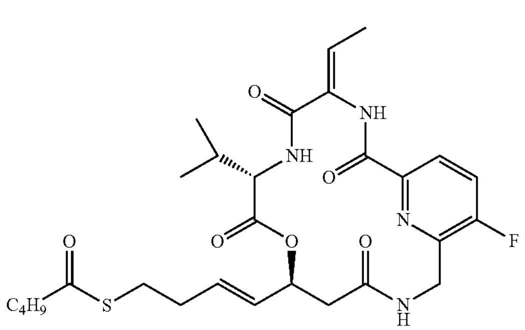
-continued
42
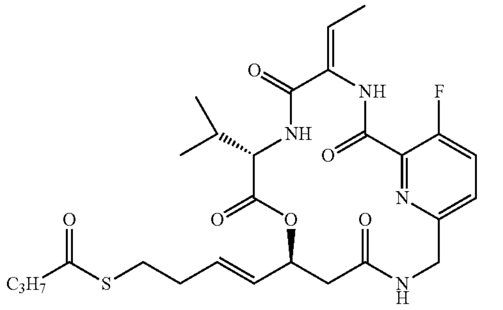
43
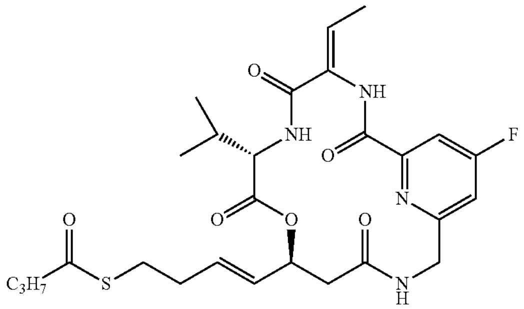
44
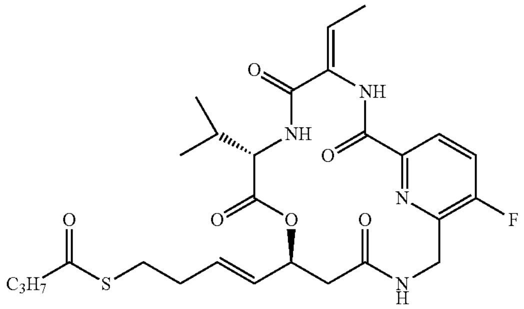
45
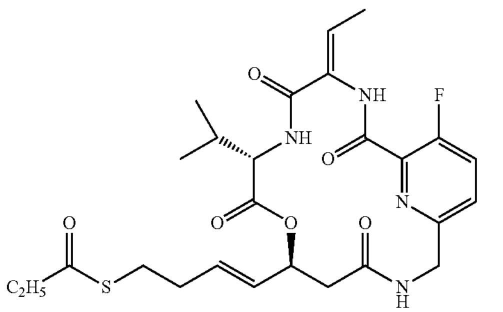
46
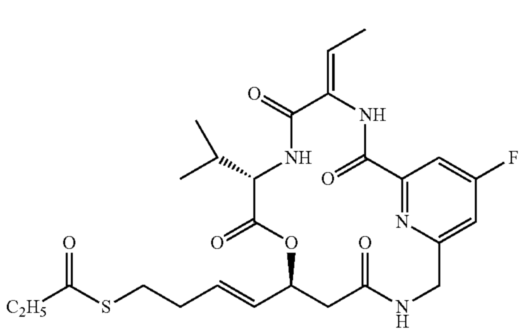

-continued
47
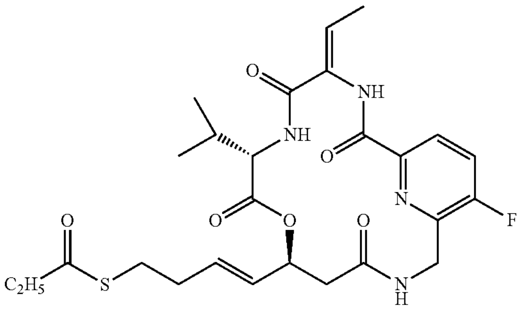
48
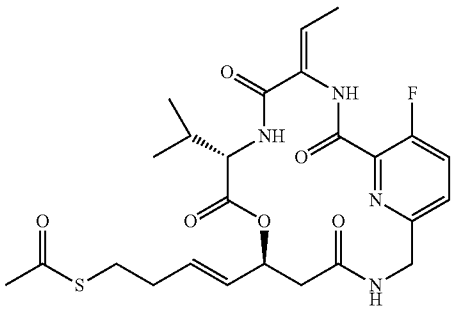
49
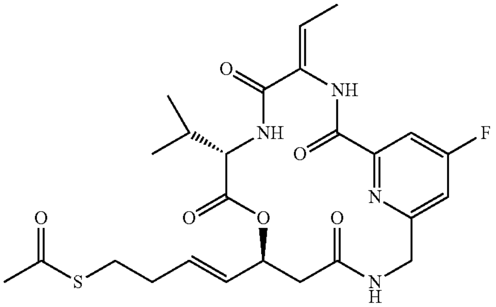
50
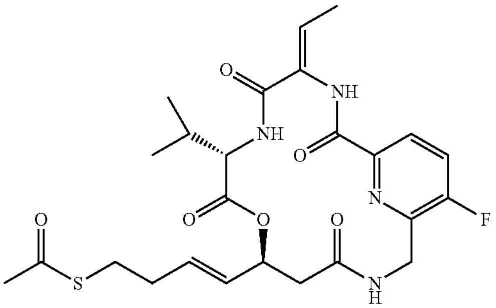
51
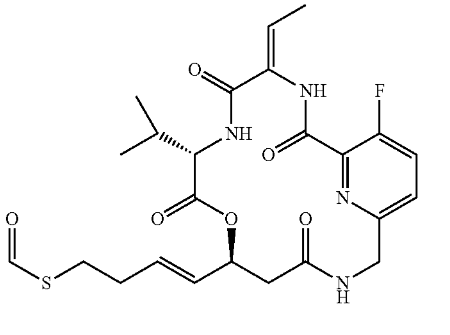
-continued
52
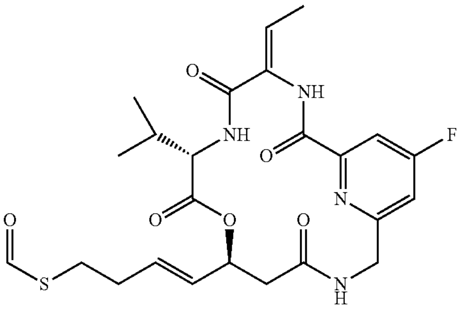
53
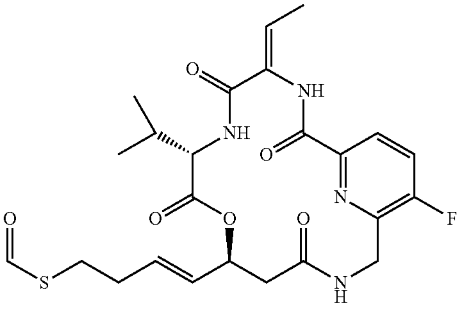
54
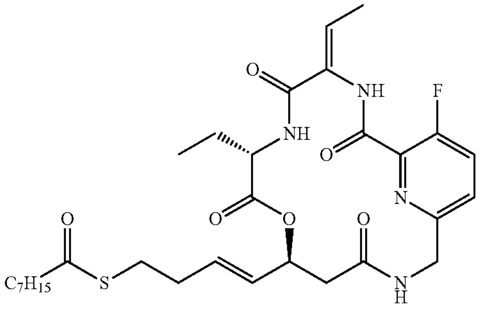
55
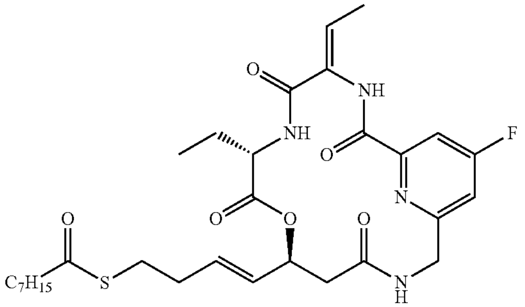
56
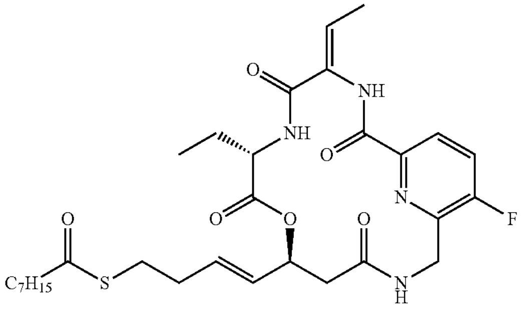

-continued
57
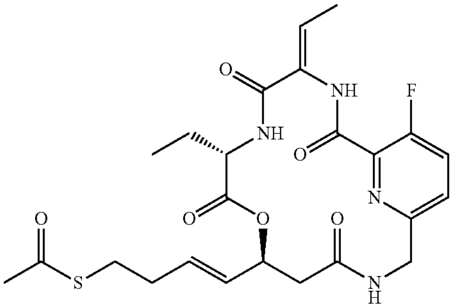
58
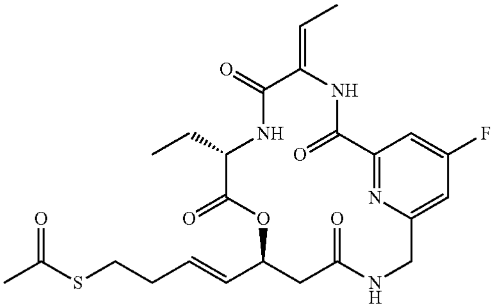
59
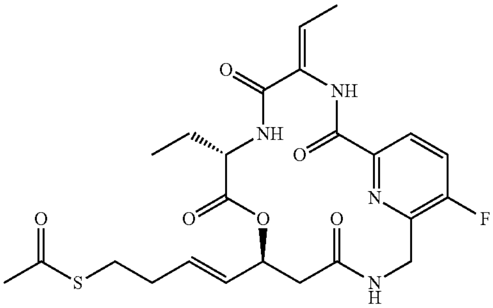
60
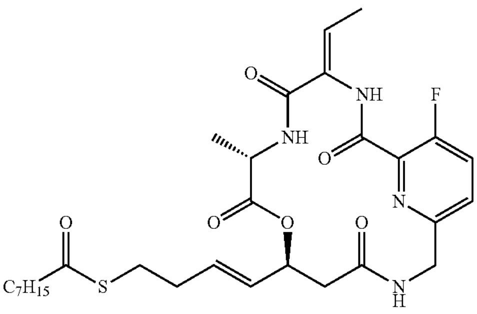
61
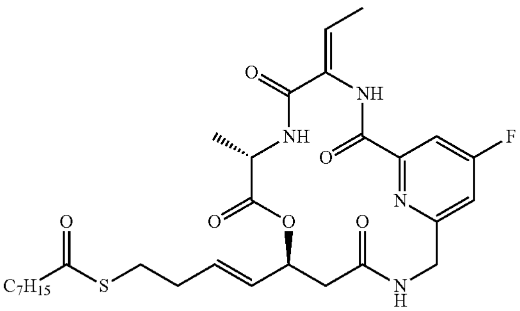
-continued
62
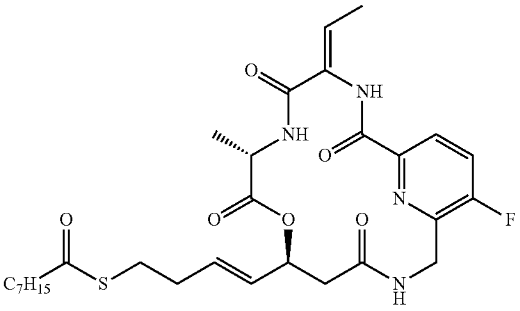
63
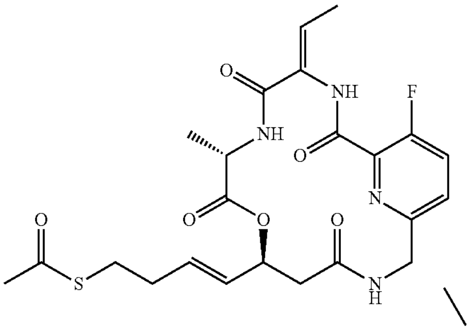
64
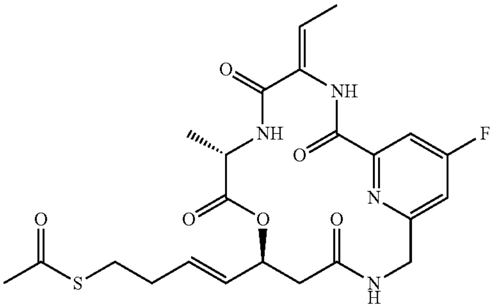
65
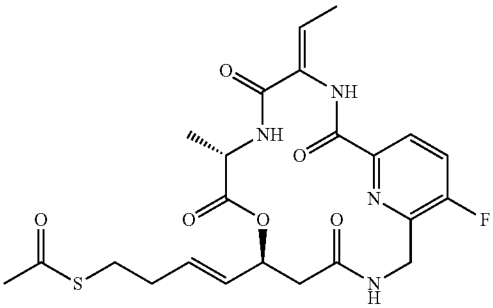
66
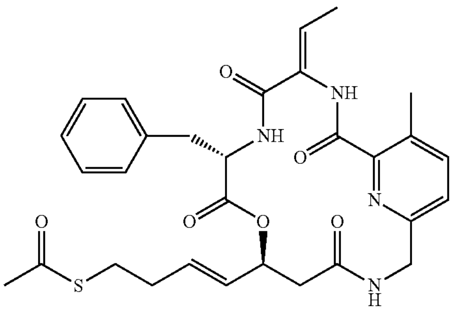

-continued
67
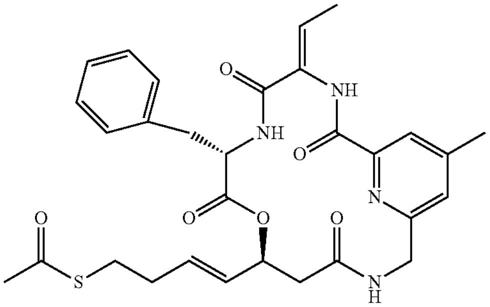
68
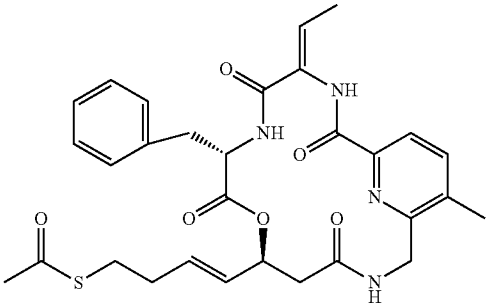
69
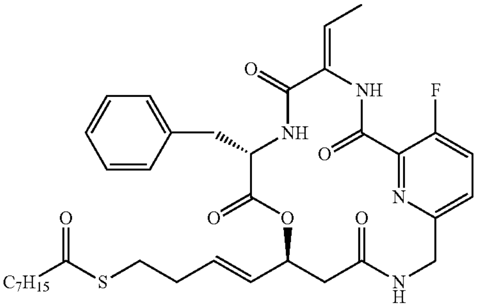
70
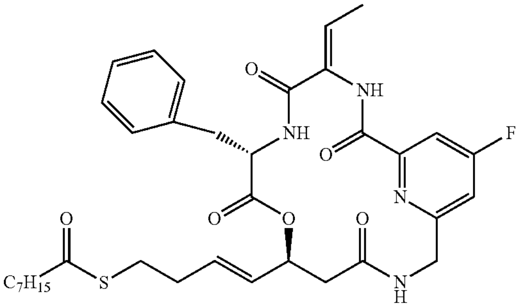
71
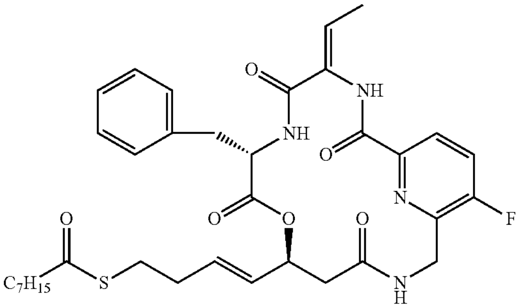
-continued
72
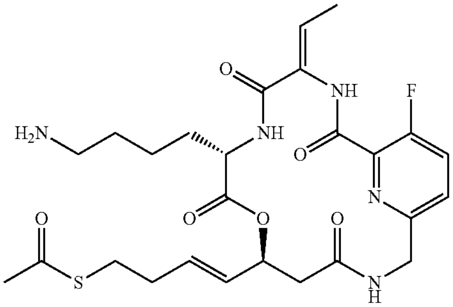
73
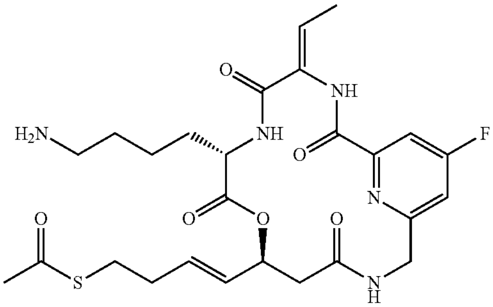
74
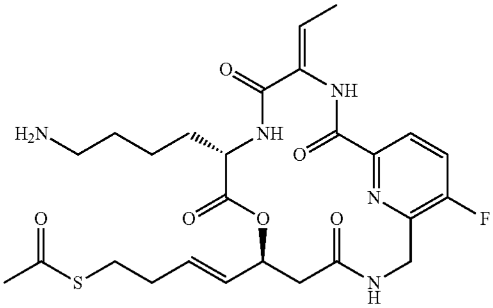
75
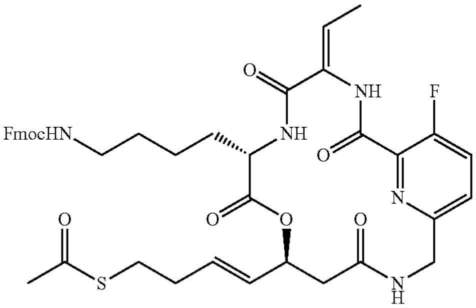
76
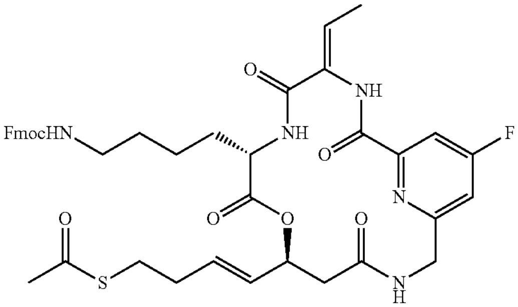

-continued
77
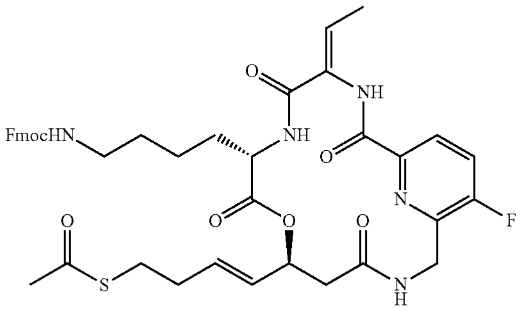
78
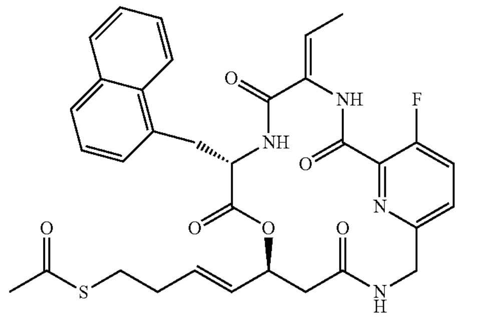
79
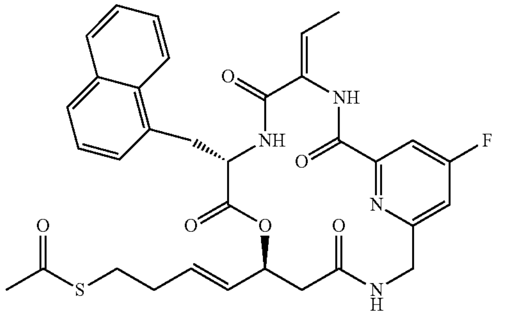
80
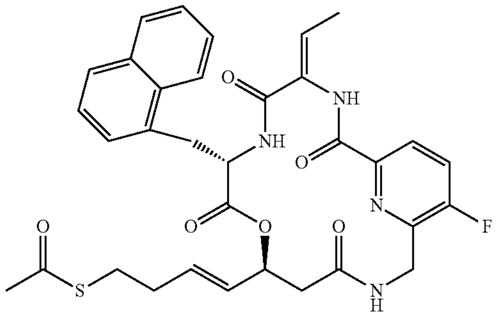
81
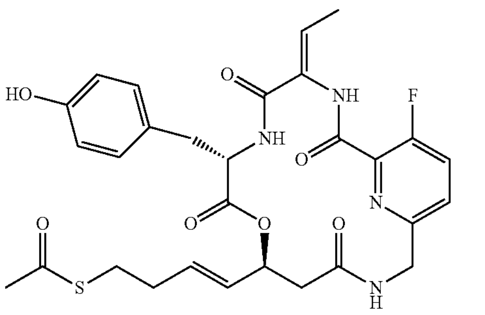
-continued
82
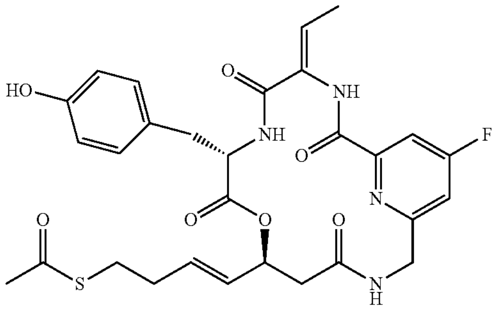
83
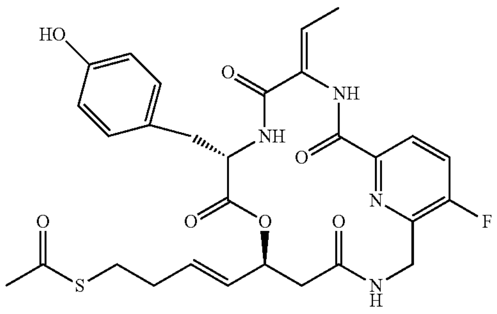
84
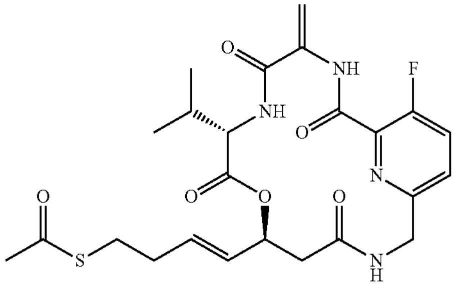
85
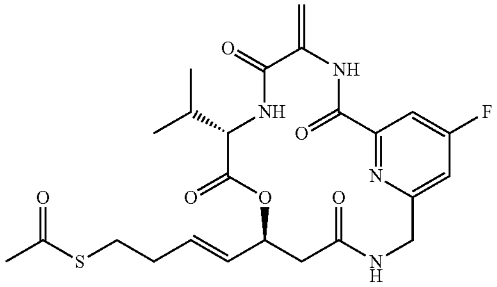
86
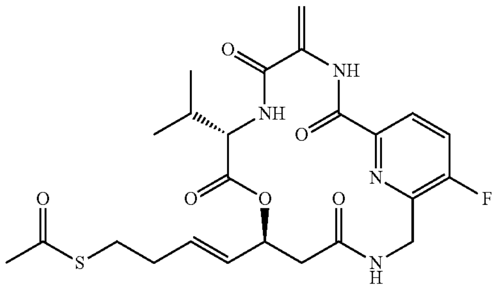

-continued
87
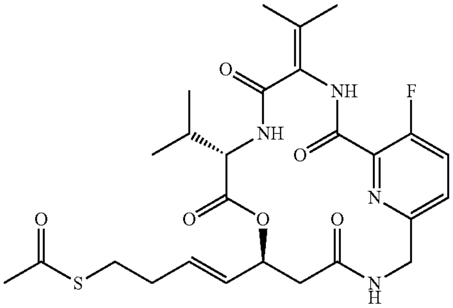
88
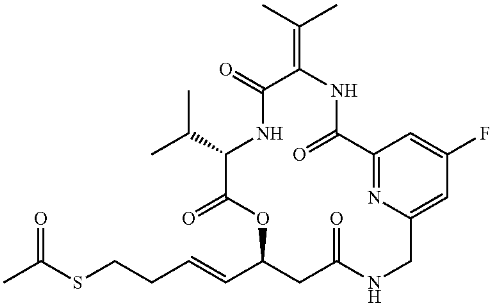
89
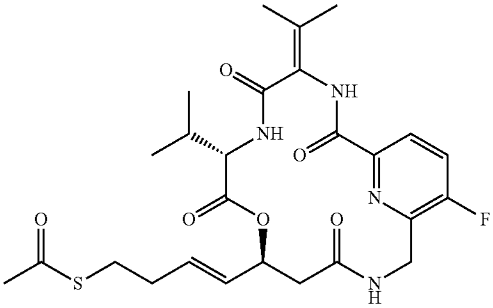
90
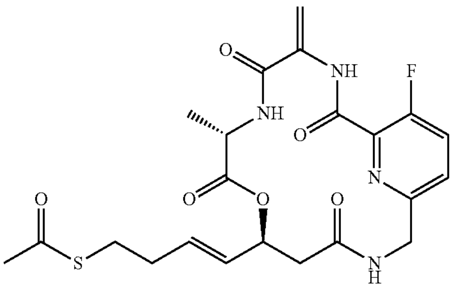
91
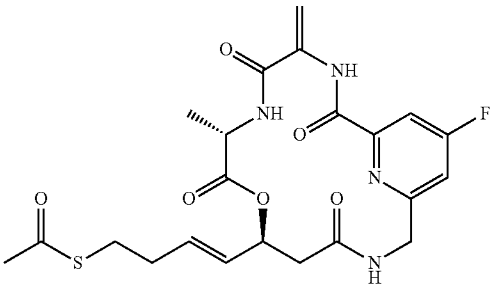
-continued
92
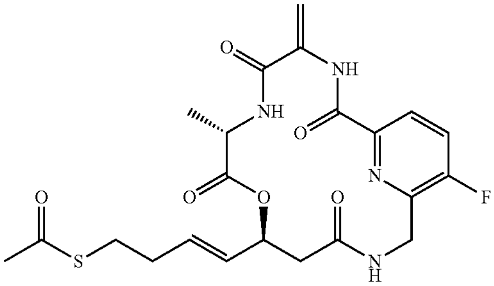
93
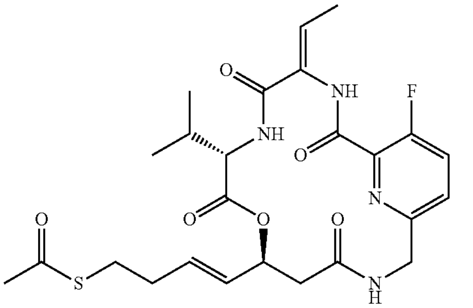
94
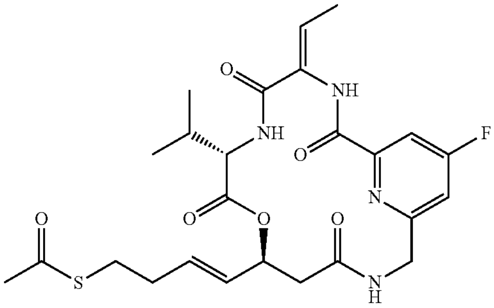
95
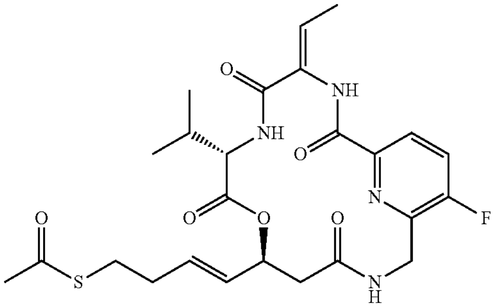
96
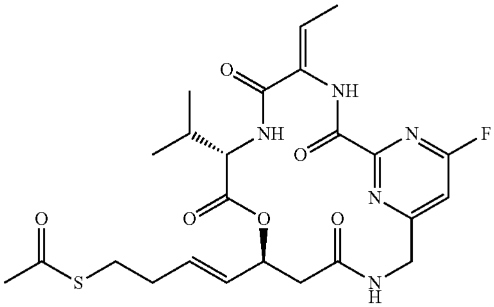

-continued
97
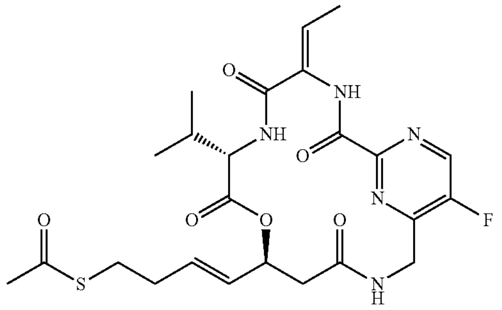
98
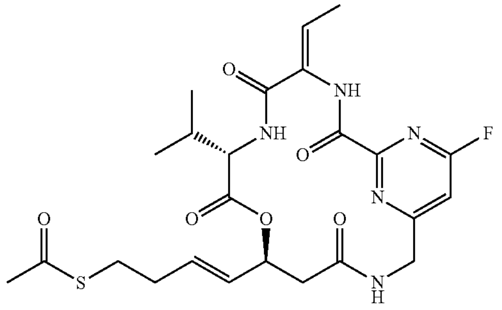
99
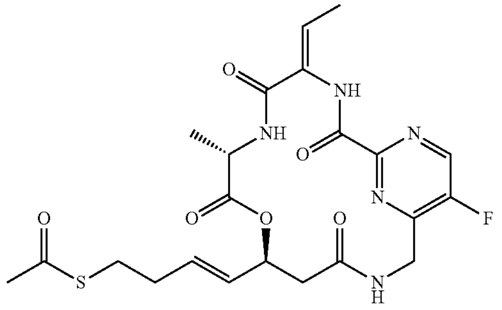
100
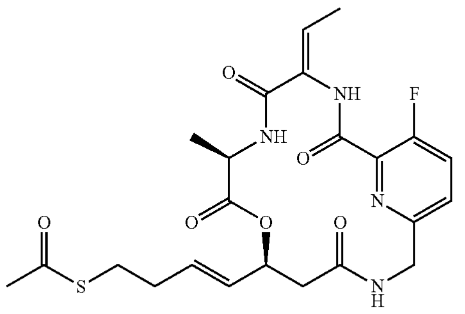
101
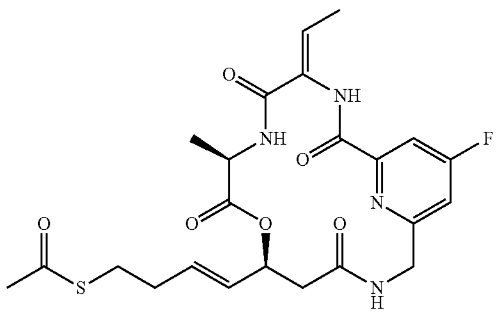
-continued
102
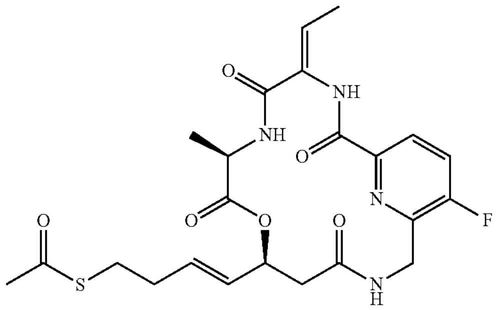
103
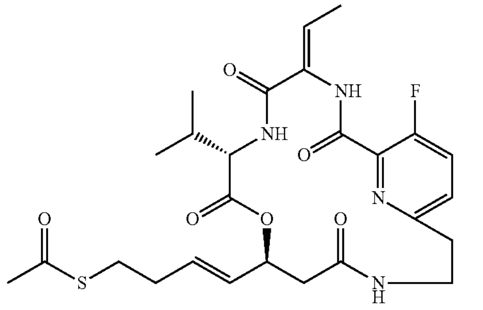
104
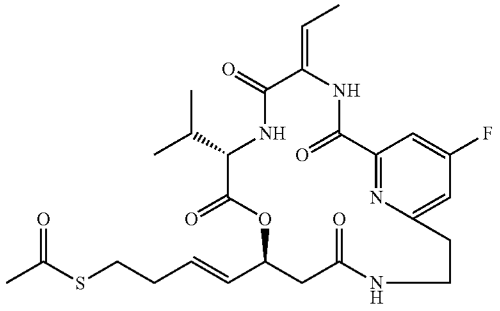
105
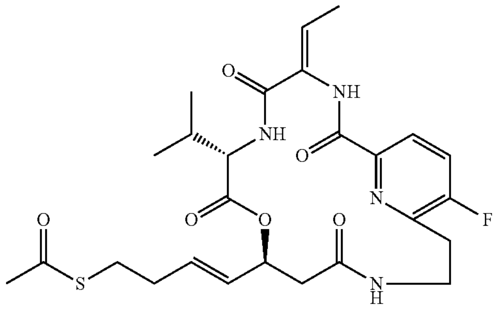
106
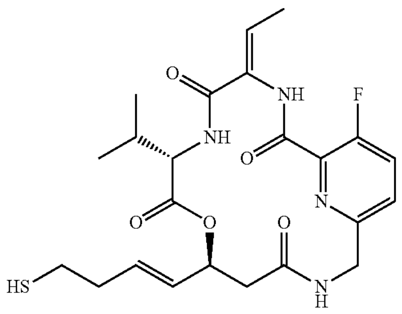

-continued
107
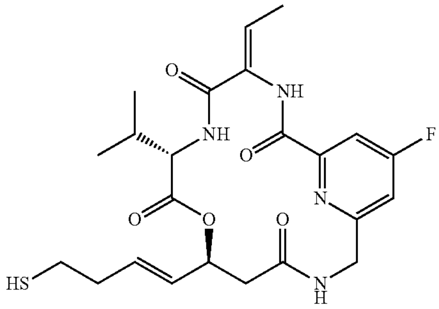
108
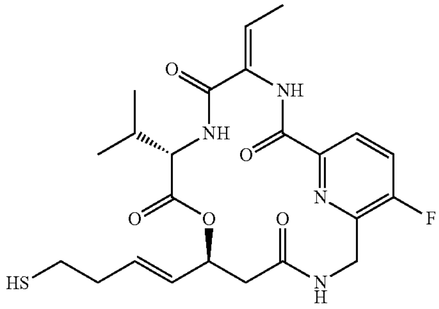
109
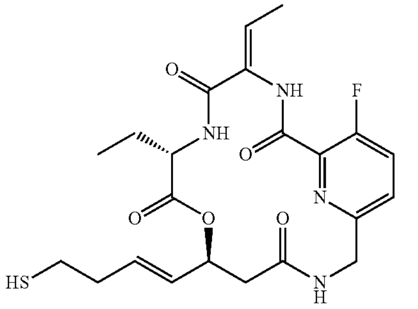
110
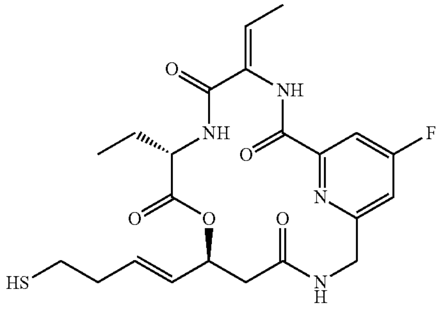
111
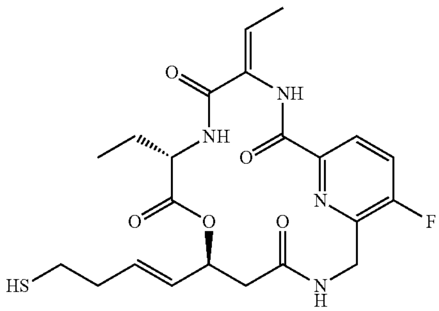
-continued
112
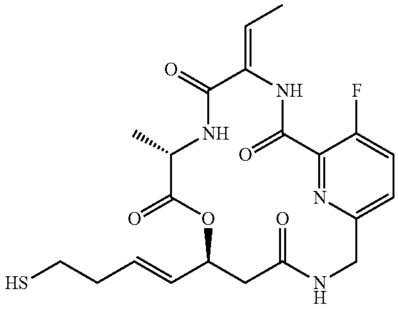
113
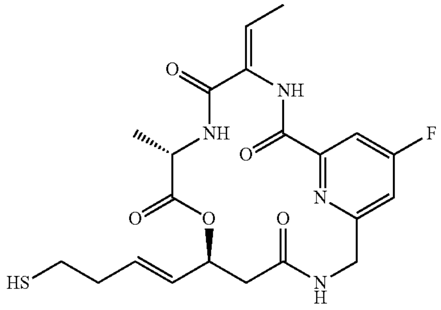
114
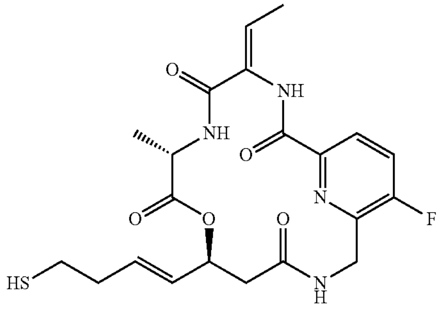
115
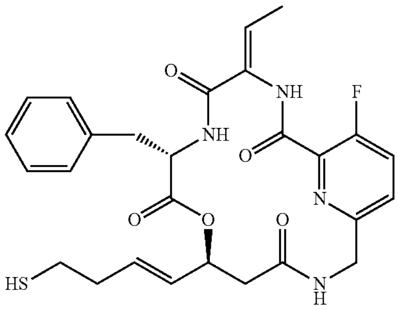
116
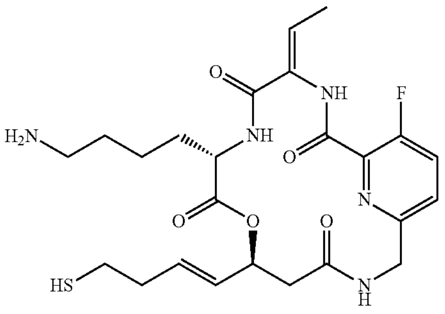

-continued
117
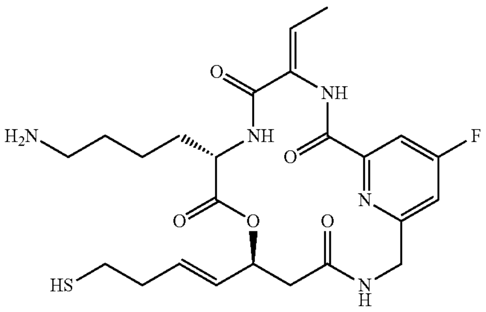
118
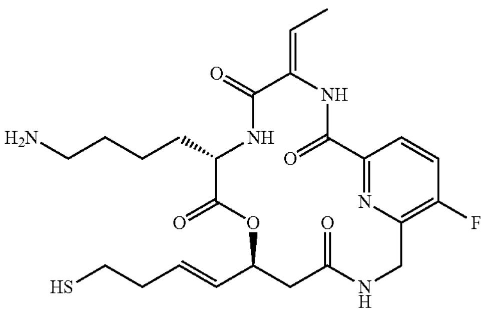
119
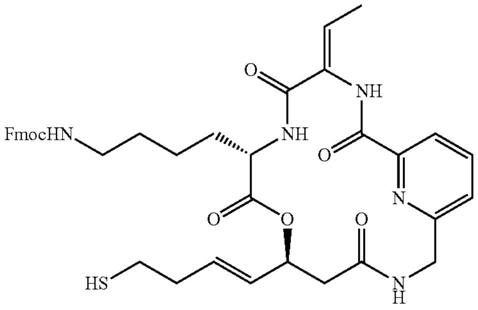
120
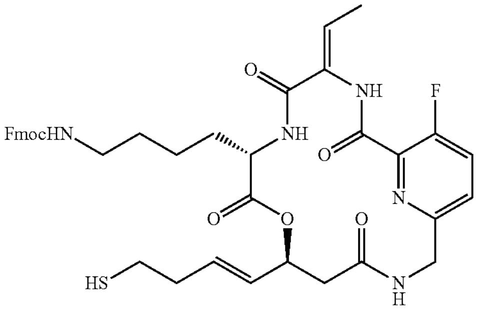
121
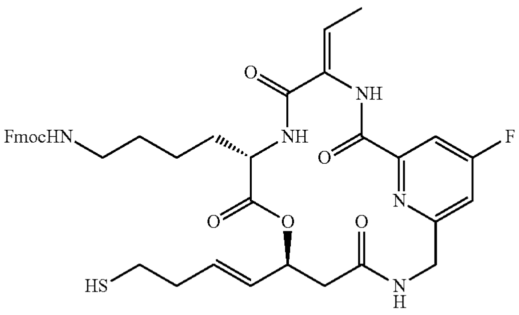
-continued
122
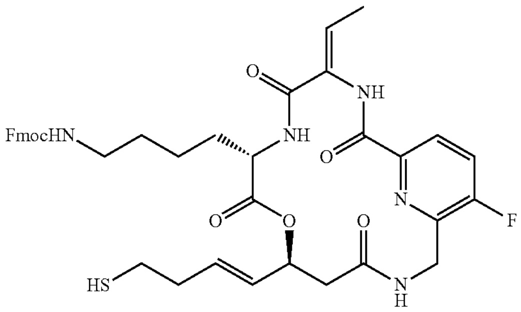
123
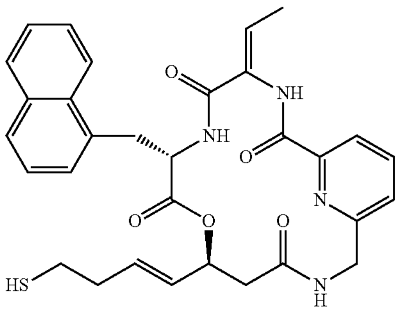
124
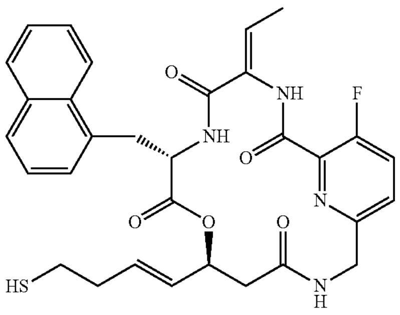
125
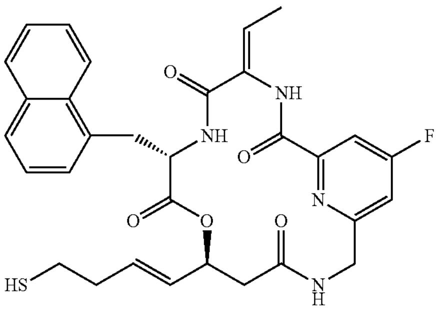
126
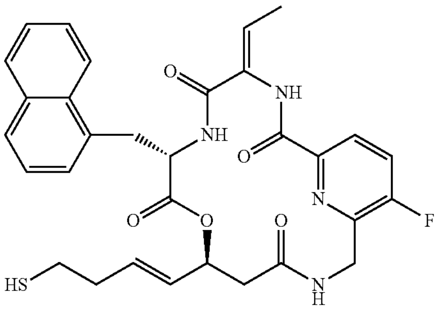

-continued
127
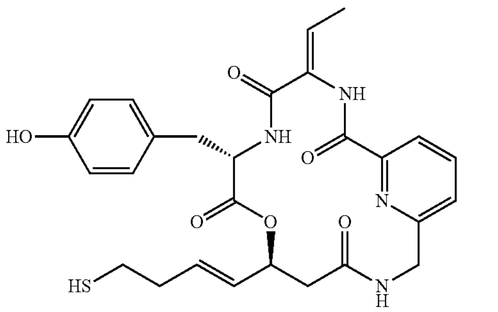
128
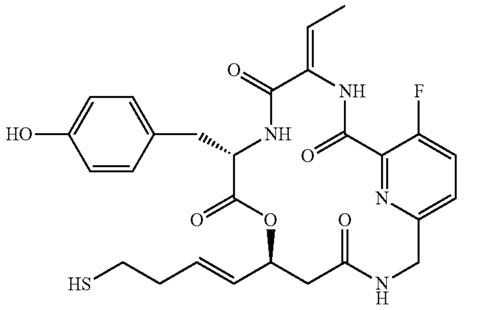
129
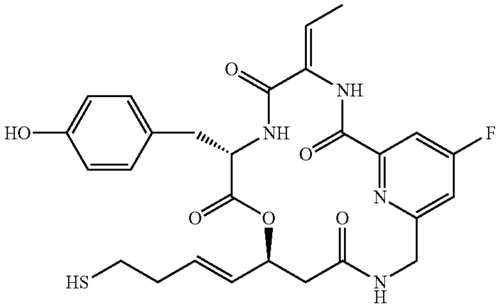
130
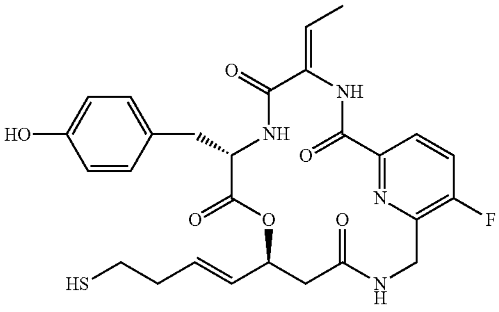
131
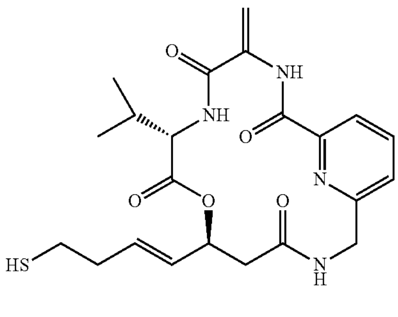
-continued
132
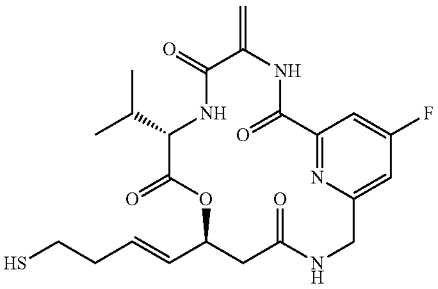
133
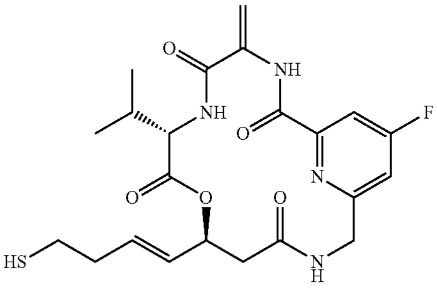
134
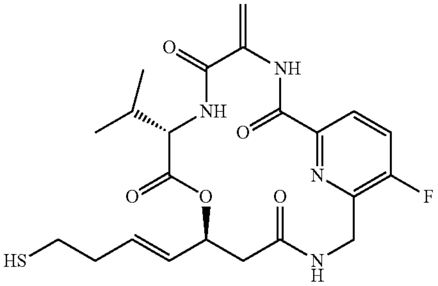
135
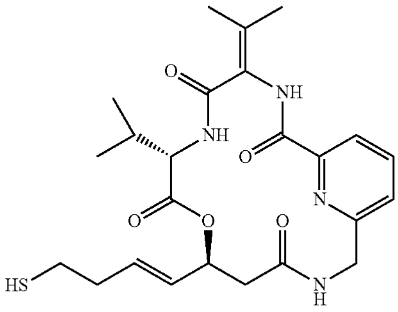
136
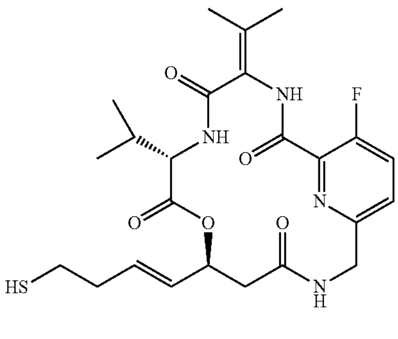

137
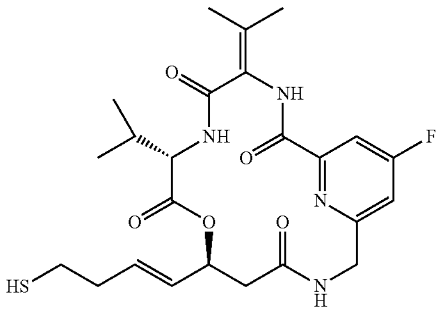
138
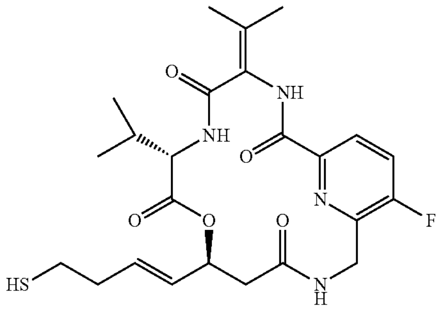
139
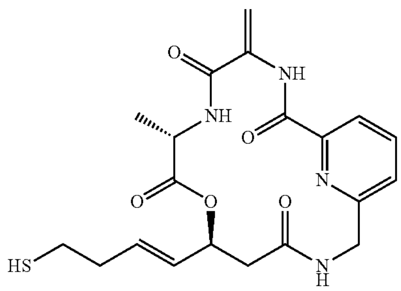
140
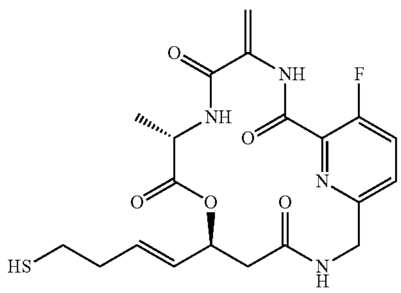
141
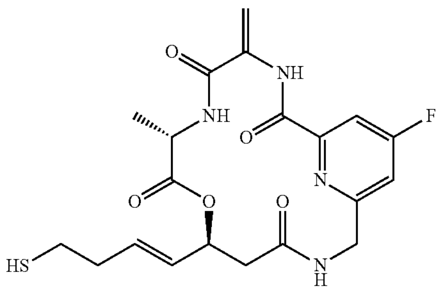
142
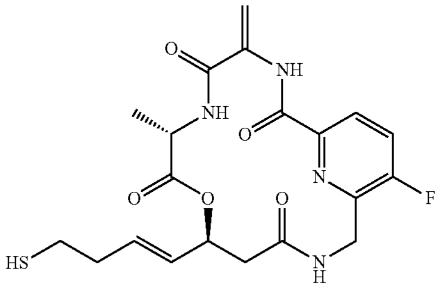
143
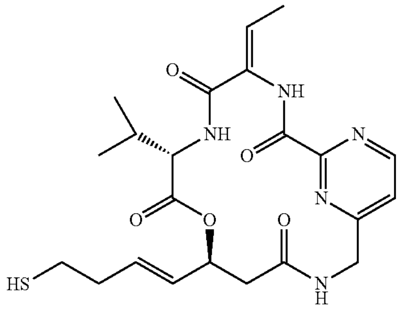
144
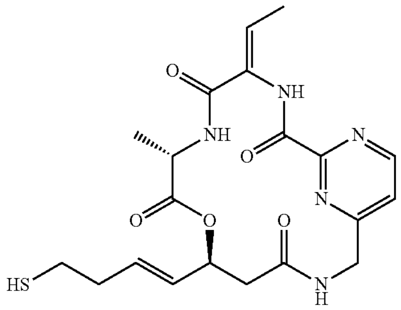
145
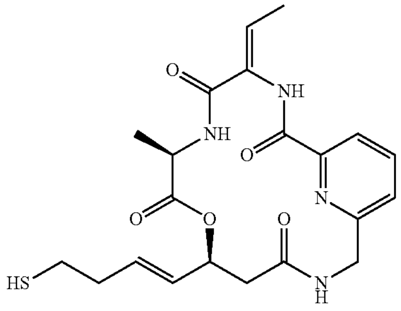
146
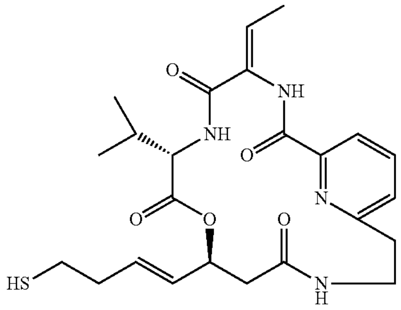

-continued
147
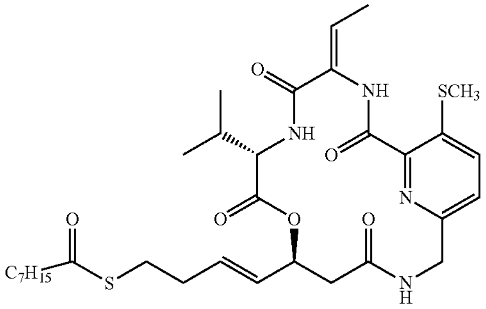
148
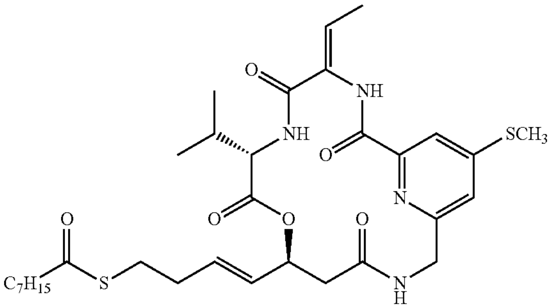
149
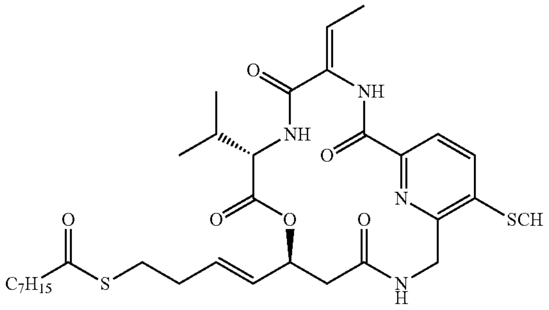
150
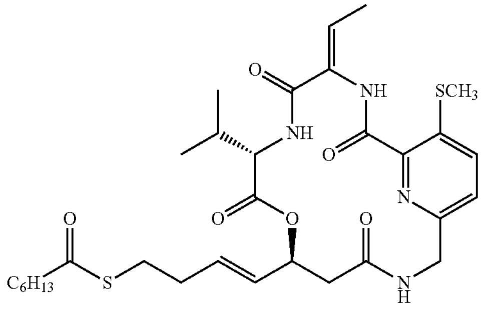
151
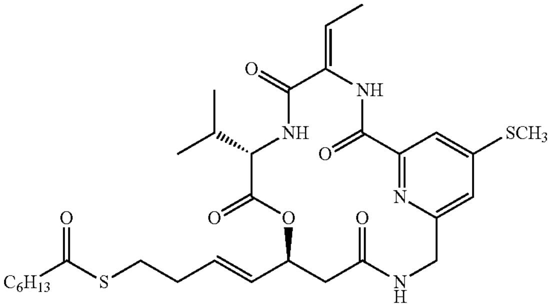
-continued
152
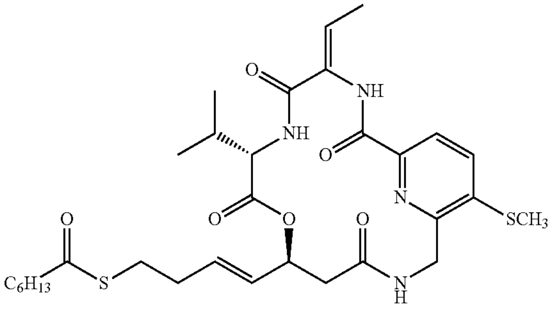
153
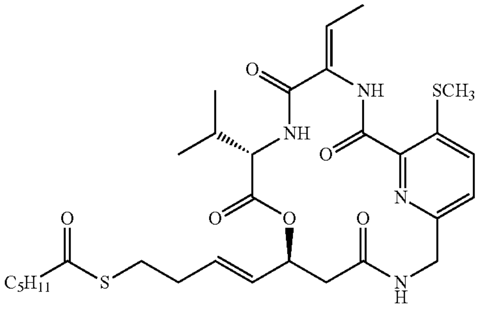
154
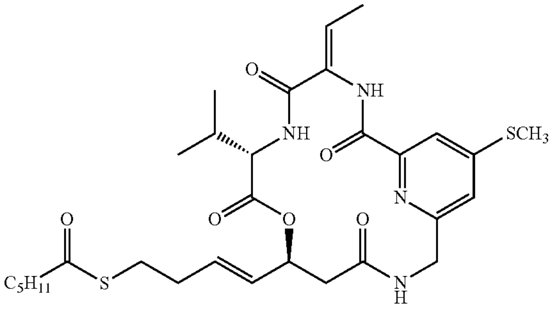
155
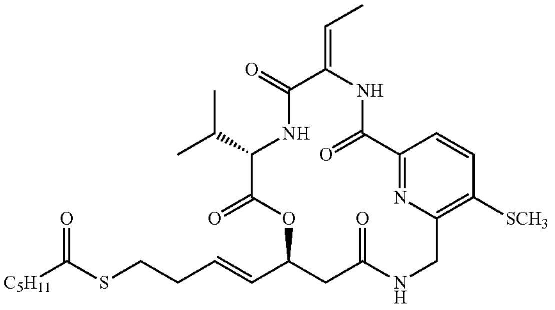
156
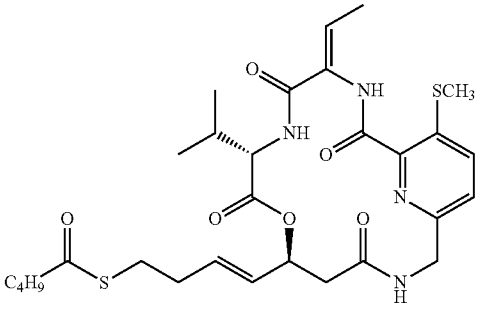

-continued
157
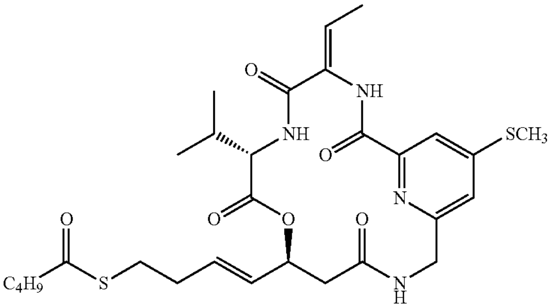
158
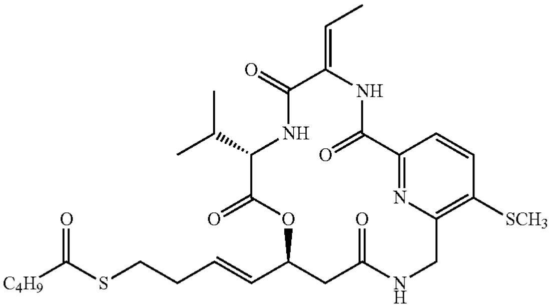
159
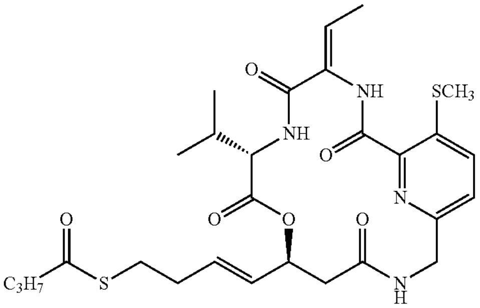
160
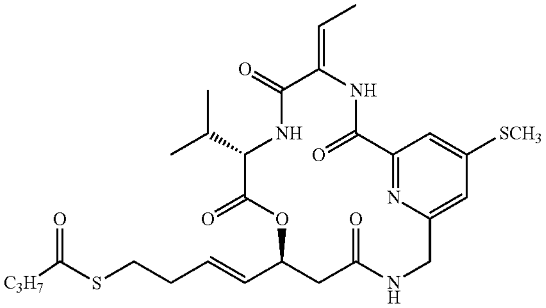
-continued
161
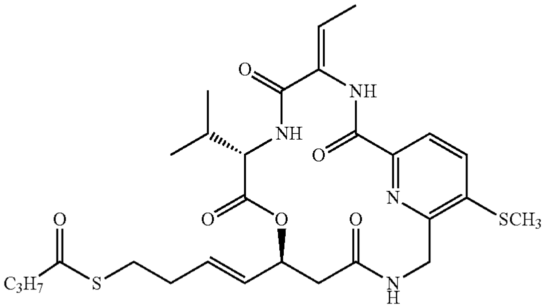
162
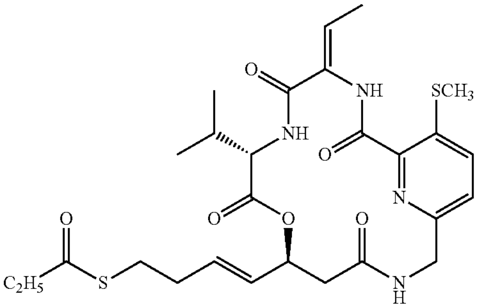
163
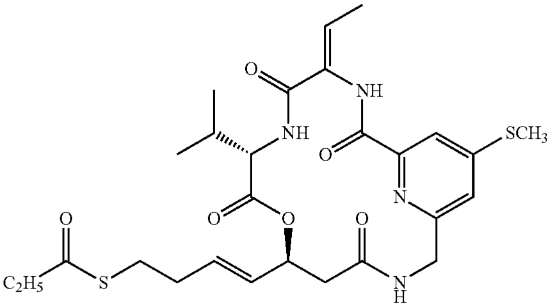
164
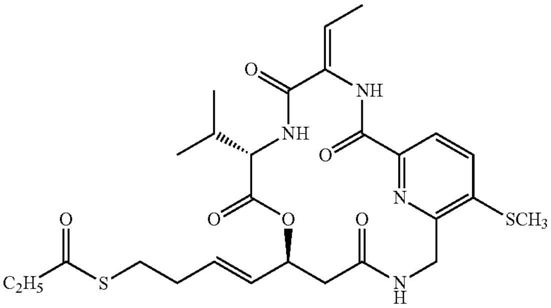
165
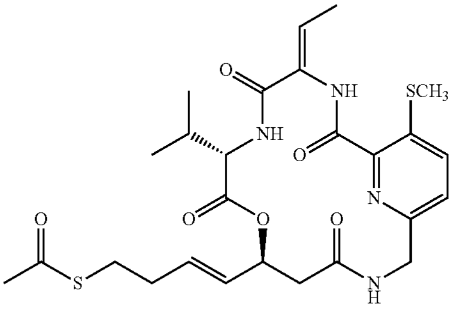

-continued
166
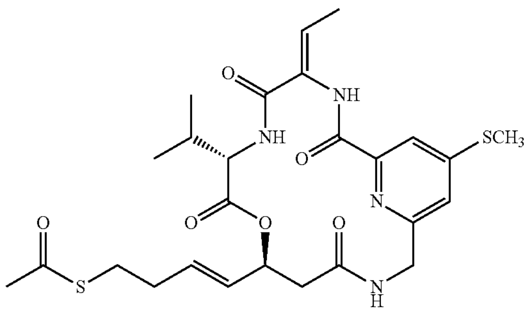
167
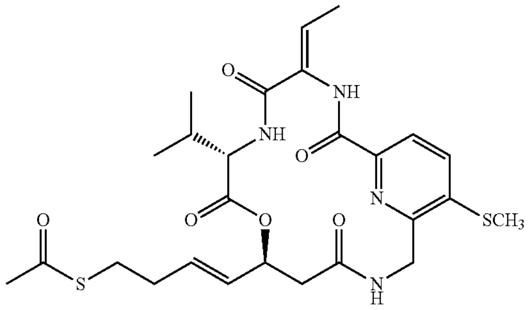
168
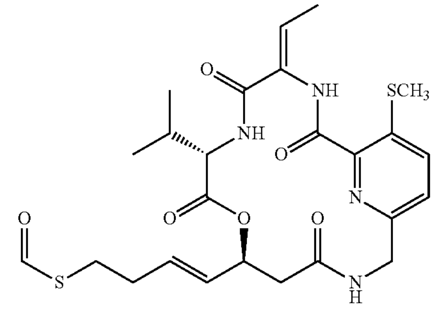
169
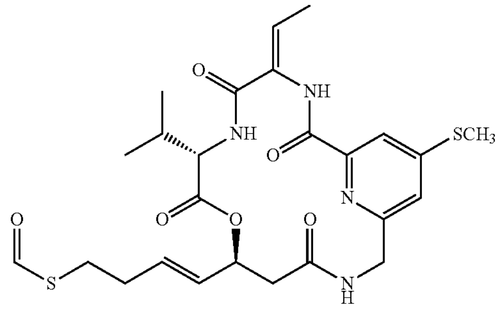
170
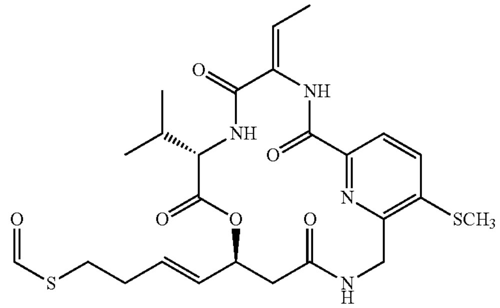
-continued
171
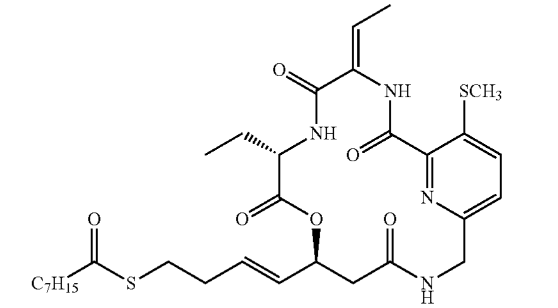
172
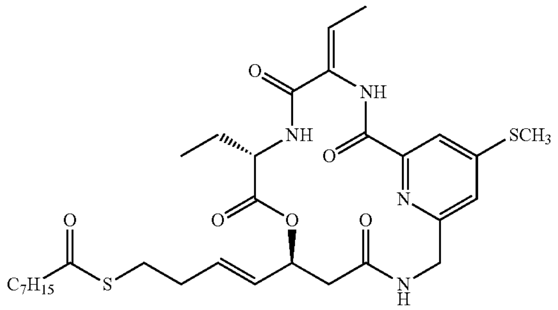
173
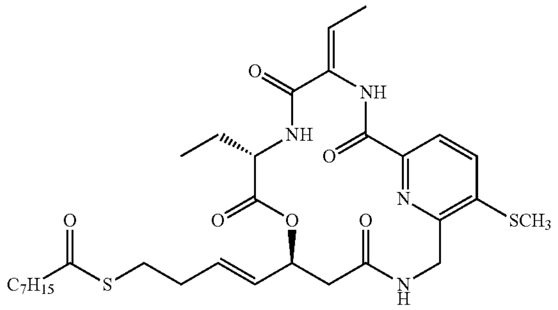
174
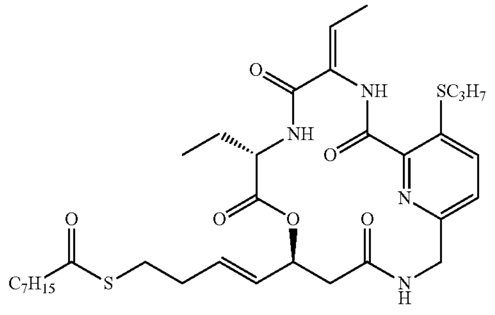
175
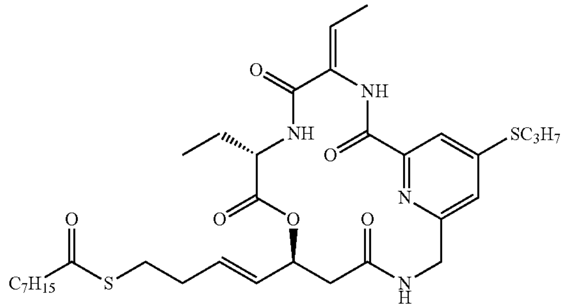

-continued
176
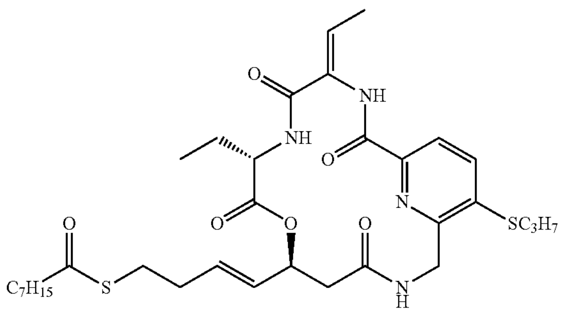
177
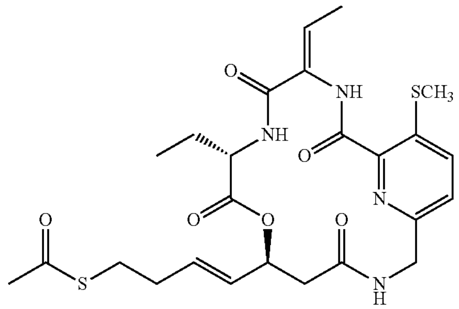
178
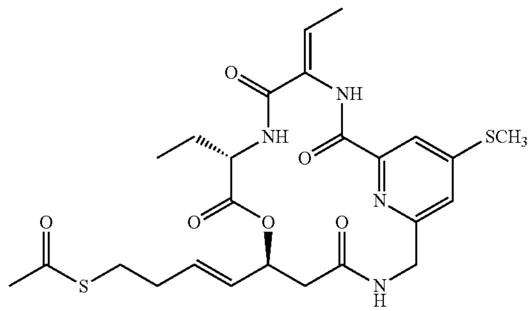
179
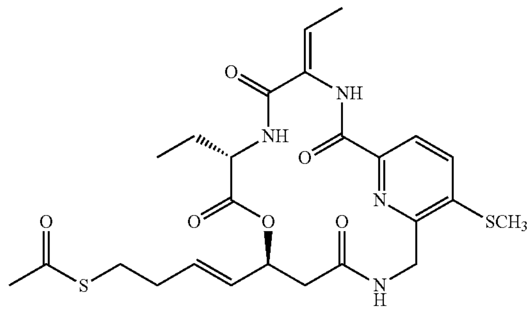
180
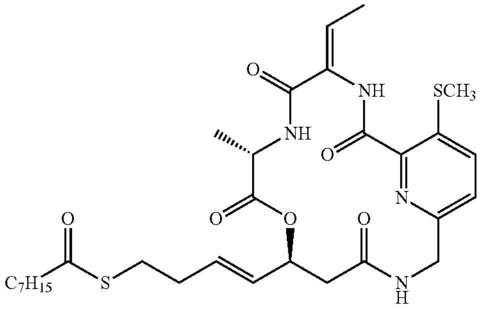
-continued
181
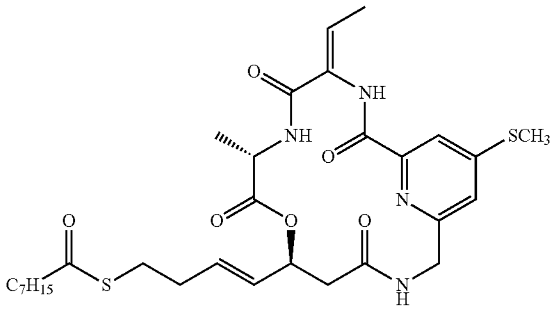
182
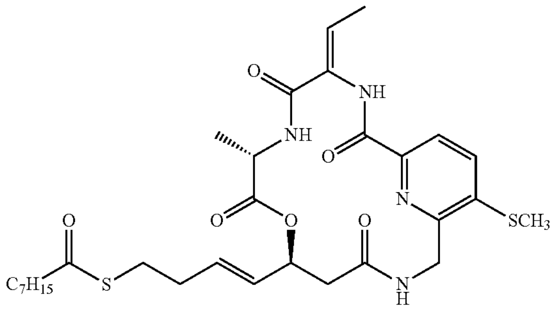
183
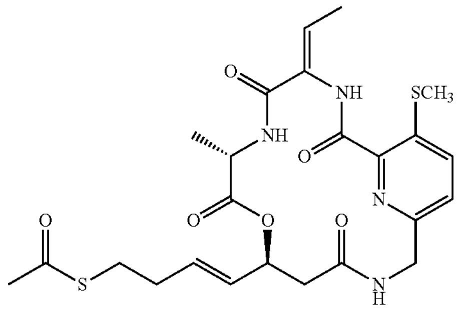
184
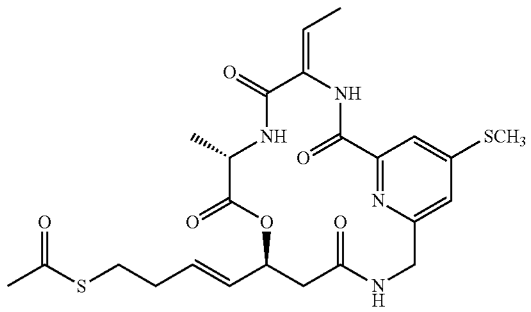
185
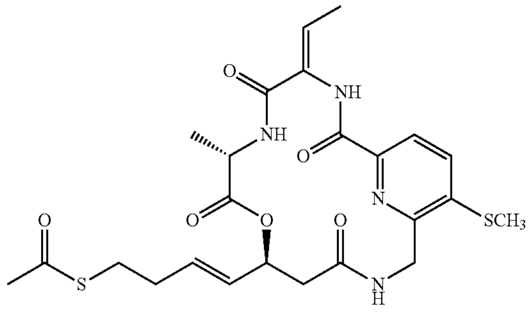

-continued
186
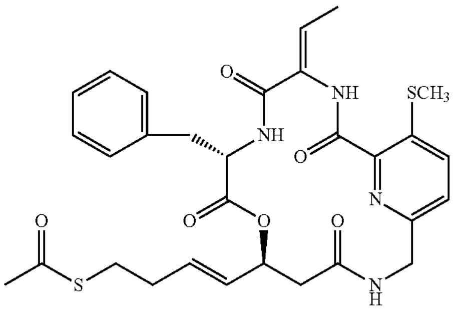
187
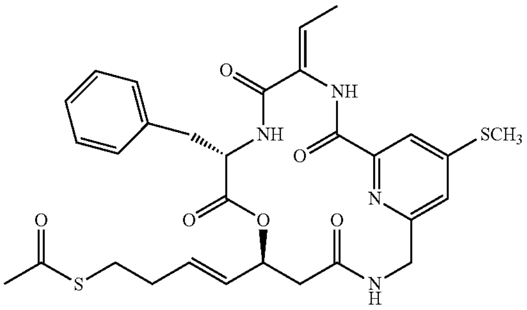
188
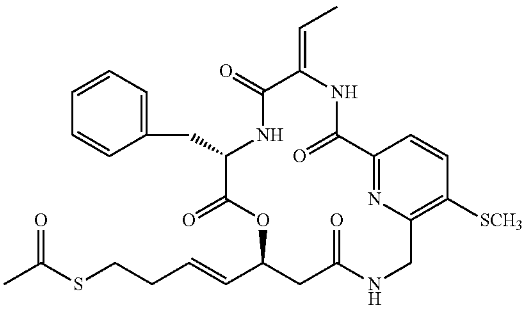
189
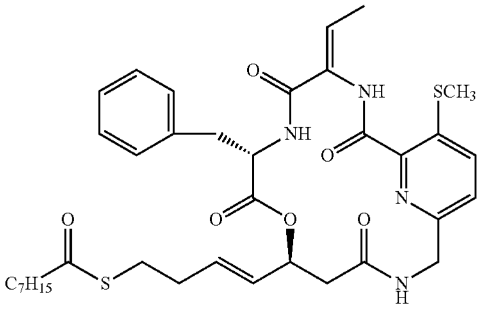
190
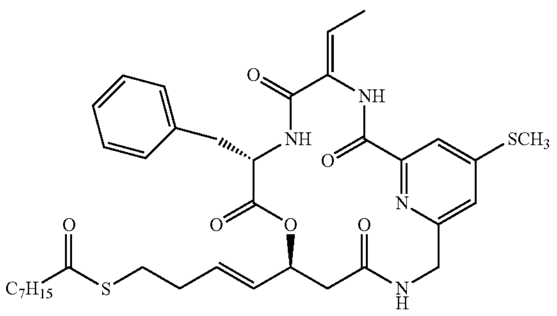
-continued
191
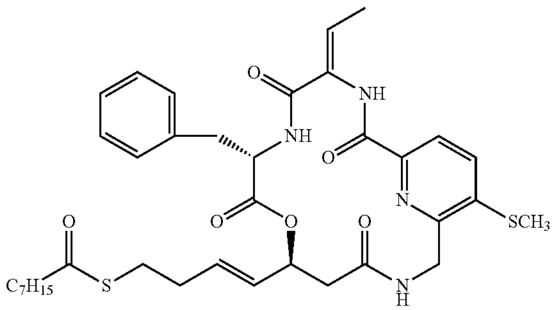
192
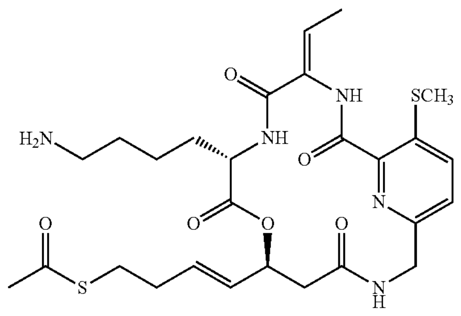
193
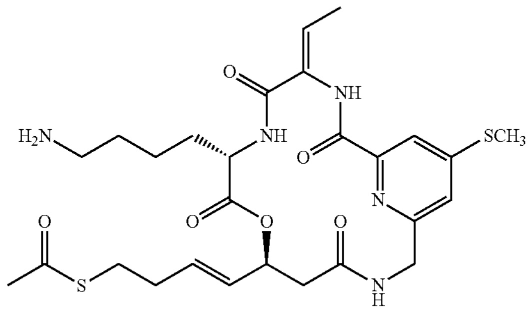
194
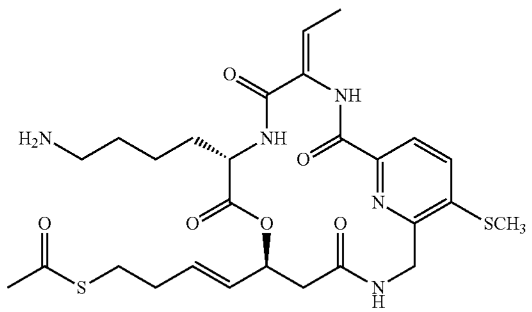
195
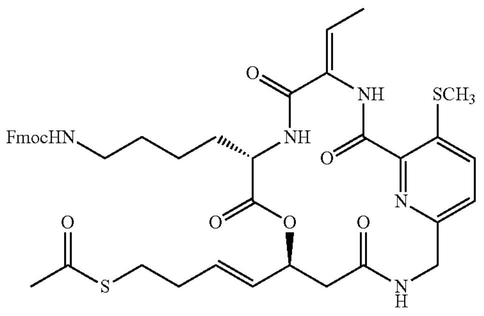

-continued
196
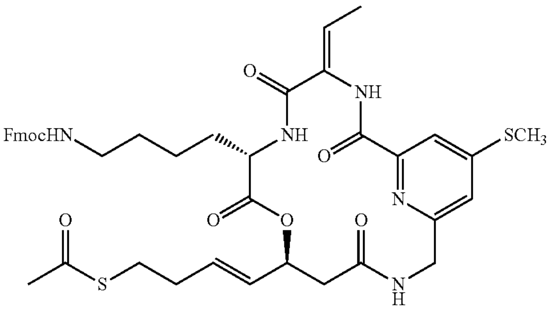
197
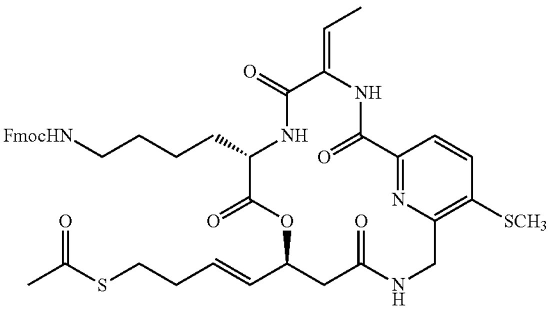
198
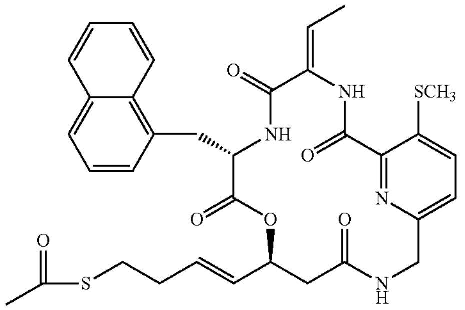
199
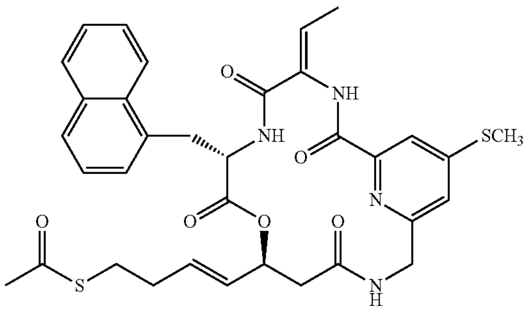
200
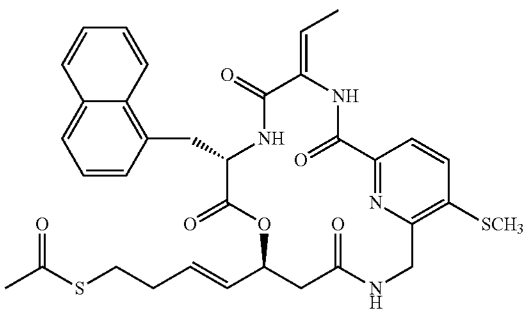
-continued
201
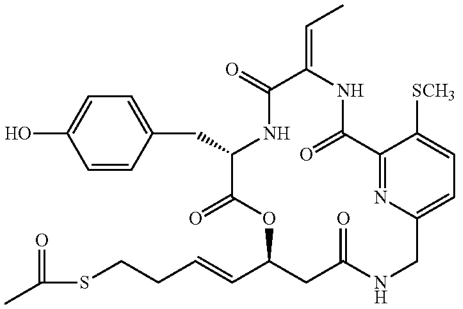
202
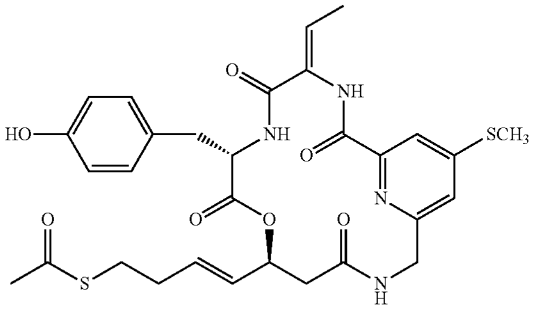
203
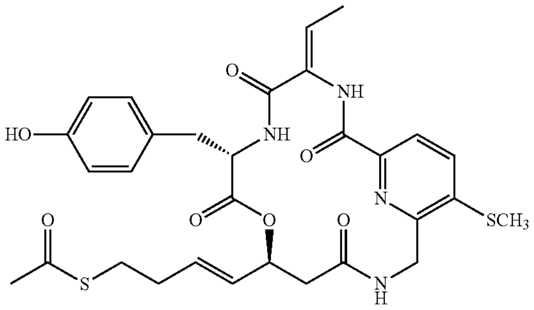
204
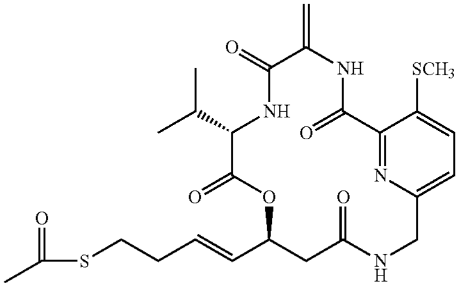
205
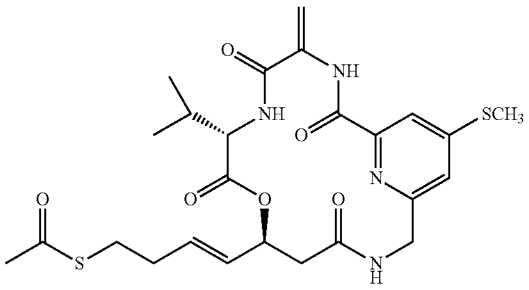

-continued
206
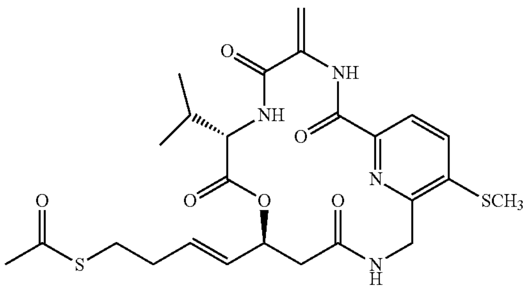
207
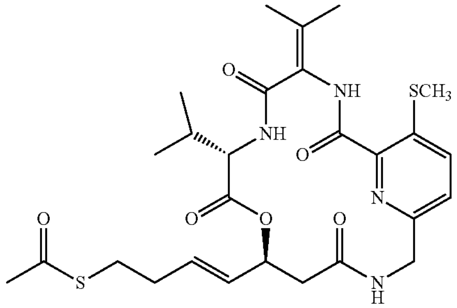
208
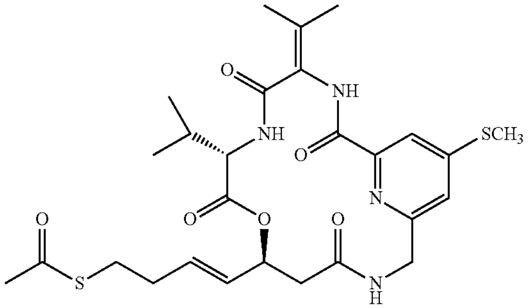
209
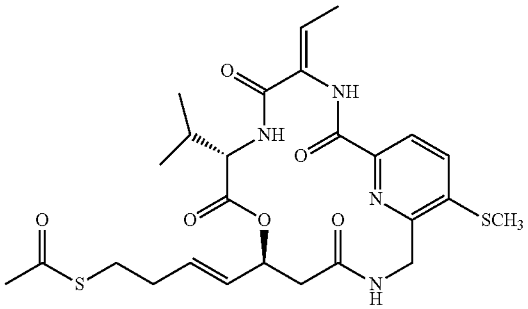
210
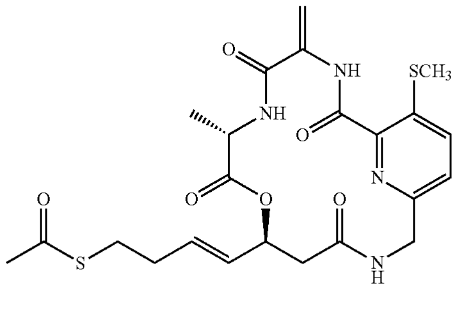
-continued
211
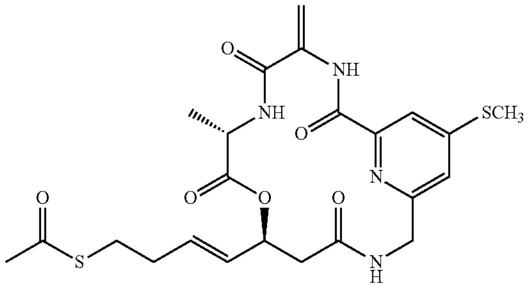
212
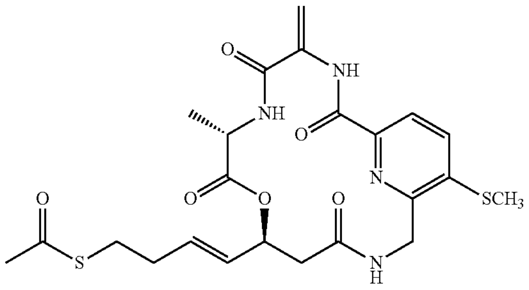
213
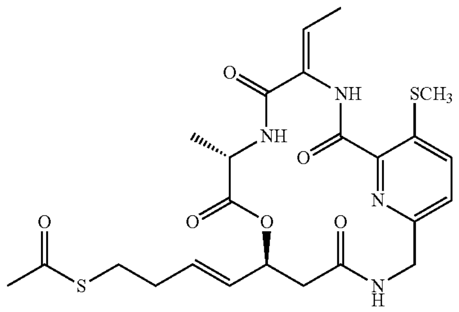
214
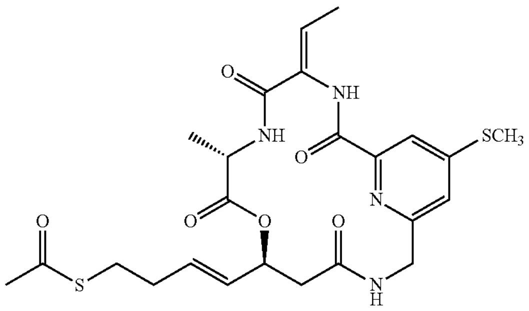
215
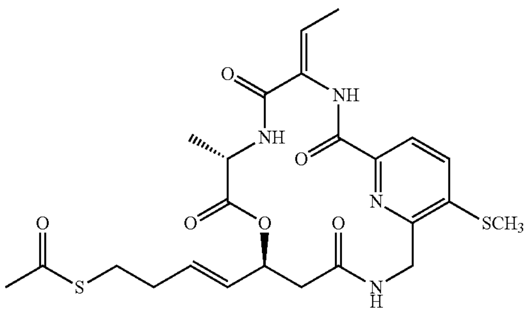

216
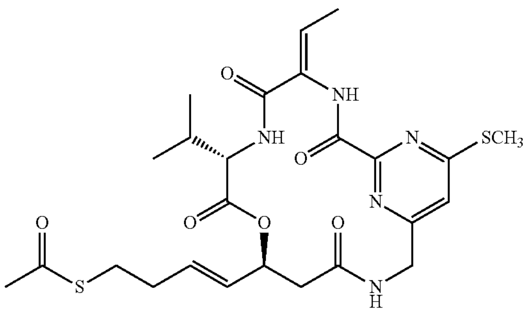
217
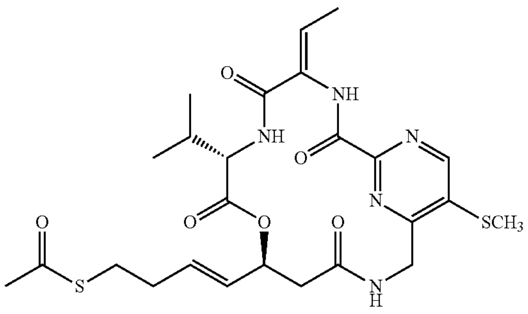
218
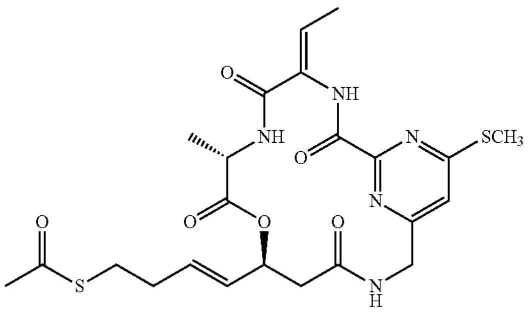
219
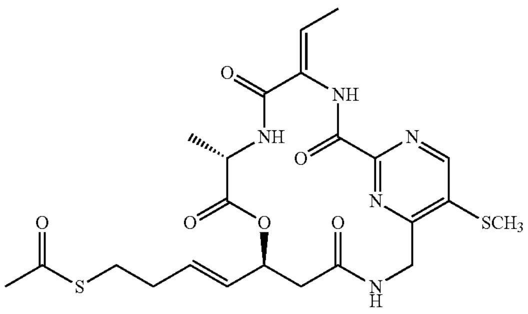
220
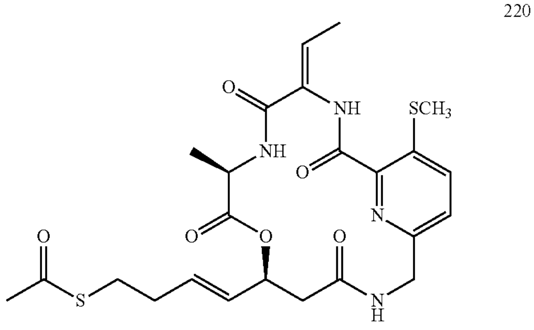
221
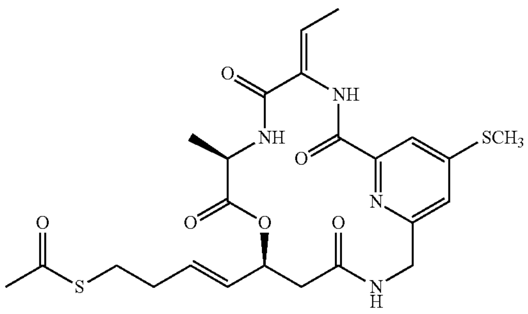
222
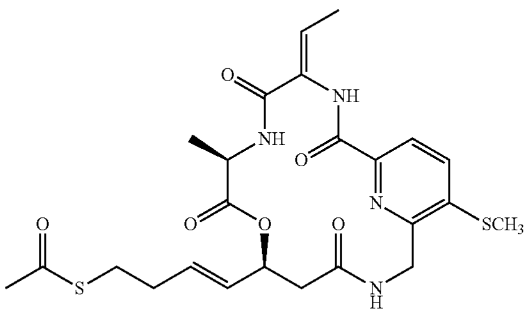
223
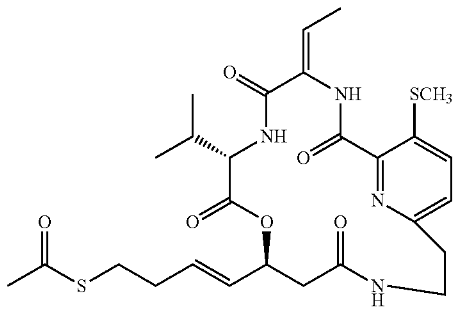
224
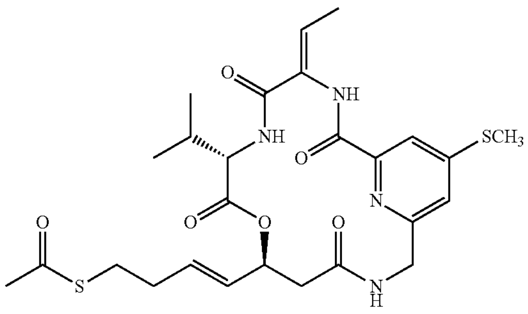
225
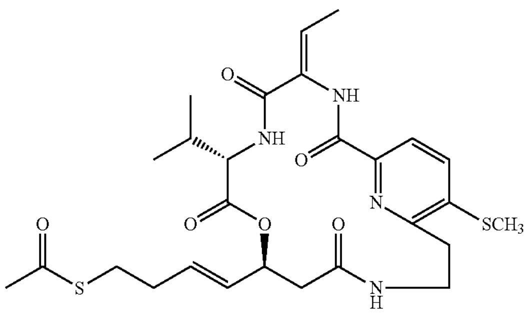

-continued
226
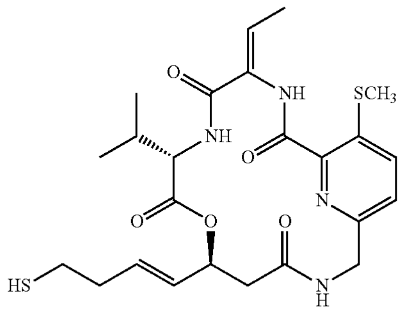
227
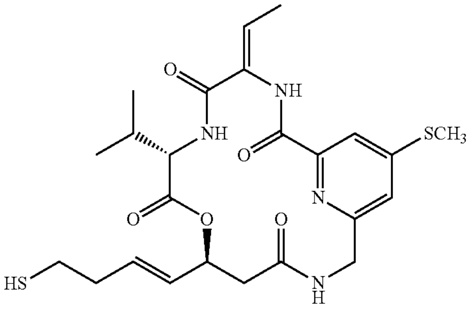
228
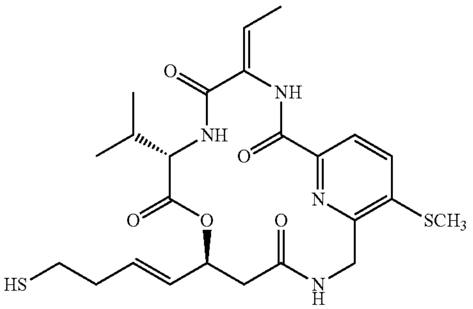
229
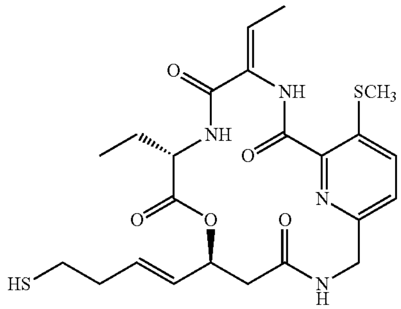
230
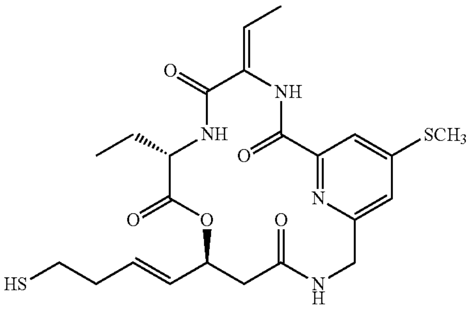
-continued
231
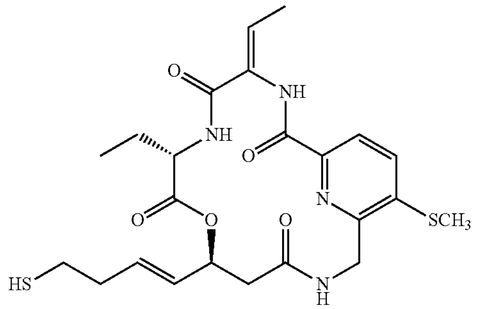
232
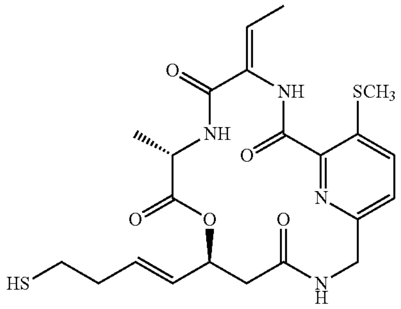
233
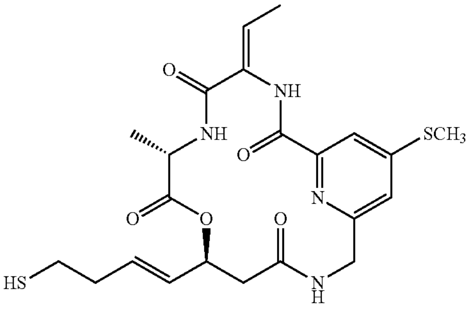
234
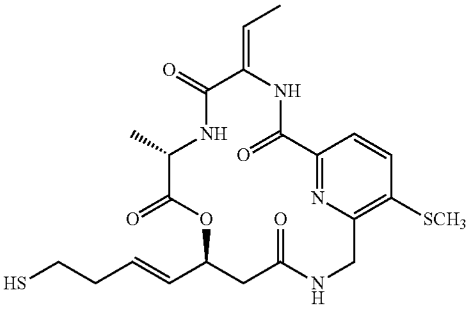
235
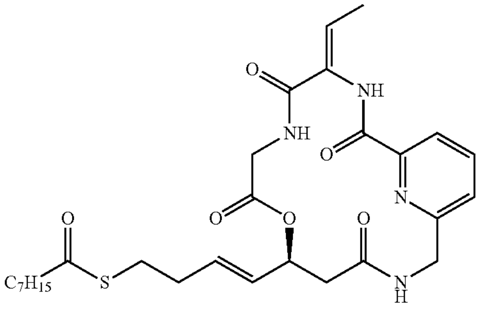

-continued
236
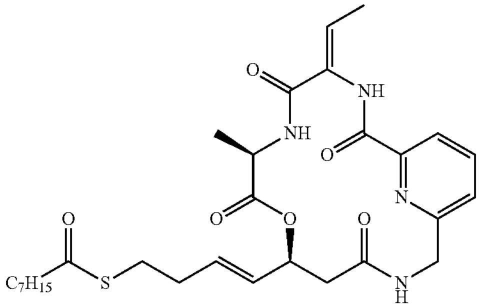
237
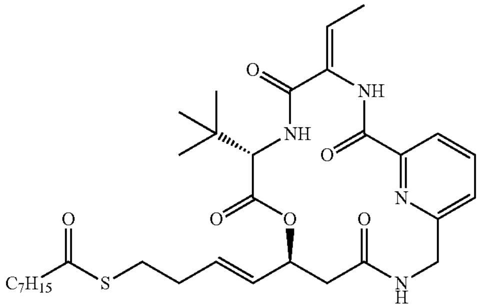
238
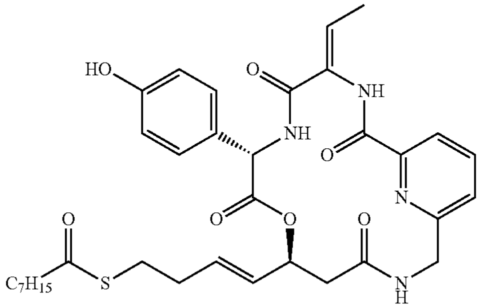
239
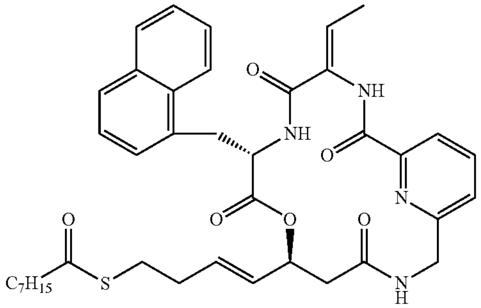
240
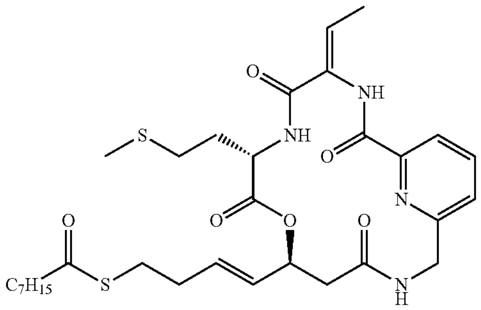
-continued
241
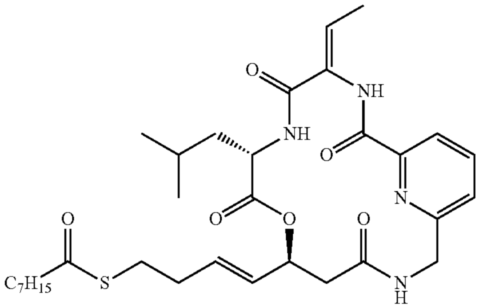
242
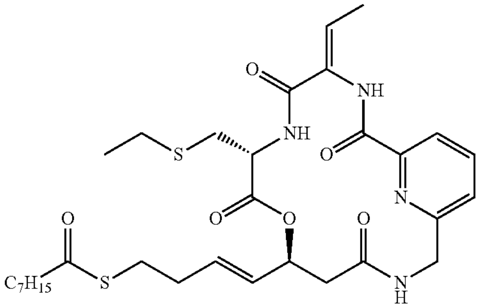
243
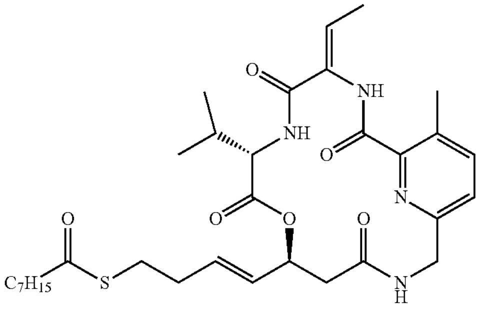
244
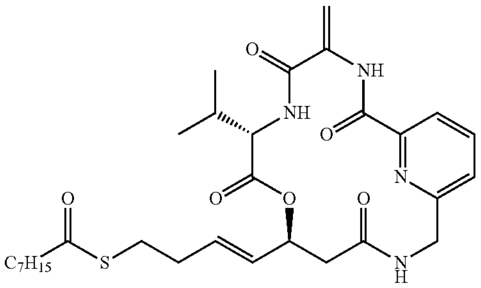
245
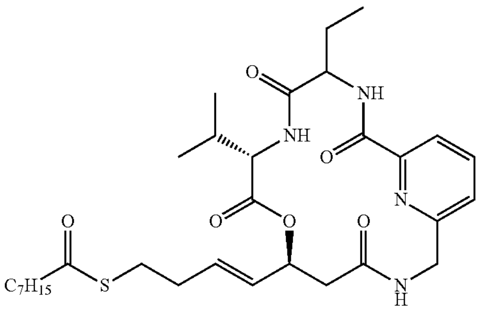

-continued
246
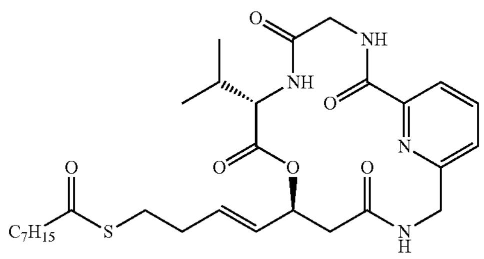
247
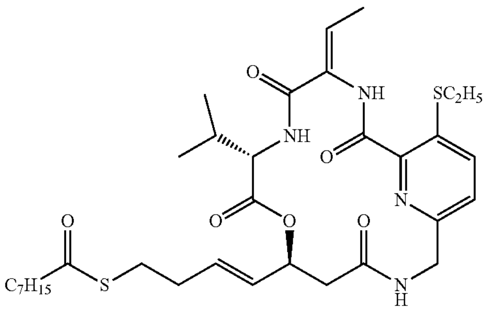
248
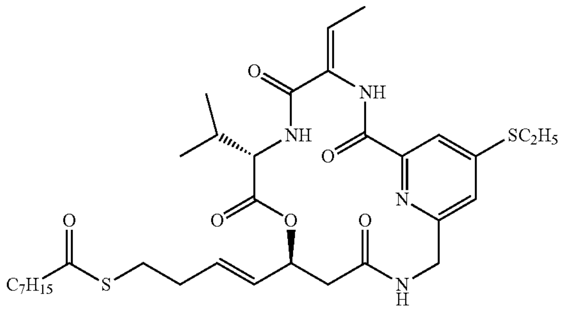
249
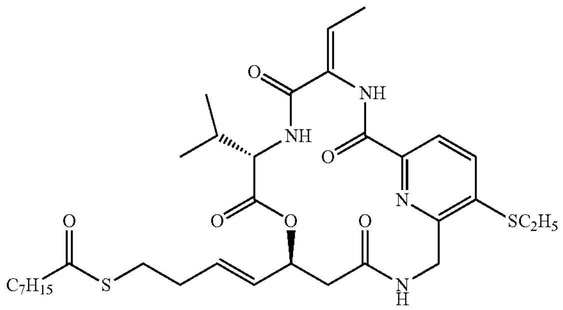
250
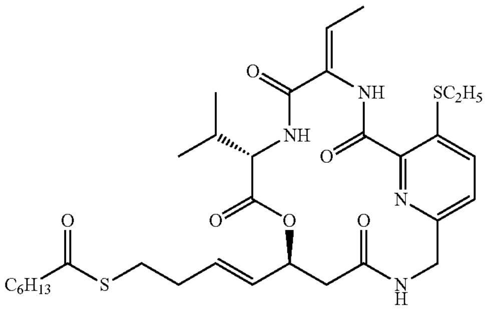
-continued
251
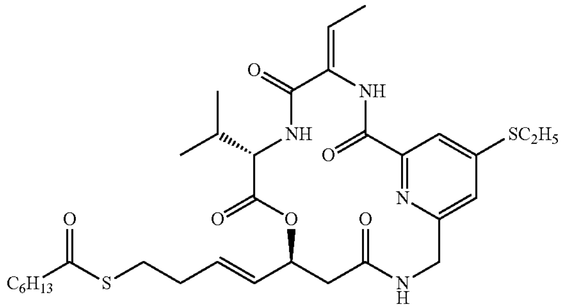
252
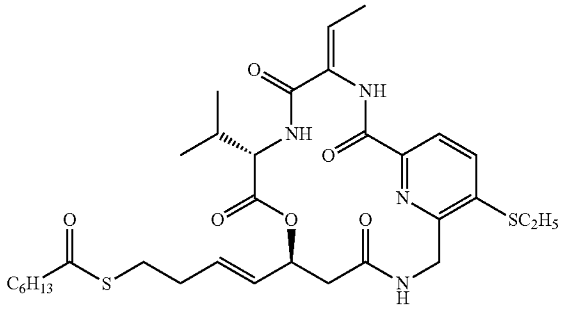
253
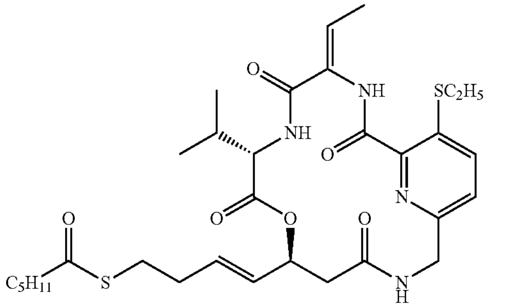
254
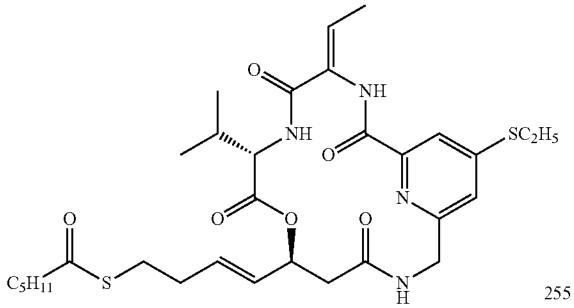
255
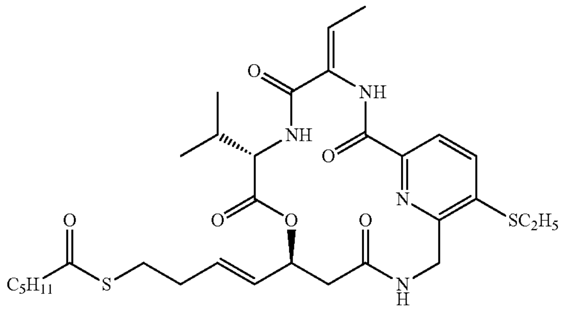

The present invention also provides a method of preparing compound of Formula (I), comprising the following steps:

(1) The compound of Formula (II) with alkali affords the compound of Formula (III) via hydrolysis reaction; the reaction process is shown as follows:

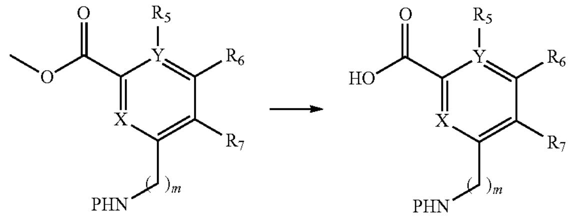

II III (2) Compound of Formula (III) and compound of Formula (IV) with organic alkali under condensation agent affords compound of Formula (V) compound; the reaction process is shown as follows:

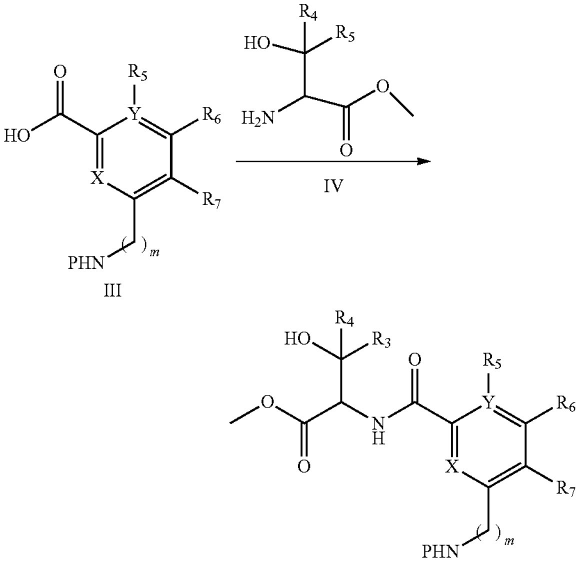

III IV V (3) The compound of Formula (V) and MsCl with organic alkali affords the compound of Formula (VI) via condensation reaction; the reaction process is shown as follows:

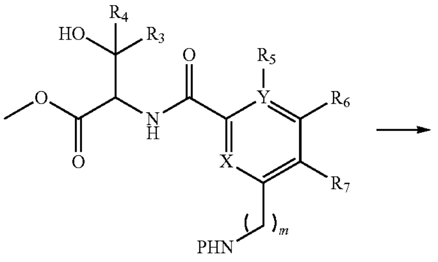

V

-continued

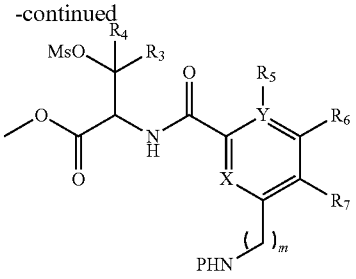

VI (4) The compound of Formula (VI) affords the compound of Formula (VII) via elimination reaction; the reaction process is shown as follows:

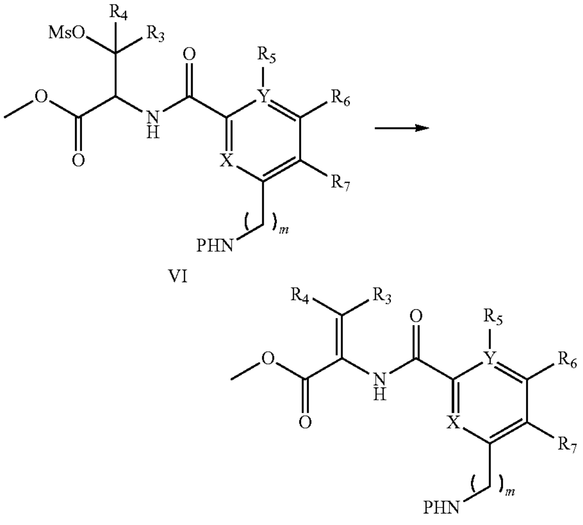

VI VII (5) The compound of Formula (VII) with alkali affords the compound of Formula (VIII) via hydrolysis reaction; the reaction process is shown as follows:

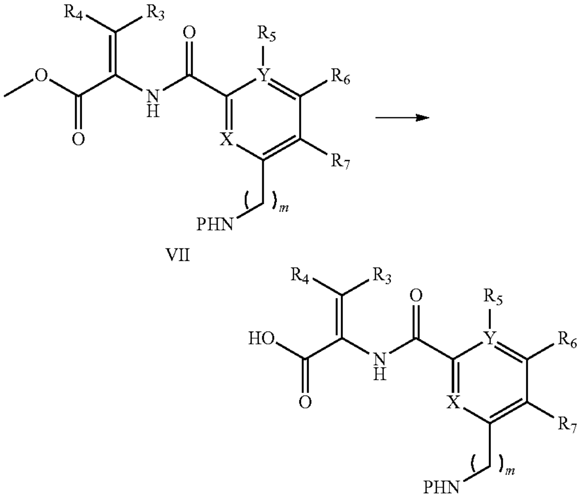

VII VIII (6) Compound of Formula (VIII) and compound of Formula (IX) with organic alkali under condensation agent affords the compound of Formula (X) via condensation reaction; the reaction process is shown as follows:

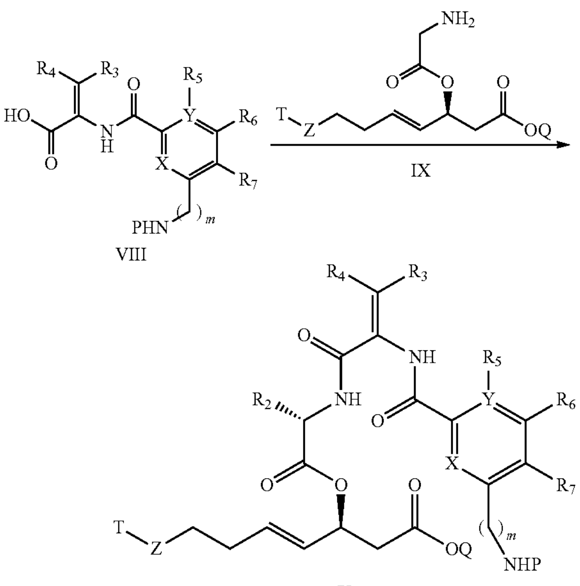

VIII IX X (7) Remove the amino protecting group P and carboxyl protecting group Q of the compound of Formula (X), and then under condensation agent with organic alkali affords the compound of Formula (XI) via the intramolecular closed loop reaction; the reaction procedure is shown as follows:

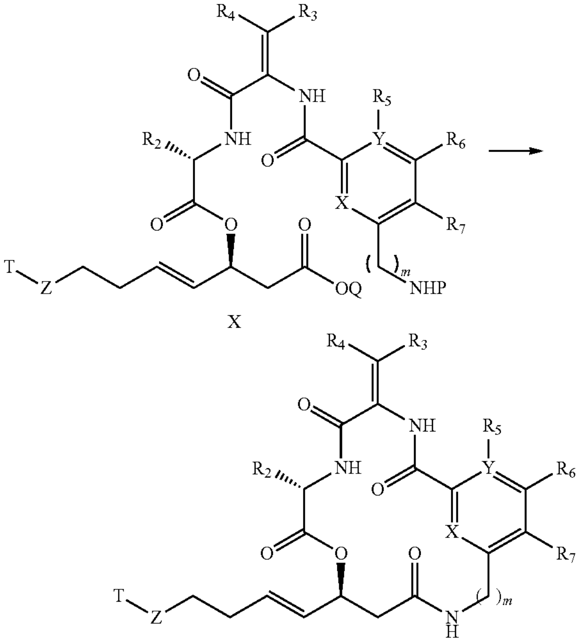

X XI (8) To remove protecting group T of the compound of Formula (XI), the compound of Formula (XII) was obtained; the reaction procedure is shown as follows:

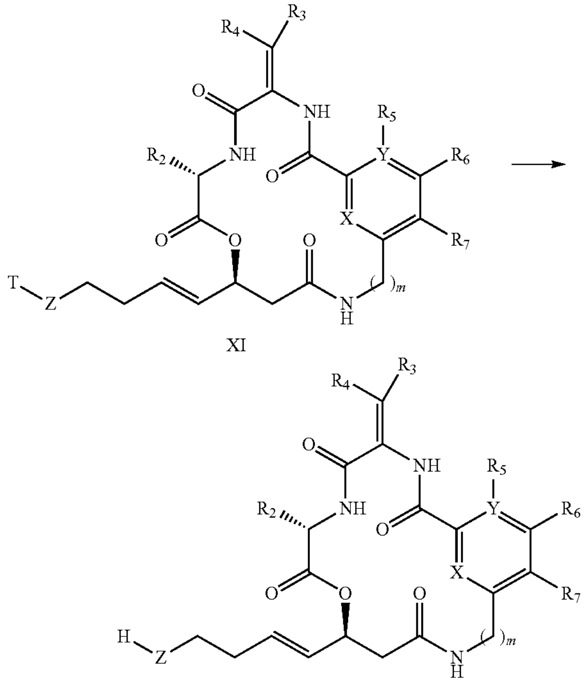

XI XII (9) The compound of Formula (XII) and compound $R_1$-L affords the compound of Formula (XIII); the reaction procedure is shown as follows:

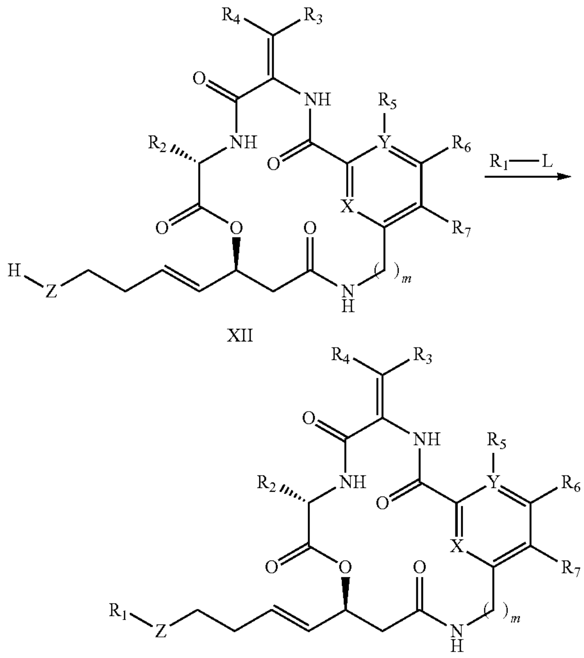

XII XIII

Wherein, the definition of $R_1$~$R_7$, X, Y, Z, m are the same as above;

P is an amino protecting group;

Q is a carboxyl protecting group;

T is O, S, NH heteroatom protecting group;

L is selected from halo, OH, OMs, SH, MeO, t-butO.

Further,

The organic alkalis in the step (2), (3), (6) and (7) are selected from imidazole, triethylamine, diisopropylethylamine, piperidine, dimethyl pyridine, LiHMDS, NaHMDS, khmds, N-methyl morpholine, DABCO or pyridine;

The condensing agents in the step (2), (6) are selected from DCC, EDC, HATU, HOAt, HOBt, DEAD, HBTU or PyBOP;

The amino protecting P is selected from Boc, Cbz, Bn, Fmoc, Alloc, Tos, Trt, or Bn;

The carboxyl protecting Q is selected from TMSOH, tertiary-butyl, ethyl, methyl.

The synthesis process described above, the organic solvent used may be selected from dichloromethane, tetrahydrofuran (THF), dimethylformamide (DMF), ethylene glycol dimethyl ether, 1,2-dichloroethane, dimethyl phthalate (DMP), methanol, ethanol, petroleum ether, hexane or diethyl ether; necessary inorganic alkali can selected from sodium hydroxide, lithium hydroxide, potassium carbonate, sodium carbonate, sodium bicarbonate, calcium carbonate; necessary acid may be selected from trifluoroacetic acid, hydrochloric acid, sulfuric acid or nitric acid. The oxidant may be Dess-Martin oxidant, Swern oxidizing agent, m-chloroperbenzoic acid, chlorine pyridinium dichromate (PDC) or pyridinium chlorochromate (PCC).

Further, the present invention provides applications of the compound of formula (I), its isomers, racemates, pharmaceutically acceptable salts, crystalline hydrate, solvate or a mixture thereof in preparing pharmaceuticals for preventing or treating mammalian diseases related to the dysregulation of histone deacetylase. The mammalian diseases related to the dysregulation of histone deacetylase include cancer, neurodegenerative diseases, malaria and AIDS, and more particularly include lymphoma, lung cancer, stomach cancer, pancreatic cancer, breast cancer, prostate cancer, leukemia and cervical cancer.

The present invention also provides a pharmaceutical composition which comprises a therapeutically effective amount of a compound of formula (I), its isomers, racemates, pharmaceutically acceptable salts, crystalline hydrate, solvate or their mixture, and one or more pharmaceutically acceptable carriers. Pharmaceutically acceptable salts include non-toxic salts with inorganic or organic acids formed by the reaction, the inorganic acids include hydrochloric acid, hydrobromic acid, sulfuric acid, nitric acid, phosphoric acid and amine, the organic acids include propionic acid, oxalic acid, malonic acid, succinic acid, fumaric acid, maleic acid, lactic acid, malic acid, tartaric acid, citric acid, aspartic acid.

The compound and the pharmaceutical composition provided by the invention can be in a variety of forms, such as tablet, capsule, powder, syrup, like solution, suspending liquid and aerosol agent, and can be present in the suitable solid or liquid carrier or diluent and suitable for injection or infusion of fire toxic instruments in.

It should be explained that the terms used in this paper, such as “alkyl”, “aryl”, “miscellaneous aryl group”, “halogen”, “acyl” and so on, are not significantly different from the general meaning of the term in the field.

For example, the term “alkyl” refers to the straight or branched chain, C1~n alkyl said 1~n carbon atoms of saturated aliphatic group, include straight chain and branched one, for example “C1 to C12 alkyl” refers to is the group is alkyl and alkyl carbon chain of carbon atoms number in 1~12 between. It should be stated that, when there is no special restriction on the number of carbon atoms, only the number of carbon atoms in the alkyl moiety is specified, and the number of substituents on the alkyl group is not included.

The general technical personnel in the field shall know the meaning of the following terms or abbreviations.

The term “pharmaceutically acceptable salt” refers to that which applies to mammals, especially human contact with the tissues without undue toxicity, irritation, allergic response, and with a reasonable benefit/risk ratio of salt within reasonable medical judgment. For example, medical amines, carboxylic acids, and other types of compounds acceptable salts in the art is well known.

The term “isomer” refers to two or more compounds with the same molecular structure, but with different structures and properties.

The term “racemate” refers to a equimolar mixture having its optically active enantiomers of chiral molecules, which is opposite to the direction of rotation, optical rotatory power mixing equal amounts of the same molecule, these molecules due to its optical rotation the role of the inter offset each other, so it is optically inactive.

The term “solvate” refers to a mixture of compound and solvent composition, i.e., e.g., a crystalline solvate.

The material corresponding to the English abbreviations used in the statement of claim or statement are:

DCC (N,N'-dicyclohexylcarbodiimide, Cas No.: 538-75-0), EDCI [1-ethyl-(3-dimethylaminopropyl) carbodiimide hydrochloride, Cas No.: 25952-53-8], HATU (Cas No.: 148893-10-1), HOAt (Cas No.: 39968-33-7), HOBt (1-hydroxy-benzo-triazole, Cas No.: 2592-95-2), DEAD (diethyl azodicarboxylate, Cas No.: 1972-28-7), HBTU (Cas No.: 94790-37-1), PyBOP (hexafluorophosphate benzotriazol-1-yl-yloxy tripyrrolidinophosphonium phosphorus, Cas No.: 132705-51-2), DIPEA (N,N-diisopropylethylamine, CAS: 7087-68-5); LiHMDS [bis (trimethylsilyl) amide], NaHMDS (sodium hexamethyldisilazide amino), KHMDS (potassium hexamethyldisilazide amine), DABCO (1,4-diazepine bicyclo [2.2.2] octane); Boc (tert-butoxycarbonyl), Cbz (benzyloxycarbonyl), Bn (benzyl), Fmoc (Fluorenylmethoxycarbonyl), Alloc (propoxycarbonyl), Tos (tosyl), Tfa (trifluoroacetyl) or Trt (trityl), OMs (methylsulfonyl oxy), MeO (oxymethyl), t-butO (tert-butoxy).

EXAMPLES

The following examples will further illustrate the present invention. These examples are intended to illustrate the present invention but not in any way limit the present invention only.

The present invention is used in the starting reactant unless otherwise specified, are commercially available It should be noted that in the following examples, the conventional post-processing method is: After completion of the reaction, adding an appropriate amount of water in the reaction mixture to separate the organic and aqueous phases, and combine organic phase; if necessary, followed by the use of 5% HCl solution and/or saturated NaSO4 dried, filtered under reduced pressure after the election anhydrousness to give the crude product, after column chromatography purification of the final product.

Example 1

1.1

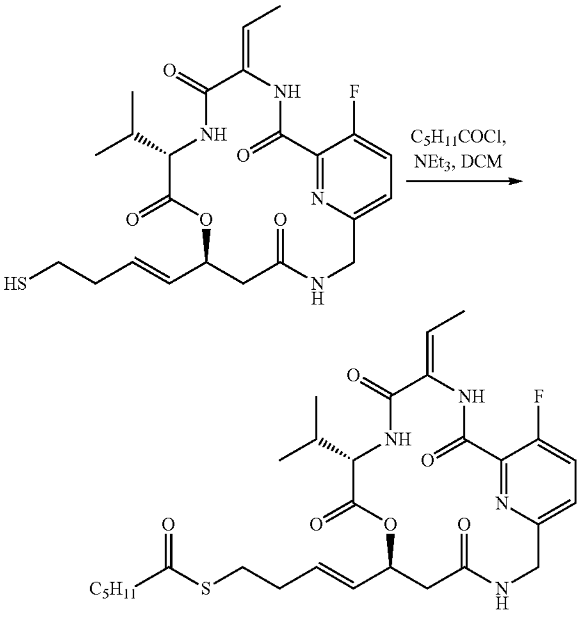

15 ml LiOH aqueous solution (456 mg, 19 mmol) were added dropwise to the reactant (2 g, 7.6 mmol) of 30 ml THF, then reacted for 2 h at room temperature. The reaction solution was adjusted by dilute hydrochloric acid to with the pH value of 3, then 100 ml ethyl acetate was added. The organic matter was washed by water and saturated salt water. The organic layer was dried by anhydrous sodium sulfate, and the solvent evaporated to give a 1.86 g white flocculent solid, and the yield was 97%.

1.2

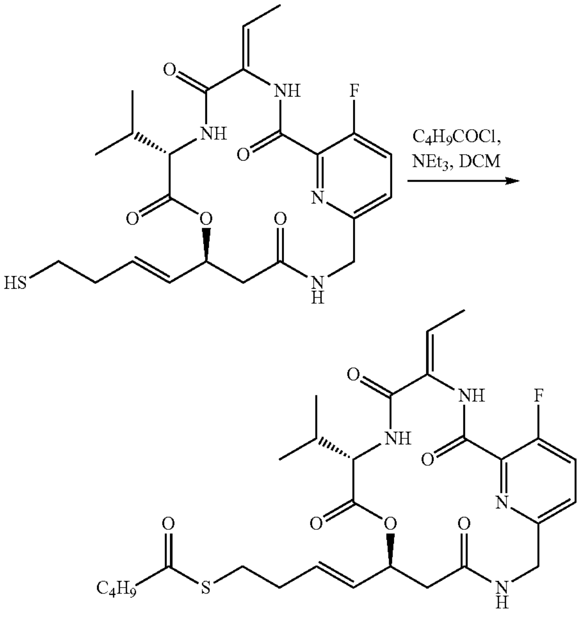

At 0° C., DIPEA (1.2 ml, 6 mmol) was added slowly to the reactant (0.7 g, 2.7 mmol), stirred slightly, then added S2 (456 mg, 2.7 mmol), PyBop (2.5 g, 4 mmol), and then stirred at room temperature overnight. The reaction solution was washed with saturated sodium bicarbonate solution, dilute hydrochloric acid solution, saturated sodium chloride solution. The product was dried with anhydrous sodium sulfate and spinned solvent by column chromatography and 0.7 g white floc was obtained, and the yield was 75%. $^1H$ NMR (400 MHz, $CDCl_3$): δ 8.64 (d, J=8.4 Hz, 1H), 8.05 (d, J=8 Hz, 1H), 7.81 (t, J=8 Hz, 1H), 7.44 (d, J=7.6 Hz, 1H), 5.44 (s, 1H), 4.77 (d, J=7.2 Hz, 1H), 4.48-4.45 (m, J=3H), 3.78 (s, 3H), 1.45 (s, 9H), 1.26 (d, J=5.6 Hz, 3H) ppm. $^{13}C$ NMR (100 MHz, CDCl3) δ 171.1, 164.6, 157.4, 156.0, 148.9, 137.9, 134.6, 124.2, 121.8, 121.0, 80.7, 79.8, 78.7, 70.3, 68.2, 61.1, 57.8, 52.7, 52.2, 47.7, 32.1, 28.3, 28.2, 28.1, 28.0, 22.6, 19.8 ppm.

1.3

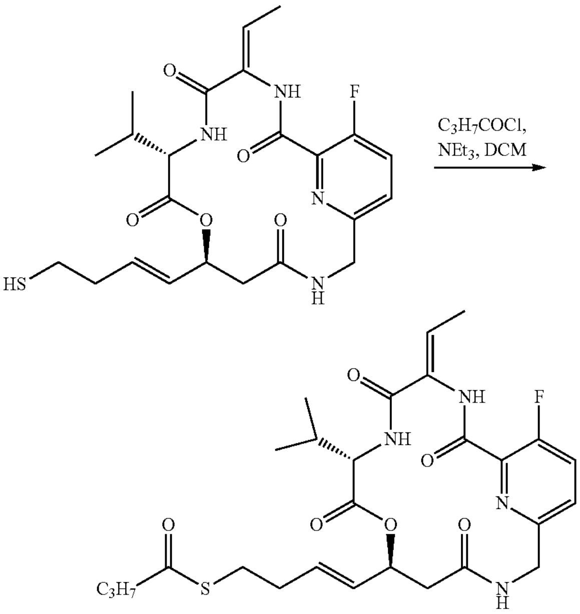

At 0° C., DMAP (25 mg, 0.184 mmol), $NEt_3$ (0.42 ml, 3 mmol), MsCl (0.186 ml, 2.4 mmol) was added to the reactants (675 mg, 1.84 mmol) in anhydrous DCM (10 ml) successively, then raised to room temperature and stirred overnight. The product was spinned anhydrous, pumped with oil pump and directly put into next step.

1.4

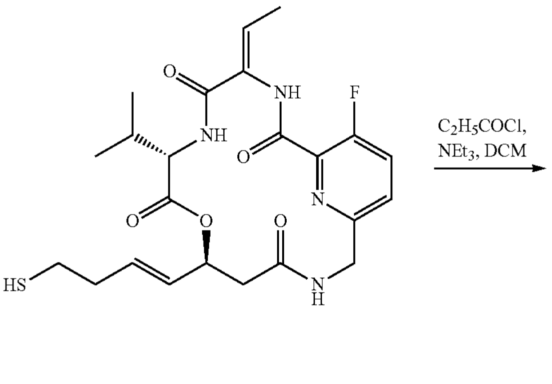

-continued

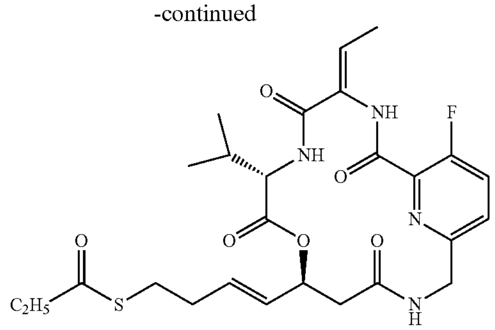

DABOCO (1 g, 9.22 mmol) was added to the anhydrous DCM liquid (10 ml) obtained above and stirred 8 h at room temperature. The reaction solution was washed by saturated sodium bicarbonate solution, saturated ammonium chloride solution, saturated sodium chloride solution in sequence, and dried by anhydrous sodium sulfate. The product was filtered and spinned solvent by column chromatography and 500 mg white floc was obtained, and the yield was 76%. $^1H$ NMR (400 MHz, $CDCl_3$): δ 9.38 (s, 1H), 8.01 (d, J=7.6 Hz, 1H), 7.78 (t, J=8 Hz, 1H), 7.41 (d, J=7.6 Hz, 1H), 6.86 (q, J=7.6 Hz, 1H), 5.57 (s, 1H), 4.44 (d, J=5.6 Hz, 2H), 3.74 (s, 9H), 1.80 (d, J=7.6 Hz, 3H), 1.40 (s, 9H) ppm. $^{13}C$ NMR (100 MHz, $CDCl_3$) δ 164.8, 162.1, 157.4, 156.0, 148.9, 148.8, 138.1, 133.9, 126.3, 124.2, 121.7, 121.0, 79.7, 52.1, 45.9, 28.3, 14.6 ppm.

1.5

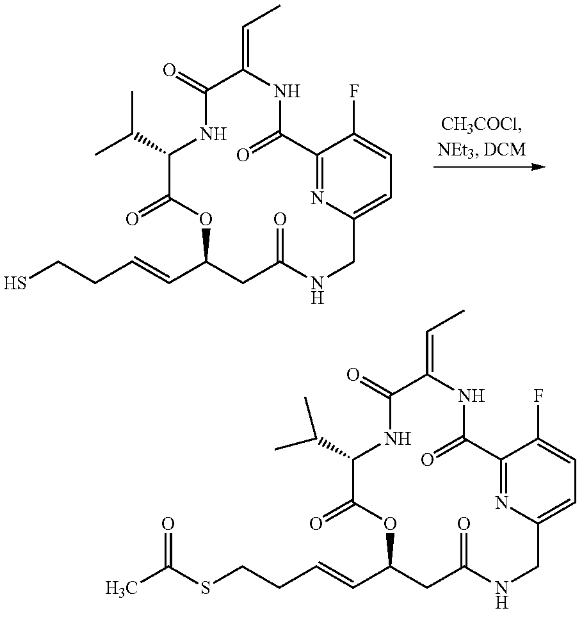

5 ml LiOH aqueous solution (90 mg, 3.6 mmol) were added dropwise to reactants (500 mg, 1.44 mmol) with THF (10 ml), then spinned anhydrous the organic phase after three hours. 10 ml water and 15 ml ethyl acetate were added to the organic phase. The aqueous phase was removed after liquid separation. Then the solution was added 15 ml ethyl acetate, adjusted the acid. Anhydrous sodium sulfate was used for the separation of organic phase after liquid separation. 453 mg solid white floc was obtained after spinned anhydrous. The yield was 94%. $^1H$ NMR (400 MHz, $CDCl_3$): δ 9.40 (s, 1H), 8.03 (d, J=7.6 Hz, 1H), 7.80 (t, J=8.2 Hz, 1H), 7.43 (d, J=7.8 Hz, 1H), 6.88 (q, J=7.8 Hz, 1H), 5.58 (s, 1H), 4.46 (d, J=5.8 Hz, 2H), 3.76 (s, 9H), 1.83 (d, J=7.8 Hz, 3H), 1.43 (s, 9H) ppm. $^{13}C$ NMR (100 MHz, $CDCl_3$) δ 165.3, 162.7, 157.8, 156.2, 149.0, 148.8, 138.3, 133.7, 126.5, 124.5, 121.9, 121.0, 52.5, 46.3, 28.5, 14.8 ppm.

1.6

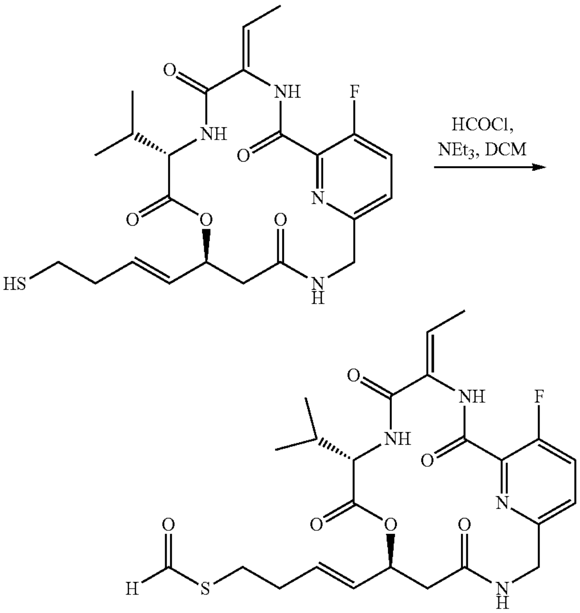

At 0° C., DIPEA (0.7 ml), carboxylic acid (610 mg), HATU (760 mg), HOAT (326 mg) were sequentially added to the reactant (336 mg, 1 mmol) in DCM solution (10 ml). Then raised to room temperature with stirring. After 8 h, the reaction was washed with saturated sodium bicarbonate solution, dilute hydrochloric acid solution, saturated sodium chloride solution, and dried over anhydrous sodium sulfate. The product was filtered and spinned solvent by column chromatography and 750 mg white flocculent solid was obtained, and the yield was 92%. $^1H$ NMR (400 MHz, $CDCl_3$): δ 9.41 (s, 1H), 8.10 (d, J=7.6 Hz, 1H), 7.84 (t, J=7.6 Hz, 1H), 7.48 (d, J=7.6 Hz, 1H), 7.39-7.17 (m, 12H), 6.66-6.61 (m, 2H), 5.68-5.59 (m, 2H), 5.46 (s, 1H), 5.38-5.32 (m, 1H), 4.59 (dd, J=8.8 Hz, 4 Hz, 1H), 4.49 (d, J=4.2 Hz, 2H), 4.15-4.10 (m, 3H), 2.66 (dd, J=15.6 Hz, 7.6 Hz, 1H), 2.52 (dd, J=15.6 Hz, 5.6 Hz, 1H), 2.18-2.14 (m, 3H), 2.04 (t, J=6.8 Hz, 4H), 1.82 (d, J=7.2 Hz, 3H), 1.46 (s, 9H), 1.25 (t, J=6.8 Hz, 2H), 0.97-0.90 (m, 5H), 0.80 (d, J=6.8 Hz, 3H), 0.02 (s, 9H) ppm. $^{13}C$ NMR (125 MHz, CDCl3) δ 171.0, 170.7, 169.5, 164.3, 162.6, 157.3, 155.9, 148.5, 144.7, 138.2, 133.9, 129.6, 129.4, 129.0, 127.7, 127.6, 126.5, 124.6, 121.1, 79.7, 71.8, 66.5, 63.0, 60.3, 57.0, 45.6, 39.5, 31.5, 31.2, 31.0, 28.3, 20.9, 18.8, 17.5, 17.2, 14.1, 13.8, 0.9, −1.5, −1.6 ppm.

1.7

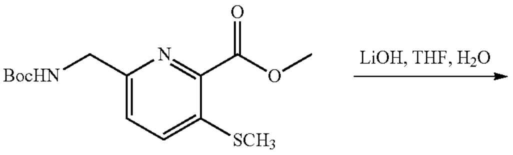

-continued

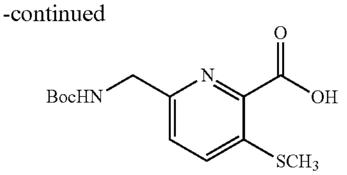

Tetrabutylammonium fluoride in tetrahydrofuran solution (1 mol/l, 2.3 ml) was added to the reaction (750 mg, 0.92 mmol) in redistilled THF (5 ml). After 3 h, the reaction was immediately spinned anhydrous by column chromatography to obtain a white solid.

Trifluoroacetic acid (6 ml) was added to DCM solution (25 ml) of the resulting resultant of the last step. After 5 h, spinned and removed DCM, the residue was added toluene (8 ml). Without further treatment, a brown viscous material was obtained after pumped organic solvent with oil pump. Chromatography pure acetonitrile (200 ml) obtained above was dissolved, slowly dropped in HATU (3 g), DIPEA (4 ml) of HPLC grade acetonitrile (550 ml). After 24 h, spinned anhydrous solvents, the product was diluted with ethyl acetate (20 ml) and then washed with saturated sodium bicarbonate solution, dilute hydrochloric acid solution, saturated sodium chloride solution and dried over anhydrous sodium sulfate. The product was filtered and spinned anhydrous by column chromatography and 540 mg pale yellow solid was obtained. The yield was 82%. $^{1}$H NMR (400 MHz, CDCl3): δ 9.17 (s, 1H), 8.10 (d, J=7.6 Hz, 1H), 7.87 (t, J=7.6 Hz, 1H), 7.37-7.16 (m, 15H), 7.07 (q, J=7.2 Hz, 1H), 6.67 (d, J=4.4 Hz, 1H), 6.43 (d, J=10.4 Hz, 1H), 5.62-5.56 (m, 2H), 5.39-5.34 (m, 1H), 5.06 (dd, J=17.2 Hz, 8 Hz, 1H), 4.74 (dd, J=6.4 Hz, 3.6 Hz, 1H), 4.19-4.08 (m, 2H), 2.69-2.64 (m, 2H), 2.30-2.27 (m, 1H), 2.21-2.17 (m, 2H), 1.84 (d, J=7.2 Hz, 3H), 0.79 (d, J=6.8 Hz, 3H), 0.59 (d, J=6.8 Hz, 3H) ppm. 13C NMR (125 MHz, DMSO) δ 133.6, 132.0, 131.3, 126.1, 124.7, 118.4, 111.1, 107.1, 101.0, 97.3, 95.2, 92.0, 90.4, 90.3, 89.5, 89.1, 87.5, 83.8, 39.8, 39.5, 39.3, 34.1, 29.1, 22.9, 19.5 ppm.

1.8

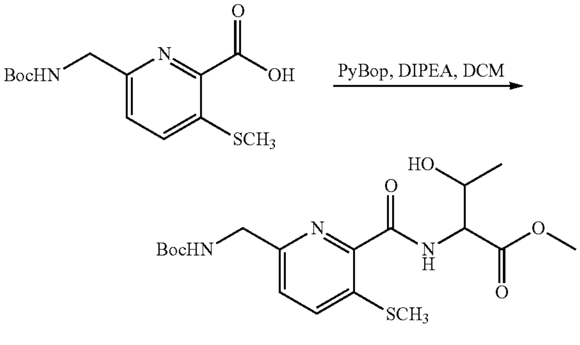

At 0° C., TES (0.1 ml), TFA (0.65 ml) were sequentially added to the reactants (150 mg, 0.21 mmol) in anhydrous DCM solution (5 ml). 15 min later, the product was directly spinned anhydrous solvent by column chromatography and 63 mg pale yellow solid was obtained, and the yield was 63%. [α]$^{20}$D: 6.13 (c 0.5, $CHCl_3$). $^{1}$H NMR (400 MHz, $CDCl_3$): δ 8.18 (d, J=7.6 Hz, 1H), 7.89 (t, J=7.6 Hz, 1H), 7.45 (d, J=7.6 Hz, 1H), 7.06 (dd, J=14.4 Hz J=7.2 Hz, 1H), 6.58 (dd, J=7.6 Hz, J=3.6 Hz, 1H), 6.45 (d, J=8 Hz, 1H), 5.74-5.64 (m, 2H), 5.50 (dd, J=15.6 Hz, J=6.8 Hz, 1H), 5.10 (m, 1H), 4.74 (dd, J=10 Hz, J=3.6 Hz, 1H), 4.34-4.28 (m, 1H), 2.74-2.69 (m, 2H), 2.56-2.50 (m, 2H), 2.34-2.29 (m, 3H), 1.36 (t, J=7.6 Hz, 1H), 0.80 (d, J=6.8 Hz, 3H), 0.6 (d, J=6.8 Hz, 3H) ppm. $^{13}$C NMR (125 MHz, CDCl3) δ 169.6, 168.9, 163.6, 162.9, 155.7, 148.6, 138.3, 134.7, 132.4, 128.6, 127.0, 124.9, 121.4, 71.9, 56.9, 43.3, 41.0, 36.0, 30.8, 23.7, 18.9, 16.5, 14.6 ppm.

Example 2

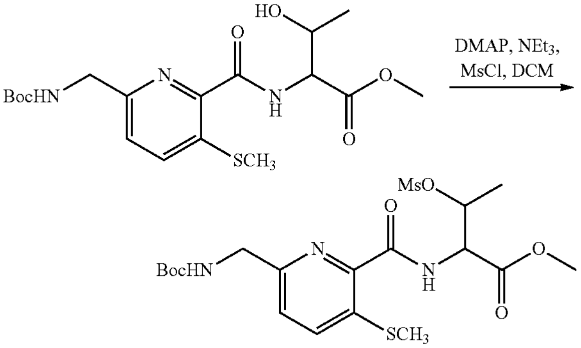

At 0° C., redistilled $NEt_3$ (0.04 ml) was added to the reactant (60 mg, 0.126 mmol) in anhydrous DCM (5 ml), stirred slightly, then caprylate chloride (0.1 ml) was added. After 7 h, The product was directly spinned anhydrous solvent by column chromatography and 60 mg pale yellow solid was obtained, and the yield was 80%. [α]$^{20}$D: 3.71 (c 0.5, CHCl3). $^{1}$H NMR (400 MHz, CDCl3): δ 9.21 (s, 1H), 8.10 (d, J=7.6 Hz, 1H), 7.91 (t, J=7.6 Hz, 1H), 7.44 (d, J=7.6 Hz, 1H), 7.06 (m, J=7.2 Hz, 1H), 6.70 (d, J=4.4 Hz, 1H), 6.46 (d, J=10 Hz, 1H), 5.70-5.64 (m, 2H), 5.59-5.46 (m, 1H), 5.13 (dd, J=17.2 Hz, 8 Hz, 1H), 4.73-4.70 (m, 2H), 4.27 (d, J=J=17.2 Hz, 1H), 2.85-2.71 (m, 4H), 2.62-2.61 (m, 1H), 2.49 (t, J=7.6 Hz, 3H), 2.29-2.23 (m, 3H), 1.84-1.81 (m, 3H), 1.61-1.58 (m, 2H), 1.24 (s, 11H), 0.86-0.57 (m, 7H), 0.53 (d, J=7.6 Hz, 3H) ppm. $^{13}$C NMR (125 MHz, $CDCl_3$) δ169.6, 169.1, 167.6, 165.7, 163.7, 162.3, 155.8, 148.6, 138.5, 134.7, 132.5, 132.2, 130.8, 128.7, 128.2, 127.2, 124.9, 121.3, 72.0, 71.6, 56.9, 44.0, 43.2, 40.8, 38.5, 33.7, 32.1, 31.5, 30.8, 29.6, 29.0, 28.8, 28.8, 27.7, 27.6, 25.5, 24.7, 22.5, 19.0, 18.9, 16.4, 14.6, 13.9 ppm.

Example 3

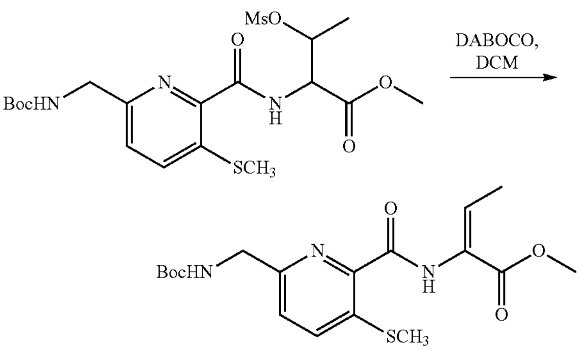

At 0° C., redistilled $NEt_3$ (0.02 ml) was added to the reactant (30 mg, 0.063 mmol) in anhydrous DCM (2 ml), stirred slightly, then heptanoyl chloride (0.05 ml) was added. After 7 h, The product was directly spinned anhydrous solvent by column chromatography and 31 mg pale yellow solid was obtained, and the yield was 83%. $[\alpha]^{20}D$: 4.11 (c 0.7, $CHCl_3$). 1H NMR (400 MHz, $CDCl_3$): δ 9.23 (s, 1H), 8.12 (d, J=7.8 Hz, 1H), 7.93 (t, J=7.6 Hz, 1H), 7.45 (d, J=7.6 Hz, 1H), 7.08 (m, J=7.2 Hz, 1H), 6.73 (d, J=4.4 Hz, 1H), 6.48 (d, J=10 Hz, 1H), 5.72-5.63 (m, 2H), 5.62-5.45 (m, 1H), 5.15 (dd, J=17.2 Hz, 8 Hz, 1H), 4.75-4.71 (m, 2H), 4.28 (d, J=17.2 Hz, 1H), 2.86-2.71 (m, 4H), 2.63-2.62 (m, 1H), 2.50 (t, J=7.8 Hz, 3H), 2.30-2.25 (m, 3H), 1.85-1.82 (m, 3H), 1.62-1.59 (m, 2H), 1.26-1.24 (m, 9H), 0.85 (m, 3H), 0.78 (d, J=7.6 Hz, 3H), 0.57 (d, J=7.6 Hz, 3H) ppm. $^{13}C$ NMR (125 MHz, $CDCl_3$) δ 169.5, 169.0, 163.5, 162.1, 155.7, 148.8, 138.6, 134.5, 132.6, 132.1, 130.9, 128.9, 128.5, 127.5, 125.1, 121.3, 72.2, 71.7, 57.3, 44.1, 43.2, 40.9, 38.6, 33.8, 32.2, 31.5, 30.9, 29.7, 29.1, 28.8, 27.7, 27.6, 25.5, 22.5, 19.1, 18.9, 16.4, 14.6, 14.0 ppm.

Example 4

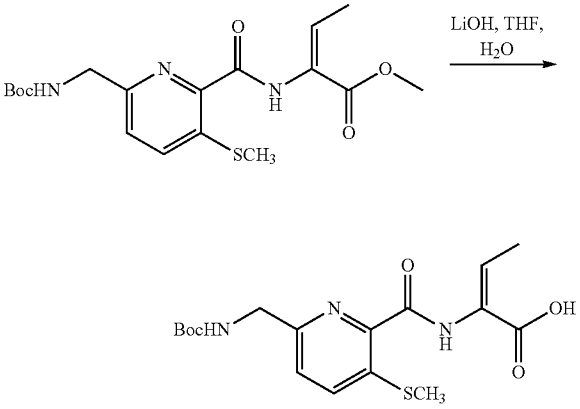

At 0° C., redistilled $NEt_3$ (0.02 ml) was added to the reactant (30 mg, 0.063 mmol) in anhydrous DCM (2 ml), stirred slightly, then hexanoyl chloride (0.04 ml) was added. After 7 h, The product was directly spinned anhydrous solvent by column chromatography and 32 mg pale yellow solid was obtained, and the yield was 85%. $[\alpha]^{20}D$: 3.11 (c 0.3, $CHCl_3$). 1H NMR (400 MHz, $CDCl_3$): δ 9.22 (s, 1H), 8.10 (d, J=7.8 Hz, 1H), 7.95 (t, J=7.6 Hz, 1H), 7.46 (d, J=7.6 Hz, 1H), 7.06 (m, J=7.2 Hz, 1H), 6.75 (d, J=4.4 Hz, 1H), 6.46 (d, J=10.0 Hz, 1H), 5.74-5.68 (m, 2H), 5.50 (m, 1H), 5.17 (dd, J=17.2 Hz, 8.0 Hz, 1H), 4.76-4.73 (m, 2H), 4.28 (d, J=17.2 Hz, 1H), 2.88-2.75 (m, 4H), 2.63 (m, 1H), 2.49 (t, J=7.8 Hz, 3H), 2.30-2.25 (m, 3H), 1.84-1.82 (m, 3H), 1.63-1.60 (m, 2H), 1.26-1.24 (m, 7H), 0.84 (m, 3H), 0.79 (d, J=7.6 Hz, 3H), 0.59 (d, J=7.6 Hz, 3H) ppm. $^{13}C$ NMR (125 MHz, CDCl3) δ 169.3, 169.0, 163.2, 162.0, 155.6, 148.9, 138.8, 134.8, 132.7, 132.0, 130.9, 128.9, 128.6, 127.7, 125.3, 121.5, 72.3, 71.8, 57.5, 44.3, 43.4, 41.2, 38.9, 33.9, 32.5, 31.7, 30.9, 29.8, 29.2, 28.9, 27.8, 27.6, 25.6, 22.6, 19.0, 16.5, 14.7, 13.9 ppm.

Example 5

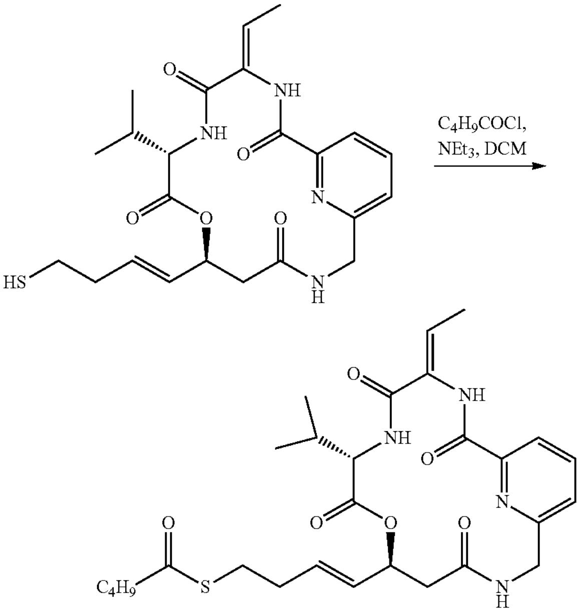

At 0° C., redistilled $NEt_3$ (0.02 ml) was added to the reactant (30 mg, 0.063 mmol) in anhydrous DCM (2 ml), stirred slightly, thenpivaloyl chloride (0.04 ml) was added. After 7 h, The product was directly spinned anhydrous solvent by column chromatography and 30 mg pale yellow solid was obtained, and the yield was 84%. $[\alpha]^{20}D$: 3.31 (c 0.6, CHCl3). $^{1}H$ NMR (400 MHz, CDCl3): δ 9.20 (s, 1H), 8.12 (d, J=7.8 Hz, 1H), 7.96 (t, J=7.6 Hz, 1H), 7.47 (d, J=7.6 Hz, 1H), 7.08 (d, J=7.2 Hz, 1H), 6.73 (d, J=4.4 Hz, 1H), 6.49 (d, J=10.0 Hz, 1H), 5.73-5.69 (m, 2H), 5.51 (m, 1H), 5.15 (dd, J=17.2 Hz, 8.0 Hz, 1H), 4.75-4.73 (m, 2H), 4.29 (d, J=17.2 Hz, 1H), 2.89-2.75 (m, 4H), 2.62 (m, 1H), 2.47 (t, J=7.8 Hz, 3H), 2.31-2.26 (m, 3H), 1.85-1.83 (m, 3H), 1.62-1.60 (m, 2H), 1.25-1.23 (m, 5H), 0.83 (m, 3H), 0.78 (d, J=7.6 Hz, 3H), 0.58 (d, J=7.6 Hz, 3H) ppm. $^{13}C$ NMR (125 MHz, CDCl3) δ 169.2, 169.0, 163.3, 162.2, 155.7, 148.7, 138.9, 134.5, 132.8, 132.1, 130.8, 128.9, 128.5, 127.6, 125.2, 121.3, 72.1, 71.6, 57.8, 44.2, 43.5, 41.3, 38.8, 33.8, 32.6, 31.6, 30.8, 29.9, 29.3, 28.8, 27.6, 25.7, 22.7, 19.1, 16.6, 14.9, 13.8 ppm.

Example 6

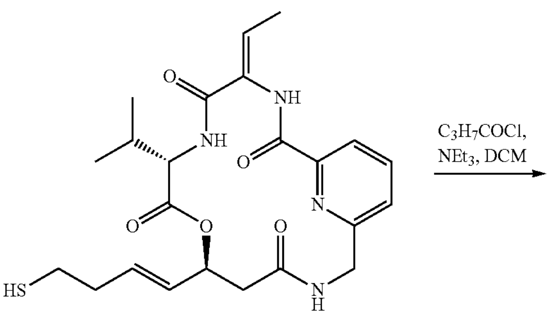

-continued

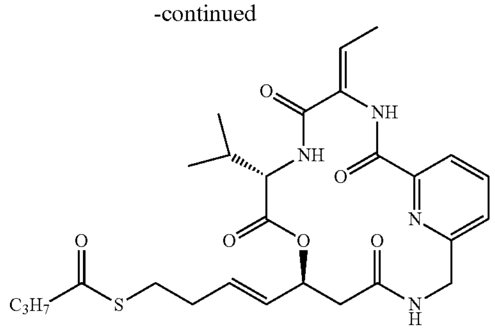

At 0° C., redistilled $NEt_3$ (0.02 ml) was added to the reactant (30 mg, 0.063 mmol) in anhydrous DCM (2 ml), stirred slightly, then butyryl chloride (0.05 ml) was added. After 7 h, The product was directly spinned anhydrous solvent by column chromatography and 29 mg pale yellow solid was obtained, and the yield was 86%. $[\alpha]^{20D}$: 6.51 (c 0.5, $CHCl_3$). 1H NMR (400 MHz, $CDCl_3$): δ 9.23 (s, 1H), 8.12 (d, J=7.8 Hz, 1H), 7.98 (t, J=7.6 Hz, 1H), 7.49 (d, J=7.6 Hz, 1H), 7.09 (d, J=7.2 Hz, 1H), 6.75 (d, J=4.4 Hz, 1H), 6.47 (d, J=10.0 Hz, 1H), 5.76-5.71 (m, 2H), 5.53 (m, 1H), 5.18 (dd, J=17.2 Hz, 8.0 Hz, 1H), 4.77-4.74 (m, 2H), 4.27 (d, J=17.2 Hz, 1H), 2.88-2.74 (m, 4H), 2.63 (m, 1H), 2.49 (t, J=7.8 Hz, 3H), 2.33-2.28 (m, 3H), 1.86-1.83 (m, 3H), 1.66-1.62 (m, 2H), 1.27-1.24 (m, 3H), 0.86 (m, 3H), 0.79 (d, J=7.6 Hz, 3H), 0.56 (d, J=7.6 Hz, 3H) ppm. $^{13}C$ NMR (125 MHz, CDCl3) δ 169.4, 169.1, 163.5, 162.3, 155.8, 148.8, 138.9, 134.7, 132.9, 132.3, 130.9, 128.9, 128.4, 127.5, 125.3, 121.5, 72.2, 71.7, 57.6, 44.5, 43.6, 41.4, 38.9, 33.9, 32.7, 31.7, 30.9, 29.9, 29.5, 28.9, 27.7, 25.8, 22.9, 19.3, 15.5, 13.8 ppm.

Example 7

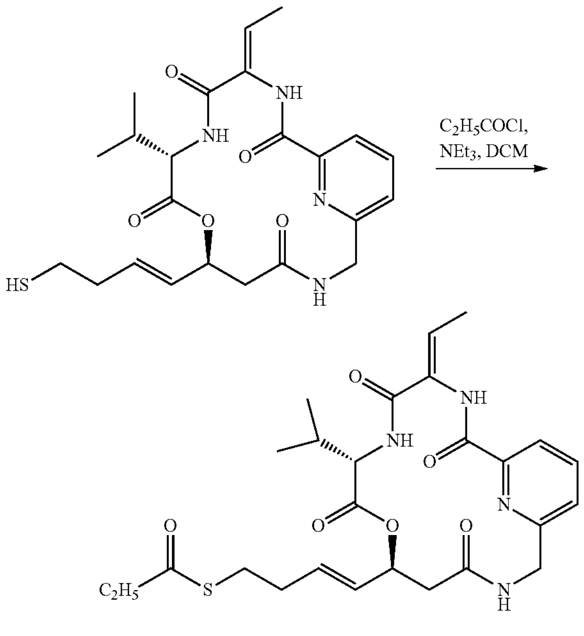

At 0° C., redistilled $NEt_3$ (0.02 ml) was added to the reactant (30 mg, 0.063 mmol) in anhydrous DCM (2 ml), stirred slightly, propionyl chloride (0.05 ml) was added. After 7 h, The product was directly spinned anhydrous solvent by column chromatography and 35 mg pale yellow solid was obtained, and the yield was 88%. $[\alpha]^{20}$D: 5.50 (c 0.3, $CHCl_3$). $^1H$ NMR (400 MHz, $CDCl_3$): δ 9.25 (s, 1H), 8.14 (d, J=7.8 Hz, 1H), 7.99 (t, J=7.6 Hz, 1H), 7.48 (d, J=7.6 Hz, 1H), 7.08 (d, J=7.2 Hz, 1H), 6.77 (d, J=4.4 Hz, 1H), 6.48 (d, J=10.0 Hz, 1H), 5.75-5.72 (m, 2H), 5.55 (m, 1H), 5.19 (dd, J=17.2 Hz, 8.0 Hz, 1H), 4.78-4.75 (m, 2H), 4.28 (d, J=17.2 Hz, 1H), 2.89-2.75 (m, 4H), 2.65 (m, 1H), 2.48 (t, J=7.8 Hz, 3H), 2.35-2.29 (m, 3H), 1.88-1.85 (m, 3H), 1.66 (m, 2H), 0.86 (m, 3H), 0.77 (d, J=7.6 Hz, 3H), 0.57 (d, J=7.6 Hz, 3H) ppm. $^{13}C$ NMR (125 MHz, $CDCl_3$) δ 169.6, 169.2, 163.3, 162.2, 155.9, 148.9, 138.8, 134.8, 132.9, 132.2, 130.8, 128.9, 128.5, 127.6, 125.5, 121.6, 72.3, 71.8, 57.8, 44.6, 43.7, 41.5, 38.8, 33.9, 32.8, 31.8, 30.8, 29.9, 29.6, 28.9, 27.8, 25.9, 22.9, 19.5, 14.8 ppm.

Example 8

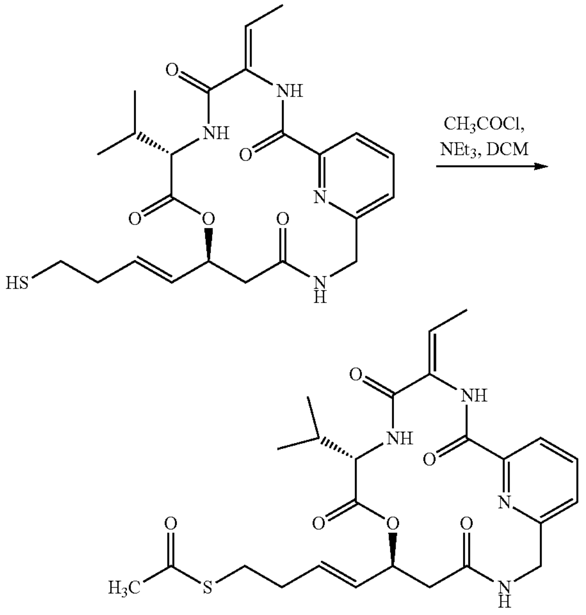

At 0° C., redistilled $NEt_3$ (0.02 ml) was added to the reactant (30 mg, 0.063 mmol) in anhydrous DCM (2 ml), stirred slightly, acetyl chloride (0.05 ml) was added. After 7 h, the product was directly spinned anhydrous solvent by column chromatography and 33 mg pale yellow solid was obtained, and the yield was 85%. [α]20D: 4.66 (c 0.6, CHCl3). 1H NMR (400 MHz, CDCl3): δ 9.26 (s, 1H), 8.15 (d, J=7.8 Hz, 1H), 7.98 (t, J=7.6 Hz, 1H), 7.49 (d, J=7.6 Hz, 1H), 7.09 (d, J=7.2 Hz, 1H), 6.79 (d, J=4.4 Hz, 1H), 6.47 (d, J=10.0 Hz, 1H), 5.73-5.70 (m, 2H), 5.53 (m, 1H), 5.18 (dd, J=17.2 Hz, 8.0 Hz, 1H), 4.77 (m, 2H), 4.28 (d, J=17.2 Hz, 1H), 2.88-2.78 (m, 4H), 2.67 (m, 1H), 2.49 (t, J=7.8 Hz, 3H), 2.36-2.33 (m, 3H), 1.89-1.86 (m, 3H), 0.88 (m, 3H), 0.78 (d, J=7.6 Hz, 3H), 0.58 (d, J=7.6 Hz, 3H) ppm. 13C NMR (125 MHz, CDCl3) δ 169.8, 169.3, 163.5, 162.5, 155.8, 148.8, 138.7, 134.7, 132.8, 132.3, 130.9, 128.8, 128.7, 127.7, 125.6, 121.7, 72.5, 71.9, 57.9, 44.7, 43.9, 41.6, 38.9, 33.8, 32.9, 31.9, 30.9, 29.8, 29.5, 28.8, 27.7, 15.0 ppm.

Example 9

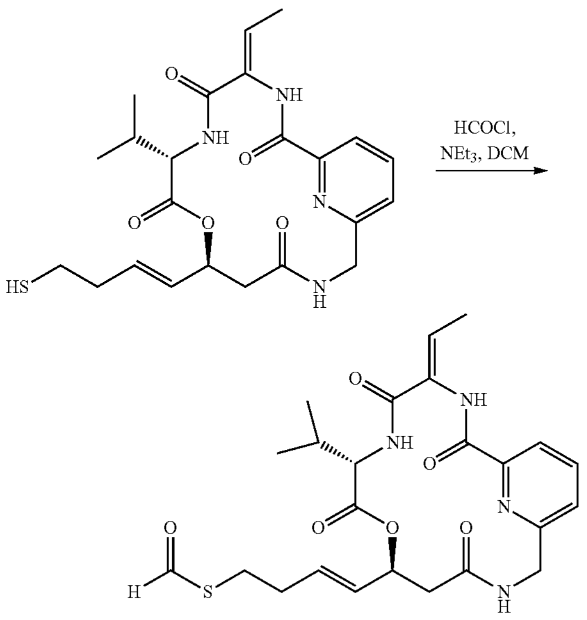

At 0° C., redistilled $NEt_3$ (0.02 ml) was added to the reactant (30 mg, 0.063 mmol) in anhydrous DCM (2 ml), stirred slightly, methanesulfonyl chloride (0.02 ml) was added. After 7 h, the product was directly spinned anhydrous solvent by column chromatography and 26 mg pale yellow solid was obtained, and the yield was 75%. $[\alpha]^{20}D$: 1.96 (c 0.1, CHCl3). $^1H$ NMR (400 MHz, $CDCl_3$): δ 9.63 (s, 1H), 9.23 (s, 1H), 8.16 (d, J=7.6 Hz, 1H), 7.88 (t, J=7.6 Hz, 1H), 7.42 (d, J=7.6 Hz, 1H), 7.07 (dd, J=14.4 Hz, J=7.2 Hz, 1H), 6.56 (dd, J=7.6 Hz, J=3.6 Hz, 1H), 6.48 (d, J=8 Hz, 1H), 5.73 (m, 2H), 5.52 (dd, J=15.6 Hz, J=6.8 Hz, 1H), 5.12 (m, 1H), 4.76 (dd, J=10 Hz, J=3.6 Hz, 1H), 4.33 (m, 1H), 2.72 (m, 2H), 2.53 (m, 2H), 2.34-2.29 (m, 3H), 1.38 (t, J=7.6 Hz, 1H), 0.82 (d, J=6.8 Hz, 3H), 0.62 (d, J=6.8 Hz, 3H) ppm. $^{13}C$ NMR (125 MHz, $CDCl_3$) δ 176.5, 169.8, 169.4, 163.6, 162.6, 155.7, 148.8, 138.5, 134.7, 132.5, 132.3, 130.9, 128.8, 127.8, 125.6, 121.8, 72.5, 71.7, 56.9, 44.8, 43.6, 41.5, 36.0, 30.8, 23.7, 18.9, 16.5, 14.6 ppm.

Example 10

10.1

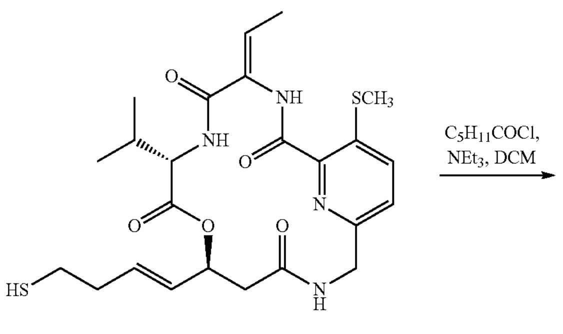

-continued

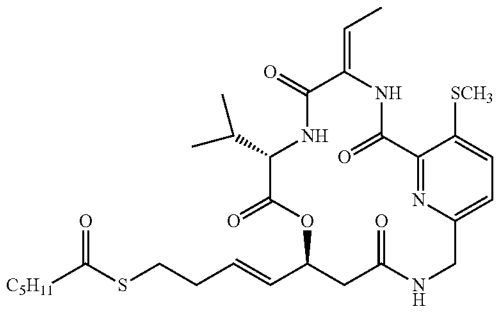

The Fmoc-L-Pra (0.976 g, 3.00 mmol), EDCI (584 mg, 3.05 mmol) and DMAP (25 mg, 0.203 mmol) was dissolved in anhydrous dichloromethane (15 mL), DIPEA (0.50 mL, 3.05 mmol) and the alcohol (526 mg, 1.02 mmol) was added at 0° C., was stirred for 12 h at room temperature, and added diluted with methylene chloride. The reaction solution was washed with sodium bicarbonate solution (50 mL×3). The organic phase was washed with saturated brine, and dried over anhydrous sodium sulfate, concentrated and the residue was purified by silica gel column chromatography to give a pale yellow solid compound (716 mg, 85%). $^1H$ NMR (400 MHz, $CDCl_3$): δ 7.77 (d, J=7.6 Hz, 2H), 7.61 (m, 2H), 7.42-7.32 (m 19H), 5.85-5.78 (m, 1H), 5.68 (dd, J=13.6, 7.2 Hz, 1H), 5.55 (dd, J=15.2, 7.2 Hz, 1H), 5.35 (d, J=8.8 Hz, 1H), 4.37 (t, J=6.8 Hz, 2H), 4.28 (dd, J=9.2, 4.4 Hz, 1H), 4.25 (t, J=7.2, 1H), 4.18 (t, J=8.4 Hz, 2H), 2.89 (t, J=7.2 Hz, 2H), 2.73 (dd, J=15.6, 7.6 Hz, 1H), 2.61 (dd, J=15.6, 5.6 Hz, 1H), 2.55 (t, J=7.2 Hz, 2H), 2.28 (dt, J=13.6, 6.8 Hz, 2H), 2.19 (m, 1H), 1.67 (m, 2H), 0.90-0.85 (m, 4H), 0.03 (s, 9H) ppm.

10.2

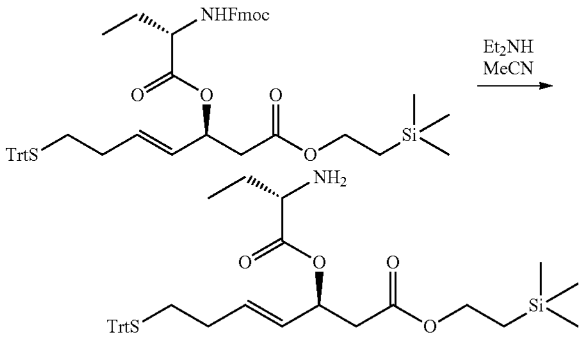

The reaction (660 mg, 0.80 mmol) was dissolved in acetonitrile (8 mL), diethylamine (0.25 mL, 2.44 mmol) was added and stirred for 2 h, decompressed and removed acetonitrile. The residue was purified by silica gel column chromatography and 463 mg anhydrous oil was obtained. The yield was 96%. $^1H$ NMR (400 MHz, CDCl3): δ 7.41-7.39 (m, 6H), 7.29-7.24 (m, 6H), 7.21-7.18 (m, 3H), 5.69-5.57 (m, 2H), 5.37 (dd, J=15.4 Hz, 7.4 Hz, 1H), 4.15-4.09 (m, 2H), 3.23 (d, J=4.8 Hz, 1H), 2.65 (dd, J=15.6 Hz, 8.4 Hz, 1H), 2.54 (dd, J=15.6 Hz, 5.2 Hz, 1H), 2.19-2.16 (m, 2H), 2.07-1.98 (m, 2H), 1.97-1.93 (m, 1H), 0.95 (m, 1H), 0.82 (d, J=6.8 Hz, 3H), 0.03 (s, 9H) ppm.

10.3

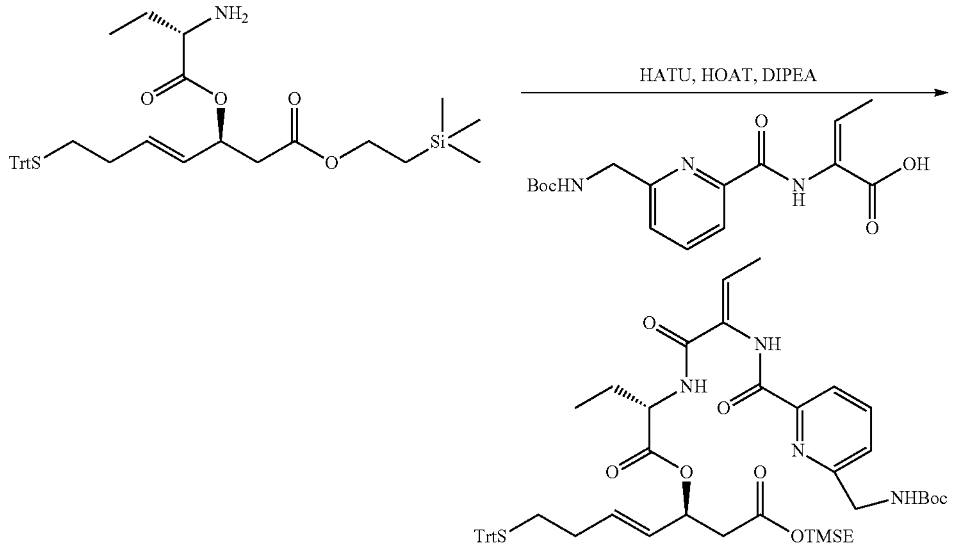

At 0° C., DIPEA (0.7 ml), the product (610 mg) of Example 1.5, HATU (760 mg), HOAT (326 mg) were added sequentially to the reactant (603 mg, 1 mmol) in DCM solution (10 ml), And raised to room temperature with stirring. After 8 h, the reaction was washed with saturated sodium bicarbonate solution, dilute hydrochloric acid solution, saturated sodium chloride solution, dried over anhydrous sodium sulfate. The product was filtered and spinned anhydrous by column chromatography and 739 mg white flocculent solid solid was obtained. The yield was 93%. $^1$H NMR (400 MHz, $CDCl_3$): δ 9.36 (s, 1H), 8.11 (d, J=7.6 Hz, 1H), 7.85 (t, J=7.6 Hz, 1H), 7.47 (d, J=7.6 Hz, 1H), 7.39-7.18 (m, 12H), 6.68-6.63 (m, 2H), 5.66-5.60 (m, 2H), 5.47 (s, 1H), 5.38-5.32 (m, 1H), 4.61 (dd, J=8.8 Hz, 4 Hz, 1H), 4.51 (d, J=4.2 Hz, 2H), 4.16-4.11 (m, 3H), 2.67 (dd, J=15.6 Hz, 7.6 Hz, 1H), 2.53 (dd, J=15.6 Hz, 5.6 Hz, 1H), 2.19-2.15 (m, 3H), 2.05 (t, J=6.8 Hz, 4H), 1.83 (d, J=7.2 Hz, 3H), 1.49 (s, 9H), 1.27 (t, J=6.8 Hz, 2H), 0.95-0.91 (m, 3H), 0.82 (d, J=6.8 Hz, 3H), 0.02 (s, 9H) ppm. $^{13}$C NMR (125 MHz, $CDCl_3$) δ 171.1, 170.8, 169.6, 164.2, 162.7, 157.4, 155.9, 148.6, 144.7, 138.4, 133.9, 129.7, 129.4, 129.0, 127.6, 126.5, 124.6, 121.1, 79.7, 71.8, 66.5, 63.0, 60.3, 57.0, 45.6, 39.5, 31.5, 31.2, 31.0, 28.3, 20.9, 18.8, 17.5, 17.2, 14.1, 0.9, −1.5, −1.6 ppm.

10.4

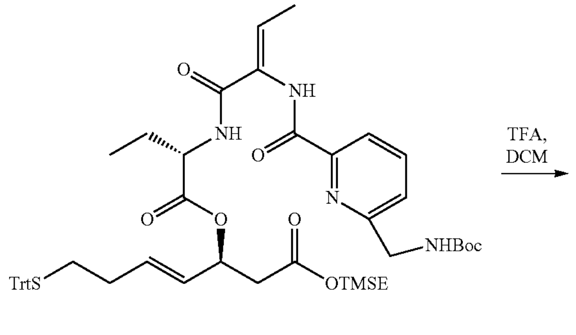

-continued

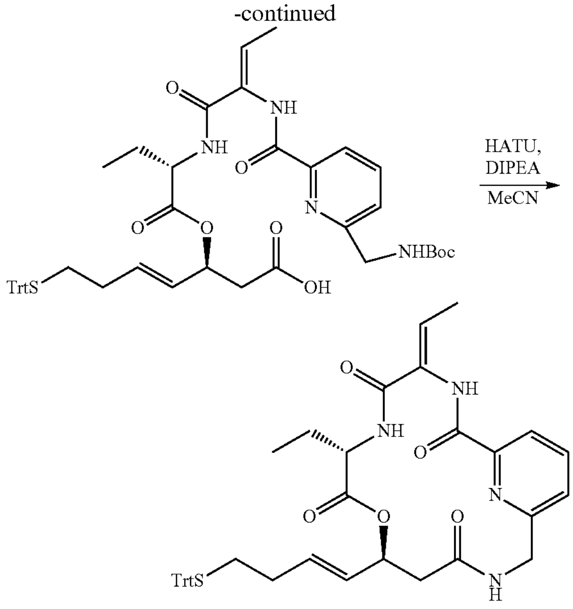

Tetrabutylammonium fluoride in tetrahydrofuran solution (1 mol/l, 2.3 ml) was added to the reaction (723 mg, 0.90 mmol) in redistilled THF (5 ml). After 3 h, the reaction was immediately spinned anhydrous by column chromatography to obtain a white solid. DCM solution (25 ml) of the resulting resultant was added trifluoroacetic acid (6 ml). After 5 h, spinned and removed DCM, the residue was added toluene (8 ml). Without further treatment, a brown viscous material was obtained after pumped organic solvent with oil pump. Chromatography pure acetonitrile (200 ml) obtained above was dissolved, slowly dropped in HATU (3 g), DIPEA (4 ml) of HPLC grade acetonitrile (550 ml). After 24 h, spinned anhydrous solvents, the product was diluted with ethyl acetate (20 ml) and then washed with saturated sodium bicarbonate solution, dilute hydrochloric acid solution, saturated sodium chloride solution and dried over anhydrous sodium sulfate. The product was filtered and spinned anhydrous by column chromatography and 537 mg pale yellow solid was obtained. The yield was 85%. $^{1}$H NMR (400 MHz, $CDCl_3$): δ 9.17 (s, 1H), 8.10 (d, J=7.6 Hz, 1H), 7.87 (t, J=7.6 Hz, 1H), 7.37-7.16 (m, 15H), 7.07 (q, J=7.2 Hz, 1H), 6.67 (d, J=4.4 Hz, 1H), 6.43 (d, J=10.4 Hz, 1H), 5.62-5.56 (m, 2H), 5.39-5.34 (m, 1H), 5.06 (dd, J=17.2 Hz, 8 Hz, 1H), 4.74 (dd, J=6.4 Hz, 3.6 Hz, 1H), 4.19-4.08 (m, 2H), 2.69-2.64 (m, 2H), 2.30-2.27 (m, 1H), 2.21-2.17 (m, 2H), 1.84 (d, J=7.2 Hz, 3H), 0.79 (d, J=6.8 Hz, 3H), 0.59 (d, J=6.8 Hz, 3H) ppm. $^{13}$C NMR (125 MHz, DMSO) δ 133.64, 132.05, 131.39, 126.08, 124.66, 118.36, 111.05, 107.13, 100.97, 97.27, 95.22, 91.96, 90.37, 90.32, 89.54, 89.11, 87.45, 83.79, 39.76, 39.50, 39.25, 34.06, 29.13, 22.85, 19.48 ppm.

10.5

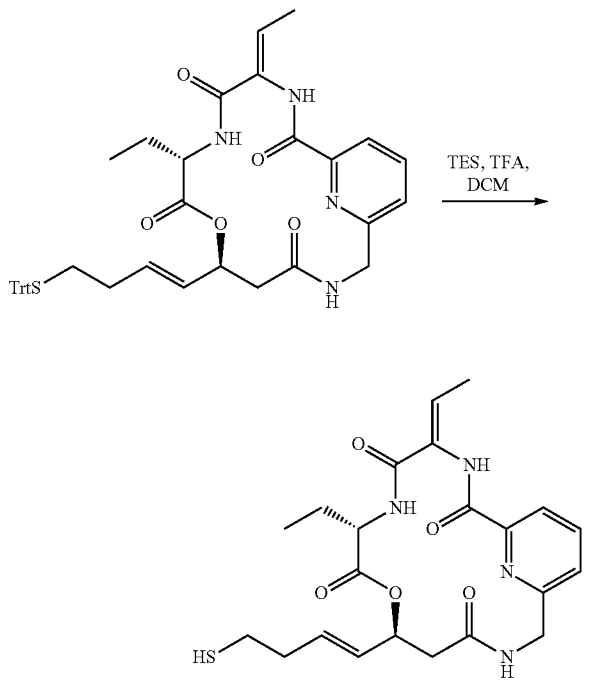

At 0° C., TES (0.1 ml), TFA (0.65 ml) were sequentially added to the reactants (150 mg, 0.21 mmol) in anhydrous DCM solution (5 ml). 15 min later, the product was directly spinned anhydrous solvent by column chromatography and 63 mg yellow solid was obtained, and the yield was 63%. [α]$^{20}$D: 6.13 (c 0.5, CHCl3). $^{1}$H NMR (400 MHz, CDCl3): δ 8.18 (d, J=7.6 Hz, 1H), 7.89 (t, J=7.6 Hz, 1H), 7.45 (d, J=7.6 Hz, 1H), 7.06 (dd, J=14.4 Hz J=7.2 Hz, 1H), 6.58 (dd, J=7.6 Hz, J=3.6 Hz, 1H), 6.45 (d, J=8 Hz, 1H), 5.74-5.64 (m, 2H), 5.50 (dd, J=15.6 Hz, J=6.8 Hz, 1H), 5.10 (m, 1H), 4.74 (dd, J=10 Hz, J=3.6 Hz, 1H), 4.34-4.28 (m, 1H), 2.74-2.69 (m, 2H), 2.56-2.50 (m, 2H), 2.34-2.29 (m, 3H), 1.36 (t, J=7.6 Hz, 1H), 0.80 (d, J=6.8 Hz, 3H), 0.6 (d, J=6.8 Hz, 3H) ppm. $^{13}$C NMR (125 MHz, $CDCl_3$) δ 169.6, 168.9, 163.6, 162.9, 155.7, 148.6, 138.3, 134.7, 132.4, 128.6, 127.0, 124.9, 121.4, 77.2, 76.9, 76.7, 71.9, 56.9, 43.3, 41.0, 36.0, 30.8, 23.7, 18.9, 16.5, 14.6 ppm.

Example 11

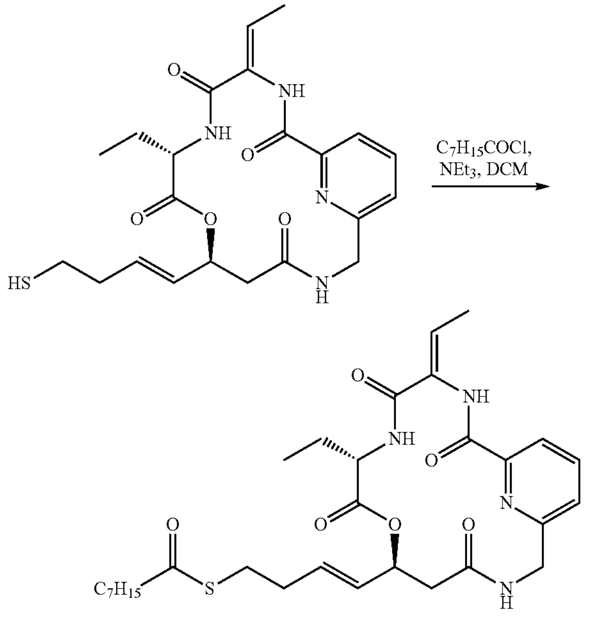

At 0° C., redistilled $NEt_3$ (0.04 ml) was added to the reactant (60 mg, 0.126 mmol) in anhydrous DCM (5 ml), stirred slightly, then added caprylate chloride (0.1 ml). After 7 h, The product was directly spinned anhydrous solvent by column chromatography and 60 mg pale yellow solid was obtained, and the yield was 80%. [α]$^{20}$D: 3.71 (c 0.5, $CHCl_3$). 1H NMR (400 MHz, $CDCl_3$): δ 9.21 (s, 1H), 8.10 (d, J=7.6 Hz, 1H), 7.91 (t, J=7.6 Hz, 1H), 7.44 (d, J=7.6 Hz, 1H), 7.06 (m, J=7.2 Hz, 1H), 6.70 (d, J=4.4 Hz, 1H), 6.46 (d, J=10 Hz, 1H), 5.70-5.64 (m, 2H), 5.59-5.46 (m, 1H), 5.13 (dd, J=17.2 Hz, 8 Hz, 1H), 4.73-4.70 (m, 2H), 4.27 (d, J=J=17.2 Hz, 1H), 2.85-2.71 (m, 4H), 2.62-2.61 (m, 1H), 2.49 (t, J=7.6 Hz, 3H), 2.29-2.23 (m, 3H), 1.84-1.81 (m, 3H), 1.61-1.58 (m, 2H), 1.24 (s, 11H), 0.86-0.57 (m, 7H), 0.53 (d, J=7.6 Hz, 3H) ppm. $^{13}$C NMR (125 MHz, $CDCl_3$) δ 199.5, 169.6, 169.1, 167.6, 165.7, 163.7, 162.3, 155.8, 148.6, 138.5, 134.7, 132.5, 132.2, 130.8, 128.7, 128.2, 127.2, 124.9, 121.3, 77.2, 77.0, 76.7, 72.0, 71.6, 56.9, 44.0, 43.2, 40.8, 38.5, 33.7, 32.1, 31.5, 30.8, 29.6, 29.0, 28.8, 28.8, 27.7, 27.6, 25.5, 24.7, 22.5, 19.0, 18.9, 16.4, 14.6, 13.9 ppm.

Example 12

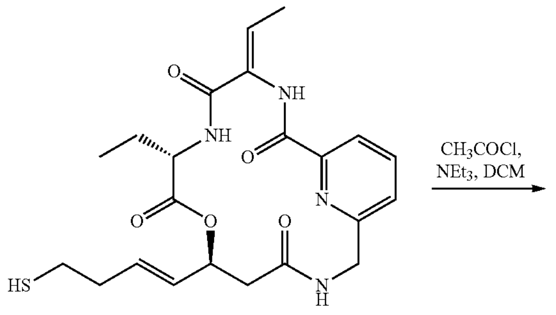

-continued

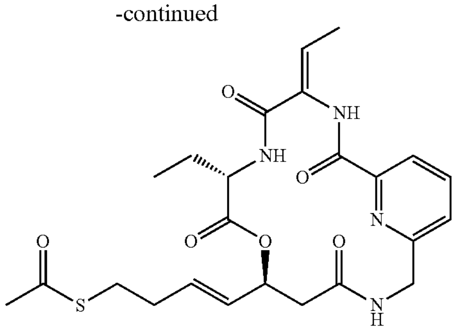

At 0° C., redistilled $NEt_3$ (0.04 ml) was added to the reactant (60 mg, 0.126 mmol) in anhydrous DCM (5 ml), stirred slightly, then added caprylate chloride (0.1 ml). After 7 h, The product was directly spinned anhydrous solvent by column chromatography and 60 mg yellow solid was obtained, and the yield was 80%. $[\alpha]^{20}D$: 3.71 (c 0.5, $CHCl_3$). 1'H NMR (400 MHz, $CDCl_3$): δ 9.21 (s, 1H), 8.10 (d, J=7.6 Hz, 1H), 7.91 (t, J=7.6 Hz, 1H), 7.44 (d, J=7.6 Hz, 1H), 7.06 (m, J=7.2 Hz, 1H), 6.70 (d, J=4.4 Hz, 1H), 6.46 (d, J=10 Hz, 1H), 5.70-5.64 (m, 2H), 5.59-5.46 (m, 1H), 5.13 (dd, J=17.2 Hz, 8 Hz, 1H), 4.73-4.70 (m, 2H), 4.27 (d, J=J=17.2 Hz, 1H), 2.85-2.71 (m, 4H), 2.62-2.61 (m, 1H), 2.49 (t, J=7.6 Hz, 3H), 2.29-2.23 (m, 3H), 1.84-1.81 (m, 3H), 1.61-1.58 (m, 2H), 1.24 (s, 11H), 0.86-0.57 (m, 7H), 0.53 (d, J=7.6 Hz, 3H) ppm. $^{13}C$ NMR (125 MHz, $CDCl_3$) δ 199.5, 169.6, 169.1, 167.6, 165.7, 163.7, 162.3, 155.8, 148.6, 138.5, 134.7, 132.5, 132.2, 130.8, 128.7, 128.2, 127.2, 124.9, 121.3, 77.2, 77.0, 76.7, 72.0, 71.6, 56.9, 44.0, 43.2, 40.8, 38.5, 33.7, 32.1, 31.5, 30.8, 29.6, 29.0, 28.8, 28.8, 27.7, 27.6, 25.5, 24.7, 22.5, 19.0, 18.9, 16.4, 14.6, 13.9 ppm.

Example 13

13.1

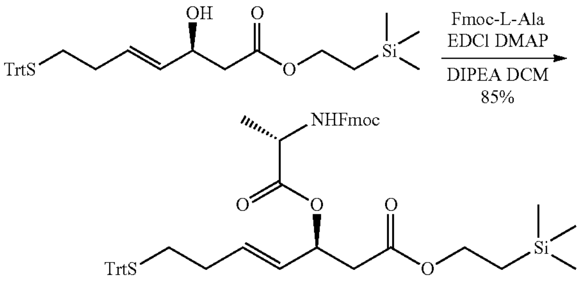

The Fmoc-L-Pra (0.976 g, 3.05 mmol), EDCI (584 mg, 3.045 mmol) and DMAP (25 mg, 0.203 mmol) was dissolved in anhydrous dichloromethane (15 mL), DIPEA (0.50 mL, 3.045 mmol) and the compound 2-23 (526 mg, 1.02 mmol) were added at 0° C., was stirred for 12 h at room temperature, and added diluted with methylene chloride. The reaction solution was washed with sodium bicarbonate solution (50 mL×3). The organic phase was washed with saturated brine, and dried over anhydrous sodium sulfate, concentrated and the residue was purified by silica gel column chromatography to give a pale yellow solid compound 2-24 (682 mg, 80%). $^1H$ NMR (400 MHz, $CDCl_3$): δ 7.76 (d, J=7.6 Hz, 2H), 7.60 (m, 2H), 7.40-7.31 (m 19H), 5.84 and 5.76 (m, 1H), 5.67 (dd, J=13.6, 7.2 Hz, 1H), 5.53 (dd, J=15.2, 7.2 Hz, 1H), 5.32 (d, J=8.8 Hz, 1H), 4.39 (t, J=6.8 Hz, 2H), 4.29 (dd, J=9.2, 4.4 Hz, 1H), 4.23 (t, J=7.2, 1H), 4.17 (t, J=8.4 Hz, 2H), 2.88 (t, J=7.2 Hz, 2H), 2.71 (dd, J=15.6, 7.6 Hz, 1H), 2.59 (dd, J=15.6, 5.6 Hz, 1H), 2.52 (t, J=7.2 Hz, 2H), 2.29 (dt, J=13.6, 6.8 Hz, 2H), 2.18 (m, 1H), 1.65 (m, 2H), 0.97-0.83 (m, 8H), 0.03 (s, 9H) ppm.

13.2

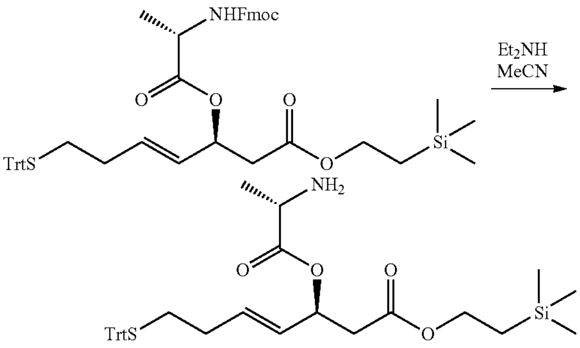

The reaction (682 mg, 0.81 mmol) was dissolved in acetonitrile (8 mL), diethylamine (0.25 mL, 2.44 mmol) was added and stirred for 2 h, decompressed and removed acetonitrile. The residue was purified by silica gel column chromatography and 477 mg anhydrous oil was obtained. The yield was 95%. $^1H$ NMR (400 MHz, $CDCl_3$): δ 7.40-7.38 (m, 6H), 7.29-7.25 (m, 6H), 7.22-7.18 (m, 3H), 5.69-5.57 (m, 2H), 5.36 (dd, J=15.4 Hz, 7.4 Hz, 1H), 4.16-4.09 (m, 2H), 3.21 (d, J=4.8 Hz, 1H), 2.64 (dd, J=15.6 Hz, 8.4 Hz, 1H), 2.53 (dd, J=15.6 Hz, 5.2 Hz, 1H), 2.19-2.15 (m, 2H), 2.07-1.98 (m, 2H), 1.97-1.93 (m, 1H), 0.98-0.93 (m, 2H), 0.92 (d, J=6.8 Hz, 3H), 0.81 (d, J=6.8 Hz, 3H), 0.03 (s, 9H) ppm.

13.3

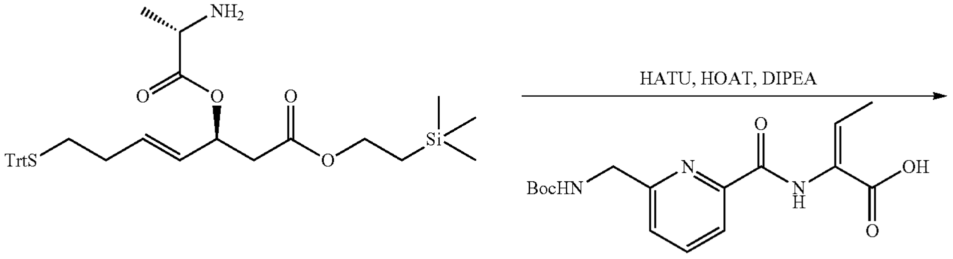

-continued

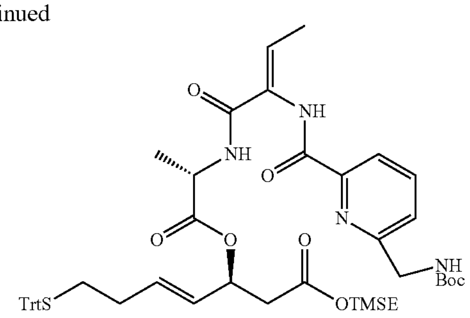

At 0° C., DIPEA (0.7 ml) the product (610 mg) of Example 1.5, HATU (760 mg), HOAT (326 mg) were sequentially added to the reactant (336 mg, 1 mmol) in DCM solution (10 ml), and raised to room temperature with stirring. After 8 h, the reaction was washed with saturated sodium bicarbonate solution, dilute hydrochloric acid solution, saturated sodium chloride solution, dried over anhydrous sodium sulfate. The product was filtered and spinned anhydrous by column chromatography and 750 mg white flocculent solid solid was obtained. The yield was 92%. $^{1}$H NMR (400 MHz, $CDCl_3$): δ 9.41 (s, 1H), 8.10 (d, J=7.6 Hz, 1H), 7.84 (t, J=7.6 Hz, 1H), 7.48 (d, J=7.6 Hz, 1H), 7.39-7.17 (m, 12H), 6.66-6.61 (m, 2H), 5.68-5.59 (m, 2H), 5.46 (s, 1H), 5.38-5.32 (m, 1H), 4.59 (dd, J=8.8 Hz, 4 Hz, 1H), 4.49 (d, J=4.2 Hz, 2H), 4.15-4.10 (m, 3H), 2.66 (dd, J=15.6 Hz, 7.6 Hz, 1H), 2.52 (dd, J=15.6 Hz, 5.6 Hz, 1H), 2.18-2.14 (m, 3H), 2.04 (t, J=6.8 Hz, 4H), 1.82 (d, J=7.2 Hz, 3H), 1.46 (s, 9H), 1.25 (t, J=6.8 Hz, 2H), 0.97-0.90 (m, 5H), 0.80 (d, J=6.8 Hz, 3H), 0.02 (s, 9H) ppm. $^{13}$C NMR (125 MHz, $CDCl_3$) δ 171.0, 170.7, 169.5, 164.3, 162.6, 157.3, 155.9, 148.5, 144.7, 138.2, 133.9, 129.6, 129.4, 129.0, 127.7, 127.6, 126.5, 124.6, 121.1, 79.7, 77.2, 77.0, 76.7, 71.8, 66.5, 63.0, 60.3, 57.0, 45.6, 39.5, 31.5, 31.2, 31.0, 28.3, 20.9, 18.8, 17.5, 17.2, 14.1, 13.8, 0.9, −1.5, −1.6 ppm.

13.4

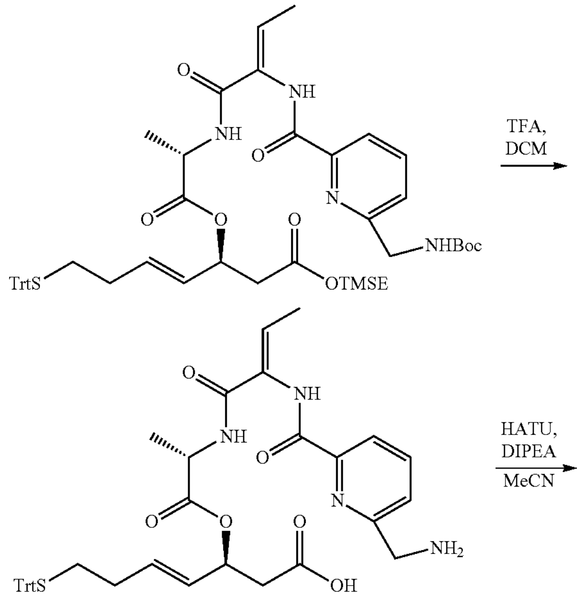

-continued

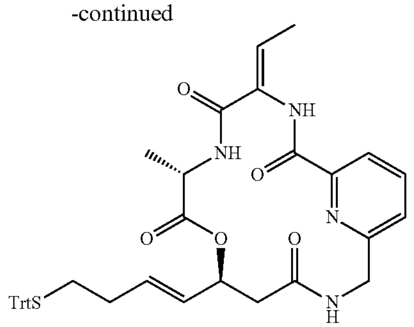

Tetrabutylammonium fluoride in tetrahydrofuran solution (1 mol/l, 2.3 ml) was added to the reaction (750 mg, 0.92 mmol) in redistilled THF (5 ml). After 3 h, the reaction was immediately spinned anhydrous by column chromatography to obtain a white solid.

Trifluoroacetic acid (6 ml) was added to DCM solution (25 ml) of the resulting resultant. After 5 h, spinned and removed DCM, the residue was added toluene (8 ml). Without further treatment, a brown viscous material was obtained after pumped organic solvent with oil pump. Chromatography pure acetonitrile (200 ml) obtained above was dissolved, slowly dropped in HATU (3 g), DIPEA (4 ml) of HPLC grade acetonitrile (550 ml). After 24 h, spinned anhydrous solvents, the product was diluted with ethyl acetate (20 ml) and then washed with saturated sodium bicarbonate solution, dilute hydrochloric acid solution, saturated sodium chloride solution and dried over anhydrous sodium sulfate. The product was filtered and spinned anhydrous by column chromatography and 540 mg pale yellow solid was obtained. The yield was 82%. $^{1}$H NMR (400 MHz, $CDCl_3$): δ 9.17 (s, 1H), 8.10 (d, J=7.6 Hz, 1H), 7.87 (t, J=7.6 Hz, 1H), 7.37-7.16 (m, 15H), 7.07 (q, J=7.2 Hz, 1H), 6.67 (d, J=4.4 Hz, 1H), 6.43 (d, J=10.4 Hz, 1H), 5.62-5.56 (m, 2H), 5.39-5.34 (m, 1H), 5.06 (dd, J=17.2 Hz, 8 Hz, 1H), 4.74 (dd, J=6.4 Hz, 3.6 Hz, 1H), 4.19-4.08 (m, 2H), 2.69-2.64 (m, 2H), 2.30-2.27 (m, 1H), 2.21-2.17 (m, 2H), 1.84 (d, J=7.2 Hz, 3H), 0.79 (d, J=6.8 Hz, 3H), 0.59 (d, J=6.8 Hz, 3H) ppm. $^{13}$C NMR (125 MHz, DMSO) δ 133.64, 132.05, 131.39, 126.08, 124.66, 118.36, 111.05, 107.13, 100.97, 97.27, 95.22, 91.96, 90.37, 90.32, 89.54, 89.11, 87.45, 83.79, 39.76, 39.50, 39.25, 34.06, 29.13, 22.85, 19.48 ppm.

13.5

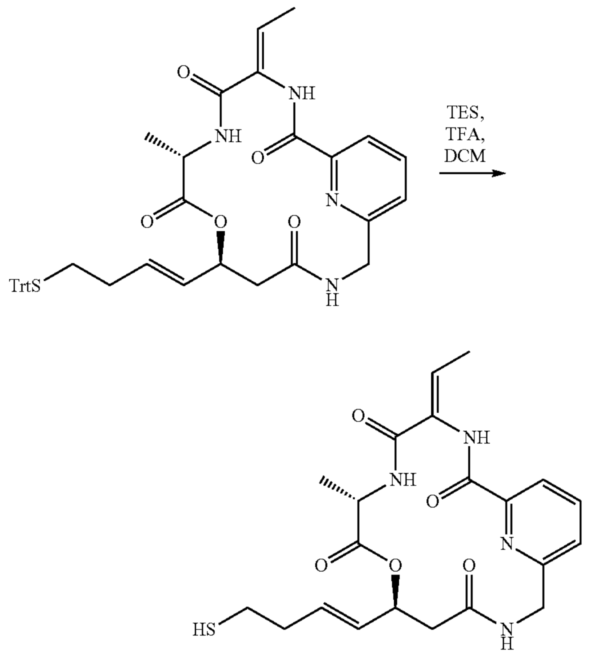

At 0° C., TES (0.1 ml), TFA (0.65 ml) were sequentially added to the reactants (150 mg, 0.21 mmol) in anhydrous DCM solution (5 ml). 15 min later, the product was directly spinned anhydrous solvent by column chromatography and 63 mg yellow solid was obtained, and the yield was 63%. $[\alpha]^{20}D$: 6.13 (c 0.5, $CHCl_3$). $^1H$ NMR (400 MHz, $CDCl_3$): δ 8.18 (d, J=7.6 Hz, 1H), 7.89 (t, J=7.6 Hz, 1H), 7.45 (d, J=7.6 Hz, 1H), 7.06 (dd, J=14.4 Hz J=7.2 Hz, 1H), 6.58 (dd, J=7.6 Hz, J=3.6 Hz, 1H), 6.45 (d, J=8 Hz, 1H), 5.74-5.64 (m, 2H), 5.50 (dd, J=15.6 Hz, J=6.8 Hz, 1H), 5.10 (m, 1H), 4.74 (dd, J=10 Hz, J=3.6 Hz, 1H), 4.34-4.28 (m, 1H), 2.74-2.69 (m, 2H), 2.56-2.50 (m, 2H), 2.34-2.29 (m, 3H), 1.36 (t, J=7.6 Hz, 1H), 0.80 (d, J=6.8 Hz, 3H), 0.6 (d, J=6.8 Hz, 3H) ppm. $^{13}C$ NMR (125 MHz, $CDCl_3$) δ 169.6, 168.9, 163.6, 162.9, 155.7, 148.6, 138.3, 134.7, 132.4, 128.6, 127.0, 124.9, 121.4, 77.2, 76.9, 76.7, 71.9, 56.9, 43.3, 41.0, 36.0, 30.8, 23.7, 18.9, 16.5, 14.6 ppm.

Example 14

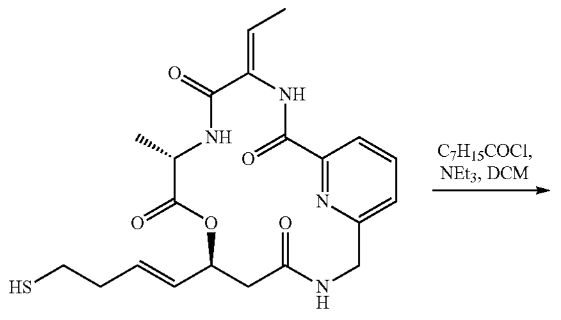

-continued

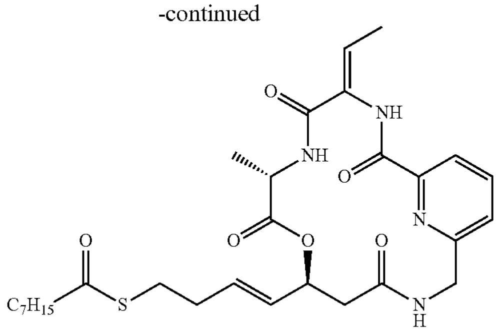

At 0° C., redistilled $NEt_3$ (0.04 ml) was added to the reactant (60 mg, 0.126 mmol) in anhydrous DCM (5 ml), stirred slightly, then added caprylate chloride (0.1 ml). After 7 h, The product was directly spinned anhydrous solvent by column chromatography and 60 mg yellow solid was obtained, and the yield was 80%. $[\alpha]^{20}D$: 3.71 (c 0.5, $CHCl_3$). 1H NMR (400 MHz, $CDCl_3$): δ 9.21 (s, 1H), 8.10 (d, J=7.6 Hz, 1H), 7.91 (t, J=7.6 Hz, 1H), 7.44 (d, J=7.6 Hz, 1H), 7.06 (m, J=7.2 Hz, 1H), 6.70 (d, J=4.4 Hz, 1H), 6.46 (d, J=10 Hz, 1H), 5.70-5.64 (m, 2H), 5.59-5.46 (m, 1H), 5.13 (dd, J=17.2 Hz, 8 Hz, 1H), 4.73-4.70 (m, 2H), 4.27 (d, J=J=17.2 Hz, 1H), 2.85-2.71 (m, 4H), 2.62-2.61 (m, 1H), 2.49 (t, J=7.6 Hz, 3H), 2.29-2.23 (m, 3H), 1.84-1.81 (m, 3H), 1.61-1.58 (m, 2H), 1.24 (s, 11H), 0.86-0.57 (m, 7H), 0.53 (d, J=7.6 Hz, 3H) ppm. $^{13}C$ NMR (125 MHz, $CDCl_3$) δ 199.5, 169.6, 169.1, 167.6, 165.7, 163.7, 162.3, 155.8, 148.6, 138.5, 134.7, 132.5, 132.2, 130.8, 128.7, 128.2, 127.2, 124.9, 121.3, 77.2, 77.0, 76.7, 72.0, 71.6, 56.9, 44.0, 43.2, 40.8, 38.5, 33.7, 32.1, 31.5, 30.8, 29.6, 29.0, 28.8, 28.8, 27.7, 27.6, 25.5, 24.7, 22.5, 19.0, 18.9, 16.4, 14.6, 13.9 ppm.

Example 15

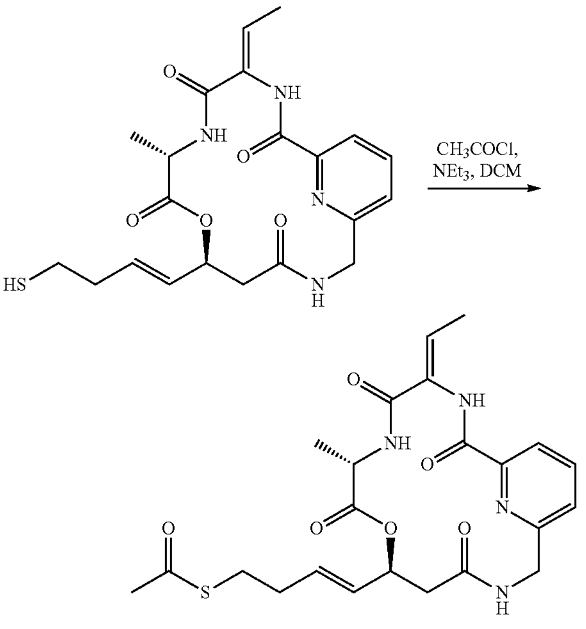

At 0° C., redistilled $NEt_3$ (0.04 ml) was added to the reactant (60 mg, 0.126 mmol) in anhydrous DCM (5 ml), stirred slightly, then added caprylate chloride (0.1 ml). After 7 h, The product was directly spinned anhydrous solvent by column chromatography and 60 mg yellow solid was obtained, and the yield was 80%. [α]$^{20}$D: 3.71 (c 0.5, $CHCl_3$). 1H NMR (400 MHz, $CDCl_3$): δ 9.21 (s, 1H), 8.10 (d, J=7.6 Hz, 1H), 7.91 (t, J=7.6 Hz, 1H), 7.44 (d, J=7.6 Hz, 1H), 7.06 (m, J=7.2 Hz, 1H), 6.70 (d, J=4.4 Hz, 1H), 6.46 (d, J=10 Hz, 1H), 5.70-5.64 (m, 2H), 5.59-5.46 (m, 1H), 5.13 (dd, J=17.2 Hz, 8 Hz, 1H), 4.73-4.70 (m, 2H), 4.27 (d, J=J=17.2 Hz, 1H), 2.85-2.71 (m, 4H), 2.62-2.61 (m, 1H), 2.49 (t, J=7.6 Hz, 3H), 2.29-2.23 (m, 3H), 1.84-1.81 (m, 3H), 1.61-1.58 (m, 2H), 1.24 (s, 11H), 0.86-0.57 (m, 7H), 0.53 (d, J=7.6 Hz, 3H) ppm. $^{13}$C NMR (125 MHz, CDCl3) δ 199.5, 169.6, 169.1, 167.6, 165.7, 163.7, 162.3, 155.8, 148.6, 138.5, 134.7, 132.5, 132.2, 130.8, 128.7, 128.2, 127.2, 124.9, 121.3, 77.2, 77.0, 76.7, 72.0, 71.6, 56.9, 44.0, 43.2, 40.8, 38.5, 33.7, 32.1, 31.5, 30.8, 29.6, 29.0, 28.8, 28.8, 27.7, 27.6, 25.5, 24.7, 22.5, 19.0, 18.9, 16.4, 14.6, 13.9 ppm.

Example 16

16.1

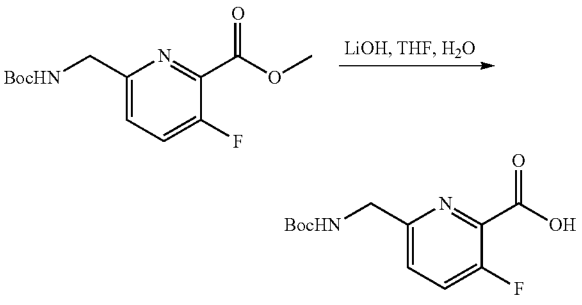

15 ml LiOH aqueous (19 mmol) solution (7.6 mmol) were added dropwise to the reactant (7.6 mmol) of 30 ml THF, then reacted 2 h at room temperature. The reaction solution was adjusted by dilute hydrochloric acid to with the pH value of 3, then 100 ml ethyl acetate was added. The organic matter was washed by water and saturated salt water. The organic layer was dried by anhydrous sodium sulfate, and the solvent evaporated to give a white flocculent solid. $^{1}$H NMR (400 MHz, $CDCl_3$): δ 8.05 (s, J=8.0 Hz, 1H), 7.85 (d, J=7.6 Hz, 1H), 7.61 (d, J=7.8 Hz, 1H), 5.55 (s, 1H), 4.48 (d, J=4.2 Hz, 1H), 1.34 (s, 9H) ppm.

16.2

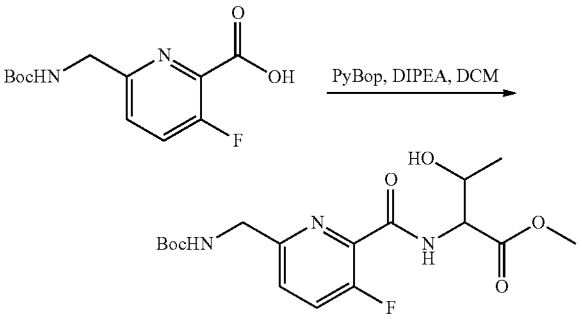

At 0° C., S2 (2.7 mmol), PyBop (4 mmol) and DIPEA (6 mmol) were added slowly to the reactant (2.7 mmol), stirred slightly, then added, and then stirred at room temperature overnight. The reaction solution was washed with saturated sodium bicarbonate solution, dilute hydrochloric acid solution, saturated sodium chloride solution. The product was dried with anhydrous sodium sulfate and spinned solvent by column chromatography and white floc was obtained. $^{1}$H NMR (400 MHz, $CDCl_3$): δ 8.64 (d, J=8.4 Hz, 1H), 8.05 (d, J=8 Hz, 1H), 7.81 (d, J=8 Hz, 1H), 5.44 (s, 1H), 4.48-4.45 (m, J=3H), 3.78 (s, 3H), 1.45 (s, 9H), 1.26 (d, J=5.6 Hz, 3H) ppm. $^{13}$C NMR (100 MHz, $CDCl_3$) δ 171.1, 164.6, 157.4, 156.0, 148.9, 137.9, 134.6, 124.2, 121.8, 121.0, 80.7, 79.8, 78.7, 70.3, 68.2, 61.1, 57.8, 52.7, 52.2, 47.7, 32.1, 28.3, 28.2, 28.1, 28.0, 22.6, 19.8 ppm.

16.3

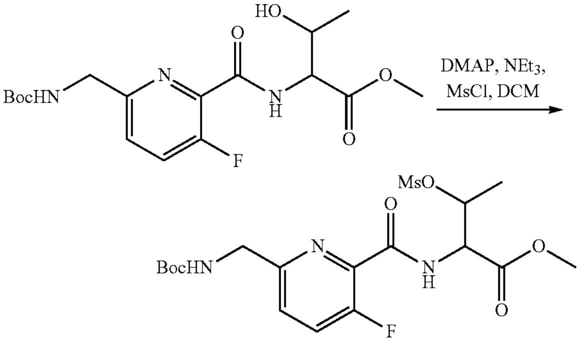

At 0° C., DMAP (0.184 mmol), $NEt_3$ (3 mmol), MsCl (2.4 mmol) were successively added to anhydrous DCM (10 ml) of the reactants (1.84 mmol), then raised to room temperature and stirred overnight. The product was spinned anhydrous, pumped with oil pump and directly put into next step.

16.4

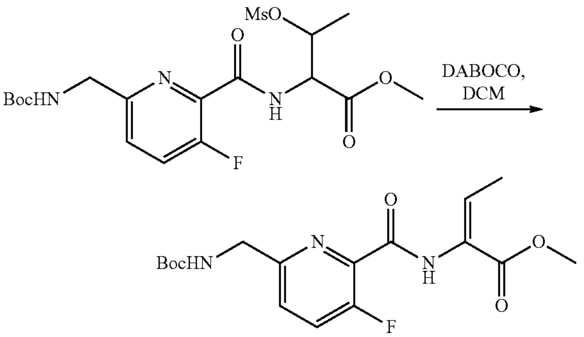

DABOCO (9.22 mmol) was added to Anhydrous DCM liquid (10 ml) obtained above and stirred 8 h at room temperature. The reaction solution was washed by saturated sodium bicarbonate solution, saturated ammonium chloride solution, saturated sodium chloride solution in sequence, and dried by anhydrous sodium sulfate. The product was filtered and spinned solvent by column chromatography and white floc was obtained. $^{1}$H NMR (400 MHz, $CDCl_3$): δ 9.38 (s, 1H), 8.01 (d, J=7.6 Hz, 1H), 7.78 (d, J=8 Hz, 1H), 7.41 (d, J=7.6 Hz, 1H), 6.86 (q, J=7.6 Hz, 1H), 5.57 (s, 1H), 4.44 (d, J=5.6 Hz, 1H), 3.74 (s, 9H), 1.80 (d, J=7.6 Hz, 3H), 1.40 (s, 9H) ppm. $^{13}$C NMR (100 MHz, $CDCl_3$) δ 164.8, 162.1, 157.4, 156.0, 148.9, 148.8, 138.1, 133.9, 126.3, 124.2, 121.7, 121.0, 79.7, 52.1, 45.9, 28.3, 14.6 ppm.

16.5

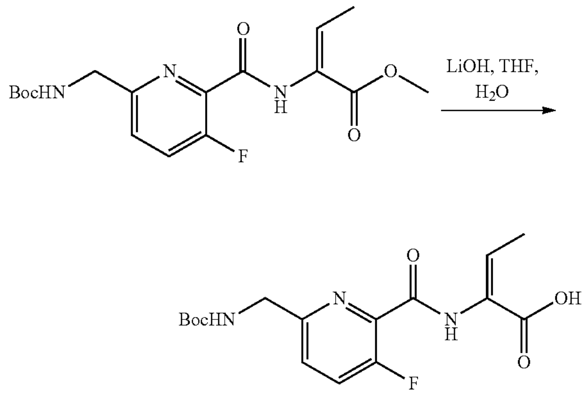

5 ml LiOH aqueous solution (3.6 mmol) were added dropwise to reactants (1.44 mmol) with THF (10 ml), then spinned anhydrous the organic phase after three hours. 10 ml water and 15 ml ethyl acetate were added to the organic phase. The aqueous phase was removed after liquid separation. Then the solution was added 15 ml ethyl acetate, adjusted the acid. Anhydrous sodium sulfate was used for the separation of organic phase after liquid separation. 453 mg solid white floc was obtained after spinned anhydrous. $^{1}$H NMR (400 MHz, $CDCl_3$): δ 9.40 (s, 1H), 8.03 (d, J=7.6 Hz, 1H), 7.80 (d, J=8.2 Hz, 1H), 6.88 (q, J=7.8 Hz, 1H), 5.58 (s, 1H), 3.76 (s, 9H), 1.83 (d, J=7.8 Hz, 3H), 1.43 (s, 9H) ppm. $^{13}$C NMR (100 MHz, $CDCl_3$) δ 165.3, 162.7, 157.8, 156.2, 149.0, 148.8, 138.3, 133.7, 126.5, 124.5, 121.9, 121.0, 52.5, 46.3, 28.5, 14.8 ppm.

16.6

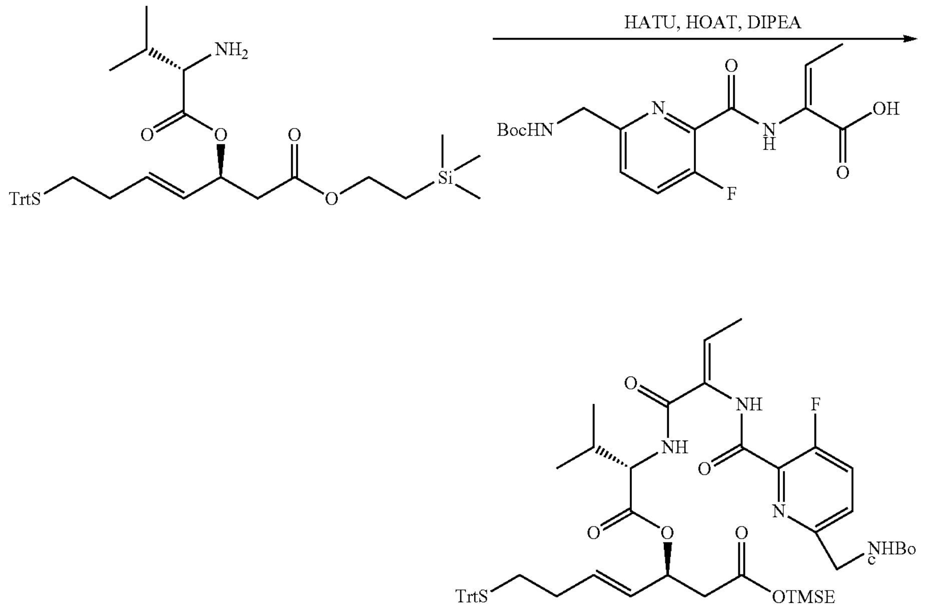

At 0° C., DIPEA (0.7 ml), carboxylic acid, HATU, HOAT were sequentially added to the reactant (1 mmol) in DCM solution (10 ml). Then raised to room temperature with stirring. After 8 h, the reaction was washed with saturated sodium bicarbonate solution, dilute hydrochloric acid solution, saturated sodium chloride solution, and dried over anhydrous sodium sulfate. The product was filtered and spinned solvent by column chromatography and white flocculent solid was obtained. $^{1}$H NMR (400 MHz, $CDCl_3$): δ 9.41 (s, 1H), 8.10 (d, J=7.6 Hz, 1H), 7.48 (d, J=7.6 Hz, 1H), 7.39-7.17 (m, 12H), 6.66-6.61 (m, 2H), 5.68-5.59 (m, 2H), 5.46 (s, 1H), 5.38-5.32 (m, 1H), 4.59 (dd, J=8.8 Hz, 4 Hz, 1H), 4.49 (d, J=4.2 Hz, 1H), 4.15-4.10 (m, 3H), 2.66 (dd, J=15.6 Hz, 7.6 Hz, 1H), 2.52 (dd, J=15.6 Hz, 5.6 Hz, 1H), 2.18-2.14 (m, 3H), 2.04 (t, J=6.8 Hz, 4H), 1.82 (d, J=7.2 Hz, 3H), 1.46 (s, 9H), 1.25 (t, J=6.8 Hz, 2H), 0.97-0.90 (m, 5H), 0.80 (d, J=6.8 Hz, 3H), 0.02 (s, 9H) ppm. $^{13}$C NMR (125 MHz, $CDCl_3$) δ 171.0, 170.7, 169.5, 164.3, 162.6, 157.3, 155.9, 148.5, 144.7, 138.2, 133.9, 129.6, 129.4, 129.0, 127.7, 127.6, 126.5, 124.6, 121.1, 79.7, 71.8, 66.5, 63.0, 60.3, 57.0, 45.6, 39.5, 31.5, 31.2, 31.0, 28.3, 20.9, 18.8, 17.5, 17.2, 14.1, 13.8, 0.9, −1.5, −1.6 ppm.

16.7

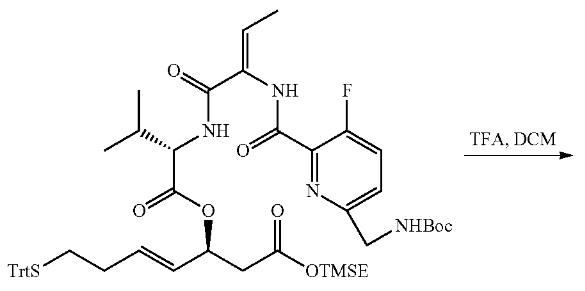

-continued 16.8

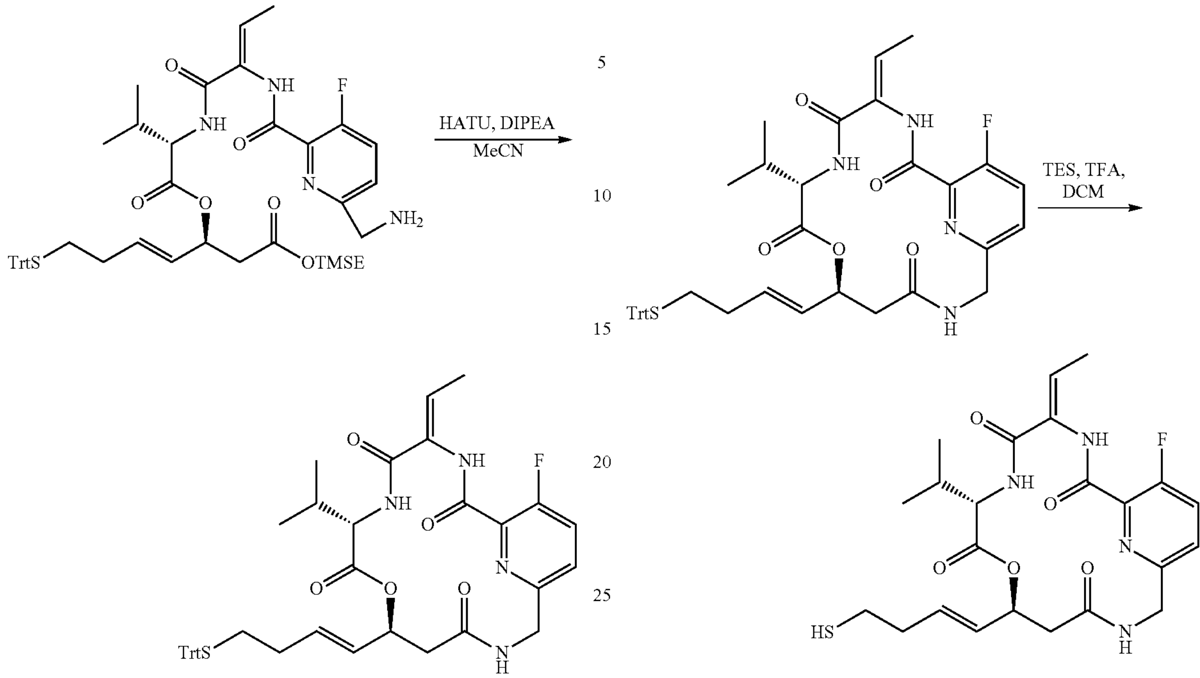

Tetrabutylammonium fluoride in tetrahydrofuran solution (1 mol/l, 2.3 ml) was added to the reaction (0.92 mmol) in redistilled THF (5 ml). After 3 h, the reaction was immediately spinned anhydrous by column chromatography to obtain a white solid.

Trifluoroacetic acid (6 ml) was added to DCM solution (25 ml) of the resulting resultant. After 5 h, spinned and removed DCM, toluene (8 ml) was added to the residue. Without further treatment, a brown viscous material was obtained after pumped organic solvent with oil pump. Chromatography pure acetonitrile (200 ml) obtained above was dissolved, slowly dropped in HATU (3 g), DIPEA (4 ml) of HPLC grade acetonitrile (550 ml). After 24 h, spinned anhydrous solvents, the product was diluted with ethyl acetate (20 ml) and then washed with saturated sodium bicarbonate solution, dilute hydrochloric acid solution, saturated sodium chloride solution and dried over anhydrous sodium sulfate. The product was filtered and spinned anhydrous by column chromatography and 540 mg pale yellow solid was obtained. The yield was 82%. $^{1}$H NMR (400 MHz, $CDCl_3$): δ 9.17 (s, 1H), 8.10 (d, J=7.6 Hz, 1H), 7.87 (d, J=7.6 Hz, 1H), 7.37-7.16 (m, 15H), 7.07 (q, J=7.2 Hz, 1H), 6.67 (d, J=4.4 Hz, 1H), 5.62-5.56 (m, 2H), 5.39-5.34 (m, 1H), 5.06 (dd, J=17.2 Hz, 8 Hz, 1H), 4.74 (dd, J=6.4 Hz, 3.6 Hz, 1H), 4.19-4.08 (m, 2H), 2.69-2.64 (m, 2H), 2.30-2.27 (m, 1H), 2.21-2.17 (m, 2H), 1.84 (d, J=7.2 Hz, 3H), 0.79 (d, J=6.8 Hz, 3H), 0.59 (d, J=6.8 Hz, 3H) ppm. $^{13}$C NMR (125 MHz, DMSO) δ 133.6, 132.0, 131.3, 126.1, 124.7, 118.4, 111.1, 107.1, 101.0, 97.3, 95.2, 92.0, 90.4, 90.3, 89.5, 89.1, 87.5, 83.8, 39.8, 39.5, 39.3, 34.1, 29.1, 22.9, 19.5 ppm.

At 0° C., TES (0.1 ml), TFA (0.65 ml) were sequentially added to the reactants (0.21 mmol) in anhydrous DCM solution (5 ml). 15 min later, the product was directly spinned anhydrous solvent by column chromatography and yellow solid was obtained. $[\alpha]^{20}_{D}$: 6.13 (c 0.5, $CHCl_3$). $^{1}$H NMR (400 MHz, $CDCl_3$): δ 8.18 (d, J=7.6 Hz, 1H), 7.89 (d, J=7.6 Hz, 1H), 7.06 (dd, J=14.4 Hz J=7.2 Hz, 1H), 6.58 (dd, J=7.6 Hz, J=3.6 Hz, 1H), 6.45 (d, J=8 Hz, 1H), 5.74-5.64 (m, 2H), 5.50 (dd, J=15.6 Hz, J=6.8 Hz, 1H), 5.10 (m, 1H), 4.74 (dd, J=10 Hz, J=3.6 Hz, 1H), 4.34-4.28 (m, 1H), 2.74-2.69 (m, 2H), 2.56-2.50 (m, 2H), 2.34-2.29 (m, 3H), 1.36 (t, J=7.6 Hz, 1H), 0.80 (d, J=6.8 Hz, 3H), 0.6 (d, J=6.8 Hz, 3H) ppm. $^{13}$C NMR (125 MHz, $CDCl_3$) δ 169.6, 168.9, 163.6, 162.9, 155.7, 148.6, 138.3, 134.7, 132.4, 128.6, 127.0, 124.9, 121.4, 71.9, 56.9, 43.3, 41.0, 36.0, 30.8, 23.7, 18.9, 16.5, 14.6 ppm.

Example 17

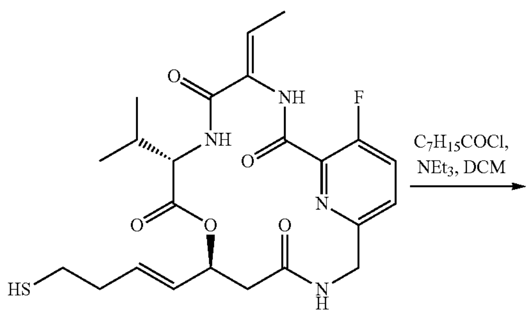

-continued

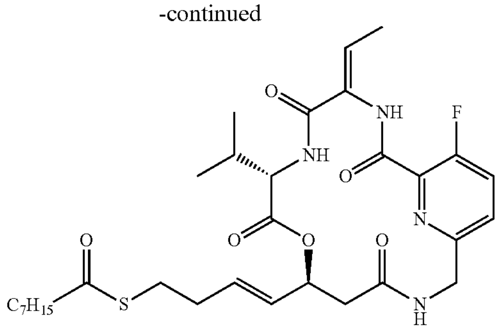

At 0° C., redistilled $NEt_3$ (0.04 ml) was added to the reactant (0.126 mmol) in anhydrous DCM (5 ml), stirred slightly, then added caprylate chloride (0.1 ml). After 7 h, The product was directly spinned anhydrous solvent by column chromatography and yellow solid was obtained. $[\alpha]^{20}_{D}$: 3.71 (c 0.5, $CHCl_3$). $^1H$ NMR (400 MHz, $CDCl_3$): δ 9.21 (s, 1H), 8.10 (d, J=7.6 Hz, 1H), 7.91 (d, J=7.6 Hz, 1H), 7.06 (m, J=7.2 Hz, 1H), 6.70 (d, J=4.4 Hz, 1H), 5.70-5.64 (m, 2H), 5.59-5.46 (m, 1H), 5.13 (dd, J=17.2 Hz, 8 Hz, 1H), 4.73-4.70 (m, 2H), 4.27 (d, J=J=17.2 Hz, 1H), 2.85-2.71 (m, 4H), 2.62-2.61 (m, 1H), 2.49 (t, J=7.6 Hz, 3H), 2.29-2.23 (m, 3H), 1.84-1.81 (m, 3H), 1.61-1.58 (m, 2H), 1.24 (s, 11H), 0.86-0.57 (m, 7H), 0.53 (d, J=7.6 Hz, 3H) ppm. $^{13}C$ NMR (125 MHz, $CDCl_3$) δ169.6, 169.1, 167.6, 165.7, 163.7, 162.3, 155.8, 148.6, 138.5, 134.7, 132.5, 132.2, 130.8, 128.7, 128.2, 127.2, 124.9, 121.3, 72.0, 71.6, 56.9, 44.0, 43.2, 40.8, 38.5, 33.7, 32.1, 31.5, 30.8, 29.6, 29.0, 28.8, 28.8, 27.7, 27.6, 25.5, 24.7, 22.5, 19.0, 18.9, 16.4, 14.6, 13.9 ppm.

Example 18

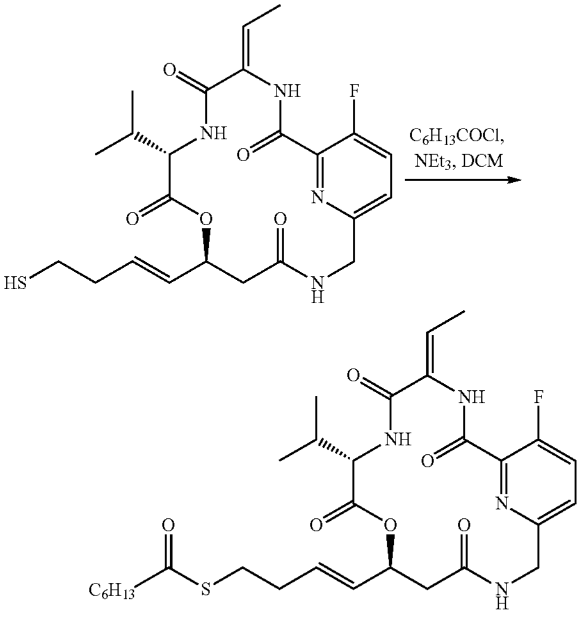

At 0° C., redistilled $NEt_3$ (0.02 ml) was added to the reactant (0.063 mmol) in anhydrous DCM (2 ml), stirred slightly, then added heptanoyl chloride (0.05 ml). After 7 h, The product was directly spinned anhydrous solvent by column chromatography and yellow solid was obtained. $[\alpha]^{20}_{D}$: 4.11 (c 0.7, $CHCl_3$). $^1H$ NMR (400 MHz, $CDCl_3$): δ 9.23 (s, 1H), 8.12 (d, J=7.8 Hz, 1H), 7.93 (d, J=7.6 Hz, 1H), 7.08 (m, J=7.2 Hz, 1H), 6.73 (d, J=4.4 Hz, 1H), 6.48 (d, J=10 Hz, 1H), 5.72-5.63 (m, 2H), 5.62-5.45 (m, 1H), 5.15 (dd, J=17.2 Hz, 8 Hz, 1H), 4.75-4.71 (m, 2H), 4.28 (d, J=17.2 Hz, 1H), 2.86-2.71 (m, 4H), 2.63-2.62 (m, 1H), 2.50 (t, J=7.8 Hz, 3H), 2.30-2.25 (m, 3H), 1.85-1.82 (m, 3H), 1.62-1.59 (m, 2H), 1.26-1.24 (m, 9H), 0.85 (m, 3H), 0.78 (d, J=7.6 Hz, 3H), 0.57 (d, J=7.6 Hz, 3H) ppm. $^{13}C$ NMR (125 MHz, $CDCl_3$) δ 169.5, 169.0, 163.5, 162.1, 155.7, 148.8, 138.6, 134.5, 132.6, 132.1, 130.9, 128.9, 128.5, 127.5, 125.1, 121.3, 72.2, 71.7, 57.3, 44.1, 43.2, 40.9, 38.6, 33.8, 32.2, 31.5, 30.9, 29.7, 29.1, 28.8, 27.7, 27.6, 25.5, 22.5, 19.1, 18.9, 16.4, 14.6, 14.0 ppm.

Example 19

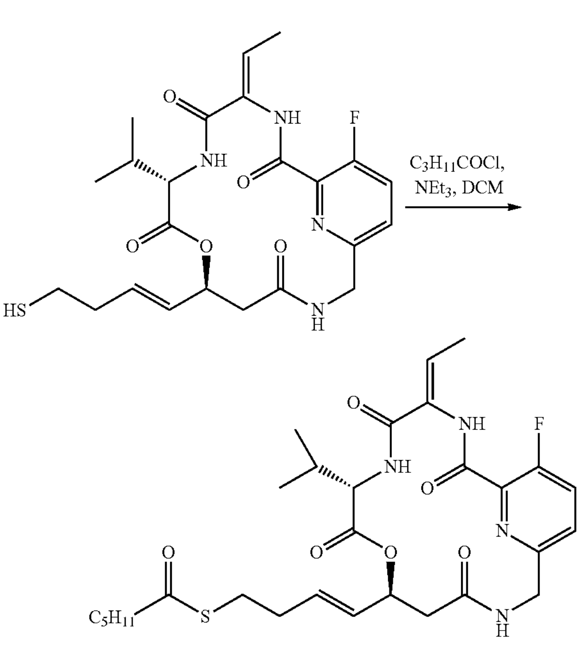

At 0° C., redistilled $NEt_3$ (0.02 ml) was added to the reactant (0.063 mmol) in anhydrous DCM (2 ml), stirred slightly, then added hexanoyl chloride (0.04 ml). After 7 h, The product was directly spinned anhydrous solvent by column chromatography and yellow solid was obtained. $[\alpha]^{20}_{D}$: 3.11 (c 0.3, $CHCl_3$). $^1H$ NMR (400 MHz, $CDCl_3$): δ 9.22 (s, 1H), 8.10 (d, J=7.8 Hz, 1H), 7.95 (d, J=7.6 Hz, 1H), 7.06 (m, J=7.2 Hz, 1H), 6.75 (d, J=4.4 Hz, 1H), 6.46 (d, J=10.0 Hz, 1H), 5.74-5.68 (m, 2H), 5.50 (m, 1H), 5.17 (dd, J=17.2 Hz, 8.0 Hz, 1H), 4.76-4.73 (m, 2H), 4.28 (d, J=17.2 Hz, 1H), 2.88-2.75 (m, 4H), 2.63 (m, 1H), 2.49 (t, J=7.8 Hz, 3H), 2.30-2.25 (m, 3H), 1.84-1.82 (m, 3H), 1.63-1.60 (m, 2H), 1.26-1.24 (m, 7H), 0.84 (m, 3H), 0.79 (d, J=7.6 Hz, 3H), 0.59 (d, J=7.6 Hz, 3H) ppm. $^{13}C$ NMR (125 MHz, $CDCl_3$) δ 169.3, 169.0, 163.2, 162.0, 155.6, 148.9, 138.8, 134.8, 132.7, 132.0, 130.9, 128.9, 128.6, 127.7, 125.3, 121.5, 72.3, 71.8, 57.5, 44.3, 43.4, 41.2, 38.9, 33.9, 32.5, 31.7, 30.9, 29.8, 29.2, 28.9, 27.8, 27.6, 25.6, 22.6, 19.0, 16.5, 14.7, 13.9 ppm.

Example 20

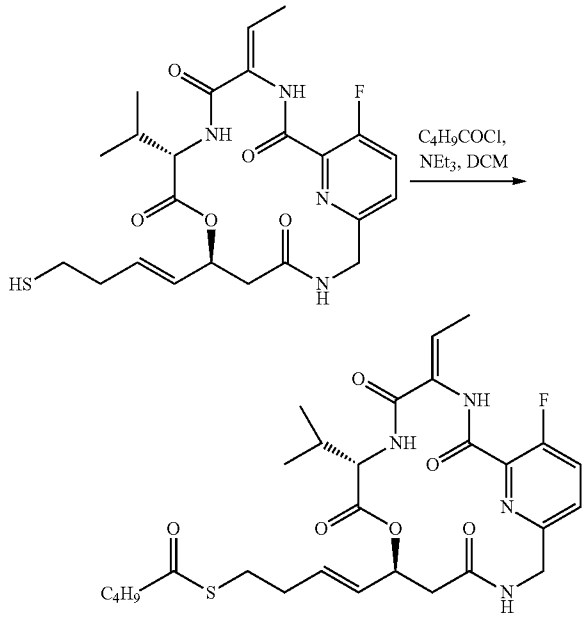

At 0° C., redistilled $NEt_3$ (0.02 ml) was added to the reactant (0.063 mmol) in anhydrous DCM (2 ml), stirred slightly, then added pivaloyl chloride (0.04 ml). After 7 h, The product was directly spinned anhydrous solvent by column chromatography and yellow solid was obtained. $[\alpha]^{20}_{D}$: 3.31 (c 0.6, $CHCl_3$). $^1H$ NMR (400 MHz, $CDCl_3$): δ 9.20 (s, 1H), 8.12 (d, J=7.8 Hz, 1H), 7.96 (d, J=7.6 Hz, 1H), 7.08 (d, J=7.2 Hz, 1H), 6.73 (d, J=4.4 Hz, 1H), 6.49 (d, J=10.0 Hz, 1H), 5.73-5.69 (m, 2H), 5.51 (m, 1H), 5.15 (dd, J=17.2 Hz, 8.0 Hz, 1H), 4.75-4.73 (m, 2H), 4.29 (d, J=17.2 Hz, 1H), 2.89-2.75 (m, 4H), 2.62 (m, 1H), 2.47 (t, J=7.8 Hz, 3H), 2.31-2.26 (m, 3H), 1.85-1.83 (m, 3H), 1.62-1.60 (m, 2H), 1.25-1.23 (m, 5H), 0.83 (m, 3H), 0.78 (d, J=7.6 Hz, 3H), 0.58 (d, J=7.6 Hz, 3H) ppm. $^{13}C$ NMR (125 MHz, $CDCl_3$) δ 169.2, 169.0, 163.3, 162.2, 155.7, 148.7, 138.9, 134.5, 132.8, 132.1, 130.8, 128.9, 128.5, 127.6, 125.2, 121.3, 72.1, 71.6, 57.8, 44.2, 43.5, 41.3, 38.8, 33.8, 32.6, 31.6, 30.8, 29.9, 29.3, 28.8, 27.6, 25.7, 22.7, 19.1, 16.6, 14.9, 13.8 ppm.

Example 21

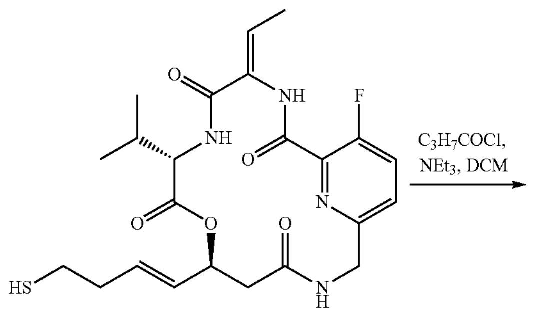

-continued

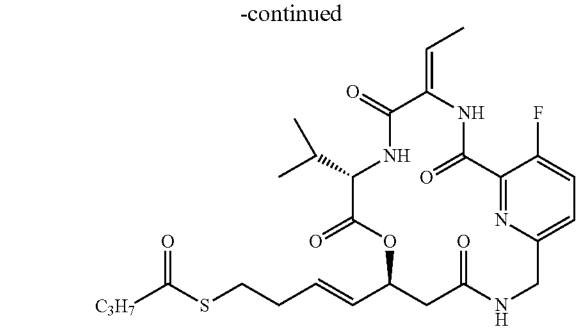

At 0° C., redistilled $NEt_3$ (0.02 ml) was added to the reactant (0.063 mmol) in anhydrous DCM (2 ml), stirred slightly, then added butyryl chloride (0.05 ml). After 7 h, The product was directly spinned anhydrous solvent by column chromatography and yellow solid was obtained. $[\alpha]^{20}_{D}$: 6.51 (c 0.5, $CHCl_3$). $^1H$ NMR (400 MHz, $CDCl_3$): δ 9.23 (s, 1H), 8.12 (d, J=7.8 Hz, 1H), 7.98 (d, J=7.6 Hz, 1H), 7.09 (d, J=7.2 Hz, 1H), 6.75 (d, J=4.4 Hz, 1H), 6.47 (d, J=10.0 Hz, 1H), 5.76-5.71 (m, 2H), 5.53 (m, 1H), 5.18 (dd, J=17.2 Hz, 8.0 Hz, 1H), 4.77-4.74 (m, 2H), 4.27 (d, J=17.2 Hz, 1H), 2.88-2.74 (m, 4H), 2.63 (m, 1H), 2.49 (t, J=7.8 Hz, 3H), 2.33-2.28 (m, 3H), 1.86-1.83 (m, 3H), 1.66-1.62 (m, 2H), 1.27-1.24 (m, 3H), 0.86 (m, 3H), 0.79 (d, J=7.6 Hz, 3H), 0.56 (d, J=7.6 Hz, 3H) ppm. $^{13}C$ NMR (125 MHz, $CDCl_3$) δ 169.4, 169.1, 163.5, 162.3, 155.8, 148.8, 138.9, 134.7, 132.9, 132.3, 130.9, 128.9, 128.4, 127.5, 125.3, 121.5, 72.2, 71.7, 57.6, 44.5, 43.6, 41.4, 38.9, 33.9, 32.7, 31.7, 30.9, 29.9, 29.5, 28.9, 27.7, 25.8, 22.9, 19.3, 15.5, 13.8 ppm.

Example 22

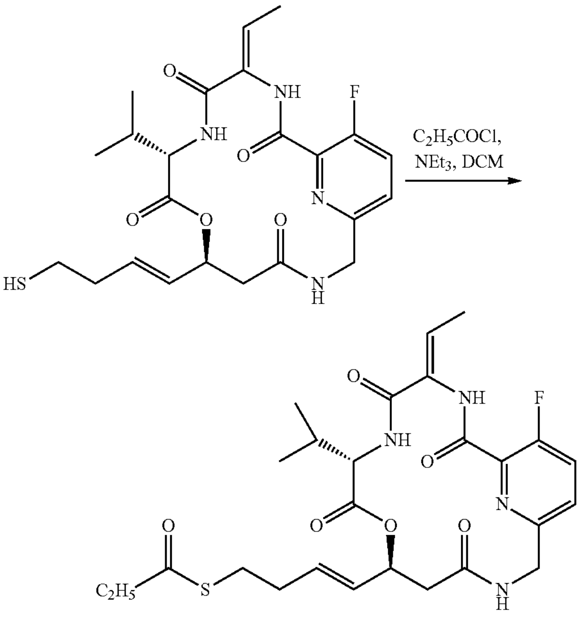

At 0° C., redistilled $NEt_3$ (0.02 ml) was added to the reactant (0.063 mmol) in anhydrous DCM (2 ml), stirred slightly, was added propionyl chloride (0.05 ml). After 7 h, The product was directly spinned anhydrous solvent by column chromatography and yellow solid was obtained. $[\alpha]^{20}_D$: 5.50 (c 0.3, $CHCl_3$). $^1H$ NMR (400 MHz, $CDCl_3$): δ 9.25 (s, 1H), 8.14 (d, J=7.8 Hz, 1H), 7.99 (d, J=7.6 Hz, 1H), 7.08 (d, J=7.2 Hz, 1H), 6.77 (d, J=4.4 Hz, 1H), 6.48 (d, J=10.0 Hz, 1H), 5.75-5.72 (m, 2H), 5.55 (m, 1H), 5.19 (dd, J=17.2 Hz, 8.0 Hz, 1H), 4.78-4.75 (m, 2H), 4.28 (d, J=17.2 Hz, 1H), 2.89-2.75 (m, 4H), 2.65 (m, 1H), 2.48 (t, J=7.8 Hz, 3H), 2.35-2.29 (m, 3H), 1.88-1.85 (m, 3H), 1.66 (m, 2H), 0.86 (m, 3H), 0.77 (d, J=7.6 Hz, 3H), 0.57 (d, J=7.6 Hz, 3H) ppm. $^{13}C$ NMR (125 MHz, $CDCl_3$) δ 169.6, 169.2, 163.3, 162.2, 155.9, 148.9, 138.8, 134.8, 132.9, 132.2, 130.8, 128.9, 128.5, 127.6, 125.5, 121.6, 72.3, 71.8, 57.8, 44.6, 43.7, 41.5, 38.8, 33.9, 32.8, 31.8, 30.8, 29.9, 29.6, 28.9, 27.8, 25.9, 22.9, 19.5, 14.8 ppm.

Example 23

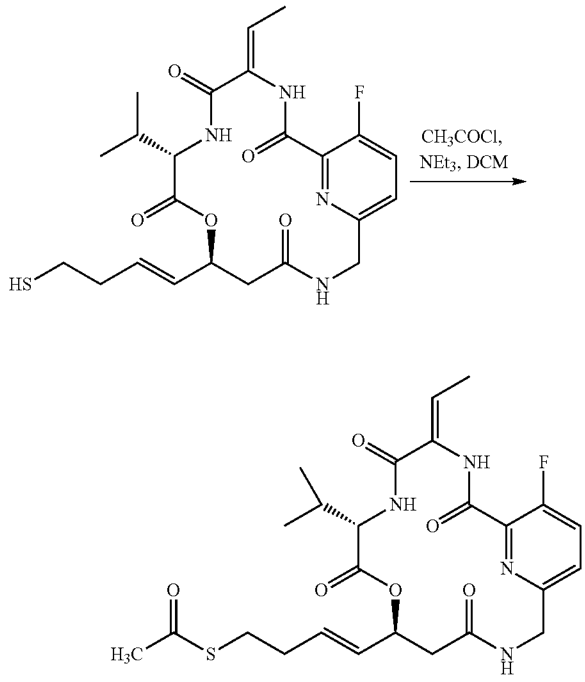

At 0° C., redistilled $NEt_3$ (0.02 ml) was added to the reactant (0.063 mmol) in anhydrous DCM (2 ml), stirred slightly, acetyl chloride (0.05 ml) was added. After 7 h, the product was directly spinned anhydrous solvent by column chromatography and yellow solid was obtained. $[\alpha]^{20}_D$: 4.66 (c 0.6, $CHCl_3$). $^1H$ NMR (400 MHz, $CDCl_3$): δ 9.26 (s, 1H), 8.15 (d, J=7.8 Hz, 1H), 7.98 (d, J=7.6 Hz, 1H), 7.09 (d, J=7.2 Hz, 1H), 6.79 (d, J=4.4 Hz, 1H), 6.47 (d, J=10.0 Hz, 1H), 5.73-5.70 (m, 2H), 5.53 (m, 1H), 5.18 (dd, J=17.2 Hz, 8.0 Hz, 1H), 4.77 (m, 2H), 4.28 (d, J=17.2 Hz, 1H), 2.88-2.78 (m, 4H), 2.67 (m, 1H), 2.49 (t, J=7.8 Hz, 3H), 2.36-2.33 (m, 3H), 1.89-1.86 (m, 3H), 0.88 (m, 3H), 0.78 (d, J=7.6 Hz, 3H), 0.58 (d, J=7.6 Hz, 3H) ppm. $^{13}C$ NMR (125 MHz, $CDCl_3$) δ 169.8, 169.3, 163.5, 162.5, 155.8, 148.8, 138.7, 134.7, 132.8, 132.3, 130.9, 128.8, 128.7, 127.7, 125.6, 121.7, 72.5, 71.9, 57.9, 44.7, 43.9, 41.6, 38.9, 33.8, 32.9, 31.9, 30.9, 29.8, 29.5, 28.8, 27.7, 15.0 ppm.

Example 24

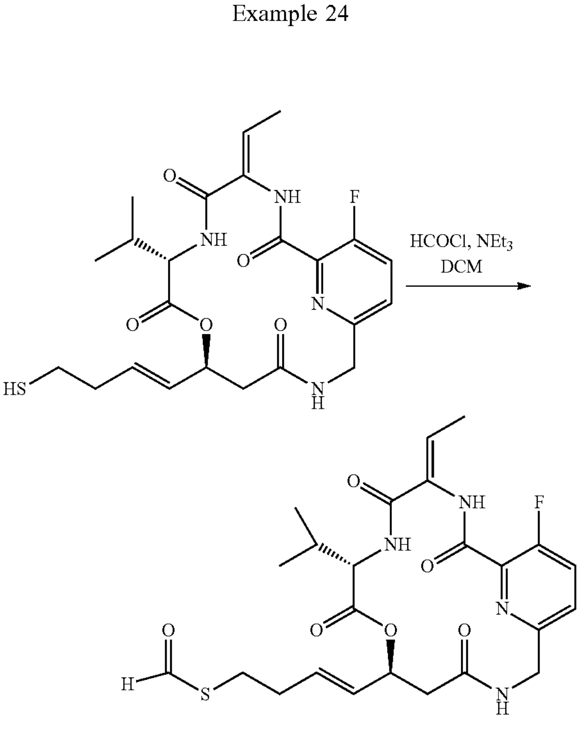

At 0° C., redistilled $NEt_3$ (0.02 ml) was added to the reactant (0.063 mmol) in anhydrous DCM (2 ml), stirred slightly, methanesulfonyl chloride (0.02 ml) was added. After 7 h, the product was directly spinned anhydrous solvent by column chromatography and yellow solid was obtained. $[\alpha]^{20}_D$: 1.96 (c 0.1, $CHCl_3$). $^1H$ NMR (400 MHz, $CDCl_3$): δ 9.63 (s, 1H), 9.23 (s, 1H), 8.16 (d, J=7.6 Hz, 1H), 7.88 (d, J=7.6 Hz, 1H), 7.07 (dd, J=14.4 Hz, J=7.2 Hz, 1H), 6.56 (dd, J=7.6 Hz, J=3.6 Hz, 1H), 6.48 (d, J=8 Hz, 1H), 5.73 (m, 2H), 5.52 (dd, J=15.6 Hz, J=6.8 Hz, 1H), 5.12 (m, 1H), 4.76 (dd, J=10 Hz, J=3.6 Hz, 1H), 4.33 (m, 1H), 2.72 (m, 2H), 2.53 (m, 2H), 2.34-2.29 (m, 3H), 1.38 (t, J=7.6 Hz, 1H), 0.82 (d, J=6.8 Hz, 3H), 0.62 (d, J=6.8 Hz, 3H) ppm. $^{13}C$ NMR (125 MHz, $CDCl_3$) δ 176.5, 169.8, 169.4, 163.6, 162.6, 155.7, 148.8, 138.5, 134.7, 132.5, 132.3, 130.9, 128.8, 127.8, 125.6, 121.8, 72.5, 71.7, 56.9, 44.8, 43.6, 41.5, 36.0, 30.8, 23.7, 18.9, 16.5, 14.6 ppm.

Example 25

25.1

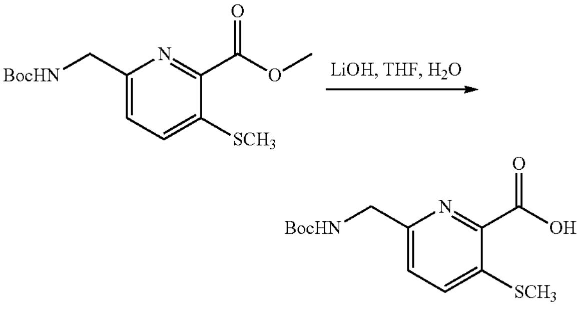

15 ml LiOH aqueous solution (19 mmol) were added dropwise to the reactant (7.6 mmol) of 30 ml THF, then reacted 2 h at room temperature. The reaction solution was adjusted by dilute hydrochloric acid to with the pH value of 3, then 100 ml ethyl acetate was added. The organic matter was washed by water and saturated salt water. The organic layer was dried by anhydrous sodium sulfate, and the solvent evaporated to give white flocculent solid. $^1$H NMR (400 MHz, $CDCl_3$): δ 7.66 (d, J=8.0 Hz, 1H), 7.48 (d, J=7.8 Hz, 1H), 5.55 (s, 1H), 4.48 (d, J=4.2 Hz, 2H), 3.48 (s, 3H), 1.36 (s, 9H) ppm.

25.2

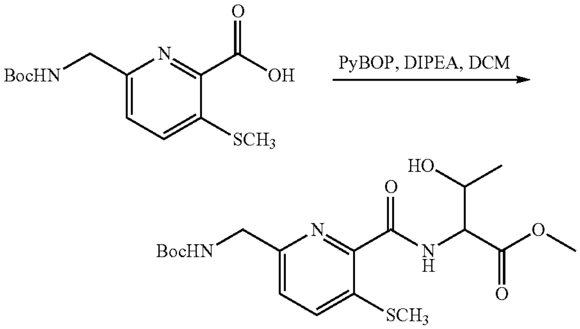

At 0° C., DIPEA (1.2 ml, 6 mmol) was added to the reactant (2.7 mmol) slowly, stirred slightly, then added S2 (2.7 mmol), PyBop (4 mmol), and then stirred at room temperature overnight. The reaction solution was washed with saturated sodium bicarbonate solution, dilute hydrochloric acid solution, saturated sodium chloride solution. The product was dried with anhydrous sodium sulfate and spinned solvent by column chromatography and white floc was obtained. $^1$H NMR (400 MHz, $CDCl_3$): δ 8.64 (d, J=8.4 Hz, 1H), 8.05 (d, J=8 Hz, 1H), 7.44 (d, J=7.6 Hz, 1H), 5.44 (s, 1H), 4.77 (d, J=7.2 Hz, 1H), 4.48-4.45 (m, J=3H), 3.78 (s, 3H), 3.48 (s, 3H), 1.45 (s, 9H), 1.26 (d, J=5.6 Hz, 3H) ppm. $^{13}$C NMR (100 MHz, $CDCl_3$) δ 171.1, 164.6, 157.4, 156.0, 148.9, 137.9, 134.6, 124.2, 121.8, 121.0, 80.7, 79.8, 78.7, 70.3, 68.2, 61.1, 57.8, 52.7, 52.2, 47.7, 32.1, 28.3, 28.2, 28.1, 28.0, 22.6, 19.8 ppm.

25.3

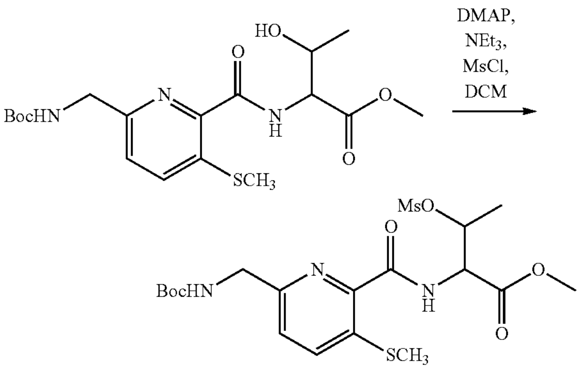

At 0° C., DMAP (0.184 mmol), $NEt_3$ (0.42 ml, 3 mmol), MsCl (0.186 ml, 2.4 mmol) were added to anhydrous DCM (10 ml) of the reactants (1.84 mmol) successively, then raised to room temperature and stirred overnight. The product was spinned anhydrous, pumped with oil pump and directly put into next step.

25.4

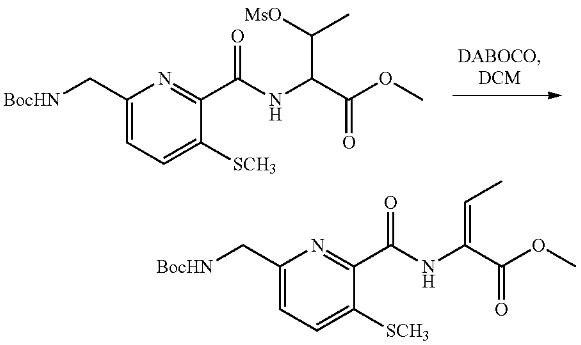

DABOCO (1 g, 9.22 mmol) was added to anhydrous DCM liquid (10 ml) obtained above and stirred 8 h at room temperature. The reaction solution was washed by saturated sodium bicarbonate solution, saturated ammonium chloride solution, saturated sodium chloride solution in sequence, and dried by anhydrous sodium sulfate. The product was filtered and spinned solvent by column chromatography and white floc was obtained. $^1$H NMR (400 MHz, $CDCl_3$): δ 9.38 (s, 1H), 8.01 (d, J=7.6 Hz, 1H), 7.78 (d, J=8 Hz, 1H), 6.86 (q, J=7.6 Hz, 1H), 5.57 (s, 1H), 4.44 (d, J=5.6 Hz, 2H), 3.74 (s, 9H), 3.48 (s, 3H), 3.48 (s, 3H), 1.80 (d, J=7.6 Hz, 3H), 1.40 (s, 9H) ppm. $^{13}$C NMR (100 MHz, $CDCl_3$) δ 164.8, 162.1, 157.4, 156.0, 148.9, 148.8, 138.1, 133.9, 126.3, 124.2, 123.5, 121.7, 121.0, 79.7, 52.1, 45.9, 28.3, 14.6 ppm.

25.5

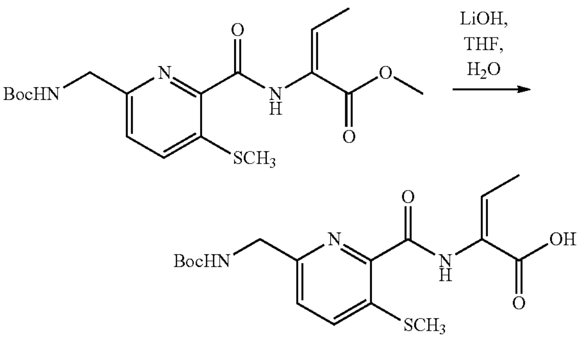

5 ml LiOH aqueous solution (90 mg, 3.6 mmol) were added dropwise to reactants (1.44 mmol) with THF (10 ml), then spinned anhydrous the organic phase after three hours. 10 ml water and 15 ml ethyl acetate were added to the organic phase. The aqueous phase was removed after liquid separation. Then the solution was added 15 ml ethyl acetate, adjusted the acid. Anhydrous sodium sulfate was used for the separation of organic phase after liquid separation. Solid white floc was obtained after spinned anhydrous. $^1$H NMR (400 MHz, $CDCl_3$): δ 9.40 (s, 1H), 8.03 (d, J=7.6 Hz, 1H), 7.80 (d, J=8.2 Hz, 1H), 6.88 (q, J=7.8 Hz, 1H), 5.58 (s, 1H), 4.46 (d, J=5.8 Hz, 2H), 3.76 (s, 9H), 3.48 (s, 3H), 1.83 (d, J=7.8 Hz, 3H), 1.43 (s, 9H) ppm. $^{13}$C NMR (100 MHz, $CDCl_3$) δ 165.3, 162.7, 157.8, 156.2, 149.0, 148.8, 138.3, 133.7, 126.5, 124.5, 123.7, 121.9, 121.0, 52.5, 46.3, 28.5, 14.8 ppm.

25.6

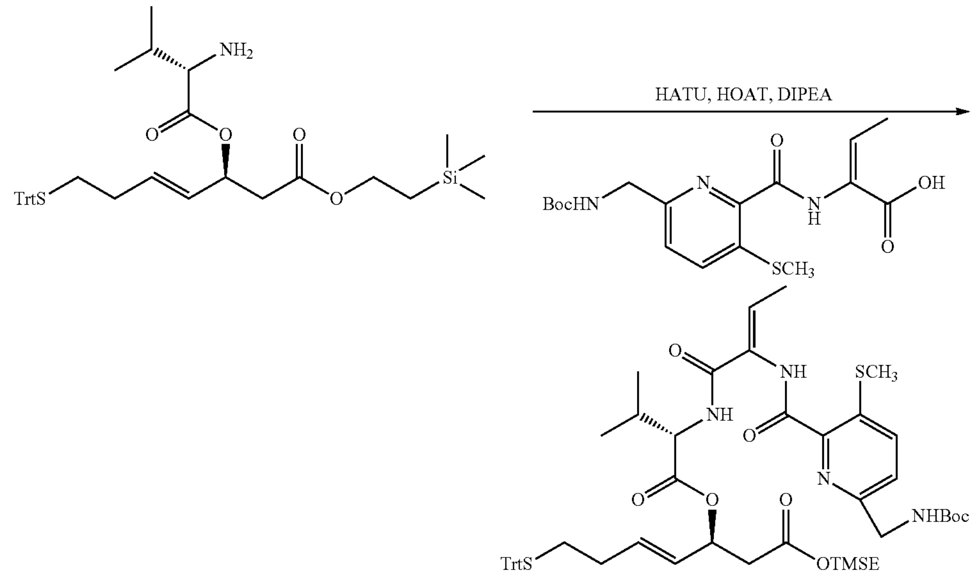

At 0° C., DIPEA (0.7 ml), carboxylic acid (610 mg), HATU (760 mg), HOAT (326 mg) were added to the reactant (336 mg, 1 mmol) in DCM solution (10 ml) sequentially. Then raised to room temperature with stirring. After 8 h, the reaction was washed with saturated sodium bicarbonate solution, dilute hydrochloric acid solution, saturated sodium chloride solution, and dried over anhydrous sodium sulfate. The product was filtered and spinned solvent by column chromatography and white flocculent solid was obtained. $^1H$ NMR (400 MHz, $CDCl_3$): δ 9.41 (s, 1H), 8.10 (d, J=7.6 Hz, 1H), 7.48 (d, J=7.6 Hz, 1H), 7.39-7.17 (m, 12H), 6.66-6.61 (m, 2H), 5.68-5.59 (m, 2H), 5.46 (s, 1H), 5.38-5.32 (m, 1H), 4.59 (dd, J=8.8 Hz, 4 Hz, 1H), 4.49 (d, J=4.2 Hz, 2H), 4.15-4.10 (m, 3H), 3.48 (s, 3H), 2.66 (dd, J=15.6 Hz, 7.6 Hz, 1H), 2.52 (dd, J=15.6 Hz, 5.6 Hz, 1H), 2.18-2.14 (m, 3H), 2.04 (t, J=6.8 Hz, 4H), 1.82 (d, J=7.2 Hz, 3H), 1.46 (s, 9H), 1.25 (t, J=6.8 Hz, 2H), 0.97-0.90 (m, 5H), 0.80 (d, J=6.8 Hz, 3H), 0.02 (s, 9H) ppm. $^{13}C$ NMR (125 MHz, $CDCl_3$) δ 171.0, 170.7, 169.5, 164.3, 162.6, 157.3, 155.9, 148.5, 144.7, 138.2, 133.9, 129.6, 129.4, 129.0, 127.7, 127.6, 126.5, 124.6, 123.5, 121.1, 79.7, 71.8, 66.5, 63.0, 60.3, 57.0, 45.6, 39.5, 31.5, 31.2, 31.0, 28.3, 20.9, 18.8, 17.5, 17.2, 14.1, 13.8, 0.9, −1.5, −1.6 ppm.

25.7

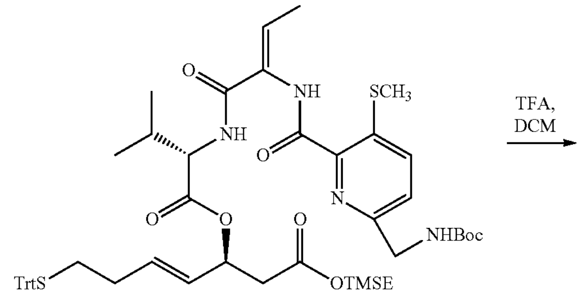

-continued

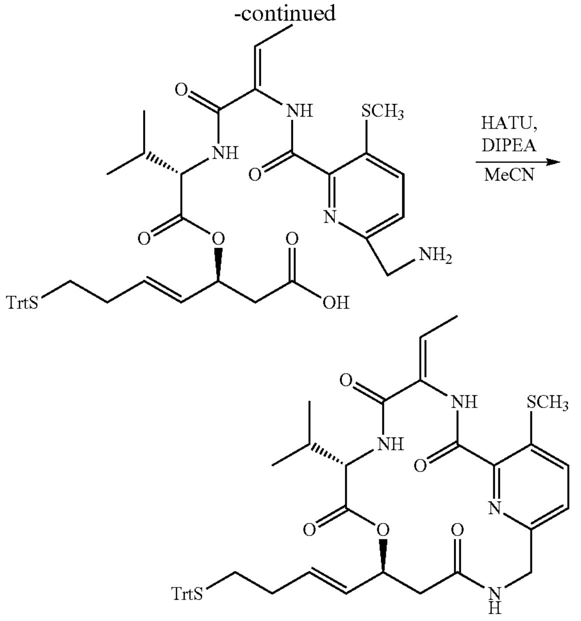

Tetrabutylammonium fluoride in tetrahydrofuran solution (1 mol/l, 2.3 ml) was added to the reaction (0.92 mmol) in redistilled THF (5 ml). After 3 h, the reaction was immediately spinned anhydrous by column chromatography to obtain a white solid. DCM solution (25 ml) of the resulting resultant was added trifluoroacetic acid (6 ml). After 5 h, spinned and removed DCM, the residue was added toluene (8 ml). Without further treatment, a brown viscous material was obtained after pumped organic solvent with oil pump. Chromatography pure acetonitrile (200 ml) obtained above was dissolved, slowly dropped in HATU (3 g), DIPEA (4 ml) of HPLC grade acetonitrile (550 ml). After 24 h, spinned anhydrous solvents, the product was diluted with ethyl acetate (20 ml) and then washed with saturated sodium bicarbonate solution, dilute hydrochloric acid solution, saturated sodium chloride solution and dried over anhydrous sodium sulfate. The product was filtered and spinned anhydrous by column chromatography and pale yellow solid was obtained. $^1$H NMR (400 MHz, $CDCl_3$): δ 9.17 (s, 1H), 8.10 (d, J=7.6 Hz, 1H), 7.87 (d, J=7.6 Hz, 1H), 7.37-7.16 (m, 15H), 7.07 (q, J=7.2 Hz, 1H), 6.43 (d, J=10.4 Hz, 1H), 5.62-5.56 (m, 2H), 5.39-5.34 (m, 1H), 5.06 (dd, J=17.2 Hz, 8 Hz, 1H), 4.74 (dd, J=6.4 Hz, 3.6 Hz, 1H), 4.19-4.08 (m, 2H), 3.48 (s, 3H), 2.69-2.64 (m, 2H), 2.30-2.27 (m, 1H), 2.21-2.17 (m, 2H), 1.84 (d, J=7.2 Hz, 3H), 0.79 (d, J=6.8 Hz, 3H), 0.59 (d, J=6.8 Hz, 3H) ppm. $^{13}$C NMR (125 MHz, DMSO) δ 133.6, 132.0, 131.3, 126.1, 124.7, 123.3, 118.4, 111.1, 107.1, 101.0, 97.3, 95.2, 92.0, 90.4, 90.3, 89.5, 89.1, 87.5, 83.8, 39.8, 39.5, 39.3, 34.1, 29.1, 22.9, 19.5 ppm.

25.8

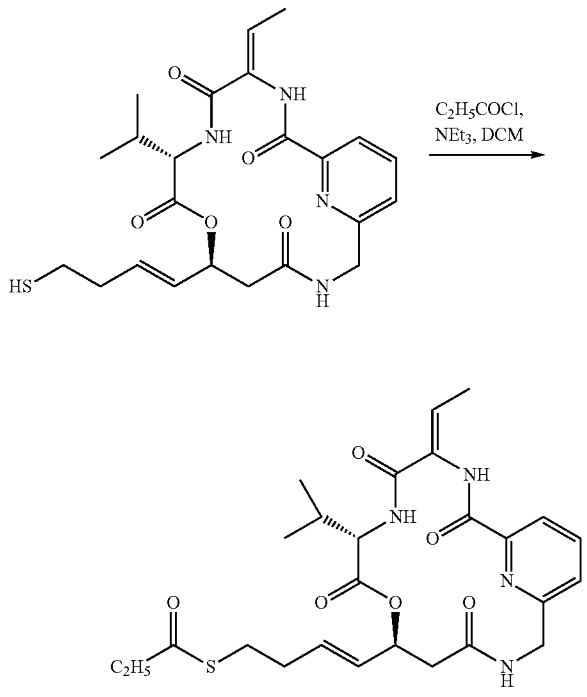

At 0° C., TES (0.1 ml), TFA (0.65 ml) were added to the reactants (150 mg, 0.21 mmol) in anhydrous DCM solution (5 ml) sequentially. 15 min later, the product was directly spinned anhydrous solvent by column chromatography and pale yellow solid was obtained. $[\alpha]^{20}_D$: 6.13 (c 0.5, $CHCl_3$). $^1$H NMR (400 MHz, $CDCl_3$): δ 8.18 (d, J=7.6 Hz, 1H), 7.89 (d, J=7.6 Hz, 1H), 7.06 (dd, J=14.4 Hz J=7.2 Hz, 1H), 6.58 (dd, J=7.6 Hz, J=3.6 Hz, 1H), 6.45 (d, J=8 Hz, 1H), 5.74-5.64 (m, 2H), 5.50 (dd, J=15.6 Hz, J=6.8 Hz, 1H), 5.10 (m, 1H), 4.74 (dd, J=10 Hz, J=3.6 Hz, 1H), 4.34-4.28 (m, 1H), 3.48 (s, 3H), 2.74-2.69 (m, 2H), 2.56-2.50 (m, 2H), 2.34-2.29 (m, 3H), 1.36 (t, J=7.6 Hz, 1H), 0.80 (d, J=6.8 Hz, 3H), 0.6 (d, J=6.8 Hz, 3H) ppm. $^{13}$C NMR (125 MHz, $CDCl_3$) δ 169.6, 168.9, 163.6, 162.9, 155.7, 148.6, 138.3, 134.7, 132.4, 128.6, 127.0, 124.9, 123.8, 121.4, 71.9, 56.9, 43.3, 41.0, 36.0, 30.8, 23.7, 18.9, 16.5, 14.6 ppm.

Example 26

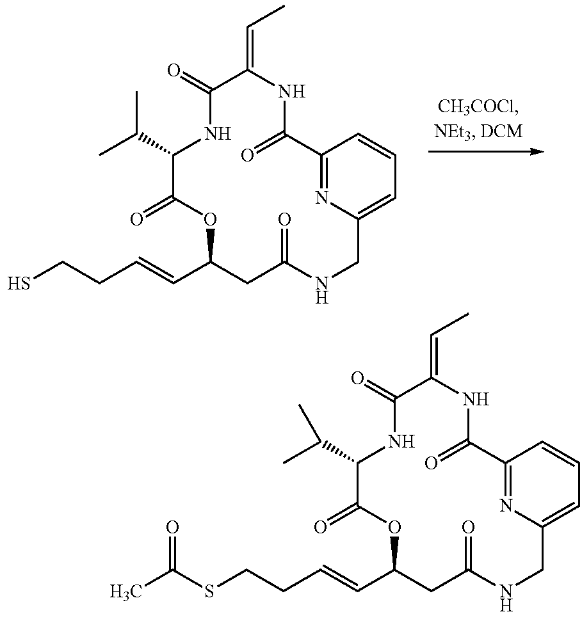

At 0° C., redistilled $NEt_3$ (0.04 ml) was added to the reactant (0.126 mmol) in anhydrous DCM (5 ml), stirred slightly, then added caprylate chloride (0.1 ml). After 7 h, The product was directly spinned anhydrous solvent by column chromatography and pale yellow solid was obtained. $[\alpha]^{20}_D$: 3.71 (c 0.5, $CHCl_3$). $^1$H NMR (400 MHz, $CDCl_3$): δ 9.21 (s, 1H), 8.10 (d, J=7.6 Hz, 1H), 7.91 (d, J=7.6 Hz, 1H), 7.06 (m, J=7.2 Hz, 1H), 6.70 (d, J=4.4 Hz, 1H), 6.46 (d, J=10 Hz, 1H), 5.70-5.64 (m, 2H), 5.59-5.46 (m, 1H), 5.13 (dd, J=17.2 Hz, 8 Hz, 1H), 4.73-4.70 (m, 2H), 4.27 (d, J=J=17.2 Hz, 1H), 3.48 (s, 3H), 2.85-2.71 (m, 4H), 2.62-2.61 (m, 1H), 2.49 (t, J=7.6 Hz, 3H), 2.29-2.23 (m, 3H), 1.84-1.81 (m, 3H), 1.61-1.58 (m, 2H), 1.24 (s, 11H), 0.86-0.57 (m, 7H), 0.53 (d, J=7.6 Hz, 3H) ppm. $^{13}$C NMR (125 MHz, $CDCl_3$) δ169.6, 169.1, 167.6, 165.7, 163.7, 162.3, 155.8, 148.6, 138.5, 134.7, 132.5, 132.2, 130.8, 128.7, 128.2, 127.2, 124.9, 123.6, 121.3, 72.0, 71.6, 56.9, 44.0, 43.2, 40.8, 38.5, 33.7, 32.1, 31.5, 30.8, 29.6, 29.0, 28.8, 28.8, 27.7, 27.6, 25.5, 24.7, 22.5, 19.0, 18.9, 16.4, 14.6, 13.9 ppm.

Example 27

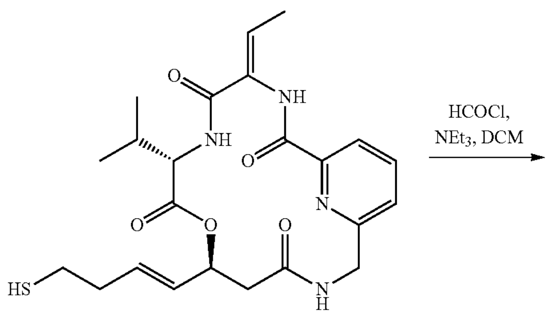

-continued

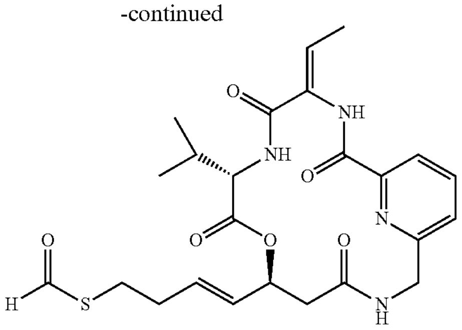

At 0° C., redistilled $NEt_3$ (0.02 ml) was added to the reactant (0.063 mmol) in anhydrous DCM (2 ml), stirred slightly, then added heptanoyl chloride (0.05 ml). After 7 h, The product was directly spinned anhydrous solvent by column chromatography and pale yellow solid was obtained. $[\alpha]^{20}_{D}$: 4.11 (c 0.7, $CHCl_3$). $^{1}H$ NMR (400 MHz, $CDCl_3$): δ 9.23 (s, 1H), 8.12 (d, J=7.8 Hz, 1H), 7.93 (d, J=7.6 Hz, 1H), 7.08 (m, J=7.2 Hz, 1H), 6.73 (d, J=4.4 Hz, 1H), 6.48 (d, J=10 Hz, 1H), 5.72-5.63 (m, 2H), 5.62-5.45 (m, 1H), 5.15 (dd, J=17.2 Hz, 8 Hz, 1H), 4.75-4.71 (m, 2H), 4.28 (d, J=17.2 Hz, 1H), 3.48 (s, 3H), 2.86-2.71 (m, 4H), 2.63-2.62 (m, 1H), 2.50 (t, J=7.8 Hz, 3H), 2.30-2.25 (m, 3H), 1.85-1.82 (m, 3H), 1.62-1.59 (m, 2H), 1.26-1.24 (m, 9H), 0.85 (m, 3H), 0.78 (d, J=7.6 Hz, 3H), 0.57 (d, J=7.6 Hz, 3H) ppm. $^{13}C$ NMR (125 MHz, $CDCl_3$) δ 169.5, 169.0, 163.5, 162.1, 155.7, 148.8, 138.6, 134.5, 132.6, 132.1, 130.9, 128.9, 128.5, 127.5, 125.1, 124.1, 121.3, 72.2, 71.7, 57.3, 44.1, 43.2, 40.9, 38.6, 33.8, 32.2, 31.5, 30.9, 29.7, 29.1, 28.8, 27.7, 27.6, 25.5, 22.5, 19.1, 18.9, 16.4, 14.6, 14.0 ppm.

Example 28

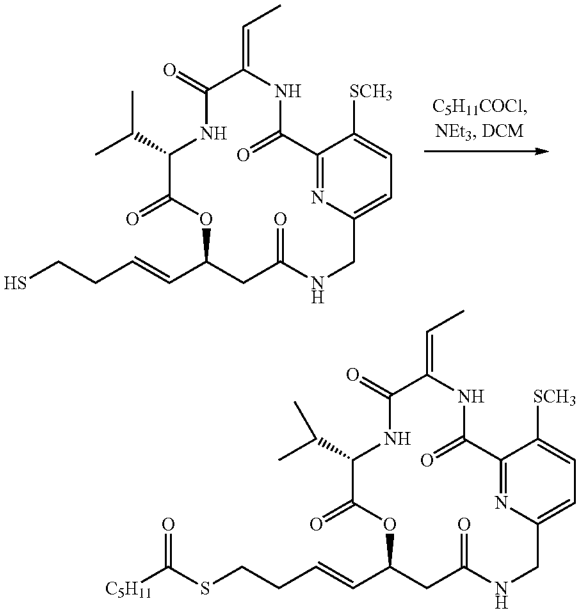

At 0° C., redistilled $NEt_3$ (0.02 ml) was added to the reactant (30 mg, 0.063 mmol) in anhydrous DCM (2 ml), stirred slightly, then added hexanoyl chloride (0.04 ml). After 7 h, The product was directly spinned anhydrous solvent by column chromatography and pale yellow solid was obtained. $[\alpha]^{20}_{D}$: 3.11 (c 0.3, $CHCl_3$). $^{1}H$ NMR (400 MHz, $CDCl_3$): δ 9.22 (s, 1H), 8.10 (d, J=7.8 Hz, 1H), 7.95 (d, J=7.6 Hz, 1H), 7.06 (m, J=7.2 Hz, 1H), 6.75 (d, J=4.4 Hz, 1H), 6.46 (d, J=10.0 Hz, 1H), 5.74-5.68 (m, 2H), 5.50 (m, 1H), 5.17 (dd, J=17.2 Hz, 8.0 Hz, 1H), 4.76-4.73 (m, 2H), 4.28 (d, J=17.2 Hz, 1H), 3.48 (s, 3H), 2.88-2.75 (m, 4H), 2.63 (m, 1H), 2.49 (t, J=7.8 Hz, 3H), 2.30-2.25 (m, 3H), 1.84-1.82 (m, 3H), 1.63-1.60 (m, 2H), 1.26-1.24 (m, 7H), 0.84 (m, 3H), 0.79 (d, J=7.6 Hz, 3H), 0.59 (d, J=7.6 Hz, 3H) ppm. $^{13}C$ NMR (125 MHz, $CDCl_3$) δ 169.3, 169.0, 163.2, 162.0, 155.6, 148.9, 138.8, 134.8, 132.7, 132.0, 130.9, 128.9, 128.6, 127.7, 125.3, 124.3, 121.5, 72.3, 71.8, 57.5, 44.3, 43.4, 41.2, 38.9, 33.9, 32.5, 31.7, 30.9, 29.8, 29.2, 28.9, 27.8, 27.6, 25.6, 22.6, 19.0, 16.5, 14.7, 13.9 ppm.

Example 29

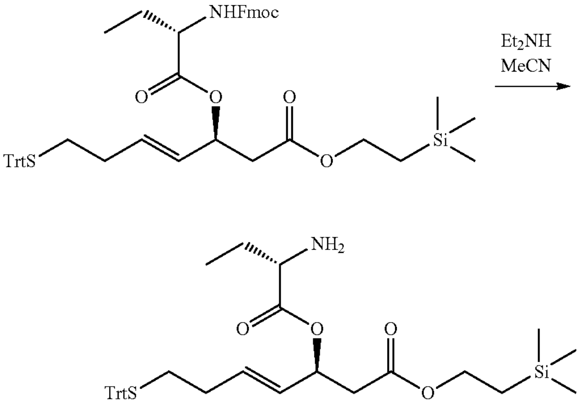

At 0° C., redistilled $NEt_3$ (0.02 ml) was added to the reactant (30 mg, 0.063 mmol) in anhydrous DCM (2 ml), stirred slightly, then added pivaloyl chloride (0.04 ml). After 7 h, The product was directly spinned anhydrous solvent by column chromatography and pale yellow solid was obtained. $[\alpha]^{20}_{D}$: 3.31 (c 0.6, $CHCl_3$). $^{1}H$ NMR (400 MHz, $CDCl_3$): δ 9.20 (s, 1H), 8.12 (d, J=7.8 Hz, 1H), 7.96 (d, J=7.6 Hz, 1H), 7.08 (d, J=7.2 Hz, 1H), 6.73 (d, J=4.4 Hz, 1H), 6.49 (d, J=10.0 Hz, 1H), 5.73-5.69 (m, 2H), 5.51 (m, 1H), 5.15 (dd, J=17.2 Hz, 8.0 Hz, 1H), 4.75-4.73 (m, 2H), 4.29 (d, J=17.2 Hz, 1H), 3.48 (s, 3H), 2.89-2.75 (m, 4H), 2.62 (m, 1H), 2.47 (t, J=7.8 Hz, 3H), 2.31-2.26 (m, 3H), 1.85-1.83 (m, 3H), 1.62-1.60 (m, 2H), 1.25-1.23 (m, 5H), 0.83 (m, 3H), 0.78 (d, J=7.6 Hz, 3H), 0.58 (d, J=7.6 Hz, 3H) ppm. $^{13}C$ NMR (125 MHz, $CDCl_3$) δ 169.2, 169.0, 163.3, 162.2, 155.7, 148.7, 138.9, 134.5, 132.8, 132.1, 130.8, 128.9, 128.5, 127.6, 125.2, 123.1, 121.3, 72.1, 71.6, 57.8, 44.2, 43.5, 41.3, 38.8, 33.8, 32.6, 31.6, 30.8, 29.9, 29.3, 28.8, 27.6, 25.7, 22.7, 19.1, 16.6, 14.9, 13.8 ppm.

Example 30

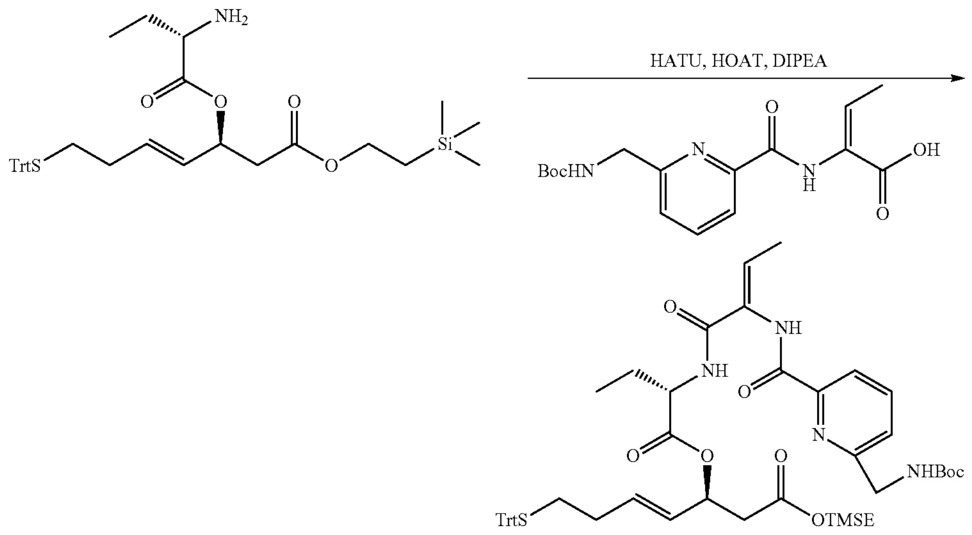

At 0° C., redistilled $NEt_3$ (0.02 ml) was added to the reactant (0.063 mmol) in anhydrous DCM (2 ml), stirred slightly, then added butyryl chloride (0.05 ml). After 7 h, The product was directly spinned anhydrous solvent by column chromatography and pale yellow solid was obtained. $[\alpha]^{20}_D$: 6.51 (c 0.5, $CHCl_3$). $^1H$ NMR (400 MHz, $CDCl_3$): δ 9.23 (s, 1H), 8.12 (d, J=7.8 Hz, 1H), 7.98 (d, J=7.6 Hz, 1H), 7.49 (d, J=7.6 Hz, 1H), 6.75 (d, J=4.4 Hz, 1H), 6.47 (d, J=10.0 Hz, 1H), 5.76-5.71 (m, 2H), 5.53 (m, 1H), 5.18 (dd, J=17.2 Hz, 8.0 Hz, 1H), 4.77-4.74 (m, 2H), 4.27 (d, J=17.2 Hz, 1H), 3.48 (s, 3H), 2.88-2.74 (m, 4H), 2.63 (m, 1H), 2.49 (t, J=7.8 Hz, 3H), 2.33-2.28 (m, 3H), 1.86-1.83 (m, 3H), 1.66-1.62 (m, 2H), 1.27-1.24 (m, 3H), 0.86 (m, 3H), 0.79 (d, J=7.6 Hz, 3H), 0.56 (d, J=7.6 Hz, 3H) ppm. $^{13}C$ NMR (125 MHz, $CDCl_3$) δ 169.4, 169.1, 163.5, 162.3, 155.8, 148.8, 138.9, 134.7, 132.9, 132.3, 130.9, 128.9, 128.4, 127.5, 125.3, 123.9, 121.5, 72.2, 71.7, 57.6, 44.5, 43.6, 41.4, 38.9, 33.9, 32.7, 31.7, 30.9, 29.9, 29.5, 28.9, 27.7, 25.8, 22.9, 19.3, 15.5, 13.8 ppm.

Example 31

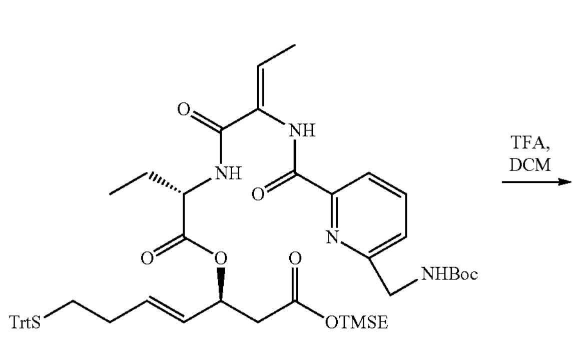

-continued

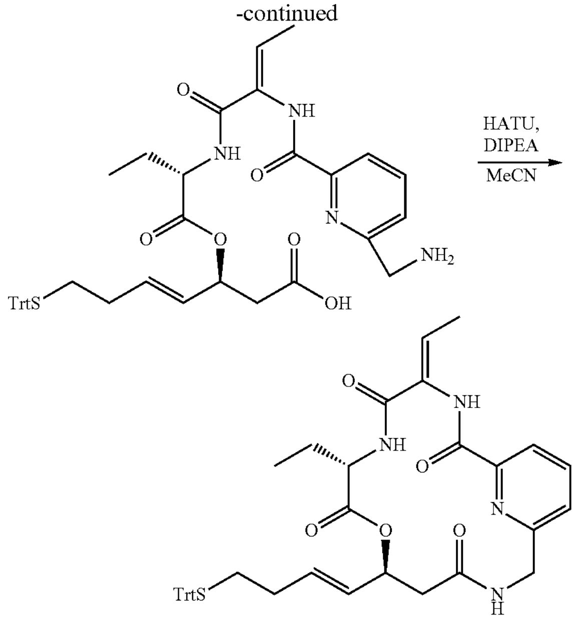

At 0° C., redistilled $NEt_3$ (0.02 ml) was added to the reactant (0.063 mmol) in anhydrous DCM (2 ml), stirred slightly, was added propionyl chloride (0.05 ml). After 7 h, The product was directly spinned anhydrous solvent by column chromatography and pale yellow solid was obtained. $[\alpha]^{20}_D$: 5.50 (c 0.3, $CHCl_3$). $^1H$ NMR (400 MHz, $CDCl_3$): δ 9.25 (s, 1H), 8.14 (d, J=7.8 Hz, 1H), 7.99 (d, J=7.6 Hz, 1H), 7.48 (d, J=7.6 Hz, 1H), 6.77 (d, J=4.4 Hz, 1H), 6.48 (d, J=10.0 Hz, 1H), 5.75-5.72 (m, 2H), 5.55 (m, 1H), 5.19 (dd, J=17.2 Hz, 8.0 Hz, 1H), 4.78-4.75 (m, 2H), 4.28 (d, J=17.2 Hz, 1H), 3.48 (s, 3H), 2.89-2.75 (m, 4H), 2.65 (m, 1H), 2.48 (t, J=7.8 Hz, 3H), 2.35-2.29 (m, 3H), 1.88-1.85 (m, 3H), 1.66 (m, 2H), 0.86 (m, 3H), 0.77 (d, J=7.6 Hz, 3H), 0.57 (d, J=7.6 Hz, 3H) ppm. $^{13}C$ NMR (125 MHz, $CDCl_3$) δ 169.6, 169.2, 163.3, 162.2, 155.9, 148.9, 138.8, 134.8, 132.9, 132.2, 130.8, 128.9, 128.5, 127.6, 125.5, 124.7, 121.6, 72.3, 71.8, 57.8, 44.6, 43.7, 41.5, 38.8, 33.9, 32.8, 31.8, 30.8, 29.9, 29.6, 28.9, 27.8, 25.9, 22.9, 19.5, 14.8 ppm.

Example 32

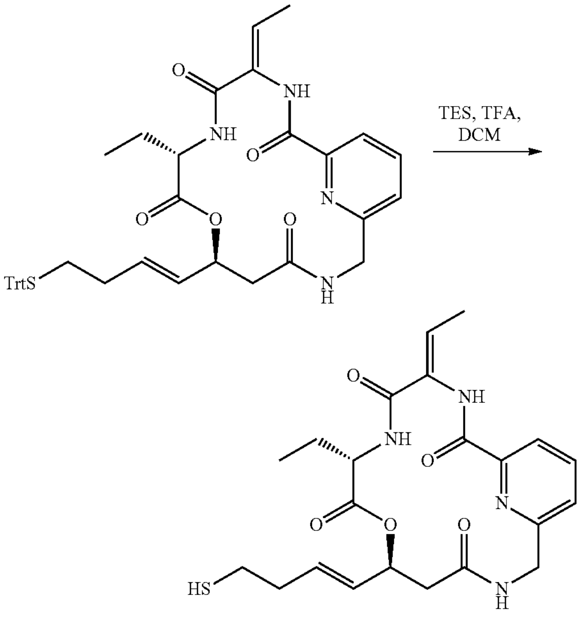

At 0° C., redistilled $NEt_3$ (0.02 ml) was added to the reactant (0.063 mmol) in anhydrous DCM (2 ml), stirred slightly, acetyl chloride (0.05 ml) was added. After 7 h, the product was directly spinned anhydrous solvent by column chromatography and pale yellow solid was obtained. $[\alpha]^{20}_{D}$: 4.66 (c 0.6, $CHCl_3$). $^1$H NMR (400 MHz, $CDCl_3$): δ 9.26 (s, 1H), 8.15 (d, J=7.8 Hz, 1H), 7.98 (d, J=7.6 Hz, 1H), 7.49 (d, J=7.6 Hz, 1H), 6.79 (d, J=4.4 Hz, 1H), 6.47 (d, J=10.0 Hz, 1H), 5.73-5.70 (m, 2H), 5.53 (m, 1H), 5.18 (dd, J=17.2 Hz, 8.0 Hz, 1H), 4.77 (m, 2H), 4.28 (d, J=17.2 Hz, 1H), 3.48 (s, 3H), 2.88-2.78 (m, 4H), 2.67 (m, 1H), 2.49 (t, J=7.8 Hz, 3H), 2.36-2.33 (m, 3H), 1.89-1.86 (m, 3H), 0.88 (m, 3H), 0.78 (d, J=7.6 Hz, 3H), 0.58 (d, J=7.6 Hz, 3H) ppm. $^{13}$C NMR (125 MHz, $CDCl_3$) δ 169.8, 169.3, 163.5, 162.5, 155.8, 148.8, 138.7, 134.7, 132.8, 132.3, 130.9, 128.8, 128.7, 127.7, 125.6, 123.4, 121.7, 72.5, 71.9, 57.9, 44.7, 43.9, 41.6, 38.9, 33.8, 32.9, 31.9, 30.9, 29.8, 29.5, 28.8, 27.7, 15.0 ppm.

Example 33

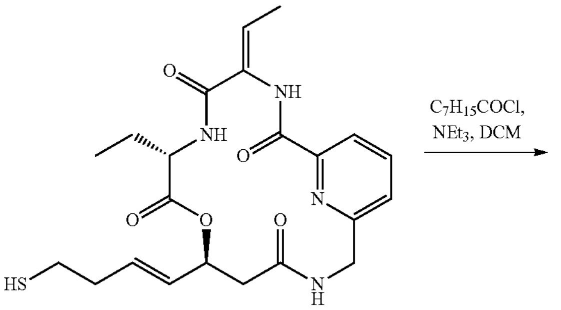

-continued

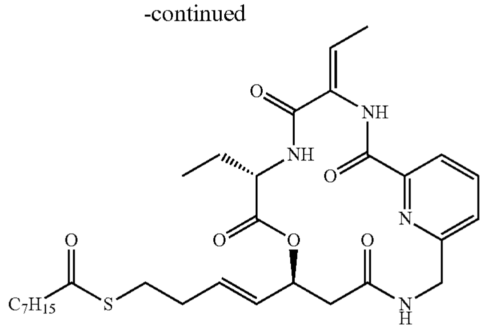

At 0° C., redistilled $NEt_3$ (0.02 ml) was added to the reactant (0.063 mmol) in anhydrous DCM (2 ml), stirred slightly, was added methanesulfonyl chloride (0.02 ml). After 7 h, the product was directly spinned anhydrous solvent by column chromatography and pale yellow solid was obtained. $[\alpha]^{20}_{D}$: 1.96 (c 0.1, $CHCl_3$). $^1$H NMR (400 MHz, $CDCl_3$): δ 9.63 (s, 1H), 9.23 (s, 1H), 8.16 (d, J=7.6 Hz, 1H), 7.88 (d, J=7.6 Hz, 1H), 7.07 (dd, J=14.4 Hz, J=7.2 Hz, 1H), 6.56 (dd, J=7.6 Hz, J=3.6 Hz, 1H), 6.48 (d, J=8 Hz, 1H), 5.73 (m, 2H), 5.52 (dd, J=15.6 Hz, J=6.8 Hz, 1H), 5.12 (m, 1H), 4.76 (dd, J=10 Hz, J=3.6 Hz, 1H), 4.33 (m, 1H), 3.48 (s, 3H), 2.72 (m, 2H), 2.53 (m, 2H), 2.34-2.29 (m, 3H), 1.38 (t, J=7.6 Hz, 1H), 0.82 (d, J=6.8 Hz, 3H), 0.62 (d, J=6.8 Hz, 3H) ppm. $^{13}$C NMR (125 MHz, $CDCl_3$) δ 176.5, 169.8, 169.4, 163.6, 162.6, 155.7, 148.8, 138.5, 134.7, 132.5, 132.3, 130.9, 128.8, 127.8, 125.6, 123.6, 121.8, 72.5, 71.7, 56.9, 44.8, 43.6, 41.5, 36.0, 30.8, 23.7, 18.9, 16.5, 14.6 ppm.

Example 34

34.1

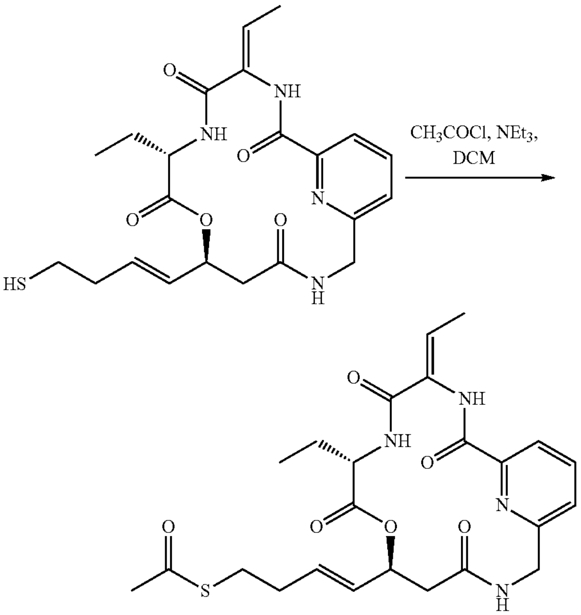

The Fmoc-L-Pra (3.00 mmol), EDCI (584 mg, 3.05 mmol) and DMAP (25 mg, 0.203 mmol) was dissolved in anhydrous dichloromethane (15 mL), DIPEA (0.50 mL, 3.05 mmol) and the alcohol (526 mg, 1.02 mmol) was added at 0° C., was stirred for 12 h at room temperature, and added diluted with methylene chloride. The reaction solution was washed with sodium bicarbonate solution (50 mL×3). The organic phase was washed with saturated brine, and dried over anhydrous sodium sulfate, concentrated and the residue was purified by silica gel column chromatography to give a pale yellow solid compound. $^1H$ NMR (400 MHz, $CDCl_3$): δ 7.77 (d, J=7.6 Hz, 2H), 7.61 (m, 2H), 7.42-7.32 (m 19H), 5.85-5.78 (m, 1H), 5.68 (dd, J=13.6, 7.2 Hz, 1H), 5.55 (dd, J=15.2, 7.2 Hz, 1H), 5.35 (d, J=8.8 Hz, 1H), 4.37 (t, J=6.8 Hz, 2H), 4.28 (dd, J=9.2, 4.4 Hz, 1H), 4.25 (t, J=7.2, 1H), 4.18 (t, J=8.4 Hz, 2H), 3.48 (s, 3H), 2.89 (t, J=7.2 Hz, 2H), 2.73 (dd, J=15.6, 7.6 Hz, 1H), 2.61 (dd, J=15.6, 5.6 Hz, 1H), 2.55 (t, J=7.2 Hz, 2H), 2.28 (dt, J=13.6, 6.8 Hz, 2H), 2.19 (m, 1H), 1.67 (m, 2H), 0.90-0.85 (m, 4H), 0.03 (s, 9H) ppm.

34.2

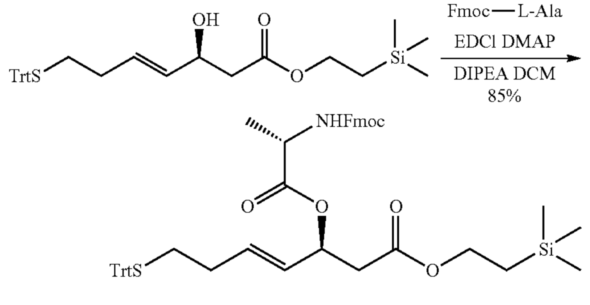

The reaction (0.80 mmol) was dissolved in acetonitrile (8 mL), diethylamine (0.25 mL, 2.44 mmol) was added and stirred for 2 h, decompressed and removed acetonitrile. The residue was purified by silica gel column chromatography and anhydrous oil was obtained. $^1H$ NMR (400 MHz, $CDCl_3$): δ 7.40-7.38 (m, 6H), 7.29-7.25 (m, 6H), 7.22-7.18 (m, 3H), 5.69-5.57 (m, 2H), 5.36 (dd, J=15.4 Hz, 7.4 Hz, 1H), 4.16-4.09 (m, 2H), 3.21 (d, J=4.8 Hz, 1H), 2.64 (dd, J=15.6 Hz, 8.4 Hz, 1H), 2.53 (dd, J=15.6 Hz, 5.2 Hz, 1H), 2.19-2.15 (m, 2H), 2.07-1.98 (m, 2H), 1.97-1.93 (m, 1H), 0.98-0.93 (m, 2H), 0.92 (d, J=6.8 Hz, 3H), 0.81 (d, J=6.8 Hz, 3H), 0.03 (s, 9H) ppm.

34.3

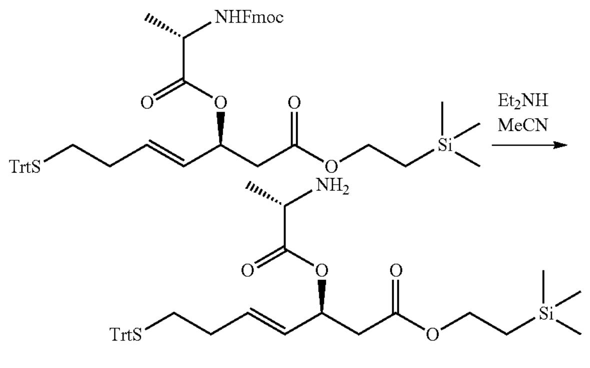

At 0° C., DIPEA (0.7 ml), the product (610 mg) of Example 16.5, HATU (760 mg), HOAT (326 mg) were sequentially added to the reactant (1 mmol) in DCM solution (10 ml), and raised to room temperature with stirring. After 8 h, the reaction was washed with saturated sodium bicarbonate solution, dilute hydrochloric acid solution, saturated sodium chloride solution, dried over anhydrous sodium sulfate. The product was filtered and spinned anhydrous by column chromatography and white flocculent solid solid was obtained. $^1H$ NMR (400 MHz, $CDCl_3$): δ 9.41 (s, 1H), 8.10 (d, J=7.6 Hz, 1H), 7.53 (d, J=7.6 Hz, 1H), 7.39-7.17 (m, 12H), 6.66-6.61 (m, 2H), 5.68-5.59 (m, 2H), 5.46 (s, 1H), 5.38-5.32 (m, 1H), 4.59 (dd, J=8.8 Hz, 4 Hz, 1H), 4.49 (d, J=4.2 Hz, 2H), 4.15-4.10 (m, 3H), 2.66 (dd, J=15.6 Hz, 7.6 Hz, 1H), 2.52 (dd, J=15.6 Hz, 5.6 Hz, 1H), 2.18-2.14 (m, 3H), 2.04 (t, J=6.8 Hz, 4H), 1.82 (d, J=7.2 Hz, 3H), 1.46 (s, 9H), 1.25 (t, J=6.8 Hz, 2H), 0.97-0.90 (m, 5H), 0.80 (d, J=6.8 Hz, 3H), 0.02 (s, 9H) ppm. $^{13}C$ NMR (125 MHz, $CDCl_3$) δ 171.0, 170.7, 169.5, 164.3, 162.6, 157.3, 155.9, 148.5, 144.7, 138.2, 133.9, 129.6, 129.4, 129.0, 127.7, 127.6, 126.5, 124.6, 121.1, 79.7, 77.2, 77.0, 76.7, 71.8, 66.5, 63.0, 60.3, 57.0, 45.6, 39.5, 31.5, 31.2, 31.0, 28.3, 20.9, 18.8, 17.5, 17.2, 14.1, 13.8, 0.9, −1.5, −1.6 ppm.

34.4

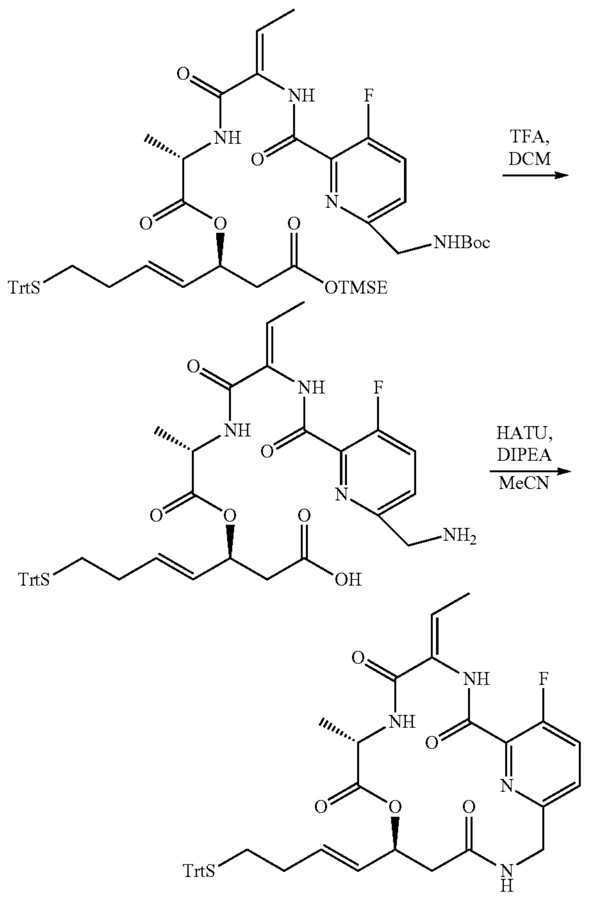

Tetrabutylammonium fluoride in tetrahydrofuran solution (1 mol/l, 2.3 ml) was added to the reaction (0.90 mmol) in redistilled THF (5 ml). After 3 h, the reaction was immediately spinned anhydrous by column chromatography to obtain a white solid. DCM solution (25 ml) of the resulting resultant was added trifluoroacetic acid (6 ml). After 5 h, spinned and removed DCM, the residue was added toluene (8 ml). Without further treatment, a brown viscous material was obtained after pumped organic solvent with oil pump. Chromatography pure acetonitrile (200 ml) obtained above was dissolved, slowly dropped in HATU (3 g), DIPEA (4 ml) of HPLC grade acetonitrile (550 ml). After 24 h, spinned anhydrous solvents, the product was diluted with ethyl acetate (20 ml) and then washed with saturated sodium bicarbonate solution, dilute hydrochloric acid solution, saturated sodium chloride solution and dried over anhydrous sodium sulfate. The product was filtered and spinned anhydrous by column chromatography and pale yellow solid was obtained. $^1$H NMR (400 MHz, $CDCl_3$): δ 9.17 (s, 1H), 8.10 (d, J=7.6 Hz, 1H), 7.87 (d, J=7.6 Hz, 1H), 7.37-7.16 (m, 15H), 7.07 (q, J=7.2 Hz, 1H), 6.43 (d, J=10.4 Hz, 1H), 5.62-5.56 (m, 2H), 5.39-5.34 (m, 1H), 5.06 (dd, J=17.2 Hz, 8 Hz, 1H), 4.74 (dd, J=6.4 Hz, 3.6 Hz, 1H), 4.19-4.08 (m, 2H), 2.69-2.64 (m, 2H), 2.30-2.27 (m, 1H), 2.21-2.17 (m, 2H), 1.84 (d, J=7.2 Hz, 3H), 0.79 (d, J=6.8 Hz, 3H), 0.59 (d, J=6.8 Hz, 3H) ppm. $^{13}$C NMR (125 MHz, DMSO) δ 133.64, 132.05, 131.39, 126.08, 124.66, 118.36, 111.05, 107.13, 100.97, 97.27, 95.22, 91.96, 90.37, 90.32, 89.54, 89.11, 87.45, 83.79, 39.76, 39.50, 39.25, 34.06, 29.13, 22.85, 19.48 ppm.

34.5

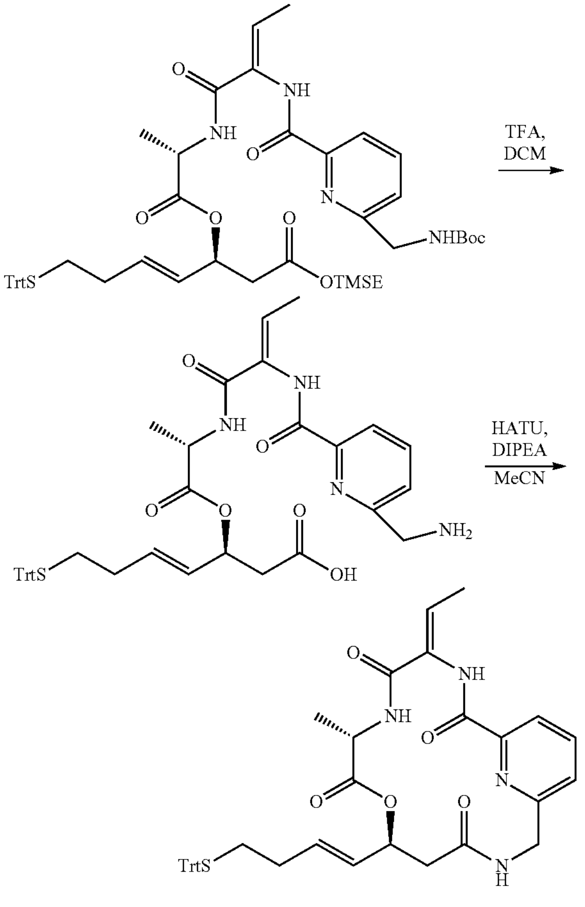

At 0° C., TES (0.1 ml), TFA (0.65 ml) were sequentially added to the reactants (0.21 mmol) in anhydrous DCM solution (5 ml). 15 min later, the product was directly spinned anhydrous solvent by column chromatography and pale yellow solid was obtained. $[\alpha]^{20}_D$: 6.13 (c 0.5, $CHCl_3$). $^1$H NMR (400 MHz, $CDCl_3$): δ 8.18 (d, J=7.6 Hz, 1H), 7.89 (d, J=7.6 Hz, 1H), 7.06 (dd, J=14.4 Hz J=7.2 Hz, 1H), 6.58 (dd, J=7.6 Hz, J=3.6 Hz, 1H), 6.45 (d, J=8 Hz, 1H), 5.74-5.64 (m, 2H), 5.50 (dd, J=15.6 Hz, J=6.8 Hz, 1H), 5.10 (m, 1H), 4.74 (dd, J=10 Hz, J=3.6 Hz, 1H), 4.34-4.28 (m, 1H), 2.74-2.69 (m, 2H), 2.56-2.50 (m, 2H), 2.34-2.29 (m, 3H), 1.36 (t, J=7.6 Hz, 1H), 0.80 (d, J=6.8 Hz, 3H), 0.6 (d, J=6.8 Hz, 3H) ppm. $^{13}$C NMR (125 MHz, $CDCl_3$) δ 169.6, 168.9, 163.6, 162.9, 155.7, 148.6, 138.3, 134.7, 132.4, 128.6, 127.0, 124.9, 121.4, 77.2, 76.9, 76.7, 71.9, 56.9, 43.3, 41.0, 36.0, 30.8, 23.7, 18.9, 16.5, 14.6 ppm.

Example 35

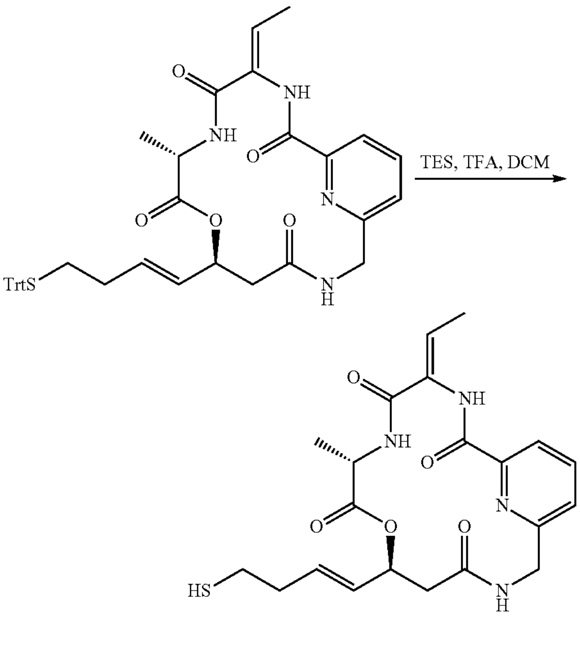

At 0° C., redistilled $NEt_3$ (0.04 ml) was added to the reactant (0.126 mmol) in anhydrous DCM (5 ml), stirred slightly, then added caprylate chloride (0.1 ml). After 7 h, The product was directly spinned anhydrous solvent by column chromatography and pale yellow solid was obtained. $[\alpha]^{20}_D$: 3.71 (c 0.5, $CHCl_3$). $^1$H NMR (400 MHz, $CDCl_3$): δ 9.21 (s, 1H), 8.10 (d, J=7.6 Hz, 1H), 7.91 (d, J=7.6 Hz, 1H), 7.06 (m, J=7.2 Hz, 1H), 6.70 (d, J=4.4 Hz, 1H), 6.46 (d, J=10 Hz, 1H), 5.70-5.64 (m, 2H), 5.59-5.46 (m, 1H), 5.13 (dd, J=17.2 Hz, 8 Hz, 1H), 4.73-4.70 (m, 2H), 4.27 (d, J=J=17.2 Hz, 1H), 2.85-2.71 (m, 4H), 2.62-2.61 (m, 1H), 2.49 (t, J=7.6 Hz, 3H), 2.29-2.23 (m, 3H), 1.84-1.81 (m, 3H), 1.61-1.58 (m, 2H), 1.24 (s, 11H), 0.86-0.57 (m, 7H), 0.53 (d, J=7.6 Hz, 3H) ppm. $^{13}$C NMR (125 MHz, $CDCl_3$) δ 199.5, 169.6, 169.1, 167.6, 165.7, 163.7, 162.3, 155.8, 148.6, 138.5, 134.7, 132.5, 132.2, 130.8, 128.7, 128.2, 127.2, 124.9, 121.3, 77.2, 77.0, 76.7, 72.0, 71.6, 56.9, 44.0, 43.2, 40.8, 38.5, 33.7, 32.1, 31.5, 30.8, 29.6, 29.0, 28.8, 28.8, 27.7, 27.6, 25.5, 24.7, 22.5, 19.0, 18.9, 16.4, 14.6, 13.9 ppm.

Example 36

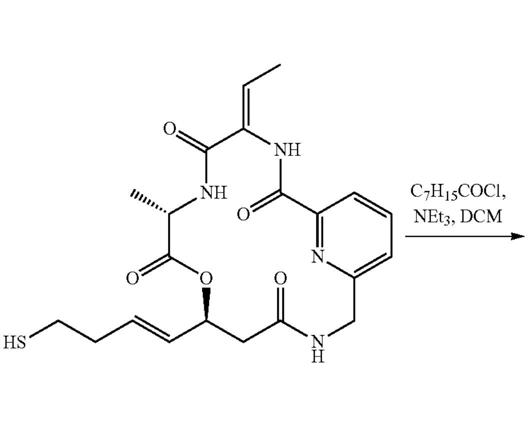

-continued

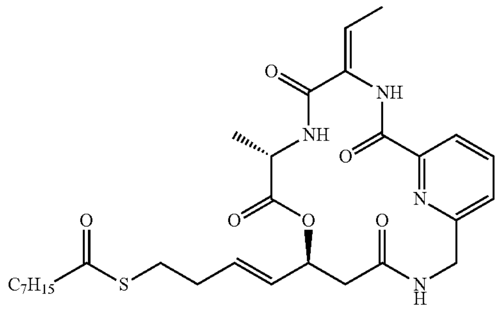

At 0° C., redistilled $NEt_3$ (0.02 ml) was added to the reactant (0.063 mmol) in anhydrous DCM (2 ml), stirred slightly, then added acetyl chloride (0.05 ml). After 7 h, The product was directly spinned anhydrous solvent by column chromatography and pale yellow solid was obtained. $[\alpha]^{20}_{D}$: 4.66 (c 0.6, $CHCl_3$). $^1H$ NMR (400 MHz, $CDCl_3$): δ 9.26 (s, 1H), 8.15 (d, J=7.8 Hz, 1H), 7.98 (d, J=7.6 Hz, 1H), 7.09 (d, J=7.2 Hz, 1H), 6.79 (d, J=4.4 Hz, 1H), 6.47 (d, J=10.0 Hz, 1H), 5.73-5.70 (m, 2H), 5.53 (m, 1H), 5.18 (dd, J=17.2 Hz, 8.0 Hz, 1H), 4.77 (m, 2H), 4.28 (d, J=17.2 Hz, 1H), 2.88-2.78 (m, 4H), 2.67 (m, 1H), 2.49 (t, J=7.8 Hz, 3H), 2.36-2.33 (m, 3H), 1.89-1.86 (m, 3H), 0.88 (m, 3H), 0.78 (d, J=7.6 Hz, 3H), 0.58 (d, J=7.6 Hz, 3H) ppm. $^{13}C$ NMR (125 MHz, $CDCl_3$) δ 169.8, 169.3, 163.5, 162.5, 155.8, 148.8, 138.7, 134.7, 132.8, 132.3, 130.9, 128.8, 128.7, 127.7, 125.6, 121.7, 72.5, 71.9, 57.9, 44.7, 43.9, 41.6, 38.9, 33.8, 32.9, 31.9, 30.9, 29.8, 29.5, 28.8, 27.7, 15.0 ppm.

Example 37

37.1

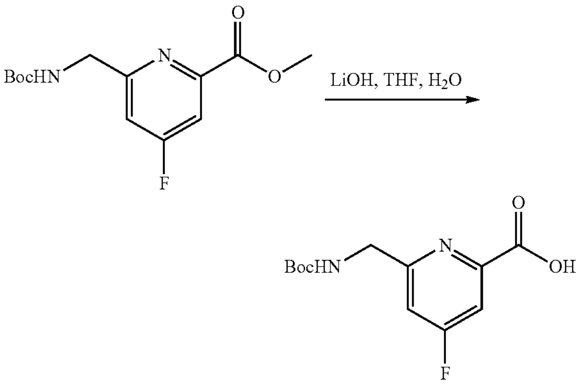

15 ml LiOH aqueous solution (19 mmol) were added dropwise to the reactant (7.6 mmol) of 30 ml THF, then reacted 2 h at room temperature. The reaction solution was adjusted by dilute hydrochloric acid to with the pH value of 3, then 100 ml ethyl acetate was added. The organic matter was washed by water and saturated salt water. The organic layer was dried by anhydrous sodium sulfate, and the solvent evaporated to give a white flocculent solid. $^1H$ NMR (400 MHz, $CDCl_3$): δ 8.05 (s, J=8.0 Hz, 1H), 7.75 (s, 1H), 7.61 (s, 1H), 5.55 (s, 1H), 4.48 (d, J=4.2 Hz, 2H), 1.34 (s, 9H) ppm.

37.2

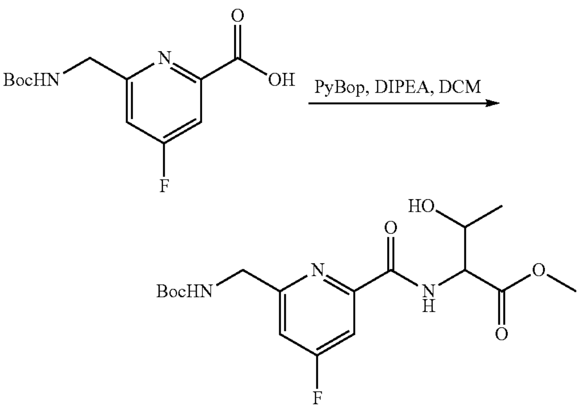

At 0° C., S2 (2.7 mmol), PyBop (4 mmol) were added to the reactant (2.7 mmol), stirred slightly, then added, and then stirred at room temperature overnight. The reaction solution was washed with saturated sodium bicarbonate solution, dilute hydrochloric acid solution, saturated sodium chloride solution. The product was dried with anhydrous sodium sulfate and spinned solvent by column chromatography and white floc was obtained. $^1H$ NMR (400 MHz, $CDCl_3$): δ 8.64 (d, J=8.4 Hz, 1H), 7.51 (s, 1H), 7.44 (s, 1H), 5.44 (s, 1H), 4.48-4.45 (m, J=3H), 3.78 (s, 3H), 1.45 (s, 9H), 1.26 (d, J=5.6 Hz, 3H) ppm. $^{13}C$ NMR (100 MHz, $CDCl_3$) δ 171.1, 164.6, 157.4, 156.0, 148.9, 137.9, 134.6, 124.2, 121.8, 121.0, 80.7, 79.8, 78.7, 70.3, 68.2, 61.1, 57.8, 52.7, 52.2, 47.7, 32.1, 28.3, 28.2, 28.1, 28.0, 22.6, 19.8 ppm.

37.3

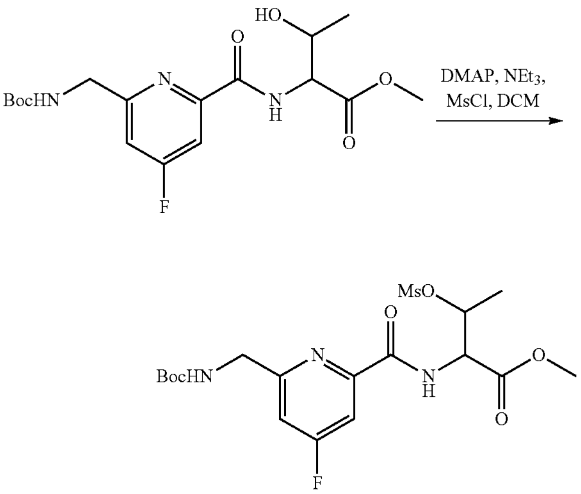 [SMILES: COC(=O)C(NC(=O)c1cc(F)cc(CNC(=O)OC(C)(C)C)n1)C(C)O ; COC(=O)C(NC(=O)c1cc(F)cc(CNC(=O)OC(C)(C)C)n1)C(C)OS(C)(=O)=O]

At 0° C., DMAP (0.184 mmol), $NEt_3$ (3 mmol), MsCl (2.4 mmol) were added to anhydrous DCM (10 ml) of the reactants (1.84 mmol) successively, then raised to room temperature and stirred overnight. The product was spinned anhydrous, pumped with oil pump and directly put into next step.

37.4

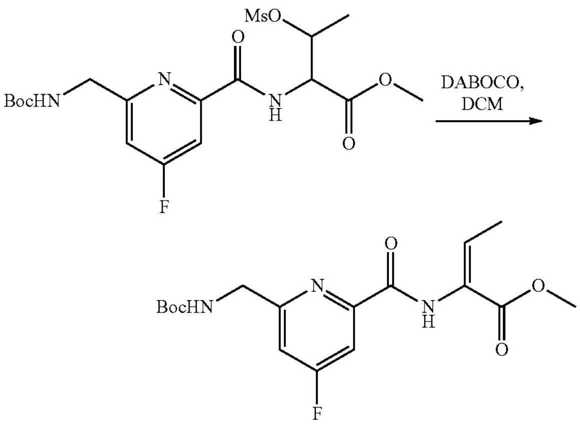

DABOCO (9.22 mmol) was added to anhydrous DCM liquid (10 ml) obtained above, and stirred 8 h at room temperature. The reaction solution was washed by saturated sodium bicarbonate solution, saturated ammonium chloride solution, saturated sodium chloride solution in sequence, and dried by anhydrous sodium sulfate. The product was filtered and spinned solvent by column chromatography and white floc was obtained. $^{1}H$ NMR (400 MHz, $CDCl_3$): δ 9.38 (s, 1H), 7.45 (s, 1H), 7.41 (s, 1H), 6.86 (q, J=7.6 Hz, 1H), 5.57 (s, 1H), 4.44 (d, J=5.6 Hz, 1H), 3.74 (s, 9H), 1.80 (d, J=7.6 Hz, 3H), 1.40 (s, 9H) ppm. $^{13}C$ NMR (100 MHz, $CDCl_3$) δ 164.8, 162.1, 157.4, 156.0, 148.9, 148.8, 138.1, 133.9, 126.3, 124.2, 121.7, 121.0, 79.7, 52.1, 45.9, 28.3, 14.6 ppm.

37.5

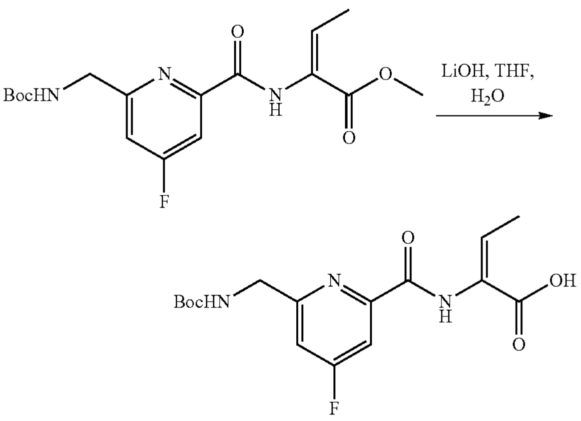

5 ml LiOH aqueous solution (3.6 mmol) were added dropwise to reactants (1.44 mmol) with THF (10 ml), then spinned anhydrous the organic phase after three hours. 10 ml water and 15 ml ethyl acetate were added to the organic phase. The aqueous phase was removed after liquid separation. Then the solution was added 15 ml ethyl acetate, adjusted the acid. Anhydrous sodium sulfate was used for the separation of organic phase after liquid separation. White floc solid was obtained after spinned anhydrous. $^{1}H$ NMR (400 MHz, $CDCl_3$): δ 9.40 (s, 1H), 8.03 (s, 1H), 7.11 (s, 1H), 6.88 (q, J=7.8 Hz, 1H), 5.58 (s, 1H), 3.76 (s, 9H), 1.83 (d, J=7.8 Hz, 3H), 1.43 (s, 9H) ppm. $^{13}C$ NMR (100 MHz, $CDCl_3$) δ 165.3, 162.7, 157.8, 156.2, 149.0, 148.8, 138.3, 133.7, 126.5, 124.5, 121.9, 121.0, 52.5, 46.3, 28.5, 14.8 ppm.

37.6

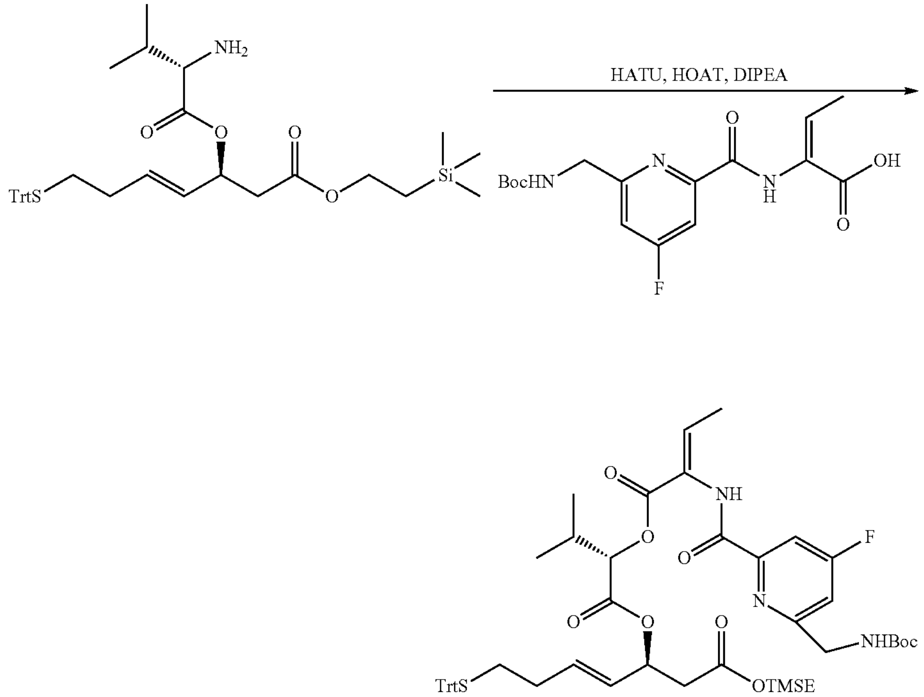

At 0° C., DIPEA (0.7 ml), carboxylic acid, HATU, HOAT were added to the reactant (1 mmol) in DCM solution (10 ml) sequentially. Then raised to room temperature with stirring. After 8 h, the reaction was washed with saturated sodium bicarbonate solution, dilute hydrochloric acid solution, saturated sodium chloride solution, and dried over anhydrous sodium sulfate. The product was filtered and spinned solvent by column chromatography and white flocculent solid was obtained. $^1$H NMR (400 MHz, $CDCl_3$): δ 9.41 (s, 1H), 7.51 (s, 1H), 7.48 (s, 1H), 7.39-7.17 (m, 12H), 6.66-6.61 (m, 2H), 5.68-5.59 (m, 2H), 5.46 (s, 1H), 5.38-5.32 (m, 1H), 4.59 (dd, J=8.8 Hz, 4 Hz, 1H), 4.49 (d, J=4.2 Hz, 1H), 4.15-4.10 (m, 3H), 2.66 (dd, J=15.6 Hz, 7.6 Hz, 1H), 2.52 (dd, J=15.6 Hz, 5.6 Hz, 1H), 2.18-2.14 (m, 3H), 2.04 (t, J=6.8 Hz, 4H), 1.82 (d, J=7.2 Hz, 3H), 1.46 (s, 9H), 1.25 (t, J=6.8 Hz, 2H), 0.97-0.90 (m, 5H), 0.80 (d, J=6.8 Hz, 3H), 0.02 (s, 9H) ppm. $^{13}$C NMR (125 MHz, $CDCl_3$) δ 171.0, 170.7, 169.5, 164.3, 162.6, 157.3, 155.9, 148.5, 144.7, 138.2, 133.9, 129.6, 129.4, 129.0, 127.7, 127.6, 126.5, 124.6, 121.1, 79.7, 71.8, 66.5, 63.0, 60.3, 57.0, 45.6, 39.5, 31.5, 31.2, 31.0, 28.3, 20.9, 18.8, 17.5, 17.2, 14.1, 13.8, 0.9, −1.5, −1.6 ppm.

37.7

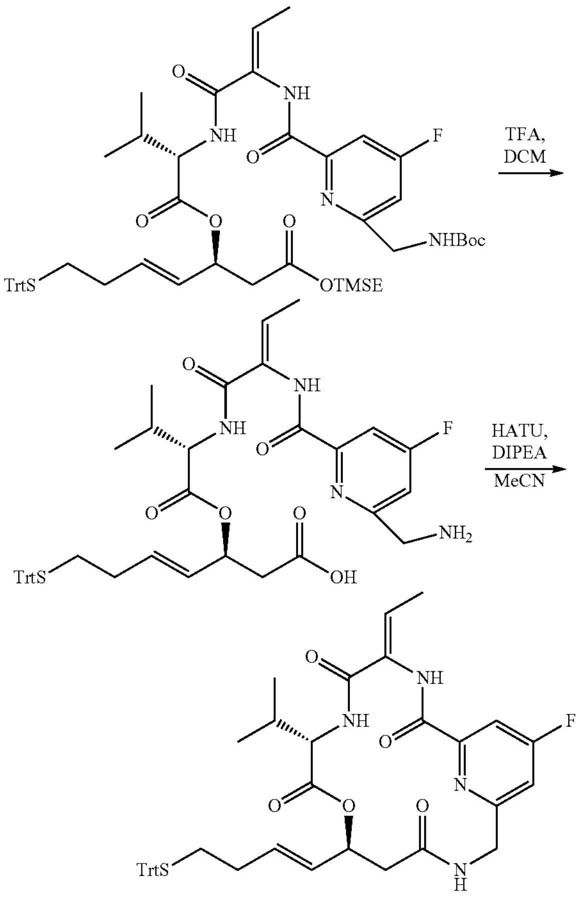

Tetrabutylammonium fluoride in tetrahydrofuran solution (1 mol/l, 2.3 ml) was added to the reaction (0.92 mmol) in redistilled THF (5 ml). After 3 h, the reaction was immediately spinned anhydrous by column chromatography to obtain a white solid. DCM solution (25 ml) of the resulting resultant was added trifluoroacetic acid (6 ml). After 5 h, spinned and removed DCM, the residue was added toluene (8 ml). Without further treatment, a brown viscous material was obtained after pumped organic solvent with oil pump. Chromatography pure acetonitrile (200 ml) obtained above was dissolved, slowly dropped in HATU (3 g), DIPEA (4 ml) of HPLC grade acetonitrile (550 ml). After 24 h, spinned anhydrous solvents, the product was diluted with ethyl acetate (20 ml) and then washed with saturated sodium bicarbonate solution, dilute hydrochloric acid solution, saturated sodium chloride solution and dried over anhydrous sodium sulfate. The product was filtered and spinned anhydrous by column chromatography and 540 mg pale yellow solid was obtained. The yield was 82%. $^1$H NMR (400 MHz, $CDCl_3$): δ 9.17 (s, 1H), 8.10 (s, 1H), 7.37-7.16 (m, 15H), 7.07 (q, J=7.2 Hz, 1H), 6.67 (d, J=4.4 Hz, 1H), 6.51 (d, J=10.3 Hz, 1H), 5.62-5.56 (m, 2H), 5.39-5.34 (m, 1H), 5.06 (dd, J=17.2 Hz, 8 Hz, 1H), 4.74 (dd, J=6.4 Hz, 3.6 Hz, 1H), 4.19-4.08 (m, 2H), 2.69-2.64 (m, 2H), 2.30-2.27 (m, 1H), 2.21-2.17 (m, 2H), 1.84 (d, J=7.2 Hz, 3H), 0.79 (d, J=6.8 Hz, 3H), 0.59 (d, J=6.8 Hz, 3H) ppm. $^{13}$C NMR (125 MHz, DMSO) δ 133.6, 132.0, 131.3, 126.1, 124.7, 118.4, 111.1, 107.1, 101.0, 97.3, 95.2, 92.0, 90.4, 90.3, 89.5, 89.1, 87.5, 83.8, 39.8, 39.5, 39.3, 34.1, 29.1, 22.9, 19.5 ppm.

37.8

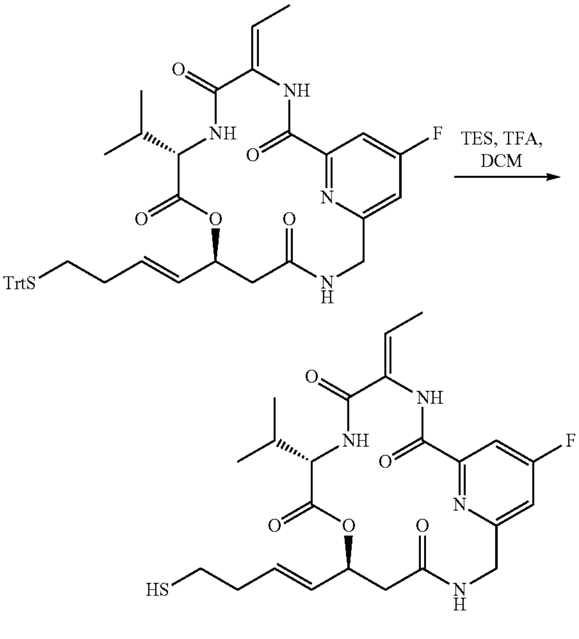

At 0° C., TES (0.1 ml), TFA (0.65 ml) were added to the reactants (0.21 mmol) in anhydrous DCM solution (5 ml) sequentially. 15 min later, the product was directly spinned anhydrous solvent by column chromatography and pale yellow solid was obtained. $[\alpha]^{20}_D$: 6.13 (c 0.5, $CHCl_3$). $^1$H NMR (400 MHz, $CDCl_3$): δ 8.18 (s, 1H), 7.41 (s, 1H), 7.06 (dd, J=14.4 Hz J=7.2 Hz, 1H), 6.58 (dd, J=7.6 Hz, J=3.6 Hz, 1H), 6.45 (s, 1H), 5.74-5.64 (m, 2H), 5.50 (dd, J=15.6 Hz, J=6.8 Hz, 1H), 5.10 (m, 1H), 4.74 (dd, J=10 Hz, J=3.6 Hz, 1H), 4.34-4.28 (m, 1H), 2.74-2.69 (m, 2H), 2.56-2.50 (m, 2H), 2.34-2.29 (m, 3H), 1.36 (t, J=7.6 Hz, 1H), 0.80 (d, J=6.8 Hz, 3H), 0.6 (d, J=6.8 Hz, 3H) ppm. $^{13}$C NMR (125 MHz, $CDCl_3$) δ 169.6, 168.9, 163.6, 162.9, 155.7, 148.6, 138.3, 134.7, 132.4, 128.6, 127.0, 124.9, 121.4, 71.9, 56.9, 43.3, 41.0, 36.0, 30.8, 23.7, 18.9, 16.5, 14.6 ppm.

Example 38

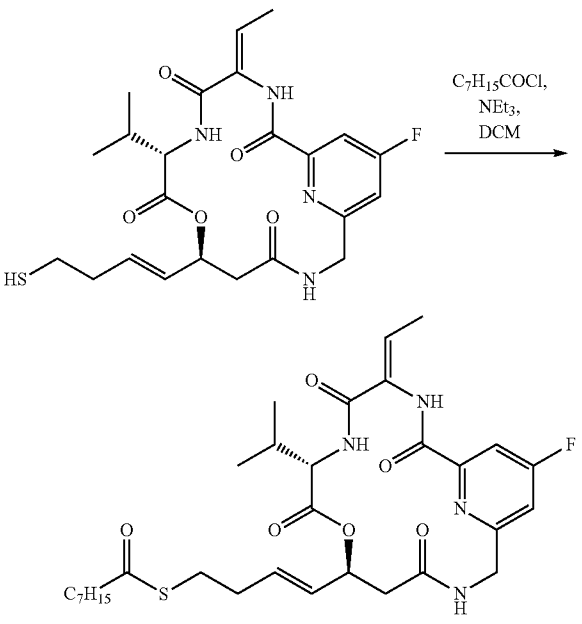

At 0° C., redistilled $NEt_3$ (0.04 ml) was added to the reactant (0.126 mmol) in anhydrous DCM (5 ml), stirred slightly, then added caprylate chloride (0.1 ml). After 7 h, The product was directly spinned anhydrous solvent by column chromatography and pale yellow solid was obtained. $[\alpha]^{20}_{D}$: 3.71 (c 0.5, $CHCl_3$). $^1H$ NMR (400 MHz, $CDCl_3$): δ 9.21 (s, 1H), 8.10 (s, J=7.6 Hz, 1H), 7.91 (s, 1H), 7.06 (m, J=7.2 Hz, 1H), 6.70 (s, 1H), 6.46 (d, J=10 Hz, 1H), 5.70-5.64 (m, 2H), 5.59-5.46 (m, 1H), 5.13 (dd, J=17.2 Hz, 8 Hz, 1H), 4.73-4.70 (m, 2H), 4.27 (d, J=J=17.2 Hz, 1H), 2.85-2.71 (m, 4H), 2.62-2.61 (m, 1H), 2.49 (t, J=7.6 Hz, 3H), 2.29-2.23 (m, 3H), 1.84-1.81 (m, 3H), 1.61-1.58 (m, 2H), 1.24 (s, 11H), 0.86-0.57 (m, 7H), 0.53 (d, J=7.6 Hz, 3H) ppm. $^{13}C$ NMR (125 MHz, $CDCl_3$) δ169.6, 169.1, 167.6, 165.7, 163.7, 162.3, 155.8, 148.6, 138.5, 134.7, 132.5, 132.2, 130.8, 128.7, 128.2, 127.2, 124.9, 121.3, 72.0, 71.6, 56.9, 44.0, 43.2, 40.8, 38.5, 33.7, 32.1, 31.5, 30.8, 29.6, 29.0, 28.8, 28.8, 27.7, 27.6, 25.5, 24.7, 22.5, 19.0, 18.9, 16.4, 14.6, 13.9 ppm.

Example 39

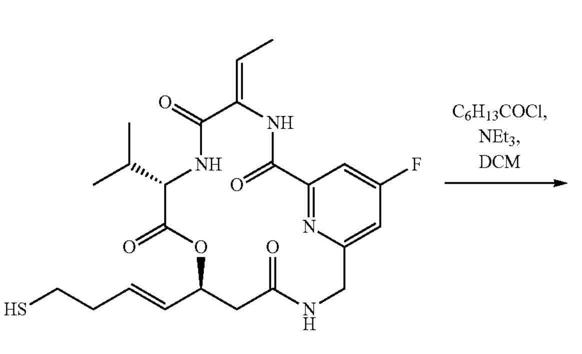

-continued

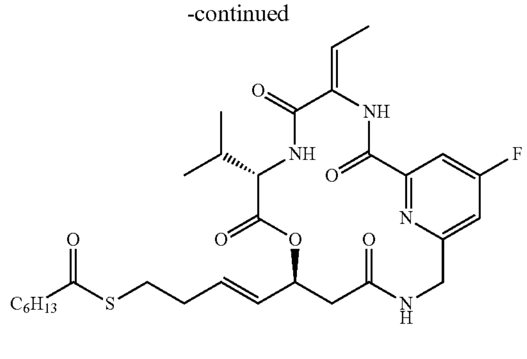

At 0° C., redistilled $NEt_3$ (0.02 ml) was added to the reactant (0.063 mmol) in anhydrous DCM (2 ml), stirred slightly, then added heptanoyl chloride (0.05 ml). After 7 h, The product was directly spinned anhydrous solvent by column chromatography and 31 mg pale yellow solid was obtained. $[\alpha]^{20}_{D}$: 4.11 (c 0.7, $CHCl_3$). $^1H$ NMR (400 MHz, $CDCl_3$): δ 9.23 (s, 1H), 8.12 (d, J=7.8 Hz, 1H), 7.93 (s, 1H), 7.08 (m, J=7.2 Hz, 1H), 6.73 (s, 1H), 6.48 (d, J=10 Hz, 1H), 5.72-5.63 (m, 2H), 5.62-5.45 (m, 1H), 5.15 (dd, J=17.2 Hz, 8 Hz, 1H), 4.75-4.71 (m, 2H), 4.28 (d, J=17.2 Hz, 1H), 2.86-2.71 (m, 4H), 2.63-2.62 (m, 1H), 2.50 (t, J=7.8 Hz, 3H), 2.30-2.25 (m, 3H), 1.85-1.82 (m, 3H), 1.62-1.59 (m, 2H), 1.26-1.24 (m, 9H), 0.85 (m, 3H), 0.78 (d, J=7.6 Hz, 3H), 0.57 (d, J=7.6 Hz, 3H) ppm. $^{13}C$ NMR (125 MHz, $CDCl_3$) δ 169.5, 169.0, 163.5, 162.1, 155.7, 148.8, 138.6, 134.5, 132.6, 132.1, 130.9, 128.9, 128.5, 127.5, 125.1, 121.3, 72.2, 71.7, 57.3, 44.1, 43.2, 40.9, 38.6, 33.8, 32.2, 31.5, 30.9, 29.7, 29.1, 28.8, 27.7, 27.6, 25.5, 22.5, 19.1, 18.9, 16.4, 14.6, 14.0 ppm.

Example 40

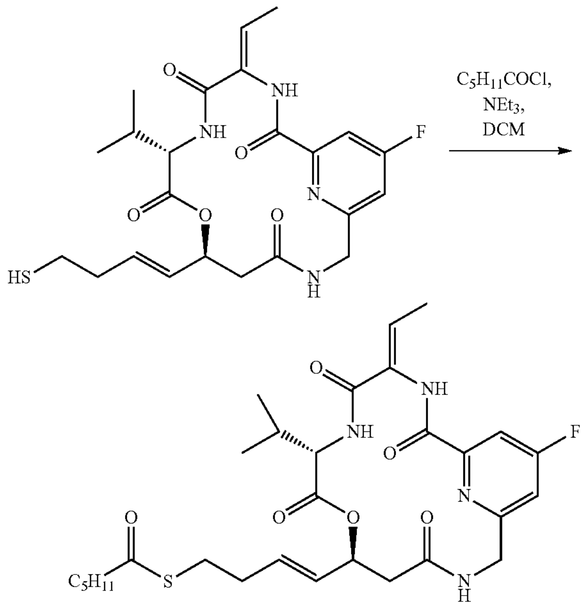

At 0° C., redistilled $NEt_3$ (0.02 ml) was added to the reactant (0.063 mmol) in anhydrous DCM (2 ml), stirred slightly, then added hexanoyl chloride (0.04 ml). After 7 h, The product was directly spinned anhydrous solvent by column chromatography and pale yellow solid was obtained.

[α]$^{20}_{D}$: 3.11 (c 0.3, $CHCl_3$). $^1$H NMR (400 MHz, $CDCl_3$): δ 9.22 (s, 1H), 8.10 (d, J=7.8 Hz, 1H), 7.95 (s, 1H), 7.06 (m, J=7.2 Hz, 1H), 6.75 (s, 1H), 6.46 (d, J=10.0 Hz, 1H), 5.74-5.68 (m, 2H), 5.50 (m, 1H), 5.17 (dd, J=17.2 Hz, 8.0 Hz, 1H), 4.76-4.73 (m, 2H), 4.28 (d, J=17.2 Hz, 1H), 2.88-2.75 (m, 4H), 2.63 (m, 1H), 2.49 (t, J=7.8 Hz, 3H), 2.30-2.25 (m, 3H), 1.84-1.82 (m, 3H), 1.63-1.60 (m, 2H), 1.26-1.24 (m, 7H), 0.84 (m, 3H), 0.79 (d, J=7.6 Hz, 3H), 0.59 (d, J=7.6 Hz, 3H) ppm. $^{13}$C NMR (125 MHz, $CDCl_3$) δ 169.3, 169.0, 163.2, 162.0, 155.6, 148.9, 138.8, 134.8, 132.7, 132.0, 130.9, 128.9, 128.6, 127.7, 125.3, 121.5, 72.3, 71.8, 57.5, 44.3, 43.4, 41.2, 38.9, 33.9, 32.5, 31.7, 30.9, 29.8, 29.2, 28.9, 27.8, 27.6, 25.6, 22.6, 19.0, 16.5, 14.7, 13.9 ppm.

Example 41

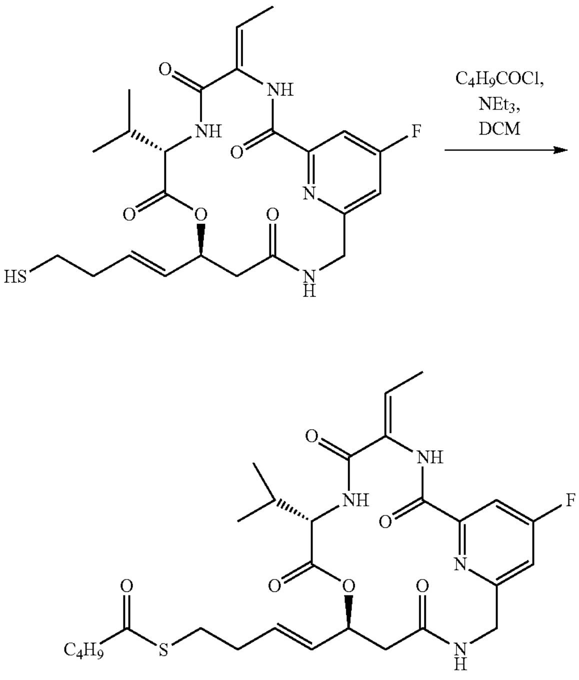

At 0° C., redistilled $NEt_3$ (0.02 ml) was added to the reactant (0.063 mmol) in anhydrous DCM (2 ml), stirred slightly, then added pivaloyl chloride (0.04 ml). After 7 h, The product was directly spinned anhydrous solvent by column chromatography and pale yellow solid was obtained. [α]$^{20}_{D}$: 3.11 (c 0.3, $CHCl_3$). $^1$H NMR (400 MHz, $CDCl_3$): δ 9.22 (s, 1H), 8.10 (d, J=7.8 Hz, 1H), 7.95 (s, 1H), 7.06 (m, J=7.2 Hz, 1H), 6.75 (s, 1H), 6.46 (d, J=10.0 Hz, 1H), 5.74-5.68 (m, 2H), 5.50 (m, 1H), 5.17 (dd, J=17.2 Hz, 8.0 Hz, 1H), 4.76-4.73 (m, 2H), 4.28 (d, J=17.2 Hz, 1H), 2.88-2.75 (m, 4H), 2.63 (m, 1H), 2.49 (t, J=7.8 Hz, 3H), 2.30-2.25 (m, 3H), 1.84-1.82 (m, 3H), 1.63-1.60 (m, 2H), 1.26-1.24 (m, 7H), 0.84 (m, 3H), 0.79 (d, J=7.6 Hz, 3H), 0.59 (d, J=7.6 Hz, 3H) ppm. $^{13}$C NMR (125 MHz, $CDCl_3$) δ 169.3, 169.0, 163.2, 162.0, 155.6, 148.9, 138.8, 134.8, 132.7, 132.0, 130.9, 128.9, 128.6, 127.7, 125.3, 121.5, 72.3, 71.8, 57.5, 44.3, 43.4, 41.2, 38.9, 33.9, 32.5, 31.7, 30.9, 29.8, 29.2, 28.9, 27.8, 27.6, 25.6, 22.6, 19.0, 16.5, 14.7, 13.9 ppm.

Example 42

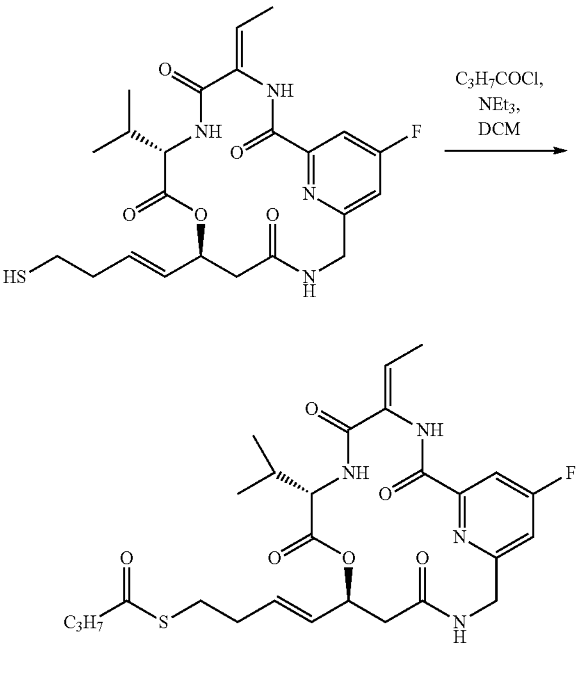

At 0° C., redistilled $NEt_3$ (0.02 ml) was added to the reactant (0.063 mmol) in anhydrous DCM (2 ml), stirred slightly, then added butyryl chloride (0.05 ml). After 7 h, The product was directly spinned anhydrous solvent by column chromatography and pale yellow solid was obtained. [α]$^{20}_{D}$: 6.51 (c 0.5, $CHCl_3$). $^1$H NMR (400 MHz, $CDCl_3$): δ 9.23 (s, 1H), 8.12 (d, J=7.8 Hz, 1H), 7.98 (s, 1H), 7.09 (s, 1H), 6.75 (d, J=4.4 Hz, 1H), 6.47 (d, J=10.0 Hz, 1H), 5.76-5.71 (m, 2H), 5.53 (m, 1H), 5.18 (dd, J=17.2 Hz, 8.0 Hz, 1H), 4.77-4.74 (m, 2H), 4.27 (d, J=17.2 Hz, 1H), 2.88-2.74 (m, 4H), 2.63 (m, 1H), 2.49 (t, J=7.8 Hz, 3H), 2.33-2.28 (m, 3H), 1.86-1.83 (m, 3H), 1.66-1.62 (m, 2H), 1.27-1.24 (m, 3H), 0.86 (m, 3H), 0.79 (d, J=7.6 Hz, 3H), 0.56 (d, J=7.6 Hz, 3H) ppm. $^{13}$C NMR (125 MHz, $CDCl_3$) δ 169.4, 169.1, 163.5, 162.3, 155.8, 148.8, 138.9, 134.7, 132.9, 132.3, 130.9, 128.9, 128.4, 127.5, 125.3, 121.5, 72.2, 71.7, 57.6, 44.5, 43.6, 41.4, 38.9, 33.9, 32.7, 31.7, 30.9, 29.9, 29.5, 28.9, 27.7, 25.8, 22.9, 19.3, 15.5, 13.8 ppm.

Example 43

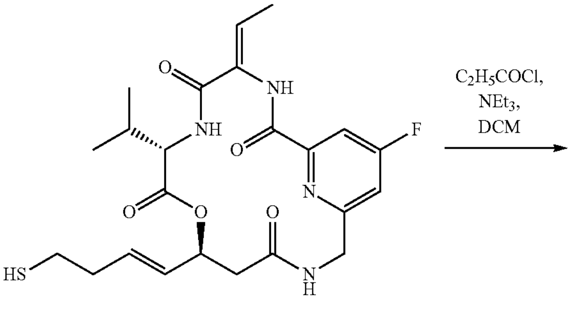

-continued

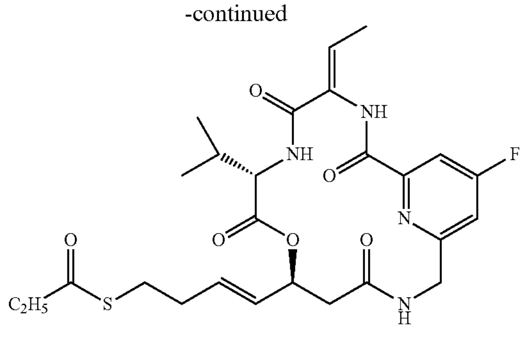

At 0° C., redistilled $NEt_3$ (0.02 ml) was added to the reactant (0.063 mmol) in anhydrous DCM (2 ml), stirred slightly, propionyl chloride (0.05 ml) was added. After 7 h, The product was directly spinned anhydrous solvent by column chromatography and pale yellow solid was obtained. $[\alpha]^{20}_{D}$: 5.50 (c 0.3, $CHCl_3$). $^1$H NMR (400 MHz, $CDCl_3$): δ 9.25 (s, 1H), 8.14 (d, J=7.8 Hz, 1H), 7.99 (d, J=7.6 Hz, 1H), 7.08 (s, 1H), 6.77 (s, 1H), 6.48 (d, J=10.0 Hz, 1H), 5.75-5.72 (m, 2H), 5.55 (m, 1H), 5.19 (dd, J=17.2 Hz, 8.0 Hz, 1H), 4.78-4.75 (m, 2H), 4.28 (d, J=17.2 Hz, 1H), 2.89-2.75 (m, 4H), 2.65 (m, 1H), 2.48 (t, J=7.8 Hz, 3H), 2.35-2.29 (m, 3H), 1.88-1.85 (m, 3H), 1.66 (m, 2H), 0.86 (m, 3H), 0.77 (d, J=7.6 Hz, 3H), 0.57 (d, J=7.6 Hz, 3H) ppm. $^{13}$C NMR (125 MHz, $CDCl_3$) δ 169.6, 169.2, 163.3, 162.2, 155.9, 148.9, 138.8, 134.8, 132.9, 132.2, 130.8, 128.9, 128.5, 127.6, 125.5, 121.6, 72.3, 71.8, 57.8, 44.6, 43.7, 41.5, 38.8, 33.9, 32.8, 31.8, 30.8, 29.9, 29.6, 28.9, 27.8, 25.9, 22.9, 19.5, 14.8 ppm.

Example 44

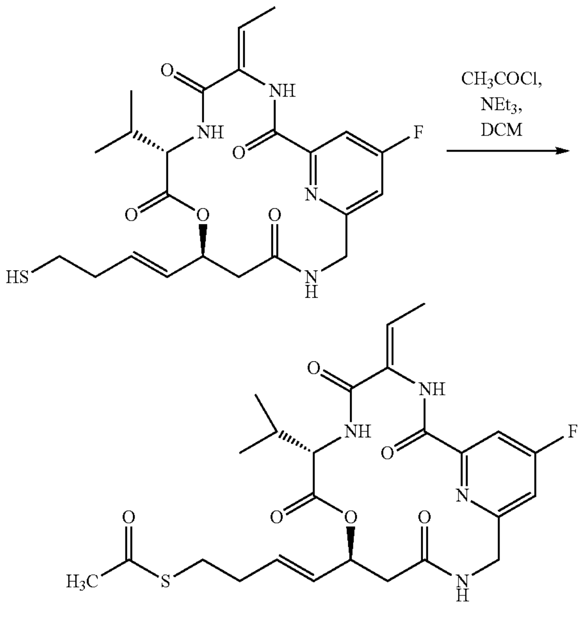

At 0° C., redistilled $NEt_3$ (0.02 ml) was added to the reactant (0.063 mmol) in anhydrous DCM (2 ml), stirred slightly, acetyl chloride (0.05 ml) was added. After 7 h, the product was directly spinned anhydrous solvent by column chromatography and pale yellow solid was obtained. $[\alpha]^{20}_{D}$: 4.66 (c 0.6, $CHCl_3$). $^1$H NMR (400 MHz, $CDCl_3$): δ 9.26 (s, 1H), 8.15 (d, J=7.8 Hz, 1H), 7.98 (d, J=7.6 Hz, 1H), 7.09 (s, 1H), 6.79 (s, 1H), 6.47 (d, J=10.0 Hz, 1H), 5.73-5.70 (m, 2H), 5.53 (m, 1H), 5.18 (dd, J=17.2 Hz, 8.0 Hz, 1H), 4.77 (m, 2H), 4.28 (d, J=17.2 Hz, 1H), 2.88-2.78 (m, 4H), 2.67 (m, 1H), 2.49 (t, J=7.8 Hz, 3H), 2.36-2.33 (m, 3H), 1.89-1.86 (m, 3H), 0.88 (m, 3H), 0.78 (d, J=7.6 Hz, 3H), 0.58 (d, J=7.6 Hz, 3H) ppm. $^{13}$C NMR (125 MHz, $CDCl_3$) δ 169.8, 169.3, 163.5, 162.5, 155.8, 148.8, 138.7, 134.7, 132.8, 132.3, 130.9, 128.8, 128.7, 127.7, 125.6, 121.7, 72.5, 71.9, 57.9, 44.7, 43.9, 41.6, 38.9, 33.8, 32.9, 31.9, 30.9, 29.8, 29.5, 28.8, 27.7, 15.0 ppm.

Example 45

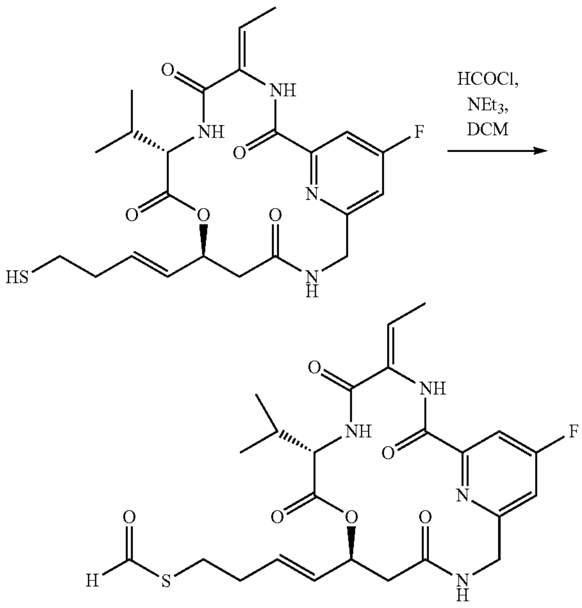

At 0° C., redistilled $NEt_3$ (0.02 ml) was added to the reactant (0.063 mmol) in anhydrous DCM (2 ml), stirred slightly, methanesulfonyl chloride (0.02 ml) was added. After 7 h, the product was directly spinned anhydrous solvent by column chromatography and pale yellow solid was obtained. $[\alpha]^{20}_{D}$: 1.96 (c 0.1, $CHCl_3$). $^1$H NMR (400 MHz, $CDCl_3$): δ 9.63 (s, 1H), 9.23 (s, 1H), 8.16 (d, J=7.6 Hz, 1H), 7.88 (s, 1H), 7.07 (dd, J=14.4 Hz, J=7.2 Hz, 1H), 6.56 (dd, J=7.6 Hz, J=3.6 Hz, 1H), 6.48 (s, 1H), 5.73 (m, 2H), 5.52 (dd, J=15.6 Hz, J=6.8 Hz, 1H), 5.12 (m, 1H), 4.76 (dd, J=10 Hz, J=3.6 Hz, 1H), 4.33 (m, 1H), 2.72 (m, 2H), 2.53 (m, 2H), 2.34-2.29 (m, 3H), 1.38 (t, J=7.6 Hz, 1H), 0.82 (d, J=6.8 Hz, 3H), 0.62 (d, J=6.8 Hz, 3H) ppm. $^{13}$C NMR (125 MHz, $CDCl_3$) δ 176.5, 169.8, 169.4, 163.6, 162.6, 155.7, 148.8, 138.5, 134.7, 132.5, 132.3, 130.9, 128.8, 127.8, 125.6, 121.8, 72.5, 71.7, 56.9, 44.8, 43.6, 41.5, 36.0, 30.8, 23.7, 18.9, 16.5, 14.6 ppm.

Example 46

46.1

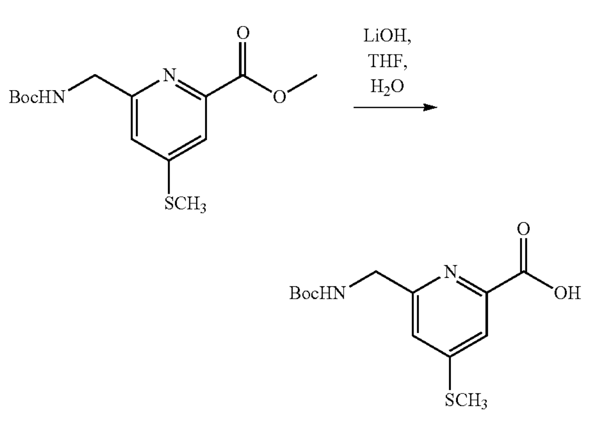

15 ml LiOH aqueous solution (19 mmol) were added dropwise to the reactant (7.6 mmol) of 30 ml THF, then reacted 2 h at room temperature. The reaction solution was adjusted by dilute hydrochloric acid to with the pH value of 3, then 100 ml ethyl acetate was added. The organic matter was washed by water and saturated salt water. The organic layer was dried by anhydrous sodium sulfate, and the solvent evaporated to give a white flocculent solid. $^1H$ NMR (400 MHz, $CDCl_3$): δ7.77 (d, J=7.8 Hz, 1H), 7.56 (s, 1H), 7.48 (s, 1H), 5.55 (s, 1H), 4.48 (d, J=4.2 Hz, 2H), 3.48 (s, 3H), 1.36 (s, 9H) ppm.

46.2

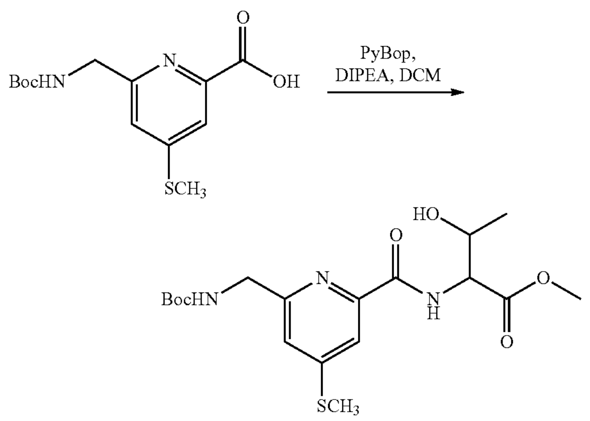

At 0° C., DIPEA (1.2 ml, 6 mmol) was added to the reactant (2.7 mmol) slowly, stirred slightly, then added S2 (2.7 mmol), PyBop (4 mmol), and then stirred at room temperature overnight. The reaction solution was washed with saturated sodium bicarbonate solution, dilute hydrochloric acid solution, saturated sodium chloride solution. The product was dried with anhydrous sodium sulfate and spinned solvent by column chromatography and white floc was obtained. $^1H$ NMR (400 MHz, $CDCl_3$): δ 8.64 (d, J=8.4 Hz, 1H), 7.95 (s, 1H), 7.81 (s, 1H), 7.44 (s, 1H), 5.44 (s, 1H), 4.77 (d, J=7.2 Hz, 1H), 4.48-4.45 (m, J=3H), 3.78 (s, 3H), 3.48 (s, 3H), 1.45 (s, 9H), 1.26 (d, J=5.6 Hz, 3H) ppm. $^{13}C$ NMR (100 MHz, $CDCl_3$) δ 171.1, 164.6, 157.4, 156.0, 148.9, 137.9, 134.6, 124.2, 121.8, 121.0, 80.7, 79.8, 78.7, 70.3, 68.2, 61.1, 57.8, 52.7, 52.2, 47.7, 32.1, 28.3, 28.2, 28.1, 28.0, 22.6, 19.8 ppm.

46.3

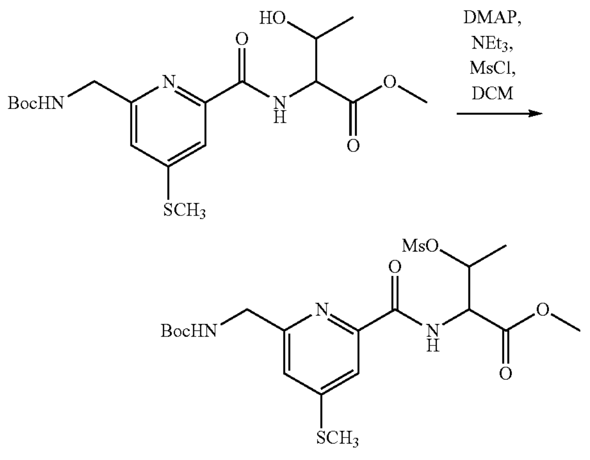

At 0° C., DMAP (0.184 mmol), $NEt_3$ (0.42 ml, 3 mmol), MsCl (0.186 ml, 2.4 mmol) were added to anhydrous DCM (10 ml) of the reactants (1.84 mmol) successively, then raised to room temperature and stirred overnight. The product was spinned anhydrous, pumped with oil pump and directly put into next step.

46.4

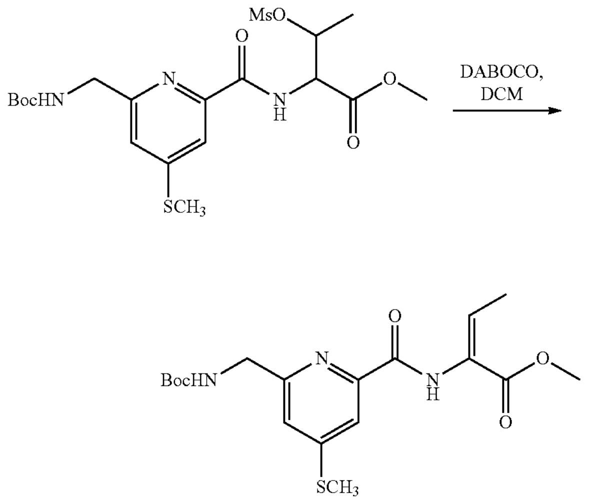

DABOCO (1 g, 9.22 mmol) was added to anhydrous DCM liquid (10 ml) obtained above, and stirred 8 h at room temperature. The reaction solution was washed by saturated sodium bicarbonate solution, saturated ammonium chloride solution, saturated sodium chloride solution in sequence, and dried by anhydrous sodium sulfate. The product was filtered and spinned solvent by column chromatography and white floc was obtained. $^1H$ NMR (400 MHz, $CDCl_3$): δ 9.38 (s, 1H), 7.78 (s, 1H), 7.41 (s, 1H), 6.86 (q, J=7.6 Hz, 1H), 5.57 (s, 1H), 4.44 (d, J=5.6 Hz, 2H), 3.74 (s, 9H), 3.48 (s, 3H), 3.48 (s, 3H), 1.80 (d, J=7.6 Hz, 3H), 1.40 (s, 9H) ppm. $^{13}C$ NMR (100 MHz, $CDCl_3$) δ 164.8, 162.1, 157.4, 156.0, 148.9, 148.8, 138.1, 133.9, 126.3, 124.2, 123.5, 121.7, 121.0, 79.7, 52.1, 45.9, 28.3, 14.6 ppm.

46.5

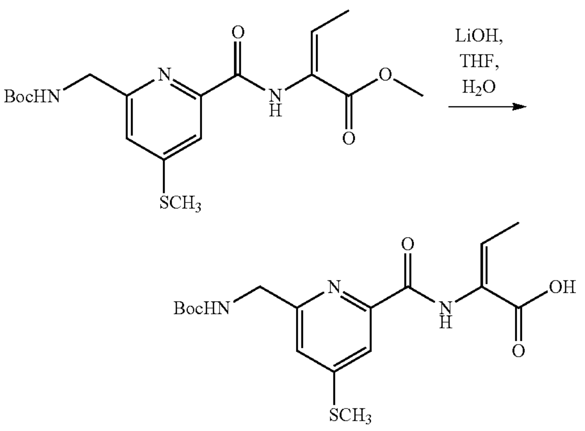

5 ml LiOH aqueous solution (90 mg, 3.6 mmol) were added dropwise to reactants (1.44 mmol) with THF (10 ml), then spinned anhydrous the organic phase after three hours. 10 ml water and 15 ml ethyl acetate were added to the organic phase. The aqueous phase was removed after liquid separation. Then the solution was added 15 ml ethyl acetate, adjusted the acid. Anhydrous sodium sulfate was used for the separation of organic phase after liquid separation. Solid white floc was obtained after spinned anhydrous. $^{1}$H NMR (400 MHz, $CDCl_3$): δ 9.40 (s, 1H), 7.51 (s, 1H), 7.43 (s, 1H), 6.88 (q, J=7.8 Hz, 1H), 5.58 (s, 1H), 4.46 (d, J=5.8 Hz, 2H), 3.76 (s, 9H), 3.48 (s, 3H), 1.83 (d, J=7.8 Hz, 3H), 1.43 (s, 9H) ppm. $^{13}$C NMR (100 MHz, $CDCl_3$) δ 165.3, 162.7, 157.8, 156.2, 149.0, 148.8, 138.3, 133.7, 126.5, 124.5, 123.7, 121.9, 121.0, 52.5, 46.3, 28.5, 14.8 ppm.

46.6

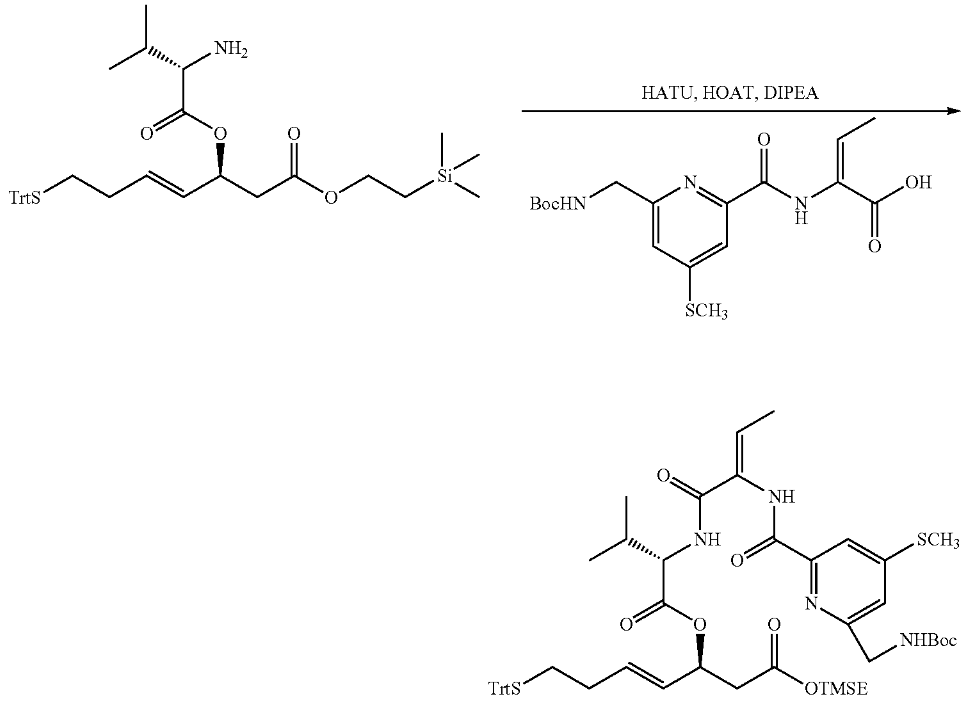

At 0° C., DIPEA (0.7 ml), carboxylic acid (610 mg), HATU (760 mg), HOAT (326 mg) were added to the reactant (336 mg, 1 mmol) in DCM solution (10 ml) sequentially. Then raised to room temperature with stirring. After 8 h, the reaction was washed with saturated sodium bicarbonate solution, dilute hydrochloric acid solution, saturated sodium chloride solution, and dried over anhydrous sodium sulfate. The product was filtered and spinned solvent by column chromatography and white flocculent solid was obtained. $^{1}$H NMR (400 MHz, $CDCl_3$): δ 9.41 (s, 1H), 7.48 (s, 1H), 7.34 (s, 1H), 7.39-7.17 (m, 12H), 6.66-6.61 (m, 2H), 5.68-5.59 (m, 2H), 5.46 (s, 1H), 5.38-5.32 (m, 1H), 4.59 (dd, J=8.8 Hz, 4 Hz, 1H), 4.49 (d, J=4.2 Hz, 2H), 4.15-4.10 (m, 3H), 3.48 (s, 3H), 2.66 (dd, J=15.6 Hz, 7.6 Hz, 1H), 2.52 (dd, J=15.6 Hz, 5.6 Hz, 1H), 2.18-2.14 (m, 3H), 2.04 (t, J=6.8 Hz, 4H), 1.82 (d, J=7.2 Hz, 3H), 1.46 (s, 9H), 1.25 (t, J=6.8 Hz, 2H), 0.97-0.90 (m, 5H), 0.80 (d, J=6.8 Hz, 3H), 0.02 (s, 9H) ppm. $^{13}$C NMR (125 MHz, $CDCl_3$) δ 171.0, 170.7, 169.5, 164.3, 162.6, 157.3, 155.9, 148.5, 144.7, 138.2, 133.9, 129.6, 129.4, 129.0, 127.7, 127.6, 126.5, 124.6, 123.5, 121.1, 79.7, 71.8, 66.5, 63.0, 60.3, 57.0, 45.6, 39.5, 31.5, 31.2, 31.0, 28.3, 20.9, 18.8, 17.5, 17.2, 14.1, 13.8, 0.9, −1.5, −1.6 ppm.

46.7

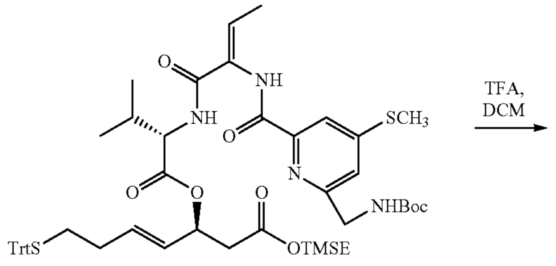

-continued

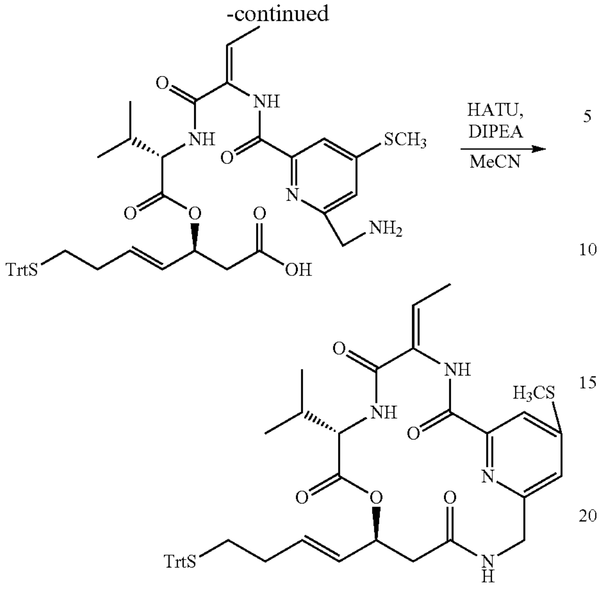

Tetrabutylammonium fluoride in tetrahydrofuran solution (1 mol/l, 2.3 ml) was added to the reaction (0.92 mmol) in redistilled THF (5 ml). After 3 h, the reaction was immediately spinned anhydrous by column chromatography to obtain a white solid. DCM solution (25 ml) of the resulting resultant was added trifluoroacetic acid (6 ml). After 5 h, spinned and removed DCM, the residue was added toluene (8 ml). Without further treatment, a brown viscous material was obtained after pumped organic solvent with oil pump. Chromatography pure acetonitrile (200 ml) obtained above was dissolved, slowly dropped in HATU (3 g), DIPEA (4 ml) of HPLC grade acetonitrile (550 ml). After 24 h, spinned anhydrous solvents, the product was diluted with ethyl acetate (20 ml) and then washed with saturated sodium bicarbonate solution, dilute hydrochloric acid solution, saturated sodium chloride solution and dried over anhydrous sodium sulfate. The product was filtered and spinned anhydrous by column chromatography and pale yellow solid was obtained. $^{1}H$ NMR (400 MHz, $CDCl_3$): δ 9.17 (s, 1H), 8.10 (d, J=7.6 Hz, 1H), 7.37-7.16 (m, 15H), 7.07 (q, J=7.2 Hz, 1H), 6.67 (s, 1H), 6.43 (s, 1H), 5.62-5.56 (m, 2H), 5.39-5.34 (m, 1H), 5.06 (dd, J=17.2 Hz, 8 Hz, 1H), 4.74 (dd, J=6.4 Hz, 3.6 Hz, 1H), 4.19-4.08 (m, 2H), 3.48 (s, 3H), 2.69-2.64 (m, 2H), 2.30-2.27 (m, 1H), 2.21-2.17 (m, 2H), 1.84 (d, J=7.2 Hz, 3H), 0.79 (d, J=6.8 Hz, 3H), 0.59 (d, J=6.8 Hz, 3H) ppm. $^{13}C$ NMR (125 MHz, DMSO) δ 133.6, 132.0, 131.3, 126.1, 124.7, 123.3, 118.4, 111.1, 107.1, 101.0, 97.3, 95.2, 92.0, 90.4, 90.3, 89.5, 89.1, 87.5, 83.8, 39.8, 39.5, 39.3, 34.1, 29.1, 22.9, 19.5 ppm.

46.8

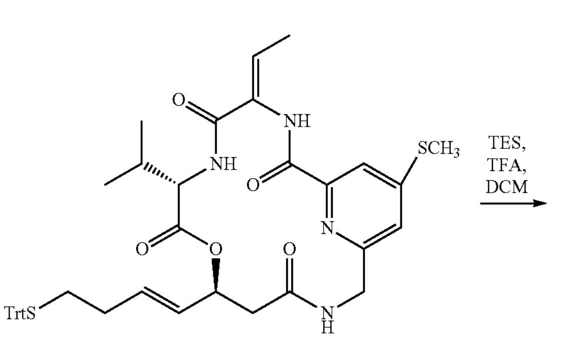

-continued

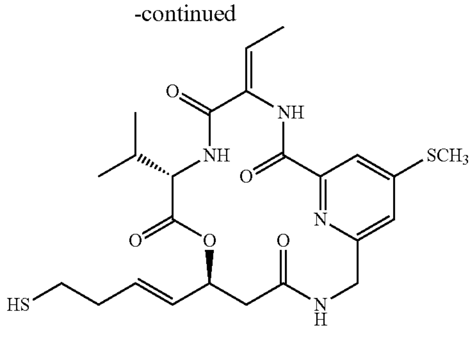

At 0° C., TES (0.1 ml), TFA (0.65 ml) were added to the reactants (150 mg, 0.21 mmol) in anhydrous DCM solution (5 ml) sequentially. 15 min later, the product was directly spinned anhydrous solvent by column chromatography and pale yellow solid was obtained. $[\alpha]^{20}_{D}$: 6.13 (c 0.5, $CHCl_3$). $^{1}H$ NMR (400 MHz, $CDCl_3$): δ7.41 (s, 1H), 7.21 (s, 1H), 7.06 (dd, J=14.4 Hz J=7.2 Hz, 1H), 6.58 (dd, J=7.6 Hz, J=3.6 Hz, 1H), 6.45 (d, J=8 Hz, 1H), 5.74-5.64 (m, 2H), 5.50 (dd, J=15.6 Hz, J=6.8 Hz, 1H), 5.10 (m, 1H), 4.74 (dd, J=10 Hz, J=3.6 Hz, 1H), 4.34-4.28 (m, 1H), 3.48 (s, 3H), 2.74-2.69 (m, 2H), 2.56-2.50 (m, 2H), 2.34-2.29 (m, 3H), 1.36 (t, J=7.6 Hz, 1H), 0.80 (d, J=6.8 Hz, 3H), 0.6 (d, J=6.8 Hz, 3H) ppm. $^{13}C$ NMR (125 MHz, $CDCl_3$) δ 169.6, 168.9, 163.6, 162.9, 155.7, 148.6, 138.3, 134.7, 132.4, 128.6, 127.0, 124.9, 123.8, 121.4, 71.9, 56.9, 43.3, 41.0, 36.0, 30.8, 23.7, 18.9, 16.5, 14.6 ppm.

Example 47

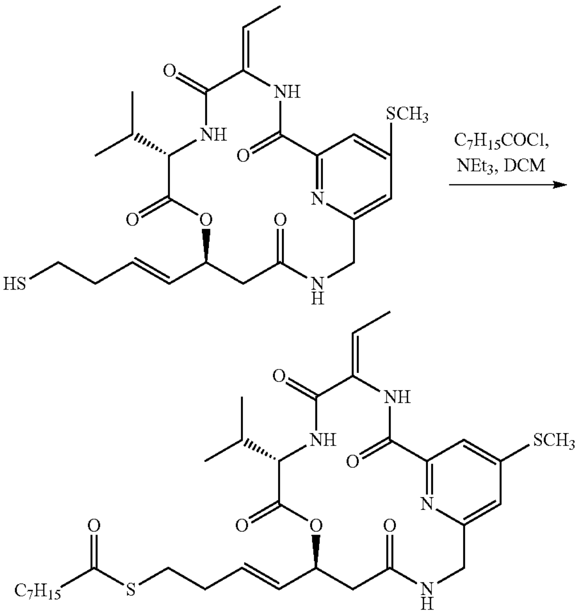

At 0° C., redistilled $NEt_3$ (0.04 ml) was added to the reactant (0.126 mmol) in anhydrous DCM (5 ml), stirred slightly, then added caprylate chloride (0.1 ml). After 7 h, The product was directly spinned anhydrous solvent by column chromatography and pale yellow solid was obtained. $[\alpha]^{20}_{D}$: 3.71 (c 0.5, $CHCl_3$). $^{1}H$ NMR (400 MHz, $CDCl_3$): δ 9.21 (s, 1H), 7.24 (s, 1H), 7.11 (s, 1H), 7.06 (m, J=7.2 Hz, 1H), 6.70 (d, J=4.4 Hz, 1H), 6.46 (d, J=10 Hz, 1H), 5.70-5.64 (m, 2H), 5.59-5.46 (m, 1H), 5.13 (dd, J=17.2 Hz, 8 Hz, 1H), 4.73-4.70 (m, 2H), 4.27 (d, J=J=17.2 Hz, 1H), 3.48 (s, 3H), 2.85-2.71 (m, 4H), 2.62-2.61 (m, 1H), 2.49 (t, J=7.6 Hz, 3H), 2.29-2.23 (m, 3H), 1.84-1.81 (m, 3H), 1.61-1.58 (m, 2H), 1.24 (s, 11H), 0.86-0.57 (m, 7H), 0.53 (d, J=7.6 Hz, 3H) ppm. $^{13}C$ NMR (125 MHz, $CDCl_3$) δ169.6, 169.1, 167.6, 165.7, 163.7, 162.3, 155.8, 148.6, 138.5, 134.7, 132.5, 132.2, 130.8, 128.7, 128.2, 127.2, 124.9, 123.6, 121.3, 72.0, 71.6, 56.9, 44.0, 43.2, 40.8, 38.5, 33.7, 32.1, 31.5, 30.8, 29.6, 29.0, 28.8, 28.8, 27.7, 27.6, 25.5, 24.7, 22.5, 19.0, 18.9, 16.4, 14.6, 13.9 ppm.

Example 48

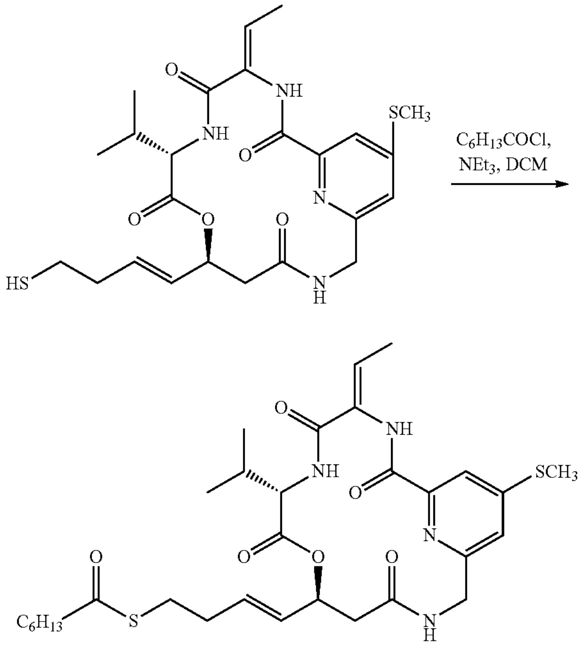

At 0° C., redistilled $NEt_3$ (0.02 ml) was added to the reactant (0.063 mmol) in anhydrous DCM (2 ml), stirred slightly, then added heptanoyl chloride (0.05 ml). After 7 h, The product was directly spinned anhydrous solvent by column chromatography and pale yellow solid was obtained. $[\alpha]^{20}_{D}$: 4.11 (c 0.7, $CHCl_3$). $^{1}H$ NMR (400 MHz, $CDCl_3$): δ 9.23 (s, 1H), 7.33 (s, 1H), 7.25 (s, 1H), 7.08 (m, J=7.2 Hz, 1H), 6.73 (d, J=4.4 Hz, 1H), 6.48 (d, J=10 Hz, 1H), 5.72-5.63 (m, 2H), 5.62-5.45 (m, 1H), 5.15 (dd, J=17.2 Hz, 8 Hz, 1H), 4.75-4.71 (m, 2H), 4.28 (d, J=17.2 Hz, 1H), 3.48 (s, 3H), 2.86-2.71 (m, 4H), 2.63-2.62 (m, 1H), 2.50 (t, J=7.8 Hz, 3H), 2.30-2.25 (m, 3H), 1.85-1.82 (m, 3H), 1.62-1.59 (m, 2H), 1.26-1.24 (m, 9H), 0.85 (m, 3H), 0.78 (d, J=7.6 Hz, 3H), 0.57 (d, J=7.6 Hz, 3H) ppm. $^{13}C$ NMR (125 MHz, $CDCl_3$) δ 169.5, 169.0, 163.5, 162.1, 155.7, 148.8, 138.6, 134.5, 132.6, 132.1, 130.9, 128.9, 128.5, 127.5, 125.1, 124.1, 121.3, 72.2, 71.7, 57.3, 44.1, 43.2, 40.9, 38.6, 33.8, 32.2, 31.5, 30.9, 29.7, 29.1, 28.8, 27.7, 27.6, 25.5, 22.5, 19.1, 18.9, 16.4, 14.6, 14.0 ppm.

Example 49

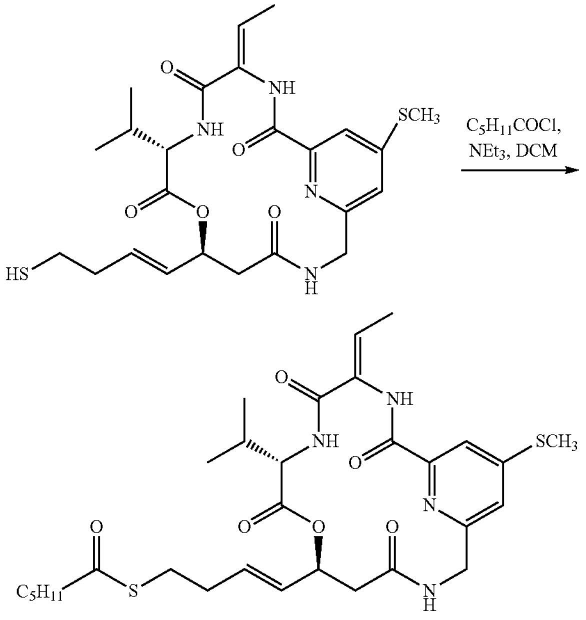

At 0° C., redistilled $NEt_3$ (0.02 ml) was added to the reactant (30 mg, 0.063 mmol) in anhydrous DCM (2 ml), stirred slightly, then added hexanoyl chloride (0.04 ml). After 7 h, The product was directly spinned anhydrous solvent by column chromatography and pale yellow solid was obtained. $[\alpha]^{20}_{D}$: 3.11 (c 0.3, $CHCl_3$). $^{1}H$ NMR (400 MHz, $CDCl_3$): δ 9.22 (s, 1H), 7.45 (s, 1H), 7.16 (s, 1H), 7.06 (m, J=7.2 Hz, 1H), 6.75 (d, J=4.4 Hz, 1H), 6.46 (d, J=10.0 Hz, 1H), 5.74-5.68 (m, 2H), 5.50 (m, 1H), 5.17 (dd, J=17.2 Hz, 8.0 Hz, 1H), 4.76-4.73 (m, 2H), 4.28 (d, J=17.2 Hz, 1H), 3.48 (s, 3H), 2.88-2.75 (m, 4H), 2.63 (m, 1H), 2.49 (t, J=7.8 Hz, 3H), 2.30-2.25 (m, 3H), 1.84-1.82 (m, 3H), 1.63-1.60 (m, 2H), 1.26-1.24 (m, 7H), 0.84 (m, 3H), 0.79 (d, J=7.6 Hz, 3H), 0.59 (d, J=7.6 Hz, 3H) ppm. $^{13}C$ NMR (125 MHz, $CDCl_3$) δ 169.3, 169.0, 163.2, 162.0, 155.6, 148.9, 138.8, 134.8, 132.7, 132.0, 130.9, 128.9, 128.6, 127.7, 125.3, 124.3, 121.5, 72.3, 71.8, 57.5, 44.3, 43.4, 41.2, 38.9, 33.9, 32.5, 31.7, 30.9, 29.8, 29.2, 28.9, 27.8, 27.6, 25.6, 22.6, 19.0, 16.5, 14.7, 13.9 ppm.

Example 50

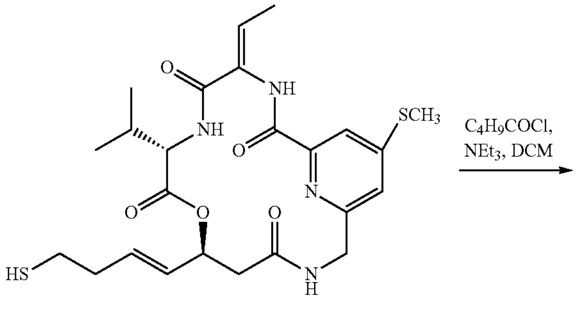

-continued

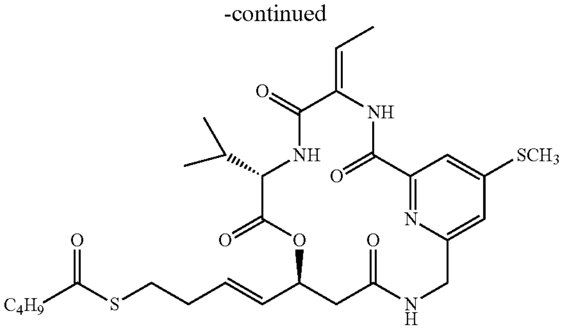

At 0° C., redistilled $NEt_3$ (0.02 ml) was added to the reactant (30 mg, 0.063 mmol) in anhydrous DCM (2 ml), stirred slightly, then added pivaloyl chloride (0.04 ml). After 7 h, The product was directly spinned anhydrous solvent by column chromatography and 30 mg pale yellow solid was obtained. The yield was 84%. $[\alpha]^{20}_{D}$: 3.31 (c 0.6, $CHCl_3$). $^1H$ NMR (400 MHz, $CDCl_3$): δ 9.20 (s, 1H), 7.96 (d, J=7.6 Hz, 1H), 7.21 (s, 1H), 7.08 (s, 1H), 6.73 (d, J=4.4 Hz, 1H), 6.49 (d, J=10.0 Hz, 1H), 5.73-5.69 (m, 2H), 5.51 (m, 1H), 5.15 (dd, J=17.2 Hz, 8.0 Hz, 1H), 4.75-4.73 (m, 2H), 4.29 (d, J=17.2 Hz, 1H), 3.48 (s, 3H), 2.89-2.75 (m, 4H), 2.62 (m, 1H), 2.47 (t, J=7.8 Hz, 3H), 2.31-2.26 (m, 3H), 1.85-1.83 (m, 3H), 1.62-1.60 (m, 2H), 1.25-1.23 (m, 5H), 0.83 (m, 3H), 0.78 (d, J=7.6 Hz, 3H), 0.58 (d, J=7.6 Hz, 3H) ppm. $^{13}C$ NMR (125 MHz, $CDCl_3$) δ 169.2, 169.0, 163.3, 162.2, 155.7, 148.7, 138.9, 134.5, 132.8, 132.1, 130.8, 128.9, 128.5, 127.6, 125.2, 123.1, 121.3, 72.1, 71.6, 57.8, 44.2, 43.5, 41.3, 38.8, 33.8, 32.6, 31.6, 30.8, 29.9, 29.3, 28.8, 27.6, 25.7, 22.7, 19.1, 16.6, 14.9, 13.8 ppm.

Example 51

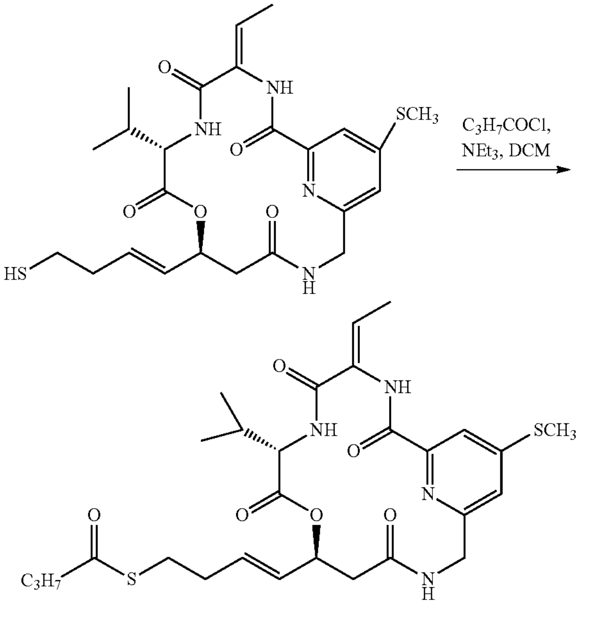

At 0° C., redistilled $NEt_3$ (0.02 ml) was added to the reactant (0.063 mmol) in anhydrous DCM (2 ml), stirred slightly, then added butyryl chloride (0.05 ml). After 7 h, The product was directly spinned anhydrous solvent by column chromatography and pale yellow solid was obtained. $[\alpha]^{20}_{D}$: 6.51 (c 0.5, $CHCl_3$). $^1H$ NMR (400 MHz, $CDCl_3$): δ 9.23 (s, 1H), 7.98 (d, J=7.6 Hz, 1H), 7.49 (d, J=7.6 Hz, 1H), 7.09 (s, 1H), 6.75 (s, 1H), 6.47 (d, J=10.0 Hz, 1H), 5.76-5.71 (m, 2H), 5.53 (m, 1H), 5.18 (dd, J=17.2 Hz, 8.0 Hz, 1H), 4.77-4.74 (m, 2H), 4.27 (d, J=17.2 Hz, 1H), 3.48 (s, 3H), 2.88-2.74 (m, 4H), 2.63 (m, 1H), 2.49 (t, J=7.8 Hz, 3H), 2.33-2.28 (m, 3H), 1.86-1.83 (m, 3H), 1.66-1.62 (m, 2H), 1.27-1.24 (m, 3H), 0.86 (m, 3H), 0.79 (d, J=7.6 Hz, 3H), 0.56 (d, J=7.6 Hz, 3H) ppm. $^{13}C$ NMR (125 MHz, $CDCl_3$) δ 169.4, 169.1, 163.5, 162.3, 155.8, 148.8, 138.9, 134.7, 132.9, 132.3, 130.9, 128.9, 128.4, 127.5, 125.3, 123.9, 121.5, 72.2, 71.7, 57.6, 44.5, 43.6, 41.4, 38.9, 33.9, 32.7, 31.7, 30.9, 29.9, 29.5, 28.9, 27.7, 25.8, 22.9, 19.3, 15.5, 13.8 ppm.

Example 52

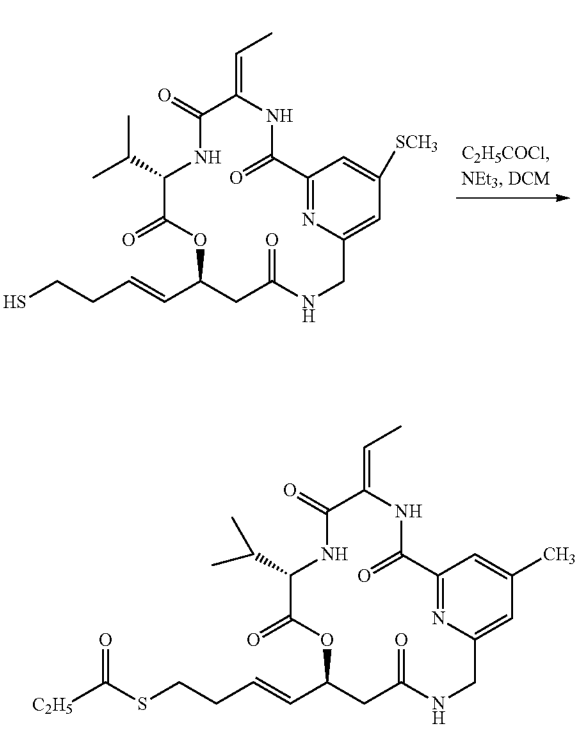

At 0° C., redistilled $NEt_3$ (0.02 ml) was added to the reactant (0.063 mmol) in anhydrous DCM (2 ml), stirred slightly, was added propionyl chloride (0.05 ml). After 7 h, The product was directly spinned anhydrous solvent by column chromatography and pale yellow solid was obtained. $[\alpha]^{20}_{D}$: 5.50 (c 0.3, $CHCl_3$). $^1H$ NMR (400 MHz, $CDCl_3$): δ 9.25 (s, 1H), 7.99 (d, J=7.6 Hz, 1H), 7.48 (d, J=7.6 Hz, 1H), 7.08 (s, 1H), 6.77 (s, 1H), 6.48 (d, J=10.0 Hz, 1H), 5.75-5.72 (m, 2H), 5.55 (m, 1H), 5.19 (dd, J=17.2 Hz, 8.0 Hz, 1H), 4.78-4.75 (m, 2H), 4.28 (d, J=17.2 Hz, 1H), 3.48 (s, 3H), 2.89-2.75 (m, 4H), 2.65 (m, 1H), 2.48 (t, J=7.8 Hz, 3H), 2.35-2.29 (m, 3H), 1.88-1.85 (m, 3H), 1.66 (m, 2H), 0.86 (m, 3H), 0.77 (d, J=7.6 Hz, 3H), 0.57 (d, J=7.6 Hz, 3H) ppm. $^{13}C$ NMR (125 MHz, $CDCl_3$) δ 169.6, 169.2, 163.3, 162.2, 155.9, 148.9, 138.8, 134.8, 132.9, 132.2, 130.8, 128.9, 128.5, 127.6, 125.5, 124.7, 121.6, 72.3, 71.8, 57.8, 44.6, 43.7, 41.5, 38.8, 33.9, 32.8, 31.8, 30.8, 29.9, 29.6, 28.9, 27.8, 25.9, 22.9, 19.5, 14.8 ppm.

Example 53

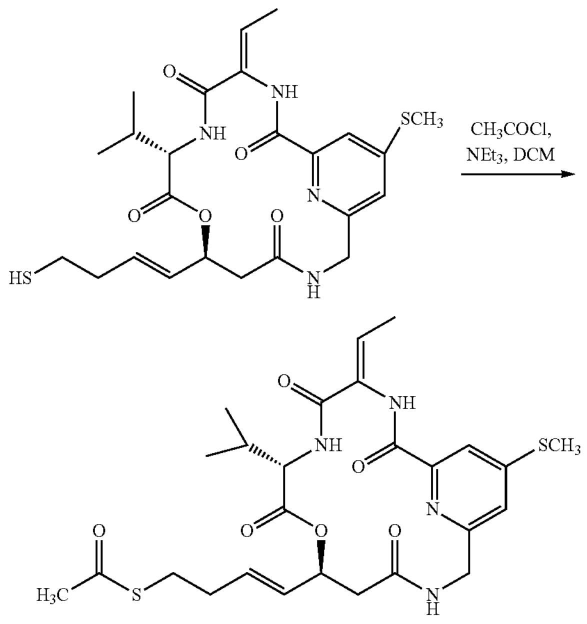

At 0° C., redistilled $NEt_3$ (0.02 ml) was added to the reactant (0.063 mmol) in anhydrous DCM (2 ml), stirred slightly, acetyl chloride (0.05 ml) was added. After 7 h, the product was directly spinned anhydrous solvent by column chromatography and pale yellow solid was obtained. $[\alpha]^{20}_{D}$: 4.66 (c 0.6, $CHCl_3$). $^1$H NMR (400 MHz, $CDCl_3$): δ 9.26 (s, 1H), 7.98 (d, J=7.6 Hz, 1H), 7.49 (d, J=7.6 Hz, 1H), 7.09 (s, 1H), 6.79 (s, 1H), 6.47 (d, J=10.0 Hz, 1H), 5.73-5.70 (m, 2H), 5.53 (m, 1H), 5.18 (dd, J=17.2 Hz, 8.0 Hz, 1H), 4.77 (m, 2H), 4.28 (d, J=17.2 Hz, 1H), 3.48 (s, 3H), 2.88-2.78 (m, 4H), 2.67 (m, 1H), 2.49 (t, J=7.8 Hz, 3H), 2.36-2.33 (m, 3H), 1.89-1.86 (m, 3H), 0.88 (m, 3H), 0.78 (d, J=7.6 Hz, 3H), 0.58 (d, J=7.6 Hz, 3H) ppm. $^{13}$C NMR (125 MHz, $CDCl_3$) δ 169.8, 169.3, 163.5, 162.5, 155.8, 148.8, 138.7, 134.7, 132.8, 132.3, 130.9, 128.8, 128.7, 127.7, 125.6, 123.4, 121.7, 72.5, 71.9, 57.9, 44.7, 43.9, 41.6, 38.9, 33.8, 32.9, 31.9, 30.9, 29.8, 29.5, 28.8, 27.7, 15.0 ppm.

Example 54

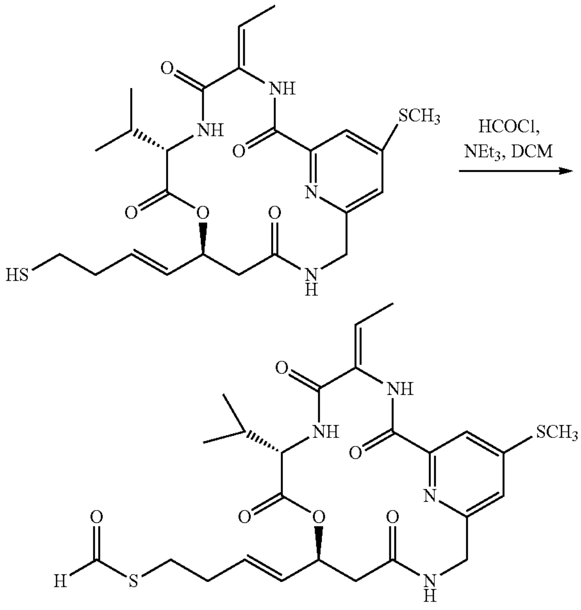

At 0° C., redistilled $NEt_3$ (0.02 ml) was added to the reactant (0.063 mmol) in anhydrous DCM (2 ml), stirred slightly, methanesulfonyl chloride (0.02 ml) was added. After 7 h, the product was directly spinned anhydrous solvent by column chromatography and pale yellow solid was obtained. $[\alpha]^{20}_{D}$: 1.96 (c 0.1, $CHCl_3$). $^1$H NMR (400 MHz, $CDCl_3$): δ 9.63 (s, 1H), 9.23 (s, 1H), 7.18 (s, 1H), 7.02 (s, 1H), 7.07 (dd, J=14.4 Hz, J=7.2 Hz, 1H), 6.56 (dd, J=7.6 Hz, J=3.6 Hz, 1H), 6.48 (d, J=8 Hz, 1H), 5.73 (m, 2H), 5.52 (dd, J=15.6 Hz, J=6.8 Hz, 1H), 5.12 (m, 1H), 4.76 (dd, J=10 Hz, J=3.6 Hz, 1H), 4.33 (m, 1H), 3.48 (s, 3H), 2.72 (m, 2H), 2.53 (m, 2H), 2.34-2.29 (m, 3H), 1.38 (t, J=7.6 Hz, 1H), 0.82 (d, J=6.8 Hz, 3H), 0.62 (d, J=6.8 Hz, 3H) ppm. $^{13}$C NMR (125 MHz, $CDCl_3$) δ 176.5, 169.8, 169.4, 163.6, 162.6, 155.7, 148.8, 138.5, 134.7, 132.5, 132.3, 130.9, 128.8, 127.8, 125.6, 123.6, 121.8, 72.5, 71.7, 56.9, 44.8, 43.6, 41.5, 36.0, 30.8, 23.7, 18.9, 16.5, 14.6 ppm.

Example 55

55.1

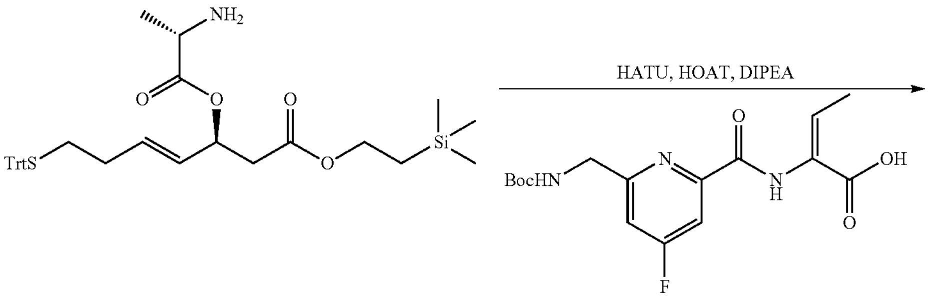

-continued

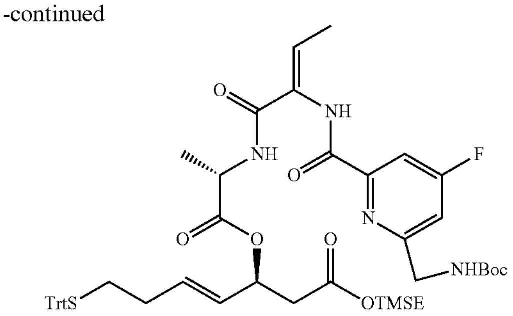

At 0° C., DIPEA (0.7 ml), the product of Example 37.5, HATU (760 mg), HOAT (326 mg) were added to the reactant (1 mmol) in DCM solution (10 ml) sequentially, and raised to room temperature with stirring. After 8 h, the reaction was washed with saturated sodium bicarbonate solution, dilute hydrochloric acid solution, saturated sodium chloride solution, dried over anhydrous sodium sulfate. The product was filtered and spinned anhydrous by column chromatography and white flocculent solid solid was obtained. $^{1}$H NMR (400 MHz, $CDCl_3$): δ 9.41 (s, 1H), 7.14 (s, 1H), 7.08 (s, 1H), 7.39-7.17 (m, 12H), 6.66-6.61 (m, 2H), 5.68-5.59 (m, 2H), 5.46 (s, 1H), 5.38-5.32 (m, 1H), 4.59 (dd, J=8.8 Hz, 4 Hz, 1H), 4.49 (d, J=4.2 Hz, 2H), 4.15-4.10 (m, 3H), 2.66 (dd, J=15.6 Hz, 7.6 Hz, 1H), 2.52 (dd, J=15.6 Hz, 5.6 Hz, 1H), 2.18-2.14 (m, 3H), 2.04 (t, J=6.8 Hz, 4H), 1.82 (d, J=7.2 Hz, 3H), 1.46 (s, 9H), 1.25 (t, J=6.8 Hz, 2H), 0.97-0.90 (m, 5H), 0.80 (d, J=6.8 Hz, 3H), 0.02 (s, 9H) ppm. $^{13}$C NMR (125 MHz, $CDCl_3$) δ 171.0, 170.7, 169.5, 164.3, 162.6, 157.3, 155.9, 148.5, 144.7, 138.2, 133.9, 129.6, 129.4, 129.0, 127.7, 127.6, 126.5, 124.6, 121.1, 79.7, 77.2, 77.0, 76.7, 71.8, 66.5, 63.0, 60.3, 57.0, 45.6, 39.5, 31.5, 31.2, 31.0, 28.3, 20.9, 18.8, 17.5, 17.2, 14.1, 13.8, 0.9, −1.5, −1.6 ppm.

55.2

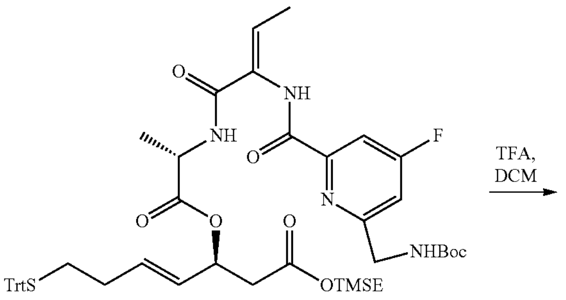

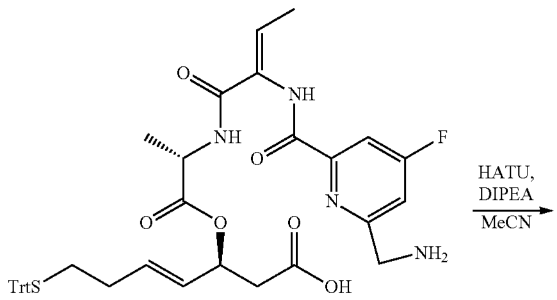

-continued

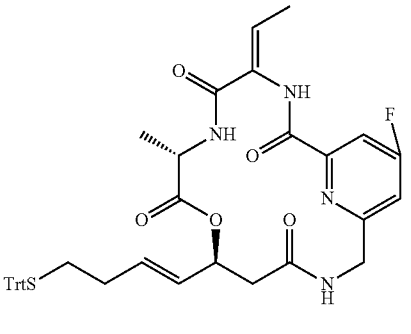

Tetrabutylammonium fluoride in tetrahydrofuran solution (1 mol/l, 2.3 ml) was added to the reaction (0.90 mmol) in redistilled THF (5 ml). After 3 h, the reaction was immediately spinned anhydrous by column chromatography to obtain a white solid. DCM solution (25 ml) of the resulting resultant was added trifluoroacetic acid (6 ml). After 5 h, spinned and removed DCM, the residue was added toluene (8 ml). Without further treatment, a brown viscous material was obtained after pumped organic solvent with oil pump. Chromatography pure acetonitrile (200 ml) obtained above was dissolved, slowly dropped in HATU (3 g), DIPEA (4 ml) of HPLC grade acetonitrile (550 ml). After 24 h, spinned anhydrous solvents, the product was diluted with ethyl acetate (20 ml) and then washed with saturated sodium bicarbonate solution, dilute hydrochloric acid solution, saturated sodium chloride solution and dried over anhydrous sodium sulfate. The product was filtered and spinned anhydrous by column chromatography and pale yellow solid was obtained. $^{1}$H NMR (400 MHz, $CDCl_3$): δ 9.17 (s, 1H), 8.10 (d, J=7.6 Hz, 1H), 7.07 (s, 1H), 7.37-7.16 (m, 15H), 7.07 (q, J=7.2 Hz, 1H), 6.33 (s, 1H), 5.62-5.56 (m, 2H), 5.39-5.34 (m, 1H), 5.06 (dd, J=17.2 Hz, 8 Hz, 1H), 4.74 (dd, J=6.4 Hz, 3.6 Hz, 1H), 4.19-4.08 (m, 2H), 2.69-2.64 (m, 2H), 2.30-2.27 (m, 1H), 2.21-2.17 (m, 2H), 1.84 (d, J=7.2 Hz, 3H), 0.79 (d, J=6.8 Hz, 3H), 0.59 (d, J=6.8 Hz, 3H) ppm. $^{13}$C NMR (125 MHz, DMSO) δ 133.64, 132.05, 131.39, 126.08, 124.66, 118.36, 111.05, 107.13, 100.97, 97.27, 95.22, 91.96, 90.37, 90.32, 89.54, 89.11, 87.45, 83.79, 39.76, 39.50, 39.25, 34.06, 29.13, 22.85, 19.48 ppm.

55.3

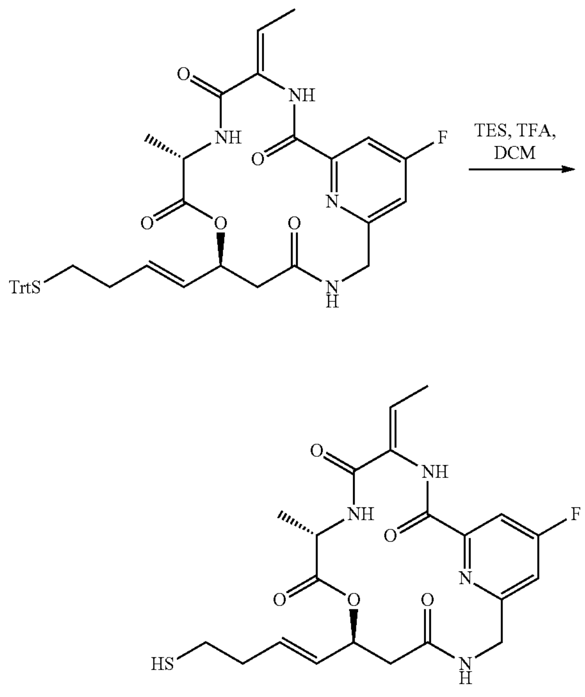

At 0° C., TES (0.1 ml), TFA (0.65 ml) were added to the reactants (0.21 mmol) in anhydrous DCM solution (5 ml) sequentially. 15 min later, the product was directly spinned anhydrous solvent by column chromatography and yellow solid was obtained. $[\alpha]^{20}_{D}$: 6.13 (c 0.5, $CHCl_3$). $^1H$ NMR (400 MHz, $CDCl_3$): δ7.88 (d, J=7.6 Hz, 1H), 7.19 (s, 1H), 7.06 (dd, J=14.4 Hz J=7.2 Hz, 1H), 6.58 (dd, J=7.6 Hz, J=3.6 Hz, 1H), 6.45 (s, 1H), 5.74-5.64 (m, 2H), 5.50 (dd, J=15.6 Hz, J=6.8 Hz, 1H), 5.10 (m, 1H), 4.74 (dd, J=10 Hz, J=3.6 Hz, 1H), 4.34-4.28 (m, 1H), 2.74-2.69 (m, 2H), 2.56-2.50 (m, 2H), 2.34-2.29 (m, 3H), 1.36 (t, J=7.6 Hz, 1H), 0.80 (d, J=6.8 Hz, 3H), 0.6 (d, J=6.8 Hz, 3H) ppm. $^{13}C$ NMR (125 MHz, $CDCl_3$) δ 169.6, 168.9, 163.6, 162.9, 155.7, 148.6, 138.3, 134.7, 132.4, 128.6, 127.0, 124.9, 121.4, 77.2, 76.9, 76.7, 71.9, 56.9, 43.3, 41.0, 36.0, 30.8, 23.7, 18.9, 16.5, 14.6 ppm.

Example 56

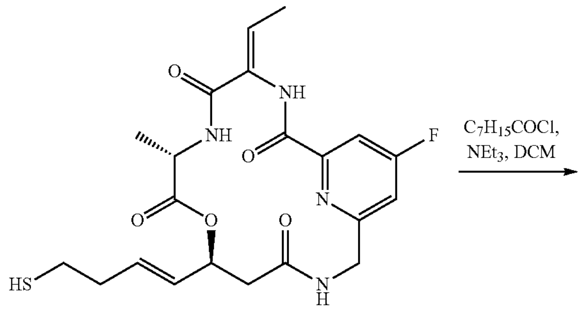

-continued

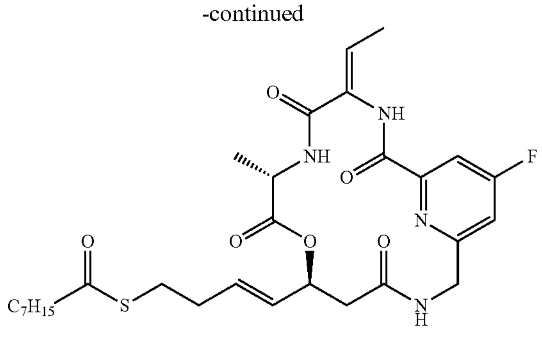

At 0° C., redistilled $NEt_3$ (0.04 ml) was added to the reactant (0.126 mmol) in anhydrous DCM (5 ml), stirred slightly, then added caprylate chloride (0.1 ml). After 7 h, The product was directly spinned anhydrous solvent by column chromatography and pale yellow solid was obtained. $[\alpha]^{20}_{D}$: 3.71 (c 0.5, $CHCl_3$). $^1H$ NMR (400 MHz, $CDCl_3$): δ 9.21 (s, 1H), 7.52 (d, J=7.6 Hz, 1H), 7.11 (s, 1H), 7.06 (m, J=7.2 Hz, 1H), 6.70 (d, J=4.4 Hz, 1H), 6.36 (s, 1H), 5.70-5.64 (m, 2H), 5.59-5.46 (m, 1H), 5.13 (dd, J=17.2 Hz, 8 Hz, 1H), 4.73-4.70 (m, 2H), 4.27 (d, J=J=17.2 Hz, 1H), 2.85-2.71 (m, 4H), 2.62-2.61 (m, 1H), 2.49 (t, J=7.6 Hz, 3H), 2.29-2.23 (m, 3H), 1.84-1.81 (m, 3H), 1.61-1.58 (m, 2H), 1.24 (s, 11H), 0.86-0.57 (m, 7H), 0.53 (d, J=7.6 Hz, 3H) ppm. $^{13}C$ NMR (125 MHz, $CDCl_3$) δ 199.5, 169.6, 169.1, 167.6, 165.7, 163.7, 162.3, 155.8, 148.6, 138.5, 134.7, 132.5, 132.2, 130.8, 128.7, 128.2, 127.2, 124.9, 121.3, 77.2, 77.0, 76.7, 72.0, 71.6, 56.9, 44.0, 43.2, 40.8, 38.5, 33.7, 32.1, 31.5, 30.8, 29.6, 29.0, 28.8, 28.8, 27.7, 27.6, 25.5, 24.7, 22.5, 19.0, 18.9, 16.4, 14.6, 13.9 ppm.

Example 57

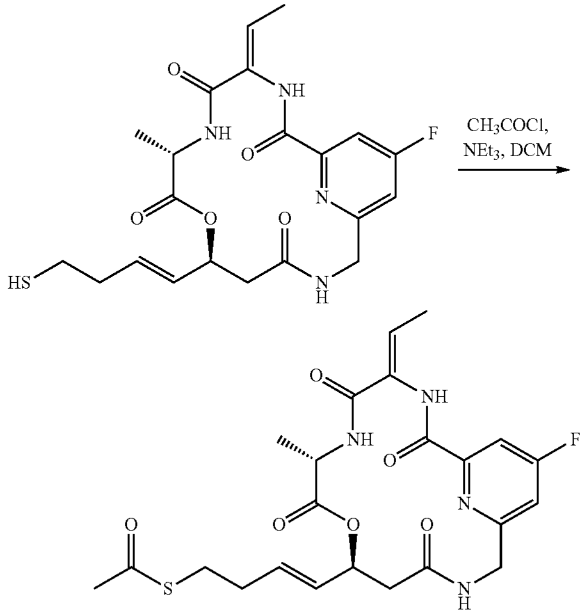

At 0° C., redistilled $NEt_3$ (0.02 ml) was added to the reactant (0.063 mmol) in anhydrous DCM (2 ml), stirred slightly, acetyl chloride (0.05 ml) was added. After 7 h, the product was directly spinned anhydrous solvent by column chromatography and yellow solid was obtained. $[\alpha]^{20}_{D}$: 4.66 (c 0.6, $CHCl_3$). $^{1}$H NMR (400 MHz, $CDCl_3$): δ 9.26 (s, 1H), 7.98 (d, J=7.6 Hz, 1H), 7.15 (d, J=7.8 Hz, 1H), 7.09 (m, J=7.8 Hz, 1H), 6.79 (s, 1H), 6.47 (s, J=10.0 Hz, 1H), 5.73-5.70 (m, 2H), 5.53 (m, 1H), 5.18 (dd, J=17.2 Hz, 8.0 Hz, 1H), 4.77 (m, 2H), 4.28 (d, J=17.2 Hz, 1H), 2.88-2.78 (m, 4H), 2.67 (m, 1H), 2.49 (t, J=7.8 Hz, 3H), 2.36-2.33 (m, 3H), 1.89-1.86 (m, 3H), 0.88 (m, 3H), 0.78 (d, J=7.6 Hz, 3H), 0.58 (d, J=7.6 Hz, 3H) ppm. $^{13}$C NMR (125 MHz, $CDCl_3$) δ 169.8, 169.3, 163.5, 162.5, 155.8, 148.8, 138.7, 134.7, 132.8, 132.3, 130.9, 128.8, 128.7, 127.7, 125.6, 121.7, 72.5, 71.9, 57.9, 44.7, 43.9, 41.6, 38.9, 33.8, 32.9, 31.9, 30.9, 29.8, 29.5, 28.8, 27.7, 15.0 ppm.

Example 58

58.1

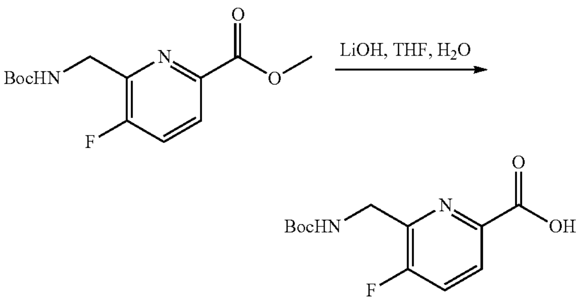

15 ml LiOH aqueous solution (456 mg, 19 mmol) were added dropwise to the reactant (7.6 mmol) of 30 ml THF, then reacted 2 h at room temperature. The reaction solution was adjusted by dilute hydrochloric acid to with the pH value of 3, then 100 ml ethyl acetate was added. The organic matter was washed by water and saturated salt water. The organic layer was dried by anhydrous sodium sulfate, and the solvent evaporated to give white flocculent solid. $^{1}$H NMR (400 MHz, $CDCl_3$): δ 7.96 (d, J=8.0 Hz, 1H), 7.47 (d, J=7.6 Hz, 1H), 5.55 (s, 1H), 4.48 (d, J=4.2 Hz, 2H), 1.36 (s, 9H) ppm.

58.2

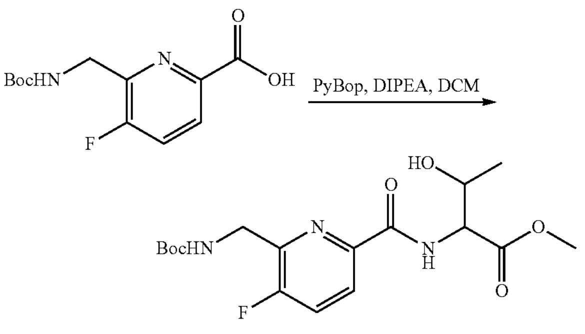

At 0° C., DIPEA (1.2 ml, 6 mmol) was added to the reactant (2.7 mmol) slowly, stirred slightly, then added S2 (2.7 mmol), PyBop (2.5 g, 4 mmol), and then stirred at room temperature overnight. The reaction solution was washed with saturated sodium bicarbonate solution, dilute hydrochloric acid solution, saturated sodium chloride solution. The product was dried with anhydrous sodium sulfate and spinned solvent by column chromatography and white floc was obtained. $^{1}$H NMR (400 MHz, $CDCl_3$): δ 8.64 (d, J=8.4 Hz, 1H), 8.05 (d, J=8 Hz, 1H), 7.41 (d, J=8 Hz, 1H), 5.44 (s, 1H), 4.77 (d, J=7.2 Hz, 1H), 4.48-4.45 (m, J=3H), 3.78 (s, 3H), 1.45 (s, 9H), 1.26 (d, J=5.6 Hz, 3H) ppm. $^{13}$C NMR (100 MHz, $CDCl_3$) δ 171.1, 164.6, 157.4, 156.0, 148.9, 137.9, 134.6, 124.2, 121.8, 121.0, 80.7, 79.8, 78.7, 70.3, 68.2, 61.1, 57.8, 52.7, 52.2, 47.7, 32.1, 28.3, 28.2, 28.1, 28.0, 22.6, 19.8 ppm.

58.3

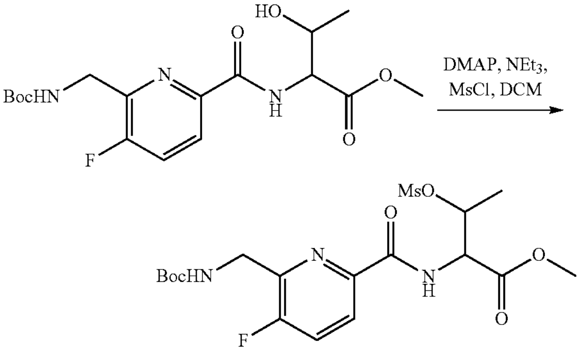

At 0° C., DMAP (25 mg, 0.184 mmol), $NEt_3$ (0.42 ml, 3 mmol), MsCl (0.186 ml, 2.4 mmol) were added to anhydrous DCM (10 ml) of the reactants (1.84 mmol) successively, then raised to room temperature and stirred overnight. The product was spinned anhydrous, pumped with oil pump and directly put into next step.

58.4

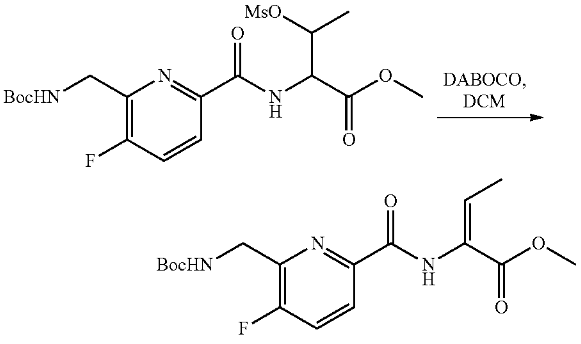

DABOCO (1 g, 9.22 mmol) was added to anhydrous DCM liquid (10 ml) obtained above and stirred 8 h at room temperature. The reaction solution was washed by saturated sodium bicarbonate solution, saturated ammonium chloride solution, saturated sodium chloride solution in sequence, and dried by anhydrous sodium sulfate. The product was filtered and spinned solvent by column chromatography and white floc was obtained. $^{1}$H NMR (400 MHz, $CDCl_3$): δ 9.38 (s, 1H), 7.88 (d, J=8 Hz, 1H), 7.51 (d, J=7.6 Hz, 1H), 6.86 (q, J=7.6 Hz, 1H), 5.57 (s, 1H), 4.44 (d, J=5.6 Hz, 2H), 3.74 (s, 9H), 1.80 (d, J=7.6 Hz, 3H), 1.40 (s, 9H) ppm. $^{13}$C NMR (100 MHz, $CDCl_3$) δ 164.8, 162.1, 157.4, 156.0, 148.9, 148.8, 138.1, 133.9, 126.3, 124.2, 121.7, 121.0, 79.7, 52.1, 45.9, 28.3, 14.6 ppm.

58.5

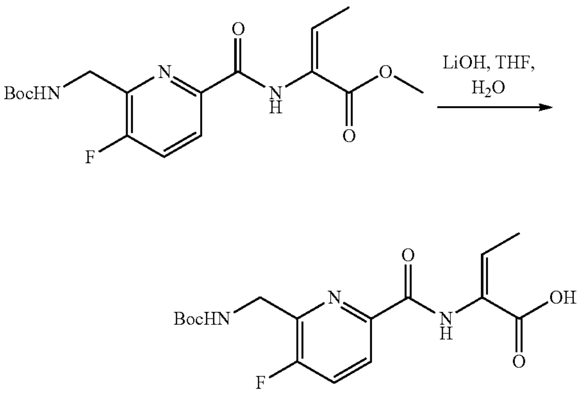

5 ml LiOH aqueous solution (90 mg, 3.6 mmol) were added dropwise to reactants (1.44 mmol) with THF (10 ml), then spinned anhydrous the organic phase after three hours. 10 ml water and 15 ml ethyl acetate were added to the organic phase. The aqueous phase was removed after liquid separation. Then the solution was added 15 ml ethyl acetate, adjusted the acid. Anhydrous sodium sulfate was used for the separation of organic phase after liquid separation. Solid white floc was obtained after spinned anhydrous. $^{1}$H NMR (400 MHz, $CDCl_3$): δ 9.40 (s, 1H), 7.83 (d, J=7.6 Hz, 1H), 7.80 (d, J=8.2 Hz, 1H), 6.88 (q, J=7.8 Hz, 1H), 5.58 (s, 1H), 4.46 (d, J=5.8 Hz, 2H), 3.76 (s, 9H), 1.83 (d, J=7.8 Hz, 3H), 1.43 (s, 9H) ppm. $^{13}$C NMR (100 MHz, $CDCl_3$) δ 165.3, 162.7, 157.8, 156.2, 149.0, 148.8, 138.3, 133.7, 126.5, 124.5, 121.9, 121.0, 52.5, 46.3, 28.5, 14.8 ppm.

58.6

At 0° C., DIPEA (0.7 ml), carboxylic acid (610 mg), HATU (760 mg), HOAT (326 mg) were added to the reactant (1 mmol) in DCM solution (10 ml) sequentially. Then raised to room temperature with stirring. After 8 h, the reaction was washed with saturated sodium bicarbonate solution, dilute hydrochloric acid solution, saturated sodium chloride solution, and dried over anhydrous sodium sulfate. The product was filtered and spinned solvent by column chromatography and white flocculent solid was obtained. $^{1}$H NMR (400 MHz, $CDCl_3$): δ 9.41 (s, 1H), 7.91 (d, J=7.6 Hz, 1H), 7.44 (d, J=7.6 Hz, 1H), 7.39-7.17 (m, 12H), 6.66-6.61 (m, 2H), 5.68-5.59 (m, 2H), 5.46 (s, 1H), 5.38-5.32 (m, 1H), 4.59 (dd, J=8.8 Hz, 4 Hz, 1H), 4.49 (d, J=4.2 Hz, 2H), 4.15-4.10 (m, 3H), 2.66 (dd, J=15.6 Hz, 7.6 Hz, 1H), 2.52 (dd, J=15.6 Hz, 5.6 Hz, 1H), 2.18-2.14 (m, 3H), 2.04 (t, J=6.8 Hz, 4H), 1.82 (d, J=7.2 Hz, 3H), 1.46 (s, 9H), 1.25 (t, J=6.8 Hz, 2H), 0.97-0.90 (m, 5H), 0.80 (d, J=6.8 Hz, 3H), 0.02 (s, 9H) ppm. $^{13}$C NMR (125 MHz, $CDCl_3$) δ 171.0, 170.7, 169.5, 164.3, 162.6, 157.3, 155.9, 148.5, 144.7, 138.2, 133.9, 129.6, 129.4, 129.0, 127.7, 127.6, 126.5, 124.6, 121.1, 79.7, 71.8, 66.5, 63.0, 60.3, 57.0, 45.6, 39.5, 31.5, 31.2, 31.0, 28.3, 20.9, 18.8, 17.5, 17.2, 14.1, 13.8, 0.9, −1.5, −1.6 ppm.

58.7

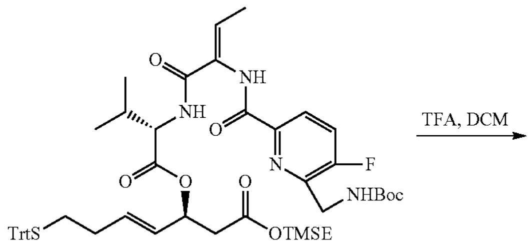

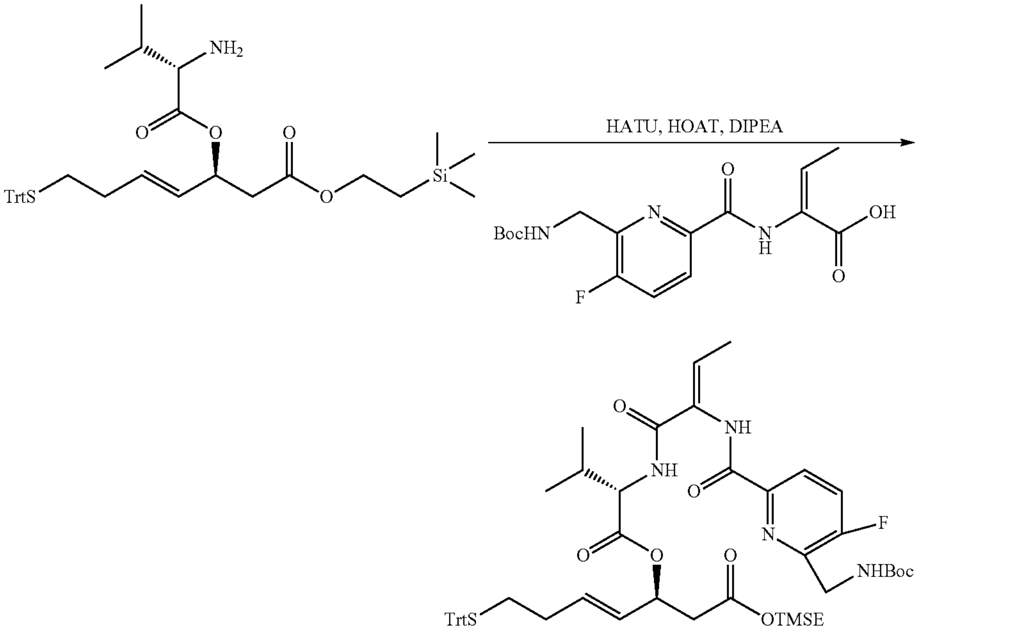

-continued

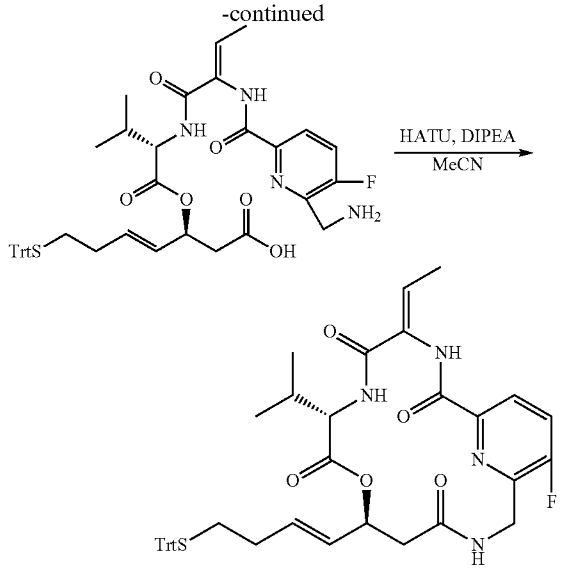

Tetrabutylammonium fluoride in tetrahydrofuran solution (1 mol/l, 2.3 ml) was added to the reaction (0.92 mmol) in redistilled THF (5 ml). After 3 h, the reaction was immediately spinned anhydrous by column chromatography to obtain a white solid. DCM solution (25 ml) of the resulting resultant was added trifluoroacetic acid (6 ml). After 5 h, spinned and removed DCM, the residue was added toluene (8 ml). Without further treatment, a brown viscous material was obtained after pumped organic solvent with oil pump. Chromatography pure acetonitrile (200 ml) obtained above was dissolved, slowly dropped in HATU (3 g), DIPEA (4 ml) of HPLC grade acetonitrile (550 ml). After 24 h, spinned anhydrous solvents, the product was diluted with ethyl acetate (20 ml) and then washed with saturated sodium bicarbonate solution, dilute hydrochloric acid solution, saturated sodium chloride solution and dried over anhydrous sodium sulfate. The product was filtered and spinned anhydrous by column chromatography and pale yellow solid was obtained. $^1$H NMR (400 MHz, $CDCl_3$): δ 9.17 (s, 1H), 7.89 (d, J=7.6 Hz, 1H), 7.68 (d, J=7.6 Hz, 1H), 7.37-7.16 (m, 15H), 7.07 (q, J=7.2 Hz, 1H), 6.43 (d, J=10.4 Hz, 1H), 5.62-5.56 (m, 2H), 5.39-5.34 (m, 1H), 5.06 (dd, J=17.2 Hz, 8 Hz, 1H), 4.74 (dd, J=6.4 Hz, 3.6 Hz, 1H), 4.19-4.08 (m, 2H), 2.69-2.64 (m, 2H), 2.30-2.27 (m, 1H), 2.21-2.17 (m, 2H), 1.84 (d, J=7.2 Hz, 3H), 0.79 (d, J=6.8 Hz, 3H), 0.59 (d, J=6.8 Hz, 3H) ppm. $^{13}$C NMR (125 MHz, DMSO) δ 133.6, 132.0, 131.3, 126.1, 124.7, 118.4, 111.1, 107.1, 101.0, 97.3, 95.2, 92.0, 90.4, 90.3, 89.5, 89.1, 87.5, 83.8, 39.8, 39.5, 39.3, 34.1, 29.1, 22.9, 19.5 ppm.

58.8

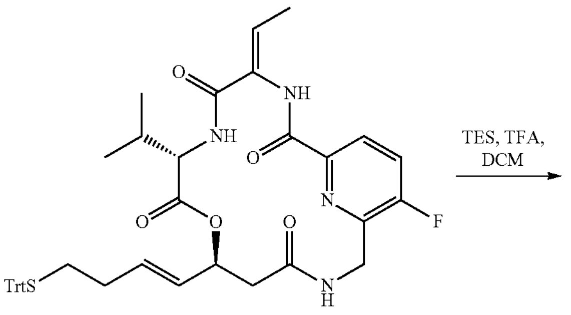

-continued

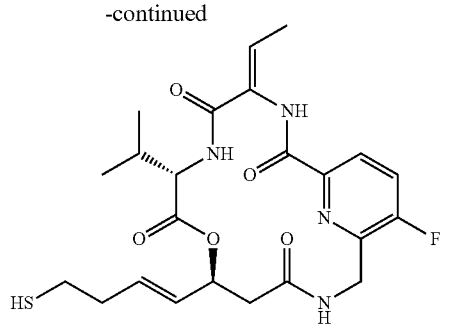

At 0° C., TES (0.1 ml), TFA (0.65 ml) were added to the reactants (0.21 mmol) in anhydrous DCM solution (5 ml) sequentially. 15 min later, the product was directly spinned anhydrous solvent by column chromatography and pale yellow solid was obtained. $[\alpha]^{20}_D$: 6.13 (c 0.5, $CHCl_3$). $^1$H NMR (400 MHz, $CDCl_3$): δ 8.18 (d, J=7.6 Hz, 1H), 7.49 (d, J=7.6 Hz, 1H), 7.06 (dd, J=14.4 Hz J=7.2 Hz, 1H), 6.58 (dd, J=7.6 Hz, J=3.6 Hz, 1H), 6.45 (d, J=8 Hz, H), 5.74-5.64 (m, 2H), 5.50 (dd, J=15.6 Hz, J=6.8 Hz, 1H), 5.10 (m, 1H), 4.74 (dd, J=10 Hz, J=3.6 Hz, 1H), 4.34-4.28 (m, 1H), 2.74-2.69 (m, 2H), 2.56-2.50 (m, 2H), 2.34-2.29 (m, 3H), 1.36 (t, J=7.6 Hz, 1H), 0.80 (d, J=6.8 Hz, 3H), 0.6 (d, J=6.8 Hz, 3H) ppm. $^{13}$C NMR (125 MHz, $CDCl_3$) δ 169.6, 168.9, 163.6, 162.9, 155.7, 148.6, 138.3, 134.7, 132.4, 128.6, 127.0, 124.9, 121.4, 71.9, 56.9, 43.3, 41.0, 36.0, 30.8, 23.7, 18.9, 16.5, 14.6 ppm.

Example 59

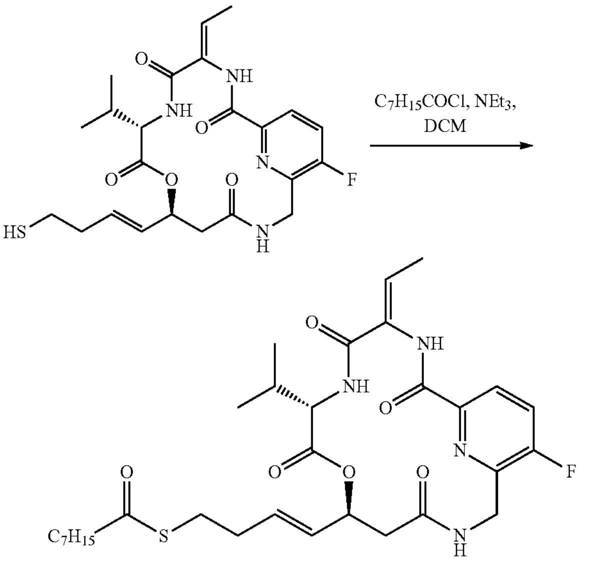

At 0° C., redistilled $NEt_3$ (0.04 ml) was added to the reactant (0.126 mmol) in anhydrous DCM (5 ml), stirred slightly, then added caprylate chloride (0.1 ml). After 7 h, The product was directly spinned anhydrous solvent by column chromatography and pale yellow solid was obtained. $[\alpha]^{20}_D$: 3.71 (c 0.5, $CHCl_3$). $^1$H NMR (400 MHz, $CDCl_3$): δ 9.21 (s, 1H), 8.10 (d, J=7.6 Hz, 1H), 7.51 (d, 1H), 7.14 (d, J=7.6 Hz, 1H), 7.06 (m, J=7.2 Hz, 1H), 6.46 (d, J=10 Hz, 1H), 5.70-5.64 (m, 2H), 5.59-5.46 (m, 1H), 5.13 (dd, J=17.2

Hz, 8 Hz, 1H), 4.73-4.70 (m, 2H), 4.27 (d, J=J=17.2 Hz, 1H), 2.85-2.71 (m, 4H), 2.62-2.61 (m, 1H), 2.49 (t, J=7.6 Hz, 3H), 2.29-2.23 (m, 3H), 1.84-1.81 (m, 3H), 1.61-1.58 (m, 2H), 1.24 (s, 11H), 0.86-0.57 (m, 7H), 0.53 (d, J=7.6 Hz, 3H) ppm. $^{13}C$ NMR (125 MHz, $CDCl_3$) δ169.6, 169.1, 167.6, 165.7, 163.7, 162.3, 155.8, 148.6, 138.5, 134.7, 132.5, 132.2, 130.8, 128.7, 128.2, 127.2, 124.9, 121.3, 72.0, 71.6, 56.9, 44.0, 43.2, 40.8, 38.5, 33.7, 32.1, 31.5, 30.8, 29.6, 29.0, 28.8, 28.8, 27.7, 27.6, 25.5, 24.7, 22.5, 19.0, 18.9, 16.4, 14.6, 13.9 ppm.

Example 60

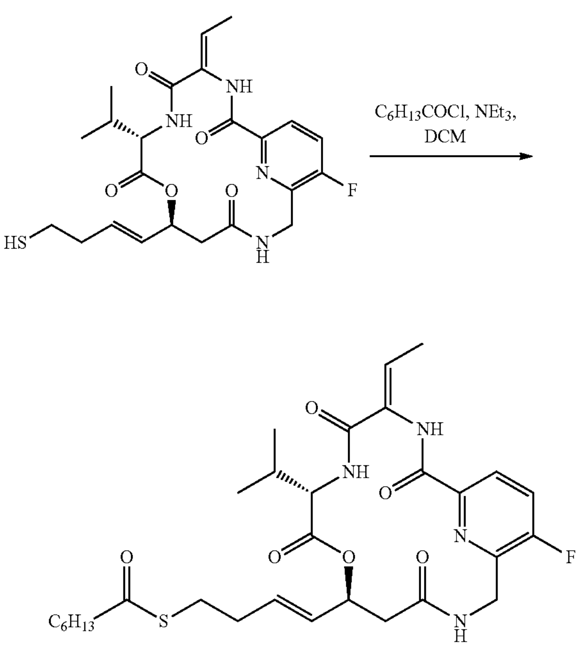

At 0° C., redistilled $NEt_3$ (0.02 ml) was added to the reactant (0.063 mmol) in anhydrous DCM (2 ml), stirred slightly, then added heptanoyl chloride (0.05 ml). After 7 h, The product was directly spinned anhydrous solvent by column chromatography and pale yellow solid was obtained. $[\alpha]^{20}_{D}$: 4.11 (c 0.7, $CHCl_3$). $^{1}H$ NMR (400 MHz, $CDCl_3$): δ 9.23 (s, 1H), 8.12 (d, J=7.8 Hz, 1H), 7.53 (d, J=7.6 Hz, 1H), 7.08 (m, J=7.2 Hz, 1H), 6.73 (d, J=4.4 Hz, 1H), 6.48 (d, J=10 Hz, 1H), 5.72-5.63 (m, 2H), 5.62-5.45 (m, 1H), 5.15 (dd, J=17.2 Hz, 8 Hz, 1H), 4.75-4.71 (m, 2H), 4.28 (d, J=17.2 Hz, 1H), 2.86-2.71 (m, 4H), 2.63-2.62 (m, 1H), 2.50 (t, J=7.8 Hz, 3H), 2.30-2.25 (m, 3H), 1.85-1.82 (m, 3H), 1.62-1.59 (m, 2H), 1.26-1.24 (m, 9H), 0.85 (m, 3H), 0.78 (d, J=7.6 Hz, 3H), 0.57 (d, J=7.6 Hz, 3H) ppm. $^{13}C$ NMR (125 MHz, $CDCl_3$) δ 169.5, 169.0, 163.5, 162.1, 155.7, 148.8, 138.6, 134.5, 132.6, 132.1, 130.9, 128.9, 128.5, 127.5, 125.1, 121.3, 72.2, 71.7, 57.3, 44.1, 43.2, 40.9, 38.6, 33.8, 32.2, 31.5, 30.9, 29.7, 29.1, 28.8, 27.7, 27.6, 25.5, 22.5, 19.1, 18.9, 16.4, 14.6, 14.0 ppm.

Example 61

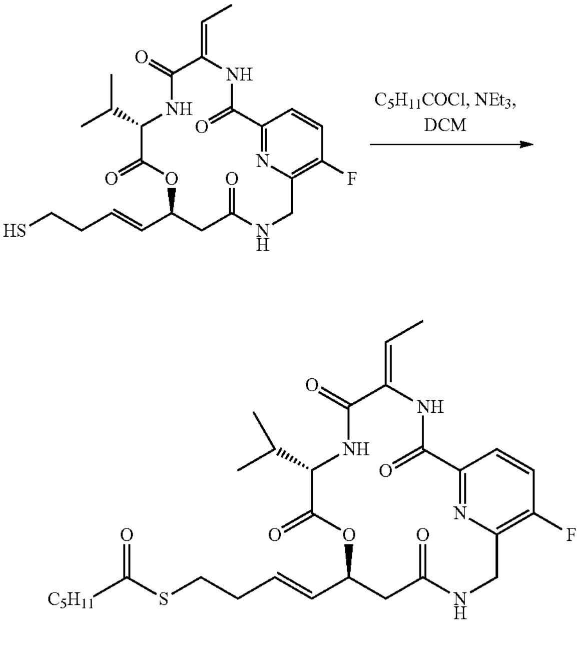

At 0° C., redistilled $NEt_3$ (0.02 ml) was added to the reactant (0.063 mmol) in anhydrous DCM (2 ml), stirred slightly, then added hexanoyl chloride (0.04 ml). After 7 h, The product was directly spinned anhydrous solvent by column chromatography and pale yellow solid was obtained. $[\alpha]^{20}_{D}$: 3.11 (c 0.3, $CHCl_3$). $^{1}H$ NMR (400 MHz, $CDCl_3$): δ 9.22 (s, 1H), 8.10 (d, J=7.8 Hz, 1H), 7.55 (d, J=7.6 Hz, 1H), 7.06 (m, J=7.2 Hz, 1H), 6.75 (d, J=4.4 Hz, 1H), 6.46 (d, J=10.0 Hz, 1H), 5.74-5.68 (m, 2H), 5.50 (m, 1H), 5.17 (dd, J=17.2 Hz, 8.0 Hz, 1H), 4.76-4.73 (m, 2H), 4.28 (d, J=17.2 Hz, 1H), 2.88-2.75 (m, 4H), 2.63 (m, 1H), 2.49 (t, J=7.8 Hz, 3H), 2.30-2.25 (m, 3H), 1.84-1.82 (m, 3H), 1.63-1.60 (m, 2H), 1.26-1.24 (m, 7H), 0.84 (m, 3H), 0.79 (d, J=7.6 Hz, 3H), 0.59 (d, J=7.6 Hz, 3H) ppm. $^{13}C$ NMR (125 MHz, $CDCl_3$) δ 169.3, 169.0, 163.2, 162.0, 155.6, 148.9, 138.8, 134.8, 132.7, 132.0, 130.9, 128.9, 128.6, 127.7, 125.3, 121.5, 72.3, 71.8, 57.5, 44.3, 43.4, 41.2, 38.9, 33.9, 32.5, 31.7, 30.9, 29.8, 29.2, 28.9, 27.8, 27.6, 25.6, 22.6, 19.0, 16.5, 14.7, 13.9 ppm.

Example 62

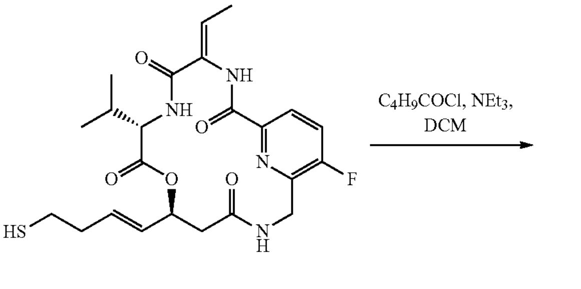

-continued

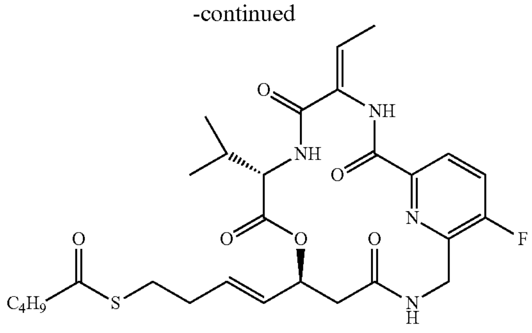

At 0° C., redistilled $NEt_3$ (0.02 ml) was added to the reactant (0.063 mmol) in anhydrous DCM (2 ml), stirred slightly, then added pivaloyl chloride (0.04 ml). After 7 h, The product was directly spinned anhydrous solvent by column chromatography and pale yellow solid was obtained. $[\alpha]^{20}_{D}$: 3.31 (c 0.6, $CHCl_3$). $^1H$ NMR (400 MHz, $CDCl_3$): δ 9.20 (s, 1H), 8.12 (d, J=7.8 Hz, 1H), 7.66 (d, J=7.6 Hz, 1H), 7.08 (d, J=7.2 Hz, 1H), 6.73 (d, J=4.4 Hz, 1H), 6.49 (d, J=10.0 Hz, 1H), 5.73-5.69 (m, 2H), 5.51 (m, 1H), 5.15 (dd, J=17.2 Hz, 8.0 Hz, 1H), 4.75-4.73 (m, 2H), 4.29 (d, J=17.2 Hz, 1H), 2.89-2.75 (m, 4H), 2.62 (m, 1H), 2.47 (t, J=7.8 Hz, 3H), 2.31-2.26 (m, 3H), 1.85-1.83 (m, 3H), 1.62-1.60 (m, 2H), 1.25-1.23 (m, 5H), 0.83 (m, 3H), 0.78 (d, J=7.6 Hz, 3H), 0.58 (d, J=7.6 Hz, 3H) ppm. $^{13}C$ NMR (125 MHz, $CDCl_3$) δ 169.2, 169.0, 163.3, 162.2, 155.7, 148.7, 138.9, 134.5, 132.8, 132.1, 130.8, 128.9, 128.5, 127.6, 125.2, 121.3, 72.1, 71.6, 57.8, 44.2, 43.5, 41.3, 38.8, 33.8, 32.6, 31.6, 30.8, 29.9, 29.3, 28.8, 27.6, 25.7, 22.7, 19.1, 16.6, 14.9, 13.8 ppm.

Example 63

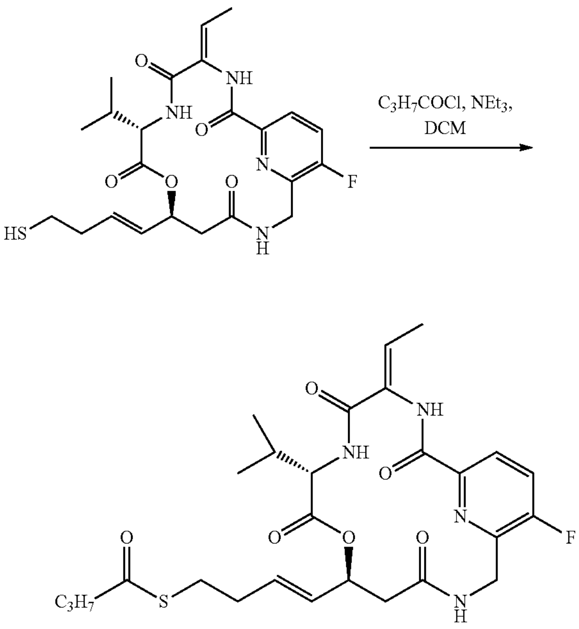

At 0° C., redistilled $NEt_3$ (0.02 ml) was added to the reactant (0.063 mmol) in anhydrous DCM (2 ml), stirred slightly, then added butyryl chloride (0.05 ml). After 7 h, The product was directly spinned anhydrous solvent by column chromatography and pale yellow solid was obtained. $[\alpha]^{20}_{D}$: 6.51 (c 0.5, $CHCl_3$). $^1H$ NMR (400 MHz, $CDCl_3$): δ 9.23 (s, 1H), 8.12 (d, J=7.8 Hz, 1H), 7.98 (d, J=7.6 Hz, 1H), 7.49 (d, J=7.6 Hz, 1H), 6.75 (d, J=4.4 Hz, 1H), 6.47 (d, J=10.0 Hz, 1H), 5.76-5.71 (m, 2H), 5.53 (m, 1H), 5.18 (dd, J=17.2 Hz, 8.0 Hz, 1H), 4.77-4.74 (m, 2H), 4.27 (d, J=17.2 Hz, 1H), 2.88-2.74 (m, 4H), 2.63 (m, 1H), 2.49 (t, J=7.8 Hz, 3H), 2.33-2.28 (m, 3H), 1.86-1.83 (m, 3H), 1.66-1.62 (m, 2H), 1.27-1.24 (m, 3H), 0.86 (m, 3H), 0.79 (d, J=7.6 Hz, 3H), 0.56 (d, J=7.6 Hz, 3H) ppm. $^{13}C$ NMR (125 MHz, $CDCl_3$) δ 169.4, 169.1, 163.5, 162.3, 155.8, 148.8, 138.9, 134.7, 132.9, 132.3, 130.9, 128.9, 128.4, 127.5, 125.3, 121.5, 72.2, 71.7, 57.6, 44.5, 43.6, 41.4, 38.9, 33.9, 32.7, 31.7, 30.9, 29.9, 29.5, 28.9, 27.7, 25.8, 22.9, 19.3, 15.5, 13.8 ppm.

Example 64

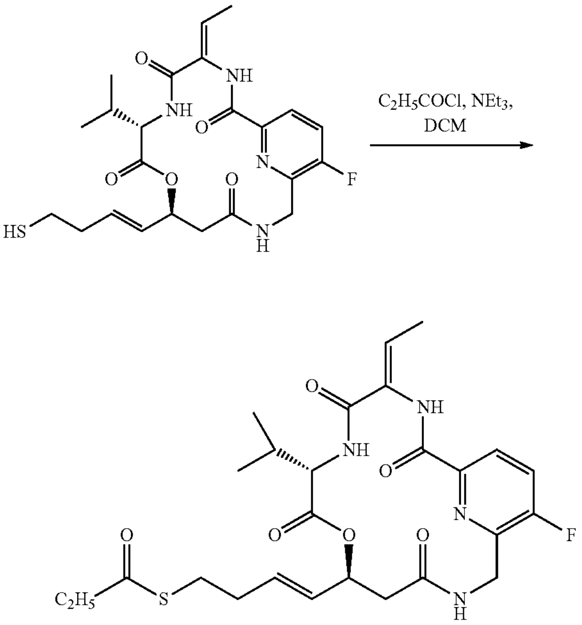

At 0° C., redistilled $NEt_3$ (0.02 ml) was added to the reactant (0.063 mmol) in anhydrous DCM (2 ml), stirred slightly, was added propionyl chloride (0.05 ml). After 7 h, The product was directly spinned anhydrous solvent by column chromatography and pale yellow solid was obtained. $[\alpha]^{20}_{D}$: 5.50 (c 0.3, $CHCl_3$). $^1H$ NMR (400 MHz, $CDCl_3$): δ 9.25 (s, 1H), 8.14 (d, J=7.8 Hz, 1H), 7.51 (d, J=7.6 Hz, 1H), 7.08 (d, J=7.2 Hz, 1H), 6.77 (d, J=4.4 Hz, 1H), 6.48 (d, J=10.0 Hz, 1H), 5.75-5.72 (m, 2H), 5.55 (m, 1H), 5.19 (dd, J=17.2 Hz, 8.0 Hz, 1H), 4.78-4.75 (m, 2H), 4.28 (d, J=17.2 Hz, 1H), 2.89-2.75 (m, 4H), 2.65 (m, 1H), 2.48 (t, J=7.8 Hz, 3H), 2.35-2.29 (m, 3H), 1.88-1.85 (m, 3H), 1.66 (m, 2H), 0.86 (m, 3H), 0.77 (d, J=7.6 Hz, 3H), 0.57 (d, J=7.6 Hz, 3H) ppm. $^{13}C$ NMR (125 MHz, $CDCl_3$) δ 169.6, 169.2, 163.3, 162.2, 155.9, 148.9, 138.8, 134.8, 132.9, 132.2, 130.8, 128.9, 128.5, 127.6, 125.5, 121.6, 72.3, 71.8, 57.8, 44.6, 43.7, 41.5, 38.8, 33.9, 32.8, 31.8, 30.8, 29.9, 29.6, 28.9, 27.8, 25.9, 22.9, 19.5, 14.8 ppm.

Example 65

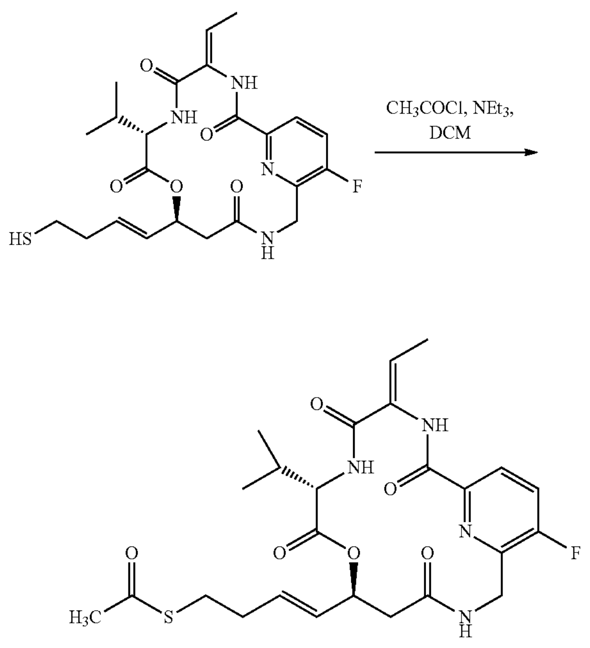

At 0° C., redistilled $NEt_3$ (0.02 ml) was added to the reactant (0.063 mmol) in anhydrous DCM (2 ml), stirred slightly, acetyl chloride (0.05 ml) was added. After 7 h, the product was directly spinned anhydrous solvent by column chromatography and pale yellow solid was obtained. $[\alpha]^{20}_{D}$: 4.66 (c 0.6, $CHCl_3$). $^1H$ NMR (400 MHz, $CDCl_3$): δ 9.26 (s, 1H), 8.15 (d, J=7.8 Hz, 1H), 7.48 (d, J=7.6 Hz, 1H), 7.09 (d, J=7.2 Hz, 1H), 6.79 (d, J=4.4 Hz, 1H), 6.47 (d, J=10.0 Hz, 1H), 5.73-5.70 (m, 2H), 5.53 (m, 1H), 5.18 (dd, J=17.2 Hz, 8.0 Hz, 1H), 4.77 (m, 2H), 4.28 (d, J=17.2 Hz, 1H), 2.88-2.78 (m, 4H), 2.67 (m, 1H), 2.49 (t, J=7.8 Hz, 3H), 2.36-2.33 (m, 3H), 1.89-1.86 (m, 3H), 0.88 (m, 3H), 0.78 (d, J=7.6 Hz, 3H), 0.58 (d, J=7.6 Hz, 3H) ppm. $^{13}C$ NMR (125 MHz, $CDCl_3$) δ 169.8, 169.3, 163.5, 162.5, 155.8, 148.8, 138.7, 134.7, 132.8, 132.3, 130.9, 128.8, 128.7, 127.7, 125.6, 121.7, 72.5, 71.9, 57.9, 44.7, 43.9, 41.6, 38.9, 33.8, 32.9, 31.9, 30.9, 29.8, 29.5, 28.8, 27.7, 15.0 ppm.

Example 66

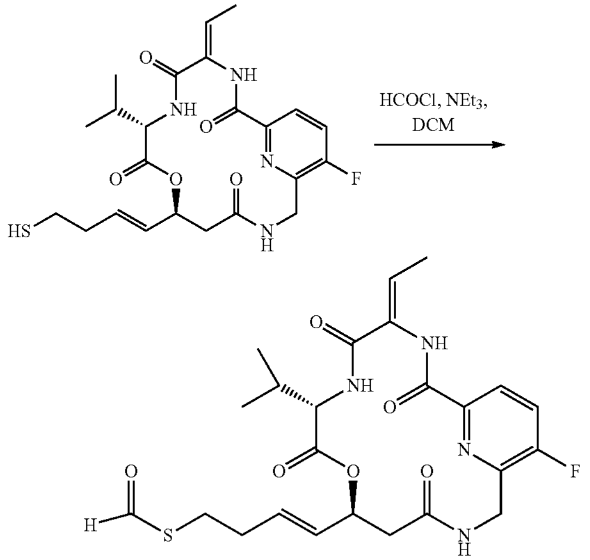

At 0° C., redistilled $NEt_3$ (0.02 ml) was added to the reactant (30 mg, 0.063 mmol) in anhydrous DCM (2 ml), stirred slightly, methanesulfonyl chloride (0.02 ml) was added. After 7 h, the product was directly spinned anhydrous solvent by column chromatography and 26 mg pale yellow solid was obtained. The yield was 75%. $[\alpha]^{20}_{D}$: 1.96 (c 0.1, $CHCl_3$). $^1H$ NMR (400 MHz, $CDCl_3$): δ 9.63 (s, 1H), 9.23 (s, 1H), 8.16 (d, J=7.6 Hz, 1H), 7.48 (d, J=7.6 Hz, 1H), 7.07 (dd, J=14.4 Hz, J=7.2 Hz, 1H), 6.56 (dd, J=7.6 Hz, J=3.6 Hz, 1H), 6.48 (d, J=8 Hz, 1H), 5.73 (m, 2H), 5.52 (dd, J=15.6 Hz, J=6.8 Hz, 1H), 5.12 (m, 1H), 4.76 (dd, J=10 Hz, J=3.6 Hz, 1H), 4.33 (m, 1H), 2.72 (m, 2H), 2.53 (m, 2H), 2.34-2.29 (m, 3H), 1.38 (t, J=7.6 Hz, 1H), 0.82 (d, J=6.8 Hz, 3H), 0.62 (d, J=6.8 Hz, 3H) ppm. $^{13}C$ NMR (125 MHz, $CDCl_3$) δ 176.5, 169.8, 169.4, 163.6, 162.6, 155.7, 148.8, 138.5, 134.7, 132.5, 132.3, 130.9, 128.8, 127.8, 125.6, 121.8, 72.5, 71.7, 56.9, 44.8, 43.6, 41.5, 36.0, 30.8, 23.7, 18.9, 16.5, 14.6 ppm.

Example 67

67.1

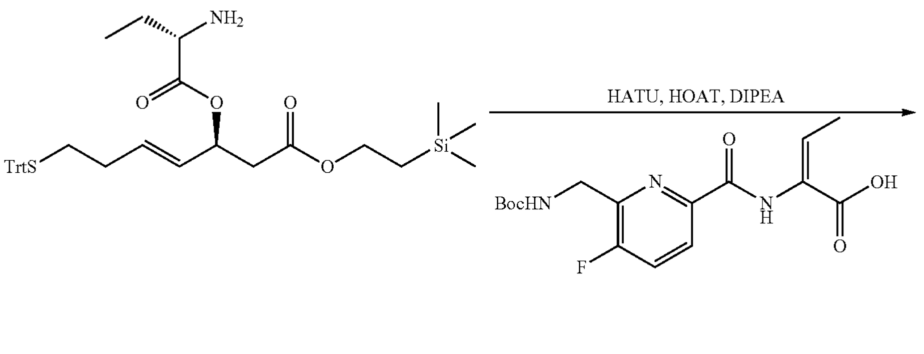

-continued

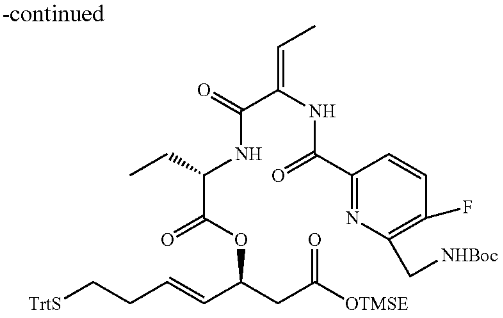

At 0° C., DIPEA (0.7 ml), the product (610 mg) of Example 58.5, HATU (760 mg), HOAT (326 mg) were added to the reactant (1 mmol) in DCM solution (10 ml) sequentially, and raised to room temperature with stirring. After 8 h, the reaction was washed with saturated sodium bicarbonate solution, dilute hydrochloric acid solution, saturated sodium chloride solution, dried over anhydrous sodium sulfate. The product was filtered and spinned anhydrous by column chromatography and white flocculent solid solid was obtained. $^{1}H$ NMR (400 MHz, $CDCl_3$): δ 9.36 (s, 1H), 8.11 (d, J=7.6 Hz, 1H), 7.55 (d, J=7.6 Hz, 1H), 7.39-7.18 (m, 12H), 6.68-6.63 (m, 2H), 5.66-5.60 (m, 2H), 5.47 (s, 1H), 5.38-5.32 (m, 1H), 4.61 (dd, J=8.8 Hz, 4 Hz, 1H), 4.51 (d, J=4.2 Hz, 2H), 4.16-4.11 (m, 3H), 2.67 (dd, J=15.6 Hz, 7.6 Hz, 1H), 2.53 (dd, J=15.6 Hz, 5.6 Hz, 1H), 2.19-2.15 (m, 3H), 2.05 (t, J=6.8 Hz, 4H), 1.83 (d, J=7.2 Hz, 3H), 1.49 (s, 9H), 1.27 (t, J=6.8 Hz, 2H), 0.95-0.91 (m, 3H), 0.82 (d, J=6.8 Hz, 3H), 0.02 (s, 9H) ppm. $^{13}C$ NMR (125 MHz, $CDCl_3$) δ 171.1, 170.8, 169.6, 164.2, 162.7, 157.4, 155.9, 148.6, 144.7, 138.4, 133.9, 129.7, 129.4, 129.0, 127.6, 126.5, 124.6, 121.1, 79.7, 71.8, 66.5, 63.0, 60.3, 57.0, 45.6, 39.5, 31.5, 31.2, 31.0, 28.3, 20.9, 18.8, 17.5, 17.2, 14.1, 0.9, −1.5, −1.6 ppm.

67.2

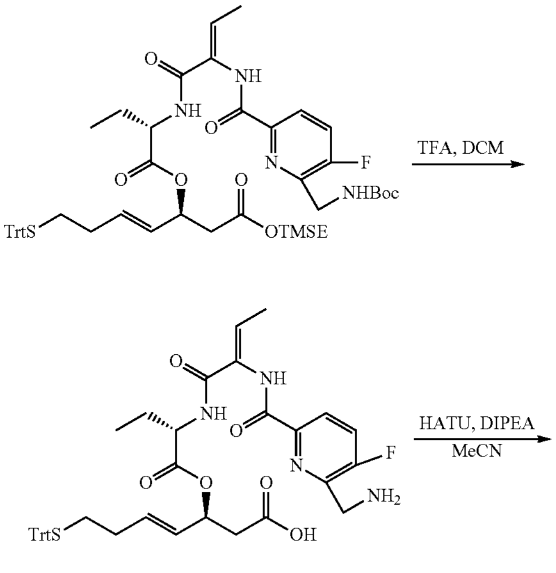

-continued

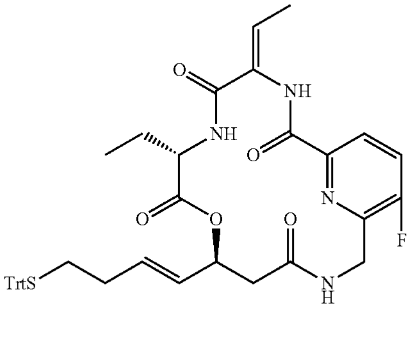

Tetrabutylammonium fluoride in tetrahydrofuran solution (1 mol/l, 2.3 ml) was added to the reaction (0.90 mmol) in redistilled THF (5 ml). After 3 h, the reaction was immediately spinned anhydrous by column chromatography to obtain a white solid. DCM solution (25 ml) of the resulting resultant was added trifluoroacetic acid (6 ml). After 5 h, spinned and removed DCM, the residue was added toluene (8 ml). Without further treatment, a brown viscous material was obtained after pumped organic solvent with oil pump. Chromatography pure acetonitrile (200 ml) obtained above was dissolved, slowly dropped in HATU (3 g), DIPEA (4 ml) of HPLC grade acetonitrile (550 ml). After 24 h, spinned anhydrous solvents, the product was diluted with ethyl acetate (20 ml) and then washed with saturated sodium bicarbonate solution, dilute hydrochloric acid solution, saturated sodium chloride solution and dried over anhydrous sodium sulfate. The product was filtered and spinned anhydrous by column chromatography and pale yellow solid was obtained. $^{1}H$ NMR (400 MHz, $CDCl_3$): δ 9.17 (s, 1H), 8.10 (d, J=7.6 Hz, 1H), 7.37-7.16 (m, 15H), 7.17 (d, J=7.6 Hz, 1H), 7.07 (q, J=7.2 Hz, 1H), 6.43 (d, J=10.4 Hz, 1H), 5.62-5.56 (m, 2H), 5.39-5.34 (m, 1H), 5.06 (dd, J=17.2 Hz, 8 Hz, 1H), 4.74 (dd, J=6.4 Hz, 3.6 Hz, 1H), 4.19-4.08 (m, 2H), 2.69-2.64 (m, 2H), 2.30-2.27 (m, 1H), 2.21-2.17 (m, 2H), 1.84 (d, J=7.2 Hz, 3H), 0.79 (d, J=6.8 Hz, 3H), 0.59 (d, J=6.8 Hz, 3H) ppm. $^{13}C$ NMR (125 MHz, DMSO) δ 133.64, 132.05, 131.39, 126.08, 124.66, 118.36, 111.05, 107.13, 100.97, 97.27, 95.22, 91.96, 90.37, 90.32, 89.54, 89.11, 87.45, 83.79, 39.76, 39.50, 39.25, 34.06, 29.13, 22.85, 19.48 ppm.

67.3

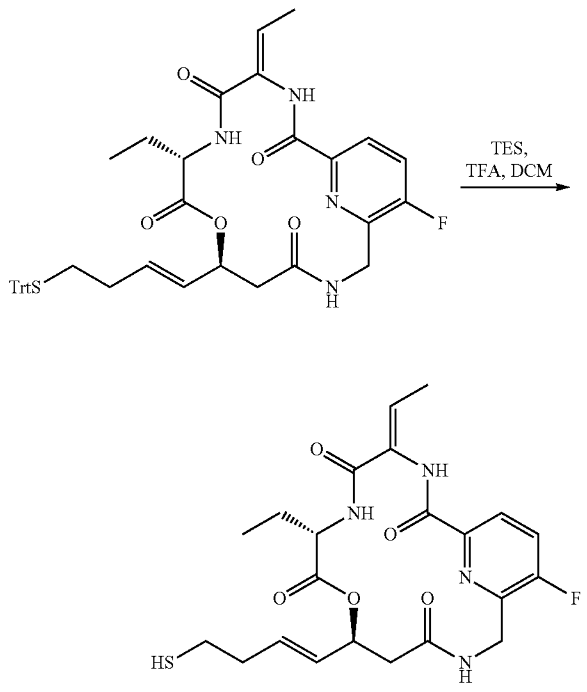

At 0° C., TES (0.1 ml), TFA (0.65 ml) were added to the reactants (0.21 mmol) in anhydrous DCM solution (5 ml) sequentially. 15 min later, the product was directly spinned anhydrous solvent by column chromatography and pale yellow solid was obtained. $[\alpha]^{20}_{D}$: 6.13 (c 0.5, $CHCl_3$). $^{1}H$ NMR (400 MHz, $CDCl_3$): δ 8.18 (d, J=7.6 Hz, 1H), 7.39 (d, J=7.6 Hz, 1H), 7.06 (dd, J=14.4 Hz J=7.2 Hz, 1H), 6.58 (dd, J=7.6 Hz, J=3.6 Hz, 1H), 6.45 (d, J=8 Hz, 1H), 5.74-5.64 (m, 2H), 5.50 (dd, J=15.6 Hz, J=6.8 Hz, 1H), 5.10 (m, 1H), 4.74 (dd, J=10 Hz, J=3.6 Hz, 1H), 4.34-4.28 (m, 1H), 2.74-2.69 (m, 2H), 2.56-2.50 (m, 2H), 2.34-2.29 (m, 3H), 1.36 (t, J=7.6 Hz, 1H), 0.80 (d, J=6.8 Hz, 3H), 0.6 (d, J=6.8 Hz, 3H) ppm. $^{13}C$ NMR (125 MHz, $CDCl_3$) δ 169.6, 168.9, 163.6, 162.9, 155.7, 148.6, 138.3, 134.7, 132.4, 128.6, 127.0, 124.9, 121.4, 77.2, 76.9, 76.7, 71.9, 56.9, 43.3, 41.0, 36.0, 30.8, 23.7, 18.9, 16.5, 14.6 ppm.

Example 68

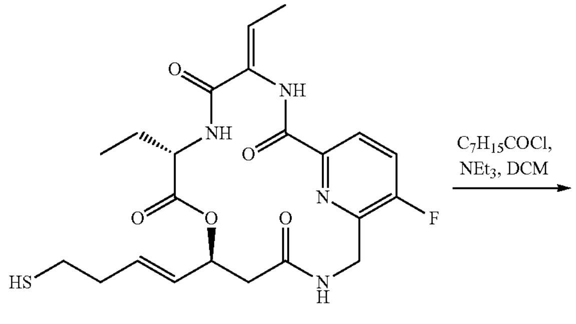

-continued

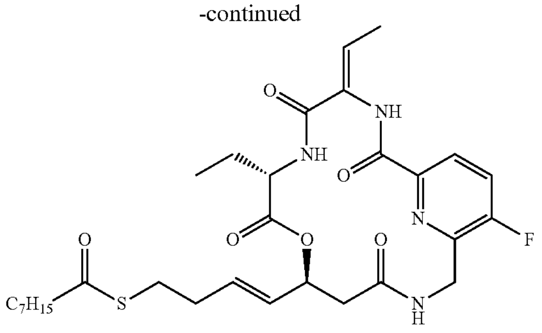

At 0° C., redistilled $NEt_3$ (0.04 ml) was added to the reactant (0.126 mmol) in anhydrous DCM (5 ml), stirred slightly, then added caprylate chloride (0.1 ml). After 7 h, The product was directly spinned anhydrous solvent by column chromatography and pale yellow solid was obtained. $[\alpha]^{20}_{D}$: 3.71 (c 0.5, $CHCl_3$). $^{1}H$ NMR (400 MHz, $CDCl_3$): δ 9.21 (s, 1H), 8.10 (d, J=7.6 Hz, 1H), 7.41 (d, J=7.6 Hz, 1H), 7.06 (m, J=7.2 Hz, 1H), 6.70 (d, J=4.4 Hz, 1H), 6.46 (d, J=10 Hz, 1H), 5.70-5.64 (m, 2H), 5.59-5.46 (m, 1H), 5.13 (dd, J=17.2 Hz, 8 Hz, 1H), 4.73-4.70 (m, 2H), 4.27 (d, J=J=17.2 Hz, 1H), 2.85-2.71 (m, 4H), 2.62-2.61 (m, 1H), 2.49 (t, J=7.6 Hz, 3H), 2.29-2.23 (m, 3H), 1.84-1.81 (m, 3H), 1.61-1.58 (m, 2H), 1.24 (s, 11H), 0.86-0.57 (m, 7H), 0.53 (d, J=7.6 Hz, 3H) ppm. $^{13}C$ NMR (125 MHz, $CDCl_3$) δ 199.5, 169.6, 169.1, 167.6, 165.7, 163.7, 162.3, 155.8, 148.6, 138.5, 134.7, 132.5, 132.2, 130.8, 128.7, 128.2, 127.2, 124.9, 121.3, 77.2, 77.0, 76.7, 72.0, 71.6, 56.9, 44.0, 43.2, 40.8, 38.5, 33.7, 32.1, 31.5, 30.8, 29.6, 29.0, 28.8, 28.8, 27.7, 27.6, 25.5, 24.7, 22.5, 19.0, 18.9, 16.4, 14.6, 13.9 ppm.

Example 69

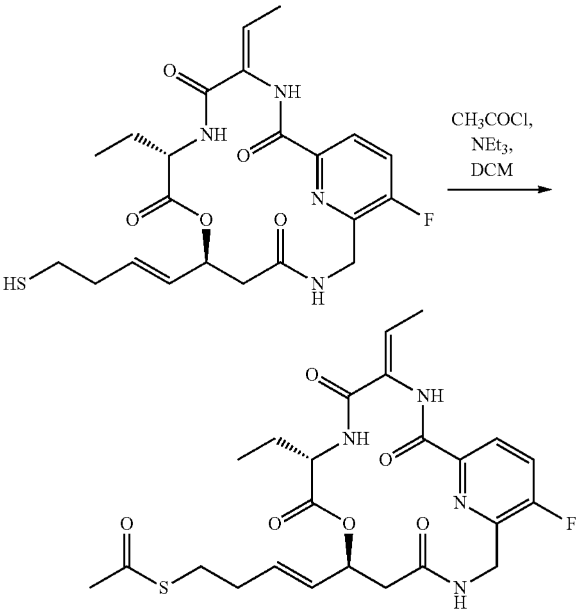

At 0° C., redistilled $NEt_3$ (0.04 ml) was added to the reactant (0.126 mmol) in anhydrous DCM (5 ml), stirred slightly, then added caprylate chloride (0.1 ml). After 7 h, The product was directly spinned anhydrous solvent by column chromatography and pale yellow solid was obtained. $[\alpha]^{20}_{D}$: 3.71 (c 0.5, $CHCl_3$). $^1$H NMR (400 MHz, $CDCl_3$): δ 9.21 (s, 1H), 8.10 (d, J=7.6 Hz, 1H), 7.41 (d, J=7.6 Hz, 1H), 7.06 (m, J=7.2 Hz, 1H), 6.70 (d, J=4.4 Hz, 1H), 6.46 (d, J=10 Hz, 1H), 5.70-5.64 (m, 2H), 5.59-5.46 (m, 1H), 5.13 (dd, J=17.2 Hz, 8 Hz, 1H), 4.73-4.70 (m, 2H), 4.27 (d, J=J=17.2 Hz, 1H), 2.85-2.71 (m, 4H), 2.62-2.61 (m, 1H), 2.49 (t, J=7.6 Hz, 3H), 2.29-2.23 (m, 3H), 1.84-1.81 (m, 3H), 1.61-1.58 (m, 2H), 1.24 (s, 11H), 0.86-0.57 (m, 7H), 0.53 (d, J=7.6 Hz, 3H) ppm. $^{13}$C NMR (125 MHz, $CDCl_3$) δ 199.5, 169.6, 169.1, 167.6, 165.7, 163.7, 162.3, 155.8, 148.6, 138.5, 134.7, 132.5, 132.2, 130.8, 128.7, 128.2, 127.2, 124.9, 121.3, 77.2, 77.0, 76.7, 72.0, 71.6, 56.9, 44.0, 43.2, 40.8, 38.5, 33.7, 32.1, 31.5, 30.8, 29.6, 29.0, 28.8, 28.8, 27.7, 27.6, 25.5, 24.7, 22.5, 19.0, 18.9, 16.4, 14.6, 13.9 ppm.

Example 70

70.1

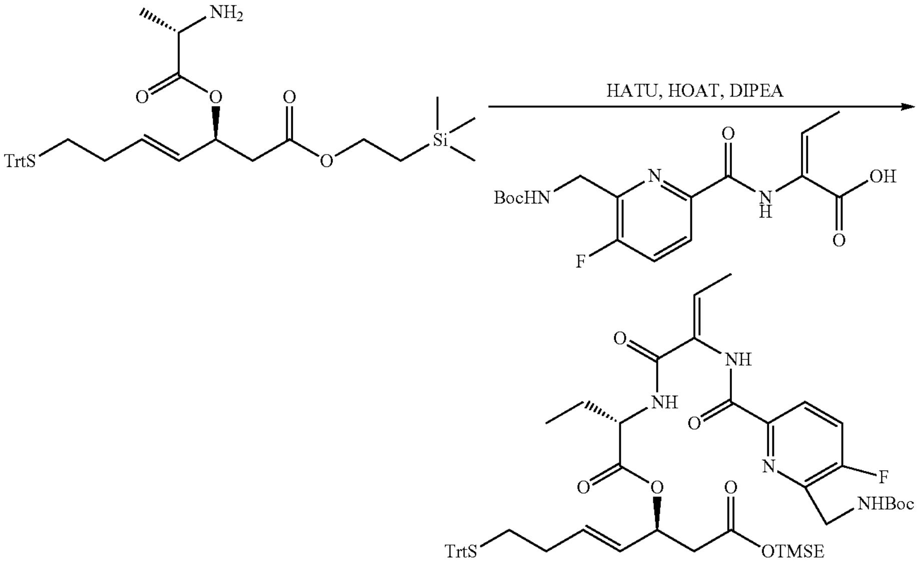

At 0° C., DIPEA (0.7 ml), the product (610 mg) of Example 1.5, HATU (760 mg), HOAT (326 mg) were added to the reactant (1 mmol) in DCM solution (10 ml) sequentially, and raised to room temperature with stirring. After 8 h, the reaction was washed with saturated sodium bicarbonate solution, dilute hydrochloric acid solution, saturated sodium chloride solution, dried over anhydrous sodium sulfate. The product was filtered and spinned anhydrous by column chromatography and white flocculent solid solid was obtained. $^1$H NMR (400 MHz, $CDCl_3$): δ 9.41 (s, 1H), 8.10 (d, J=7.6 Hz, 1H), 7.44 (d, J=7.6 Hz, 1H), 7.39-7.17 (m, 12H), 6.66-6.61 (m, 2H), 5.68-5.59 (m, 2H), 5.46 (s, 1H), 5.38-5.32 (m, 1H), 4.59 (dd, J=8.8 Hz, 4 Hz, 1H), 4.49 (d, J=4.2 Hz, 2H), 4.15-4.10 (m, 3H), 2.66 (dd, J=15.6 Hz, 7.6 Hz, 1H), 2.52 (dd, J=15.6 Hz, 5.6 Hz, 1H), 2.18-2.14 (m, 3H), 2.04 (t, J=6.8 Hz, 4H), 1.82 (d, J=7.2 Hz, 3H), 1.46 (s, 9H), 1.25 (t, J=6.8 Hz, 2H), 0.97-0.90 (m, 5H), 0.80 (d, J=6.8 Hz, 3H), 0.02 (s, 9H) ppm. $^{13}$C NMR (125 MHz, $CDCl_3$) δ 171.0, 170.7, 169.5, 164.3, 162.6, 157.3, 155.9, 148.5, 144.7, 138.2, 133.9, 129.6, 129.4, 129.0, 127.7, 127.6, 126.5, 124.6, 121.1, 79.7, 77.2, 77.0, 76.7, 71.8, 66.5, 63.0, 60.3, 57.0, 45.6, 39.5, 31.5, 31.2, 31.0, 28.3, 20.9, 18.8, 17.5, 17.2, 14.1, 13.8, 0.9, −1.5, −1.6 ppm.

70.2

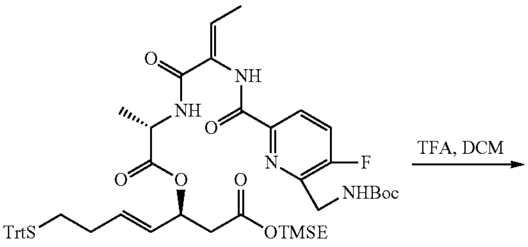

-continued

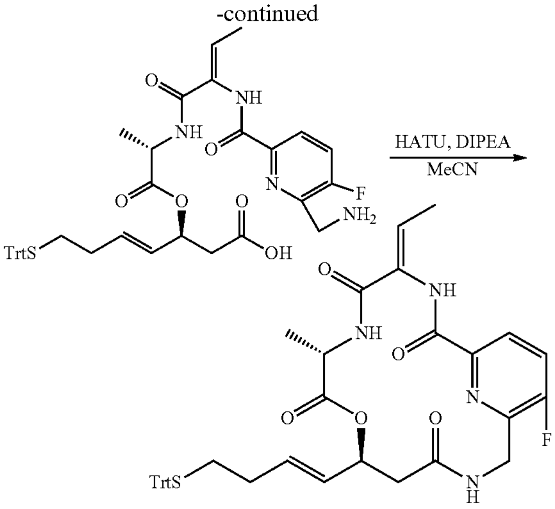

Tetrabutylammonium fluoride in tetrahydrofuran solution (1 mol/l, 2.3 ml) was added to the reaction (0.90 mmol) in redistilled THF (5 ml). After 3 h, the reaction was immediately spinned anhydrous by column chromatography to obtain a white solid. DCM solution (25 ml) of the resulting resultant was added trifluoroacetic acid (6 ml). After 5 h, spinned and removed DCM, the residue was added toluene (8 ml). Without further treatment, a brown viscous material was obtained after pumped organic solvent with oil pump. Chromatography pure acetonitrile (200 ml) obtained above was dissolved, slowly dropped in HATU (3 g), DIPEA (4 ml) of HPLC grade acetonitrile (550 ml). After 24 h, spinned anhydrous solvents, the product was diluted with ethyl acetate (20 ml) and then washed with saturated sodium bicarbonate solution, dilute hydrochloric acid solution, saturated sodium chloride solution and dried over anhydrous sodium sulfate. The product was filtered and spinned anhydrous by column chromatography and pale yellow solid was obtained. $^{1}$H NMR (400 MHz, $CDCl_3$): δ 9.17 (s, 1H), 8.10 (d, J=7.6 Hz, 1H), 7.47 (d, J=7.6 Hz, 1H), 7.37-7.16 (m, 15H), 7.07 (q, J=7.2 Hz, 1H), 6.43 (d, J=10.4 Hz, 1H), 5.62-5.56 (m, 2H), 5.39-5.34 (m, 1H), 5.06 (dd, J=17.2 Hz, 8 Hz, 1H), 4.74 (dd, J=6.4 Hz, 3.6 Hz, 1H), 4.19-4.08 (m, 2H), 2.69-2.64 (m, 2H), 2.30-2.27 (m, 1H), 2.21-2.17 (m, 2H), 1.84 (d, J=7.2 Hz, 3H), 0.79 (d, J=6.8 Hz, 3H), 0.59 (d, J=6.8 Hz, 3H) ppm. $^{13}$C NMR (125 MHz, DMSO) δ 133.64, 132.05, 131.39, 126.08, 124.66, 118.36, 111.05, 107.13, 100.97, 97.27, 95.22, 91.96, 90.37, 90.32, 89.54, 89.11, 87.45, 83.79, 39.76, 39.50, 39.25, 34.06, 29.13, 22.85, 19.48 ppm.

70.3

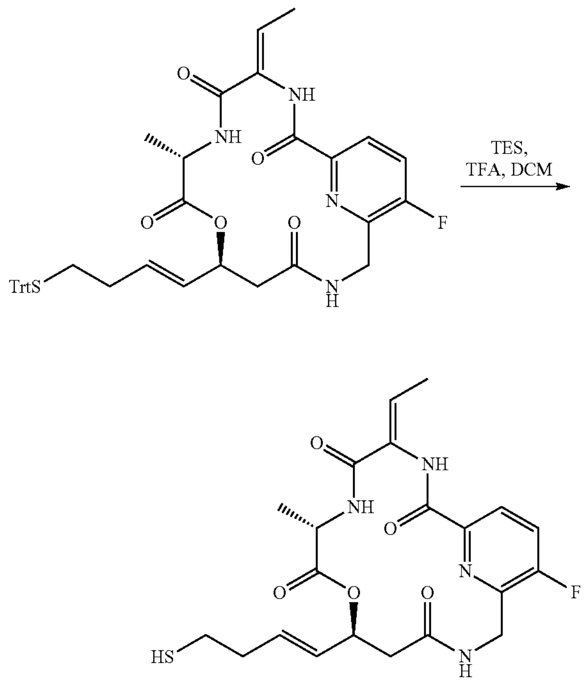

At 0° C., TES (0.1 ml), TFA (0.65 ml) were added to the reactants (150 mg, 0.21 mmol) in anhydrous DCM solution (5 ml) sequentially. 15 min later, the product was directly spinned anhydrous solvent by column chromatography and 63 mg yellow solid was obtained, and the yield was 63%. $[\alpha]^{20}_{D}$: 6.13 (c 0.5, $CHCl_3$). $^{1}$H NMR (400 MHz, $CDCl_3$): δ 8.18 (d, J=7.6 Hz, 1H), 7.49 (d, J=7.6 Hz, 1H), 7.06 (dd, J=14.4 Hz J=7.2 Hz, 1H), 6.58 (dd, J=7.6 Hz, J=3.6 Hz, 1H), 6.45 (d, J=8 Hz, 1H), 5.74-5.64 (m, 2H), 5.50 (dd, J=15.6 Hz, J=6.8 Hz, 1H), 5.10 (m, 1H), 4.74 (dd, J=10 Hz, J=3.6 Hz, 1H), 4.34-4.28 (m, 1H), 2.74-2.69 (m, 2H), 2.56-2.50 (m, 2H), 2.34-2.29 (m, 3H), 1.36 (t, J=7.6 Hz, 1H), 0.80 (d, J=6.8 Hz, 3H), 0.6 (d, J=6.8 Hz, 3H) ppm. $^{13}$C NMR (125 MHz, $CDCl_3$) δ 169.6, 168.9, 163.6, 162.9, 155.7, 148.6, 138.3, 134.7, 132.4, 128.6, 127.0, 124.9, 121.4, 77.2, 76.9, 76.7, 71.9, 56.9, 43.3, 41.0, 36.0, 30.8, 23.7, 18.9, 16.5, 14.6 ppm.

Example 71

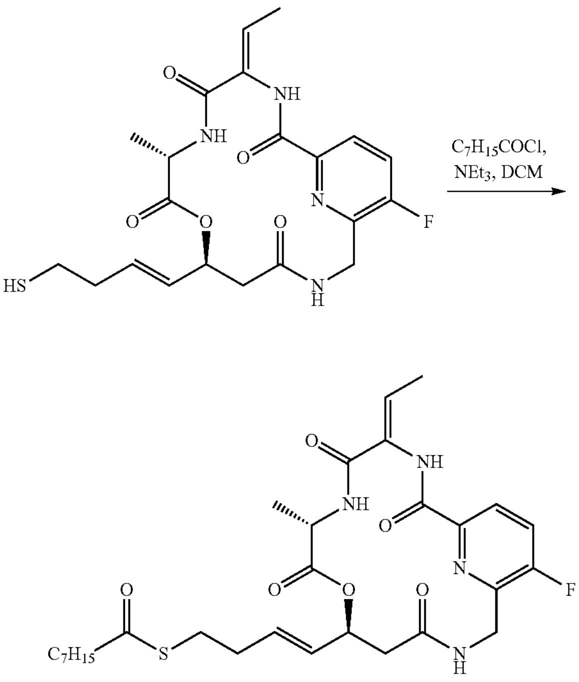

At 0° C., redistilled $NEt_3$ (0.04 ml) was added to the reactant (0.126 mmol) in anhydrous DCM (5 ml), stirred slightly, then added caprylate chloride (0.1 ml). After 7 h, The product was directly spinned anhydrous solvent by column chromatography and pale yellow solid was obtained. $[\alpha]^{20}_{D}$: 3.71 (c 0.5, $CHCl_3$). $^{1}$H NMR (400 MHz, $CDCl_3$): δ 9.21 (s, 1H), 8.10 (d, J=7.6 Hz, 1H), 7.31 (d, J=7.6 Hz, 1H), 7.06 (m, J=7.2 Hz, 1H), 6.70 (d, J=4.4 Hz, 1H), 6.46 (d, J=10 Hz, 1H), 5.70-5.64 (m, 2H), 5.59-5.46 (m, 1H), 5.13 (dd, J=17.2 Hz, 8 Hz, 1H), 4.73-4.70 (m, 2H), 4.27 (d, J=J=17.2 Hz, 1H), 2.85-2.71 (m, 4H), 2.62-2.61 (m, 1H), 2.49 (t, J=7.6 Hz, 3H), 2.29-2.23 (m, 3H), 1.84-1.81 (m, 3H), 1.61-1.58 (m, 2H), 1.24 (s, 11H), 0.86-0.57 (m, 7H), 0.53 (d, J=7.6 Hz, 3H) ppm. $^{13}$C NMR (125 MHz, $CDCl_3$) δ 199.5, 169.6, 169.1, 167.6, 165.7, 163.7, 162.3, 155.8, 148.6, 138.5, 134.7, 132.5, 132.2, 130.8, 128.7, 128.2, 127.2, 124.9, 121.3, 77.2, 77.0, 76.7, 72.0, 71.6, 56.9, 44.0, 43.2, 40.8, 38.5, 33.7, 32.1, 31.5, 30.8, 29.6, 29.0, 28.8, 28.8, 27.7, 27.6, 25.5, 24.7, 22.5, 19.0, 18.9, 16.4, 14.6, 13.9 ppm.

Example 72

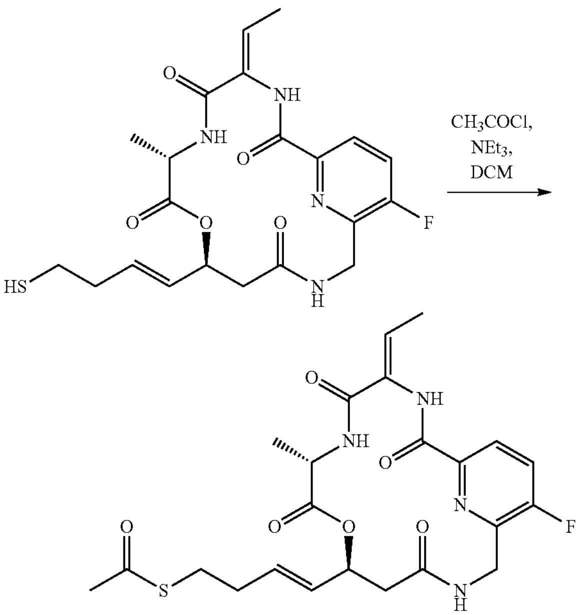

At 0° C., redistilled $NEt_3$ (0.04 ml) was added to the reactant (0.126 mmol) in anhydrous DCM (5 ml), stirred slightly, then added caprylate chloride (0.1 ml). After 7 h, The product was directly spinned anhydrous solvent by column chromatography and yellow solid was obtained. $[\alpha]^{20}_D$: 3.71 (c 0.5, $CHCl_3$). $^1$H NMR (400 MHz, $CDCl_3$): δ 9.21 (s, 1H), 8.10 (d, J=7.6 Hz, 1H), 7.41 (d, J=7.6 Hz, 1H), 7.06 (m, J=7.2 Hz, 1H), 6.70 (d, J=4.4 Hz, 1H), 6.46 (d, J=10 Hz, 1H), 5.70-5.64 (m, 2H), 5.59-5.46 (m, 1H), 5.13 (dd, J=17.2 Hz, 8 Hz, 1H), 4.73-4.70 (m, 2H), 4.27 (d, J=J=17.2 Hz, 1H), 2.85-2.71 (m, 4H), 2.62-2.61 (m, 1H), 2.49 (t, J=7.6 Hz, 3H), 2.29-2.23 (m, 3H), 1.84-1.81 (m, 3H), 1.61-1.58 (m, 2H), 1.24 (s, 11H), 0.86-0.57 (m, 7H), 0.53 (d, J=7.6 Hz, 3H) ppm. $^{13}$C NMR (125 MHz, $CDCl_3$) δ 199.5, 169.6, 169.1, 167.6, 165.7, 163.7, 162.3, 155.8, 148.6, 138.5, 134.7, 132.5, 132.2, 130.8, 128.7, 128.2, 127.2, 124.9, 121.3, 77.2, 77.0, 76.7, 72.0, 71.6, 56.9, 44.0, 43.2, 40.8, 38.5, 33.7, 32.1, 31.5, 30.8, 29.6, 29.0, 28.8, 28.8, 27.7, 27.6, 25.5, 24.7, 22.5, 19.0, 18.9, 16.4, 14.6, 13.9 ppm.

Example 73

73.1

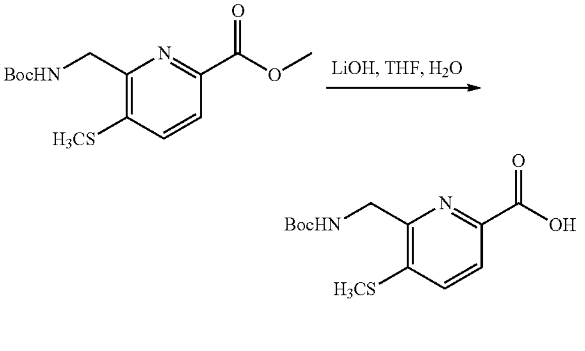

15 ml LiOH aqueous (19 mmol) solution (7.6 mmol) were added dropwise to the reactant (7.6 mmol) of 30 ml THF, then reacted 2 h at room temperature. The reaction solution was adjusted by dilute hydrochloric acid to with the pH value of 3, then 100 ml ethyl acetate was added. The organic matter was washed by water and saturated salt water. The organic layer was dried by anhydrous sodium sulfate, and the solvent evaporated to give a white flocculent solid. $^1$H NMR (400 MHz, $CDCl_3$): δ 7.77 (d, J=8.0 Hz, 1H), 7.48 (d, J=7.8 Hz, 1H), 5.55 (s, 1H), 4.48 (d, J=4.2 Hz, 2H), 3.48 (s, 3H), 1.36 (s, 9H) ppm.

73.2

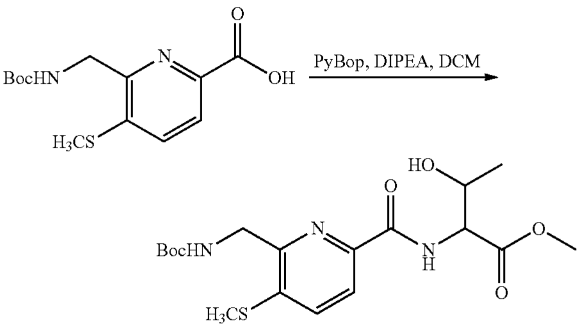

At 0° C., DIPEA (1.2 ml, 6 mmol) was added to the reactant (2.7 mmol) slowly, stirred slightly, then added S2 (2.7 mmol), PyBop (4 mmol), and then stirred at room temperature overnight. The reaction solution was washed with saturated sodium bicarbonate solution, dilute hydrochloric acid solution, saturated sodium chloride solution. The product was dried with anhydrous sodium sulfate and spinned solvent by column chromatography and white floc was obtained. $^1$H NMR (400 MHz, $CDCl_3$): δ 8.64 (d, J=8.4 Hz, 1H), 8.05 (d, J=8 Hz, 1H), 7.81 (d, J=8 Hz, 1H), 5.44 (s, 1H), 4.77 (d, J=7.2 Hz, 1H), 4.48-4.45 (m, J=3H), 3.78 (s, 3H), 3.48 (s, 3H), 1.45 (s, 9H), 1.26 (d, J=5.6 Hz, 3H) ppm. $^{13}$C NMR (100 MHz, $CDCl_3$) δ 171.1, 164.6, 157.4, 156.0, 148.9, 137.9, 134.6, 124.2, 123.2, 121.8, 121.0, 80.7, 79.8, 78.7, 70.3, 68.2, 61.1, 57.8, 52.7, 52.2, 47.7, 32.1, 28.3, 28.2, 28.1, 28.0, 22.6, 19.8 ppm.

73.3

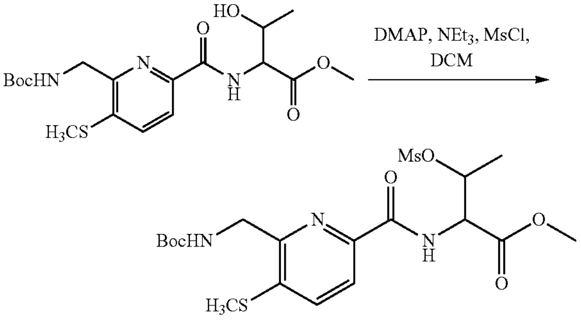

At 0° C., DMAP (0.184 mmol), $NEt_3$ (0.42 ml, 3 mmol), MsCl (0.186 ml, 2.4 mmol) were added to anhydrous DCM (10 ml) of the reactants (1.84 mmol) successively, then raised to room temperature and stirred overnight. The product was spinned anhydrous, pumped with oil pump and directly put into next step.

73.4

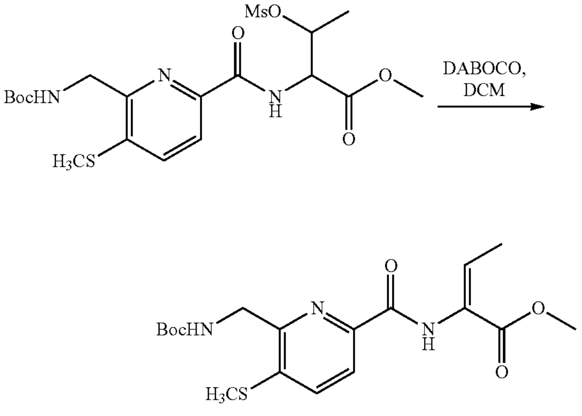

DABOCO (1 g, 9.22 mmol) was added to anhydrous DCM liquid (10 ml) obtained above and stirred 8 h at room temperature. The reaction solution was washed by saturated sodium bicarbonate solution, saturated ammonium chloride solution, saturated sodium chloride solution in sequence, and dried by anhydrous sodium sulfate. The product was filtered and spinned solvent by column chromatography and white floc was obtained. $^{1}$H NMR (400 MHz, $CDCl_3$): δ 9.38 (s, 1H), 8.01 (d, J=7.6 Hz, 1H), 7.41 (d, J=7.6 Hz, 1H), 6.86 (q, J=7.6 Hz, 1H), 5.57 (s, 1H), 4.44 (d, J=5.6 Hz, 2H), 3.74 (s, 9H), 3.48 (s, 3H), 3.48 (s, 3H), 1.80 (d, J=7.6 Hz, 3H), 1.40 (s, 9H) ppm. $^{13}$C NMR (100 MHz, $CDCl_3$) δ 164.8, 162.1, 157.4, 156.0, 148.9, 148.8, 138.1, 133.9, 126.3, 124.2, 123.5, 121.7, 121.0, 79.7, 52.1, 45.9, 28.3, 14.6 ppm.

73.5

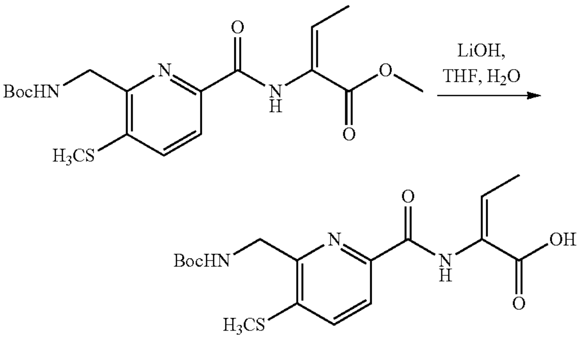

5 ml LiOH aqueous solution (90 mg, 3.6 mmol) were added dropwise to reactants (1.44 mmol) with THF (10 ml), then spinned anhydrous the organic phase after three hours. 10 ml water and 15 ml ethyl acetate were added to the organic phase. The aqueous phase was removed after liquid separation. Then the solution was added 15 ml ethyl acetate, adjusted the acid. Anhydrous sodium sulfate was used for the separation of organic phase after liquid separation. Solid white floc was obtained after spinned anhydrous. $^{1}$H NMR (400 MHz, $CDCl_3$): δ 9.40 (s, 1H), 8.03 (d, J=7.6 Hz, 1H), 7.43 (d, J=7.8 Hz, 1H), 6.88 (q, J=7.8 Hz, 1H), 5.58 (s, 1H), 4.46 (d, J=5.8 Hz, 2H), 3.76 (s, 9H), 3.48 (s, 3H), 1.83 (d, J=7.8 Hz, 3H), 1.43 (s, 9H) ppm. $^{13}$C NMR (100 MHz, $CDCl_3$) δ 165.3, 162.7, 157.8, 156.2, 149.0, 148.8, 138.3, 133.7, 126.5, 124.5, 123.7, 121.9, 121.0, 52.5, 46.3, 28.5, 14.8 ppm.

73.6

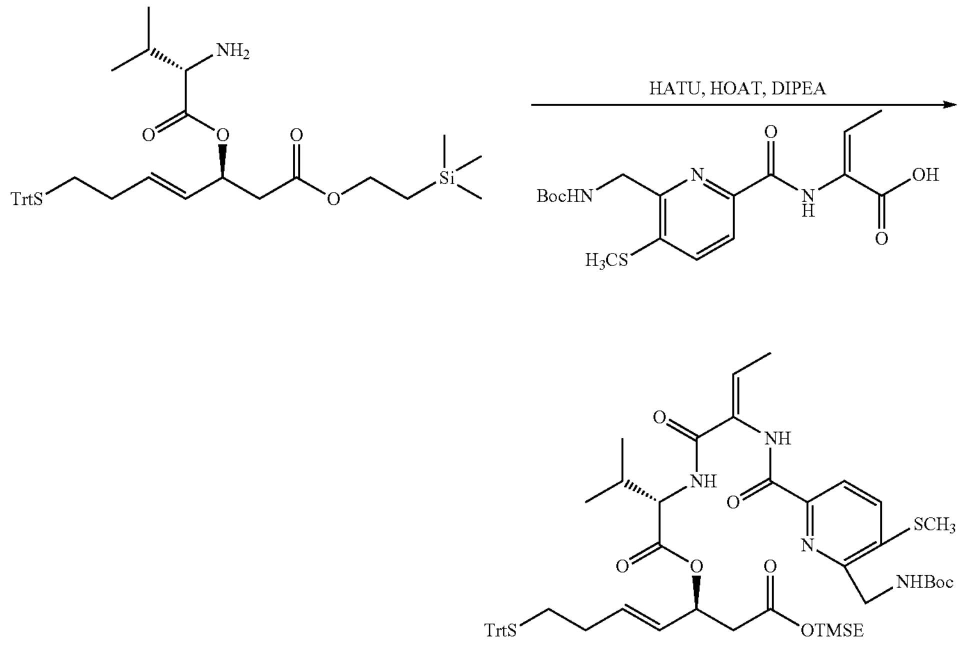

At 0° C., DIPEA (0.7 ml), carboxylic acid (610 mg), HATU (760 mg), HOAT (326 mg) were added to the reactant (1 mmol) in DCM solution (10 ml) sequentially. Then raised to room temperature with stirring. After 8 h, the reaction was washed with saturated sodium bicarbonate solution, dilute hydrochloric acid solution, saturated sodium chloride solution, and dried over anhydrous sodium sulfate. The product was filtered and spinned solvent by column chromatography and white flocculent solid was obtained. $^{1}$H NMR (400 MHz, $CDCl_3$): δ 9.41 (s, 1H), 8.10 (d, J=7.6 Hz, 1H), 7.48 (d, J=7.6 Hz, 1H), 7.39-7.17 (m, 12H), 6.66-6.61 (m, 2H), 5.68-5.59 (m, 2H), 5.46 (s, 1H), 5.38-5.32 (m, 1H), 4.59 (dd, J=8.8 Hz, 4 Hz, 1H), 4.49 (d, J=4.2 Hz, 2H), 4.15-4.10 (m, 3H), 3.48 (s, 3H), 2.66 (dd, J=15.6 Hz, 7.6 Hz, 1H), 2.52 (dd, J=15.6 Hz, 5.6 Hz, 1H), 2.18-2.14 (m, 3H), 2.04 (t, J=6.8 Hz, 4H), 1.82 (d, J=7.2 Hz, 3H), 1.46 (s, 9H), 1.25 (t, J=6.8 Hz, 2H), 0.97-0.90 (m, 5H), 0.80 (d, J=6.8 Hz, 3H), 0.02 (s, 9H) ppm. $^{13}$C NMR (125 MHz, $CDCl_3$) δ 171.0, 170.7, 169.5, 164.3, 162.6, 157.3, 155.9, 148.5, 144.7, 138.2, 133.9, 129.6, 129.4, 129.0, 127.7, 127.6, 126.5, 124.6, 123.5, 121.1, 79.7, 71.8, 66.5, 63.0, 60.3, 57.0, 45.6, 39.5, 31.5, 31.2, 31.0, 28.3, 20.9, 18.8, 17.5, 17.2, 14.1, 13.8, 0.9, −1.5, −1.6 ppm.

73.7

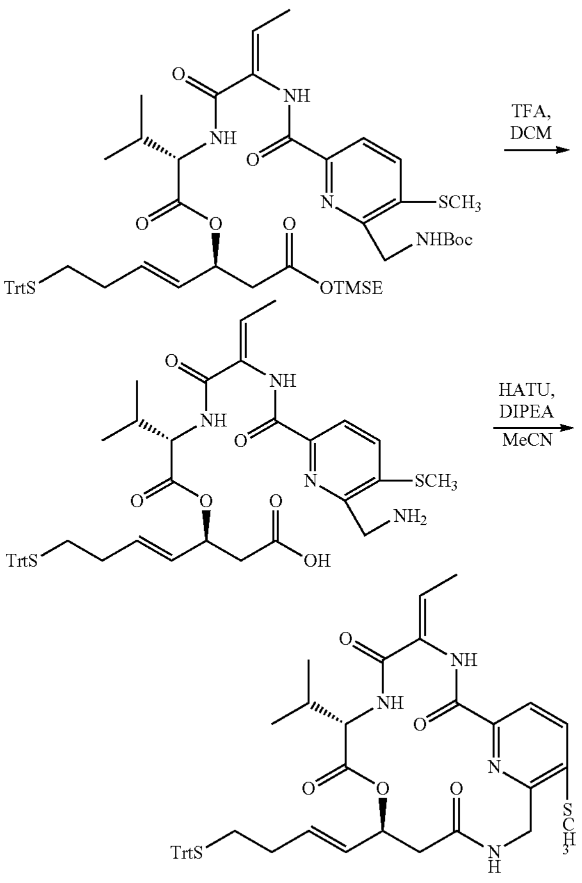

Tetrabutylammonium fluoride in tetrahydrofuran solution (1 mol/l, 2.3 ml) was added to the reaction (0.92 mmol) in redistilled THF (5 ml). After 3 h, the reaction was immediately spinned anhydrous by column chromatography to obtain a white solid. DCM solution (25 ml) of the resulting resultant was added trifluoroacetic acid (6 ml). After 5 h, spinned and removed DCM, the residue was added toluene (8 ml). Without further treatment, a brown viscous material was obtained after pumped organic solvent with oil pump. Chromatography pure acetonitrile (200 ml) obtained above was dissolved, slowly dropped in HATU (3 g), DIPEA (4 ml) of HPLC grade acetonitrile (550 ml). After 24 h, spinned anhydrous solvents, the product was diluted with ethyl acetate (20 ml) and then washed with saturated sodium bicarbonate solution, dilute hydrochloric acid solution, saturated sodium chloride solution and dried over anhydrous sodium sulfate. The product was filtered and spinned anhydrous by column chromatography and pale yellow solid was obtained. $^{1}$H NMR (400 MHz, $CDCl_3$): δ 9.17 (s, 1H), 8.10 (d, J=7.6 Hz, 1H), 7.37-7.16 (m, 15H), 7.07 (q, J=7.2 Hz, 1H), 6.67 (d, J=4.4 Hz, 1H), 6.43 (d, J=10.4 Hz, 1H), 5.62-5.56 (m, 2H), 5.39-5.34 (m, 1H), 5.06 (dd, J=17.2 Hz, 8 Hz, 1H), 4.74 (dd, J=6.4 Hz, 3.6 Hz, 1H), 4.19-4.08 (m, 2H), 3.48 (s, 3H), 2.69-2.64 (m, 2H), 2.30-2.27 (m, 1H), 2.21-2.17 (m, 2H), 1.84 (d, J=7.2 Hz, 3H), 0.79 (d, J=6.8 Hz, 3H), 0.59 (d, J=6.8 Hz, 3H) ppm. $^{13}$C NMR (125 MHz, DMSO) δ 133.6, 132.0, 131.3, 126.1, 124.7, 123.3, 118.4, 111.1, 107.1, 101.0, 97.3, 95.2, 92.0, 90.4, 90.3, 89.5, 89.1, 87.5, 83.8, 39.8, 39.5, 39.3, 34.1, 29.1, 22.9, 19.5 ppm.

Example 74

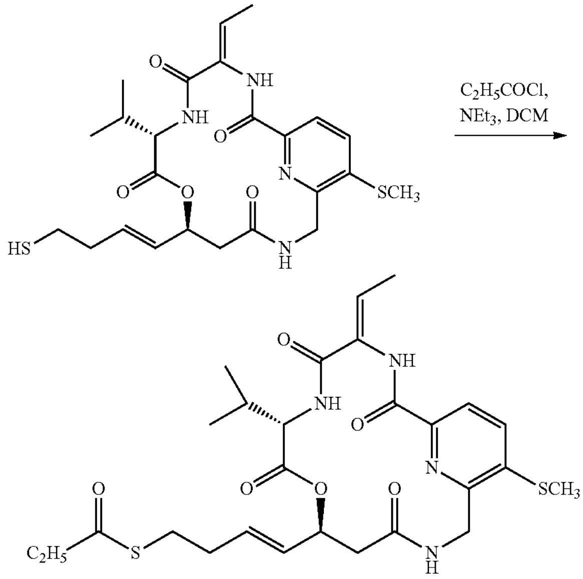

At 0° C., redistilled $NEt_3$ (0.02 ml) was added to the reactant (0.063 mmol) in anhydrous DCM (2 ml), stirred slightly, was added propionyl chloride (0.05 ml). After 7 h, The product was directly spinned anhydrous solvent by column chromatography and pale yellow solid was obtained. $[\alpha]^{20}_{D}$: 5.50 (c 0.3, $CHCl_3$). $^{1}$H NMR (400 MHz, $CDCl_3$): δ 9.25 (s, 1H), 8.14 (d, J=7.8 Hz, 1H), 7.99 (d, J=7.6 Hz, 1H), 7.48 (d, J=7.6 Hz, 1H), 6.77 (d, J=4.4 Hz, 1H), 6.48 (d, J=10.0 Hz, 1H), 5.75-5.72 (m, 2H), 5.55 (m, 1H), 5.19 (dd, J=17.2 Hz, 8.0 Hz, 1H), 4.78-4.75 (m, 2H), 4.28 (d, J=17.2 Hz, 1H), 2.89-2.75 (m, 4H), 2.65 (m, 1H), 2.48 (t, J=7.8 Hz, 3H), 2.35-2.29 (m, 3H), 1.88-1.85 (m, 3H), 1.66 (m, 2H), 0.86 (m, 3H), 0.77 (d, J=7.6 Hz, 3H), 0.57 (d, J=7.6 Hz, 3H) ppm. $^{13}$C NMR (125 MHz, $CDCl_3$) δ 169.6, 169.2, 163.3, 162.2, 155.9, 148.9, 138.8, 134.8, 132.9, 132.2, 130.8, 128.9, 128.5, 127.6, 125.5, 123.4, 121.6, 72.3, 71.8, 57.8, 44.6, 43.7, 41.5, 38.8, 33.9, 32.8, 31.8, 30.8, 29.9, 29.6, 28.9, 27.8, 25.9, 22.9, 19.5, 14.8 ppm.

Example 75

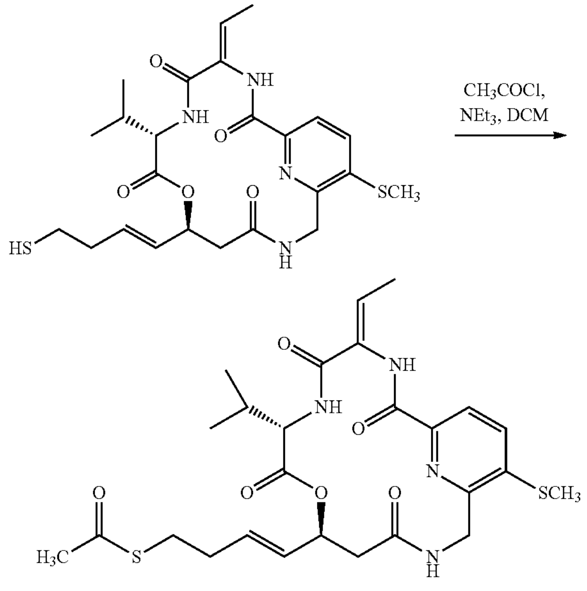

At 0° C., redistilled $NEt_3$ (0.02 ml) was added to the reactant (30 mg, 0.063 mmol) in anhydrous DCM (2 ml), stirred slightly, acetyl chloride (0.05 ml) was added. After 7 h, the product was directly spinned anhydrous solvent by column chromatography and 33 mg pale yellow solid was obtained, and the yield was 85%. $[\alpha]^{20}_{D}$: 4.66 (c 0.6, $CHCl_3$). $^1H$ NMR (400 MHz, $CDCl_3$): δ 9.26 (s, 1H), 8.15 (d, J=7.8 Hz, 1H), 7.49 (d, J=7.6 Hz, 1H), 7.09 (d, J=7.2 Hz, 1H), 6.79 (d, J=4.4 Hz, 1H), 6.47 (d, J=10.0 Hz, 1H), 5.73-5.70 (m, 2H), 5.53 (m, 1H), 5.18 (dd, J=17.2 Hz, 8.0 Hz, 1H), 4.77 (m, 2H), 4.28 (d, J=17.2 Hz, 1H), 2.88-2.78 (m, 4H), 2.67 (m, 1H), 2.49 (t, J=7.8 Hz, 3H), 2.36-2.33 (m, 3H), 1.89-1.86 (m, 3H), 0.88 (m, 3H), 0.78 (d, J=7.6 Hz, 3H), 0.58 (d, J=7.6 Hz, 3H) ppm. $^{13}C$ NMR (125 MHz, $CDCl_3$) δ 169.8, 169.3, 163.5, 162.5, 155.8, 148.8, 138.7, 134.7, 132.8, 132.3, 130.9, 128.8, 128.7, 127.7, 125.6, 123.4, 121.7, 72.5, 71.9, 57.9, 44.7, 43.9, 41.6, 38.9, 33.8, 32.9, 31.9, 30.9, 29.8, 29.5, 28.8, 27.7, 15.0 ppm.

Example 76

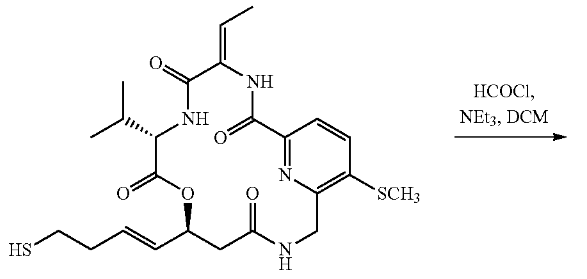

-continued

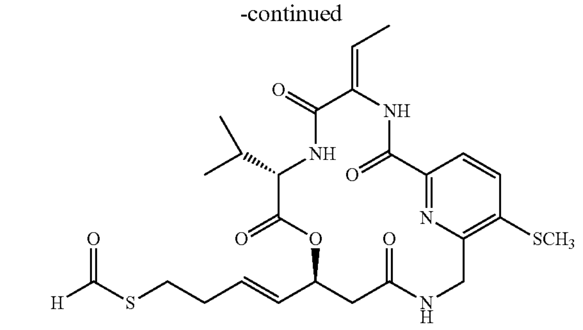

At 0° C., redistilled $NEt_3$ (0.02 ml) was added to the reactant (0.063 mmol) in anhydrous DCM (2 ml), stirred slightly, then added heptanoyl chloride (0.05 ml). After 7 h, The product was directly spinned anhydrous solvent by column chromatography and pale yellow solid was obtained. $[\alpha]^{20}_{D}$: 4.11 (c 0.7, $CHCl_3$). $^1H$ NMR (400 MHz, $CDCl_3$): δ9.63 (s, 1H), 9.23 (s, 1H), 8.12 (d, J=7.8 Hz, 1H), 7.45 (d, J=7.6 Hz, 1H), 7.08 (dd, J=14.4, 7.2 Hz, 1H), 6.73 (d, J=4.4 Hz, 1H), 6.48 (d, J=10 Hz, 1H), 5.72-5.63 (m, 2H), 5.62-5.45 (m, 1H), 5.15 (dd, J=17.2 Hz, 8 Hz, 1H), 4.75-4.71 (m, 2H), 4.28 (d, J=17.2 Hz, 1H), 3.48 (s, 3H), 2.86-2.71 (m, 4H), 2.63-2.62 (m, 1H), 2.50 (t, J=7.8 Hz, 3H), 2.30-2.25 (m, 3H), 1.85-1.82 (m, 3H), 1.62-1.59 (m, 2H), 1.26-1.24 (m, 9H), 0.85 (m, 3H), 0.78 (d, J=7.6 Hz, 3H), 0.57 (d, J=7.6 Hz, 3H) ppm. $^{13}C$ NMR (125 MHz, $CDCl_3$) δ 169.5, 169.0, 163.5, 162.1, 155.7, 148.8, 138.6, 134.5, 132.6, 132.1, 130.9, 128.9, 128.5, 127.5, 125.1, 124.1, 121.3, 72.2, 71.7, 57.3, 44.1, 43.2, 40.9, 38.6, 33.8, 32.2, 31.5, 30.9, 29.7, 29.1, 28.8, 27.7, 27.6, 25.5, 22.5, 19.1, 18.9, 16.4, 14.6, 14.0 ppm.

Example 77

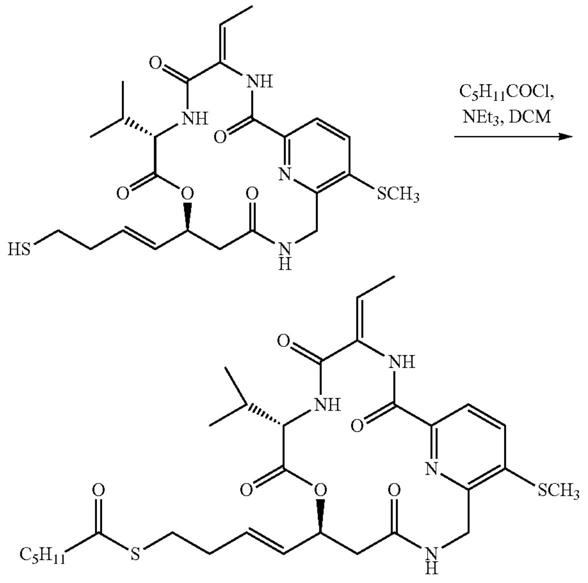

At 0° C., redistilled $NEt_3$ (0.02 ml) was added to the reactant (0.063 mmol) in anhydrous DCM (2 ml), stirred slightly, then added hexanoyl chloride (0.04 ml). After 7 h, The product was directly spinned anhydrous solvent by column chromatography and pale yellow solid was obtained. $[\alpha]^{20}_{D}$: 3.11 (c 0.3, $CHCl_3$). $^1H$ NMR (400 MHz, $CDCl_3$):

δ 9.22 (s, 1H), 8.10 (d, J=7.8 Hz, 1H), 7.51 (d, J=7.6 Hz, 1H), 7.06 (m, J=7.2 Hz, 1H), 6.75 (d, J=4.4 Hz, 1H), 6.46 (d, J=10.0 Hz, 1H), 5.74-5.68 (m, 2H), 5.50 (m, 1H), 5.17 (dd, J=17.2 Hz, 8.0 Hz, 1H), 4.76-4.73 (m, 2H), 4.28 (d, J=17.2 Hz, 1H), 3.48 (s, 3H), 2.88-2.75 (m, 4H), 2.63 (m, 1H), 2.49 (t, J=7.8 Hz, 3H), 2.30-2.25 (m, 3H), 1.84-1.82 (m, 3H), 1.63-1.60 (m, 2H), 1.26-1.24 (m, 7H), 0.84 (m, 3H), 0.79 (d, J=7.6 Hz, 3H), 0.59 (d, J=7.6 Hz, 3H) ppm. $^{13}C$ NMR (125 MHz, $CDCl_3$) δ 169.3, 169.0, 163.2, 162.0, 155.6, 148.9, 138.8, 134.8, 132.7, 132.0, 130.9, 128.9, 128.6, 127.7, 125.3, 124.3, 121.5, 72.3, 71.8, 57.5, 44.3, 43.4, 41.2, 38.9, 33.9, 32.5, 31.7, 30.9, 29.8, 29.2, 28.9, 27.8, 27.6, 25.6, 22.6, 19.0, 16.5, 14.7, 13.9 ppm.

Example 78

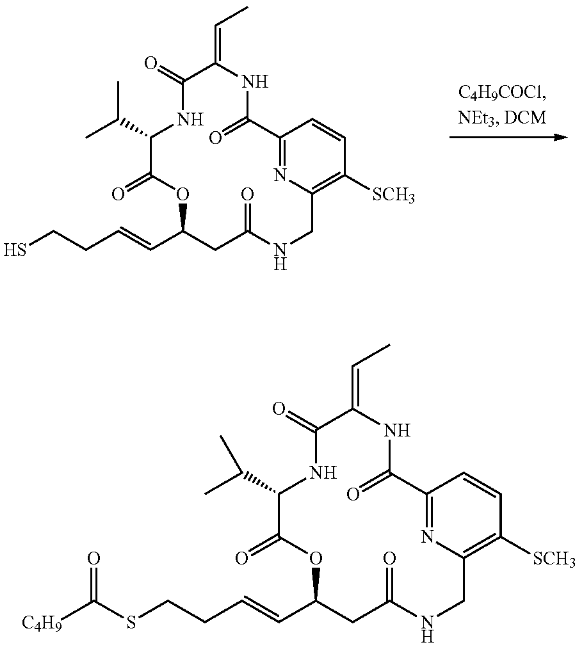

At 0° C., redistilled $NEt_3$ (0.02 ml) was added to the reactant (0.063 mmol) in anhydrous DCM (2 ml), stirred slightly, then added pivaloyl chloride (0.04 ml). After 7 h, The product was directly spinned anhydrous solvent by column chromatography and pale yellow solid was obtained. $[\alpha]^{20}_{D}$: 3.31 (c 0.6, $CHCl_3$). $^1H$ NMR (400 MHz, $CDCl_3$): δ 9.20 (s, 1H), 8.12 (d, J=7.8 Hz, 1H), 7.47 (d, J=7.6 Hz, 1H), 7.08 (d, J=7.2 Hz, 1H), 6.73 (d, J=4.4 Hz, 1H), 6.49 (d, J=10.0 Hz, 1H), 5.73-5.69 (m, 2H), 5.51 (m, 1H), 5.15 (dd, J=17.2 Hz, 8.0 Hz, 1H), 4.75-4.73 (m, 2H), 4.29 (d, J=17.2 Hz, 1H), 3.48 (s, 3H), 2.89-2.75 (m, 4H), 2.62 (m, 1H), 2.47 (t, J=7.8 Hz, 3H), 2.31-2.26 (m, 3H), 1.85-1.83 (m, 3H), 1.62-1.60 (m, 2H), 1.25-1.23 (m, 5H), 0.83 (m, 3H), 0.78 (d, J=7.6 Hz, 3H), 0.58 (d, J=7.6 Hz, 3H) ppm. $^{13}C$ NMR (125 MHz, $CDCl_3$) δ 169.2, 169.0, 163.3, 162.2, 155.7, 148.7, 138.9, 134.5, 132.8, 132.1, 130.8, 128.9, 128.5, 127.6, 125.2, 123.1, 121.3, 72.1, 71.6, 57.8, 44.2, 43.5, 41.3, 38.8, 33.8, 32.6, 31.6, 30.8, 29.9, 29.3, 28.8, 27.6, 25.7, 22.7, 19.1, 16.6, 14.9, 13.8 ppm.

Example 79

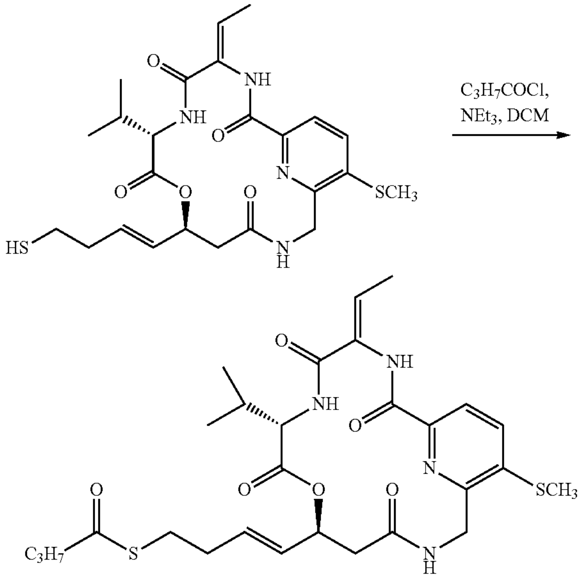

At 0° C., redistilled $NEt_3$ (0.02 ml) was added to the reactant (0.063 mmol) in anhydrous DCM (2 ml), stirred slightly, then added butyryl chloride (0.05 ml). After 7 h, The product was directly spinned anhydrous solvent by column chromatography and pale yellow solid was obtained. $[\alpha]^{20}_{D}$: 6.51 (c 0.5, $CHCl_3$). $^1H$ NMR (400 MHz, $CDCl_3$): δ 9.23 (s, 1H), 8.12 (d, J=7.8 Hz, 1H), 7.49 (d, J=7.6 Hz, 1H), 7.09 (d, J=7.2 Hz, 1H), 6.75 (d, J=4.4 Hz, 1H), 6.47 (d, J=10.0 Hz, 1H), 5.76-5.71 (m, 2H), 5.53 (m, 1H), 5.18 (dd, J=17.2 Hz, 8.0 Hz, 1H), 4.77-4.74 (m, 2H), 4.27 (d, J=17.2 Hz, 1H), 3.48 (s, 3H), 2.88-2.74 (m, 4H), 2.63 (m, 1H), 2.49 (t, J=7.8 Hz, 3H), 2.33-2.28 (m, 3H), 1.86-1.83 (m, 3H), 1.66-1.62 (m, 2H), 1.27-1.24 (m, 3H), 0.86 (m, 3H), 0.79 (d, J=7.6 Hz, 3H), 0.56 (d, J=7.6 Hz, 3H) ppm. $^{13}C$ NMR (125 MHz, $CDCl_3$) δ 169.4, 169.1, 163.5, 162.3, 155.8, 148.8, 138.9, 134.7, 132.9, 132.3, 130.9, 128.9, 128.4, 127.5, 125.3, 123.9, 121.5, 72.2, 71.7, 57.6, 44.5, 43.6, 41.4, 38.9, 33.9, 32.7, 31.7, 30.9, 29.9, 29.5, 28.9, 27.7, 25.8, 22.9, 19.3, 15.5, 13.8 ppm Example 80

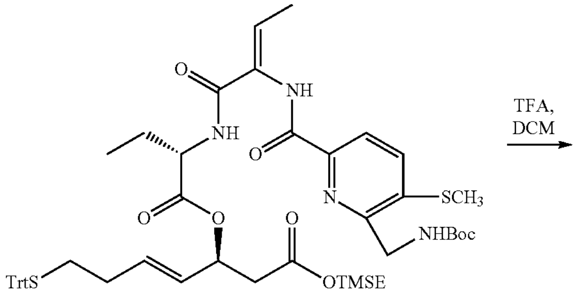

-continued

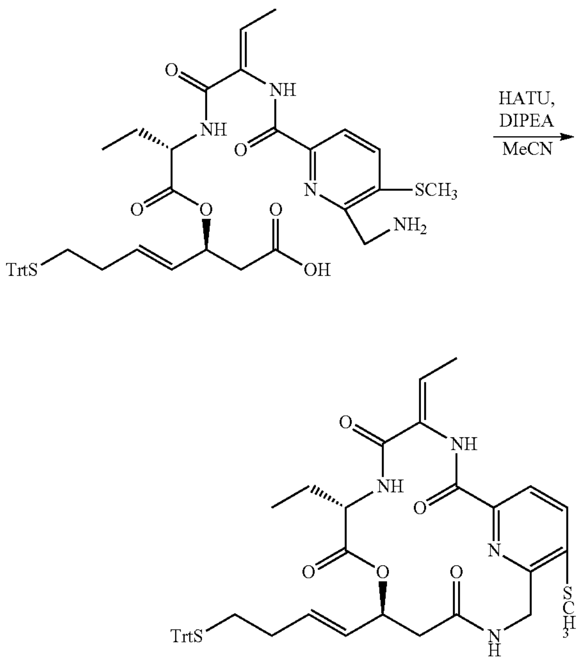

At 0° C., redistilled $NEt_3$ (0.02 ml) was added to the reactant (0.063 mmol) in anhydrous DCM (2 ml), stirred slightly, was added propionyl chloride (0.05 ml). After 7 h, The product was directly spinned anhydrous solvent by column chromatography and pale yellow solid was obtained. $[\alpha]^{20}_D$: 5.50 (c 0.3, $CHCl_3$). $^1H$ NMR (400 MHz, $CDCl_3$): δ 9.25 (s, 1H), 8.14 (d, J=7.8 Hz, 1H), 7.48 (d, J=7.6 Hz, 1H), 7.08 (d, J=7.2 Hz, 1H), 6.77 (d, J=4.4 Hz, 1H), 6.48 (d, J=10.0 Hz, 1H), 5.75-5.72 (m, 2H), 5.55 (m, 1H), 5.19 (dd, J=17.2 Hz, 8.0 Hz, 1H), 4.78-4.75 (m, 2H), 4.28 (d, J=17.2 Hz, 1H), 3.48 (s, 3H), 2.89-2.75 (m, 4H), 2.65 (m, 1H), 2.48 (t, J=7.8 Hz, 3H), 2.35-2.29 (m, 3H), 1.88-1.85 (m, 3H), 1.66 (m, 2H), 0.86 (m, 3H), 0.77 (d, J=7.6 Hz, 3H), 0.57 (d, J=7.6 Hz, 3H) ppm. $^{13}C$ NMR (125 MHz, $CDCl_3$) δ 169.6, 169.2, 163.3, 162.2, 155.9, 148.9, 138.8, 134.8, 132.9, 132.2, 130.8, 128.9, 128.5, 127.6, 125.5, 124.7, 121.6, 72.3, 71.8, 57.8, 44.6, 43.7, 41.5, 38.8, 33.9, 32.8, 31.8, 30.8, 29.9, 29.6, 28.9, 27.8, 25.9, 22.9, 19.5, 14.8 ppm.

Example 81

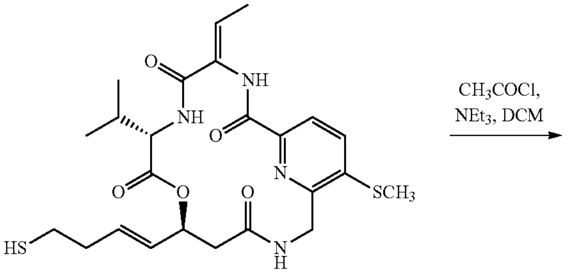

-continued

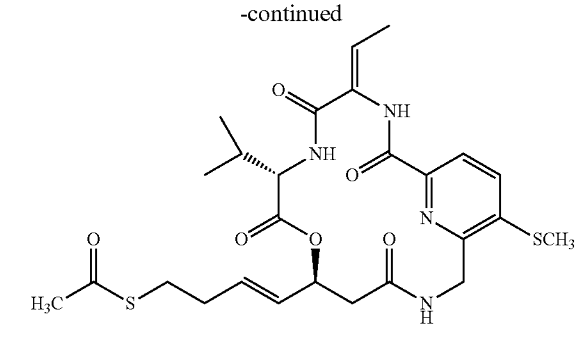

At 0° C., redistilled $NEt_3$ (0.02 ml) was added to the reactant (0.063 mmol) in anhydrous DCM (2 ml), stirred slightly, acetyl chloride (0.05 ml) was added. After 7 h, the product was directly spinned anhydrous solvent by column chromatography and pale yellow solid was obtained. $[\alpha]^{20}_D$: 4.66 (c 0.6, $CHCl_3$). $^1H$ NMR (400 MHz, $CDCl_3$): δ 9.26 (s, 1H), 8.15 (d, J=7.8 Hz, 1H), 7.49 (d, J=7.6 Hz, 1H), 7.09 (d, J=7.2 Hz, 1H), 6.79 (d, J=4.4 Hz, 1H), 6.47 (d, J=10.0 Hz, 1H), 5.73-5.70 (m, 2H), 5.53 (m, 1H), 5.18 (dd, J=17.2 Hz, 8.0 Hz, 1H), 4.77 (m, 2H), 4.28 (d, J=17.2 Hz, 1H), 3.48 (s, 3H), 2.88-2.78 (m, 4H), 2.67 (m, 1H), 2.49 (t, J=7.8 Hz, 3H), 2.36-2.33 (m, 3H), 1.89-1.86 (m, 3H), 0.88 (m, 3H), 0.78 (d, J=7.6 Hz, 3H), 0.58 (d, J=7.6 Hz, 3H) ppm. $^{13}C$ NMR (125 MHz, $CDCl_3$) δ 169.8, 169.3, 163.5, 162.5, 155.8, 148.8, 138.7, 134.7, 132.8, 132.3, 130.9, 128.8, 128.7, 127.7, 125.6, 123.4, 121.7, 72.5, 71.9, 57.9, 44.7, 43.9, 41.6, 38.9, 33.8, 32.9, 31.9, 30.9, 29.8, 29.5, 28.8, 27.7, 15.0 ppm.

Example 82

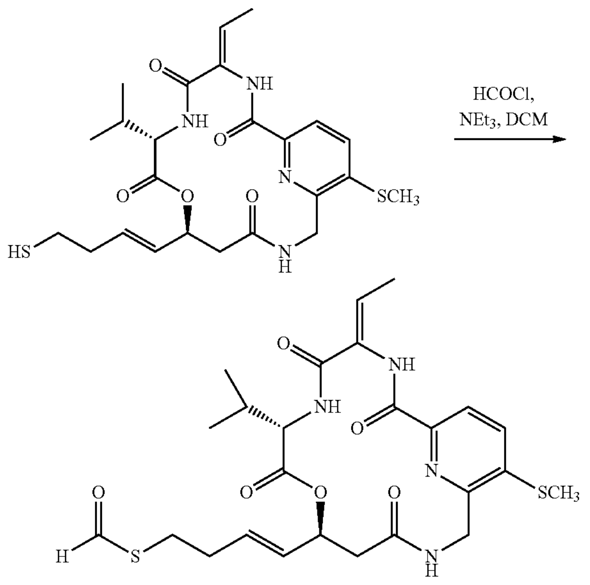

At 0° C., redistilled $NEt_3$ (0.02 ml) was added to the reactant (30 mg, 0.063 mmol) in anhydrous DCM (2 ml), stirred slightly, methanesulfonyl chloride (0.02 ml). After 7 h, the product was directly spinned anhydrous solvent by column chromatography and 26 mg pale yellow solid was obtained, and the yield was 75%. $[\alpha]^{20}_D$: 1.96 (c 0.1, $CHCl_3$). $^1H$ NMR (400 MHz, $CDCl_3$): δ 9.63 (s, 1H), 9.23 (s, 1H), 7.42 (d, J=7.6 Hz, 1H), 7.07 (dd, J=14.4 Hz, J=7.2

Hz, 1H), 6.56 (dd, J=7.6 Hz, J=3.6 Hz, 1H), 6.48 (d, J=8 Hz, 1H), 5.73 (m, 2H), 5.52 (dd, J=15.6 Hz, J=6.8 Hz, 1H), 5.12 (m, 1H), 4.76 (dd, J=10 Hz, J=3.6 Hz, 1H), 4.33 (m, 1H), 2.72 (m, 2H), 2.53 (m, 2H), 2.34-2.29 (m, 3H), 1.38 (t, J=7.6 Hz, 1H), 0.82 (d, J=6.8 Hz, 3H), 0.62 (d, J=6.8 Hz, 3H) ppm. $^{13}C$ NMR (125 MHz, $CDCl_3$) δ 176.5, 169.8, 169.4, 163.6, 162.6, 155.7, 148.8, 138.5, 134.7, 132.5, 132.3, 130.9, 128.8, 127.8, 125.6, 124.3, 121.8, 72.5, 71.7, 56.9, 44.8, 43.6, 41.5, 36.0, 30.8, 23.7, 18.9, 16.5, 14.6 ppm.

Example 83 HDAC Biochemical Activity Measurement

1. Measurement Principle:

The chemical activity of the compound is determined according to the degree of deacetylation inhibition of the HDAC enzyme. This experiment measured the degree of deacetylation related to tumor proliferation and metastasis of HDAC1, HDAC2, HDAC3, HDAC8, HDAC11 five sub-types HDAC enzymes. After the substrate containing an acetylated lysine side chain and HDAC enzyme are labeled with a fluorescent label, the fluorescent substrate is de acetyl. The fluorescent labeled substrate is cleaved by the enzyme, and the fluorescent substance is released, which generates 460 nm emission light under the excitation of 360 nm light.

2. Specific Steps:

HDAC substrate was diluted with reaction buffer to 200M (reaction concentration of 20M), the HDAC enzyme was diluted to the appropriate concentration, then added different concentrations of the test compounds and acted at 37° C. 30 minutes, and then added the same volume of 2-times concentration substrate developing solution (developer), incubated at room temperature for 15 minutes. Finally, the last reading measured with a microplate plate reader, excitation light was 360 nm, the emitted light was 460 nm, data processing software was Prime 4, and the results are shown in Table 1. In the embodiment of the invention, SAHA is suberoylanilide hydroxamic acid; no activity indicates no activity.

TABLE 1

HDAC activity and biochemical test results

| Compound No. | IC50 (μM) HDAC1 | HDAC2 | HDAC3 | HDAC8 | HDAC11 | HDAC7 |
|---|---|---|---|---|---|---|
| SAHA | 0.18 | 0.35 | 0.56 | 0.78 | 0.62 | no activity |
| 1 | 0.041 | 0.022 | 0.035 | 0.03 | 0.38 | no activity |
| 2 | 0.192 | 0.163 | 0.177 | 0.252 | 0.102 | no activity |
| 3 | 0.171 | 0.158 | 0.145 | 0.169 | 0.100 | no activity |
| 4 | 0.183 | 0.251 | 0.152 | 0.161 | 0.201 | no activity |
| 5 | 0.074 | 0.053 | 0.049 | 0.067 | 0.111 | no activity |
| 6 | 0.075 | 0.059 | 0.061 | 0.063 | 0.135 | no activity |
| 7 | 0.087 | 0.017 | 0.007 | 0.039 | 0.011 | no activity |
| 8 | 0.153 | 0.162 | 0.051 | 0.041 | 0.097 | no activity |
| 9 | 0.045 | 0.064 | 0.034 | 0.049 | 0.101 | no activity |
| 10 | 0.092 | 0.067 | 0.041 | 0.050 | 0.103 | no activity |
| 11 | 0.029 | 0.055 | 0.045 | 0.071 | 0.081 | no activity |
| 12 | 0.081 | 0.054 | 0.052 | 0.038 | 0.091 | no activity |
| 13 | 0.187 | 0.261 | 0.337 | 0.159 | 0.094 | no activity |
| 14 | 0.094 | 0.059 | 0.043 | 0.057 | 0.103 | no activity |
| 15 | 0.191 | 0.047 | 0.057 | 0.043 | 0.106 | no activity |
| 16 | 0.181 | 0.056 | 0.049 | 0.061 | 0.095 | no activity |
| 17 | 0.176 | 0.061 | 0.069 | 0.081 | 0.097 | no activity |
| 18 | 0.187 | 0.055 | 0.067 | 0.073 | 0.107 | no activity |
| 19 | 0.179 | 0.063 | 0.039 | 0.069 | 0.103 | no activity |
| 20 | 0.183 | 0.077 | 0.045 | 0.065 | 0.087 | no activity |
| 21 | 0.088 | 0.067 | 0.051 | 0.053 | 0.089 | no activity |
| 22 | 0.093 | 0.054 | 0.061 | 0.047 | 0.097 | no activity |

TABLE 1-continued

HDAC activity and biochemical test results

| Compound No. | IC50 (μM) HDAC1 | HDAC2 | HDAC3 | HDAC8 | HDAC11 | HDAC7 |
|---|---|---|---|---|---|---|
| 23 | 0.061 | 0.074 | 0.059 | 0.059 | 0.105 | no activity |
| 24 | 0.074 | 0.083 | 0.043 | 0.063 | 0.097 | no activity |
| 25 | 0.081 | 0.094 | 0.038 | 0.075 | 0.089 | no activity |
| 26 | 0.091 | 0.064 | 0.046 | 0.064 | 0.094 | no activity |
| 27 | 0.004 | 0.021 | 0.033 | 0.051 | 0.024 | no activity |
| 28 | 0.055 | 0.061 | 0.074 | 0.071 | 0.079 | no activity |
| 29 | 0.043 | 0.068 | 0.079 | 0.069 | 0.103 | no activity |
| 30 | 0.012 | 0.056 | 0.034 | 0.043 | 0.084 | no activity |
| 31 | 0.057 | 0.051 | 0.043 | 0.039 | 0.091 | no activity |
| 32 | 0.069 | 0.042 | 0.068 | 0.052 | 0.097 | no activity |
| 33 | 0.023 | 0.043 | 0.036 | 0.059 | 0.089 | no activity |
| 34 | 0.043 | 0.051 | 0.026 | 0.042 | 0.082 | no activity |
| 35 | 0.056 | 0.062 | 0.024 | 0.034 | 0.083 | no activity |
| 36 | 0.011 | 0.043 | 0.037 | 0.035 | 0.085 | no activity |
| 37 | 0.071 | 0.044 | 0.048 | 0.043 | 0.091 | no activity |
| 38 | 0.061 | 0.061 | 0.059 | 0.053 | 0.095 | no activity |
| 39 | 0.059 | 0.065 | 0.036 | 0.026 | 0.082 | no activity |
| 40 | 0.043 | 0.053 | 0.042 | 0.045 | 0.096 | no activity |
| 41 | 0.076 | 0.225 | 0.119 | 0.322 | 0.056 | no activity |
| 42 | 0.062 | 0.113 | 0.092 | 0.131 | 0.077 | no activity |
| 43 | 0.027 | 0.051 | 0.046 | 0.043 | 0.094 | no activity |
| 44 | 0.051 | 0.043 | 0.043 | 0.042 | 0.091 | no activity |
| 45 | 0.064 | 0.032 | 0.041 | 0.025 | 0.092 | no activity |
| 46 | 0.022 | 0.041 | 0.025 | 0.035 | 0.082 | no activity |
| 47 | 0.071 | 0.026 | 0.039 | 0.0.16 | 0.083 | no activity |
| 48 | 0.081 | 0.015 | 0.047 | 0.014 | 0.093 | no activity |
| 49 | 0.016 | 0.046 | 0.048 | 0.038 | 0.073 | no activity |
| 50 | 0.064 | 0.043 | 0.052 | 0.037 | 0.107 | no activity |
| 51 | 0.046 | 0.052 | 0.051 | 0.041 | 0.103 | no activity |
| 52 | 0.045 | 0.062 | 0.038 | 0.053 | 0.107 | no activity |
| 53 | 0.084 | 0.043 | 0.029 | 0.026 | 0.105 | no activity |
| 54 | 0.074 | 0.024 | 0.034 | 0.034 | 0.099 | no activity |
| 55 | 0.013 | 0.034 | 0.035 | 0.043 | 0.083 | no activity |
| 56 | 0.061 | 0.035 | 0.039 | 0.035 | 0.081 | no activity |
| 57 | 0.051 | 0.026 | 0.047 | 0.044 | 0.095 | no activity |
| 58 | 0.032 | 0.021 | 0.029 | 0.051 | 0.097 | no activity |
| 59 | 0.071 | 0.029 | 0.024 | 0.061 | 0.091 | no activity |
| 60 | 0.081 | 0.037 | 0.016 | 0.053 | 0.088 | no activity |
| 61 | 0.013 | 0.038 | 0.038 | 0.038 | 0.083 | no activity |
| 62 | 0.046 | 0.027 | 0.037 | 0.037 | 0.079 | no activity |
| 63 | 0.041 | 0.058 | 0.039 | 0.029 | 0.091 | no activity |
| 64 | 0.024 | 0.029 | 0.029 | 0.027 | 0.093 | no activity |
| 65 | 0.048 | 0.026 | 0.027 | 0.035 | 0.086 | no activity |
| 66 | 0.041 | 0.016 | 0.031 | 0.026 | 0.094 | no activity |
| 67 | 0.0.64 | 0.034 | 0.028 | 0.016 | 0.092 | no activity |
| 68 | 0.079 | 0.043 | 0.037 | 0.021 | 0.082 | no activity |
| 69 | 0.061 | 0.038 | 0.028 | 0.052 | 0.081 | no activity |
| 70 | 0.033 | 0.043 | 0.024 | 0.034 | 0.097 | no activity |
| 71 | 0.051 | 0.029 | 0.034 | 0.041 | 0.096 | no activity |
| 72 | 0.064 | 0.331 | 0.135 | 0.453 | 0.276 | no activity |
| 73 | 0.182 | 0.325 | 0.426 | 0.562 | 0.375 | no activity |
| 74 | 0.273 | 0.129 | 0.231 | 0.435 | 0.672 | no activity |
| 75 | 0.443 | 0.334 | 0.543 | 0.163 | 0.181 | no activity |
| 76 | 0.051 | 0.036 | 0.042 | 0.028 | 0.094 | no activity |
| 77 | 0.094 | 0.029 | 0.026 | 0.037 | 0.088 | no activity |
| 78 | 0.063 | 0.037 | 0.038 | 0.039 | 0.094 | no activity |
| 79 | 0.057 | 0.019 | 0.027 | 0.042 | 0.093 | no activity |
| 80 | 0.067 | 0.038 | 0.034 | 0.053 | 0.097 | no activity |
| 81 | 0.037 | 0.031 | 0.016 | 0.026 | .095 | no activity |
| 82 | 0.094 | 0.049 | 0.053 | 0.034 | 0.092 | no activity |
| 83 | 0.051 | 0.046 | 0.026 | 0.038 | 0.082 | no activity |
| 84 | 0.042 | 0.043 | 0.029 | 0.029 | 0.091 | no activity |
| 85 | 0.034 | 0.038 | 0.037 | 0.027 | 0.092 | no activity |
| 86 | 0.084 | 0.033 | 0.039 | 0.034 | 0.082 | no activity |
| 87 | 0.083 | 0.022 | 0.026 | 0.035 | 0.087 | no activity |
| 88 | 0.031 | 0.035 | 0.041 | 0.043 | 0.094 | no activity |
| 89 | 0..073 | 0.036 | 0.052 | 0.062 | 0.086 | no activity |
| 90 | 0.084 | 0.029 | 0.063 | 0.051 | 0.075 | no activity |
| 91 | 0.061 | 0.037 | 0.033 | 0.034 | 0.079 | no activity |
| 92 | 0.052 | 0.035 | 0.035 | 0.037 | 0.086 | no activity |
| 93 | 0.043 | 0.024 | 0.039 | 0.029 | 0.084 | no activity |
| 94 | 0.042 | 0.035 | 0.028 | 0.028 | 0.091 | no activity |
| 95 | 0.072 | 0.026 | 0.017 | 0.034 | 0.099 | no activity |
| 96 | 0.094 | 0.034 | 0.051 | 0.032 | 0.098 | no activity |

TABLE 1-continued

| HDAC activity and biochemical test results | | | | | | |
|---|---|---|---|---|---|---|
| Compound No. | IC50 (μM) | | | | | |
| | HDAC1 | HDAC2 | HDAC3 | HDAC8 | HDAC11 | HDAC7 |
| 97 | 0.052 | 0.037 | 0.601 | 0.052 | 0.086 | no activity |
| 98 | 0.061 | 0.019 | 0.062 | 0.061 | 0.089 | no activity |
| 99 | 0.076 | 0.028 | 0.051 | 0.022 | 0.097 | no activity |
| 100 | 0.049 | 0.022 | 0.071 | 0.031 | 0.095 | no activity |
| 101 | 0.038 | 0.034 | 0.059 | 0.035 | 0.092 | no activity |
| 102 | 0.049 | 0.038 | 0.048 | 0.026 | 0.094 | no activity |
| 103 | 0.038 | 0.029 | 0.053 | 0.016 | 0.093 | no activity |
| 104 | 0.051 | 0.026 | 0.043 | 0.019 | 0.083 | no activity |
| 105 | 0.053 | 0.025 | 0.015 | 0.027 | 0.084 | no activity |
| 106 | 0.061 | 0.035 | 0.041 | 0.037 | 0.078 | no activity |
| 107 | 0.076 | 0.038 | 0.042 | 0.023 | 0.084 | no activity |
| 108 | 0.077 | 0.029 | 0.053 | 0.026 | 0.083 | no activity |
| 109 | 0.066 | 0.034 | 0.062 | 0.034 | 0.087 | no activity |
| 110 | 0.088 | 0.028 | 0.051 | 0.035 | 0.098 | no activity |
| 111 | 0.054 | 0.061 | 0.053 | 0.042 | 0.095 | no activity |
| 112 | 0.075 | 0.051 | 0.047 | 0.043 | 0.092 | no activity |
| 113 | 0.086 | 0.053 | 0.041 | 0.053 | 0.093 | no activity |
| 114 | 0.061 | 0.049 | 0.027 | 0.038 | 0.099 | no activity |
| 115 | 0.055 | 0.043 | 0.038 | 0.029 | 0.091 | no activity |
| 116 | 0.041 | 0.052 | 0.039 | 0.027 | 0.098 | no activity |
| 117 | 0.039 | 0.133 | 0.156 | 0.217 | 0.125 | no activity |
| 118 | 0.053 | 0.109 | 0.228 | 0.197 | 0.126 | no activity |
| 119 | 0.051 | 0.042 | 0.041 | 0.037 | 0.092 | no activity |
| 120 | 0.072 | 0.112 | 0.093 | 0.043 | 0.032 | no activity |
| 121 | 0.051 | 0.207 | 0.199 | 0.086 | 0.142 | no activity |
| 122 | 0.065 | 0.143 | 0.202 | 0.092 | 0.127 | no activity |
| 123 | 0.052 | 0.026 | 0.052 | 0.026 | 0.089 | no activity |
| 124 | 0.033 | 0.092 | 0.117 | 0.059 | 0.121 | no activity |
| 125 | 0.087 | 0.122 | 0.103 | 0.098 | 0.102 | no activity |
| 126 | 0.035 | 0.023 | 0.059 | 0.037 | 0.068 | no activity |
| 127 | 0.048 | 0.026 | 0.057 | 0.033 | 0.062 | no activity |
| 128 | 0.052 | 0.119 | 0.114 | 0.072 | 0.083 | no activity |
| 129 | 0.027 | 0.029 | 0.052 | 0.034 | 0.061 | no activity |
| 130 | 0.037 | 0.042 | 0.053 | 0.039 | 0.043 | no activity |
| 131 | 0.076 | 0.031 | 0.035 | 0.022 | 0.089 | no activity |
| 132 | 0.033 | 0.117 | 0.093 | 0.092 | 0.163 | no activity |
| 133 | 0.043 | 0.021 | 0.053 | 0.042 | 0.077 | no activity |
| 134 | 0.058 | 0.025 | 0.067 | 0.031 | 0.068 | no activity |
| 135 | 0.083 | 0.031 | 0.034 | 0.027 | 0.082 | no activity |
| 136 | 0.052 | 0.047 | 0.031 | 0.042 | 0.089 | no activity |
| 137 | 0.033 | 0.036 | 0.017 | 0.099 | 0.076 | no activity |
| 138 | 0.039 | 0.024 | 0.029 | 0.077 | 0.062 | no activity |
| 139 | 0.072 | 0.035 | 0.052 | 0.039 | 0.087 | no activity |
| 140 | 0.085 | 0.043 | 0.032 | 0.056 | 0.089 | no activity |
| 141 | 0.042 | 0.068 | 0.025 | 0.037 | 0.062 | no activity |
| 142 | 0.053 | 0.023 | 0.063 | 0.075 | 0.081 | no activity |
| 143 | 0.046 | 0.041 | 0.063 | 0.049 | 0.097 | no activity |
| 144 | 0.042 | 0.038 | 0.024 | 0.017 | 0.082 | no activity |
| 145 | 0.051 | 0.029 | 0.026 | 0.029 | 0.083 | no activity |
| 146 | 0.073 | 0.034 | 0.028 | 0.043 | 0.097 | no activity |
| 147 | 0.061 | 0.041 | 0.051 | 0.028 | 0.086 | no activity |
| 148 | 0.049 | 0.052 | 0.035 | 0.029 | 0.082 | no activity |
| 149 | 0.051 | 0.063 | 0.043 | 0.034 | 0.094 | no activity |
| 150 | 0.044 | 0.026 | 0.031 | 0.035 | 0.083 | no activity |
| 151 | 0.061 | 0.024 | 0.023 | 0.038 | 0.095 | no activity |
| 152 | 0.062 | 0.026 | 0.035 | 0.037 | 0.076 | no activity |
| 153 | 0.072 | 0.031 | 0.036 | 0.028 | 0.072 | no activity |
| 154 | 0.084 | 0.011 | 0.042 | 0.031 | 0.085 | no activity |
| 155 | 0.094 | 0.012 | 0.043 | 0.036 | 0.084 | no activity |
| 156 | 0.095 | 0.016 | 0.053 | 0.029 | 0.086 | no activity |
| 157 | 0.082 | 0.019 | 0.051 | 0.027 | 0.091 | no activity |
| 158 | 0.081 | 0.028 | 0.053 | 0.043 | 0.092 | no activity |
| 159 | 0.054 | 0.037 | 0.042 | 0.044 | 0.095 | no activity |
| 160 | 0.053 | 0.024 | 0.052 | 0.051 | 0.097 | no activity |
| 161 | 0.061 | 0.033 | 0.063 | 0.062 | 0.086 | no activity |
| 162 | 0.073 | 0.027 | 0.024 | 0.035 | 0.083 | no activity |
| 163 | 0.072 | 0.026 | 0.053 | 0.039 | 0.084 | no activity |
| 164 | 0.073 | 0.029 | 0.026 | 0.031 | 0.081 | no activity |
| 165 | 0.084 | 0.031 | 0.025 | 0.062 | 0.092 | no activity |
| 166 | 0.082 | 0.032 | 0.035 | 0.032 | 0.097 | no activity |
| 167 | 0.065 | 0.058 | 0.013 | 0.022 | 0.074 | no activity |
| 168 | 0.091 | 0.041 | 0.034 | 0.013 | 0.099 | no activity |
| 169 | 0.072 | 0.052 | 0.016 | 0.015 | 0.092 | no activity |
| 170 | 0.076 | 0.062 | 0.019 | 0.042 | 0.098 | no activity |

TABLE 1-continued

| HDAC activity and biochemical test results | | | | | | |
|---|---|---|---|---|---|---|
| Compound No. | IC50 (μM) | | | | | |
| | HDAC1 | HDAC2 | HDAC3 | HDAC8 | HDAC11 | HDAC7 |
| 171 | 0.068 | 0.035 | 0.018 | 0.035 | 0.095 | no activity |
| 172 | 0.059 | 0.029 | 0.029 | 0.038 | 0.093 | no activity |
| 173 | 0.0.38 | 0.031 | 0.037 | 0.039 | 0.097 | no activity |
| 174 | 0.084 | 0.032 | 0.026 | 0.021 | 0.098 | no activity |
| 175 | 0.041 | 0.032 | 0.011 | 0.069 | 0.055 | no activity |
| 176 | 0.025 | 0.039 | 0.032 | 0.059 | 0.081 | no activity |
| 177 | 0.085 | 0.033 | 0.027 | 0.042 | 0.088 | no activity |
| 178 | 0.091 | 0.026 | 0.035 | 0.036 | 0.099 | no activity |
| 179 | 0.073 | 0.051 | 0.034 | 0.042 | 0.092 | no activity |
| 180 | 0.043 | 0.037 | 0.029 | 0.033 | 0.091 | no activity |
| 181 | 0.086 | 0.061 | 0.031 | 0.022 | 0.086 | no activity |
| 182 | 0.072 | 0.032 | 0.023 | 0.055 | 0.082 | no activity |
| 183 | 0.058 | 0.033 | 0.013 | 0.065 | 0.084 | no activity |
| 184 | 0.046 | 0.041 | 0.034 | 0.054 | 0.091 | no activity |
| 185 | 0.063 | 0.053 | 0.038 | 0.041 | 0.093 | no activity |
| 186 | 0.053 | 0.083 | 0.026 | 0.053 | 0.097 | no activity |
| 187 | 0.051 | 0.073 | 0.024 | 0.026 | 0.098 | no activity |
| 188 | 0.043 | 0.063 | 0.042 | 0.023 | 0.086 | no activity |
| 189 | 0.086 | 0.024 | 0.041 | 0.037 | 0.084 | no activity |
| 190 | 0.085 | 0.025 | 0.053 | 0.029 | 0.081 | no activity |
| 191 | 0.092 | 0.036 | 0.062 | 0.018 | 0.085 | no activity |
| 192 | 0.073 | 0.026 | 0.038 | 0.053 | 0.091 | no activity |
| 193 | 0.043 | 0.025 | 0.039 | 0.049 | 0.093 | no activity |
| 194 | 0.061 | 0.032 | 0.042 | 0.043 | 0.079 | no activity |
| 195 | 0.065 | 0.035 | 0.053 | 0.059 | 0.078 | no activity |
| 196 | 0.092 | 0.026 | 0.024 | 0.048 | 0.095 | no activity |
| 197 | 0.072 | 0.024 | 0.035 | 0.052 | 0.096 | no activity |
| 198 | 0.0.84 | 0.025 | 0.037 | 0.034 | 0.098 | no activity |
| 199 | 0.082 | 0.034 | 0.041 | 0.059 | 0.092 | no activity |
| 200 | 0.088 | 0.038 | 0.052 | 0.049 | 0.093 | no activity |
| 201 | 0.081 | 0.042 | 0.037 | 0.019 | 0.089 | no activity |
| 202 | 0.072 | 0.043 | 0.043 | 0.029 | 0.082 | no activity |
| 203 | 0.083 | 0.053 | 0.062 | 0.018 | 0.084 | no activity |
| 204 | 0.086 | 0.061 | 0.053 | 0.035 | 0.087 | no activity |
| 205 | 0.091 | 0.052 | 0.038 | 0.062 | 0.077 | no activity |
| 206 | 0.051 | 0.037 | 0.037 | 0.031 | 0.086 | no activity |
| 207 | 0.062 | 0.027 | 0.042 | 0.033 | 0.092 | no activity |
| 208 | 0.051 | 0.017 | 0.031 | 0.055 | 0.098 | no activity |
| 209 | 0.061 | 0.018 | 0.041 | 0.042 | 0.096 | no activity |
| 210 | 0.2082 | 0.024 | 0.026 | 0.041 | 0.092 | no activity |
| 211 | 0.091 | 0.026 | 0.052 | 0.028 | 0.089 | no activity |
| 212 | 0.073 | 0.035 | 0.035 | 0.037 | 0.086 | no activity |
| 213 | 0.077 | 0.034 | 0.063 | 0.029 | 0.087 | no activity |
| 214 | 0.064 | 0.039 | 0.032 | 0.059 | 0.0830 | no activity |
| 215 | 0.066 | 0.041 | 0.044 | 0.057 | .086 | no activity |
| 216 | 0.155 | 0.033 | 0.062 | 0.052 | 0.081 | no activity |
| 217 | 0.035 | 0.043 | 0.122 | 0.078 | 0.093 | no activity |
| 218 | 0.043 | 0.034 | 0.352 | 0.562 | 0.178 | no activity |
| 219 | 0.055 | 0.741 | 0.922 | 0.138 | 0.291 | no activity |
| 220 | 0.167 | 0.534 | 0.821 | 0.433 | 0.320 | no activity |
| 221 | 0.296 | 0.655 | 0.813 | 0.132 | 0.211 | no activity |
| 222 | 0.175 | 0.126 | 0.516 | 0.756 | 0.377 | no activity |
| 223 | 0.156 | 0.238 | 0.762 | 0.243 | 0.273 | no activity |
| 224 | 0.184 | 0.335 | 0.563 | 0.752 | 0.279 | no activity |
| 225 | 0.142 | 0.539 | 0.438 | 0.241 | 0.668 | no activity |
| 226 | 0.062 | 0.035 | 0.046 | 0.022 | 0.083 | no activity |
| 227 | 0.072 | 0.639 | 0.538 | 0.341 | 0.198 | no activity |
| 228 | 0.135 | 0.039 | 0.061 | 0.025 | 0.086 | no activity |
| 229 | 0.097 | 0.036 | 0.057 | 0.132 | 0.119 | no activity |
| 230 | 0.028 | 0.169 | 0.041 | 0.058 | 0.112 | no activity |
| 231 | 0.053 | 0.046 | 0.057 | 0.032 | 0.103 | no activity |
| 232 | 0.066 | 0.093 | 0.021 | 0.059 | 0.152 | no activity |
| 233 | 0.107 | 0.129 | 0.028 | 0.031 | 0.053 | no activity |
| 234 | 0.018 | 0.085 | 0.032 | 0.078 | 0.065 | no activity |
| 235 | 0.008 | 0.019 | 0.035 | 0.047 | 0.019 | no activity |
| 236 | 0.043 | 0.038 | 0.066 | 0.067 | 0.072 | no activity |
| 237 | 0.072 | 0.032 | 0.035 | 0.043 | 0.077 | no activity |
| 238 | 0.044 | 0.083 | 0.059 | 0.078 | 0.065 | no activity |
| 239 | 0.077 | 0.056 | 0.047 | 0.089 | 0.028 | no activity |
| 240 | 0.045 | 0.021 | 0.053 | 0.052 | 0.056 | no activity |
| 241 | 0.028 | 0.036 | 0.062 | 0.033 | 0.069 | no activity |
| 242 | 0.019 | 0.043 | 0.032 | 0.055 | 0.067 | no activity |
| 243 | 0.087 | 0.056 | 0.048 | 0.129 | 0.187 | no activity |
| 244 | 0.092 | 0.053 | 0.032 | 0.089 | 0.037 | no activity |

TABLE 1-continued

HDAC activity and biochemical test results

| Com-pound No. | IC50 (μM) HDAC1 | HDAC2 | HDAC3 | HDAC8 | HDAC11 | HDAC7 |
|---|---|---|---|---|---|---|
| 245 | 0.066 | 0.074 | 0.052 | 0.102 | 0.126 | no activity |
| 246 | 0.090 | 0.069 | 0.087 | 0.132 | 0.235 | no activity |
| 247 | 0.062 | 0.049 | 0.037 | 0.041 | 0.088 | no activity |
| 248 | 0.056 | 0.029 | 0.022 | 0.039 | 0.051 | no activity |
| 249 | 0.038 | 0.023 | 0.028 | 0.042 | 0.076 | no activity |
| 250 | 0.077 | 0.045 | 0.063 | 0.053 | 0.035 | no activity |
| 251 | 0.033 | 0.058 | 0.027 | 0.037 | 0.039 | no activity |
| 252 | 0.042 | 0.038 | 0.056 | 0.069 | 0.077 | no activity |
| 253 | 0.053 | 0.026 | 0.083 | 0.062 | 0.045 | no activity |
| 254 | 0.061 | 0.042 | 0.069 | 0.067 | 0.062 | no activity |
| 255 | 0.032 | 0.089 | 0.049 | 0.121 | 0.072 | no activity |

3. Test Results and Analysis:

IC50 in the table above is the concentration of the inhibitor (50% inhibitory concentration), which is inhibited by half.

From the table it can be indicated that the compounds mentioned above had HDAC enzymes (mainly HDAC1, HDAC2, HDAC3, HDAC8, HDAC11) to acetylation activity with significant inhibition of tumor proliferation and metastasis, compared with the positive control (SAHA). But HDAC7 which has less relation to the tumor proliferation and metastasis has no effect.

Compared with the related compounds of the patent public CN102391359A, the compound structure of the invention is shown in Table 2, which shows a significant advantage and the difference is several times to several hundreds of times.

TABLE 2

Comparison of the results of the present invention with CN102391359A

| Compounds No. Compounds No. of the present invention (a) | Compounds No. of CN102391359A (b) | IC50 (μM) HDAC1 a | b |
|---|---|---|---|
| 235 | 1-1 | <0.01 | <0.1 |
| 9 | 1-2 | <0.05 | <0.19 |
| 1 | 1-3 | <0.05 | <10 |
| 11 | 1-4 | <0.03 | <1.0 |
| 236 | 1-5 | <0.05 | <10 |
| 237 | 1-6 | <0.08 | <10 |
| 14 | 1-7 | <0.1 | <10 |
| 238 | 1-8 | <0.05 | <0.102 |
| 239 | 1-9 | <0.10 | <10 |
| 240 | 1-10 | <0.05 | <0.10 |
| 241 | 1-11 | <0.03 | <0.10 |
| 242 | 1-12 | <0.02 | <0.1 |
| 1 | 2-1 | <0.05 | <0.1 |
| 243 | 2-2 | <0.10 | <10 |
| 243 | 2-3 | <0.10 | <10 |
| 1 | 2-4 | <0.05 | <10 |
| 1 | 2-5 | <0.05 | <10 |
| 1 | 2-6 | <0.05 | <10 |
| 1 | 2-7 | <0.05 | <10 |
| 244 | 3-1 | <0.10 | <10 |
| 245 | 3-2 | <0.10 | <10 |
| 246 | 3-3 | <0.10 | <10 |
| 27 | 6-1 | <0.005 | <0.1 |
| 7 | 6-2 | <0.5 | <10 |

Six-membered ring with substituents in the compounds of the present invention showed a significant advantage, compared to non-substituted group in related compounds in HDAC1. The results were shown in Table 3.

TABLE 3

Result comparison of six-membered ring with substituent and without substituent data

| Compounds No. of the present invention substituents (C) | non-substituent (D) | IC50 (μM) HDAC1 C | D |
|---|---|---|---|
| 30 | 1 | 0.012 | 0.041 |
| 33 | 2 | 0.023 | 0.192 |
| 36 | 3 | 0.011 | 0.171 |
| 40 | 4 | 0.043 | 0.183 |
| 43 | 5 | 0.027 | 0.074 |
| 46 | 6 | 0.022 | 0.075 |
| 49 | 7 | 0.016 | 0.087 |
| 52 | 8 | 0.045 | 0.153 |
| 55 | 9 | 0.013 | 0.045 |
| 58 | 10 | 0.032 | 0.092 |
| 61 | 11 | 0.013 | 0.029 |
| 64 | 12 | 0.024 | 0.081 |
| 66 | 13 | 0.041 | 0.187 |
| 70 | 14 | 0.033 | 0.094 |
| 72 | 15 | 0.064 | 0.191 |
| 76 | 16 | 0.051 | 0.181 |
| 78 | 17 | 0.063 | 0.176 |
| 81 | 18 | 0.037 | 0.187 |
| 84 | 19 | 0.042 | 0.179 |
| 88 | 20 | 0.031 | 0.183 |

Example 84 Detection of the Activity of Compounds on Cancer Cell

Experimental principles: compounds inhibit cancer cell growth by MTT method to detect. MTT assay principle is yellow MTT can penetrate membrane into the cell, succinic dehydrogenase of the mitochondria in living cells can make exogenous MTT reduction of insoluble in water of blue-violet acicular formazan for crystallization and deposition in the cell, crystallization can be dissolved dimethyl sulfoxide (DMSO) solution, detected its absorbance at 490 nm/570 nm wavelength by enzyme-linked immunosorbent assay, which can reflect the number of cells.

Experimental Materials: cancer cell lines used are for the Hela (human cervical cancer cells), MCF-7 (human breast cancer cells), BGC-823 (human gastric cancer cells), A549 (human lung cancer cells), HT1080 (human fibrosarcoma cells), A431 (human epidermal squamous cell carcinoma cells), HUVEC (human umbilical vein endothelial cells), DU145 (human prostate cancer cells), lncap (prostate cancer cells), K562 (human leukemia cells), U937 (human leukemia cells), Pac-1 (human pancreatic cancer cells), MOLT-4 (human acute lymphoblastic leukemia cells), KBM-5 (human chronic myelogenous leukemia), KBM5-T315I (human chronic myelogenous leukemia), SGC-7901 (human gastric cancer cells), N-87 (human gastric cancer cells), Bel-7402 (human hepatoma cells), Huh-7 (human hepatoma cells) K562 (human leukemia cells), H1975 (non-small cell lung adenocarcinoma fine), HCC827 (human non-small cell lung cancer cells), MDA-MB-231 (breast cancer cells). Using DMEM+10% FBS culture medium or using 1640+10% FBS culture, respectively.

Experimental Method and Result Analysis:

Experimental group: 190 μl cell suspension+10 μl different concentrations of drugs (the final concentration is $10^{-5}$~$10^{-10}$M)

Control group: 200 μl PBS

Negative control group: 190 μl cell suspension+10 μl 2% DMSO (DMSO final concentration is 0.1%)

Positive control group: 190 μl cell suspension+10 μl different concentrations of compounds a) Cells were seeded in 96-well plates with the inoculation of 1500/well, 190 μl/hole, 37° C., 5% of $CO_2$ incubator overnight;

b) The next day each well was added 10 μl of different drugs. The final concentration of drug was $10^{-5}$~$10^{-10}$M, three parallel holes; 37° C., 5% $CO_2$ culture incubator for 72 hours incubation;

c) Per well was added 20 μl 5 mg/ml of MTT, 37° C., 5% $CO_2$ culture incubator for 4 hours incubation;

d) The supernatant was discarded. Each well was added 100 μl of DMSO and oscillation;

e) 570 nm readings. Calculate cell viability. GI50 calculation based on the results. The results are shown in Tables 4-5.

TABLE 4

Test results of compounds on cancer cells (1)

| | GI50 (μM) | | | | | | | | | |
|---|---|---|---|---|---|---|---|---|---|---|
| Compound | Hela | MCF | A54 | BG | HT1 | lnca | Du1 | U93 | PAN | Mol |
| SAHA | 30.2 | 1.64 | 8.53 | 5.23 | 3.97 | 4.61 | 15.2 | 2.35 | 7.62 | 10.0 |
| 1 | 0.02 | 0.03 | 0.01 | 0.06 | 0.01 | 0.00 | 0.00 | 0.00 | 0.02 | 0.00 |
| 2 | 0.03 | 0.03 | 0.04 | 0.06 | 0.05 | 0.00 | 0.00 | 0.00 | 0.03 | 0.00 |
| 3 | 0.05 | 0.03 | 0.05 | 0.06 | 0.06 | 0.00 | 0.00 | 0.00 | 0.03 | 0.00 |
| 4 | 0.05 | 0.04 | 0.05 | 0.06 | 0.07 | 0.00 | 0.00 | 0.00 | 0.06 | 0.00 |
| 5 | 0.05 | 0.04 | 0.05 | 0.06 | 0.07 | 0.00 | 0.00 | 0.00 | 0.06 | 0.00 |
| 6 | 0.06 | 0.06 | 0.06 | 0.07 | 0.08 | 0.00 | 0.00 | 0.00 | 0.06 | 0.00 |
| 7 | 0.04 | 0.03 | 0.05 | 0.03 | 0.02 | 0.00 | 0.01 | 0.00 | 0.00 | 0.02 |
| 8 | 0.07 | 0.08 | 0.08 | 0.09 | 0.09 | 0.00 | 0.00 | 0.00 | 0.08 | 0.00 |
| 9 | 0.05 | 0.03 | 0.08 | 0.00 | 0.04 | 0.00 | 0.00 | 0.00 | 0.06 | 0.01 |
| 10 | 0.07 | 0.06 | 0.06 | 0.09 | 0.08 | 0.00 | 0.00 | 0.00 | 0.08 | 0.00 |
| 11 | 0.12 | 0.05 | 0.43 | 0.41 | 0.14 | 0.02 | 0.03 | 0.03 | 0.06 | 0.01 |
| 12 | 0.05 | 0.06 | 0.07 | 0.09 | 0.06 | 0.00 | 0.00 | 0.00 | 0.08 | 0.00 |
| 13 | 0.09 | 0.3 | 0.05 | 0.1 | 0.2 | 0.1 | 0.02 | 0.08 | 0.07 | 0.02 |
| 14 | 0.22 | 0.4 | 0.1 | 0.2 | 0.3 | 0.2 | 0.01 | 0.03 | 0.53 | 0.02 |
| 15 | 15.7 | 19.8 | 2.3 | 1.22 | 38.7 | 0.4 | 0.48 | 1.12 | 2.58 | 19.7 |
| 16 | 21 | 49.5 | 4.2 | 2.1 | 1.3 | 82.1 | 6.1 | 17.9 | 4.1 | 0.7 |
| 17 | 11 | 22 | 1.93 | 19.7 | 0.97 | 0.53 | 5.22 | 20.1 | 23.3 | 0.92 |
| 18 | 0.37 | 0.49 | 3.8 | 53.1 | 10.8 | 10.3 | 0.42 | 11.3 | 42.1 | 59.7 |
| 19 | 0.06 | 0.08 | 0.09 | 0.09 | 0.07 | 0.58 | 0.00 | 0.00 | 0.6 | 1.9 |
| 20 | 0.01 | 1.9 | 0.32 | 1.1 | 0.98 | 5.1 | 1.98 | 20.2 | 10.1 | 0.13 |
| 21 | 0.4 | 0.1 | 0.33 | 0.87 | 1.05 | 1.21 | 0.99 | 5.11 | 1.17 | 1.01 |
| 22 | 0.39 | 1.11 | 1.03 | 5.88 | 0.05 | 0.39 | 0.04 | 0.12 | 4.07 | 2.06 |
| 23 | 0.27 | 0.64 | 0.22 | 1.1 | 1.01 | 5.05 | 6.33 | 0.01 | 19.7 | 10.0 |
| 24 | 0.5 | 0.05 | 0.1 | 0.22 | 0.04 | 0.03 | 0.02 | 0.00 | 0.22 | 0.49 |
| 25 | 67.7 | 53.6 | 15.4 | 3.3 | 39.2 | 0.7 | 1.3 | 2.29 | 0.55 | 0.3 |
| 26 | 37 | 53.7 | 38.9 | 5.4 | 18 | 9 | 11.7 | 9.5 | 0.77 | 3.35 |
| 27 | 0.53 | 0.03 | 0.09 | 0.31 | 0.04 | 0.03 | 0.02 | 0.00 | 0.21 | 0.51 |
| 28 | 0.81 | 0.93 | 0.42 | 1.1 | 0.04 | 0.39 | 0.43 | 2.11 | 0.02 | 0.08 |
| 29 | 0.91 | 1.21 | 0.27 | 0.09 | 0.06 | 0.05 | 0.07 | 0.45 | 0.08 | 0.07 |
| 30 | 0.08 | 0.02 | 0.03 | 0.03 | 0.08 | 0.03 | 0.03 | 0.03 | 0.08 | 0.03 |
| 31 | 0.09 | 0.06 | 0.07 | 0.05 | 0.05 | 0.01 | 0.02 | 0.04 | 0.05 | 0.01 |
| 32 | 0.07 | 0.05 | 0.04 | 0.06 | 0.06 | 0.03 | 0.03 | 0.05 | 0.06 | 0.03 |
| 33 | 0.08 | 0.05 | 0.05 | 0.06 | 0.08 | 0.03 | 0.01 | 0.02 | 0.08 | 0.03 |
| 34 | 0.07 | 0.05 | 0.04 | 0.06 | 0.09 | 0.04 | 0.05 | 0.03 | 0.09 | 0.04 |
| 35 | 0.07 | 0.05 | 0.06 | 0.06 | 0.05 | 0.04 | 0.02 | 0.03 | 0.05 | 0.04 |
| 36 | 0.06 | 0.05 | 0.04 | 0.03 | 0.06 | 0.04 | 0.02 | 0.02 | 0.06 | 0.04 |
| 37 | 0.05 | 0.06 | 0.05 | 0.04 | 0.03 | 0.03 | 0.03 | 0.02 | 0.03 | 0.03 |
| 38 | 0.07 | 0.06 | 0.03 | 0.04 | 0.08 | 0.03 | 0.03 | 0.03 | 0.08 | 0.03 |
| 39 | 0.07 | 0.06 | 0.04 | 0.05 | 0.08 | 0.02 | 0.02 | 0.03 | 0.08 | 0.02 |
| 40 | 0.07 | 0.05 | 0.04 | 0.07 | 0.07 | 0.03 | 0.04 | 0.04 | 0.07 | 0.03 |
| 41 | 0.05 | 0.06 | 0.03 | 0.03 | 0.07 | 0.24 | 0.10 | 0.01 | 0.12 | 0.02 |
| 42 | 0.05 | 0.10 | 0.04 | 0.03 | 0.04 | 0.05 | 0.10 | 0.07 | 0.04 | 0.08 |
| 43 | 0.08 | 0.05 | 0.05 | 0.03 | 0.07 | 0.03 | 0.05 | 0.06 | 0..0 | 0.03 |
| 44 | 0.08 | 0.06 | 0.03 | 0.05 | 0.08 | 0.02 | 0.06 | 0.05 | 0.08 | 0.02 |
| 45 | 0.09 | 0.05 | 0.04 | 0.05 | 0.06 | 0.03 | 0.03 | 0.03 | 0.06 | 0.03 |
| 46 | 0.09 | 0.04 | 0.05 | 0.04 | 0.05 | 0.03 | 0.03 | 0.03 | 0.05 | 0.03 |
| 47 | 0.08 | 0.05 | 0.04 | 0.06 | 0.04 | 0.02 | 0.03 | 0.02 | 0.04 | 0.02 |
| 48 | 0.07 | 0.06 | 0.06 | 0.08 | 0.04 | 0.03 | 0.02 | 0.02 | 0.04 | 0.03 |
| 49 | 0.08 | 0.05 | 0.06 | 0.07 | 0.07 | 0.02 | 0.01 | 0.03 | 0.07 | 0.02 |
| 50 | 0.07 | 0.06 | 0.03 | 0.06 | 0.08 | 0.02 | 0.04 | 0.03 | 0.08 | 0.02 |
| 51 | 0.08 | 0.07 | 0.04 | 0.06 | 0.07 | 0.02 | 0.04 | 0.06 | 0.07 | 0.02 |
| 52 | 0.08 | 0.06 | 0.05 | 0.05 | 0.09 | 0.03 | 0.02 | 0.06 | 0.09 | 0.03 |
| 53 | 0.09 | 0.05 | 0.06 | 0.04 | 0.04 | 0.02 | 0.03 | 0.05 | 0.04 | 0.02 |
| 54 | 0.09 | 0.06 | 0.06 | 0.04 | 0.05 | 0.03 | 0.02 | 0.04 | 0.05 | 0.03 |
| 55 | 0.08 | 0.07 | 0.05 | 0.05 | 0.08 | 0.02 | 0.03 | 0.05 | 0.08 | 0.02 |
| 56 | 0.08 | 0.06 | 0.05 | 0.04 | 0.09 | 0.03 | 0.04 | 0.05 | 0.09 | 0.03 |
| 57 | 0.07 | 0.05 | 0.09 | 0.05 | 0.07 | 0.02 | 0.03 | 0.05 | 0.07 | 0.02 |
| 58 | 0.06 | 0.08 | 0.05 | 0.06 | 0.04 | 0.03 | 0.02 | 0.06 | 0.04 | 0.03 |
| 59 | 0.06 | 0.07 | 0.05 | 0.05 | 0.08 | 0.03 | 0.03 | 0.03 | 0.08 | 0.03 |
| 60 | 0.07 | 0.08 | 0.04 | 0.06 | 0.05 | 0.01 | 0.02 | 0.04 | 0.05 | 0.01 |
| 61 | 0.08 | 0.09 | 0.03 | 0.07 | 0.06 | 0.03 | 0.03 | 0.05 | 0.06 | 0.03 |

TABLE 4-continued

| Test results of compounds on cancer cells (1) | | | | | | | | | | |
|---|---|---|---|---|---|---|---|---|---|---|
| | GI50 (μM) | | | | | | | | | |
| Compound | Hela | MCF | A54 | BG | HT1 | lnca | Du1 | U93 | PAN | Mol |
| 62 | 0.09 | 0.06 | 0.04 | 0.06 | 0.08 | 0.03 | 0.01 | 0.02 | 0.08 | 0.03 |
| 63 | 0.09 | 0.05 | 0.05 | 0.05 | 0.09 | 0.04 | 0.05 | 0.03 | 0.09 | 0.04 |
| 64 | 0.08 | 0.02 | 0.03 | 0.03 | 0.05 | 0.04 | 0.02 | 0.03 | 0.05 | 0.04 |
| 65 | 0.09 | 0.06 | 0.07 | 0.05 | 0.06 | 0.04 | 0.02 | 0.02 | 0.06 | 0.04 |
| 66 | 0.09 | 0.03 | 0.02 | 0.06 | 0.03 | 0.03 | 0.03 | 0.02 | 0.03 | 0.03 |
| 67 | 0.04 | 0.02 | 0.03 | 0.05 | 0.08 | 0.03 | 0.03 | 0.03 | 0.08 | 0.03 |
| 68 | 0.05 | 0.03 | 0.02 | 0.04 | 0.08 | 0.02 | 0.02 | 0.03 | 0.08 | 0.02 |
| 69 | 0.08 | 0.02 | 0.03 | 0.05 | 0.07 | 0.03 | 0.04 | 0.04 | 0.07 | 0.03 |
| 70 | 0.09 | 0.03 | 0.04 | 0.05 | 0..0 | 0.03 | 0.05 | 0.06 | 0..0 | 0.03 |
| 71 | 0.07 | 0.02 | 0.03 | 0.05 | 0.08 | 0.02 | 0.06 | 0.05 | 0.08 | 0.02 |
| 72 | 0.04 | 0.03 | 0.02 | 0.06 | 0.06 | 0.03 | 0.03 | 0.03 | 0.06 | 0.03 |
| 73 | 0.08 | 0.02 | 0.02 | 0.03 | 0.05 | 0.03 | 0.03 | 0.03 | 0.05 | 0.03 |
| 74 | 0.03 | 0.35 | 0.04 | 0.03 | 0.04 | 0.02 | 0.03 | 0.02 | 0.04 | 0.02 |
| 75 | 0.06 | 0.02 | 0.04 | 0.02 | 0.04 | 0.03 | 0.02 | 0.02 | 0.04 | 0.03 |
| 76 | 0.09 | 0.03 | 0.05 | 0.03 | 0.07 | 0.02 | 0.01 | 0.03 | 0.07 | 0.02 |
| 77 | 0.05 | 0.03 | 0.60 | 0.05 | 0.08 | 0.02 | 0.04 | 0.03 | 0.08 | 0.02 |
| 78 | 0.06 | 0.01 | 0.06 | 0.06 | 0.07 | 0.02 | 0.04 | 0.06 | 0.07 | 0.02 |
| 79 | 0.07 | 0.02 | 0.05 | 0.02 | 0.09 | 0.03 | 0.02 | 0.06 | 0.09 | 0.03 |
| 80 | 0.04 | 0.02 | 0.07 | 0.03 | 0.04 | 0.02 | 0.03 | 0.05 | 0.04 | 0.02 |
| 81 | 0.03 | 0.03 | 0.05 | 0.03 | 0.05 | 0.03 | 0.02 | 0.04 | 0.05 | 0.03 |
| 82 | 0.04 | 0.03 | 0.04 | 0.02 | 0.08 | 0.02 | 0.03 | 0.05 | 0.08 | 0.02 |
| 83 | 0.03 | 0.02 | 0.05 | 0.01 | 0.09 | 0.03 | 0.04 | 0.05 | 0.09 | 0.03 |
| 84 | 0.05 | 0.02 | 0.04 | 0.01 | 0.07 | 0.02 | 0.03 | 0.05 | 0.07 | 0.02 |
| 85 | 0.05 | 0.02 | 0.01 | 0.02 | 0.04 | 0.03 | 0.02 | 0.06 | 0.04 | 0.03 |
| 86 | 0.06 | 0.03 | 0.02 | 0.03 | 0.08 | 0.03 | 0.03 | 0.03 | 0.08 | 0.03 |
| 87 | 0.08 | 0.03 | 0.03 | 0.02 | 0.05 | 0.01 | 0.02 | 0.04 | 0.05 | 0.01 |
| 88 | 0.07 | 0.02 | 0.02 | 0.03 | 0.06 | 0.03 | 0.03 | 0.05 | 0.06 | 0.03 |
| 89 | 0.09 | 0.03 | 0.03 | 0.01 | 0.08 | 0.03 | 0.01 | 0.02 | 0.08 | 0.03 |
| 90 | 0.08 | 0.02 | 0.03 | 0.03 | 0.09 | 0.04 | 0.05 | 0.03 | 0.09 | 0.04 |
| 91 | 0.09 | 0.03 | 0.04 | 0.06 | 0.05 | 0.04 | 0.02 | 0.03 | 0.05 | 0.04 |
| 92 | 0.04 | 0.02 | 0.05 | 0.01 | 0.06 | 0.04 | 0.02 | 0.02 | 0.06 | 0.04 |
| 93 | 0.05 | 0.03 | 0.06 | 0.02 | 0.03 | 0.03 | 0.03 | 0.02 | 0.03 | 0.03 |
| 94 | 0.06 | 0.03 | 0.04 | 0.03 | 0.08 | 0.03 | 0.03 | 0.03 | 0.08 | 0.03 |
| 95 | 0.07 | 0.03 | 0.04 | 0.02 | 0.08 | 0.02 | 0.02 | 0.03 | 0.08 | 0.02 |
| 96 | 0.06 | 0.02 | 0.04 | 0.02 | 0.04 | 0.03 | 0.02 | 0.02 | 0.04 | 0.03 |
| 97 | 0.09 | 0.03 | 0.05 | 0.03 | 0.07 | 0.02 | 0.01 | 0.03 | 0.07 | 0.02 |
| 98 | 0.05 | 0.03 | 0.60 | 0.05 | 0.08 | 0.02 | 0.04 | 0.03 | 0.08 | 0.02 |
| 99 | 0.06 | 0.01 | 0.06 | 0.06 | 0.07 | 0.02 | 0.04 | 0.06 | 0.07 | 0.02 |
| 100 | 0.07 | 0.02 | 0.05 | 0.02 | 0.09 | 0.03 | 0.02 | 0.06 | 0.09 | 0.03 |
| 101 | 0.04 | 0.02 | 0.07 | 0.03 | 0.04 | 0.02 | 0.03 | 0.05 | 0.04 | 0.02 |
| 102 | 0.03 | 0.03 | 0.05 | 0.03 | 0.05 | 0.03 | 0.02 | 0.04 | 0.05 | 0.03 |
| 103 | 0.04 | 0.03 | 0.04 | 0.02 | 0.08 | 0.02 | 0.03 | 0.05 | 0.08 | 0.02 |
| 104 | 0.03 | 0.02 | 0.05 | 0.01 | 0.09 | 0.03 | 0.04 | 0.05 | 0.09 | 0.03 |
| 105 | 0.05 | 0.02 | 0.04 | 0.01 | 0.07 | 0.02 | 0.03 | 0.05 | 0.07 | 0.02 |
| 106 | 0.05 | 0.03 | 0.06 | 0.02 | 0.03 | 0.03 | 0.03 | 0.02 | 0.03 | 0.03 |
| 107 | 0.06 | 0.03 | 0.04 | 0.03 | 0.08 | 0.03 | 0.03 | 0.03 | 0.08 | 0.03 |
| 108 | 0.07 | 0.03 | 0.04 | 0.02 | 0.08 | 0.02 | 0.02 | 0.03 | 0.08 | 0.02 |
| 109 | 0.07 | 0.02 | 0.05 | 0.02 | 0.07 | 0.03 | 0.04 | 0.04 | 0.07 | 0.03 |
| 110 | 0.06 | 0.03 | 0.06 | 0.03 | 0.07 | 0.03 | 0.05 | 0.06 | 0..0 | 0.03 |
| 111 | 0.08 | 0.02 | 0.05 | 0.03 | 0.08 | 0.02 | 0.06 | 0.05 | 0.08 | 0.02 |
| 112 | 0.07 | 0.06 | 0.06 | 0.08 | 0.09 | 0.07 | 0.06 | 0.06 | 0.08 | 0.09 |
| 113 | 0.08 | 0.05 | 0.06 | 0.07 | 0.10 | 0.08 | 0.05 | 0.06 | 0.07 | 0.10 |
| 114 | 0.07 | 0.06 | 0.03 | 0.06 | 0.10 | 0.07 | 0.06 | 0.03 | 0.06 | 0.10 |
| 115 | 0.08 | 0.07 | 0.04 | 0.06 | 0.08 | 0.08 | 0.07 | 0.04 | 0.06 | 0.08 |
| 116 | 0.04 | 0.06 | 0.06 | 0.05 | 0.05 | 0.03 | 0.02 | 0.02 | 0.04 | 0.03 |
| 117 | 0.08 | 0.02 | 0.06 | 0.07 | 0.04 | 0.02 | 0.01 | 0.03 | 0.06 | 0.02 |
| 118 | 0.07 | 0.06 | 0.03 | 0.06 | 0.08 | 0.02 | 0.04 | 0.03 | 0.08 | 0.02 |
| 119 | 0.09 | 0.05 | 0.06 | 0.04 | 0.09 | 0.09 | 0.05 | 0.06 | 0.04 | 0.09 |
| 120 | 0.03 | 0.10 | 0.05 | 0.03 | 0.01 | 0.03 | 0.05 | 0.01 | 0.10 | 0.02 |
| 121 | 0.05 | 0.02 | 0.21 | 0.19 | 0.07 | 0.11 | 0.03 | 0.06 | 0.07 | 0.03 |
| 122 | 0.05 | 0.03 | 0.11 | 0.02 | 0.03 | 0.03 | 0.08 | 0.11 | 0.03 | 0.10 |
| 123 | 0.09 | 0.06 | 0.06 | 0.04 | 0.09 | 0.09 | 0.06 | 0.06 | 0.04 | 0.09 |
| 124 | 0.03 | 0.03 | 0.05 | 0.03 | 0.03 | 0.07 | 0.02 | 0.10 | 0.69 | 0.05 |
| 125 | 0.05 | 0.06 | 0.06 | 0.03 | 0.04 | 0.11 | 0.03 | 0.05 | 0.12 | 0.11 |
| 126 | 0.13 | 0.02 | 0.03 | 0.10 | 0.05 | 0.02 | 0.06 | 0.07 | 0.03 | 0.09 |
| 127 | 0.08 | 0.07 | 0.05 | 0.05 | 0.08 | 0.08 | 0.07 | 0.05 | 0.05 | 0.08 |
| 128 | 0.04 | 0.05 | 0.03 | 0.07 | 0.07 | 0.10 | 0.05 | 0.05 | 0.13 | 0.02 |
| 129 | 0.04 | 0.03 | 0.08 | 0.03 | 0.13 | 0.07 | 0.03 | 0.01 | 0.05 | 0.06 |
| 130 | 0.13 | 0.07 | 0.07 | 0.05 | 0.10 | 0.02 | 0.03 | 0.03 | 0.04 | 0.03 |
| 131 | 0.08 | 0.06 | 0.05 | 0.04 | 0.08 | 0.08 | 0.06 | 0.05 | 0.04 | 0.08 |
| 132 | 0.02 | 0.10 | 0.02 | 0.04 | 0.03 | 0.03 | 0.15 | 0.04 | 0.07 | 0.03 |
| 133 | 0.02 | 0.07 | 0.05 | 0.05 | 0.08 | 0.08 | 0.07 | 0.05 | 0.05 | 0.08 |
| 134 | 0.04 | 0.08 | 0.03 | 0.17 | 0.07 | 0.10 | 0.05 | 0.05 | 0.13 | 0.05 |
| 135 | 0.07 | 0.05 | 0.09 | 0.05 | 0.09 | 0.07 | 0.05 | 0.09 | 0.05 | 0.09 |

TABLE 4-continued

| Test results of compounds on cancer cells (1) | | | | | | | | | | |
|---|---|---|---|---|---|---|---|---|---|---|
| | GI50 (μM) | | | | | | | | | |
| Compound | Hela | MCF | A54 | BG | HT1 | lnca | Du1 | U93 | PAN | Mol |
| 136 | 0.08 | 0.05 | 0.04 | 0.07 | 0.04 | 0.03 | 0.01 | 0.03 | 0.08 | 0.02 |
| 137 | 0.07 | 0.03 | 0.02 | 0.03 | 0.08 | 0.02 | 0.03 | 0.03 | 0.08 | 0.04 |
| 138 | 0.06 | 0.02 | 0.04 | 0.02 | 0.02 | 0.05 | 0.02 | 0.02 | 0.03 | 0.05 |
| 139 | 0.07 | 0.01 | 0.05 | 0.06 | 0.07 | 0.19 | 0.08 | 0.05 | 0.07 | 0.09 |
| 140 | 0.13 | 0.08 | 0.03 | 0.10 | 0.05 | 0.02 | 0.06 | 0.07 | 0.03 | 0.05 |
| 141 | 0.08 | 0.07 | 0.05 | 0.03 | 0.08 | 0.08 | 0.07 | 0.05 | 0.05 | 0.08 |
| 142 | 0.05 | 0.05 | 0.13 | 0.07 | 0.07 | 0.11 | 0.05 | 0.05 | 0.13 | 0.02 |
| 143 | 0.06 | 0.07 | 0.08 | 0.08 | 0.09 | 0.06 | 0.07 | 0.08 | 0.08 | 0.09 |
| 144 | 0.05 | 0.06 | 0.07 | 0.07 | 0.07 | 0.05 | 0.06 | 0.07 | 0.07 | 0.07 |
| 145 | 0.04 | 0.06 | 0.07 | 0.06 | 0.10 | 0.04 | 0.06 | 0.07 | 0.06 | 0.10 |
| 146 | 0.04 | 0.05 | 0.03 | | 0.08 | 0.04 | 0.05 | 0.03 | | 0.08 |
| 147 | 0.05 | 0.04 | 0.03 | 0.05 | 0.08 | 0.05 | 0.04 | 0.03 | 0.05 | 0.08 |
| 148 | 0.04 | 0.05 | 0.02 | 0.04 | 0.08 | 0.04 | 0.05 | 0.02 | 0.04 | 0.08 |
| 149 | 0.05 | 0.06 | 0.02 | 0.03 | 0.08 | 0.05 | 0.06 | 0.02 | 0.03 | 0.08 |
| 150 | 0.06 | 0.04 | 0.03 | 0.03 | 0.08 | 0.06 | 0.04 | 0.03 | 0.03 | 0.08 |
| 151 | 0.07 | 0.04 | 0.04 | 0.04 | 0.09 | 0.07 | 0.04 | 0.04 | 0.04 | 0.09 |
| 152 | 0.06 | 0.06 | 0.05 | 0.05 | 0.09 | 0.06 | 0.06 | 0.05 | 0.05 | 0.09 |
| 153 | 0.05 | 0.06 | 0.03 | 0.02 | 0.08 | 0.05 | 0.06 | 0.03 | 0.02 | 0.08 |
| 154 | 0.04 | 0.05 | 0.04 | 0.04 | 0.09 | 0.04 | 0.05 | 0.04 | 0.04 | 0.09 |
| 155 | 0.04 | 0.05 | 0.04 | 0.04 | 0.09 | 0.04 | 0.05 | 0.04 | 0.04 | 0.09 |
| 156 | 0.03 | 0.02 | 0.03 | 0.05 | 0.08 | 0.03 | 0.08 | 0.02 | 0.05 | 0.01 |
| 157 | 0.07 | 0.02 | 0.02 | 0.03 | 0.09 | 0.05 | 0.07 | 0.02 | 0.02 | 0.02 |
| 158 | 0.06 | 0.02 | 0.03 | 0.03 | 0.07 | 0.04 | 0.06 | 0.04 | 0.02 | 0.08 |
| 159 | 0.07 | 0.05 | 0.03 | 0.08 | 0.05 | 0.06 | 0.04 | 0.06 | 0.05 | 0.05 |
| 160 | 0.05 | 0.04 | 0.03 | 0.09 | 0.04 | 0.05 | 0.04 | 0.05 | 0.04 | 0.05 |
| 161 | 0.01 | 0.07 | 0.08 | 0.02 | 0.05 | 0.07 | 0.02 | 0.06 | 0.01 | 0.03 |
| 162 | 0.08 | 0.04 | 0.09 | 0.05 | 0.07 | 0.05 | 0.01 | 0.05 | 0.07 | 0.07 |
| 163 | 0.01 | 0.02 | 0.05 | 0.06 | 0.01 | 0.03 | 0.04 | 0.03 | 0.07 | 0.04 |
| 164 | 0.02 | 0.03 | 0.06 | 0.34 | 0.02 | 0.03 | 0.05 | 0.06 | 0.08 | 0.05 |
| 165 | 0.06 | 0.03 | 0.03 | 0.02 | 0.06 | 0.02 | 0.06 | 0.05 | 0.07 | 0.04 |
| 166 | 0.05 | 0.06 | 0.01 | 0.07 | 0.08 | 0.07 | 0.06 | 0.03 | 0.02 | 0.03 |
| 167 | 0.04 | 0.03 | 0.03 | 0.04 | 0.10 | 0.06 | 0.04 | 0.02 | 0.07 | 0.02 |
| 168 | 0.05 | 0.06 | 0.08 | 0.01 | 0.13 | 0.02 | 0.05 | 0.04 | 0.06 | 0.10 |
| 169 | 0.02 | 0.07 | 0.04 | 0.06 | 0.06 | 0.05 | 0.07 | 0.02 | 0.04 | 0.04 |
| 170 | 0.03 | 0.06 | 0.06 | 0.02 | 0.05 | 0.07 | 0.02 | 0.09 | 0.05 | 0.03 |
| 171 | 0.05 | 0.01 | 0.05 | 0.07 | 0.04 | 0.05 | 0.01 | 0.02 | 0.01 | 0.02 |
| 172 | 0.05 | 0.06 | 0.03 | 0.06 | 0.06 | 0.02 | 0.04 | 0.04 | 0.08 | 0.02 |
| 173 | 0.06 | 0.02 | 0.06 | 0.04 | 0.07 | 0.04 | 0.06 | 0.01 | 0.04 | 0.03 |
| 174 | 0.02 | 0.08 | 0.05 | 0.03 | 0.01 | 0.03 | 0.05 | 0.07 | 0.10 | 0.02 |
| 175 | 0.01 | 0.02 | 0.10 | 0.02 | 0.05 | 0.08 | 0.03 | 0.04 | 0.05 | 0.02 |
| 176 | 0.05 | 0.01 | 0.08 | 0.02 | 0.03 | 0.03 | 0.05 | 0.01 | 0.06 | 0.05 |
| 177 | 0.10 | 0.05 | 0.02 | 0.04 | 0.03 | 0.01 | 0.06 | 0.06 | 0.02 | 0.06 |
| 178 | 0.06 | 0.03 | 0.03 | 0.06 | 0.02 | 0.05 | 0.02 | 0.09 | 0.35 | 0.05 |
| 179 | 0.03 | 0.06 | 0.06 | 0.03 | 0.04 | 0.10 | 0.03 | 0.05 | 0.06 | 0.08 |
| 180 | 0.10 | 0.02 | 0.03 | 0.05 | 0.05 | 0.02 | 0.06 | 0.07 | 0.03 | 0.05 |
| 181 | 0.07 | 0.07 | 0.05 | 0.03 | 0.06 | 0.08 | 0.06 | 0.02 | 0.04 | 0.08 |
| 182 | 0.06 | 0.03 | 0.06 | 0.07 | 0.03 | 0.10 | 0.05 | 0.08 | 0.09 | 0.03 |
| 183 | 0.11 | 0.04 | 0.07 | 0.06 | 0.05 | 0.06 | 0.03 | 0.02 | 0.05 | 0.06 |
| 184 | 0.02 | 0.11 | 0.11 | 0.05 | 0.08 | 0.02 | 0.06 | 0.03 | 0.06 | 0.03 |
| 185 | 0.05 | 0.06 | 0.01 | 0.03 | 0.05 | 0.08 | 0.03 | 0.05 | 0.03 | 0.05 |
| 186 | 0.07 | 0.05 | 0.03 | 0.04 | 0.02 | 0.03 | 0.10 | 0.04 | 0.05 | 0.03 |
| 187 | 0.04 | 0.02 | 0.06 | 0.06 | 0.02 | 0.06 | 0.05 | 0.06 | 0.06 | 0.03 |
| 188 | 0.05 | 0.03 | 0.02 | 0.03 | 0.08 | 0.06 | 0.03 | 0.04 | 0.05 | 0.03 |
| 189 | 0.04 | 0.03 | 0.03 | 0.01 | 0.11 | 0.05 | 0.03 | 0.04 | 0.08 | 0.05 |
| 190 | 0.06 | 0.03 | 0.02 | 0.05 | 0.02 | 0.03 | 0.02 | 0.05 | 0.06 | 0.07 |
| 191 | 0.13 | 0.17 | 0.07 | 0.10 | 0.05 | 0.31 | 0.04 | 0.03 | 0.05 | 0.05 |
| 192 | 0.29 | 0.05 | 0.09 | 0.07 | 0.05 | 0.02 | 0.08 | 0.02 | 0.06 | 0.09 |
| 193 | 0.43 | 0.07 | 0.04 | 0.03 | 0.01 | 0.08 | 0.03 | 0.05 | 0.08 | 0.04 |
| 194 | 0.05 | 0.04 | 0.03 | 0.05 | 0.01 | 0.02 | 0.03 | 0.06 | 0.04 | 0.03 |
| 195 | 0.06 | 0.03 | 0.09 | 0.02 | 0.03 | 0.09 | 0.05 | 0.05 | 0.03 | 0.02 |
| 196 | 0.08 | 0.06 | 0.02 | 0.05 | 0.07 | 0.06 | 0.13 | 0.06 | 0.06 | 0.03 |
| 197 | 0.07 | 0.05 | 0.06 | 0.04 | 0.05 | 0.03 | 0.05 | 0.08 | 0.04 | 0.04 |
| 198 | 0.03 | 0.11 | 0.05 | 0.07 | 0.02 | 0.09 | 0.05 | 0.05 | 0.03 | 0.02 |
| 199 | 0.03 | 0.08 | 0.04 | 0.09 | 0.04 | 0.04 | 0.05 | 0.03 | 0.01 | 0.03 |
| 200 | 0.03 | 0.03 | 0.02 | 0.08 | 0.04 | 0.08 | 0.06 | 0.05 | 0.07 | 0.04 |
| 201 | 0.03 | 0.04 | 0.03 | 0.05 | 0.06 | 0.07 | 0.03 | 0.04 | 0.06 | 0.02 |
| 202 | 0.02 | 0.03 | 0.05 | 0.04 | 0.03 | 0.02 | 0.07 | 0.02 | 0.03 | 0.05 |
| 203 | 0.03 | 0.04 | 0.03 | 0.08 | 0.06 | 0.03 | 0.04 | 0.02 | 0.03 | 0.03 |
| 204 | 0.06 | 0.03 | 0.03 | 0.02 | 0.03 | 0.05 | 0.05 | 0.02 | 0.02 | 0.04 |
| 205 | 0.07 | 0.07 | 0.05 | 0.05 | 0.01 | 0.06 | 0.06 | 0.04 | 0.03 | 0.05 |
| 206 | 0.00 | 0.03 | 0.05 | 0.02 | 0.01 | 0.07 | 0.01 | 0.06 | 0.02 | 0.02 |
| 207 | 0.02 | 0.04 | 0.03 | 0.03 | 0.03 | 0.05 | 0.03 | 0.04 | 0.05 | 0.01 |
| 208 | 0.08 | 0.03 | 0.05 | 0.05 | 0.07 | 0.03 | 0.04 | 0.06 | 0.03 | 0.04 |
| 209 | 0.09 | 0.02 | 0.02 | 0.04 | 0.03 | 0.02 | 0.07 | 0.03 | 0.02 | 0.07 |

TABLE 4-continued

| Test results of compounds on cancer cells (1) | | | | | | | | | | |
|---|---|---|---|---|---|---|---|---|---|---|
| | GI50 (μM) | | | | | | | | | |
| Compound | Hela | MCF | A54 | BG | HT1 | lnca | Du1 | U93 | PAN | Mol |
| 210 | 0.03 | 0.03 | 0.05 | 0.01 | 0.02 | 0.05 | 0.03 | 0.02 | 0.05 | 0.05 |
| 211 | 0.06 | 0.07 | 0.04 | 0.07 | 0.04 | 0.03 | 0.06 | 0.04 | 0.07 | 0.03 |
| 212 | 0.02 | 0.07 | 0.04 | 0.06 | 0.03 | 0.08 | 0.03 | 0.06 | 0.05 | 0.07 |
| 213 | 0.05 | 0.09 | 0.07 | 0.03 | 0.02 | 0.07 | 0.02 | 0.07 | 0.08 | 0.04 |
| 214 | 0.06 | 0.05 | 0.09 | 0.02 | 0.04 | 0.11 | 0.04 | 0.05 | 0.04 | 0.05 |
| 215 | 0.02 | 0.03 | 0.05 | 0.04 | 0.02 | 0.10 | 0.03 | 0.09 | 0.04 | 0.07 |
| 216 | 0.07 | 0.05 | 0.08 | 0.06 | 0.05 | 0.01 | 0.02 | 0.08 | 0.02 | 0.04 |
| 217 | 0.01 | 0.06 | 0.07 | 0.03 | 0.02 | 0.03 | 0.02 | 0.09 | 0.07 | 0.09 |
| 218 | 0.08 | 0.04 | 0.03 | 0.06 | 0.02 | 0.05 | 0.05 | 0.06 | 0.05 | 0.09 |
| 219 | 0.09 | 0.06 | 0.03 | 0.05 | 0.07 | 0.06 | 0.05 | 0.07 | 0.08 | 0.08 |
| 220 | 0.03 | 0.02 | 0.04 | 0.03 | 0.08 | 0.06 | 0.03 | 0.08 | 0.03 | 0.05 |
| 221 | 0.03 | 0.08 | 0.02 | 0.05 | 0.08 | 0.02 | 0.05 | 0.07 | 0.05 | 0.07 |
| 222 | 0.02 | 0.07 | 0.05 | 0.04 | 0.07 | 0.06 | 0.03 | 0.08 | 0.03 | 0.03 |
| 223 | 0.05 | 0.04 | 0.02 | 0.03 | 0.08 | 0.01 | 0.06 | 0.02 | 0.05 | 0.05 |
| 224 | 0.06 | 0.04 | 0.05 | 0.03 | 0.09 | 0.03 | 0.05 | 0.03 | 0.06 | 0.03 |
| 225 | 0.07 | 0.03 | 0.04 | 0.04 | 0.02 | 0.02 | 0.02 | 0.03 | 0.03 | 0.06 |
| 226 | 0.09 | 0.02 | 0.06 | 0.05 | 0.02 | 0.03 | 0.03 | 0.04 | 0.02 | 0.03 |
| 227 | 0.07 | 0.02 | 0.02 | 0.05 | 0.07 | 0.02 | 0.06 | 0.04 | 0.01 | 0.06 |
| 228 | 0.01 | 0.03 | 0.03 | 0.06 | 0.04 | 0.02 | 0.02 | 0.04 | 0.03 | 0.05 |
| 229 | 0.03 | 0.07 | 0.06 | 0.74 | 0.01 | 0.03 | 0.05 | 0.02 | 0.05 | 0.03 |
| 230 | 0.02 | 0.07 | 0.02 | 0.03 | 0.02 | 0.05 | 0.05 | 0.02 | 0.03 | 0.03 |
| 231 | 0.04 | 0.08 | 0.06 | 0.01 | 0.03 | 0.03 | 0.05 | 0.08 | 0.01 | 0.05 |
| 232 | 0.03 | 0.08 | 0.03 | 0.05 | 0.02 | 0.03 | 0.05 | 0.09 | 0.01 | 0.05 |
| 233 | 0.05 | 0.02 | 0.02 | 0.06 | 0.07 | 0.02 | 0.05 | 0.08 | 0.02 | 0.03 |
| 234 | 0.06 | 0.03 | 0.02 | 0.08 | 0.01 | 0.02 | 0.05 | 0.02 | 0.03 | 0.03 |
| 235 | 0.04 | 0.05 | 0.03 | 0.04 | 0.02 | 0.04 | 0.03 | 0.06 | 0.23 | 0.07 |
| 236 | 0.81 | 0.76 | 0.51 | 0.09 | 0.19 | 0.05 | 0.09 | 0.07 | 0.21 | 0.86 |
| 237 | 0.88 | 0.35 | 0.42 | 0.17 | 0.99 | 0.94 | 0.04 | 0.11 | 0.93 | 0.97 |
| 238 | 0.05 | 0.02 | 0.01 | 0.14 | 0.02 | 0.11 | 0.01 | 0.01 | 0.07 | 0.00 |
| 239 | 0.011 | 0.01 | 0.01 | 0.02 | 0.01 | 0.01 | 0.00 | 0.00 | 0.13 | 0.00 |
| 240 | 0.07 | 0.00 | 0.01 | 0.19 | 0.01 | 0.01 | 0.00 | 0.03 | 0.11 | 0.03 |
| 241 | 0.011 | 0.02 | 0.11 | 0.10 | 0.03 | 0.02 | 0.00 | 0.00 | 0.17 | 0.00 |
| 242 | 0.08 | 0.07 | 0.19 | 0.01 | 0.03 | 0.17 | 0.09 | 0.01 | 0.95 | 0.03 |
| 243 | 0.23 | 0.12 | 0.94 | 0.86 | 0.84 | 0.47 | 0.13 | 0.87 | 0.52 | 0.49 |
| 244 | 0.00 | 0.33 | 0.12 | 0.39 | 0.76 | 0.99 | 0.95 | 0.89 | 0.77 | 0.11 |
| 245 | 0.53 | 0.04 | 0.11 | 0.77 | 0.65 | 0.86 | 0.13 | 0.84 | 0.14 | 0.35 |
| 246 | 0.01 | 0.31 | 0.11 | 1.02 | 0.01 | 0.13 | 0.02 | 0.11 | 0.87 | 0.91 |
| 247 | 0.05 | 0.05 | 0.06 | 0.01 | 0.06 | 0.02 | 0.02 | 0.07 | 0.05 | 0.03 |
| 248 | 0.06 | 0.03 | 0.03 | 0.06 | 0.05 | 0.03 | 0.03 | 0.08 | 0.02 | 0.03 |
| 249 | 0.08 | 0.07 | 0.05 | 0.03 | 0.04 | 0.04 | 0.03 | 0.07 | 0.02 | 0.05 |
| 250 | 0.07 | 0.04 | 0.04 | 0.04 | 0.06 | 0.05 | 0.05 | 0.08 | 0.03 | 0.03 |
| 251 | 0.02 | 0.04 | 0.06 | 0.03 | 0.02 | 0.09 | 0.02 | 0.03 | 0.05 | 0.07 |
| 252 | 0.05 | 0.02 | 0.05 | 0.03 | 0.04 | 0.05 | 0.07 | 0.04 | 0.06 | 0.09 |
| 253 | 0.05 | 0.06 | 0.03 | 0.05 | 0.05 | 0.02 | 0.02 | 0.03 | 0.06 | 0.08 |
| 254 | 0.04 | 0.05 | 0.04 | 0.06 | 0.06 | 0.01 | 0.06 | 0.04 | 0.01 | 0.04 |
| 255 | 0.01 | 0.08 | 0.03 | 0.03 | 0.06 | 0.05 | 0.04 | 0.02 | 0.04 | 0.05 |

TABLE 5

| Test results of compounds on 249 cancer cells (2) | | | | | | | | | | |
|---|---|---|---|---|---|---|---|---|---|---|
| | GI50 (μM) | | | | | | | | | |
| Compound No. | KBM-5 | KBM5-T315I | SGC-7901 | N-87 | Bel-7402 | Huh-7 | K562 | H1975 | HCC827 | MDA-MB-231 |
| SAHA | 11.2 | 86.7 | 12.5 | 13.2 | 12.7 | 18.3 | 10.1 | 15.2 | 16.7 | 22.5 |
| 1 | 0.037 | 0.046 | 0.053 | 0.018 | 0.029 | 0.033 | 0.078 | 0.122 | 0.179 | 0.095 |
| 2 | 0.051 | 0.029 | 0.026 | 0.029 | 0.083 | 0.073 | 0.051 | 0.034 | 0.042 | 0.092 |
| 3 | 0.073 | 0.034 | 0.028 | 0.043 | 0.097 | 0.043 | 0.037 | 0.029 | 0.033 | 0.091 |
| 4 | 0.074 | 0.022 | 0.034 | 0.053 | 0.092 | 0.086 | 0.061 | 0.031 | 0.022 | 0.086 |
| 5 | 0.072 | 0.033 | 0.043 | 0.037 | 0.093 | 0.072 | 0.032 | 0.023 | 0.055 | 0.082 |
| 6 | 0.061 | 0.041 | 0.051 | 0.028 | 0.086 | 0.058 | 0.033 | 0.013 | 0.065 | 0.084 |
| 7 | 0.049 | 0.052 | 0.035 | 0.029 | 0.082 | 0.046 | 0.041 | 0.034 | 0.054 | 0.091 |
| 8 | 0.051 | 0.063 | 0.043 | 0.034 | 0.094 | 0.061 | 0.053 | 0.038 | 0.041 | 0.093 |
| 9 | 0.044 | 0.026 | 0.031 | 0.035 | 0.083 | 0.053 | 0.083 | 0.026 | 0.053 | 0.097 |
| 10 | 0.061 | 0.024 | 0.023 | 0.038 | 0.095 | 0.051 | 0.073 | 0.024 | 0.026 | 0.098 |
| 11 | 0.062 | 0.026 | 0.035 | 0.037 | 0.076 | 0.043 | 0.063 | 0.042 | 0.023 | 0.086 |
| 12 | 0.072 | 0.031 | 0.036 | 0.028 | 0.072 | 0.086 | 0.024 | 0.041 | 0.037 | 0.084 |
| 13 | 0.084 | 0.011 | 0.042 | 0.031 | 0.085 | 0.085 | 0.025 | 0.053 | 0.029 | 0.081 |
| 14 | 0.094 | 0.012 | 0.043 | 0.036 | 0.084 | 0.092 | 0.036 | 0.062 | 0.018 | 0.085 |

TABLE 5-continued

Test results of compounds on 249 cancer cells (2)

| Compound No. | GI50 (μM) KBM-5 | KBM5-T315I | SGC-7901 | N-87 | Bel-7402 | Huh-7 | K562 | H1975 | HCC827 | MDA-MB-231 |
|---|---|---|---|---|---|---|---|---|---|---|
| 15 | 0.095 | 0.016 | 0.053 | 0.029 | 0.086 | 0.073 | 0.026 | 0.038 | 0.051 | 0.091 |
| 16 | 0.082 | 0.019 | 0.051 | 0.027 | 0.091 | 0.043 | 0.025 | 0.039 | 0.049 | 0.093 |
| 17 | 0.081 | 0.028 | 0.053 | 0.043 | 0.092 | 0.061 | 0.032 | 0.042 | 0.043 | 0.079 |
| 18 | 0.054 | 0.037 | 0.042 | 0.044 | 0.095 | 0.065 | 0.035 | 0.053 | 0.059 | 0.078 |
| 19 | 0.053 | 0.024 | 0.052 | 0.051 | 0.097 | 0.092 | 0.026 | 0.024 | 0.048 | 0.095 |
| 20 | 0.061 | 0.033 | 0.063 | 0.062 | 0.086 | 0.072 | 0.024 | 0.035 | 0.052 | 0.096 |
| 21 | 0.073 | 0.027 | 0.024 | 0.035 | 0.083 | 0.084 | 0.025 | 0.037 | 0.034 | 0.098 |
| 22 | 0.072 | 0.026 | 0.053 | 0.039 | 0.084 | 0.082 | 0.034 | 0.041 | 0.059 | 0.092 |
| 23 | 0.076 | 0.062 | 0.019 | 0.042 | 0.098 | 0.091 | 0.052 | 0.038 | 0.062 | 0.077 |
| 24 | 0.068 | 0.035 | 0.018 | 0.035 | 0.095 | 0.051 | 0.037 | 0.037 | 0.031 | 0.086 |
| 25 | 0.059 | 0.029 | 0.029 | 0.038 | 0.093 | 0.062 | 0.027 | 0.042 | 0.033 | 0.092 |
| 26 | 0.0.38 | 0.031 | 0.037 | 0.039 | 0.097 | 0.051 | 0.017 | 0.031 | 0.055 | 0.098 |
| 27 | 0.091 | 0.026 | 0.035 | 0.036 | 0.099 | 0.091 | 0.026 | 0.052 | 0.028 | 0.089 |
| 28 | 0.073 | 0.051 | 0.034 | 0.042 | 0.092 | 0.073 | 0.035 | 0.035 | 0.037 | 0.086 |
| 29 | 0.043 | 0.037 | 0.029 | 0.033 | 0.091 | 0.077 | 0.034 | 0.063 | 0.029 | 0.087 |
| 30 | 0.082 | 0.022 | 0.035 | 0.03 | 0.082 | 0.037 | 0.038 | 0.039 | 0.082 | 0.037 |
| 31 | 0.092 | 0.063 | 0.077 | 0.052 | 0.057 | 0.019 | 0.027 | 0.042 | 0.057 | 0.019 |
| 32 | 0.071 | 0.058 | 0.045 | 0.069 | 0.067 | 0.038 | 0.034 | 0.053 | 0.067 | 0.038 |
| 33 | 0.083 | 0.051 | 0.052 | 0.061 | 0.083 | 0.031 | 0.016 | 0.026 | 0.083 | 0.031 |
| 34 | 0.074 | 0.053 | 0.049 | 0.067 | 0.094 | 0.049 | 0.053 | 0.034 | 0.094 | 0.049 |
| 35 | 0.075 | 0.059 | 0.061 | 0.063 | 0.051 | 0.046 | 0.026 | 0.038 | 0.051 | 0.046 |
| 36 | 0.061 | 0.057 | 0.047 | 0.039 | 0.062 | 0.043 | 0.029 | 0.019 | 0.062 | 0.043 |
| 37 | 0.053 | 0.062 | 0.051 | 0.041 | 0.034 | 0.038 | 0.037 | 0.027 | 0.034 | 0.038 |
| 38 | 0.077 | 0.064 | 0.034 | 0.049 | 0.084 | 0.033 | 0.039 | 0.034 | 0.084 | 0.033 |
| 39 | 0.072 | 0.067 | 0.041 | 0.050 | 0.083 | 0.022 | 0.026 | 0.035 | 0.083 | 0.022 |
| 40 | 0.079 | 0.055 | 0.045 | 0.071 | 0.074 | 0.035 | 0.041 | 0.043 | 0.074 | 0.035 |
| 41 | 0.031 | 0.076 | 0.027 | 0.039 | 0.082 | 0.033 | 0.066 | 0.032 | 0.033 | 0.072 |
| 42 | 0.046 | 0.053 | 0.032 | 0.084 | 0.055 | 0.019 | 0.057 | 0.035 | 0.035 | 0.035 |
| 43 | 0.081 | 0.054 | 0.052 | 0.038 | 0.073 | 0.036 | 0.052 | 0.062 | 0..073 | 0.036 |
| 44 | 0.087 | 0.061 | 0.037 | 0.059 | 0.084 | 0.029 | 0.063 | 0.051 | 0.084 | 0.029 |
| 45 | 0.094 | 0.059 | 0.043 | 0.067 | 0.061 | 0.037 | 0.033 | 0.034 | 0.061 | 0.037 |
| 46 | 0.091 | 0.047 | 0.057 | 0.043 | 0.052 | 0.035 | 0.035 | 0.037 | 0.052 | 0.035 |
| 47 | 0.081 | 0.056 | 0.049 | 0.061 | 0.043 | 0.024 | 0.039 | 0.029 | 0.043 | 0.024 |
| 48 | 0.076 | 0.061 | 0.069 | 0.081 | 0.042 | 0.035 | 0.028 | 0.028 | 0.042 | 0.035 |
| 49 | 0.087 | 0.055 | 0.067 | 0.073 | 0.072 | 0.026 | 0.017 | 0.034 | 0.072 | 0.026 |
| 50 | 0.079 | 0.063 | 0.039 | 0.069 | 0.083 | 0.025 | 0.042 | 0.035 | 0.083 | 0.025 |
| 51 | 0.083 | 0.077 | 0.045 | 0.065 | 0.072 | 0.029 | 0.046 | 0.063 | 0.072 | 0.029 |
| 52 | 0.088 | 0.067 | 0.051 | 0.053 | 0.091 | 0.031 | 0.027 | 0.061 | 0.091 | 0.031 |
| 53 | 0.093 | 0.054 | 0.061 | 0.047 | 0.046 | 0.026 | 0.037 | 0.051 | 0.046 | 0.026 |
| 54 | 0.099 | 0.063 | 0.064 | 0.049 | 0.051 | 0.034 | 0.029 | 0.043 | 0.051 | 0.034 |
| 55 | 0.089 | 0.073 | 0.059 | 0.055 | 0.081 | 0.029 | 0.036 | 0.052 | 0.081 | 0.029 |
| 56 | 0.081 | 0.069 | 0.053 | 0.042 | 0.093 | 0.037 | 0.043 | 0.053 | 0.093 | 0.037 |
| 57 | 0.074 | 0.054 | 0.092 | 0.053 | 0.073 | 0.028 | 0.035 | 0.055 | 0.073 | 0.028 |
| 58 | 0.069 | 0.082 | 0.051 | 0.061 | 0.049 | 0.039 | 0.026 | 0.061 | 0.049 | 0.039 |
| 59 | 0.061 | 0.074 | 0.059 | 0.059 | 0.082 | 0.037 | 0.038 | 0.039 | 0.082 | 0.037 |
| 60 | 0.074 | 0.083 | 0.043 | 0.063 | 0.057 | 0.019 | 0.027 | 0.042 | 0.057 | 0.019 |
| 61 | 0.081 | 0.094 | 0.038 | 0.075 | 0.067 | 0.038 | 0.034 | 0.053 | 0.067 | 0.038 |
| 62 | 0.091 | 0.064 | 0.046 | 0.064 | 0.083 | 0.031 | 0.016 | 0.026 | 0.083 | 0.031 |
| 63 | 0.093 | 0.057 | 0.051 | 0.059 | 0.094 | 0.049 | 0.053 | 0.034 | 0.094 | 0.049 |
| 64 | 0.082 | 0.022 | 0.035 | 0.03 | 0.051 | 0.046 | 0.026 | 0.038 | 0.051 | 0.046 |
| 65 | 0.092 | 0.063 | 0.077 | 0.052 | 0.062 | 0.043 | 0.029 | 0.029 | 0.062 | 0.043 |
| 66 | 0.091 | 0.031 | 0.025 | 0.061 | 0.034 | 0.038 | 0.037 | 0.027 | 0.034 | 0.038 |
| 67 | 0.046 | 0.026 | 0.037 | 0.051 | 0.084 | 0.033 | 0.039 | 0.034 | 0.084 | 0.033 |
| 68 | 0.051 | 0.034 | 0.029 | 0.043 | 0.083 | 0.022 | 0.026 | 0.035 | 0.083 | 0.022 |
| 69 | 0.081 | 0.029 | 0.036 | 0.052 | 0.074 | 0.035 | 0.041 | 0.043 | 0.074 | 0.035 |
| 70 | 0.093 | 0.037 | 0.043 | 0.053 | 0..073 | 0.036 | 0.052 | 0.062 | 0..073 | 0.036 |
| 71 | 0.073 | 0.028 | 0.035 | 0.055 | 0.084 | 0.029 | 0.063 | 0.051 | 0.084 | 0.029 |
| 72 | 0.049 | 0.039 | 0.026 | 0.061 | 0.061 | 0.037 | 0.033 | 0.034 | 0.061 | 0.037 |
| 73 | 0.086 | 0.024 | 0.028 | 0.038 | 0.052 | 0.035 | 0.035 | 0.037 | 0.052 | 0.035 |
| 74 | 0.037 | 0.35 | 0.049 | 0.037 | 0.043 | 0.024 | 0.039 | 0.029 | 0.043 | 0.024 |
| 75 | 0.061 | 0.026 | 0.041 | 0.022 | 0.042 | 0.035 | 0.028 | 0.028 | 0.042 | 0.035 |
| 76 | 0.094 | 0.034 | 0.051 | 0.032 | 0.072 | 0.026 | 0.017 | 0.034 | 0.072 | 0.026 |
| 77 | 0.052 | 0.037 | 0.601 | 0.052 | 0.083 | 0.025 | 0.042 | 0.035 | 0.083 | 0.025 |
| 78 | 0.061 | 0.019 | 0.062 | 0.061 | 0.072 | 0.029 | 0.046 | 0.063 | 0.072 | 0.029 |
| 79 | 0.076 | 0.028 | 0.051 | 0.022 | 0.091 | 0.031 | 0.027 | 0.061 | 0.091 | 0.031 |
| 80 | 0.049 | 0.022 | 0.071 | 0.031 | 0.046 | 0.026 | 0.037 | 0.051 | 0.046 | 0.026 |
| 81 | 0.038 | 0.034 | 0.059 | 0.035 | 0.051 | 0.034 | 0.029 | 0.043 | 0.051 | 0.034 |
| 82 | 0.049 | 0.038 | 0.048 | 0.026 | 0.081 | 0.029 | 0.036 | 0.052 | 0.081 | 0.029 |
| 83 | 0.038 | 0.029 | 0.053 | 0.016 | 0.093 | 0.037 | 0.043 | 0.053 | 0.093 | 0.037 |
| 84 | 0.051 | 0.026 | 0.043 | 0.019 | 0.073 | 0.028 | 0.035 | 0.055 | 0.073 | 0.028 |
| 85 | 0.053 | 0.025 | 0.015 | 0.027 | 0.049 | 0.039 | 0.026 | 0.061 | 0.049 | 0.039 |
| 86 | 0.061 | 0.034 | 0.028 | 0.037 | 0.082 | 0.037 | 0.038 | 0.039 | 0.082 | 0.037 |
| 87 | 0.082 | 0.037 | 0.037 | 0.021 | 0.057 | 0.019 | 0.027 | 0.042 | 0.057 | 0.019 |

TABLE 5-continued

Test results of compounds on 249 cancer cells (2)

| Compound No. | GI50 (μM) KBM-5 | KBM5-T315I | SGC-7901 | N-87 | Bel-7402 | Huh-7 | K562 | H1975 | HCC827 | MDA-MB-231 |
|---|---|---|---|---|---|---|---|---|---|---|
| 88 | 0.071 | 0.024 | 0.029 | 0.031 | 0.067 | 0.038 | 0.034 | 0.053 | 0.067 | 0.038 |
| 89 | 0.093 | 0.038 | 0.034 | 0.013 | 0.083 | 0.031 | 0.016 | 0.026 | 0.083 | 0.031 |
| 90 | 0.083 | 0.024 | 0.036 | 0.034 | 0.094 | 0.049 | 0.053 | 0.034 | 0.094 | 0.049 |
| 91 | 0.091 | 0.031 | 0.048 | 0.062 | 0.051 | 0.046 | 0.026 | 0.038 | 0.051 | 0.046 |
| 92 | 0.042 | 0.029 | 0.057 | 0.015 | 0.062 | 0.043 | 0.022 | 0.029 | 0.062 | 0.043 |
| 93 | 0.053 | 0.034 | 0.068 | 0.028 | 0.034 | 0.038 | 0.037 | 0.027 | 0.034 | 0.038 |
| 94 | 0.061 | 0.035 | 0.041 | 0.037 | 0.084 | 0.033 | 0.039 | 0.034 | 0.084 | 0.033 |
| 95 | 0.076 | 0.038 | 0.042 | 0.023 | 0.083 | 0.022 | 0.026 | 0.035 | 0.083 | 0.022 |
| 96 | 0.072 | 0.054 | 0.037 | 0.027 | 0.061 | 0.048 | 0.019 | 0.073 | 0.065 | 0.057 |
| 97 | 0.093 | 0.026 | 0.024 | 0.031 | 0.059 | 0.013 | 0.029 | 0.042 | 0.039 | 0.031 |
| 98 | 0.029 | 0.058 | 0.036 | 0.021 | 0.043 | 0.028 | 0.037 | 0.081 | 0.035 | 0.037 |
| 99 | 0.019 | 0.022 | 0.069 | 0.031 | 0.016 | 0.031 | 0.042 | 0.058 | 0.088 | 0.024 |
| 100 | 0.035 | 0.031 | 0.057 | 0.032 | 0.071 | 0.027 | 0.034 | 0.053 | 0.017 | 0.078 |
| 101 | 0.041 | 0.036 | 0.048 | 0.026 | 0.045 | 0.036 | 0.021 | 0.069 | 0.039 | 0.052 |
| 102 | 0.067 | 0.071 | 0.031 | 0.046 | 0.011 | 0.073 | 0.028 | 0.035 | 0.058 | 0.026 |
| 103 | 0.031 | 0.051 | 0.037 | 0.051 | 0.025 | 0.047 | 0.034 | 0.026 | 0.055 | 0.039 |
| 104 | 0.079 | 0.068 | 0.026 | 0.096 | 0.057 | 0.089 | 0.033 | 0.038 | 0.049 | 0.020 |
| 105 | 0.023 | 0.053 | 0.016 | 0.093 | 0.021 | 0.056 | 0.019 | 0.097 | 0.047 | 0.086 |
| 106 | 0.056 | 0.076 | 0.035 | 0.012 | 0.066 | 0.031 | 0.027 | 0.068 | 0.043 | 0.019 |
| 107 | 0.072 | 0.041 | 0.027 | 0.035 | 0.053 | 0.024 | 0.038 | 0.057 | 0.013 | 0.027 |
| 108 | 0.011 | 0.024 | 0.036 | 0.034 | 0.076 | 0.043 | 0.059 | 0.033 | 0.093 | 0.049 |
| 109 | 0.082 | 0.071 | 0.042 | 0.061 | 0.056 | 0.046 | 0.028 | 0.031 | 0.051 | 0.126 |
| 110 | 0.041 | 0.029 | 0.057 | 0.035 | 0.062 | 0.048 | 0.017 | 0.059 | 0.062 | 0.013 |
| 111 | 0.053 | 0.035 | 0.073 | 0.028 | 0.036 | 0.038 | 0.037 | 0.027 | 0.057 | 0.038 |
| 112 | 0.021 | 0.031 | 0.041 | 0.073 | 0.023 | 0.035 | 0.055 | 0.016 | 0.073 | 0.058 |
| 113 | 0.036 | 0.051 | 0.095 | 0.042 | 0.034 | 0.021 | 0.047 | 0.024 | 0.048 | 0.031 |
| 114 | 0.099 | 0.028 | 0.043 | 0.011 | 0.042 | 0.054 | 0.038 | 0.032 | 0.071 | 0.022 |
| 115 | 0.053 | 0.028 | 0.023 | 0.045 | 0.036 | 0.099 | 0.041 | 0.023 | 0.041 | 0.036 |
| 116 | 0.018 | 0.036 | 0.021 | 0.043 | 0.028 | 0.052 | 0.016 | 0.093 | 0.021 | 0.046 |
| 117 | 0.022 | 0.059 | 0.033 | 0.016 | 0.034 | 0.066 | 0.035 | 0.072 | 0.086 | 0.058 |
| 118 | 0.041 | 0.057 | 0.039 | 0.061 | 0.027 | 0.041 | 0.029 | 0.035 | 0.053 | 0.031 |
| 119 | 0.062 | 0.028 | 0.034 | 0.038 | 0.037 | 0.026 | 0.036 | 0.038 | 0.037 | 0.027 |
| 120 | 0.045 | 0.033 | 0.084 | 0.053 | 0.066 | 0.071 | 0.023 | 0.035 | 0.055 | 0.016 |
| 121 | 0.046 | 0.023 | 0.033 | 0.023 | 0.026 | 0.045 | 0.038 | 0.028 | 0.042 | 0.075 |
| 122 | 0.038 | 0.026 | 0.061 | 0.048 | 0.049 | 0.091 | 0.046 | 0.055 | 0.032 | 0.032 |
| 123 | 0.068 | 0.067 | 0.051 | 0.062 | 0.027 | 0.035 | 0.036 | 0.021 | 0.069 | 0.039 |
| 124 | 0.057 | 0.015 | 0.042 | 0.045 | 0.072 | 0.016 | 0.076 | 0.028 | 0.035 | 0.051 |
| 125 | 0.064 | 0.058 | 0.039 | 0.031 | 0.057 | 0.025 | 0.047 | 0.036 | 0.029 | 0.075 |
| 126 | 0.041 | 0.037 | 0.081 | 0.033 | 0.049 | 0.051 | 0.079 | 0.033 | 0.038 | 0.029 |
| 127 | 0.053 | 0.028 | 0.036 | 0.046 | 0.037 | 0.071 | 0.028 | 0.036 | 0.038 | 0.037 |
| 128 | 0.041 | 0.053 | 0.023 | 0.035 | 0.053 | 0.049 | 0.073 | 0.023 | 0.039 | 0.055 |
| 129 | 0.035 | 0.042 | 0.033 | 0.021 | 0.041 | 0.038 | 0.042 | 0.033 | 0.022 | 0.041 |
| 130 | 0.023 | 0.011 | 0.042 | 0.058 | 0.032 | 0.041 | 0.028 | 0.042 | 0.054 | 0.038 |
| 131 | 0.063 | 0.045 | 0.031 | 0.095 | 0.043 | 0.023 | 0.045 | 0.016 | 0.059 | 0.046 |
| 132 | 0.024 | 0.043 | 0.028 | 0.057 | 0.077 | 0.026 | 0.048 | 0.028 | 0.052 | 0.016 |
| 133 | 0.036 | 0.016 | 0.035 | 0.066 | 0.032 | 0.033 | 0.016 | 0.031 | 0.036 | 0.035 |
| 134 | 0.031 | 0.061 | 0.027 | 0.041 | 0.029 | 0.092 | 0.038 | 0.054 | 0.035 | 0.063 |
| 135 | 0.011 | 0.051 | 0.044 | 0.026 | 0.039 | 0.087 | 0.033 | 0.079 | 0.093 | 0.041 |
| 136 | 0.009 | 0.035 | 0.051 | 0.031 | 0.022 | 0.036 | 0.046 | 0.035 | 0.041 | 0.058 |
| 137 | 0.048 | 0.026 | 0.081 | 0.029 | 0.016 | 0.043 | 0.035 | 0.053 | 0.049 | 0.045 |
| 138 | 0.042 | 0.045 | 0.072 | 0.016 | 0.076 | 0.036 | 0.021 | 0.043 | 0.022 | 0.052 |
| 139 | 0.069 | 0.021 | 0.057 | 0.025 | 0.043 | 0.051 | 0.047 | 0.015 | 0.034 | 0.067 |
| 140 | 0.031 | 0.033 | 0.044 | 0.055 | 0.079 | 0.042 | 0.039 | 0.063 | 0.021 | 0.031 |
| 141 | 0.036 | 0.043 | 0.017 | 0.067 | 0.058 | 0.028 | 0.031 | 0.038 | 0.037 | 0.026 |
| 142 | 0.073 | 0.035 | 0.053 | 0.042 | 0.073 | 0.038 | 0.084 | 0.059 | 0.066 | 0.051 |
| 143 | 0.036 | 0.034 | 0.063 | 0.032 | 0.042 | 0.075 | 0.053 | 0.049 | 0.073 | 0.025 |
| 144 | 0.011 | 0.127 | 0.041 | 0.029 | 0.035 | 0.023 | 0.011 | 0.038 | 0.012 | 0.037 |
| 145 | 0.008 | 0.031 | 0.018 | 0.031 | 0.018 | 0.058 | 0.032 | 0.031 | 0.078 | 0.041 |
| 146 | 0.033 | 0.023 | 0.035 | 0.023 | 0.035 | 0.065 | 0.043 | 0.073 | 0.045 | 0.056 |
| 147 | 0.023 | 0.026 | 0.045 | 0.083 | 0.028 | 0.057 | 0.037 | 0.026 | 0.028 | 0.078 |
| 148 | 0.035 | 0.053 | 0.051 | 0.047 | 0.053 | 0.064 | 0.062 | 0.039 | 0.016 | 0.051 |
| 149 | 0.021 | 0.041 | 0.042 | 0.039 | 0.063 | 0.075 | 0.032 | 0.070 | 0.029 | 0.035 |
| 150 | 0.026 | 0.039 | 0.087 | 0.033 | 0.058 | 0.046 | 0.055 | 0.079 | 0.063 | 0.021 |
| 151 | 0.031 | 0.022 | 0.036 | 0.046 | 0.026 | 0.035 | 0.067 | 0.058 | 0.038 | 0.037 |
| 152 | 0.041 | 0.029 | 0.023 | 0.035 | 0.047 | 0.028 | 0.011 | 0.038 | 0.035 | 0.065 |
| 153 | 0.028 | 0.031 | 0.083 | 0.028 | 0.096 | 0.075 | 0.032 | 0.031 | 0.028 | 0.057 |
| 154 | 0.029 | 0.071 | 0.012 | 0.063 | 0.053 | 0.047 | 0.028 | 0.038 | 0.075 | 0.053 |
| 155 | 0.035 | 0.056 | 0.033 | 0.032 | 0.041 | 0.038 | 0.075 | 0.023 | 0.023 | 0.011 |
| 156 | 0.017 | 0.033 | 0.045 | 0.065 | 0.023 | 0.035 | 0.031 | 0.018 | 0.043 | 0.063 |
| 157 | 0.036 | 0.023 | 0.072 | 0.036 | 0.083 | 0.029 | 0.023 | 0.035 | 0.037 | 0.026 |
| 158 | 0.046 | 0.027 | 0.027 | 0.038 | 0.045 | 0.041 | 0.048 | 0.049 | 0.091 | 0.046 |
| 159 | 0.035 | 0.053 | 0.075 | 0.063 | 0.023 | 0.058 | 0.062 | 0.024 | 0.035 | 0.036 |
| 160 | 0.028 | 0.026 | 0.081 | 0.049 | 0.036 | 0.042 | 0.042 | 0.071 | 0.016 | 0.017 |

TABLE 5-continued

| Test results of compounds on 249 cancer cells (2) | | | | | | | | | | |
|---|---|---|---|---|---|---|---|---|---|---|
| | GI50 (μM) | | | | | | | | | |
| Compound No. | KBM-5 | KBM5-T315I | SGC-7901 | N-87 | Bel-7402 | Huh-7 | K562 | H1975 | HCC827 | MDA-MB-231 |
| 161 | 0.013 | 0.012 | 0.091 | 0.037 | 0.047 | 0.079 | 0.031 | 0.057 | 0.065 | 0.046 |
| 162 | 0.042 | 0.016 | 0.078 | 0.018 | 0.035 | 0.081 | 0.073 | 0.049 | 0.051 | 0.079 |
| 163 | 0.075 | 0.023 | 0.049 | 0.039 | 0.026 | 0.107 | 0.058 | 0.045 | 0.047 | 0.058 |
| 164 | 0.073 | 0.047 | 0.028 | 0.041 | 0.038 | 0.095 | 0.062 | 0.081 | 0.028 | 0.096 |
| 165 | 0.041 | 0.034 | 0.076 | 0.032 | 0.030 | 0.028 | 0.057 | 0.012 | 0.043 | 0.053 |
| 166 | 0.05 | 0.053 | 0.042 | 0.073 | 0.068 | 0.056 | 0.046 | 0.026 | 0.031 | 0.017 |
| 167 | 0.014 | 0.033 | 0.097 | 0.042 | 0.075 | 0.029 | 0.045 | 0.043 | 0.028 | 0.091 |
| 168 | 0.022 | 0.036 | 0.034 | 0.094 | 0.044 | 0.056 | 0.034 | 0.066 | 0.035 | 0.012 |
| 169 | 0.051 | 0.047 | 0.062 | 0.055 | 0.046 | 0.061 | 0.037 | 0.044 | 0.029 | 0.035 |
| 170 | 0.049 | 0.057 | 0.037 | 0.062 | 0.043 | 0.088 | 0.037 | 0.026 | 0.096 | 0.038 |
| 171 | 0.033 | 0.068 | 0.028 | 0.039 | 0.038 | 0.053 | 0.046 | 0.071 | 0.023 | 0.065 |
| 172 | 0.035 | 0.041 | 0.031 | 0.084 | 0.073 | 0.023 | 0.026 | 0.045 | 0.032 | 0.078 |
| 173 | 0.013 | 0.012 | 0.023 | 0.083 | 0.022 | 0.071 | 0.053 | 0.036 | 0.027 | 0.048 |
| 174 | 0.015 | 0.096 | 0.026 | 0.031 | 0.041 | 0.011 | 0.013 | 0.057 | 0.046 | 0.016 |
| 175 | 0.042 | 0.047 | 0.062 | 0.049 | 0.105 | 0.027 | 0.039 | 0.042 | 0.013 | 0.029 |
| 176 | 0.034 | 0.038 | 0.031 | 0.028 | 0.031 | 0.031 | 0.021 | 0.031 | 0.038 | 0.032 |
| 177 | 0.080 | 0.013 | 0.039 | 0.037 | 0.084 | 0.035 | 0.029 | 0.083 | 0.033 | 0.049 |
| 178 | 0.093 | 0.022 | 0.076 | 0.055 | 0.058 | 0.042 | 0.053 | 0.089 | 0.032 | 0.026 |
| 179 | 0.061 | 0.028 | 0.019 | 0.073 | 0.065 | 0.015 | 0.071 | 0.054 | 0.025 | 0.051 |
| 180 | 0.029 | 0.057 | 0.035 | 0.062 | 0.048 | 0.017 | 0.049 | 0.097 | 0.013 | 0.056 |
| 181 | 0.015 | 0.033 | 0.028 | 0.036 | 0.038 | 0.037 | 0.023 | 0.035 | 0.041 | 0.018 |
| 182 | 0.031 | 0.041 | 0.071 | 0.023 | 0.035 | 0.035 | 0.083 | 0.039 | 0.023 | 0.035 |
| 183 | 0.051 | 0.065 | 0.048 | 0.037 | 0.025 | 0.047 | 0.025 | 0.041 | 0.046 | 0.049 |
| 184 | 0.078 | 0.043 | 0.011 | 0.042 | 0.056 | 0.038 | 0.023 | 0.058 | 0.062 | 0.074 |
| 185 | 0.028 | 0.013 | 0.044 | 0.026 | 0.091 | 0.071 | 0.036 | 0.012 | 0.082 | 0.071 |
| 186 | 0.036 | 0.021 | 0.043 | 0.028 | 0.052 | 0.016 | 0.039 | 0.063 | 0.089 | 0.039 |
| 187 | 0.021 | 0.041 | 0.038 | 0.042 | 0.043 | 0.085 | 0.045 | 0.023 | 0.075 | 0.011 |
| 188 | 0.018 | 0.036 | 0.071 | 0.028 | 0.042 | 0.079 | 0.036 | 0.053 | 0.029 | 0.023 |
| 189 | 0.045 | 0.043 | 0.023 | 0.045 | 0.036 | 0.021 | 0.032 | 0.041 | 0.041 | 0.038 |
| 190 | 0.057 | 0.017 | 0.086 | 0.048 | 0.028 | 0.075 | 0.063 | 0.023 | 0.056 | 0.067 |
| 191 | 0.036 | 0.032 | 0.033 | 0.011 | 0.051 | 0.089 | 0.041 | 0.032 | 0.049 | 0.052 |
| 192 | 0.021 | 0.029 | 0.099 | 0.032 | 0.054 | 0.071 | 0.023 | 0.035 | 0.037 | 0.083 |
| 193 | 0.031 | 0.041 | 0.073 | 0.023 | 0.035 | 0.033 | 0.035 | 0.011 | 0.018 | 0.043 |
| 194 | 0.051 | 0.025 | 0.043 | 0.036 | 0.027 | 0.084 | 0.029 | 0.023 | 0.035 | 0.027 |
| 195 | 0.026 | 0.043 | 0.014 | 0.042 | 0.054 | 0.045 | 0.081 | 0.038 | 0.079 | 0.091 |
| 196 | 0.028 | 0.093 | 0.045 | 0.056 | 0.089 | 0.023 | 0.058 | 0.062 | 0.064 | 0.085 |
| 197 | 0.086 | 0.021 | 0.043 | 0.028 | 0.052 | 0.076 | 0.049 | 0.045 | 0.071 | 0.016 |
| 198 | 0.099 | 0.043 | 0.016 | 0.038 | 0.063 | 0.047 | 0.079 | 0.031 | 0.057 | 0.045 |
| 199 | 0.017 | 0.029 | 0.067 | 0.027 | 0.042 | 0.035 | 0.081 | 0.078 | 0.047 | 0.051 |
| 200 | 0.028 | 0.034 | 0.058 | 0.039 | 0.026 | 0.026 | 0.107 | 0.059 | 0.045 | 0.046 |
| 201 | 0.029 | 0.035 | 0.051 | 0.032 | 0.069 | 0.09 | 0.035 | 0.073 | 0.011 | 0.038 |
| 202 | 0.038 | 0.026 | 0.031 | 0.029 | 0.076 | 0.031 | 0.015 | 0.058 | 0.032 | 0.041 |
| 203 | 0.053 | 0.026 | 0.043 | 0.077 | 0.023 | 0.022 | 0.035 | 0.065 | 0.023 | 0.073 |
| 204 | 0.063 | 0.019 | 0.073 | 0.028 | 0.036 | 0.083 | 0.028 | 0.067 | 0.037 | 0.056 |
| 205 | 0.015 | 0.027 | 0.059 | 0.049 | 0.056 | 0.047 | 0.053 | 0.064 | 0.062 | 0.039 |
| 206 | 0.027 | 0.039 | 0.082 | 0.097 | 0.048 | 0.039 | 0.061 | 0.075 | 0.012 | 0.076 |
| 207 | 0.038 | 0.021 | 0.057 | 0.019 | 0.027 | 0.033 | 0.048 | 0.046 | 0.055 | 0.079 |
| 208 | 0.018 | 0.049 | 0.026 | 0.056 | 0.017 | 0.026 | 0.076 | 0.035 | 0.067 | 0.018 |
| 209 | 0.046 | 0.031 | 0.041 | 0.051 | 0.013 | 0.023 | 0.039 | 0.017 | 0.085 | 0.035 |
| 210 | 0.052 | 0.049 | 0.105 | 0.027 | 0.047 | 0.022 | 0.086 | 0.025 | 0.056 | 0.072 |
| 211 | 0.031 | 0.028 | 0.071 | 0.031 | 0.021 | 0.024 | 0.019 | 0.073 | 0.055 | 0.085 |
| 212 | 0.069 | 0.037 | 0.084 | 0.035 | 0.039 | 0.057 | 0.035 | 0.062 | 0.048 | 0.097 |
| 213 | 0.078 | 0.054 | 0.058 | 0.042 | 0.053 | 0.035 | 0.028 | 0.076 | 0.028 | 0.037 |
| 214 | 0.019 | 0.073 | 0.068 | 0.095 | 0.071 | 0.041 | 0.071 | 0.063 | 0.035 | 0.015 |
| 215 | 0.025 | 0.042 | 0.048 | 0.017 | 0.019 | 0.065 | 0.048 | 0.037 | 0.015 | 0.047 |
| 216 | 0.038 | 0.036 | 0.038 | 0.037 | 0.023 | 0.049 | 0.056 | 0.087 | 0.059 | 0.062 |
| 217 | 0.041 | 0.083 | 0.028 | 0.057 | 0.037 | 0.019 | 0.062 | 0.043 | 0.029 | 0.019 |
| 218 | 0.021 | 0.043 | 0.053 | 0.065 | 0.062 | 0.021 | 0.036 | 0.038 | 0.037 | 0.027 |
| 219 | 0.042 | 0.039 | 0.063 | 0.075 | 0.082 | 0.049 | 0.084 | 0.033 | 0.039 | 0.034 |
| 220 | 0.083 | 0.033 | 0.028 | 0.046 | 0.055 | 0.053 | 0.083 | 0.057 | 0.026 | 0.045 |
| 221 | 0.036 | 0.041 | 0.026 | 0.065 | 0.057 | 0.041 | 0.074 | 0.035 | 0.041 | 0.043 |
| 222 | 0.043 | 0.035 | 0.047 | 0.098 | 0.014 | 0.039 | 0.083 | 0.083 | 0.063 | 0.052 |
| 223 | 0.053 | 0.028 | 0.096 | 0.075 | 0.032 | 0.054 | 0.055 | 0.019 | 0.027 | 0.035 |
| 224 | 0.016 | 0.063 | 0.093 | 0.017 | 0.023 | 0.036 | 0.023 | 0.096 | 0.052 | 0.062 |
| 225 | 0.033 | 0.038 | 0.041 | 0.038 | 0.072 | 0.059 | 0.081 | 0.029 | 0.013 | 0.071 |
| 226 | 0.075 | 0.065 | 0.023 | 0.035 | 0.031 | 0.068 | 0.061 | 0.037 | 0.033 | 0.034 |
| 227 | 0.049 | 0.055 | 0.053 | 0.019 | 0.072 | 0.017 | 0.023 | 0.035 | 0.045 | 0.051 |
| 228 | 0.062 | 0.033 | 0.012 | 0.035 | 0.056 | 0.035 | 0.062 | 0.048 | 0.017 | 0.069 |
| 229 | 0.071 | 0.053 | 0.091 | 0.077 | 0.037 | 0.028 | 0.086 | 0.038 | 0.077 | 0.023 |
| 230 | 0.026 | 0.087 | 0.048 | 0.036 | 0.023 | 0.091 | 0.023 | 0.035 | 0.035 | 0.083 |
| 231 | 0.038 | 0.057 | 0.011 | 0.036 | 0.058 | 0.048 | 0.037 | 0.025 | 0.077 | 0.025 |
| 232 | 0.008 | 0.043 | 0.063 | 0.045 | 0.035 | 0.021 | 0.042 | 0.056 | 0.038 | 0.023 |
| 233 | 0.097 | 0.046 | 0.051 | 0.035 | 0.081 | 0.041 | 0.024 | 0.051 | 0.081 | 0.036 |

TABLE 5-continued

Test results of compounds on 249 cancer cells (2)

| Compound No. | GI50 (μM) KBM-5 | KBM5-T315I | SGC-7901 | N-87 | Bel-7402 | Huh-7 | K562 | H1975 | HCC827 | MDA-MB-231 |
|---|---|---|---|---|---|---|---|---|---|---|
| 234 | 0.012 | 0.032 | 0.039 | 0.023 | 0.082 | 0.042 | 0.038 | 0.052 | 0.016 | 0.039 |
| 235 | 0.027 | 0.092 | 0.042 | 0.063 | 0.091 | 0.038 | 0.042 | 0.063 | 0.085 | 0.045 |
| 236 | 0.033 | 0.053 | 0.048 | 0.026 | 0.075 | 0.067 | 0.073 | 0.072 | 0.026 | 0.017 |
| 237 | 0.049 | 0.087 | 0.033 | 0.058 | 0.042 | 0.049 | 0.069 | 0.083 | 0.025 | 0.012 |
| 238 | 0.052 | 0.066 | 0.056 | 0.026 | 0.031 | 0.055 | 0.065 | 0.082 | 0.029 | 0.046 |
| 239 | 0.029 | 0.023 | 0.035 | 0.046 | 0.028 | 0.051 | 0.063 | 0.091 | 0.031 | 0.025 |
| 240 | 0.071 | 0.083 | 0.024 | 0.096 | 0.079 | 0.061 | 0.047 | 0.056 | 0.066 | 0.037 |
| 241 | 0.071 | 0.082 | 0.063 | 0.057 | 0.047 | 0.064 | 0.041 | 0.051 | 0.034 | 0.029 |
| 242 | 0.056 | 0.033 | 0.032 | 0.031 | 0.088 | 0.059 | 0.055 | 0.021 | 0.079 | 0.016 |
| 243 | 0.093 | 0.045 | 0.025 | 0.023 | 0.035 | 0.053 | 0.032 | 0.043 | 0.037 | 0.093 |
| 244 | 0.023 | 0.012 | 0.036 | 0.083 | 0.029 | 0.092 | 0.053 | 0.073 | 0.028 | 0.035 |
| 245 | 0.011 | 0.012 | 0.063 | 0.053 | 0.087 | 0.031 | 0.083 | 0.028 | 0.096 | 0.065 |
| 246 | 0.056 | 0.033 | 0.032 | 0.041 | 0.038 | 0.021 | 0.012 | 0.063 | 0.053 | 0.047 |
| 247 | 0.032 | 0.045 | 0.065 | 0.023 | 0.095 | 0.053 | 0.033 | 0.032 | 0.041 | 0.038 |
| 248 | 0.023 | 0.072 | 0.026 | 0.083 | 0.029 | 0.033 | 0.048 | 0.065 | 0.093 | 0.045 |
| 249 | 0.047 | 0.027 | 0.033 | 0.045 | 0.041 | 0.043 | 0.072 | 0.076 | 0.023 | 0.029 |
| 250 | 0.053 | 0.079 | 0.063 | 0.043 | 0.058 | 0.027 | 0.027 | 0.038 | 0.045 | 0.021 |
| 251 | 0.066 | 0.081 | 0.049 | 0.036 | 0.042 | 0.055 | 0.035 | 0.063 | 0.053 | 0.038 |
| 252 | 0.072 | 0.081 | 0.035 | 0.067 | 0.079 | 0.026 | 0.081 | 0.09 | 0.076 | 0.042 |
| 253 | 0.016 | 0.078 | 0.018 | 0.035 | 0.087 | 0.072 | 0.011 | 0.057 | 0.037 | 0.069 |
| 254 | 0.053 | 0.042 | 0.087 | 0.064 | 0.031 | 0.046 | 0.078 | 0.018 | 0.035 | 0.081 |
| 255 | 0.032 | 0.037 | 0.048 | 0.051 | 0.035 | 0.045 | 0.056 | 0.068 | 0.057 | 0.023 |

The GI50 in the upper table represents the drug concentration (50% growth inhibition) required for 50% of cell growth inhibition.

The results from the above table can be seen: compared with the positive control (SAHA), the above drugs significantly inhibit the growth of the tumor cells.

Compared with the related compound of patent CN102391359A, the compound of the invention has obvious advantages. The result is shown in tables 6 and 7.

TABLE 6

Comparison of the cellular activity of compounds of the present invention and patent CN102391359A (1)

| Compound No. present invention (a) | CN102391359A (b) | GI50 (μM) Hela a | Hela b | MCF7 a | MCF7 b | A549 a | A549 b | BGC823 a | BGC823 b | HT1080 a | HT1080 b |
|---|---|---|---|---|---|---|---|---|---|---|---|
| 235 | 1-1 | 0.047 | 0.4 | 0.056 | 0.09 | 0.034 | 0.09 | 0.043 | 0.1 | 0.024 | 0.05 |
| 9 | 1-2 | 0.05 | 0.1 | 0.03 | 0.05 | 0.08 | 0.3 | 0.007 | 0.02 | 0.04 | 0.1 |
| 1 | 1-3 | 0.02 | 1.0 | 0.03 | 1.2 | 0.01 | 10.0 | 0.06 | 0.06 | 0.01 | 4.0 |
| 11 | 1-4 | 0.12 | 1.3 | 0.05 | 0.2 | 0.43 | 2.9 | 0.41 | 2.5 | 0.14 | 0.8 |
| 236 | 1-5 | 0.81 | 2.0 | 0.76 | 0.8 | 0.51 | 0.6 | 0.093 | 0.1 | 0.197 | 1.0 |
| 237 | 1-6 | 0.88 | 1.0 | 0.35 | 0.6 | 0.42 | 0.5 | 0.17 | 0.4 | 0.99 | 1.3 |
| 14 | 1-7 | 0.22 | 5.0 | 0.4 | 0.7 | 0.1 | 0.4 | 0.2 | 0.3 | 0.3 | 0.3 |
| 238 | 1-8 | 0.055 | 0.1 | 0.023 | 0.1 | 0.016 | 0.1 | 0.14 | 0.3 | 0.026 | 0.07 |
| 239 | 1-9 | 0.011 | 0.05 | 0.019 | 0.05 | 0.012 | 0.03 | 0.022 | 0.05 | 0.011 | 0.04 |
| 240 | 1-10 | 0.018 | 0.1 | 0.001 | 0.001 | 0.036 | 0.1 | 0.11 | 0.2 | 0.033 | 0.1 |
| 241 | 1-11 | 0.011 | 0.1 | 0.028 | 0.09 | 0.11 | 5.09 | 0.10 | 0.16 | 0.034 | 0.08 |
| 242 | 1-12 | 0.088 | 0.9 | 0.073 | 0.8 | 0.19 | 1.2 | 0.014 | 0.06 | 0.33 | 1.0 |
| 1 | 2-1 | 0.02 | 0.2 | 0.03 | 0.5 | 0.03 | 0.9 | 0.06 | 5 | 0.03 | 4.1 |
| 243 | 2-2 | 0.23 | 0.6 | 0.12 | 2.3 | 0.94 | 2.0 | 0.86 | 1.6 | 0.84 | 4.5 |
| 243 | 2-3 | 0.23 | 26.5 | 0.12 | 21.4 | 0.94 | 2.6 | 0.86 | 1.56 | 0.84 | 40.5 |
| 1 | 2-4 | 0.02 | 23 | 0.03 | 52.6 | 0.01 | 4.5 | 0.06 | 2.6 | 0.01 | 1.6 |
| 1 | 2-5 | 0.02 | 12 | 0.03 | 26 | 0.01 | 2.13 | 0.06 | 20.6 | 0.01 | 1.02 |
| 1 | 2-6 | 0.02 | 0.5 | 0.03 | 0.65 | 0.01 | 4.2 | 0.06 | 56.2 | 0.01 | 12.0 |
| 1 | 2-7 | 0.02 | 0.1 | 0.03 | 0.09 | 0.01 | 0.09 | 0.06 | 0.1 | 0.01 | 0.08 |
| 244 | 3-1 | 0.008 | 0.01 | 0.33 | 2.1 | 0.12 | 0.35 | 0.39 | 1.2 | 0.76 | 1.06 |
| 245 | 3-2 | 0.53 | 0.6 | 0.041 | 0.1 | 0.11 | 0.36 | 0.77 | 1.02 | 0.65 | 1.35 |
| 246 | 3-3 | 0.013 | 0.45 | 0.31 | 1.20 | 0.11 | 1.09 | 1.02 | 5.94 | 0.017 | 0.06 |
| 27 | 6-1 | 0.53 | 0.6 | 0.03 | 0.059 | 0.095 | 0.1 | 0.31 | 0.36 | 0.04 | 0.05 |
| 7 | 6-2 | 0.04 | 73.5 | 0.03 | 59.6 | 0.052 | 15.6 | 0.031 | 4.6 | 0.027 | 41.02 |

TABLE 7

Comparison of the cellular activity of compounds of the present invention and patent CN102391359A (2)

| Compound No. | | GI50 (μM) | | | | | | | | | |
|---|---|---|---|---|---|---|---|---|---|---|---|
| Present Invention | | lncap | | Du145 | | U937 | | PANC-1 | | Molt-4 | |
| (a) | CN102391359A | a | b | a | b | a | b | a | b | a | b |
| 235 | 1-1 | 0.04 | 0.05 | 0.003 | 0.008 | 0.006 | 0.007 | 0.23 | 0.3 | 0.007 | 0.009 |
| 9 | 1-2 | 0.009 | 0.07 | 0.002 | 0.004 | 0.001 | 0.004 | 0.06 | 0.2 | 0.011 | 0.03 |
| 1 | 1-3 | 0.009 | 2.0 | 0.004 | 0.3 | 0.005 | 0.5 | 0.32 | 6.0 | 0.032 | 1.0 |
| 11 | 1-4 | 0.025 | 0.2 | 0.033 | 0.36 | 0.035 | 0.03 | 0.06 | 1.6 | 0.017 | 0.1 |
| 236 | 1-5 | 0.53 | 0.6 | 0.091 | 0.1 | 0.077 | 0.1 | 0.21 | 3.0 | 0.86 | 1.0 |
| 237 | 1-6 | 0.94 | 1.2 | 0.04 | 0.05 | 0.11 | 0.2 | 0.93 | 3.0 | 0.97 | 1.0 |
| 14 | 1-7 | 0.2 | 0.5 | 0.012 | 0.02 | 0.003 | 0.02 | 0.53 | 1.5 | 0.02 | 0.1 |
| 238 | 1-8 | 0.11 | 0.2 | 0.012 | 0.03 | 0.015 | 0.02 | 0.077 | 0.1 | 0.008 | 0.02 |
| 239 | 1-9 | 0.017 | 0.03 | 0.001 | 0.003 | 0.003 | 0.005 | 0.13 | 0.6 | 0.004 | 0.01 |
| 240 | 1-10 | 0.07 | 0.08 | 0.004 | 0.01 | 0.012 | 0.02 | 0.19 | 1.3 | 0.018 | 0.02 |
| 241 | 1-11 | 0.025 | 0.03 | 0.003 | 0.006 | 0.007 | 0.009 | 0.17 | 0.8 | 0.003 | 0.01 |
| 242 | 1-12 | 0.17 | 0.3 | 0.091 | 0.1 | 0.012 | 0.1 | 0.95 | 6.0 | 0.032 | 0.1 |
| 1 | 2-1 | 0.009 | 2.01 | 0.004 | 0.05 | 0.005 | 1.3 | 0.32 | 2.06 | 0.011 | 0.1 |
| 243 | 2-2 | 0.47 | 23.6 | 0.13 | 56.5 | 0.87 | 10.2 | 0.52 | 0.6 | 0.49 | 26.2 |
| 243 | 2-3 | 0.47 | 0.5 | 0.13 | 0.56 | 0.87 | 1.23 | 0.52 | 2.65 | 0.49 | 23.1 |
| 1 | 2-4 | 0.009 | 85.2 | 0.004 | 6.4 | 0.005 | 18.6 | 0.02 | 4.2 | 0.005 | 0.9 |
| 1 | 2-5 | 0.009 | 0.56 | 0.004 | 5.46 | 0.005 | 21.03 | 0.02 | 26.4 | 0.005 | 1.03 |
| 1 | 2-6 | 0.009 | 11.65 | 0.004 | 0.56 | 0.005 | 12.6 | 0.02 | 45.01 | 0.005 | 64.5 |
| 1 | 2-7 | 0.009 | 0.65 | 0.004 | 0.006 | 0.005 | 0.009 | 0.02 | 0.8 | 0.005 | 2.1 |
| 244 | 3-1 | 0.99 | 5.4 | 0.95 | 2.03 | 0.89 | 21.5 | 0.77 | 10.6 | 0.11 | 0.15 |
| 245 | 3-2 | 0.86 | 1.42 | 0.13 | 1.06 | 0.84 | 5.26 | 0.14 | 1.23 | 0.35 | 1.06 |
| 246 | 3-3 | 0.13 | 0.45 | 0.02 | 0.05 | 0.11 | 0.14 | 0.87 | 4.13 | 0.91 | 2.12 |
| 27 | 6-1 | 0.038 | 0.042 | 0.021 | 0.034 | 0.004 | 0.005 | 0.21 | 0.23 | 0.51 | 0.65 |
| 7 | 6-2 | 0.003 | 0.9 | 0.013 | 1.6 | 0.008 | 2.65 | 0.005 | 0.68 | 0.021 | 0.4 |

It should be noted that the above-described embodiments are merely illustrative and not limiting aspect of the present invention. Any equivalent replacement or change shall be deemed to have been included within the scope of the present invention.

The invention claimed is:

1. A compound with a chemical structure shown as formula (I), its isomers, racemates, pharmaceutically acceptable salts, crystalline hydrate, and solvate or their mixture:

(I)

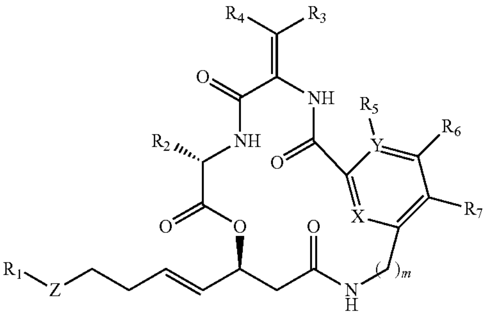

wherein, $R_1$ is hydrogen, $C_{1-16}$ alkyl, $C_{3-16}$ cycloalkyl, —(C═O)—($C_{1-16}$ alkyl), —(C═S)—($C_{1-16}$ alkyl) or —S—($C_{1-16}$ alkyl);

$R_2$ is hydrogen, $C_{1-12}$ alkyl, —$CH_2$—O—($C_{1-12}$ alkyl), —$CH_2$—NH—($C_{1-12}$ alkyl), —$CH_2$—S—($C_{1-12}$ alkyl), $C_{6-12}$ aryl, heteroaryl, —$CH_2$—($C_{6-12}$ aryl) or —$CH_2$-heteroaryl; wherein the $C_{6-12}$ aryl, heteroaryl, —$CH_2$—$C_{6-12}$ aryl, and —$CH_2$-heteroaryl, optionally comprise one or more substituents and the one or more substituents are selected from halo, amino, hydroxyl, nitro, cyano, $C_{1-12}$ alkyl, $C_{1-12}$ alkoxy, amino $C_{1-12}$ alkyl, acyl, acyloxy, thio $C_{1-12}$ alkyl, carboxyl and phenyl;

$R_3$, $R_4$ are independently selected from hydrogen, $C_{1-12}$ alkyl, —O—($C_{1-12}$ alkyl), —NH—($C_{1-12}$ alkyl), —S—($C_{1-12}$ alkyl), $C_{6-12}$ aryl and heteroaryl;

X is N and Y is C, or both X and Y are N;

$R_5$, $R_6$, $R_7$ are independently selected from hydrogen, halo, —S—($C_{1-12}$ alkyl), $C_{1-12}$ alkyl and t-butoxycarbonyl;

Z is —$CH_2$—, —NH—, —O—, —S— or

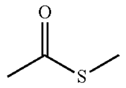

;

m is 0, 1, 2, 3, 4, 5 or 6.

2. The compound with a chemical structure shown as formula (I) according to claim 1, wherein, $R_1$ is hydrogen, $C_{1-16}$ alkyl, $C_{3-16}$ cycloalkyl, —(C═O)—($C_{1-16}$ alkyl), —(C═S)—($C_{1-16}$ alkyl) or —S—($C_{1-16}$ alkyl);

$R_2$ is hydrogen, $C_{1-12}$ alkyl, —$CH_2$—O—($C_{1-12}$ alkyl), —$CH_2$—NH—($C_{1-12}$ alkyl), —$CH_2$—S—($C_{1-12}$ alkyl), $C_{6-12}$ aryl, heteroaryl, —$CH_2$—($C_{6-12}$ aryl)-$CH_2$— or heteroaryl, wherein the $C_{6-12}$ aryl, heteroaryl, —$CH_2$—$C_{6-12}$ aryl and —$CH_2$-heteroaryl, optionally comprise one or more substituents and the one or more substituents are selected from halo, amino, hydroxyl, nitro, cyano, $C_{1-12}$ alkyl, $C_{1-12}$ alkoxy, amino $C_{1-12}$ alkyl, acyl, acyloxy, thio $C_{1-12}$ alkyl, carboxyl and phenyl;

$R_3$, $R_4$ are each independently selected from hydrogen, $C_{1-12}$ alkyl, —O—($C_{1-12}$ alkyl), —NH—($C_{1-12}$ alkyl), —S—($C_{1-12}$ alkyl), $C_{6-12}$ aryl and heteroaryl;

X is N and Y is C, or both X and Y are N;

$R_5$, $R_6$, $R_7$ groups are independently selected from hydrogen, halo, —S—($C_{1-12}$ alkyl), $C_{1-12}$ alkyl and t-butoxycarbonyl;

Z is —O—, —S— or

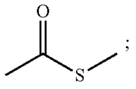
;

m is 0, 1 or 2.

3. The compound with a chemical structure shown as formula (I) according to claim 1, wherein, $R_1$ is hydrogen or $C_{1-16}$ alkyl;

$R_2$ are hydrogen, $C_{1-12}$ alkyl, or $C_{6-12}$ aryl, wherein the $C_{6-12}$ aryl optionally comprise one or more substituents and the one or more substituents are selected from halo, amino, hydroxyl, nitro, cyano, $C_{1-12}$ alkyl, $C_{1-12}$ alkoxy, amino $C_{1-12}$ alkyl, acyl, acyloxy, thio $C_{1-12}$ alkyl, carboxyl or phenyl;

$R_3$, $R_4$ groups are each independently selected from hydrogen, $C_{1-12}$ alkyl, —O—($C_{1-12}$ alkyl), —NH—($C_{1-12}$ alkyl), —S—($C_{1-12}$ alkyl), $C_{6-12}$ aryl and heteroaryl;

Y is C;

$R_5$, $R_6$, $R_7$ are independently selected from hydrogen, F, —S—($C_{1-12}$ alkyl);

Z is —S— or

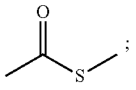
;

m is 0, 1 or 2.

4. The compound with a chemical structure shown as formula (I) according to claim 1, wherein, the compound of general formula (I) is selected from:

1

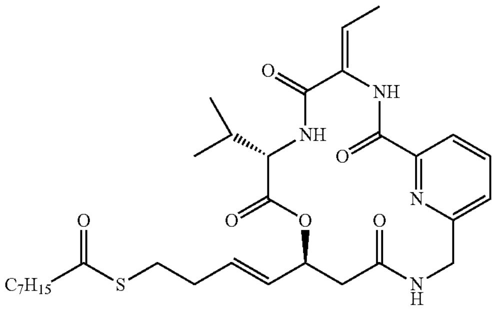

-continued

2

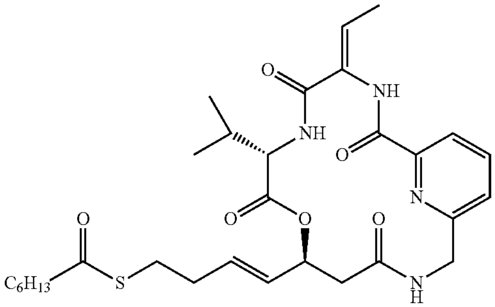

3

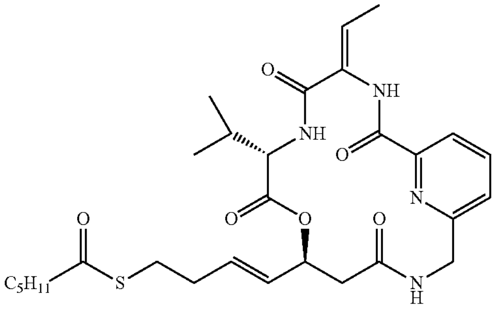

4

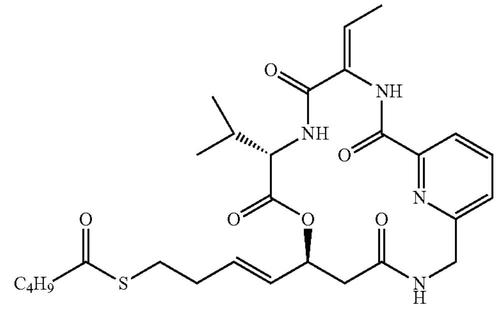

5

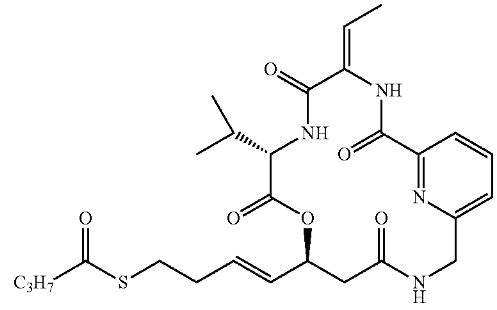

6

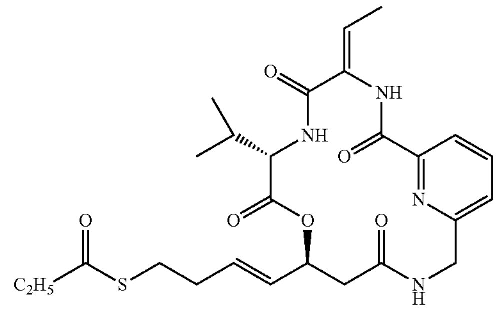

-continued
7
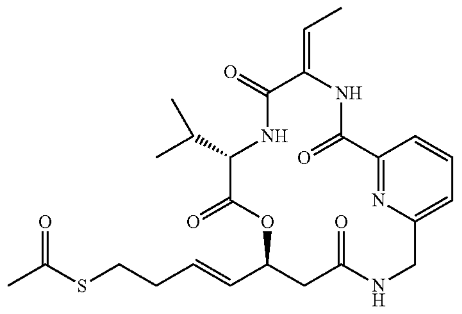
8
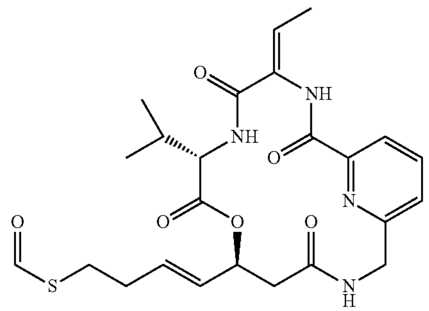
9
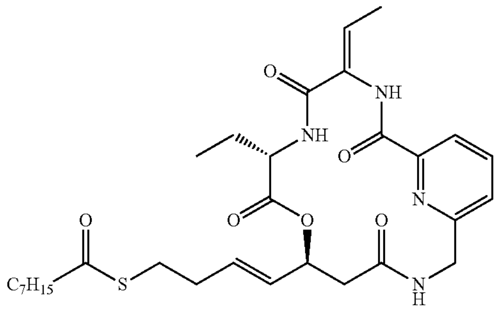
10
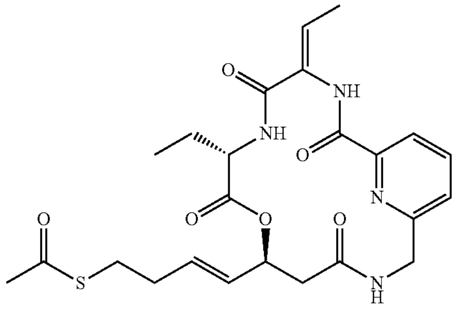
11
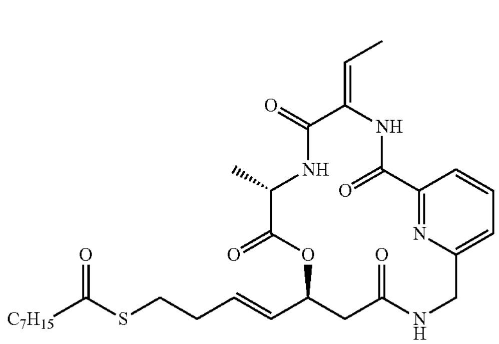
-continued
12
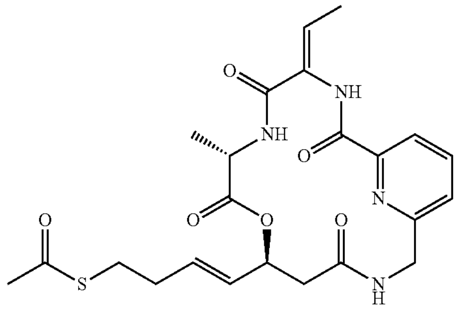
13
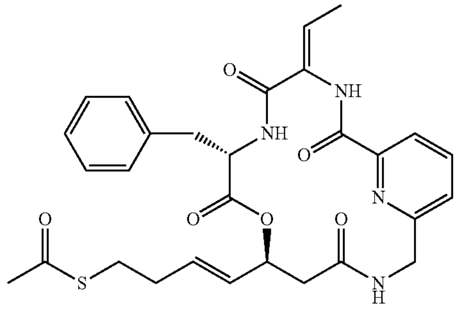
14
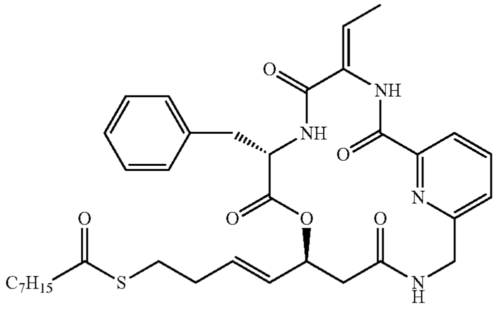
15
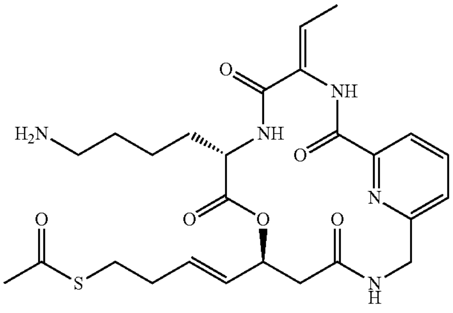
16
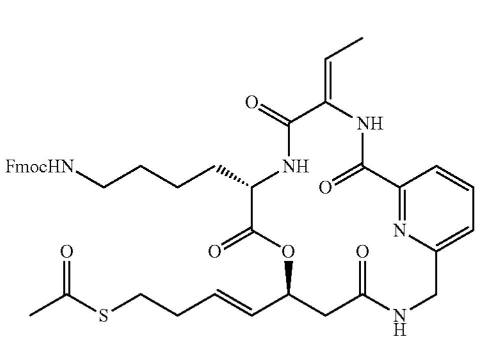

-continued
17
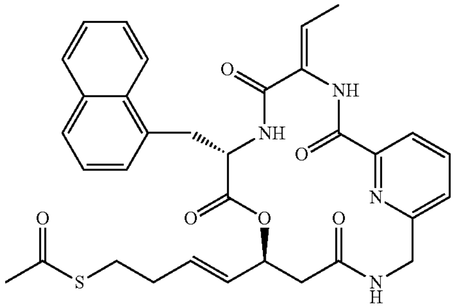
18
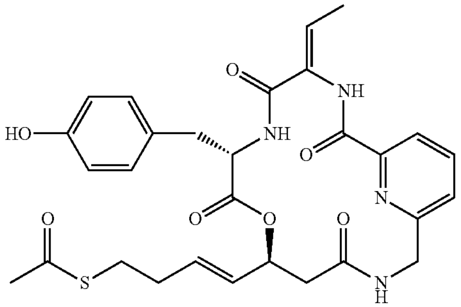
19
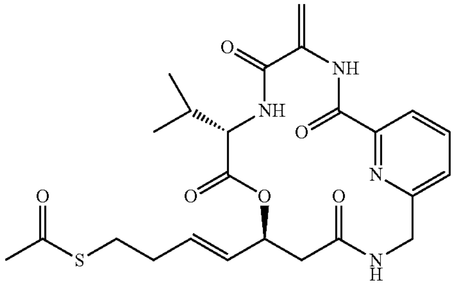
20
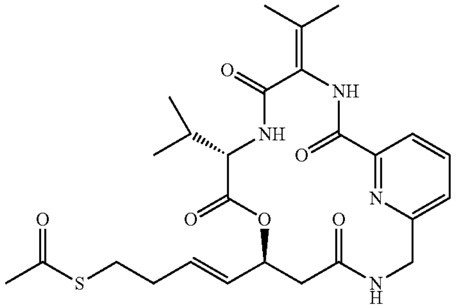
21
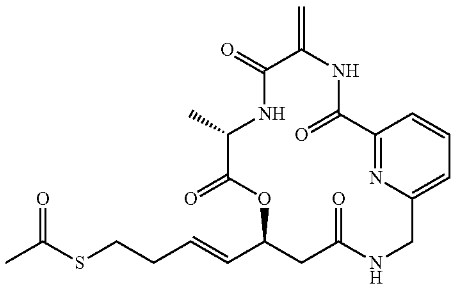
-continued
22
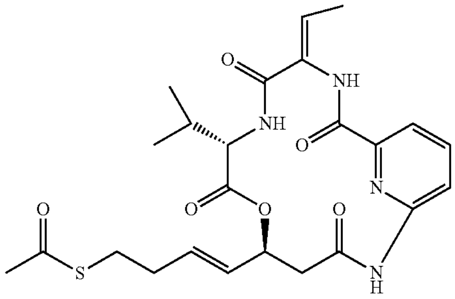
23
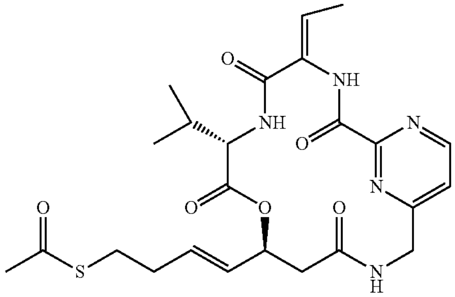
24
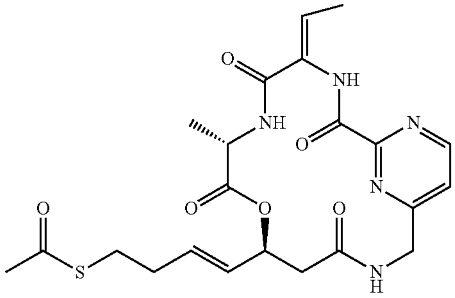
25
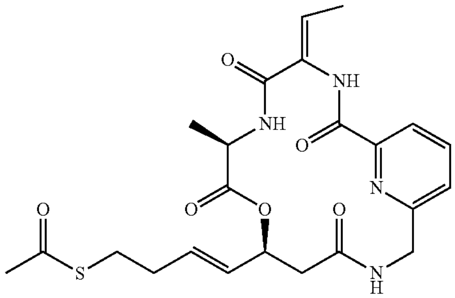
26
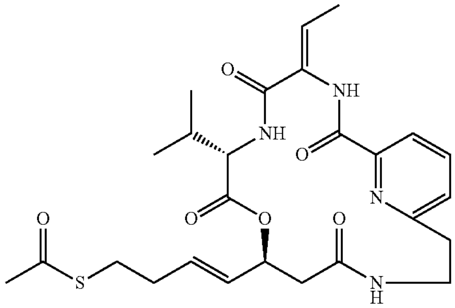

-continued
27
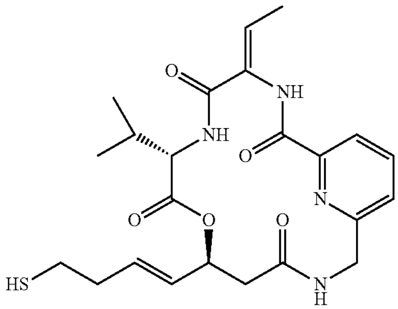
28
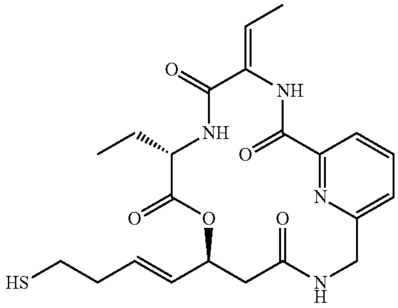
29
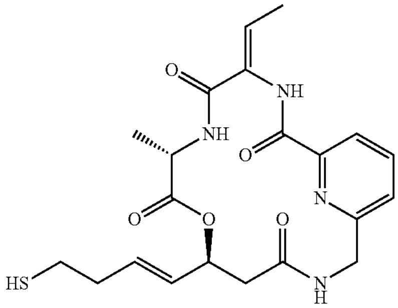
30
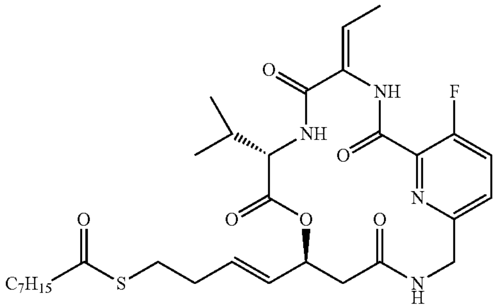
31
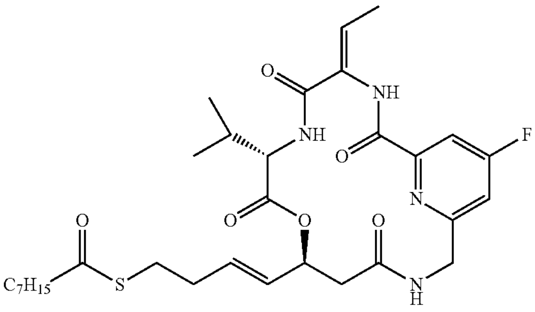
-continued
32
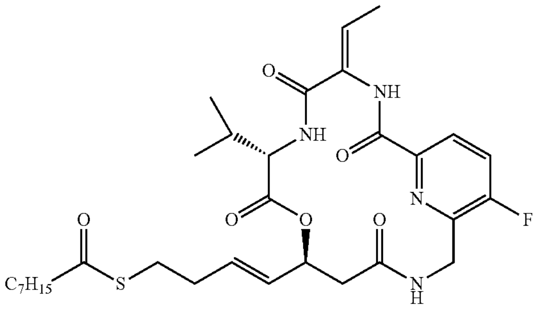
33
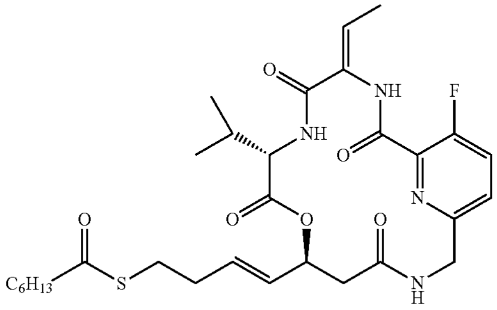
34
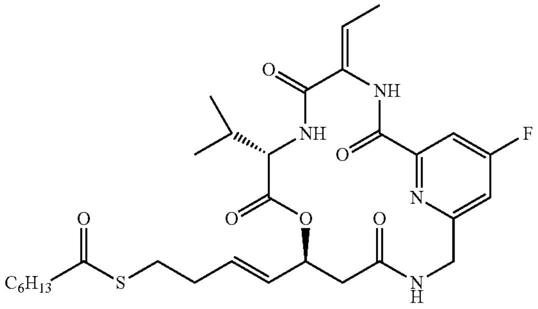
35
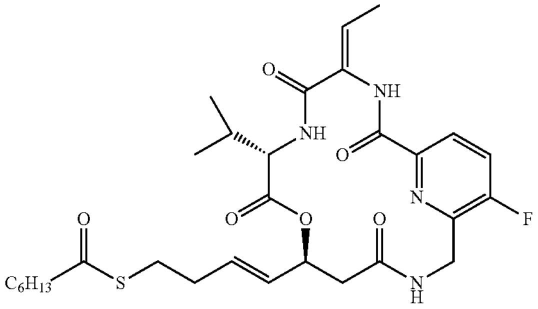
36
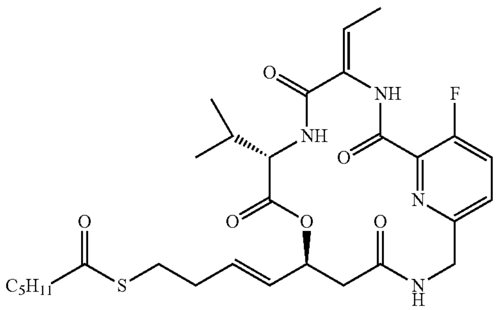

-continued
37
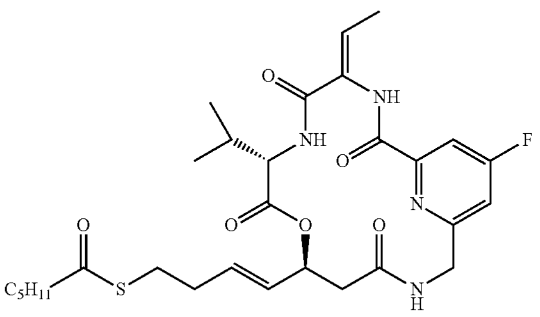
38
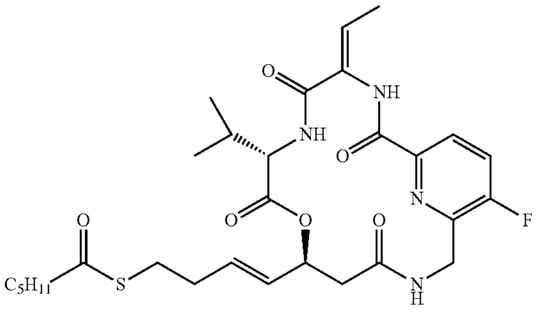
39
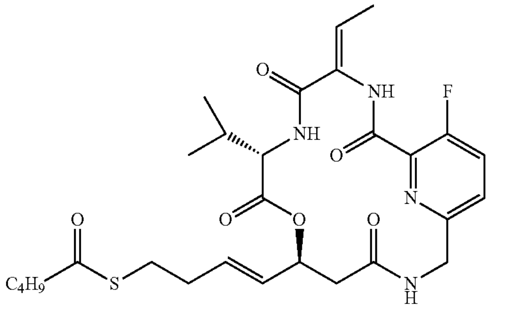
40
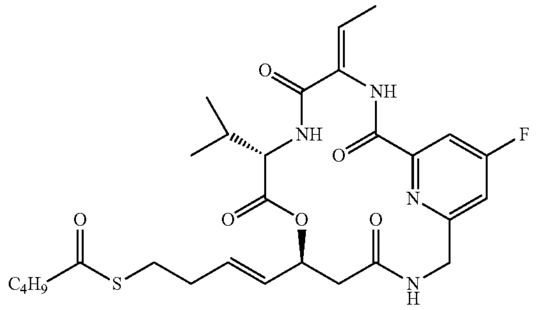
41
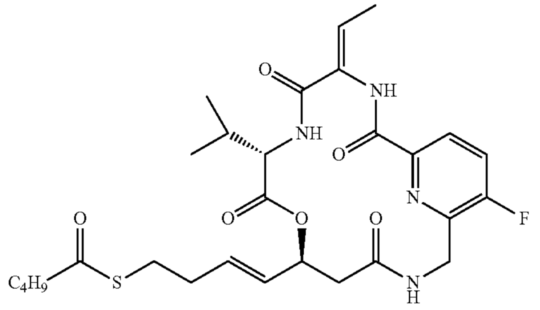
-continued
42
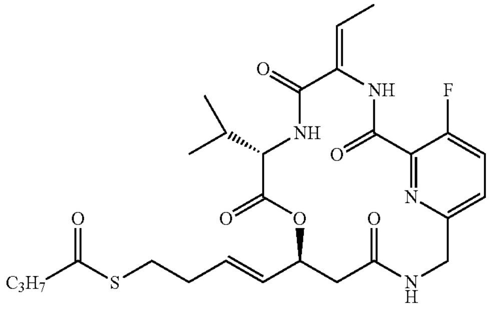
43
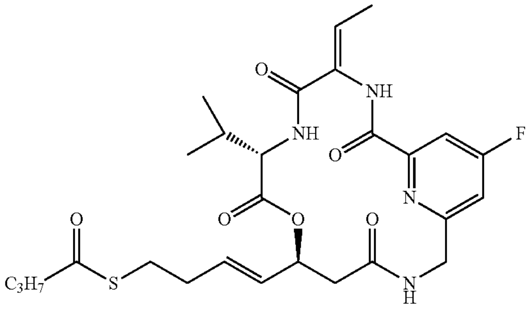
44
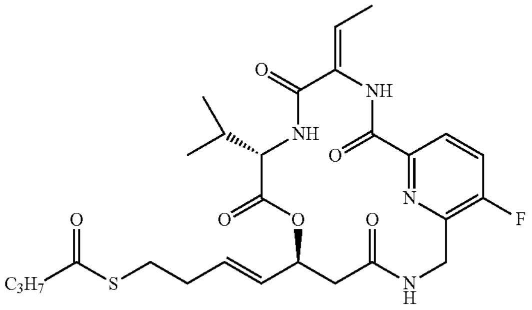
45
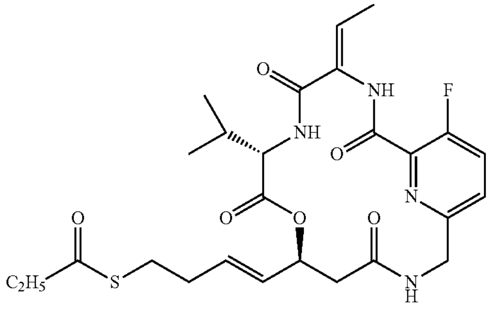
46
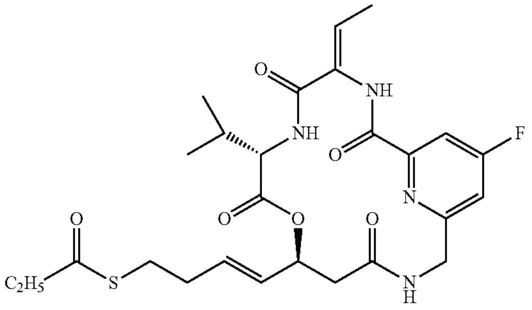

-continued
47
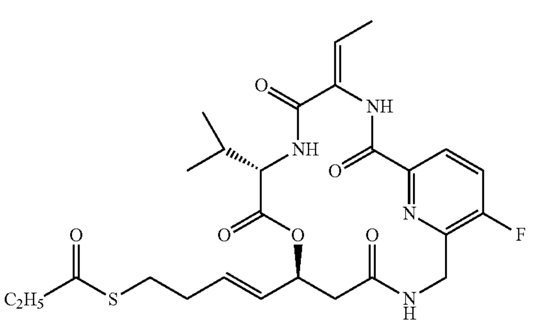
48
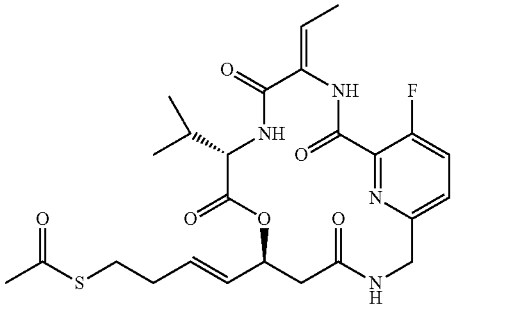
49
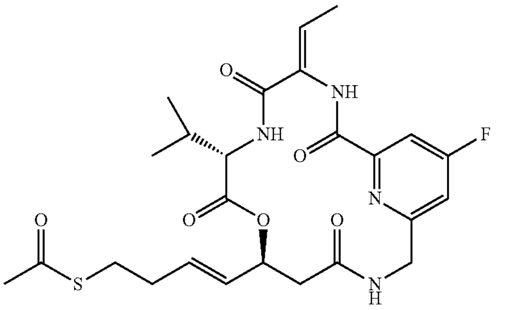
50
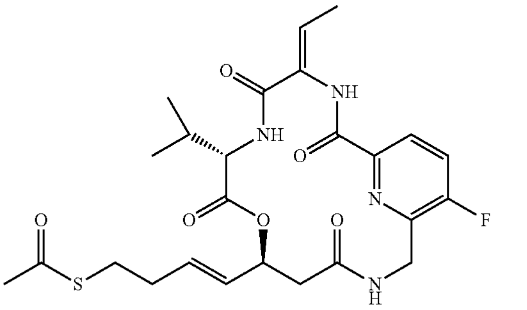
51
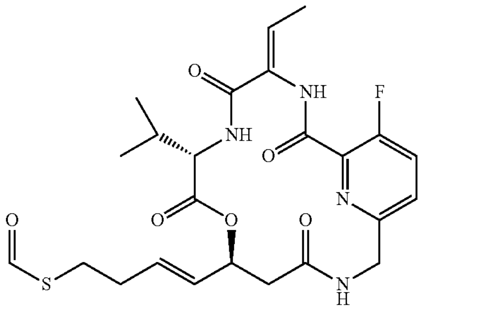
-continued
52
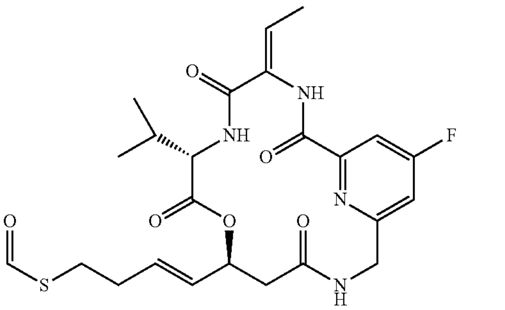
53
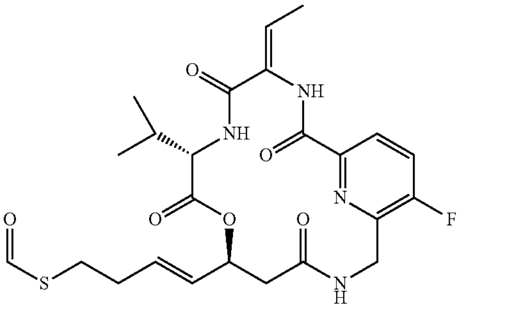
54
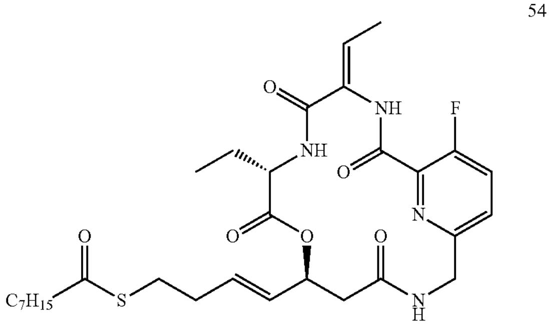
55
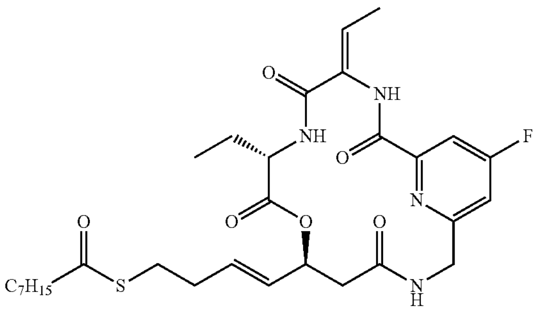
56
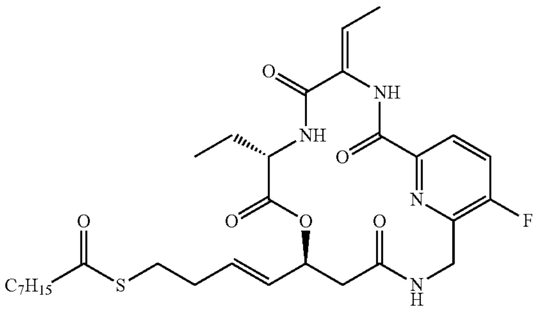

-continued
57
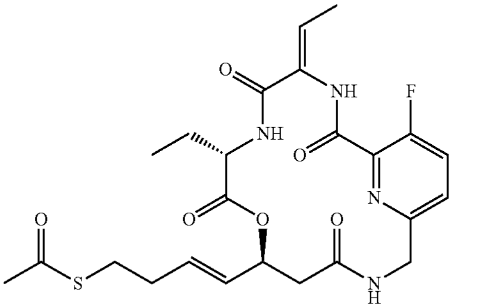
58
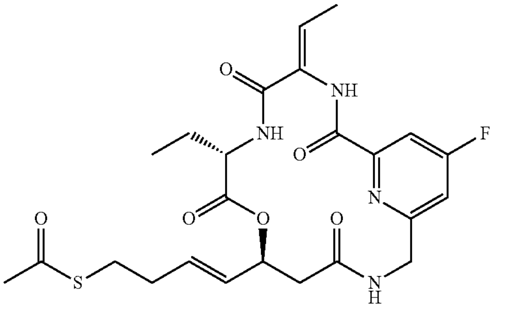
59
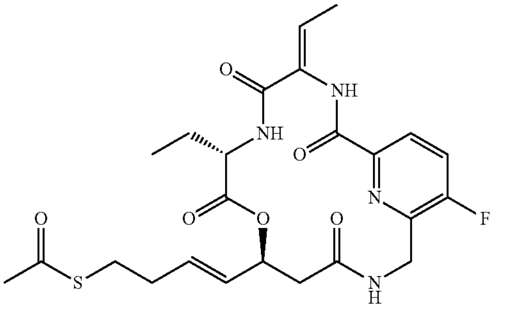
60
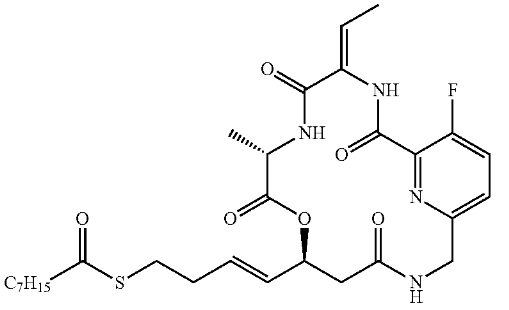
61
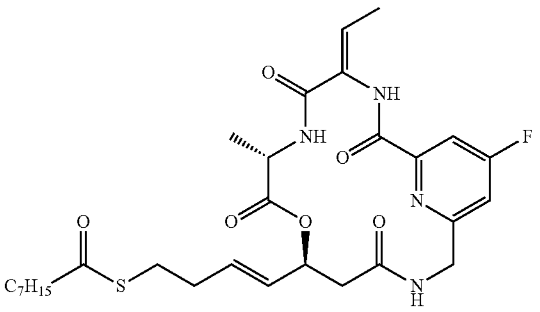
-continued
62
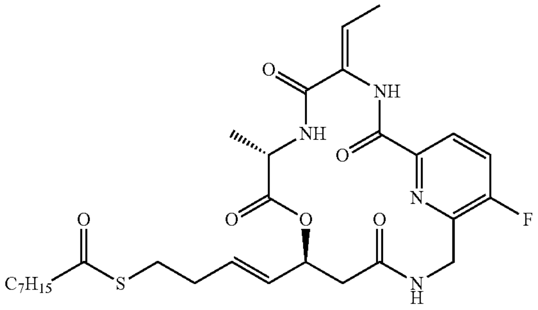
63
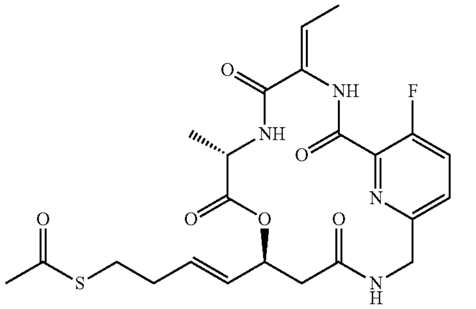
64
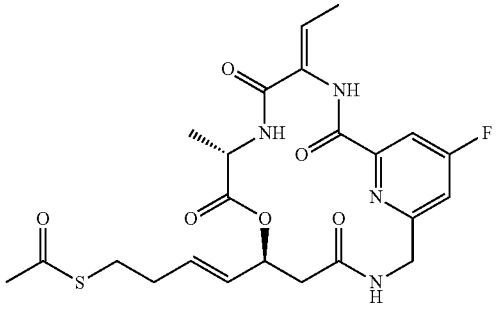
65
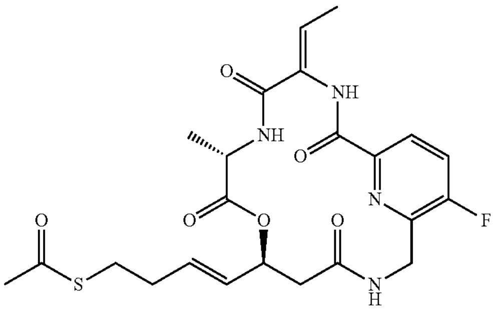
66
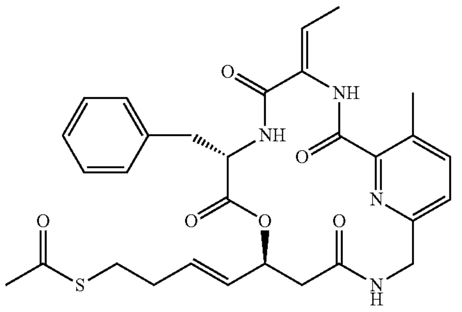

-continued
67
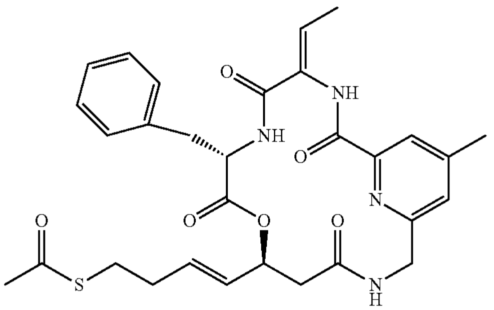
68
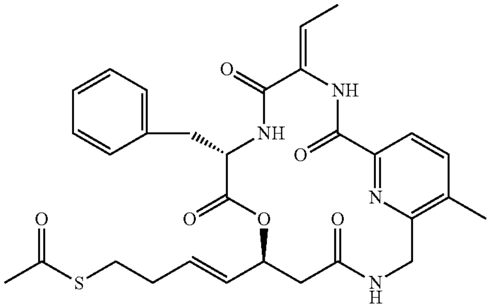
69
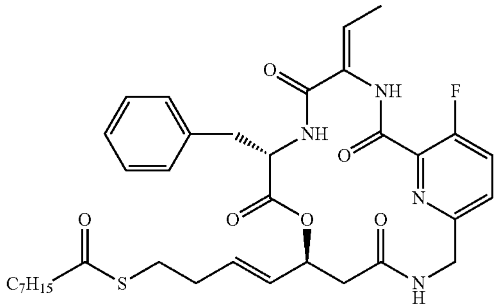
70
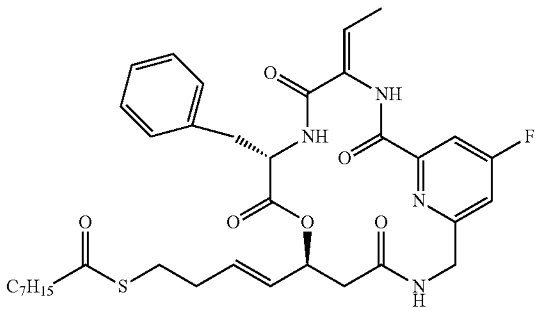
-continued
71
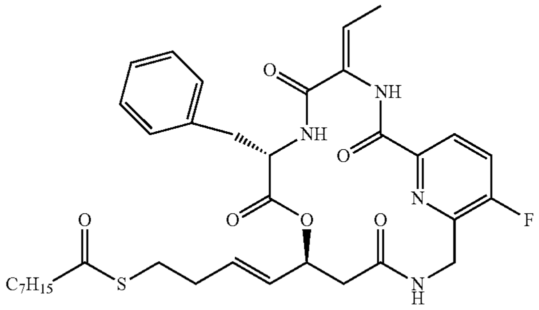
72
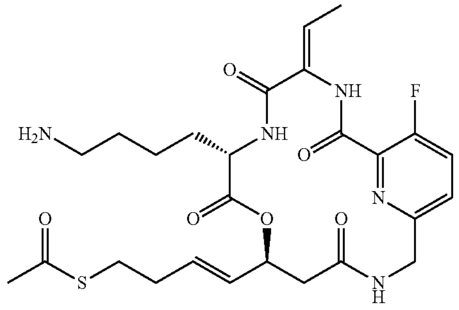
73
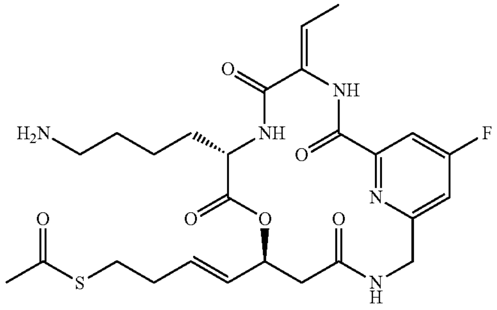
74
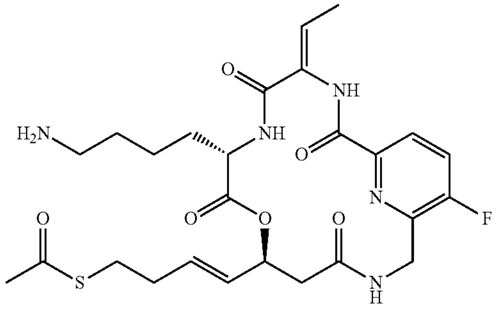
75
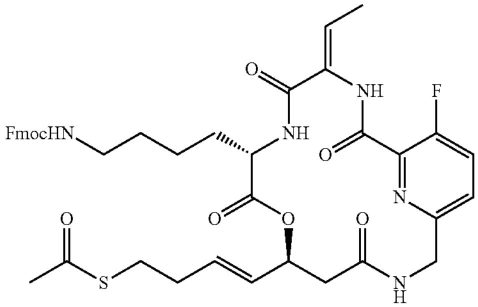

76
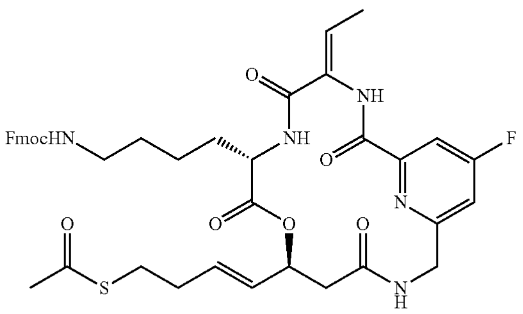
77
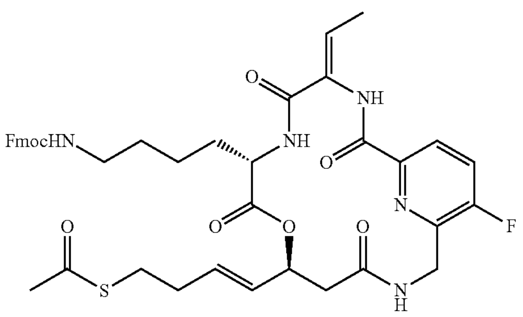
78
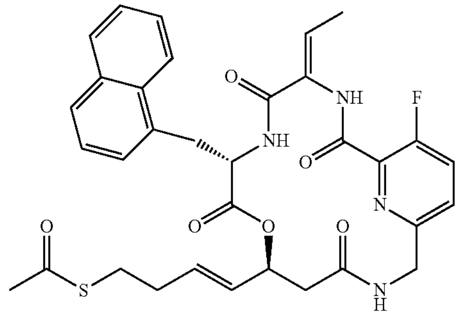
79
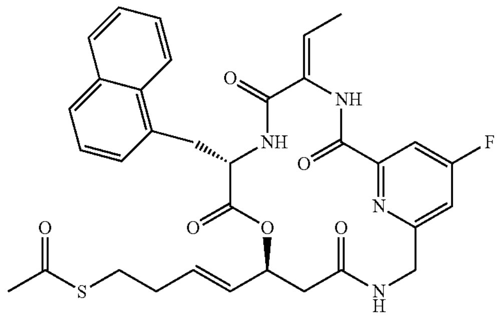
80
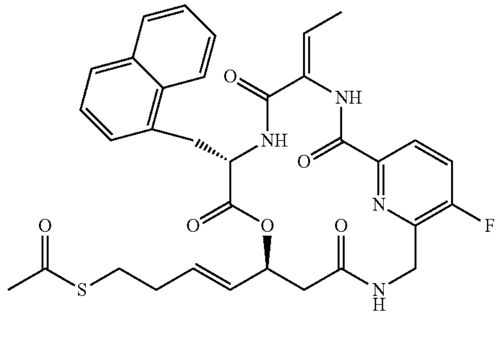
81
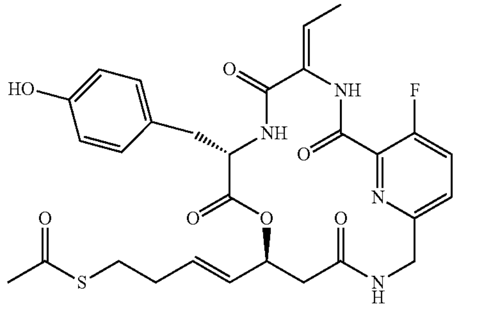
82
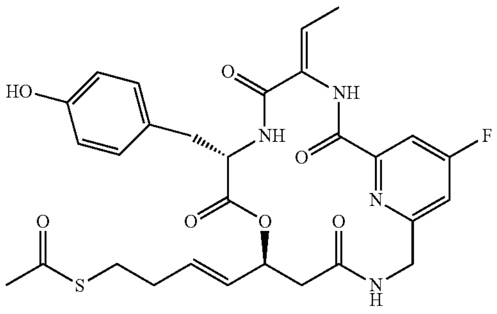
83
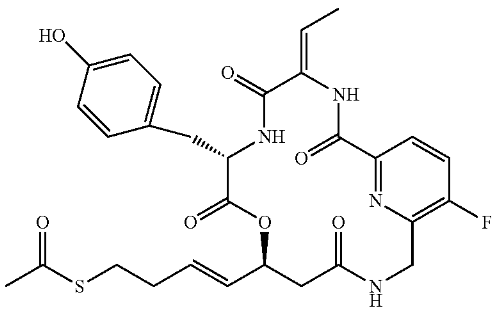
84
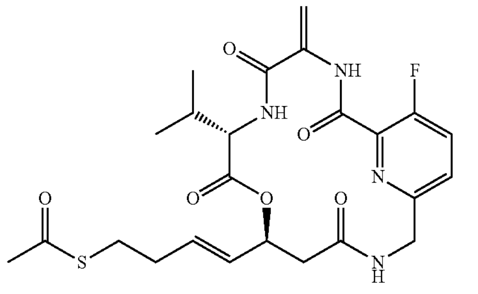
85
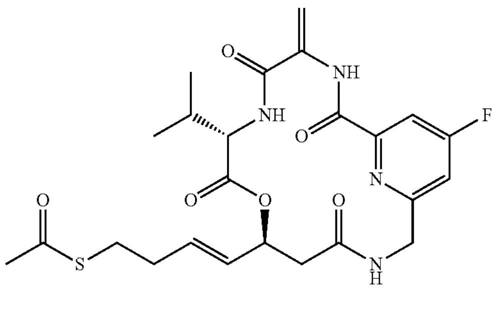

-continued
86
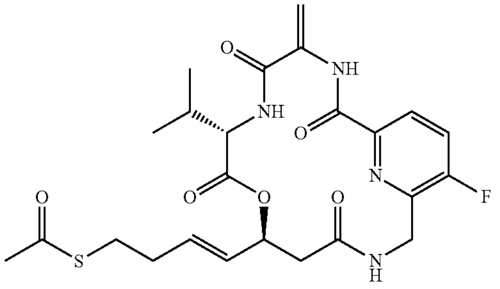
87
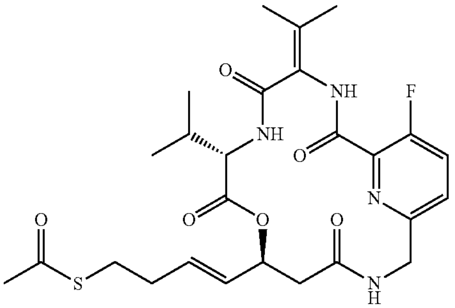
88
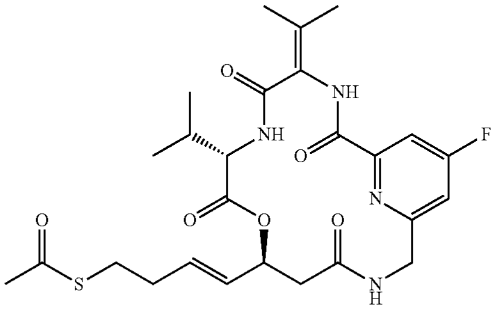
89
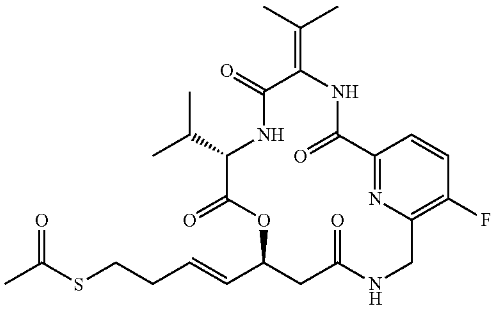
90
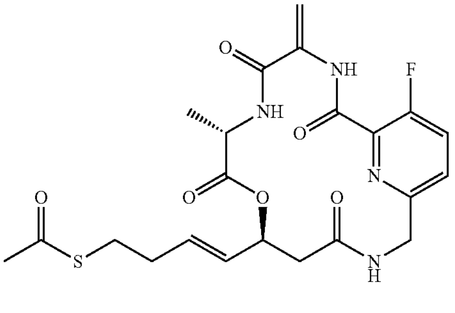
-continued
91
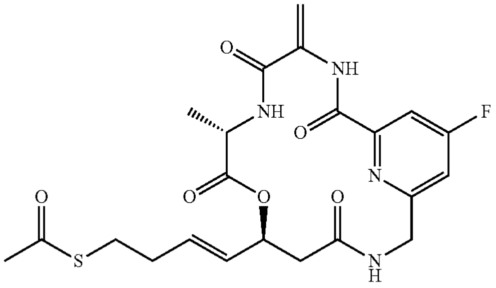
92
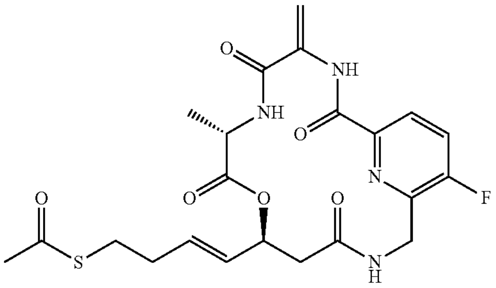
93
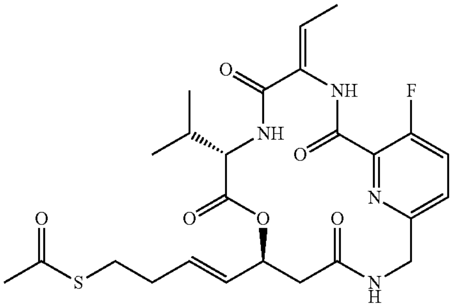
94
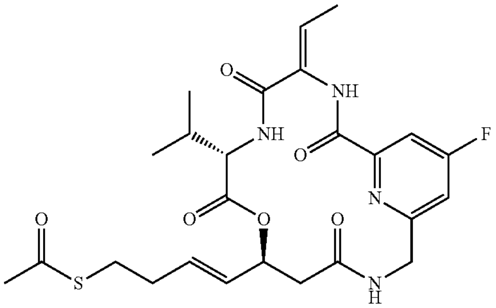
95
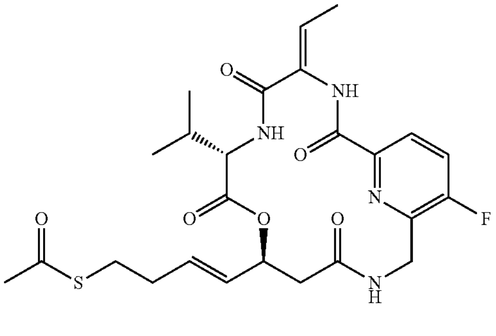

96
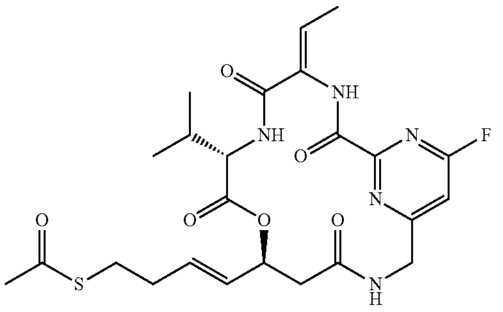
97
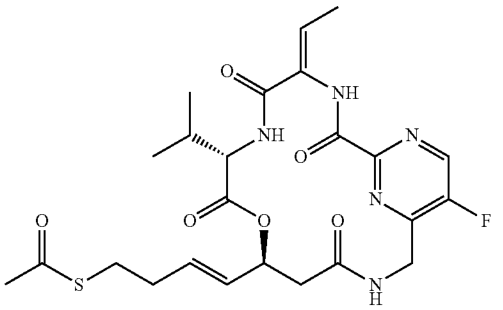
98
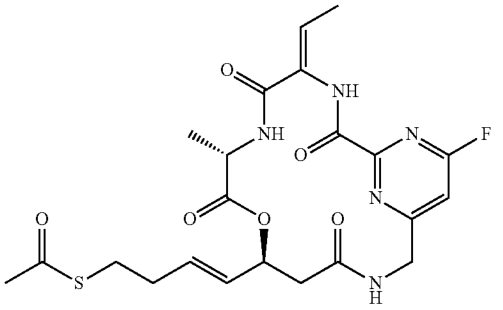
99
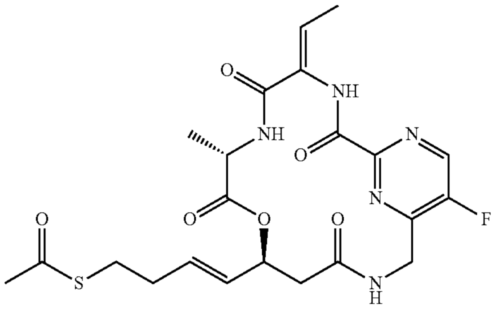
100
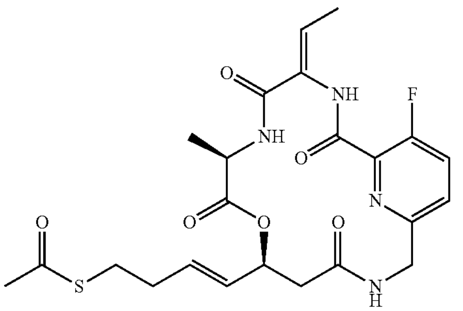
101
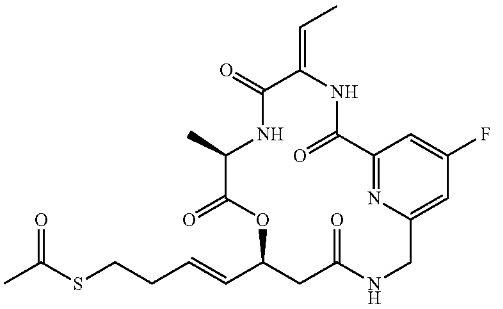
102
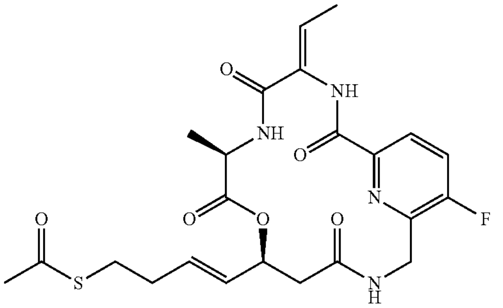
103
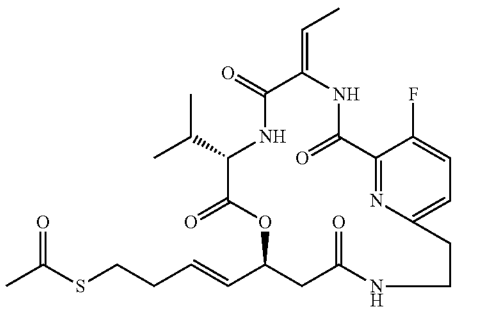
104
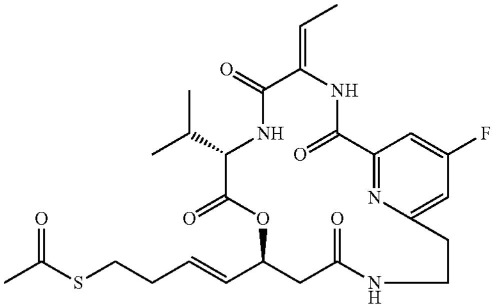
105
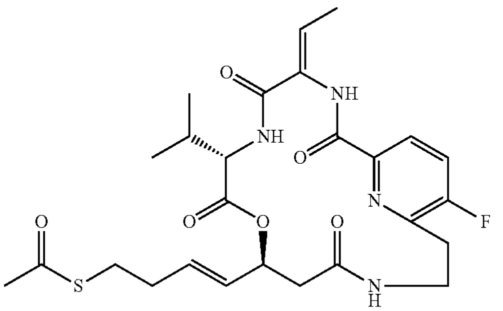

106
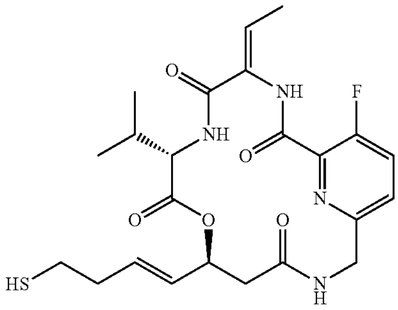
107
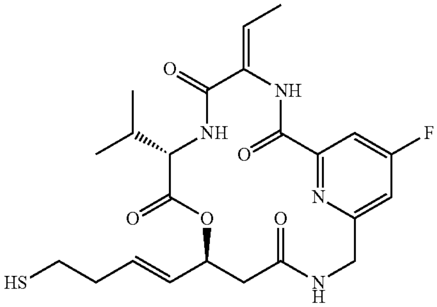
108
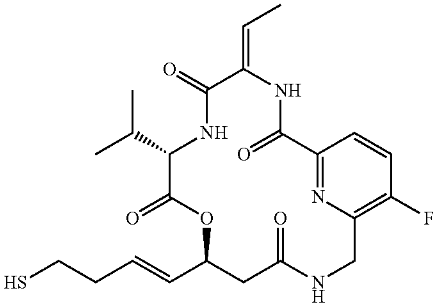
109
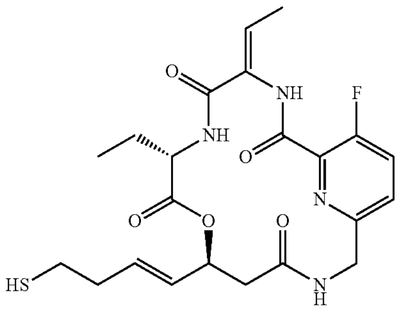
110
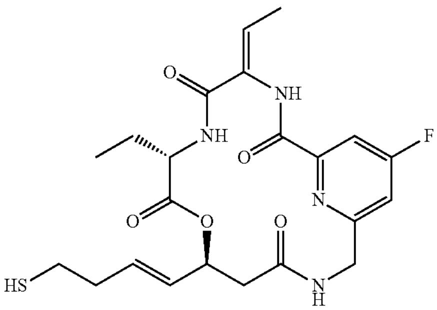
111
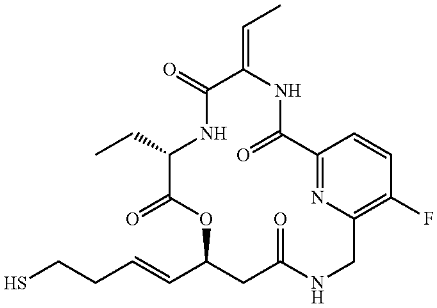
112
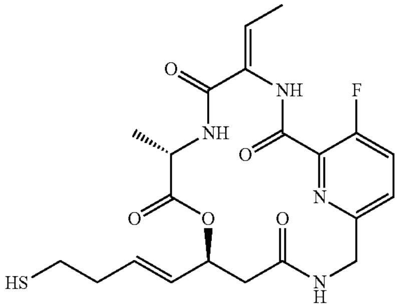
113
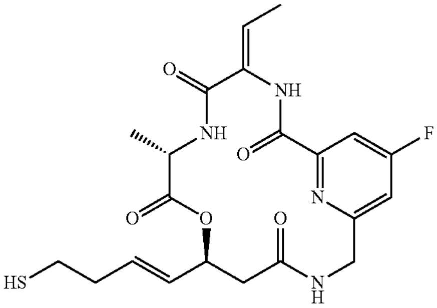
114
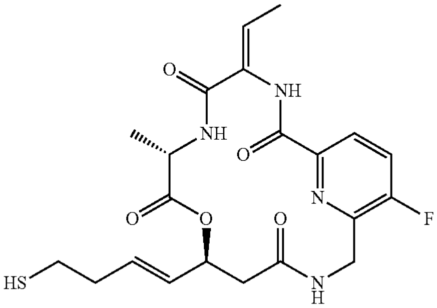
115
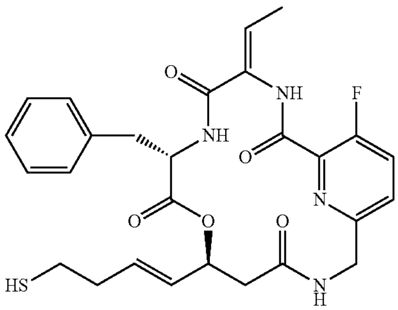

-continued
116
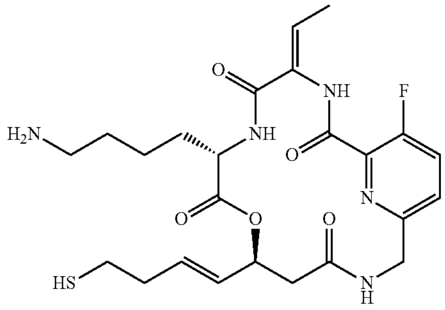
117
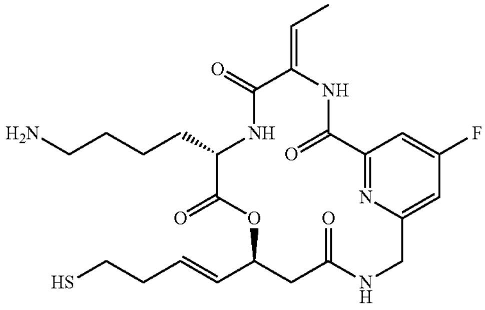
118
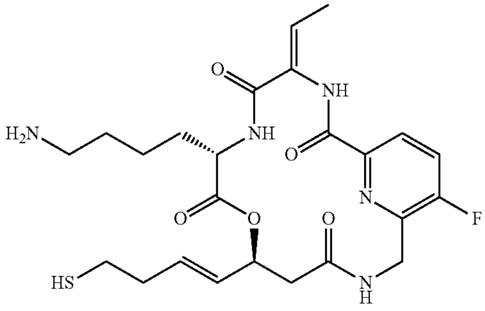
119
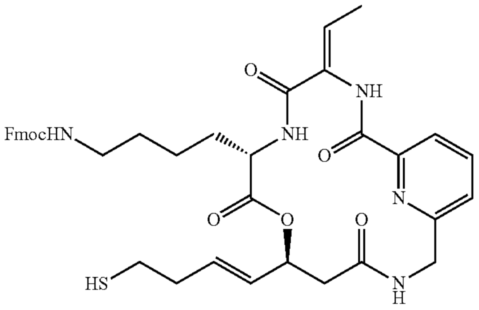
120
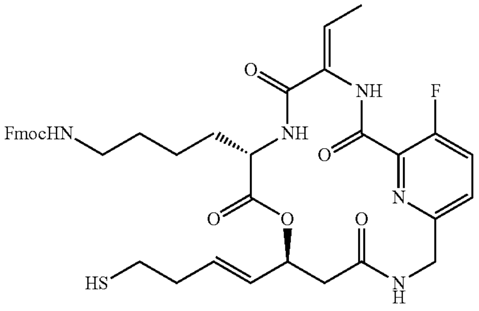
-continued
121
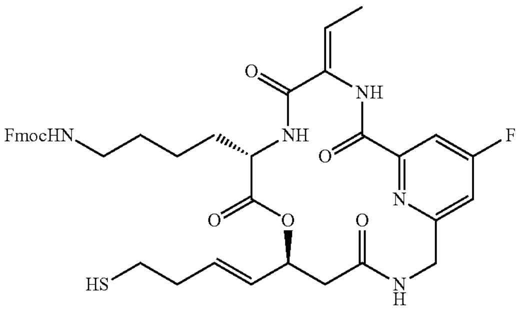
122
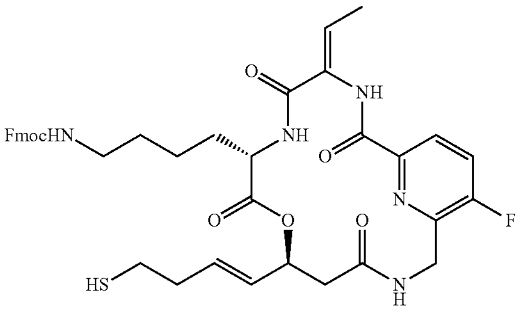
123
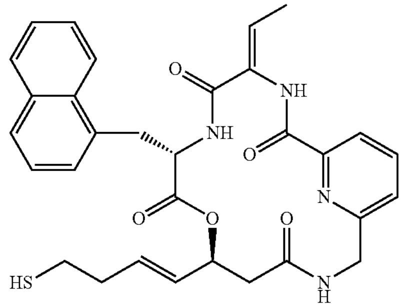
124
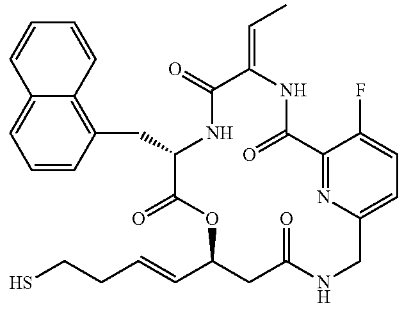
125
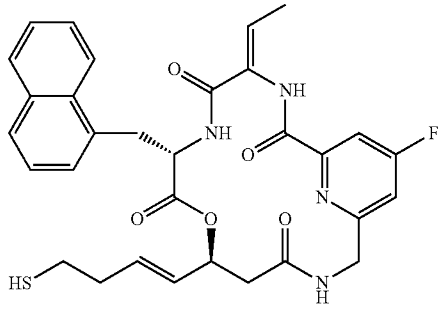

-continued
126
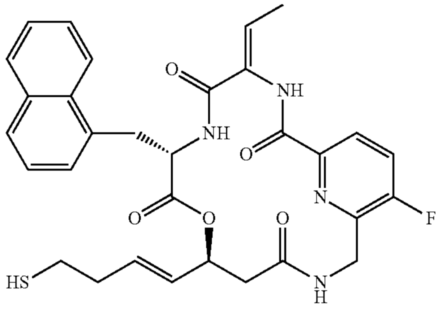
127
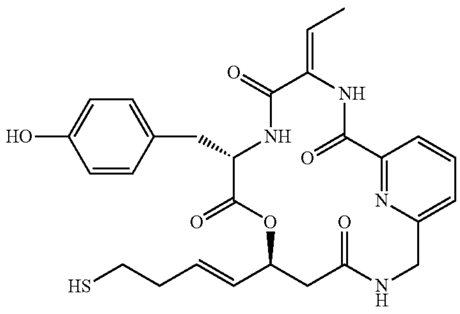
128
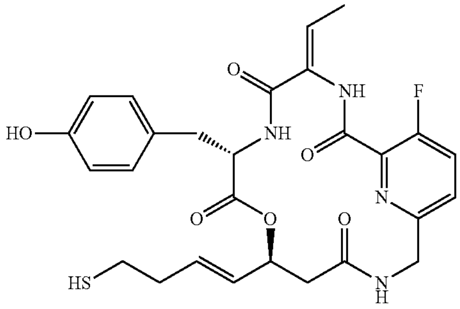
129
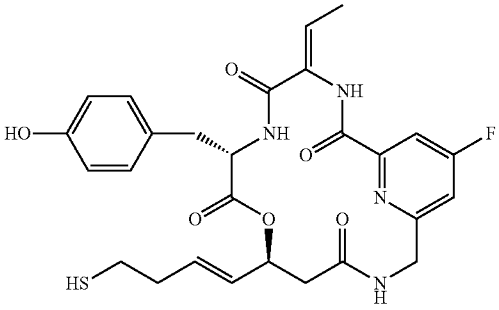
130
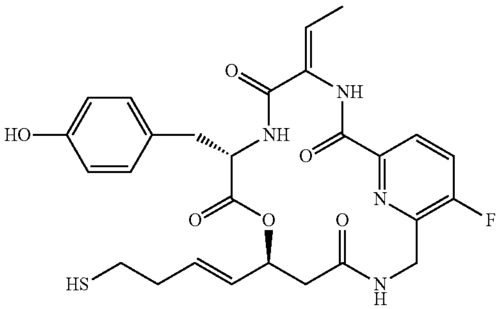
-continued
131
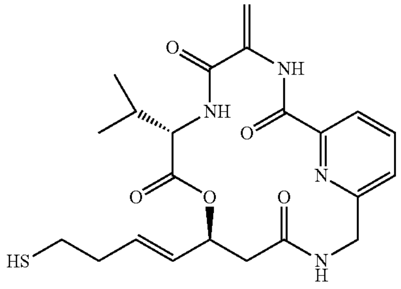
132
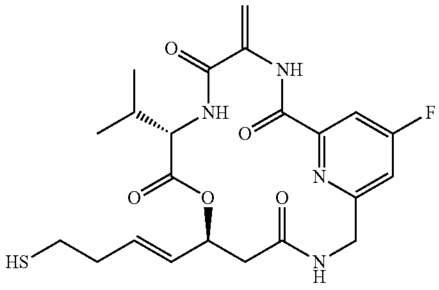
133
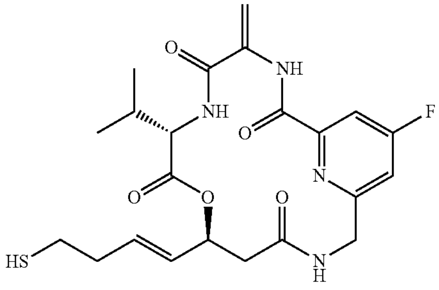
134
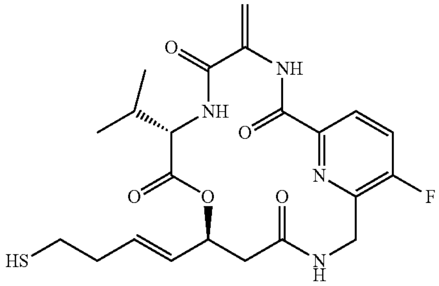
135
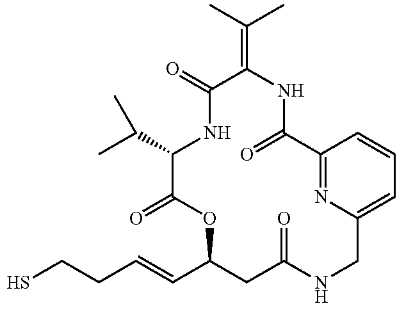

-continued
136
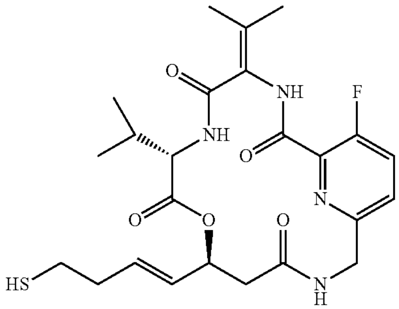
137
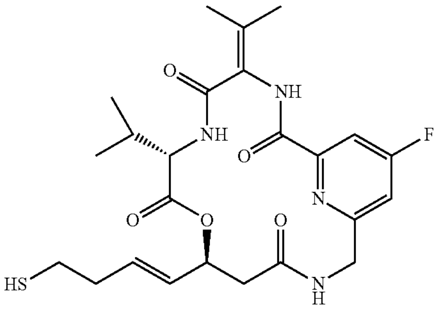
138
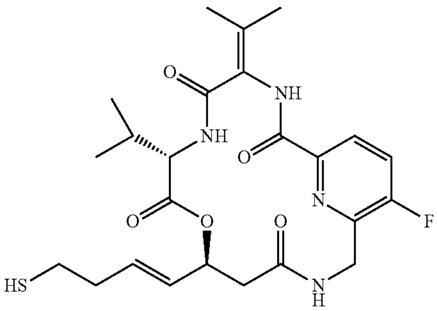
139
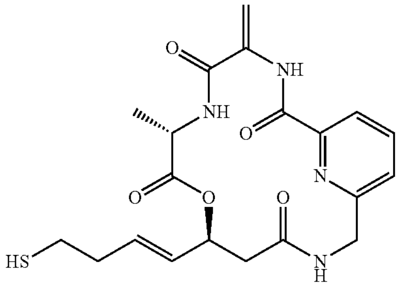
140
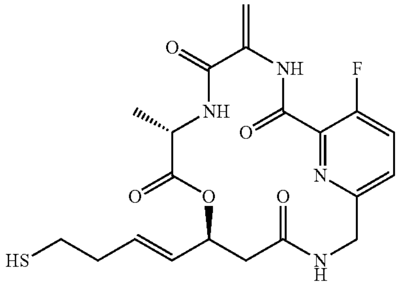
-continued
141
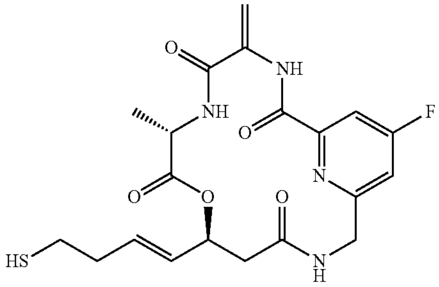
142
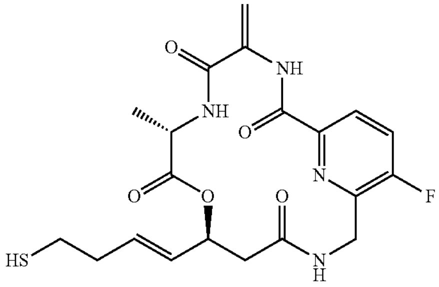
143
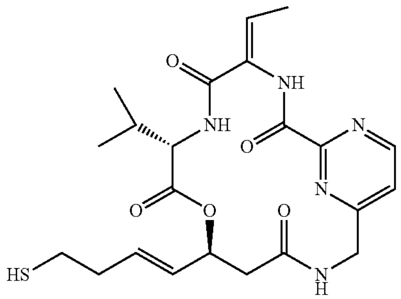
144
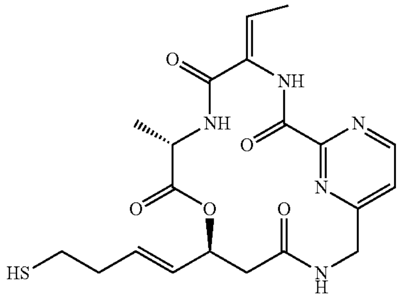
145
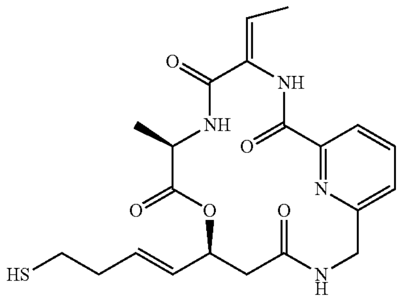

-continued
146
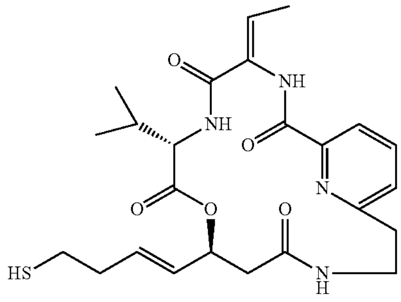
147
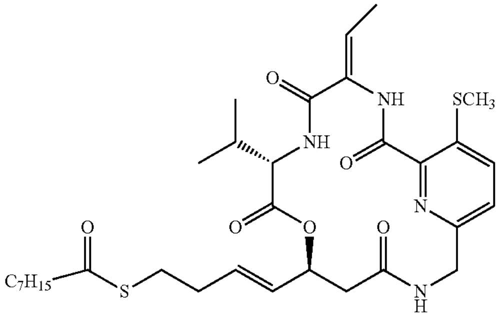
148
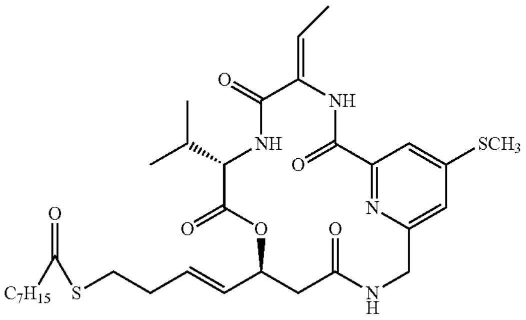
149
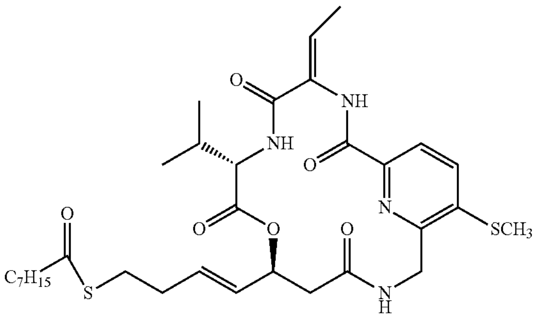
150
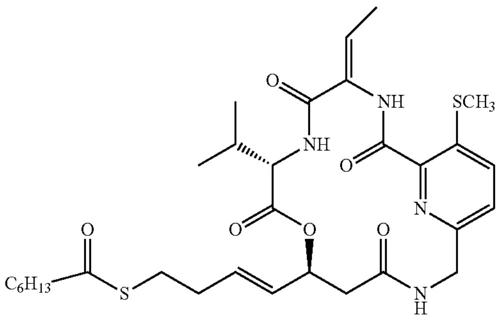
-continued
151
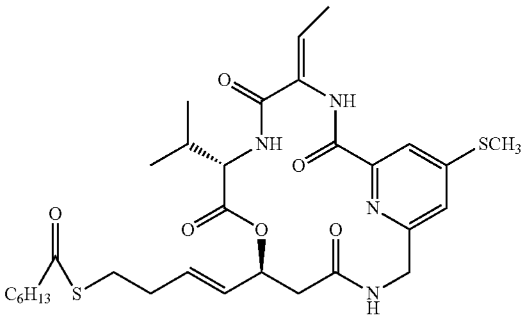
152
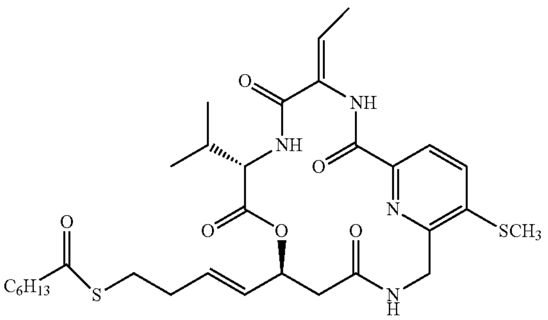
153
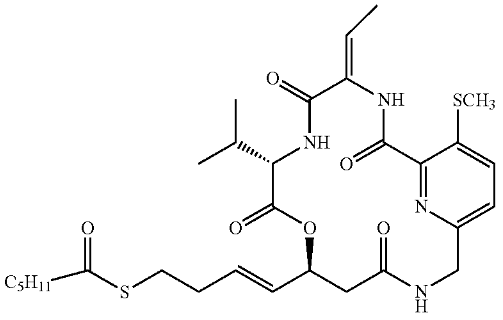
154
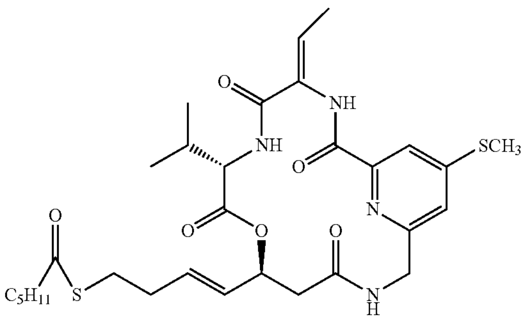

-continued
155
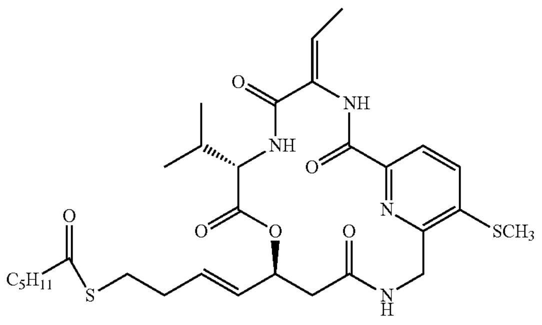
156
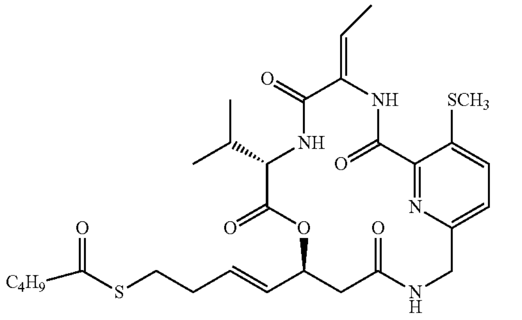
157
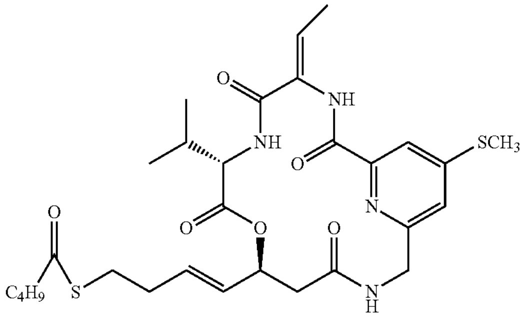
158
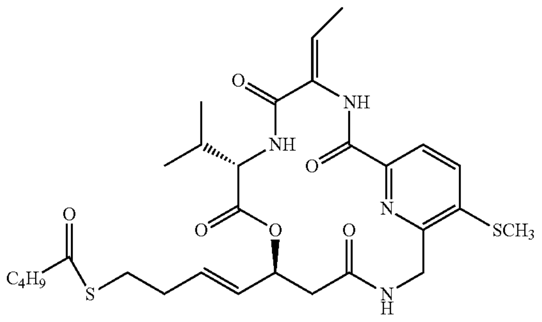
-continued
159
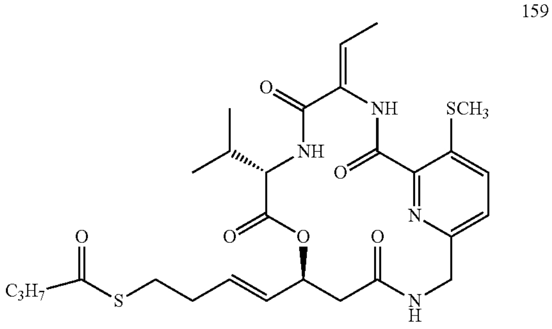
160
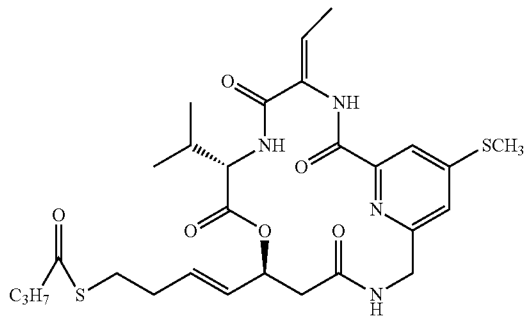
161
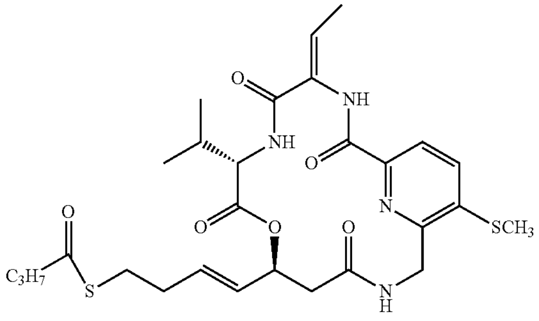
162
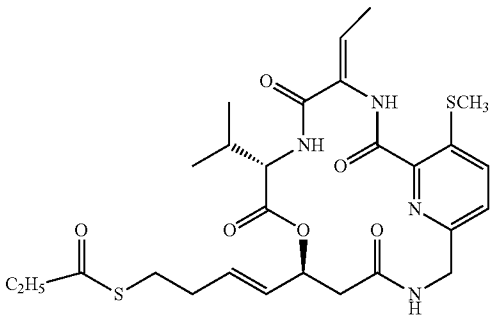

163
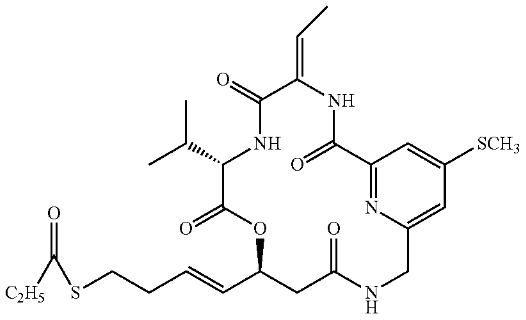
164
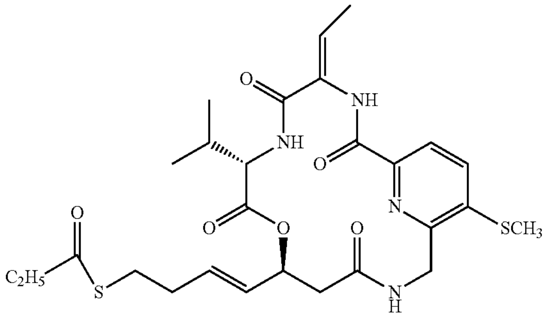
165
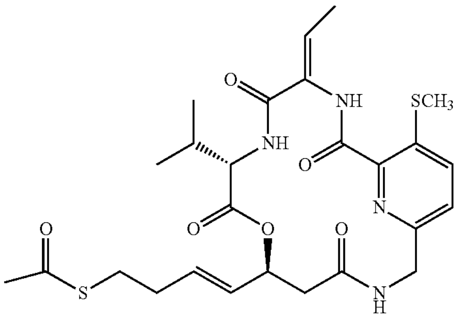
166
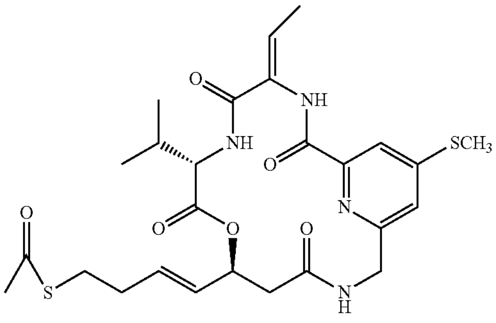
167
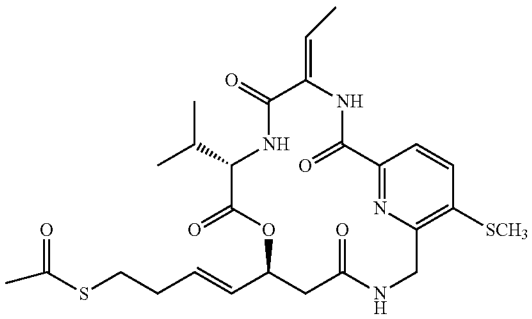
168
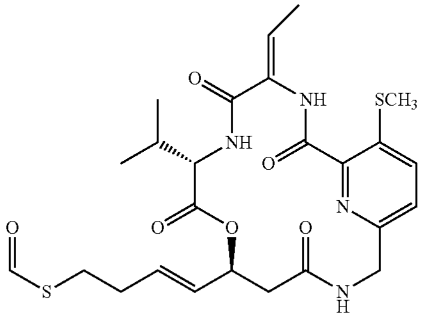
169
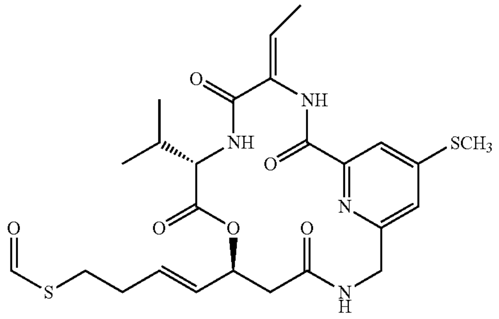
170
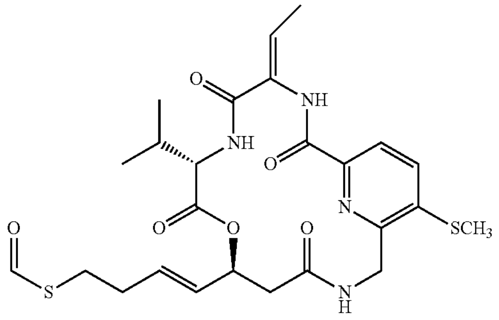
171
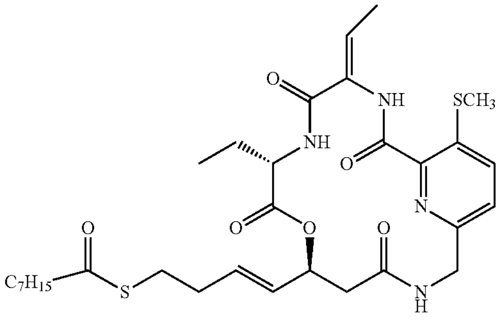

-continued
172
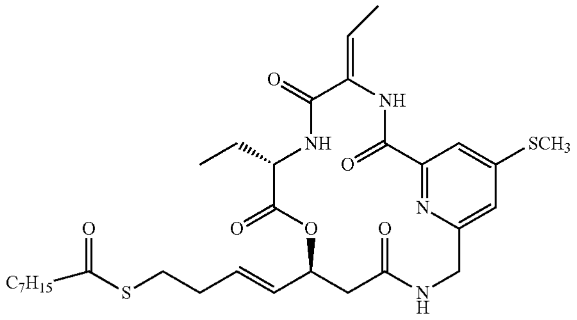
173
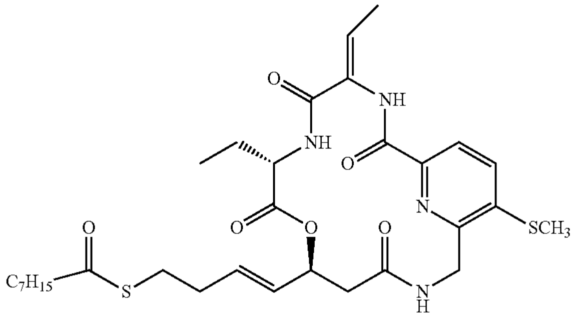
174
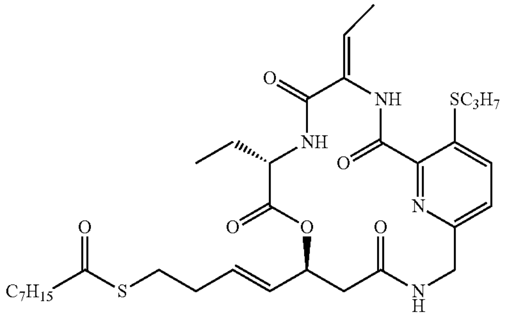
175
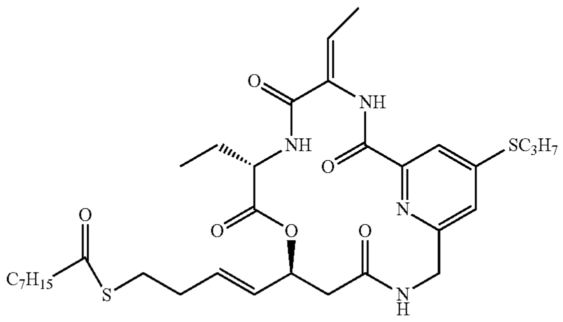
-continued
176
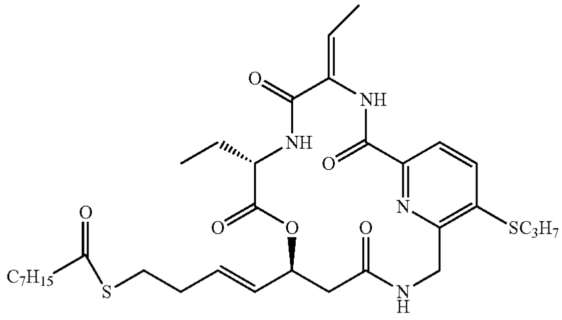
177
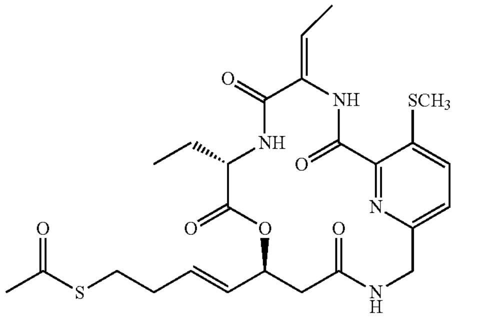
178
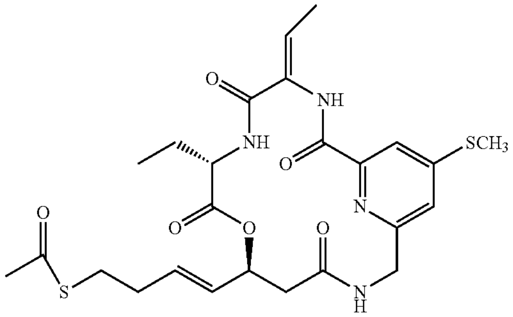
179
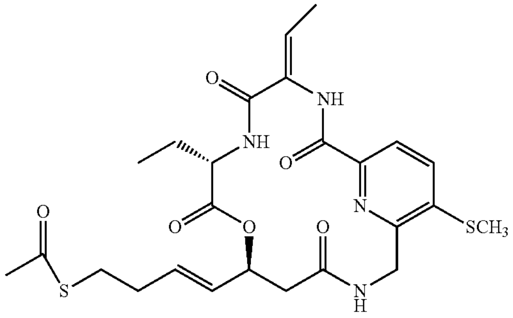
180
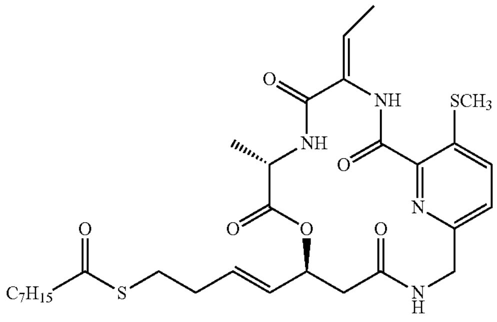

-continued
181
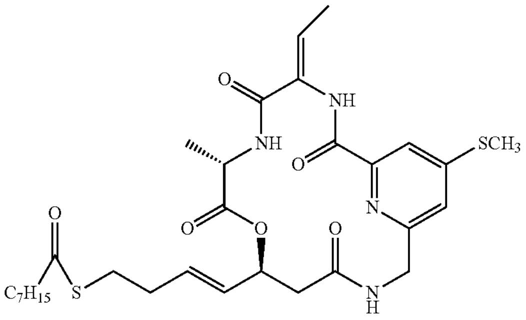
182
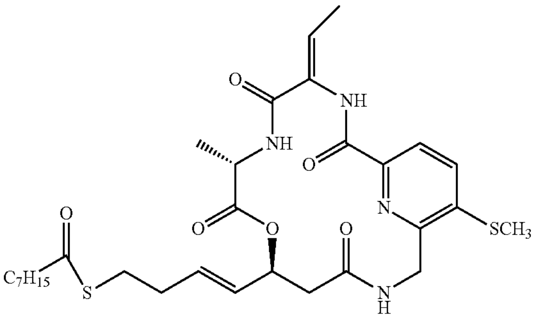
183
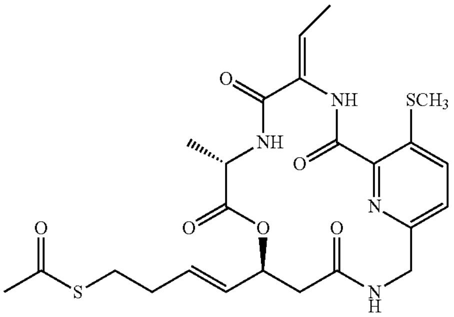
184
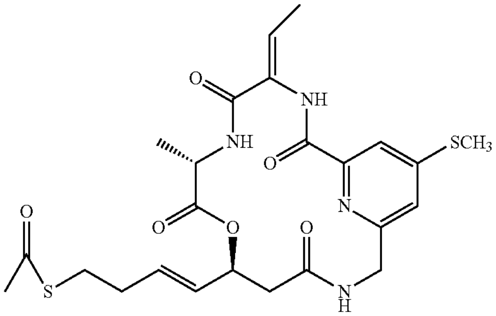
185
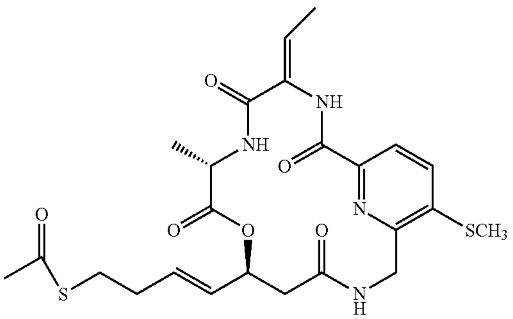
-continued
186
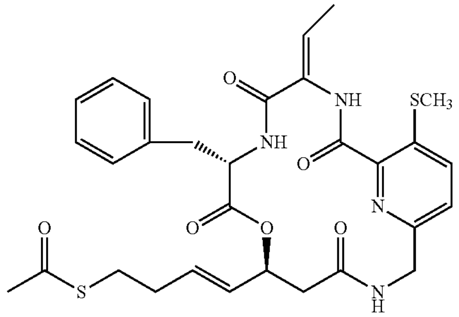
187
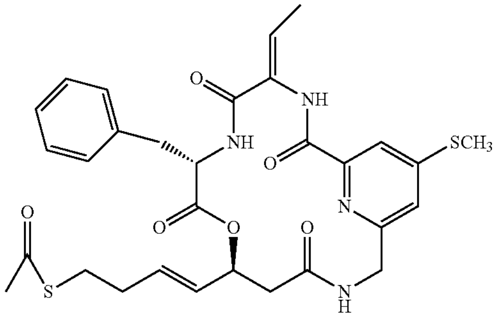
188
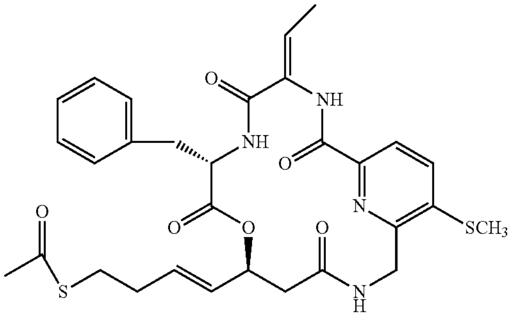
189
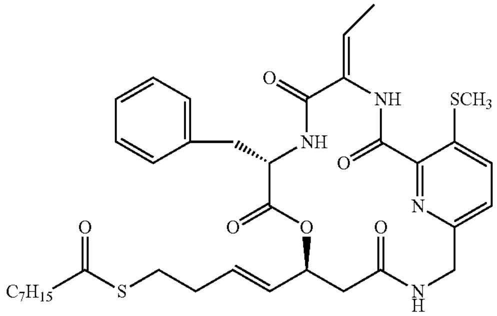
190
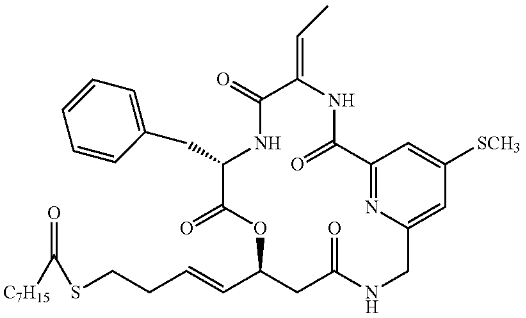

191
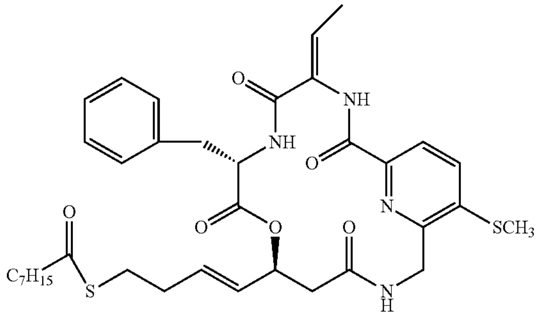
192
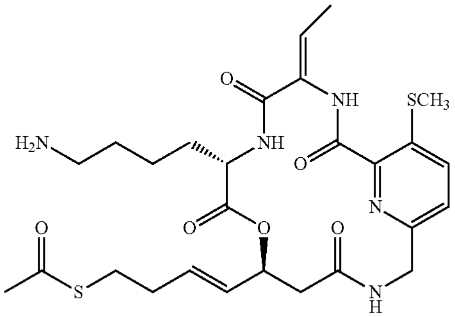
193
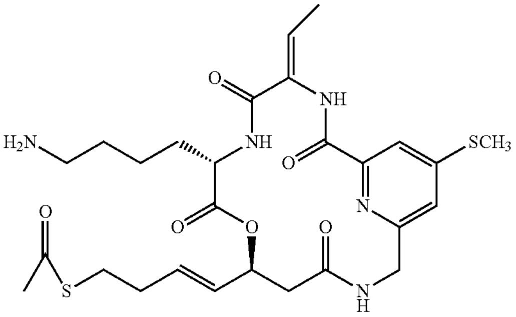
194
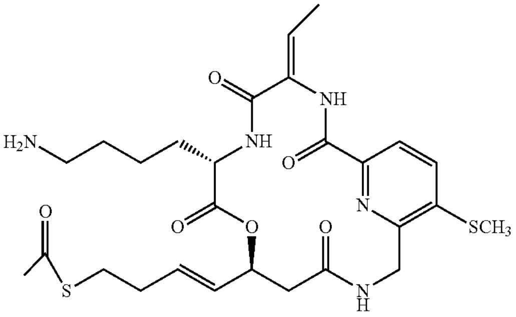
195
195
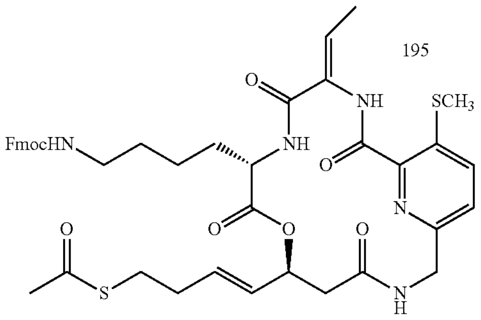
196
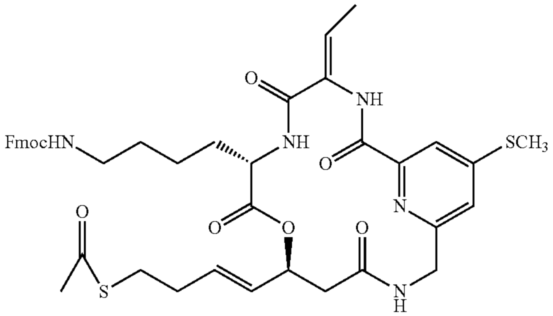
197
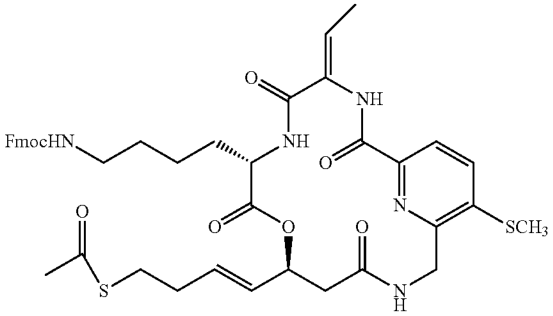
198
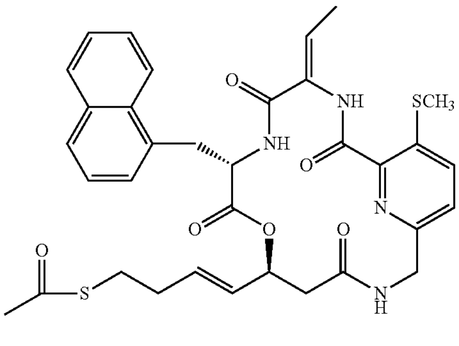

-continued
199
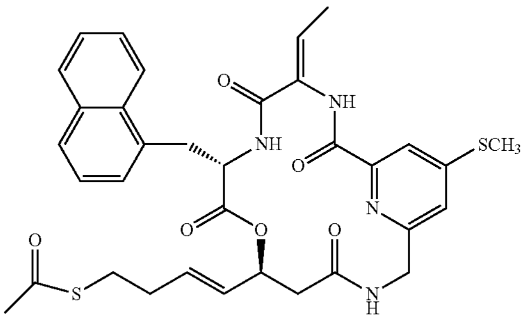
200
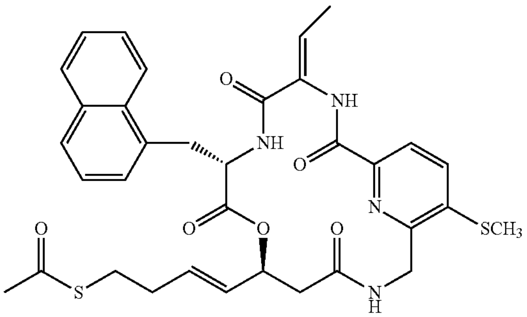
201
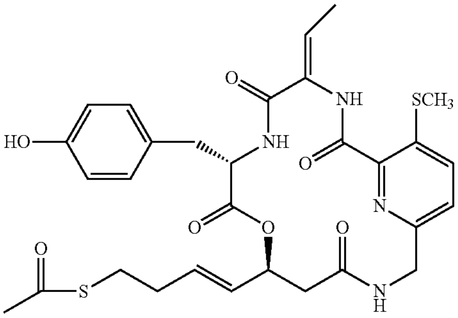
202
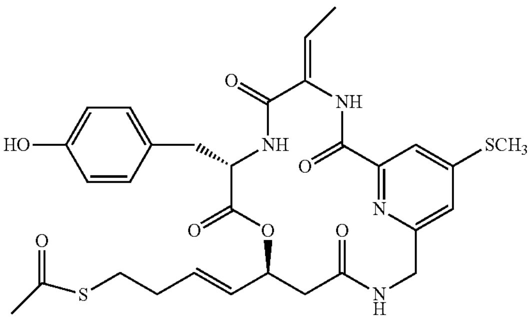
-continued
203
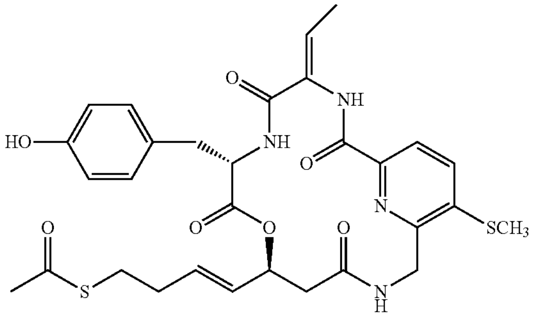
204
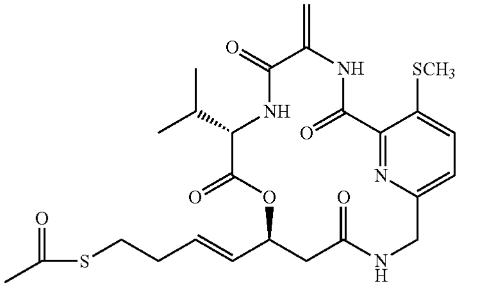
205
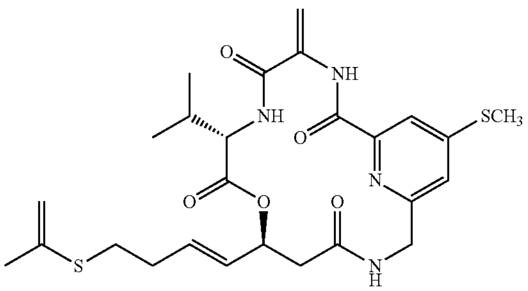
206
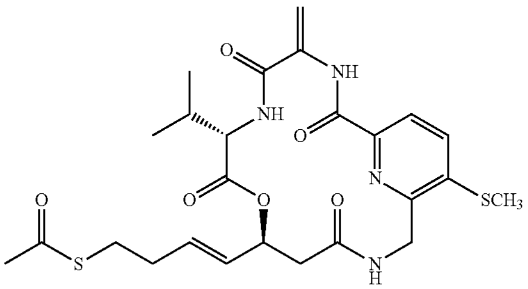
207
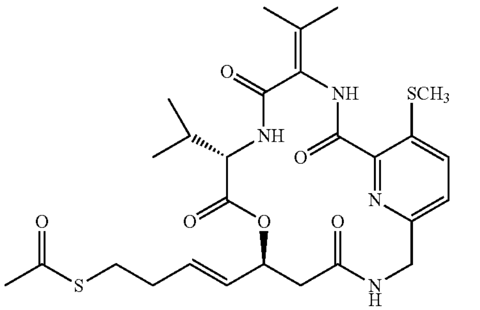

-continued
208
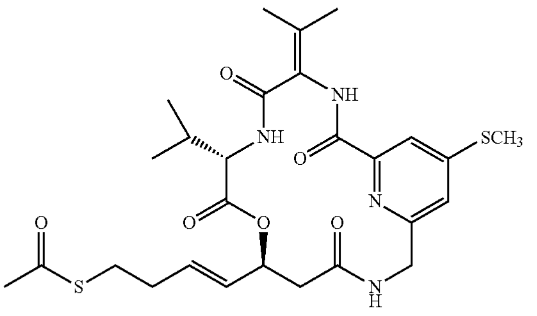
209
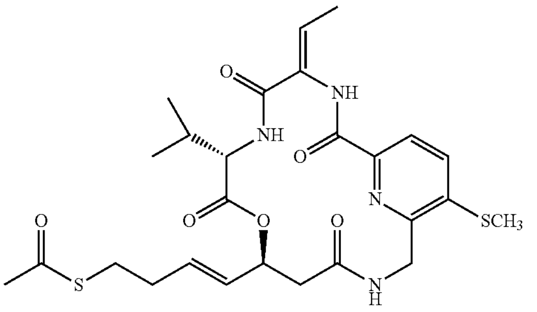
210
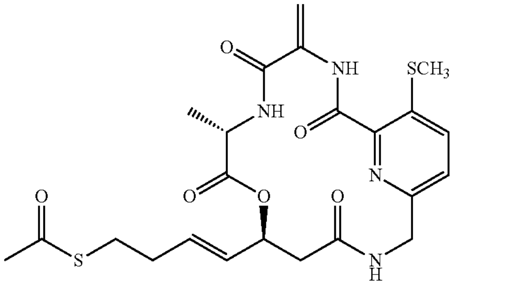
211
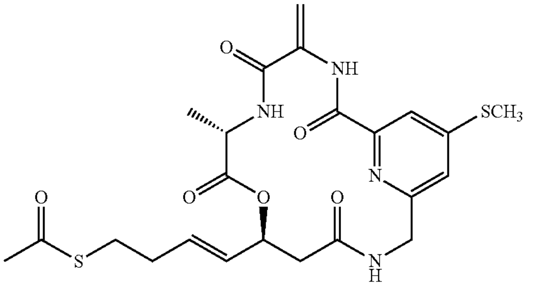
212
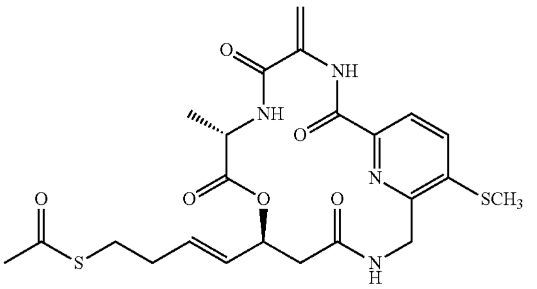
-continued
213
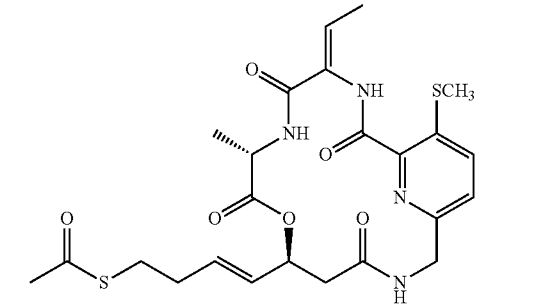
214
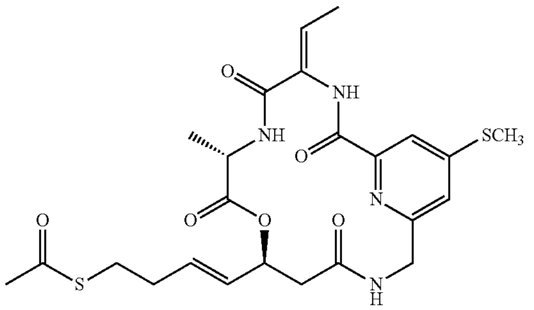
215
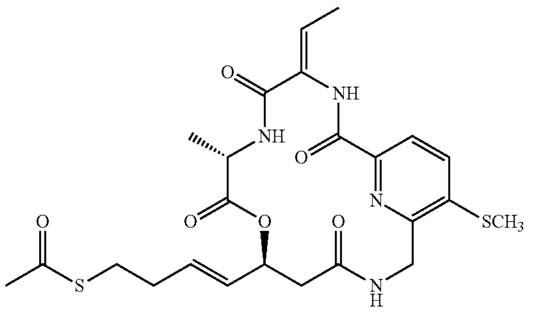
216
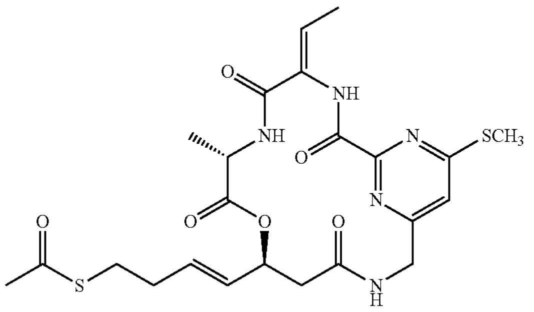
217
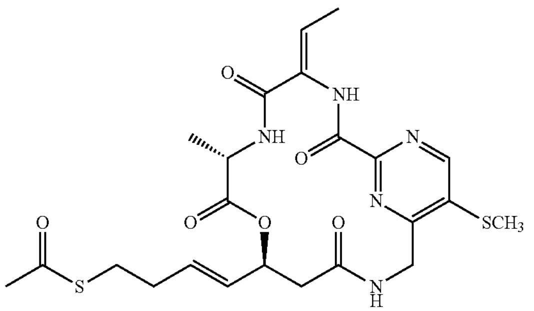

-continued
218
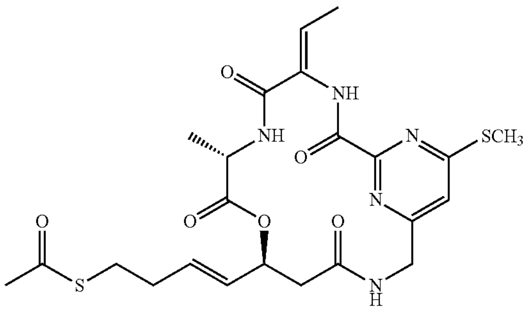
219
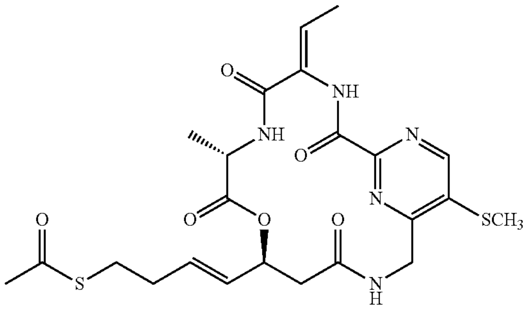
220
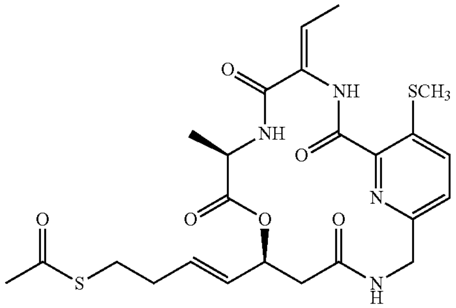
221
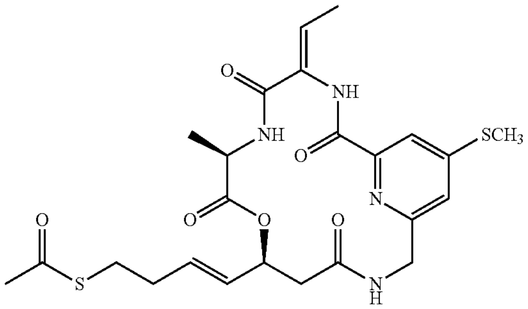
222
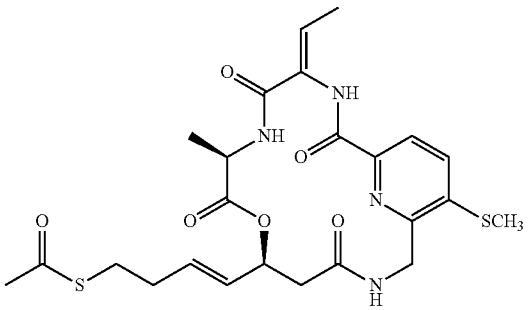
-continued
223
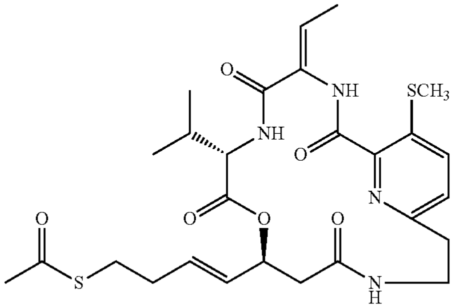
224
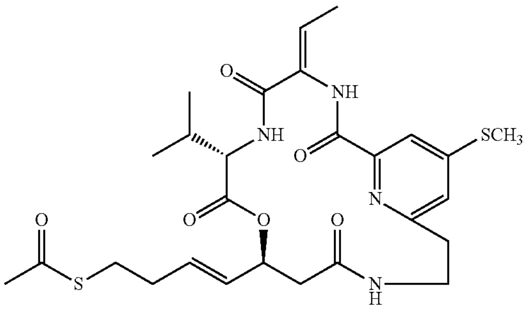
225
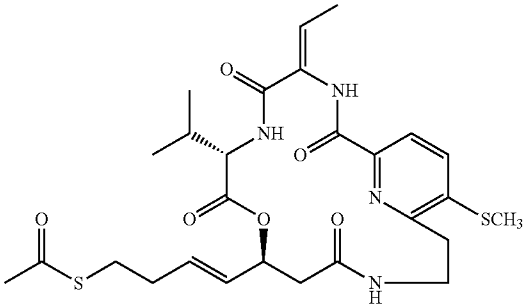
226
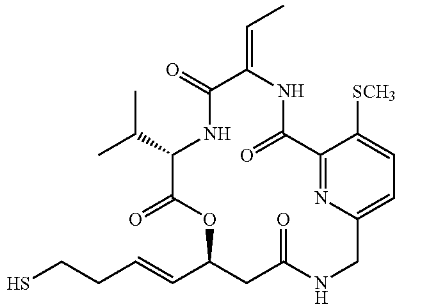
227
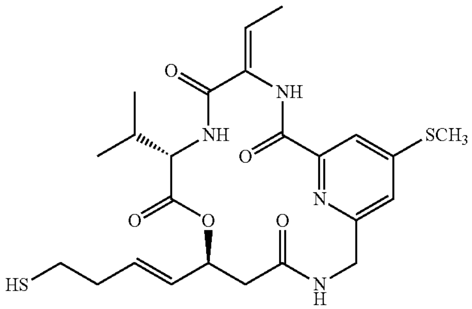

-continued
228
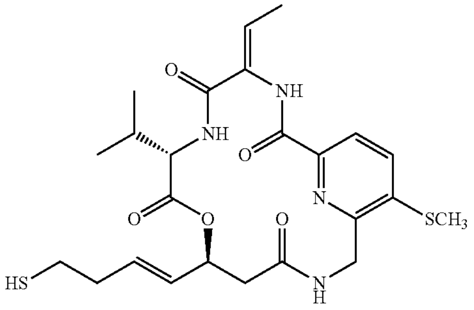
229
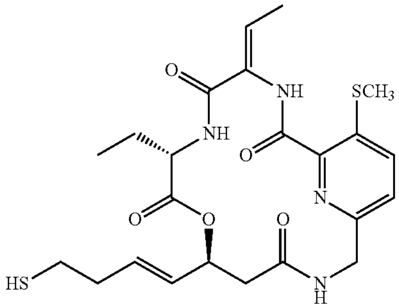
230
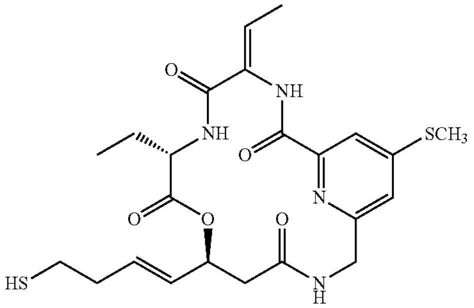
231
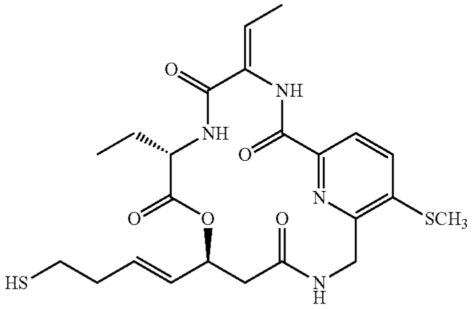
232
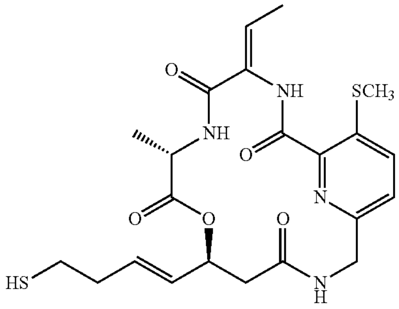
-continued
233
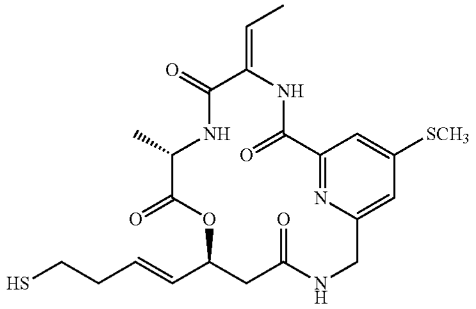
234
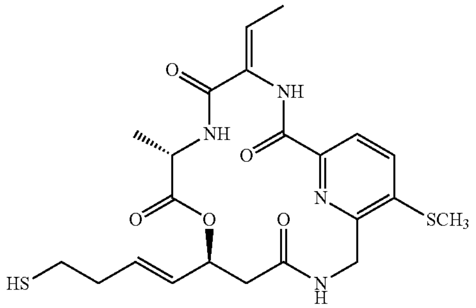
235
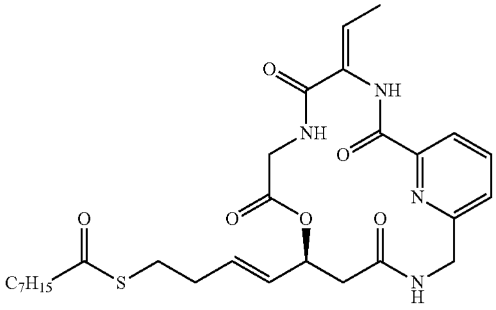
236
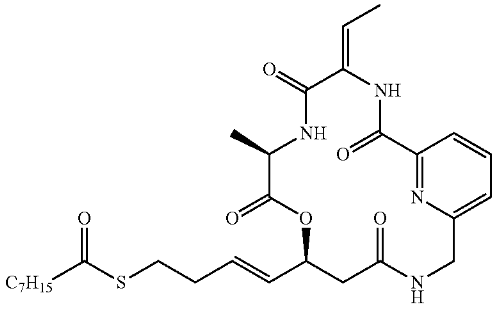
237
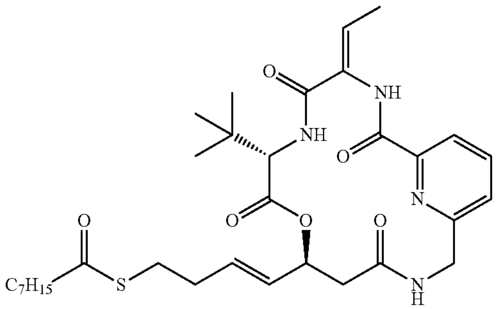

-continued
238
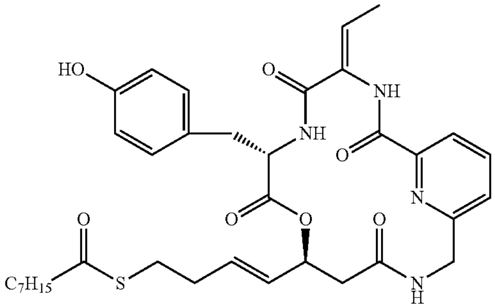
239
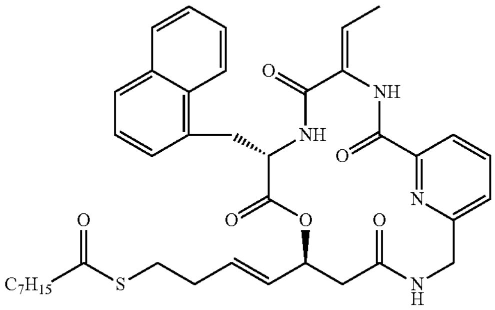
240
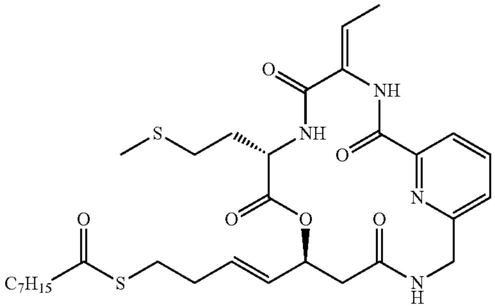
241
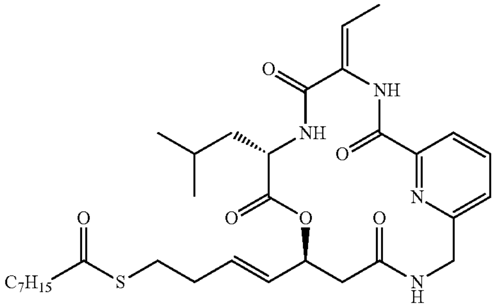
242
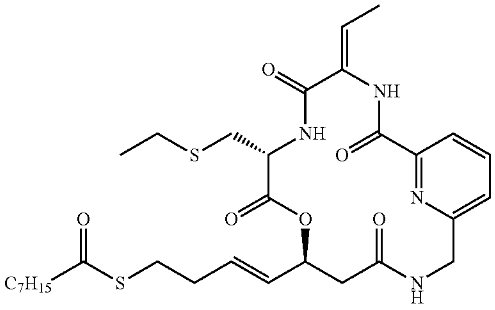
-continued
243
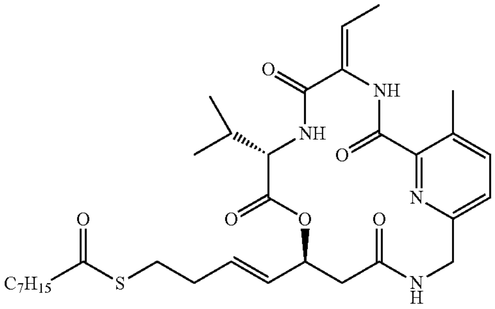
244
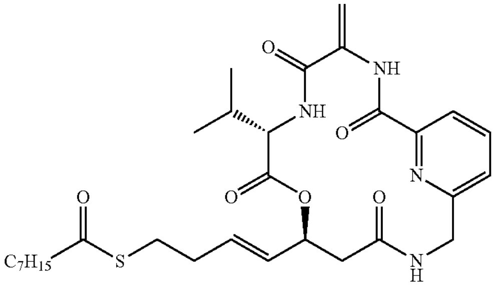
245
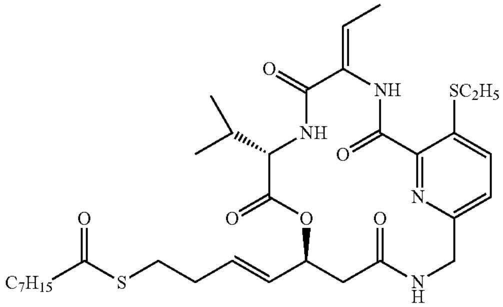
246
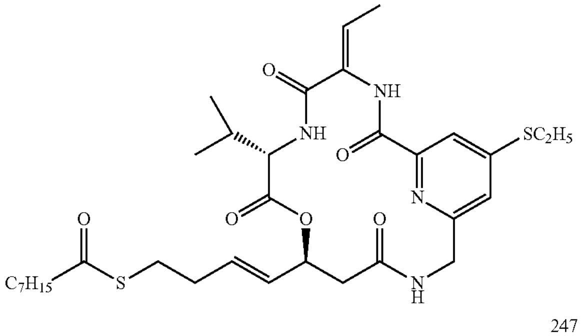
247
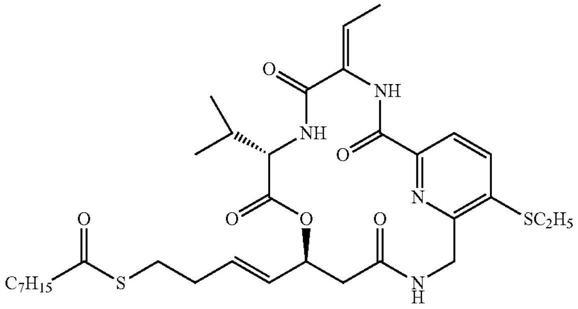

-continued

248

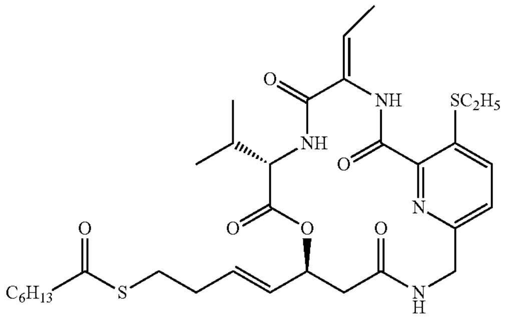

249

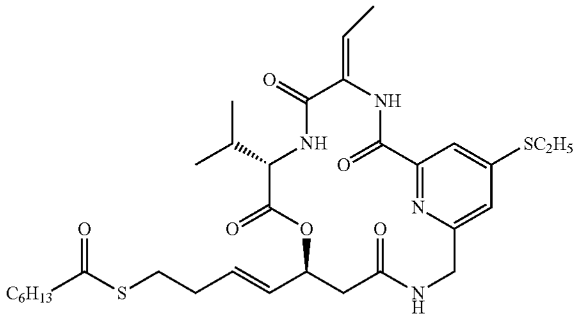

250

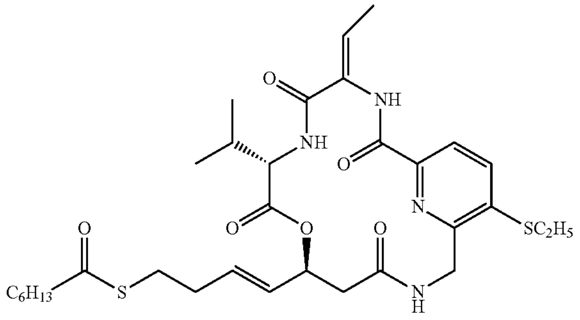

251

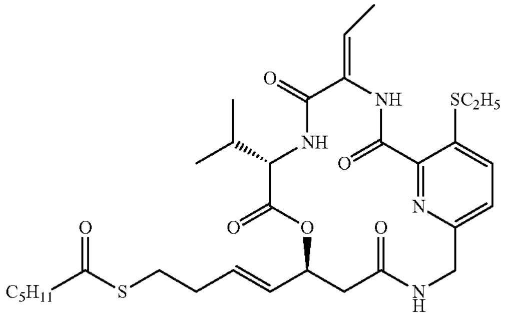

-continued

252

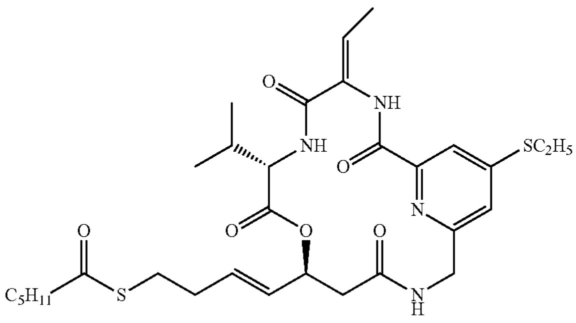

253

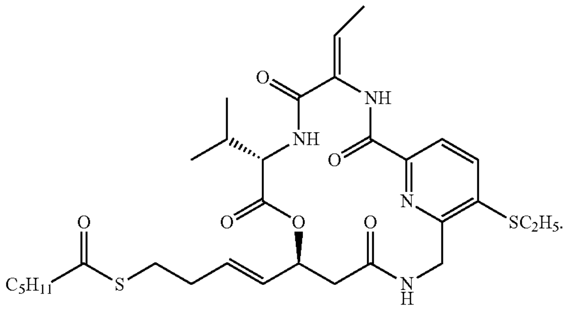

5. A method of preparing a compound with a chemical structure shown as Formula (I) according to claim 1, the method comprising:

(1) a hydrolysis reaction process of a compound of Formula (II) with alkali forming a compound of Formula (III); the hydrolysis reaction process represented as follows:

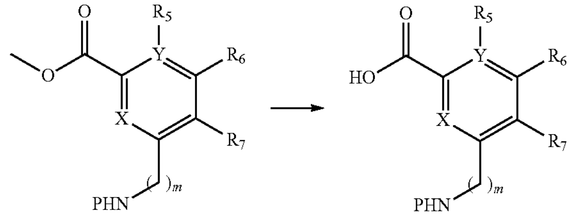

II III (2) a reaction process of the compound of Formula (III) and a compound of Formula (IV) with organic alkali under a condensation agent forming a compound of Formula (V); the reaction process represented as follows:

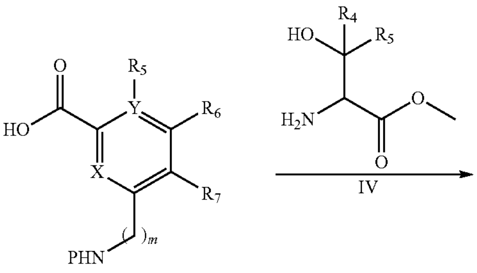

III

-continued

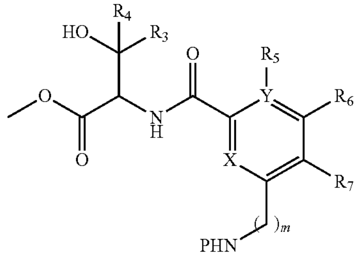

V (3) a condensation reaction process of the compound of Formula (V) and MsCl with organic alkali forming a compound of Formula (VI); the condensation reaction process represented as follows:

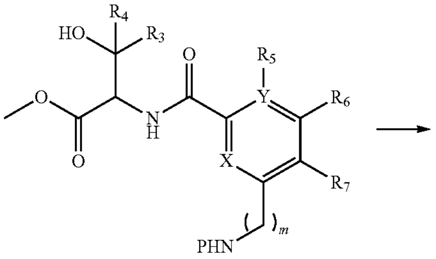

V

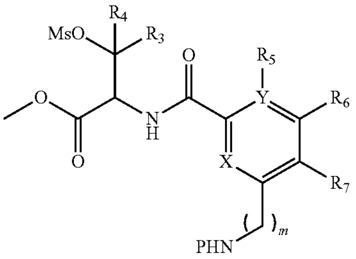

VI (4) an elimination reaction process of the compound of Formula (VI) forming a compound of Formula (VII); the elimination reaction process represented as follows:

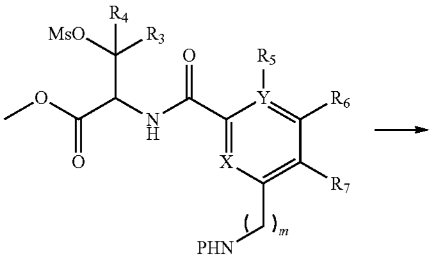

VI

-continued

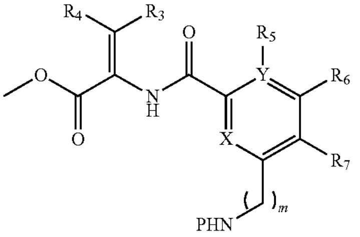

VII (5) a hydrolysis reaction process of the compound of Formula (VII) with alkali forming a compound of Formula (VIII); the hydrolysis reaction process represented as follows:

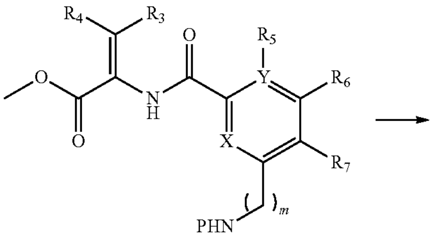

VII

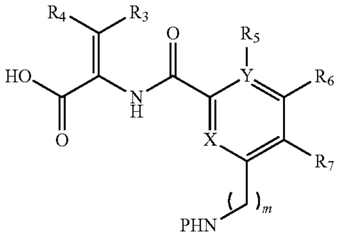

VIII (6) a condensation reaction process of the compound of Formula (VIII) and compound of Formula (IX) with organic alkali under a condensation agent forming a compound of Formula (X); the condensation reaction process represented as follows:

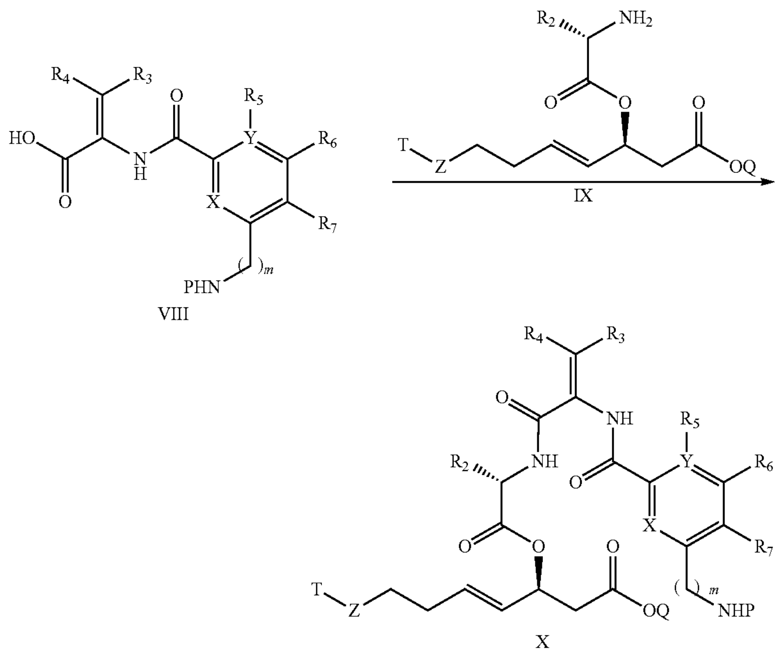

VIII

IX

X (7) removing an amino protecting group P and carboxyl protecting group Q of the compound of Formula (X), and then under a condensation agent with organic alkali forming a compound of Formula (XI) via an intramolecular closed loop reaction; the intramolecular closed loop reaction represented as follows:

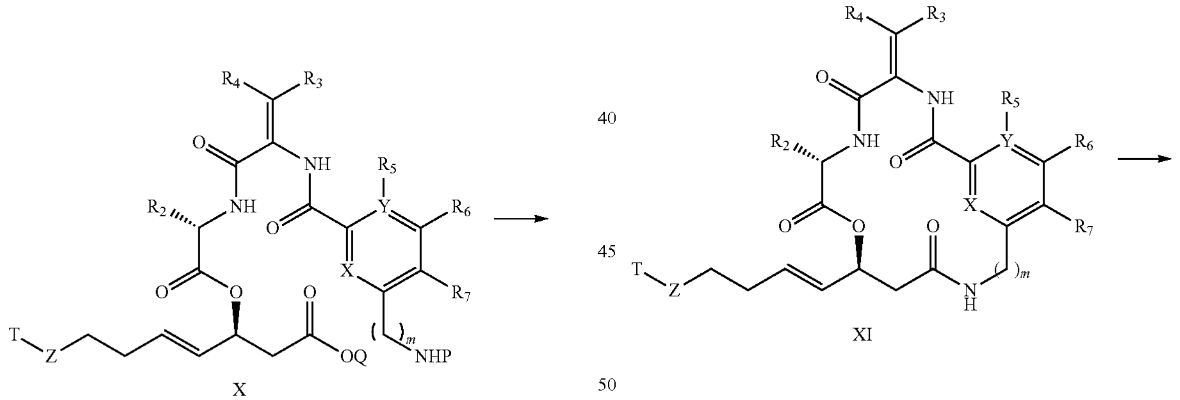

X

XI (8) removing protecting group T of the compound of Formula (XI), and forming a compound of Formula (XII); the reaction represented as follows:

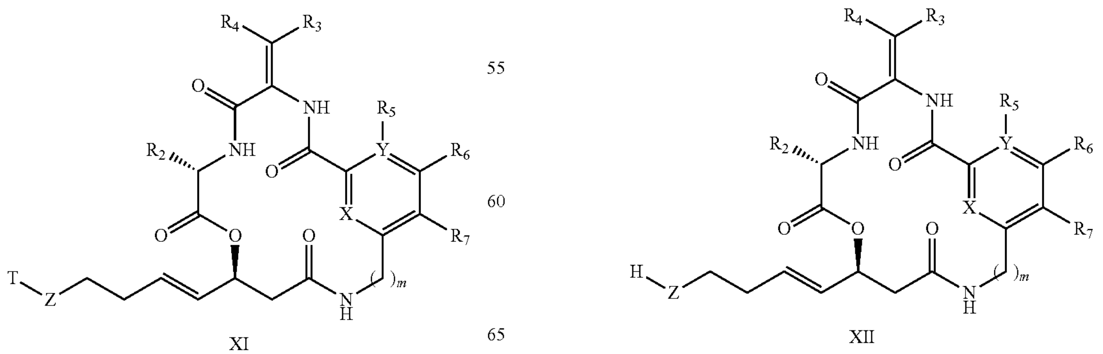

XI

XII (9) a reaction process of the compound of Formula (XII) and compound $R_1$-L forming a compound of Formula (XIII); the reaction process represented as follows:

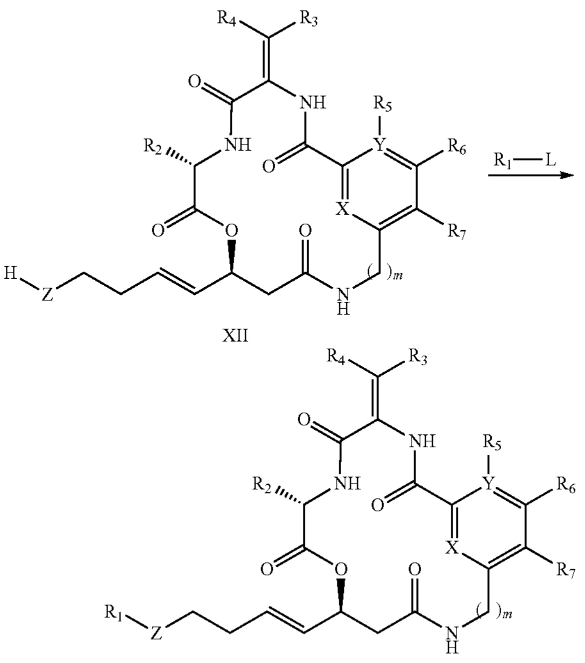

XII
XIII wherein, $R_1$ is hydrogen, $C_{1-16}$ alkyl, $C_{3-16}$ cycloalkyl, —(C═O)—($C_{1-16}$ alkyl), —(C═S)—($C_{1-16}$ alkyl) or —S—($C_{1-16}$ alkyl);

$R_2$ is hydrogen, $C_{1-12}$ alkyl, —$CH_2$—O—($C_{1-12}$ alkyl), —$CH_2$—NH—($C_{1-12}$ alkyl), —$CH_2$—S—($C_{1-12}$ alkyl), $C_{6-12}$ aryl, heteroaryl, —$CH_2$—($C_{6-12}$ aryl) or —$CH_2$-heteroaryl; wherein the $C_{6-12}$ aryl, heteroaryl, —$CH_2$—$C_{6-12}$ aryl, and —$CH_2$-heteroaryl, optionally comprise one or more substituents and the one or more substituents are selected from halo, amino, hydroxyl, nitro, cyano, $C_{1-12}$ alkyl, $C_{1-12}$ alkoxy, amino $C_{1-12}$ alkyl, acyl, acyloxy, thio $C_{1-12}$ alkyl, carboxyl and phenyl;

$R_3$, $R_4$ are independently selected from hydrogen, $C_{1-12}$ alkyl, —O—($C_{1-12}$ alkyl), —NH—($C_{1-12}$ alkyl), —S—($C_{1-12}$ alkyl), $C_{6-12}$ aryl and heteroaryl;

X is N and Y is C, or both X and Y are N;

$R_5$, $R_6$, $R_7$ are independently selected from hydrogen, halo, —S—($C_{1-12}$ alkyl), $C_{1-12}$ alkyl and t-butoxycarbonyl;

Z is —$CH_2$—, —NH—, —O—, —S— or

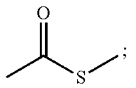

m is 0, 1, 2, 3, 4, 5 or 6;

P is an amino protecting group;

Q is a carboxyl protecting group;

T is O, S, NH heteroatom protecting group; and

L is selected from halo, OH, OMs, SH, MeO, t-butO.

6. The method according to claim 5, wherein the organic alkalis in steps (2), (3), (6) and (7) are selected from imidazole, triethylamine, diisopropylethylamine, piperidine, dimethyl pyridine, LiHMDS, NaHMDS, KHMDS, N-methyl morpholine, DABCO and pyridine;

the condensing agents in steps (2) and (6) are selected from DCC, EDC, HATU, HOAt, HOBt, DEAD, HBTU and PyBOP;

the amino protecting group P is selected from Boc, Cbz, Bn, Fmoc, Alloc, Tos, Trt, and Bn;

the carboxyl protecting group Q is selected from TMSOH, tertiary-butyl, ethyl, and methyl.

7. A pharmaceutical composition comprising a therapeutically effective amount of a compound selected from the compound of formula (I), its isomers, racemates, pharmaceutically acceptable salts, crystalline hydrate, solvate or mixtures thereof according to claim 1, and one or more of a pharmaceutically acceptable carrier.

8. A method for preventing or treating mammalian diseases related to the dysregulation of histone deacetylase comprising administering the compound of Formula (I), its isomers, racemates, pharmaceutically acceptable salts, crystalline hydrate, solvate or mixtures thereof according to claim 1.

9. The method according to claim 8, wherein the mammalian diseases related to the dysregulation of histone deacetylase selecting from the group consisting of cancer, neurodegenerative diseases, malaria and AIDS.

10. The method according to claim 9, wherein the mammalian diseases related to the dysregulation of histone deacetylase selecting from the group consisting of lymphomas, lung cancer, gastric cancer, pancreatic cancer, breast cancer, prostate cancer, cervical cancer and leukemia.

* * * * *